US012459951B2

(12) United States Patent
Hadari et al.

(10) Patent No.: US 12,459,951 B2
(45) Date of Patent: Nov. 4, 2025

(54) COMPOUNDS THAT INTERACT WITH RAS SUPERFAMILY PROTEINS FOR TREATMENT OF CANCERS, INFLAMMATORY DISEASES, RASOPATHIES, AND FIBROTIC DISEASE

(71) Applicant: SHY Therapeutics, LLC, Harrison, NY (US)

(72) Inventors: Yaron R. Hadari, Harrison, NY (US); Michael Schmertzler, St. Petersburg, FL (US); Theresa M. Williams, Harleysville, PA (US); Carolina Bigarella, Pleasantville, NY (US); Luca Carta, Scarsdale, NY (US); Rebecca Hutcheson, Stamford, CT (US); Sufang Zhang, Briarcliff Manor, NY (US); Charles H Reynolds, Austin, TX (US)

(73) Assignee: SHY Therapeutics, LLC, Harrison, NY (US)

(*) Notice: Subject to any disclaimer, the term of this patent is extended or adjusted under 35 U.S.C. 154(b) by 0 days.

(21) Appl. No.: 18/626,740

(22) Filed: Apr. 4, 2024

(65) Prior Publication Data

US 2024/0360141 A1 Oct. 31, 2024

Related U.S. Application Data

(63) Continuation of application No. PCT/US2023/065530, filed on Apr. 7, 2023.

(60) Provisional application No. 63/384,905, filed on Nov. 23, 2022, provisional application No. 63/329,141, filed on Apr. 8, 2022.

(51) Int. Cl.

| | |
|---|---|
| ***C07D 487/04*** | (2006.01) |
| ***A61K 31/53*** | (2006.01) |
| ***A61P 35/00*** | (2006.01) |

(52) U.S. Cl.
CPC ............ *C07D 487/04* (2013.01); *A61K 31/53* (2013.01); *A61P 35/00* (2018.01)

(58) Field of Classification Search
CPC ........ C07D 487/04; A61K 31/53; A61P 35/00
See application file for complete search history.

(56) References Cited

U.S. PATENT DOCUMENTS 4,838,925 A 6/1989 Tseng
6,670,357 B2 12/2003 Leftheris et al.
6,867,300 B2 3/2005 Godfrey, Jr. et al.
6,869,952 B2 3/2005 Bhide et al.
6,982,265 B1 1/2006 Hunt et al.
7,211,666 B2 5/2007 Godfrey, Jr. et al.
7,285,551 B2 10/2007 Hashimoto et al.
7,306,631 B2 12/2007 Glenn, Jr. et al.
7,531,539 B2 5/2009 Fink et al.
7,534,792 B2 5/2009 Wittman et al.
7,576,090 B2 8/2009 Herz et al.
7,713,973 B2 5/2010 Dong et al.
7,973,013 B2 7/2011 Cho et al.
8,198,438 B2 6/2012 Sampognaro et al.
8,212,031 B2 7/2012 Velaparthi et al.
8,445,676 B2 5/2013 Purandare et al.
8,455,451 B2 6/2013 Cho et al.
8,703,778 B2 4/2014 Ren et al.
9,050,345 B2 6/2015 Finlay et al.
9,174,995 B2 11/2015 Dorsch et al.
9,260,436 B2 2/2016 Takahashi et al.
9,802,904 B2 10/2017 Maloney et al.
10,292,985 B2 5/2019 Borzilleri et al.
10,336,761 B2 7/2019 Harikrishnan et al.
2004/0063707 A1* 4/2004 Bhide ..................... A61P 21/04 544/183
2006/0084650 A1 4/2006 Dong et al.
2008/0045496 A1* 2/2008 Fink ........................ A61P 35/00 514/233.2
2011/0172241 A1 7/2011 Herz et al.
2014/0256719 A1 9/2014 Finlay et al.
2015/0291593 A1 10/2015 Su et al.
2016/0089371 A1 3/2016 Liu et al.
2016/0115166 A1 4/2016 Wu et al.
2017/0000800 A1 1/2017 Yang et al.
2018/0215761 A1* 8/2018 Harikrishnan .......... A61P 35/02
2019/0276440 A1 9/2019 Zhao et al.
2020/0299285 A1 9/2020 Fletcher et al.

(Continued)

FOREIGN PATENT DOCUMENTS

CN 104974163 B 10/2015
CN 105534984 A 5/2016

(Continued)

OTHER PUBLICATIONS

Organic chemistry / Francis A. Carey.—4th ed. 2000 (Year: 2000).*
National Center for Biotechnology Information (2024). PubChem Compound Summary for CID 133525870, 5-Amino-1-phenyl-3-[3-[(1-phenyltetrazol-5-yl)amino]propyl]pyrazole-4-carbonitrile. Retrieved Oct. 24, 2024 from https://pubchem.ncbi.nlm.nih.gov/compound/133525870. (Year: 2024).*
Abstract: "Proline isosteres in a series of 2,4-disubstituted pyrrolo[1,2-*f*][1,2,4]triazine inhibitors of IGF-1R kinase and IR kinase," *Bioorganic & Medicinal Chemistry Letters*, 20:17 (Sep. 1, 2010) 5027-5030.
Abstract: "Pyrrolo[1,2-*f*][1,2,4]triazines as JAK2 inhibitors: Achieving potency and selectivity for JAK2 over JAK3," *Bioorganic & Medicinal Chemistry Letters*, 21:5 (2011) 1425-1428.

(Continued)

*Primary Examiner* — Clinton A Brooks
*Assistant Examiner* — Izabela Schmidt
(74) *Attorney, Agent, or Firm* — Jones Day

(57) ABSTRACT

Provided herein are compounds of Formula I, or a pharmaceutically acceptable form thereof, and pharmaceutical compositions comprising the same. Also provided herein methods of modulating the activity of cellular targets by administering to a subject a compound of Formula I, or a pharmaceutically acceptable form thereof. Further provided herein are methods of treating cancer, fibrotic diseases, and inflammatory diseases by administering to a subject a compound of or a pharmaceutically acceptable form thereof.

46 Claims, No Drawings

(56) References Cited

U.S. PATENT DOCUMENTS

| | | | | |
|---|---|---|---|---|
| 2022/0041607 | A1 | 2/2022 | Wang et al. | |
| 2024/0063707 | A1* | 2/2024 | Rivera Iunnissi .. | H02M 1/0074 |

FOREIGN PATENT DOCUMENTS

| | | | | | |
|---|---|---|---|---|---|
| CN | 105669680 | A | 6/2016 | | |
| CN | 108276463 | A | 7/2018 | | |
| CN | 108341819 | A | 7/2018 | | |
| CN | 109111447 | A | 1/2019 | | |
| CN | 114105989 | A | 3/2022 | | |
| EP | 0244166 | A2 | 11/1987 | | |
| EP | 1669071 | B1 | 7/2009 | | |
| EP | 4180434 | A1 | 5/2023 | | |
| WO | WO 2000/071129 | | 11/2000 | | |
| WO | WO 2002/040486 | | 5/2002 | | |
| WO | WO 2003/000254 | | 1/2003 | | |
| WO | WO 2004/009601 | | 1/2004 | | |
| WO | WO 2004/009784 | | 1/2004 | | |
| WO | WO 2004/043912 | | 5/2004 | | |
| WO | WO 2005/097052 | | 10/2005 | | |
| WO | WO 2006/012422 | | 2/2006 | | |
| WO | WO 2006/044687 | | 4/2006 | | |
| WO | WO 2006/066795 | | 6/2006 | | |
| WO | WO 2007/035428 | | 3/2007 | | |
| WO | WO 2008/005956 | | 1/2008 | | |
| WO | WO2008/021859 | | 2/2008 | | |
| WO | WO 2008/021924 | | 2/2008 | | |
| WO | WO 2008/057402 | | 5/2008 | | |
| WO | WO 2008/131050 | | 10/2008 | | |
| WO | WO 2009/111531 | | 9/2009 | | |
| WO | WO 2010/002472 | | 1/2010 | | |
| WO | WO 2010/036380 | | 4/2010 | | |
| WO | WO 2010/042684 | | 4/2010 | | |
| WO | WO 2010/091409 | | 8/2010 | | |
| WO | WO 2011/058109 | | 5/2011 | | |
| WO | WO 2011/089400 | | 7/2011 | | |
| WO | WO 2011/141713 | | 11/2011 | | |
| WO | WO 2012/012465 | | 1/2012 | | |
| WO | WO 2012/039787 | | 3/2012 | | |
| WO | WO 2012/039791 | | 3/2012 | | |
| WO | WO 2013/164061 | | 11/2013 | | |
| WO | WO 2013/178021 | | 12/2013 | | |
| WO | WO 2013/191112 | | 12/2013 | | |
| WO | WO 2014/015523 | | 1/2014 | | |
| WO | WO 2014/015675 | | 1/2014 | | |
| WO | WO 2014/015830 | | 1/2014 | | |
| WO | WO 2014/105952 | | 7/2014 | | |
| WO | WO 2014/143610 | | 9/2014 | | |
| WO | WO 2015/066371 | | 5/2015 | | |
| WO | WO 2015/126808 | | 8/2015 | | |
| WO | WO 2016/040764 | | 3/2016 | | |
| WO | WO 2016/119707 | | 8/2016 | | |
| WO | WO 2016/190847 | | 12/2016 | | |
| WO | WO 2017/004134 | | 1/2017 | | |
| WO | WO 2017/015425 | | 1/2017 | | |
| WO | WO 2017/040448 | | 3/2017 | | |
| WO | WO 2017/059191 | | 4/2017 | | |
| WO | WO 2017/070089 | | 4/2017 | | |
| WO | WO 2017/188596 | | 11/2017 | | |
| WO | WO 2017/219800 | | 12/2017 | | |
| WO | WO 2018/013867 | | 1/2018 | | |
| WO | WO 2018/195397 | | 10/2018 | | |
| WO | WO 2018/232094 | | 12/2018 | | |
| WO | WO 2018/233684 | | 12/2018 | | |
| WO | WO 2019/027765 | | 2/2019 | | |
| WO | WO 2020/052772 | | 3/2020 | | |
| WO | WO 2020/081636 | | 4/2020 | | |
| WO | WO 2020/113178 | | 6/2020 | | |
| WO | WO 2020/113182 | | 6/2020 | | |
| WO | WO 2020/119592 | | 6/2020 | | |
| WO | WO 2020/125673 | | 6/2020 | | |
| WO | WO 2020/132071 | | 6/2020 | | |
| WO | WO 2020/180768 | | 9/2020 | | |
| WO | WO 2020/210970 | | 10/2020 | | |
| WO | WO 2020/211672 | | 10/2020 | | |
| WO | WO 2020/211751 | | 10/2020 | | |
| WO | WO 2020/259601 | | 12/2020 | | |
| WO | WO 2021/011689 | | 1/2021 | | |
| WO | WO 2021/055747 | | 3/2021 | | |
| WO | WO 2021/072156 | | 4/2021 | | |
| WO | WO 2021/094209 | | 5/2021 | | |
| WO | WO 2021/097299 | | 5/2021 | | |
| WO | WO-2021127429 | A1 * | 6/2021 | .......... | A61K 31/502 |
| WO | WO 2021/151926 | | 8/2021 | | |
| WO | WO 2021/194927 | | 9/2021 | | |
| WO | WO-2021203131 | A1 * | 10/2021 | ............ | A61K 45/06 |
| WO | WO 2021/222807 | | 11/2021 | | |
| WO | WO 2022/007966 | | 1/2022 | | |
| WO | WO 2023/027948 | | 3/2023 | | |
| WO | WO 2023/110843 | | 6/2023 | | |
| WO | WO 2023/116865 | | 6/2023 | | |
| WO | WO 2023/160572 | | 8/2023 | | |

OTHER PUBLICATIONS

Abstract: "Synthesis and evaluation of pyrrolotriazine based molecules as PI3 kinase inhibitors," *Bioorganic & Medicinal Chemistry Letters*, 25:16 (2015) 3142-3146.

Abstract: "Heterobicyclic inhibitors of transforming growth factor beta receptor I (TGFβRI)," *Bioorganic & Medicinal Chemistry Letters*, 26:5 (Mar. 1, 2018) 1026-1034.

Abstract: "Discovery of cyclic guanidine-linked sulfonamides as inhibitors of LMTK3 kinase," *Bioorganic & Medicinal Chemistry Letters*, 30:9 (2020) 127108.

Abstract: "Design, synthesis and antiproliferative activity evaluation of a series of pyrrolo[2,1-*f*][1,2,4]triazine derivatives," *Bioorganic & Medicinal Chemistry Letters*, 30:12 (2020) 127194.

Abstract: "Pot, atom and step economic synthesis: a diversity-oriented approach to construct 2-substituted pyrrolo [2,1-*f*][1,2,4]triazin-4(3*H*)-ones," *RSC Advances*, 3:17 (2013) 5807.

Carboni, Joan M. et al., "BMS-754807, a small molecule inhibitor of insulin-like growth factor-1R/IR," *Mol. Cancer Ther.*, 8:12 (Dec. 2009) 3341-3349.

Chen, Yanhong et al., "A tandem copper(II)-promoted synthesis of 2-substituted pyrrolo[2,1-*f*][1,2,4]triazin-4(3*H*)-ones," *Tetrahedron*, 69:13 (Apr. 1, 2013) 2714-2719.

Cronin, Shane J.F. et al., "The metabolite BH4 controls T-cell proliferation in autoimmunity and cancer," *Nature*, 563(7732) Nov. 2018, 564-568.

Garg, Mansi et al., "Identification of new insulin growth factor receptor-1 (IGF-1R) inhibitors via exploring ATPas kinase domain of IGF-IR through virtual screening," *Medicinal Chemistry Research*, vol. 26 (2016) 205-219.

Jia, Hong et al., "Discovery, Optimization, and Evaluation of Potent and Highly Selective PI3Kγ-PI3Kδ Dual Inhibitors," *J. Med. Chem.*, vol. 62 (2019) 4936-4948.

Lim, Hyun-Suk et al., "Identification of a Peptoid Inhibitor of the Proteasome 19S Regulatory Particle," *J. Am. Chem. Soc.*, 129 (2007) 7750-7751.

Muli, Christine S. et al., "Small Molecular Inhibitors of the Proteasome's Regulatory Particle," *Chembiochem.*, 20:14 (Jul. 15, 2019) 1739-1753.

Shima, Fumi et al., "In silico discovery of small-molecule Ras inhibitors that display antitumor activity by blocking the Ras-effector interaction," *PNAS*, 110:20 (May 14, 2013) 8182-8187.

Tychhon, Boranai et al., "The prognostic value of 19S ATPase proteasome subunits in acute myeloid leukemia and other forms of cancer," *Frontiers in Medicine* (Jul. 12, 2023) doi: 10.3389/fmed.2023.1209425, 14 pages.

Wang, Xu et al., "Antipsychotic phenothiazine drugs bind to KRAS in vitro," *Journal of Biomolecular NMR*, vol. 75 (2021) 233-244.

Wittman, Mark D. et al., "Discovery of a 2,4-Disubstituted Pyrrolo[2,1-*f*][1,2,4]triazine Inhibitor (BMS-754807) of Insulin-like Growth Factor Receptor (IGF-1R) Kinase in Clinical Development," *J. Med. Chem.*, vol. 52 (2009) 7360-7363.

Xiang, Haoyue et al. "Pot, atom and step economic synthesis: a diversity-oriented approach to construct 2-substituted pyrrolo[2,1-f][1,2,4]triazin-4(3H)-ones," RSC Advances, Issue 17 (2013) Abstract only.

(56) References Cited

OTHER PUBLICATIONS

International Search Report mailed May 26, 2023 for International Application No. PCT/US2023/065530.
Written Opinion mailed May 26, 2023 for International Application No. PCT/US2023/065530.

* cited by examiner

COMPOUNDS THAT INTERACT WITH RAS SUPERFAMILY PROTEINS FOR TREATMENT OF CANCERS, INFLAMMATORY DISEASES, RASOPATHIES, AND FIBROTIC DISEASE

CROSS REFERENCE

This application is a continuation of International Application No. PCT/US2023/065530, filed Apr. 7, 2023, which designates the United States and was published in English, which further claims the benefit of priority from U.S. Provisional Application No. 63/384,905, filed Nov. 23, 2022, and U.S. Provisional Application No. 63/329,141, filed Apr. 8, 2022. Each of the foregoing related applications, in its entirety, is incorporated herein by reference.

1. FIELD

Provided herein are compounds of Formula I, or a pharmaceutically acceptable form thereof, and pharmaceutical compositions comprising the same. Also provided herein methods of modulating the activity of cellular targets by administering to a subject a compound of Formula I, or a pharmaceutically acceptable form thereof. Further provided herein are methods of treating cancer, fibrotic diseases, and inflammatory diseases by administering to a subject a compound of Formula I, or a pharmaceutically acceptable form thereof.

2. SUMMARY

Provided herein is a compound of Formula I:

Formula I

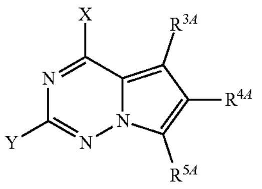

or a pharmaceutically acceptable form thereof, wherein:

X is —$NR^{1A}R^{2A}$ or $OR^{2A}$;

Y is an imidazolyl, a pyridinyl, or an 8-10-membered fused-heteroaryl; wherein the imidazolyl is optionally substituted with 1 $R^{6A}$ substituent and optionally substituted with 1-2 $R^{7A}$ substituents; and the pyridinyl or the 8-10-membered fused-heteroaryl is optionally substituted with 1-4 $R^{7A}$ substituents;

$R^{1A}$ is hydrogen or $C_{1-6}$ alkyl, wherein the $C_{1-6}$ alkyl is optionally substituted with 1-4 $R^{8A}$ substituents;

$R^{2A}$ is hydrogen, $C_{1-6}$ alkyl, $C_{3-7}$ cycloalkyl, $C_{1-6}$ heteroalkyl, $C_{3-7}$ heterocycloalkyl, $C_{5-10}$ membered aryl, —$S(O)_2R^{15A}$, —$P(O)R^{16A}R^{17A}$, or 5-10 membered heteroaryl, wherein the $C_{1-6}$ alkyl, $C_{3-7}$ cycloalkyl, $C_{1-6}$ heteroalkyl, and 5-10 membered heteroaryl are each independently optionally substituted with 1-4 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached, optionally wherein the 3-6 membered heterocycloalkyl formed by $R^{1A}$ and $R^{2A}$ is fused to a 5-6 membered heteroaryl;

$R^{3A}$ is $C_{1-6}$ alkyl, $C_{3-7}$ cycloalkyl, $C_{1-6}$ heteroalkyl, aryl, 5-10 membered heteroaryl, —$(CO)R^{11A}$, or —$C(O)NR^{12A}R^{13A}$ wherein the $C_{1-6}$ alkyl, $C_{3-7}$ cycloalkyl, $C_{1-6}$ heteroalkyl, aryl, and 5-10 membered heteroaryl are each independently optionally substituted with 1-3 $R^{9A}$ substituents;

$R^{4A}$ is hydrogen, aryl, or 5-10 membered heteroaryl, wherein the aryl and 5-10 membered heteroaryl are each independently optionally substituted with 1-4 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, $C_{1-6}$ heteroalkyl, halo, —$NR^{12A}R^{13A}$, $C_{1-6}$ alkoxy, $C_{1-6}$ haloalkoxy, —$C(O)NR^{12A}R^{13A}$, —$(CO)R^{11A}$, —$C(O)OR^{14A}$, or CN, wherein the $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, and $C_{1-6}$ heteroalkyl are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —$(CO)R^{11A}$, —$C(O)OR^{14A}$, —$C(O)NR^{12A}R^{13A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl, wherein the $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, $C_{1-6}$ alkoxy, $C_{3-6}$ cycloalkoxy, $C_{1-6}$ haloalkoxy, or 5-6 membered heteroaryl are each independently optionally substituted with 1-3 $R^{8A}$ substituents;

$R^{11A}$ is —OH, $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-7}$ cycloalkyl, $C_{1-6}$ haloalkyl, $C_{1-6}$ hydroxyalkyl, $C_{1-6}$ heteroalkyl, —OH, $C_{1-6}$ alkoxy, $C_{1-6}$ haloalkoxy, $C_{3-7}$ heterocycloalkyl, aryl, or 5-10 membered heteroaryl, wherein the $C_{1-6}$ alkyl, $C_{3-7}$ cycloalkyl, $C_{1-6}$ haloalkyl, $C_{1-6}$ hydroxyalkyl, $C_{1-6}$ heteroalkyl, $C_{1-6}$ alkoxy, $C_{1-6}$ haloalkoxy, $C_{3-7}$ heterocycloalkyl, aryl, and 5-10 membered heteroaryl are optionally substituted with 1-3 $R^{8A}$ substituents, or $R^{12A}$ and $R^{13A}$ are combined to form a 3-7 membered heterocycloalkyl including the nitrogen atom to which they are both attached;

$R^{14A}$ is hydrogen, $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{15A}$ is $C_{1-6}$ alkyl, $C_{3-6}$ cycloalkyl, $C_{1-6}$ alkoxy, or $C_{1-6}$ heteroalkyl, wherein the $C_{1-6}$ alkyl, $C_{3-6}$ cycloalkyl, $C_{1-6}$ alkoxy, and $C_{1-6}$ heteroalkyl, are each independently optionally substituted with 1-3 $R^{8A}$ substituents;

$R^{16A}$ and $R^{17A}$ are each independently selected from the group consisting $C_{1-6}$ alkyl, $C_{1-6}$ alkoxy, or $C_{1-6}$ heteroalkyl, wherein the $C_{1-6}$ alkyl, $C_{1-6}$ alkoxy, and $C_{1-6}$ heteroalkyl, are each independently optionally substituted with 1-3 $R^{8A}$ substituents, or $R^{16A}$ and $R^{17A}$ are combined to form a 3-7 membered heterocycloalkyl including the phorphorus atom to which they are both attached; and wherein, when X is OH or

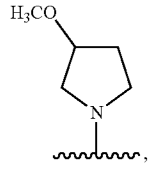

Y is N-methyl imidazoyl, and $R^{5A}$ is H, at least one of $R^{3A}$ and $R^{4A}$ is not unsubstituted phenyl.

Also provided herein is a compound of Formula II:

Formula II

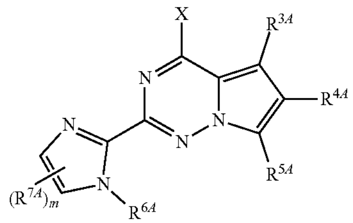

or a pharmaceutically acceptable form thereof, wherein:

X is —$NR^{1A}R^{2A}$ or —$OR^{2A}$;

$R^{1A}$ is hydrogen or $C_{1-6}$ alkyl;

$R^{2A}$ is hydrogen, $C_{1-6}$ alkyl, $C_{3-7}$ cycloalkyl, $C_{1-6}$ heteroalkyl, —$S(O)_2R^{15A}$, —$P(O)R^{16A}R^{17A}$, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached, optionally wherein the 3-6 membered heterocycloalkyl formed by $R^{1A}$ and $R^{2A}$ is fused to a 5-6 membered heteroaryl;

$R^{3A}$ is $C_{1-6}$ alkyl, $C_{3-6}$ cycloalkyl, $C_{1-6}$ heteroalkyl, phenyl, 5-10 membered heteroaryl, —$(CO)R^{11A}$, or —$C(O)NR^{12A}R^{13A}$, wherein the $C_{1-6}$ alkyl, $C_{3-6}$ cycloalkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —$(CO)R^{11A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl, wherein the $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, $C_{1-6}$ alkoxy, $C_{3-6}$ cycloalkoxy, $C_{1-6}$ haloalkoxy, or 5-6 membered heteroaryl are each independently optionally substituted with 1-3 $R^{8A}$ substituents;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-7}$ cycloalkyl, $C_{1-6}$ haloalkyl, $C_{1-6}$ hydroxyalkyl, $C_{1-6}$ heteroalkyl, —OH, $C_{1-6}$ alkoxy, or $C_{1-6}$ haloalkoxy, or $R^{12A}$ and $R^{13A}$ are combined to form a 3-6 membered heterocycloalkyl including the nitrogen atom to which they are both attached;

$R^{15A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{16A}$ and $R^{17A}$ are each independently selected from the group consisting $C_{1-6}$ alkyl, $C_{1-6}$ alkoxy, or $C_{1-6}$ heteroalkyl, wherein the $C_{1-6}$ alkyl, $C_{1-6}$ alkoxy, and $C_{1-6}$ heteroalkyl, are each independently optionally substituted with 1-3 $R^{8A}$ substituents, or $R^{16A}$ and $R^{17A}$ are combined to form a 3-7 membered heterocycloalkyl including the phorphorus atom to which they are both attached;

m is 0, 1 or 2; and wherein, when X is OH or

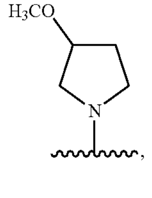 [SMILES: *N1CCC(OC)C1]

Y is N-methyl imidazoyl, and $R^{5A}$ is H, at least one of $R^{3A}$ and $R^{4A}$ is not unsubstituted phenyl.

Also provided herein is a compound of Formula IIa:

Formula IIa

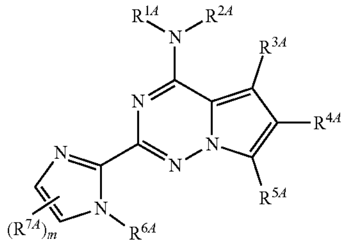

or a pharmaceutically acceptable form thereof, wherein:

$R^{1A}$ is hydrogen;

$R^{2A}$ is hydrogen, $C_{1-6}$ alkyl, $C_{3-6}$ cycloalkyl, $C_{1-6}$ heteroalkyl, —$S(O)_2R^{15A}$, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{3A}$ is $C_{1-3}$ alkyl, $C_{3-6}$ cycloalkyl, $C_{1-6}$ heteroalkyl, phenyl, 5-, 6- or 9-membered heteroaryl, —$(CO)R^{11A}$, or —$C(O)NR^{12A}R^{13A}$, wherein the $C_{1-3}$ alkyl, $C_{3-6}$ cycloalkyl, $C_{1-6}$ heteroalkyl, phenyl, and 5-, 6-, or 9-membered heteroaryl are each independently optionally substituted with 1-3 $R^{9A}$ substituents;

$R^{4A}$ is hydrogen, phenyl, or 5, 6, or 9 membered heteroaryl, wherein the phenyl and 5, 6, or 9 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is $C_{1-3}$ alkyl or $C_{1-3}$ heteroalkyl, wherein the $C_{1-3}$ alkyl or $C_{1-3}$ heteroalkyl is optionally substituted with biotinamide;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —$(CO)R^{11A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{11A}R^{12A}$, or 5-6 membered heteroaryl, wherein the $C_{1-6}$ alkyl or $C_{1-6}$ heteroalkyl is optionally substituted with biotinamide;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy, or $R^{12A}$ and $R^{13A}$ are combined to form a 5 or 6 membered heterocycloalkyl including the nitrogen atom to which they are both attached;

$R^{15A}$ is $C_{1-3}$ alkyl, $C_{3-6}$ cycloalkyl, or $C_{1-4}$ heteroalkyl;

$R^{16A}$ and $R^{17A}$ are each independently selected from the group consisting $C_{1-3}$ alkyl or $C_{1-3}$ alkoxy, or $R^{16A}$ and $R^{17A}$ are combined to form a 5 membered heterocycloalkyl including the phorphorus atom to which they are both attached; and m is 0 or 1.

Also provided herein is a compound of Formula IIa(1):

Formula IIa(1)

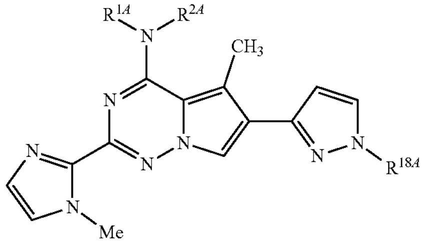

or a pharmaceutically acceptable form thereof, wherein:

$R^{1A}$ is hydrogen;

$R^{2A}$ is 5 or 6 membered heteroaryl, wherein the 5 or 6 membered heteroaryl is optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{8A}$ is selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —$(CO)R^{11A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy, or $R^{12A}$ and $R^{13A}$ are combined to form a 5 or 6 membered heterocycloalkyl including the nitrogen atom to which they are both attached; and $R^{18A}$ is $C_{1-3}$ alkyl or $C_{3-6}$ cycloalkyl.

Also provided herein is a compound of Formula IIb:

Formula IIb

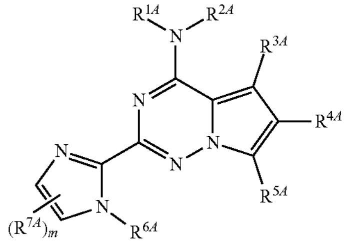

or a pharmaceutically acceptable form thereof, wherein:

$R^{1A}$ and $R^{2A}$ are combined to form a 4-6 membered heterocycloalkyl including the nitrogen atom to which they are both attached, optionally wherein the 4-6 membered heterocycloalkyl formed by $R^{1A}$ and $R^{2A}$ is fused to a 6 membered heteroaryl;

$R^{3A}$ is $C_{1-3}$ alkyl or phenyl, wherein the $C_{1-3}$ alkyl and phenyl are each independently optionally substituted with 1-3 $R^{9A}$ substituents;

$R^{4A}$ is phenyl or 5 membered heteroaryl, wherein the phenyl and 5 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is methyl;

$R^{7A}$ is methyl;

$R^{9A}$ is each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{11A}$ and $R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy;

m is 0 or 1; and wherein, when $R^{1A}$ and $R^{2A}$ are combined to form

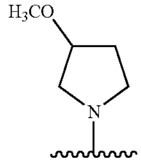, $R^{6A}$ is methyl, m is 0, and $R^{5A}$ is H, at least one of $R^{3A}$ and $R^{4A}$ is not unsubstituted phenyl.

Also provided herein is a compound of Formula IIc:

Formula IIc

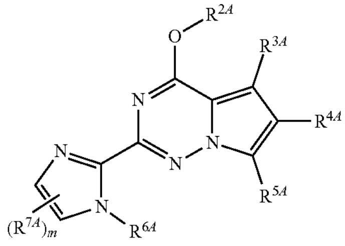

or a pharmaceutically acceptable form thereof, wherein:

$R^{2A}$ is hydrogen $C_{1-6}$ heteroalkyl, or 6 membered heteroaryl, wherein the $C_{1-6}$ heteroalkyl and 5-6 membered heteroaryl are each optionally substituted with 1-3 $R^{8A}$ substituents;

$R^{3A}$ is $C_{1-3}$ alkyl or phenyl, wherein the $C_{1-3}$ alkyl or phenyl are each independently optionally substituted with 1-3 $R^{9A}$ substituents;

$R^{4A}$ is hydrogen, phenyl, or 5 or 6 membered heteroaryl, wherein the phenyl and 5 or 6 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is methyl;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy;

m is 0 or 1; and wherein, when $R^{2A}$ is H, $R^{6A}$ is methyl, m is 0, and $R^{5A}$ is H, at least one of $R^{3A}$ and $R^{4A}$ is not unsubstituted phenyl.

Also provided herein is a compound of Formula III:

Formula III

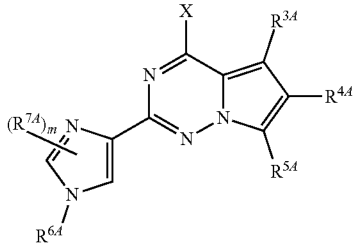

or a pharmaceutically acceptable form thereof, wherein:

X is $NR^{1A}R^{2A}$ or —$OR^{2A}$;

$R^{1A}$ is hydrogen or $C_{1-6}$ alkyl;

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

Also provided herein is a compound of Formula IIIa:

Formula IIIa

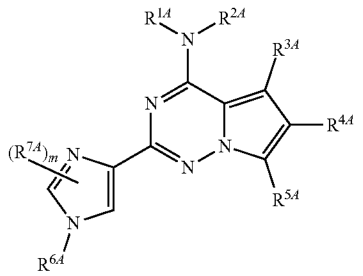

or a pharmaceutically acceptable form thereof, wherein:

$R^{1A}$ is hydrogen;

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

Also provided herein is a compound of Formula IIIb:

Formula IIIb

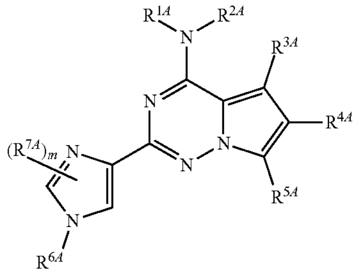

or a pharmaceutically acceptable form thereof, wherein:

$R^{1A}$ and $R^{2A}$ are combined to form a 4-6 membered heterocycloalkyl including the nitrogen atom to which they are both attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3

$R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $R^{10A}$ $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

Also provided herein is a compound of Formula IIIc:

Formula IIIc

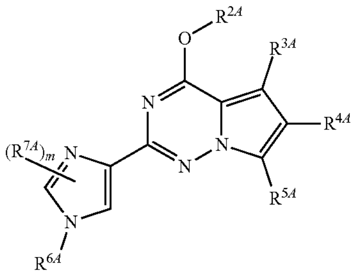

or a pharmaceutically acceptable form thereof, wherein:

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

Also provided herein is a compound of Formula IV:

Formula IV

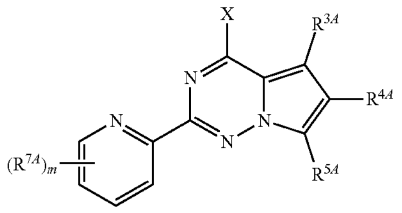

or a pharmaceutically acceptable form thereof, wherein:

X is —$NR^{1A}R^{2A}$ or —$OR^{2A}$;

$R^{1A}$ is hydrogen or $C_{1-6}$ alkyl;

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{7A}$ is $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, $C_{1-6}$ heteroalkyl, halo, —$NR^{12A}R^{13A}$, $C_{1-6}$ alkoxy, $C_{1-6}$ haloalkoxy, —$C(O)NR^{12A}R^{13A}$, —$(CO)R^{11A}$, —$C(O)OR^{14A}$, or CN, wherein the $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, and $C_{1-6}$ heteroalkyl are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$(CO)R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

Also provided herein is a compound of Formula IVa:

Formula IVa

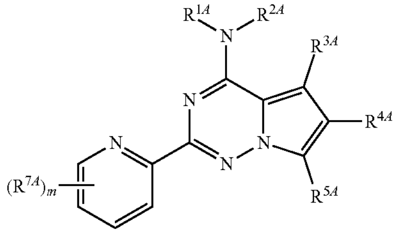

or a pharmaceutically acceptable form thereof, wherein:

$R^{1A}$ is hydrogen;

$R^{2A}$ is hydrogen, $C_{1-6}$ alkyl, $C_{3-6}$ cycloalkyl, $C_{1-6}$ heteroalkyl, or 6 membered heteroaryl, wherein the $C_{1-6}$ alkyl, $C_{3-6}$ cycloalkyl, $C_{1-6}$ heteroalkyl, and 6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{3A}$ is $C_{1-6}$ alkyl or phenyl, wherein the $C_{1-6}$ alkyl and phenyl are each independently optionally substituted with 1-3 $R^{9A}$ substituents;

$R^{4A}$ is 5 membered heteroaryl, wherein the 5 membered heteroaryl is optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$(CO)R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

Also provided herein is a compound of Formula IVb:

Formula IVb

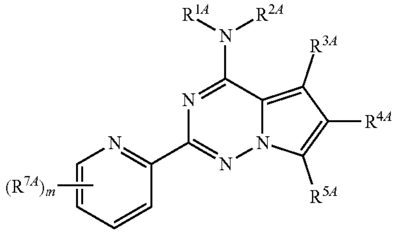

or a pharmaceutically acceptable form thereof, wherein:

$R^{1A}$ and $R^{2A}$ are combined to form a 4-6 membered heterocycloalkyl including the nitrogen atom to which they are both attached;

$R^{3A}$ is $C_{1-6}$ alkyl or phenyl, wherein the $C_{1-6}$ alkyl and phenyl are each independently optionally substituted with 1-3 $R^{9A}$ substituents;

$R^{4A}$ is 5 membered heteroaryl, wherein the 5 membered heteroaryl is optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$(CO)R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

Also provided herein is a compound of Formula IVc:

Formula IVc

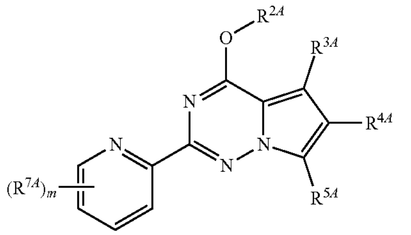

or a pharmaceutically acceptable form thereof, wherein:

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{7A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

Also provided herein is a compound of Formula I, Ia, Ib, Ic, II, IIa, IIa(1), IIb, IIc, III, IIIa, IIIb, IIIc, IV, IVa, IVb, or IVc selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, wherein the compound is a modulator of Ras superfamily activity according to a Ras Superfamily Activity Assay. In one embodiment, the compound or pharmaceutically acceptable form thereof modulates Ras superfamily activity of one or more GTPase by 50% or more, 55% or more, 60% or more, 65% or more, 70% or more, 75% or more, 80% or more, 85% or more, 90% or more, or 95% or more at 20 μM according to a Ras Superfamily Activity Assay. In one embodiment, the compound or pharmaceutically acceptable form thereof modulates Ras superfamily activity of one or more GTPase by about 50% to about 60%, about 60% to about 70%, about 70% to about 80%, about 80% to about 90%, or about 90% to about 100% at 20 μM according to a Ras Superfamily Activity Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, wherein the compound inhibits phosphorylation of Erk1/2 according to Erk1/2 Phosphorylation Assay. In one embodiment, the compound or pharmaceutically acceptable form thereof inhibits phosphorylation of Erk1/2 by 50% or more, 55% or more, 60% or more, 65% or more, 70% or more, 75% or more, 80% or more, 85% or more, 90% or more, or 95% or more at 10 μM according to Erk1/2 Phosphorylation Assay. In one embodiment, the compound or pharmaceutically acceptable form thereof inhibits phosphorylation of Erk1/2 by about 50% to about 60%, about 60% to about 70%, about 70% to about 80%, about 80% to about 90%, or about 90% to about 100% at 10 μM according to Erk1/2 Phosphorylation Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, wherein the compound activates phosphorylation of Erk1/2 according to Erk1/2 Phosphorylation Assay. In one embodiment, the compound or pharmaceutically acceptable form thereof activates phosphorylation of Erk1/2 by 50% or more, 55% or more, 60% or more, 65% or more, 70% or more, 75% or more, 80% or more, 85% or more, 90% or more, 95% or more, or equal or greater than 100% at 10 μM according to Erk1/2 Phosphorylation Assay. In one embodiment, the compound or pharmaceutically acceptable form thereof activates phosphorylation of Erk1/2 by about 50% to about 60%, about 60% to about 70%, about 70% to about 80%, about 80% to about 90%, about 90% to about 100%, or 100% or more at 10 μM according to Erk1/2 Phosphorylation Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, wherein the compound inhibits phosphorylation of Akt according to Akt Phosphorylation Assay. In one embodiment, the compound or pharmaceutically acceptable form thereof inhibits phosphorylation of Akt by 50% or more, 55% or more, 60% or more, 65% or more, 70% or more, 75% or more, 80% or more, 85% or more, 90% or more, or 95% or more at 10 μM according to Akt Phosphorylation Assay. In one embodiment, the compound or pharmaceutically acceptable form thereof inhibits phosphorylation of Akt by about 50% to about 60%, about 60% to about 70%, about 70% to about 80%, about 80% to about 90%, or about 90% to about 100% at 10 μM according to Akt Phosphorylation Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, wherein the compound activates phosphorylation of Akt according to Akt Phosphorylation Assay. In one embodiment, the compound or pharmaceutically acceptable form thereof activates phosphorylation of Akt by 50% or more, 55% or more, 60% or more, 65% or more, 70% or more, 75% or more, 80% or more, 85% or more, 90% or more, 95% or more, or equal or greater than 100% at 10 μM according to Akt Phosphorylation Assay. In one embodiment, the compound or pharmaceutically acceptable form thereof activates phosphorylation of Akt by about 50% to about 60%, about 60% to about 70%, about 70% to about 80%, about 80% to about 90%, about 90% to about 100%, or 100% or more at 10 μM according to Akt Phosphorylation Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, wherein the compound inhibits phosphorylation of Smad2/3 according to Phospho-Smad2/3 Inhibition Assay. In one embodiment, the compound or pharmaceutically acceptable form thereof inhibits phosphorylation of Smad2/3 by 50% or more, 55% or more, 60% or more, 65% or more, 70% or more, 75% or more, 80% or more, 85% or more, 90% or more, or 95% or more at 10 μM according to Phospho-Smad2/3 Inhibition Assay. In one embodiment, the compound or pharmaceutically acceptable form thereof inhibits phosphorylation of Smad2/3 by about 50% to about 60%, about 60% to about 70%, about 70% to about 80%, about 80% to about 90%, or about 90% to about 100% at 10 μM according to Phospho-Smad2/3 Inhibition Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof activates phosphorylation of Smad2/3 according to Phospho-Smad2/3 Inhibition Assay. In one embodiment, the compound or pharmaceutically acceptable form thereof activates phosphorylation of Smad2/3 by 50% or more, 55% or more, 60% or more, 65% or more, 70% or more, 75% or more, 80% or more, 85% or more, 90% or more, 95% or more, or equal or greater than 100% at 10 μM according to Phospho-Smad2/3 Inhibition Assay. In one embodiment, the compound or pharmaceutically acceptable form thereof activates phosphorylation of Smad2/3 by about 50% to about 60%, about 60% to about 70%, about 70% to about 80%, about 80% to about 90%, about 90% to about 100%, or 100% or more at 10 μM according to Phospho-Smad2/3 Inhibition Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, wherein the compound inhibits JNK according to JNK Activation Assay. In one embodiment, the compound or pharmaceutically acceptable form thereof inhibits JNK by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to JNK Activation Assay. In one embodiment, the compound or pharmaceutically acceptable form thereof inhibits JNK by about 50% to about 60%, about 60% to about 70%, about 70% to about 80%, about 80% to about 90%, or about 90% to about 100% at 10 μM according to JNK Activation Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, wherein the compound activates JNK according to JNK Activation Assay. In one embodiment, the compound or pharmaceutically acceptable form thereof activates JNK by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to JNK Activation Assay. In one embodiment, the compound or pharmaceutically acceptable form thereof activates JNK by about 50% to about 60%, about 60% to about 70%, about 70% to about 80%, about 80% to about 90%, about 90% to about 100%, or 100% or more at 10 μM according to JNK Activation Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, wherein the compound inhibits MAPK p38 according to MAPK p38 Activation Assay. In one embodiment, the compound or pharmaceutically acceptable form thereof inhibits MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to MAPK p38 Activation Assay. In one embodiment, the compound or pharmaceutically acceptable form thereof inhibits MAPK p38 by about 50% to about 60%, about 60% to about 70%, about 70% to about 80%, about 80% to about 90%, or about 90% to about 100% at 10 μM according to MAPK p38 Activation Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, wherein the compound activates MAPK p38 according to MAPK p38 Activation Assay. In one embodiment, the compound or pharmaceutically acceptable form thereof activates MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to MAPK p38 Activation Assay. In one embodiment, the compound or pharmaceutically acceptable form thereof activates MAPK p38 by about 50% to about 60%, about 60% to about 70%, about 70% to about 80%, about 80% to about 90%, about 90% to about 100%, or 100% or more at 10 μM according to MAPK p38 Activation Assay.

Also provided herein is a compound of Formula I, Ia, Ib, Ic, II, IIa, IIa(1), IIb, II, III, IIIa, IIIb, IIIc, IV, IVa, IVb, or IVc, or pharmaceutically acceptable form thereof, wherein the compound inhibits proliferation in MiaPaca2 according to Proliferation Assay. In one embodiment, the compound or pharmaceutically acceptable form thereof inhibits proliferation in MiaPaca2 with an IC50 value of 1 μM or less, 0.9 μM or less, 0.8 UM or less, 0.75 μM or less, 0.7 μM or less, 0.6 μM or less, 0.5 μM or less, 0.4 μM or less, 0.3 μM or less, 0.25 UM or less, 0.2 μM or less, 0.15 μM or less, or 0.1 μM or less according to Proliferation Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, wherein the compound inhibits IL-6 according to IL-6 Quantification Assay. In one embodiment, the compound or pharmaceutically acceptable form thereof inhibits IL-6 by 50% or more, 55% or more, 60% or more, 65% or more, 70% or more, 75% or more, 80% or more, 85% or more, 90% or more, or 95% or more at 10 μM according to IL-6 Quantification Assay. In one embodiment, the compound or pharmaceutically acceptable form thereof inhibits IL-6 by about 50% to about 60%, about 60% to about 70%, about 70% to about 80%, about 80% to about 90%, or about 90% to about 100% at 10 μM according to IL-6 Quantification Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof inhibits TNF-alpha according to TNF-alpha Quantification Assay. In one embodiment, the compound or pharmaceutically acceptable form thereof inhibits TNF-alpha by 50% or more, 55% or more, 60% or more, 65% or more, 70% or more, 75% or more, 80% or more, 85% or more, 90% or more, or 95% or more at 10 μM according to TNF-alpha Quantification Assay. In one embodiment, the compound or pharmaceutically acceptable form thereof inhibits TNF-alpha by about 50% to about 60%, about 60% to about 70%, about 70% to about 80%, about 80% to about 90%, or about 90% to about 100% at 10 μM according to TNF-alpha Quantification Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof that has a half-life of 10 minutes or more, 20 minutes or more, 30 minutes or more, 40 minutes or more, or 50 minutes or more in mouse liver microsomes according to Mouse Liver Microsome Metabolic Stability Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof that has a kinetic solubility of 10 μM or more, 20 μM or more, 30 μM or more, 40 μM or more, 5 μM or more, 60 μM or more, 70 μM or more, 80 μM or more, 90 μM or more, 100 μM or more, 150 μM or more, or 200 μM or more in pH 7.4 buffer comprising 2% DMSO according to Kinetic Solubility Assay.

Also provided herein is a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof that inhibits proliferation in NCI-H358, A375, GP2d, BT549, or MM.R1 according to Proliferation Assay. In one embodiment, the compound or pharmaceutically acceptable form thereof inhibits proliferation in NCI-H358, A375, GP2d, BT549, or MM.R1 with an IC50 value of 50 nM or less, 40 nM or less, 30 nM or less, 20 nM or less, 10 nM or less, 1 nM or less, 0.1 nM or less, or 0.01 nM or less according to Proliferation Assay. In one embodiment, the compound or pharmaceutically acceptable form thereof inhibits proliferation in MM.R1 with an IC50 value of 1 nM or less, 0.1 nM or less, or 0.01 nM or less according to Proliferation Assay.

Also provided herein are methods of modulating a Ras superfamily protein, comprising contacting the Ras superfamily protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating a Ras superfamily protein, comprising contacting the Ras superfamily protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating caspase activity, comprising contacting the caspase with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating caspase activity, comprising contacting the caspase with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating Erk1/2 activity, comprising contacting an Erk1/2 protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating Erk1/2 activity, comprising contacting an Erk1/2 protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating Akt activity, comprising contacting an Akt protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating Akt activity, comprising contacting an AKT protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating Smad2/3 activity, comprising contacting a Smad2/3 protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating Smad2/3 activity, comprising contacting a Smad2/3 protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating JNK activity, comprising contacting a JNK protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating JNK activity, comprising contacting a JNK protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating MAPK p38 activity, comprising contacting a MAPK p38 protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating MAPK p38 activity, comprising contacting a MAPK p38 protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating IL-6 activity, comprising contacting a IL-6 protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating IL-6 activity, comprising contacting a IL-6 protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating TNF-alpha activity, comprising contacting a TNF-alpha protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of modulating TNF-alpha activity, comprising contacting a TNF-alpha protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof.

Also provided herein are methods of treating cancer in a subject, comprising administering a therapeutically effective amount of the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, to the subject having cancer. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

Also provided herein are methods of treating cancer in a subject, comprising administering a therapeutically effective amount of a pharmaceutical comprising a compound of Formula I, Ia, Ib, Ic, II, IIa, IIb, IIc, III, IIIa, IIIb, IIIc, IV, IVa, IVb, or IVc, or pharmaceutically acceptable form thereof, to the subject having cancer.

Also provided herein are methods of treating a fibrotic disease in a subject, comprising administering a therapeutically effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, to the subject.

Also provided herein are methods treating a fibrotic disease in a subject, comprising administering a therapeutically effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, to the subject.

Also provided herein are methods treating an inflammatory disease in a subject, comprising administering a therapeutically effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, to the subject.

Also provided herein are methods of treating an inflammatory disease in a subject, comprising administering a therapeutically effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, to the subject.

Also provided herein are pharmaceutical compositions provided herein comprising therapeutically effective amounts of one or more of compounds provided herein (e.g. compounds of Formula I, Ia, Ib, Ic, II, IIa, IIa(1), IIb, IIc, III, IIIa, IIIb, IIIc, IV, IVa, IVb, or IVc) and a pharmaceutically acceptable carrier, diluent or excipient.

3. DETAILED DESCRIPTION

3.1. Definitions

To facilitate understanding of the disclosure set forth herein, a number of terms are defined below.

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

The singular forms "a," "an," and "the" include plural references, unless the context clearly dictates otherwise.

As used herein "subject" is an animal, such as a mammal, including human, such as a patient.

As used herein, biological activity refers to the in vivo activities of a compound or physiological responses that result upon in vivo administration of a compound, composition or other mixture. Biological activity, thus, encompasses therapeutic effects and pharmacokinetic behavior of such compounds, compositions and mixtures. Biological activities can be observed in in vitro systems designed to test for such activities.

As used herein, pharmaceutically acceptable derivatives of a compound include, but are not limited to, salts, esters, enol ethers, enol esters, acetals, ketals, orthoesters, hemiacetals, hemiketals, acids, bases, clathrates, solvates or hydrates thereof. Such derivatives may be readily prepared by those of skill in this art using known methods for such derivatization. The compounds produced may be administered to animals or humans without substantial toxic effects and either are pharmaceutically active or are prodrugs.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C═C(OR) where R is alkyl, alkenyl, alkynyl, aryl, aralkyl and cycloalkyl. Pharmaceutically acceptable enol esters include, but are not limited to, derivatives of formula C═C(OC(O)R) where R is hydrogen, alkyl, alkenyl, alkynyl, aryl, aralkyl and cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating a fibrotic disease, for example DMD.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, and unless otherwise indicated, the terms "manage," "managing" and "management" encompass preventing the recurrence of the specified disease or disorder in a subject who has already suffered from the disease or disorder, and/or lengthening the time that a subject who has suffered from the disease or disorder remains in remission. The terms encompass modulating the threshold, development and/or duration of the disease or disorder, or changing the way that a subject responds to the disease or disorder.

As used herein, the terms "fibrosis" or "fibrotic disease" may be used interchangeably and refer to any pathological wound healing process in which connective tissue replaces normal parenchymal tissue, leading to considerable tissue re-modeling and the formation of permanent scar tissue. For example, in some embodiments, the fibrotic disease may be fibrosis of the kidney, such as progressive kidney disease. In some embodiments, the fibrotic disease may be fibrosis of the cardiovascular system, such as atherosclerosis or restenosis. In some embodiments, the fibrotic disease may be pulmonary fibrosis. In some embodiments, the fibrotic disease may be cystic fibrosis. In some embodiments, the fibrotic disease may be idiopathic fibrosis, such as idiopathic pulmonary fibrosis. In some embodiments, the fibrotic disease may be fibrosis of the lung, such as progressive massive fibrosis or radiation-induced lung injury. In some embodiments, the fibrotic disease may be bridging fibrosis. In some embodiments, the fibrotic disease may be fibrosis of the liver, such as cirrhosis. In some embodiments, the fibrotic disease may be fibrosis of the intestine, such as Crohn's disease. In some embodiments, the fibrotic disease may be fibrosis of the muscular system, such as Duchenne muscular dystrophy (DMD). In some embodiments, the fibrotic disease may be fibrosis of the brain, such as glial scar. In some embodiments, the fibrotic disease may be fibrosis of the joints, such as arterial stiffness, fibrosis of the knee or fibrosis of the shoulder. In some embodiments, the fibrotic disease may be fibrosis of the skin, such as Keloid. In some embodiments, the fibrotic disease may be fibrosis of the bone marrow, such as myelofibrosis. In some embodiments, the fibrotic disease may be fibrosis of the heart, such as myocardial fibrosis. In some embodiments, the fibrotic disease may be fibrosis of the soft tissue. In some embodiments, the fibrotic disease may be fibrosis of the tendons. In some embodiments, the fibrotic disease may be fibrosis of the lymph nodes. In some embodiments, the fibrotic disease may be fibrosis of the eyes. In some embodiments, the fibrotic disease may be retroperitoneum. In some embodiments, the fibrotic disease may be scleroderma. In some embodiments, the fibrotic disease may be surgical scarring.

As used herein, "Duchenne muscular dystrophy" ("DMD") refers to muscular dystrophy and all forms of Duchenne muscular dystrophy (DMD). For example, in some embodiments, the DMD may be Becker Muscular Dystrophy (BMD), an intermediate clinical presentation between DMD and BMD, or DMD-associated dilated cardiomyopathy (heart-disease) with little or no clinical skeletal, or voluntary, muscle disease.

As used herein, the $IC_{50}$ refers to an amount, concentration or dosage of a particular test compound that achieves a 50% inhibition of a maximal response in an assay that measures such response.

As used herein, the $K_d$ refers to the measured equilibrium dissociation constant between a compound (or ligand) and a protein (or binding domain of a protein).

As used herein, "Smad 2/3" means the members of the receptor-regulated Smad (R-Smads) family of transcription factors, Smad2 and Smad3, collectively.

As used herein, "MAPK" means mitogen-activated protein kinase, which includes the stress-activated MAPK protein, MAPK p38, or simply p38.

As used herein, "JNK" means the stress-activated MAPK protein c-Jun $NH_2$-terminal kinase.

As used herein, "Ras superfamily" means the protein superfamily of small guanosine triphosphatases (GTPases) which consists of the five main families Ras, Rho, Rab, Ran and Arf, or mutants thereof. Subfamilies of the five main families are also included, e.g., the Rac subfamily of the Rho main family.

Without being bound by theory, the Ras superfamily of proteins are small GTPases with substantial amino acid sequence homology that act as signal transducers between cell surface receptors and several intracellular signaling cascades. These proteins are involved in the regulation of essential cellular functions such as cell survival, proliferation, motility and cytoskeletal organization (see Karnoub et al., Nat. Rev. Mol. Cell Biol., 9:517-531 (2008)). These proteins play essential roles in regulating many biological processes including, without limitation, cell growth, cell differentiation, cell migration, lipid vesicle trafficking, fibrosis, inflammation and apoptosis.

Research has defined a number of subfamilies of the Ras superfamily, based largely on amino acid sequence homologies. These subfamilies are often referred to in an abbreviated manner based on the most commonly studied member of the class.

The GTP binding domains of one subfamily of the Ras superfamily having substantial sequence homology is commonly referred to as the Ras family or Ras.

There are four isoforms of Ras proteins, expressed from three different genes: H-Ras (Harvey sarcoma viral oncogene), N-Ras (neuroblastoma oncogene), and the splice variants K-Ras4A and K-Ras4B (Kirsten sarcoma viral oncogene) (see Karnoub et al., supra).

The GTP binding domains of another subfamily of the Ras superfamily having substantial sequence homology is commonly referred to as the Rho family and includes proteins and groups of proteins referred to as Rho, Rac and Cdc42.

Without being bound by theory, all Ras isoforms share sequence identity in all of the regions that are responsible for GDP/GTP binding, GTPase activity, and effector interactions, suggesting a functional redundancy. However, studies clearly demonstrate that each Ras isoform can function in a unique, different way from the other Ras proteins in normal physiological processes as well as in pathogenesis (Quinlan et al., Future Oncol., 5:105-116 (2009)).

Without being bound by theory, several cell surface receptors activate Ras, such as Receptor Tyrosine Kinases (RTKs), growth factor receptors, cytokine receptors and integrins.

Without being bound by theory, Ras proteins cycle between 'on' and 'off' conformations that are conferred by the binding of GTP and GDP, respectively. Under physiological conditions, the transition between these two states is regulated by guanine nucleotide exchange factors (GEFs), such as Son of sevenless (Sos) (Bar-Sagi D, Trends Endocrin. Metab. 5, 165-169 (1994)), which promote the activation of Ras proteins by stimulating the exchange of GDP for GTP exchange, and by GTPase-activating proteins (GAPs), which accelerate Ras-mediated GTP hydrolysis to GDP.

Without being bound by theory, the region of Sos functional for nucleotide exchange on Ras spans about 500 residues, and contains blocks of sequence that are conserved in Sos and other Ras-specific GEF's such as Cdc25, Sdc25 and Ras guanine-nucleotide-release factor (GRF) (Boguske et al, Nature 366, 643-654 (1993)).

Without being bound by theory, once activated, Ras initiates signaling of the "MAPK pathway" (also referred to as the Ras-RAF-MEK-MAPK/ERK1/2 pathway) that affects cell growth, differentiation, proliferation, apoptosis and migration. The MAPK pathway operates through a sequence of interactions among kinases. Activated by Ras in the "on", GTP bound, state, a MAPK kinase kinase (MAPK3), such as Raf, MLK, or TAK, phosphorylates and activates a MAPK kinase, such as MEK, which then phosphorylates and increases the activity of one or more MAPKs, such as ERK1/2.

Without being bound by theory, Ras activation also initiates signaling of the "Akt pathway" that affects cellular survival, proliferation, migration, anti-apoptotic and cell cycle regulation. Ras in the "on", GTP bound, state, activates phosphoinositide 3-kinase (PI3K) which, in turn, induces the production of phosphatidylinositol (3,4,5) trisphosphates (PIP3). These lipids serve as plasma membrane docking sites for proteins that harbor pleckstrin-homology (PH) domains, including Akt (also known as protein kinase B or PKB) and its upstream activator PDK1. There are three highly related isoforms of Akt (Akt1, Akt2 and Akt3) that phosphorylate shared substrates, but isoform-specific Akt substrates have also been identified. At the membrane, Akt is phosphorylated and activated by PDK1, PDK2 and mTORC2. The Akt pathway can also be activated by receptor tyrosine kinases, integrins, B and T cell receptors, cytokine receptors and G-protein-coupled receptors that directly interact and activate PI3K.

Without being bound by theory, Ras activation is also associated with signaling through other molecular pathways other than phosphoinositide 3-kinases (PI3Ks), such as Rac1 GEF and the Ral-guanine nucleotide dissociation stimulator (GDS). Regarding PI3K, that is part of the PI3K/AKT/mTOR pathway regulating intracellular signaling important for several cellular functions such as survival, anti-apoptotic and cell cycle regulation.

Without being bound by theory, Ras and its downstream pathways, including ERK1/2 and Akt, have been studied extensively. They are causally associated with a range of diseases, including certain cancers, inflammatory disorders, Ras-associated autoimmune leukoproliferative disorder, type II diabetes, and certain Rasopathies.

Without being bound by theory, activation of MAPKs, in particular ERK1/2, is a component of the inflammatory response. Thus, the compounds provided herein, which are ERK1/2 inhibitors via inhibition of Ras and/or a Ras superfamily member, are useful in the treatment of inflammatory diseases.

Without being bound by theory, activation of Akt is a component of the inflammatory response. Thus, the compounds provided herein, which are Akt inhibitors via inhibition of Ras and/or a Ras superfamily member, are useful in the treatment of inflammatory diseases.

Without being bound by theory, there is more than one distinct route to aberrant Ras activation including mutational activation of Ras itself, excessive activation of the wild-type protein through upstream signaling, and loss of a GAP function that is required to terminate activity of the protein.

One million deaths per year are attributed in the literature to mutations in K-Ras alone. (Frank McCormick. "K-Ras protein as a drug target." Journal of Molecular Medicine (Berlin) 2016: 94: 253-258)

Without being bound by theory, Ras is causally associated with inflammatory diseases including the following: rheumatoid arthritis (Abreu J R, de Launay D, Sanders M E, Grabiec A M, Sande van de M G, Tak P P, Reedquist K A: The Ras guanine nucleotide exchange factor RasGRF1 promotes matrix metalloproteinase-3 production in rheumatoid arthritis synovial tissue (Arthritis Res Ther. 2009, 11: R121-10.1186/ar2785), which is the most common cause of disability (Hootman J M, Brault M W, Helmick C G, Theis K A, Armour B S. Prevalence and most common causes of disability among adults—United States 2005, MMWR, 2009, 58 (16): 421-6); atherosclerosis (Fonarow G (2003), Cleve. Clin. J. Med. 70:431-434); inflammatory bowel disease (IBD), such as Crohn's disease (Ignacio C S, Sandvik A K, Bruland T, Andreu-Ballester J C, J. Crohns Colitis, 2017 Mar. 16. doi: 10); ulcerative colitis; spondyloarthropathies; idiopathic pulmonary fibrosis; juvenile arthritis; psoriasis; psoriatic arthritis; and others.

Without being bound by theory, Ras has been causally associated with Ras-associated autoimmune leukoproliferative disorder, a nonmalignant clinical syndrome initially identified in a subset of putative autoimmune lymphoproliferative syndrome (ALPS) patients. (Katherin Calvo, et al.

"JMML and RALD (Ras-associated autoimmune leukoproliferative disorder): common genetic etiology yet clinically distinct entities" Blood, 2015 Apr. 30; 125 (18): 2753-2758)

Without being bound by theory, Ras signaling is causally implicated in rasopathies. Thus, the compounds provided herein, which inhibit the function of one or more members of the Ras superfamily, are useful in the treatment of rasopathies including neurofibromatosis type 1, Noonan's syndrome, and Costello syndrome.

As used herein, "Ras" or "Ras family" or "Ras subfamily" or "Ras group" means DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; RRAS2, or mutants thereof.

As used herein, "Rho" or "Rho family" or "Rho subfamily" or "Rho group" means RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3; CDC42, or mutants thereof.

As used herein, "Rac" or "Rac family" or "Rac subfamily" or "Rac group" means RAC1; RAC2; RAC3; RHOG, or mutants thereof.

Without being bound by theory, the Rho subfamily of the Ras superfamily currently includes approximately 22 proteins most of which scientists commonly divide into subgroups including those referred to as Cdc42, Rac, and Rho. (Boureux A, Vignal E, Faure S, Fort P (2007). "Evolution of the Rho family of ras-like GTPases in eukaryotes". Mol Biol Evol 24 (1): 203-16).

Without being bound by theory, the three most commonly studied members of the Rho subfamily have been Cdc42, Rac1, and RhoA.

Without being bound by theory, the Cdc42 group includes Cdc42, TC10, TCL, Chip, and Wrch-1.

Without being bound by theory, the Rac group includes Rac1, Rac2, Rac3, and RhoG.

Without being bound by theory, the RhoA group includes RhoA, RhoB, and RhoC.

Without being bound by theory, other Rho subfamily GTPases not included in the Cdc42, Rac, or Rho groups include RhoE/Rnd3, RhoH/TTF, Rif, RhoBTB1, RhoBTB2, Miro-1, Miro-2, RhoD, Rnd1, and Rnd2.

Without being bound by theory, like other Ras superfamily proteins, the Rho subfamily GTPases cycle between 'on' and 'off' conformations that are conferred by the binding of GTP and GDP, respectively. Under physiological conditions, the transition between these two states is regulated by guanine nucleotide exchange factors (GEFs), which promote the activation of Rho subfamily proteins by stimulating the release of GDP and the binding of GTP, and by GTPase-activating proteins (GAPs), which accelerate Rho subfamily member-mediated GTP hydrolysis to GDP. Guanine nucleotide dissociation inhibitors (GDIs) proteins form a large complex with the Rho protein, helping to prevent diffusion within the membrane and into the cytosol and thus acting as an anchor and allowing tight spatial control of Rho activation.

Without being bound by theory, the Rho subfamily members are intracellular proteins that affect a large number of downstream pathways broadly involving cytoskeleton organization, cell polarity, migration, transcription and proliferation, and, more particularly, membrane and vesicular trafficking, cell cycling, microtubule stability, actin membrane linkages, actin polymerization, myosin phosphorylation, API dependent gene expression, cell adhesion, cell contractility, cell adhesion, and MTOC orientation. (Martin Schwartz. "Rho Signalling at a Glance." Journal of Cell Science. 2004: (117: pp. 5457-5458). and (Bustelo X R, Sauzeau V, Berenjeno I M (2007). "GTP-binding proteins of the Rho/Rac family: regulation, effectors and functions in vivo" BioEssays. 29 (4): 356-370).

Without being bound by theory, Rho subfamily associated kinases (ROCK1 and ROCK2) are implicated as mediators of multiple profibrotic processes including those associated with idiopathic pulmonary fibrosis. (Knipe R S, Tager E M, and Liao J K. "The Rho kinases: critical mediators of multiple profibrotic processes and rational targets for new therapies for pulmonary fibrosis." Pharmacol Rev. 2015 67 (1): 103-17.)

Without being bound by theory, given their roles in disease processes, Rho subfamily members have been identified as potential Therapeutic Molecular Targets.

Without being bound by theory, Rho subfamily members have been identified as potential Therapeutic Molecular Targets in cancer.

Without being bound by theory, Rho subfamily members have been identified as potential Therapeutic Molecular Targets in fibrotic disease.

As used herein, "GTP binding site" or "GTP binding domain" both mean the region of a protein which binds GTP, and the surrounding region of said protein in which another compound may bind, wherein such binding blocks the ability of GTP to bind to said protein.

As used herein, "GDP binding site" or "GDP binding domain" both mean the region of a protein which binds GDP, and the surrounding region of said protein in which another compound may bind, wherein such binding blocks the ability of GDP to bind to said protein.

As used herein, "guanosine binding region" means a region of a protein which is part of the GDP binding domain or GTP binding domain, that mediates interaction with the guanosine portion of GDP or GTP.

As used herein, "metal region" means a region of a protein which is part of the GDP binding domain or GTP binding domain, that is proximal to a magnesium (Mg202) binding site.

As used herein, "alternative Tyr32 conformation" means the conformation of the GTP or GDP binding domain in the region of Tyr 32 in KRas crystal structure PDB code: 3gft in comparison to the KRas crystal structure PDB code: 4epr.

Without being bound by theory, as used herein "apoptosis" refers to a process of programmed cell death which plays important roles in physiology and pathology. It is activated during embryonic development and beyond to eliminate unwanted or damaged cells. Apoptosis also plays important roles in preventing cancer. Loss of apoptotic control allows tumor cells to survive longer and provides them time to accumulate mutations which can increase invasiveness during cancer progression, stimulate angiogenesis, deregulate cell proliferation, and interfere with differentiation.

Without being bound by theory, in regard to apoptosis, it has been demonstrated that several members of the Ras superfamily of small GTPases have pro- and anti-apoptosis functions. Members of the Rho family of GTPases such as Rho, Rac and cdc42 can activate apoptosis via the JNK or p38 pathways. On the other hand, members of the Ras and Rab families of GTPases have anti-apoptotic activity mediated by activating the PI3K/Akt/mTOR survival pathway which prevent apoptosis and leads to increased cellular proliferation. In addition, it has been demonstrated that GTPase Activating Proteins (GAPs) can promote apoptosis in tumor cells by regulating apoptosis-related proteins and pathways. It should be noted that some GAPs also exert apoptosis-inhibiting effects and thus promote tumor progression Without being bound by theory, the c-Jun N-terminal kinase (JNK) pathway is one of the major signaling cascades of the mitogen-activated protein kinase (MAPK) signaling pathway. It functions in the control of a number of cellular processes, including proliferation, embryonic development and apoptosis. The JNK pathway is activated by environmental stresses (ionizing radiation, heat, oxidative stress such as reactive oxygen species (ROS) and DNA damage), inflammatory cytokines, as well as growth factors. JNK activation often involves the Rho family of GTPases such as Rho, Cdc42 and Rac.

Without being bound by theory, JNK activates apoptotic signaling by the upregulation of pro-apoptotic genes through transactivation of c-Jun/AP1-dependent or p53/73 protein-dependent mechanisms. In these pathways directed at mitochondrial apoptotic proteins, activated JNK directly modulates the activities of mitochondrial pro-apoptotic proteins through distinct phosphorylation events.

Without being bound by theory, another member of the MAPK signaling pathway is p38 MAPK (also referred to herein as MAPK p38) which allows cells to interpret a wide range of external signals and respond by activating downstream pathways mediating several biological effects. This pathway also functions in the control of apoptosis and the release of cytokines by macrophages and neutrophils.

Without being bound by theory, apoptosis can be activated by both extrinsic (death ligand) and intrinsic (mitochondrial) pathways. Members of the Bcl-2 family of proteins, like Bax and Bak, regulate and mediate the intrinsic apoptosis process by which mitochondria contributes to cell death. Upon apoptotic stimuli, these proteins are activated and oligomerize at the mitochondrial outer membrane to mediate its permeabilization. Permeabilization enables the release of cytochrome c from mitochondria which, in turn, induces a series of biochemical reactions resulting in caspase activation and subsequent cell death.

Without being bound by theory, induction of apoptosis, such as in mammalian cells, can be mediated by several mechanisms, including inhibition of the ubiquitin proteasome system (UPS). The UPS system is a major proteolytic pathway for the removal of cytosolic, nuclear, and membrane associated proteins and has essential functions in homeostasis, which include preventing the accumulation of misfolded or deleterious proteins. The proteins targeted for degradation are selected by tagging them covalently with ubiquitin, typically with lysine48-linked tetraubiquitin chains, followed by proteolysis within the 26S proteasome. The 26S proteasome holoenzyme consists of a 19S regulatory particle (RP) which is responsible for recognizing the ubiquitin signal and unfolding the target protein, and a 20S core particle (CP), which hydrolyzes the unfolded polypeptide into short peptides of varying lengths. Accordingly, impairment of the UPS has been associated with several pathological conditions including cancers. Tumor cells can be characterized by the loss of cell cycle checkpoint control and can often be subjected to elevated levels of stress because of hyperactivation of oncogenic signaling and/or adverse microenvironmental conditions. Therefore, transformed cells can rely to a great extent on the correct function of UPS for survival and proliferation. Inhibition of the UPS, such as with proteasome inhibitors, can induce cell death and apoptosis. To date, three proteasome inhibitors have gained FDA approval to treat multiple myeloma cancer patients. The three proteasome inhibitors, Velcade (bortezomib), Kyprolis (carfilzomib), and Ninlaro (ixazomib), are reported as targeting the proteolytic sites within the 20S CP.

Without being bound by theory, as used herein "caspase (s)" refers to one or more of a family of cysteine proteases that cleave proteins following aspartic acid residues. All caspases are synthesized in cells as catalytically inactive zymogens and must undergo a cleavage activation process to yield large and small subunits which dimerize to create active enzymes. Caspases exist in a hierarchy including so-called upstream caspases 2, 8, 9, and 10 and downstream caspases 3, 6, and 7. Active caspase-9 initiates caspase cleavage which activate downstream executioner caspases 3, 6 and 7 which cleave other cellular targets and initiate apoptosis. In some embodiments, the anti-proliferative inhibitory activity of the compounds disclosed herein is mediated by the induction of apoptosis, as determined by an Anexin V apoptosis assay kit.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter enzymatic and biological activities of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as chiral reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included. For example, Formula A includes, but is not limited to, the three tautomeric structures below.

Formula A

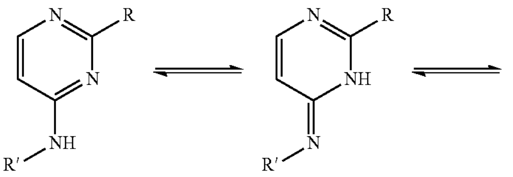

-continued

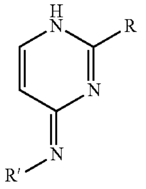

As used herein, the abbreviations for any protective groups, amino acids and other compounds, are, unless indicated otherwise, in accord with their common usage, recognized abbreviations, the IUPAC-IUB Commission on Biochemical Nomenclature (see, (1972) Biochem. 11:942-944), or the IUPAC Nomenclature of Organic Chemistry (see, Favre H A and Powell W H, Nomenclature of Organic Chemistry: IUPAC Recommendations and Preferred Names 2013, Cambridge, UK: The Royal Society of Chemistry, 2013: Print ISBN 978-0-85404-182-4, PDF eISBN 978-1-84973-306-9, DOI 10.1039/9781849733069; Nomenclature of Organic Chemistry, Sections A, B, C, D, E, F, and H, Pergamon Press, Oxford, 1979. Copyright 1979 IUPAC; and A Guide to IUPAC Nomenclature of Organic Compounds (Recommendations 1993), 1993, Blackwell Scientific publications, Copyright 1993 IUPAC).

As used herein, alkyl, alkenyl and alkynyl carbon chains, if not specified, contain from 1 to 20 carbons, or 1 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, ethenyl, propenyl, butenyl, pentenyl, acetylenyl and hexynyl. As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "heteroalkyl" refers to a straight or branched aliphatic hydrocarbon group having, inserted in the hydrocarbon chain one or more oxygen, sulfur, including S(═O) and $S(═O)_2$ groups, or substituted or unsubstituted nitrogen atoms, including —NR— and —$N^+$RR— groups, where the nitrogen substituent(s) is (are) alkyl, aryl, aralkyl, heteroaryl, heteroaralkyl, $S(═O)_2R'$ or COR', where R' is alkyl, aryl, aralkyl, heteroaryl, heteroaralkyl, —OY or —NYY', where Y and Y' are each independently hydrogen, alkyl, aryl, heteroaryl, cycloalkyl or heterocyclyl, in one embodiment having from 1 to about 20 atoms, in another embodiment having from 1 to 12 atoms in the chain.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond. In some embodiments, the cycloalkyl ring is unsaturated or partially saturated.

As used herein, "carbocyclic" refers to a mono- or multicyclic ring system, in which all of the atoms composing the ring are carbon atoms, such as benzene or cyclopropane. In some embodiments, the carbocyclic ring is unsaturated or partially saturated.

As used herein, "substituted alkyl," "substituted alkenyl," "substituted alkynyl," "substituted cycloalkyl," "substituted cycloalkenyl," and "substituted cycloalkynyl" refer to alkyl, alkenyl, alkynyl, cycloalkyl, cycloalkenyl and cycloalkynyl groups, respectively, that are substituted with one or more substituents, in certain embodiments one to three or four substituents, where the substituents are as defined herein.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, N-methylpyrrolyl, quinolinyl and isoquinolinyl. In certain embodiments, the heteroaryl may be optionally fused to a heterocycloalkyl ring. In certain embodiments, the heteroaryl may be a partially saturated heteroaryl, such as a phenyl ring fused to a heterocycloalkyl ring, for example a phenyl ring fused to a tetrahydrofuryl ring.

As used herein, "heterocycloalkyl," "heterocyclyl" or "heterocyclic" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is (are) nitrogen, the nitrogen is optionally substituted with hydrogen, alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, amidino, sulfonyl or the nitrogen may be quaternized to form an ammonium group where the substituents are selected as above. In some embodiments, the heterocyclyl ring is saturated. In some embodiments, the heterocyclyl ring is unsaturated or partially saturated.

As used herein, "substituted aryl," "substituted heteroaryl" and "substituted heterocyclyl" refer to aryl, heteroaryl and heterocyclyl groups, respectively, that are substituted with one or more substituents, in certain embodiments one to three or four substituents, where the substituents are as defined herein.

As used herein, "aralkyl" or "arylalkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO in which R is a haloalkyl group.

As used herein, "hydroxalkyl" refers to an alkyl group in which one or more of the hydrogen atoms are replaced by a hydroxyl group (—OH).

As used herein, "cycloalkoxy" refers to an —OR group, in which R is a cycloalkyl group.

As used herein, "carboxy" refers to a divalent radical, —C(O)O—.

As used herein, "aminocarbonyl" refers to —C(O)$NH_2$.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR-'COR in which R' and R are independently alkyl, including lower alkyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

Where the number of any given substituent is not specified (e.g., "haloalkyl"), there may be one or more substituents present. For example, "haloalkyl" may include one or more of the same or different halogens.

As used herein, "cyclic structure" may be a cycloalkyl, carbocyclic, heterocyclic, aryl or heteroaryl group.

As used herein, the abbreviations for any protective groups, amino acids and other compounds, are, unless indicated otherwise, in accord with their common usage, recognized abbreviations, the IUPAC-IUB Commission on Biochemical Nomenclature (see, (1972) Biochem. 11:942-944), or the IUPAC Nomenclature of Organic Chemistry (see, Favre H A and Powell W H, Nomenclature of Organic Chemistry: IUPAC Recommendations and Preferred Names 2013, Cambridge, UK: The Royal Society of Chemistry, 2013: Print ISBN 978-0-85404-182-4, PDF eISBN 978-1-84973-306-9, DOI 10.1039/9781849733069; Nomenclature of Organic Chemistry, Sections A, B, C, D, E, F, and H, Pergamon Press, Oxford, 1979. Copyright 1979 IUPAC; and A Guide to IUPAC Nomenclature of Organic Compounds (Recommendations 1993), 1993, Blackwell Scientific publications, Copyright 1993 IUPAC).

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician. A therapeutically effective amount of a compound provided herein can be administered in one dose (i.e., a single dose administration) or divided and administered over time (i.e., continuous administration or multiple sub-dose administration). Single dose administration, continuous administration, or multiple sub-dose administration can be repeated, for example, to maintain the level of the compound in a biological molecule (e.g., a protein, enzyme, RNA, or DNA), cell, tissue, system, animal, or human.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 22nd ed.; Loyd et al., Eds.; The Pharmaceutical Press, 2012; *Handbook of Pharmaceutical Excipients,* 7th ed.; Rowe et al., Eds.; The Pharmaceutical Press, 2012; *Handbook of Pharmaceutical Additives,* 3rd ed.; Ash and Ash Eds.; Synapse Information Resources, Inc., 2007; *Pharmaceutical Preformulation and Formulation,* 2nd ed.; Gibson Ed.; CRC Press LLC, 2009.

As used herein, a "pharmaceutically acceptable form" of compounds disclosed herein includes, but is not limited to, a pharmaceutically acceptable salt, solvate, isomer, and isotopologue (i.e., isotopically labeled derivative) of compounds disclosed herein. In one embodiment, a "pharmaceutically acceptable form" includes, but is not limited to, a pharmaceutically acceptable salt, solvate, isomer, and isotopologue (i.e., isotopically labeled derivative) of a compound of Formula I, Ia, Ib, Ic, II, IIa, IIa(1), IIb, IIc, III, IIIa, IIIb, IIIc, IV, IVa, IVb, or IVc, as disclosed herein.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "percent by weight" or "% by weight" refers to the weight of a specified component (e.g., an active compound or excipient) in a composition (e.g., a pharmaceutical composition) as a percentage of the total weight of the composition. Thus, the sum of the weight percentages of all the components in a composition is 100%.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "racemate" is understood to refer to an equimolar mixture of a pair of enantiomers. It does not exhibit optical activity. The chemical name or formula of a racemate is distinguished from those of the enantiomers by the prefix (±)-, or rac- (or rac. or racem-) or by the symbols RS and SR. See IUPAC Recommendations 1996, Basic Terminology of Stereochemistry, *Pure & Appl. Chem.*, Vol. 68, No. 12, pp. 2193-2222, 1996.

Racemic compounds disclosed herein that contain two asymmetric centers with known relative configuration are named using the configurational descriptors R,S or R,R, preceded by the prefix rac-. For example, Racemic Compound A below is named rac-(1R,3S)-1-bromo-3-chlorocyclohexane and is a 1:1 mixture of enantiomers (1R,3S)-1-bromo-3-chlorocyclohexane and (1S,3R)-1-bromo-3-chlorocyclohexane.

Racemic Compound A

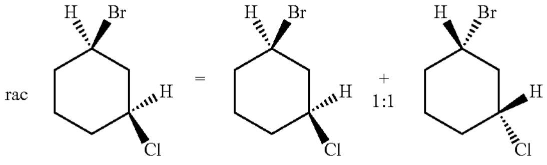

rac-(1R,3S)-1-bromo-3-chlorocyclohexane    (1R,3S)-1-bromo-3-chlorocyclohexane    (1S,3R)-1-bromo-3-chlorocyclohexane Lower case r/s stereo descriptors are used to describe pseudo-asymmetric centers, according to Cahn-Ingold-Prelog Rules (see R. S. Cahn, C. K. Ingold and V. Prelog, Angew. Chem. Internat. Ed. Eng. 5, 385-415, 511 (1966); and V. Prelog and G. Helmchen, Angew. Chem Internat. Ed. Eng. 21, 567-583 (1982)). For example, Compound B below is named (1s,4s)-1-bromo-4-chlorocyclohexane.

Compound B

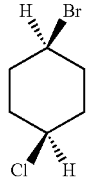

(1s,4s)-1-bromo-4-chlorocyclohexane

Compound names included herein were generated from the corresponding chemical structures using ChemDraw® versions 20.0.0.38, 20.1.0.112, and 22.2.0.3348. If there is a discrepancy between the chemical structure and the name disclosed herein, the structure shall control.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen ($^{1}H$), deuterium ($^{2}H$), tritium ($^{3}H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), and chlorine-37 ($^{37}Cl$). In certain embodiments, an "isotopic variant" of a compound is in a stable form, that is, non-radioactive. It will be understood that, in a compound as provided herein, any hydrogen can be $^{2}H$, for example, or any carbon can be $^{13}C$, as example, or any nitrogen can be $^{15}N$, as example, and any oxygen can be $^{18}O$, where feasible according to the judgment of one of skill. In certain embodiments, an "isotopic variant" of a compound contains unnatural proportions of deuterium. In some embodiments, a pharmaceutically acceptable derivative of a compound is an isotopic variant.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an isotopic variant thereof; or a pharmaceutically acceptable salt thereof; or a pharmaceutically acceptable solvate thereof" has the same meaning as the phrase "an isotopic variant of the compound referenced therein; or a pharmaceutically acceptable salt of the compound referenced therein; or a pharmaceutically acceptable salt of an isotopic variant of the compound referenced therein; or a pharmaceutically acceptable solvate of the compound referenced therein; or a pharmaceutically acceptable solvate of an isotopic variant of the compound referenced therein; or a pharmaceutically acceptable solvate of a pharmaceutically acceptable salt of the compound referenced therein; or a pharmaceutically acceptable solvate of a pharmaceutically acceptable salt of an isotopic variant of the compound referenced therein or its variant or its variant."

3.2. Compounds

Provided herein is a compound of Formula I:

Formula I

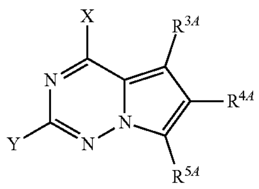

or a pharmaceutically acceptable form thereof, wherein:

X is —$NR^{1A}R^{2A}$ or $OR^{2A}$;

Y is an imidazolyl, a pyridinyl, or an 8-10-membered fused-heteroaryl; wherein the imidazolyl is optionally substituted with 1 $R^{6A}$ substituent and optionally substituted with 1-2 $R^{7A}$ substituents; and the pyridinyl or the 8-10-membered fused-heteroaryl is optionally substituted with 1-4 $R^{7A}$ substituents;

$R^{1A}$ is hydrogen or $C_{1-6}$ alkyl, wherein the $C_{1-6}$ alkyl is optionally substituted with 1-4 $R^{8A}$ substituents;

$R^{2A}$ is hydrogen, $C_{1-6}$ alkyl, $C_{3-7}$ cycloalkyl, $C_{1-6}$ heteroalkyl, $C_{3-7}$ heterocycloalkyl, $C_{5-10}$ membered aryl, —$S(O)_2R^{15A}$, —$P(O)R^{16A}R^{17A}$, or 5-10 membered heteroaryl, wherein the $C_{1-6}$ alkyl, $C_{3-7}$ cycloalkyl, $C_{1-6}$ heteroalkyl, and 5-10 membered heteroaryl are each independently optionally substituted with 1-4 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached, optionally wherein the 3-6 membered heterocycloalkyl formed by $R^{1A}$ and $R^{2A}$ is fused to a 5-6 membered heteroaryl;

$R^{3A}$ is $C_{1-6}$ alkyl, $C_{3-7}$ cycloalkyl, $C_{1-6}$ heteroalkyl, aryl, 5-10 membered heteroaryl, —$(CO)R^{11A}$, or —$C(O)NR^{12A}R^{13A}$ wherein the $C_{1-6}$ alkyl, $C_{3-7}$ cycloalkyl, $C_{1-6}$ heteroalkyl, aryl, and 5-10 membered heteroaryl are each independently optionally substituted with 1-3 $R^{9A}$ substituents;

$R^{4A}$ is hydrogen, aryl, or 5-10 membered heteroaryl, wherein the aryl and 5-10 membered heteroaryl are each independently optionally substituted with 1-4 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, $C_{1-6}$ heteroalkyl, halo, —$NR^{12A}R^{13A}$, $C_{1-6}$ alkoxy, $C_{1-6}$ haloalkoxy, —$C(O)NR^{12A}R^{13A}$, —$(CO)R^{11A}$, —$C(O)OR^{14A}$, or CN, wherein the $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, and $C_{1-6}$ heteroalkyl are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —$(CO)R^{11A}$, —$C(O)OR^{14A}$, —$C(O)NR^{12A}R^{13A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl, wherein the $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, $C_{1-6}$ alkoxy, $C_{3-6}$ cycloalkoxy, $C_{1-6}$ haloalkoxy, or 5-6 membered heteroaryl are each independently optionally substituted with 1-3 $R^{8A}$ substituents;

$R^{11A}$ is —OH, $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-7}$ cycloalkyl, $C_{1-6}$ haloalkyl, $C_{1-6}$ hydroxyalkyl, $C_{1-6}$ heteroalkyl, —OH, $C_{1-6}$ alkoxy, $C_{1-6}$ haloalkoxy, $C_{3-7}$ heterocycloalkyl, aryl, or 5-10 membered heteroaryl, wherein the $C_{1-6}$ alkyl, $C_{3-7}$ cycloalkyl, $C_{1-6}$ haloalkyl, $C_{1-6}$ hydroxyalkyl, $C_{1-6}$ heteroalkyl, $C_{1-6}$ alkoxy, $C_{1-6}$ haloalkoxy, $C_{3-7}$ heterocycloalkyl, aryl, and 5-10 membered heteroaryl are optionally substituted with 1-3 $R^{8A}$ substituents, or $R^{12A}$ and $R^{13A}$ are combined to form a 3-7 membered heterocycloalkyl including the nitrogen atom to which they are both attached;

$R^{14A}$ is hydrogen, $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{15A}$ is $C_{1-6}$ alkyl, $C_{3-6}$ cycloalkyl, $C_{1-6}$ alkoxy, or $C_{1-6}$ heteroalkyl, wherein the $C_{1-6}$ alkyl, $C_{3-6}$ cycloalkyl, $C_{1-6}$ alkoxy, and $C_{1-6}$ heteroalkyl, are each independently optionally substituted with 1-3 $R^{8A}$ substituents;

$R^{16A}$ and $R^{17A}$ are each independently selected from the group consisting $C_{1-6}$ alkyl, $C_{1-6}$ alkoxy, or $C_{1-6}$ heteroalkyl, wherein the $C_{1-6}$ alkyl, $C_{1-6}$ alkoxy, and $C_{1-6}$ heteroalkyl, are each independently optionally substituted with 1-3 $R^{8A}$ substituents, or $R^{16A}$ and $R^{17A}$ are combined to form a 3-7 membered heterocycloalkyl including the phorphorus atom to which they are both attached; and wherein, when X is OH or

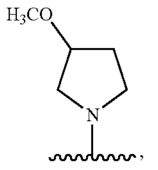 [SMILES: *N1CCC(OC)C1]

Y is N-methyl imidazoyl, and $R^{5A}$ is H, at least one of $R^{3A}$ and $R^{4A}$ is not unsubstituted phenyl.

In some embodiments, the compound of Formula I is such that Y is an imidazolyl optionally substituted with 1 $R^{6A}$ substituent and optionally substituted with 1-2 $R^{7A}$ substituents. In some embodiments, the compound of Formula I is such that Y is a C-linked imidazolyl that is substituted with 1 $R^{6A}$ substituent at a nitrogen of the imidazolyl ring and optionally substituted with 1-2 $R^{7A}$ substituents at carbons of the imidazolyl ring. In some embodiments, the compound of Formula I is a compound of Formula Ia:

Formula Ia

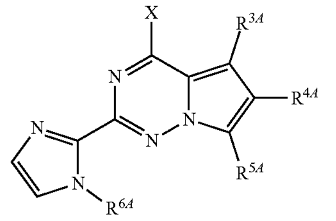

or a pharmaceutically acceptable form thereof. In some embodiments, the compound of Formula I is a compound of Formula Ib:

Formula Ib

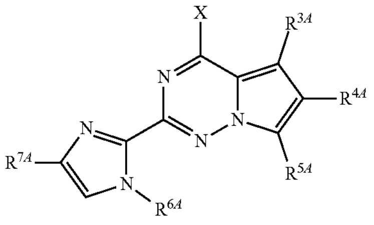

or a pharmaceutically acceptable form thereof. In some embodiments, the compound of Formula I is such that Y is a pyridinyl optionally substituted with 1-4 $R^{7A}$ substituents. In some embodiments, the compound of Formula I is a compound of Formula Ib:

Formula Ic

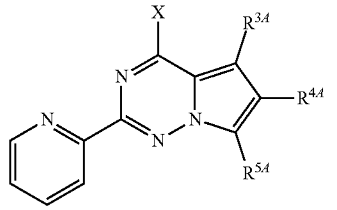

or a pharmaceutically acceptable form thereof.

In some embodiments, the compound of Formula I, Formula Ia, Formula Ib, or Formula Ic is such that no more than one of $R^{4A}$ and $R^{5A}$ is hydrogen. In some embodiments, the compound is such that $R^{5A}$ is hydrogen, methyl, ethyl, or isopropyl. In some embodiments, the compound is such that $R^{5A}$ is hydrogen.

In some embodiments, the compound of Formula I, Formula Ia, Formula Ib, or Formula Ic is such that $R^{6A}$ is $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, $C_{1-6}$ heteroalkyl, $C_{1-6}$ alkoxy, $C_{1-6}$ haloalkoxy, —C(O)NR$^{12A}$R$^{13A}$, —(CO)R$^{11A}$, or —C(O)OR$^{14A}$, wherein the $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, and $C_{1-6}$ heteroalkyl are each independently optionally substituted with 1-3 $R^{8A}$ substituents. In some embodiments, the compound is such that $R^{6A}$ is $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents. In some embodiments, the compound is such that $R^{6A}$ is methyl, ethyl, or isopropyl, wherein the methyl, ethyl, and isopropyl are each independently optionally substituted with 1-3 $R^{8A}$, wherein $R^{8A}$ is —OH, $C_{1-3}$ alkoxy, or $C_{1-3}$ haloalkoxy. In some embodiments, the compound is such that $R^{6A}$ is methyl, ethyl, or isopropyl. In some embodiments, the compound is such that $R^{6A}$ is methyl.

In some embodiments, the compound of Formula I, Formula Ia, Formula Ib, or Formula Ic is such that $R^{7A}$ is $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents. In some embodiments, the compound is such that $R^{7A}$ is methyl, ethyl, or isopropyl, wherein the methyl, ethyl, and isopropyl are each independently optionally substituted with 1-3 $R^{8A}$, wherein $R^{8A}$ is —OH, $C_{1-3}$ alkoxy, or $C_{1-3}$ haloalkoxy. In some embodiments, the compound is such that $R^{7A}$ is methyl, ethyl, or isopropyl. In some embodiments, the compound is such that $R^{7A}$ is methyl. In some embodiments, the compound is such that m is 4. In some embodiments, the compound is such that m is 3. In some embodiments, the compound is such that m is 2. In some embodiments, the compound is such that m is 1. In some embodiments, the compound is such that m is 0.

In some embodiments, the compound of Formula I, Formula Ia, Formula Ib, or Formula Ic is such that X is —OR$^{2A}$. In some embodiments, the compound of Formula I, Formula Ia, Formula Ib, or Formula Ic is such that X is —NR$^{1A}$R$^{2A}$. In some embodiments, the compound is such that X is —NR$^{1A}$R$^{2A}$, and $R^{1A}$ and $R^{2A}$ are combined to form a 3-6 membered heterocycloalkyl including the nitrogen atom to which they are both attached. In some embodiments, the compound is such that $R^{1A}$ is hydrogen or $C_{1-3}$ alkyl. In some embodiments, the compound is such that $R^{1A}$ is methyl, ethyl, or isopropyl. In some embodiments, the compound is such that $R^{14}$ is hydrogen. In some embodiments, the compound is such that $R^{2A}$ is $C_{1-4}$ alkyl, $C_{4-5}$ cycloalkyl, $C_{1-4}$ heteroalkyl, or 5-6 membered heteroaryl, wherein the $C_{1-4}$ alkyl, $C_{4-5}$ cycloalkyl, $C_{1-4}$ heteroalkyl, or 5-6 membered heteroaryl are each independently optionally substituted with 1-3 $R^{8A}$ substituents. In some embodiments, the compound is such that $R^{2A}$ is a 5-6 membered heteroaryl, wherein each are independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached. In some embodiments, the compound is such that $R^{2A}$ is a 5-6 membered heteroaryl selected from the group consisting of a pyridinyl, a pyrimidinyl, a pyrazinyl, a pyridazinyl, a triazinyl, an imidazolyl, a pyrazolyl, a triazolyl, a tetrazolyl, an oxazolyl, an isoxazolyl, an oxadiazolyl, a thiazolyl, a isothiazolyl, or a thiadiazolyl, wherein are each independently optionally substituted with 1-3 $R^{8A}$ substituents. In some embodiments, the 5-6 membered heteroaryl is substituted with 2 independent $R^{8A}$ substituents which are combined to form a 5-6 membered cycloalkyl fused to the 5-6 membered heteroaryl including the atom or atoms to which each are attached. In some embodiments, the 5-6 membered heteroaryl is substituted with 2 independent $R^{8A}$ substituents which are combined to form a 5-6 membered heterocycloalkyl fused to the 5-6 membered heteroaryl including the atom or atoms to which each are attached. In some embodiments, the 2 $R^{8A}$ substituents are combined to form a pyrazolo[5,1-b]oxazolyl ring. In some embodiments, the 2 $R^{8A}$ substituents are combined to form a 2,3-dihydropyrazolo[5,1-b]oxazolyl ring. In some embodiments, the 5-6 membered heteroaryl is a pyrazolyl. In some embodiments, the compound is such that $R^{8A}$ is independently selected from the group consisting of $C_{1-6}$ alkyl, $C_{1-6}$ haloalkyl, $C_{3-6}$ cycloalkyl, —$NR^{12A}R^{13A}$, —(CO)$R^{11A}$, oxo, $C_1$-6 hydroxyalkyl, $C_{1-6}$ heteroalkyl, 3-6 membered heterocycloalkyl, $C_{1-6}$ alkoxy, or $C_{3-6}$ cycloalkoxy. In some embodiments, the compound is such that $R^{8A}$ is independently selected from the group consisting of $C_{1-4}$ alkyl, $C_{1-4}$ haloalkyl, $C_{3-5}$ cycloalkyl, —$NR^{12A}R^{13A}$, —(CO)$R^{11A}$, oxo, $C_1$-4 hydroxyalkyl, $C_{1-4}$ heteroalkyl, 3-5 membered heterocycloalkyl, $C_{1-4}$ alkoxy, or $C_{3-5}$ cycloalkoxy. In some embodiments, the compound is such that $R^{8A}$ is independently selected from the group consisting of methyl, ethyl, isopropyl, cyclopropyl, cyclobutyl, —$NR^{12A}R^{13A}$, —(CO)$R^{11A}$, oxo, $C_{2-3}$ hydroxyalkyl, $C_{2-4}$ heteroalkyl, methoxy, ethoxy, isopropoxy, cyclopropoxy, or cyclobutoxy.

In some embodiments, the compound of Formula I, Formula Ia, Formula Ib, or Formula Ic is such that X is: —OH, —$NH_2$,

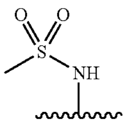,
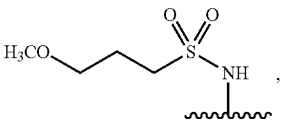,
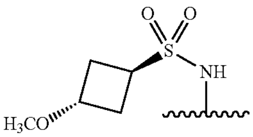,
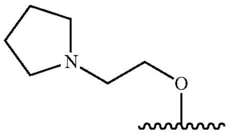,
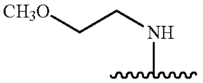,
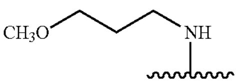,

-continued

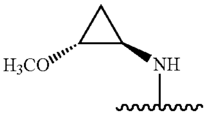,
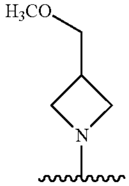,
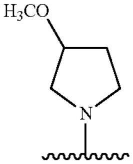,
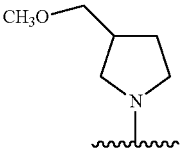,
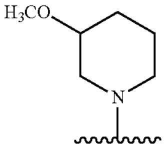,
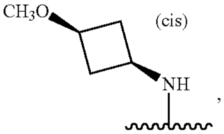

,
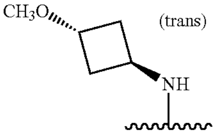

,
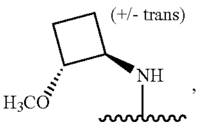

,
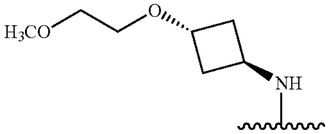,
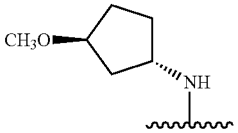,
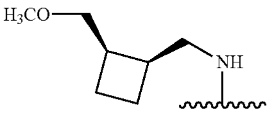,
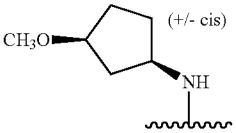

,
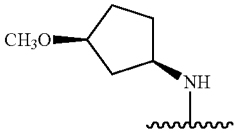,
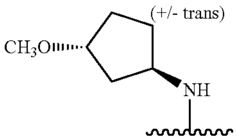

,
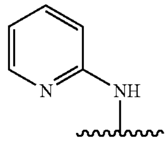,
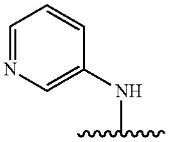,
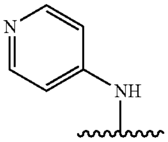,
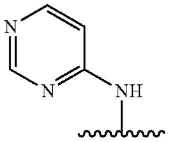,
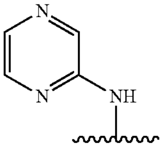,
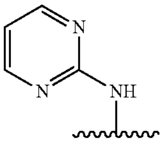,
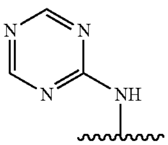,
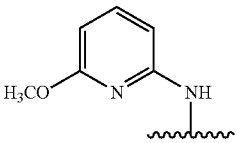,
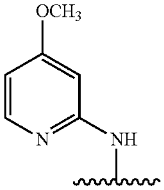,
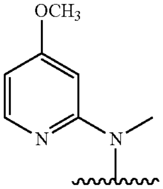,
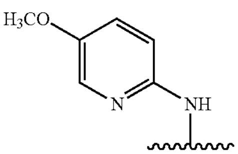, -continued
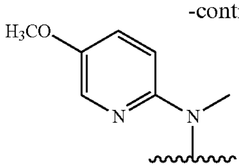,
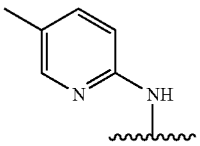,
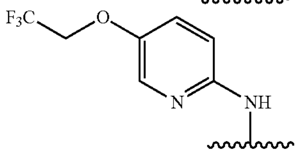,
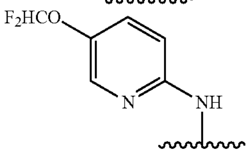,
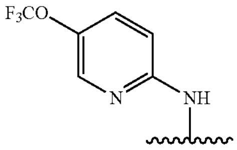,
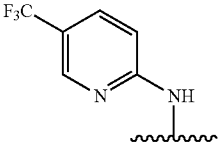,
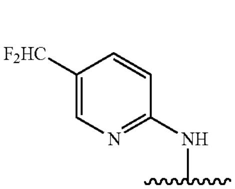,
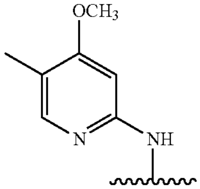,
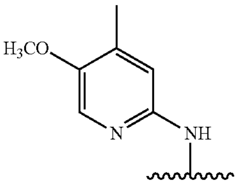,
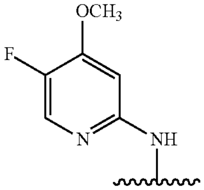,
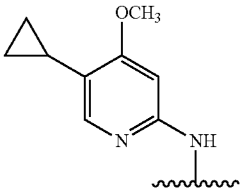,
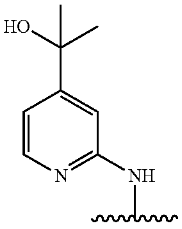,
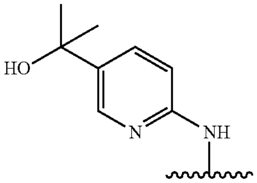,
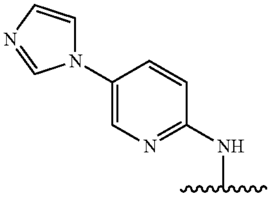,
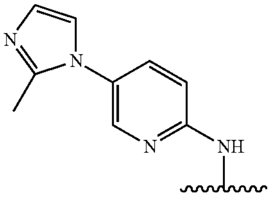,
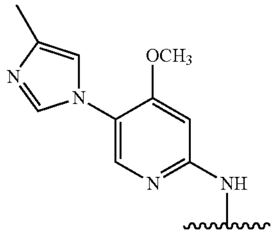,
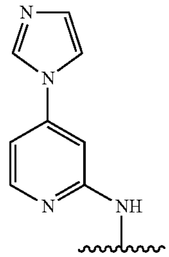,
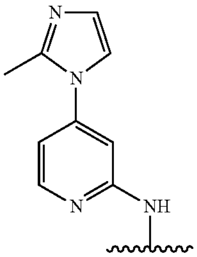,
-continued
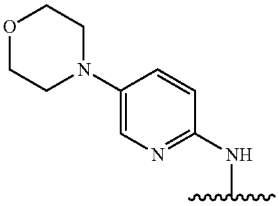,
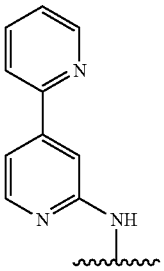,
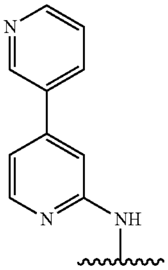,
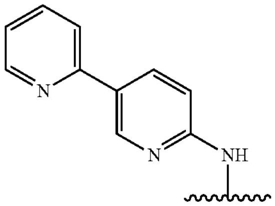,
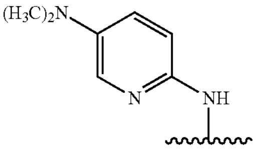,
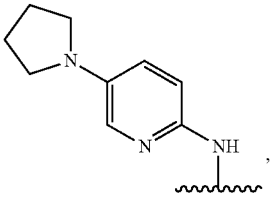,
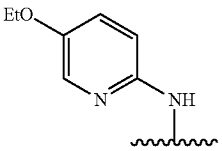,
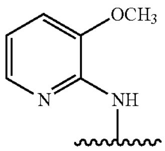,
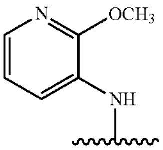,
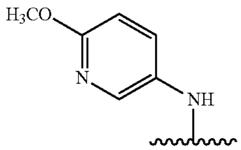,
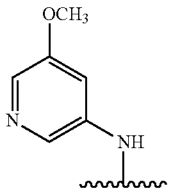,
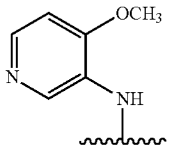,
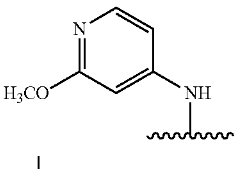,
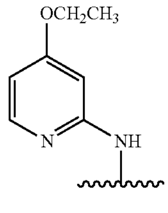,
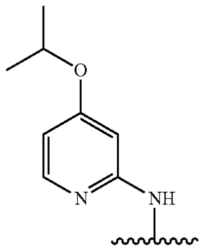,
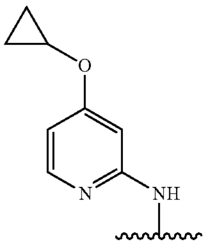, -continued
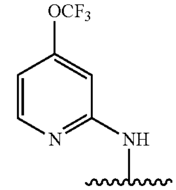,
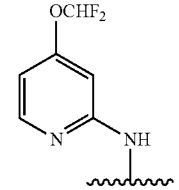,
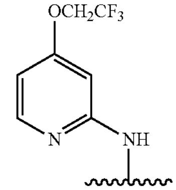,
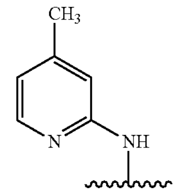,
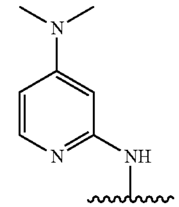,
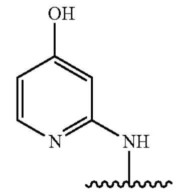,
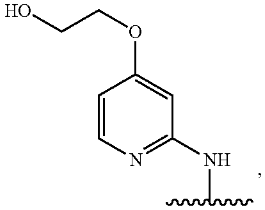,
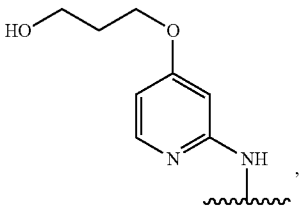,
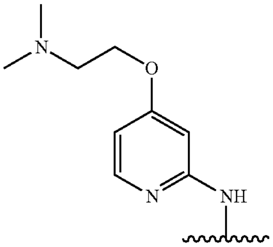,
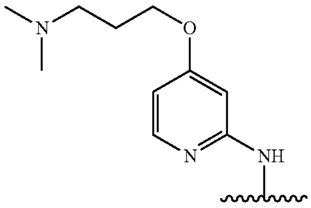,
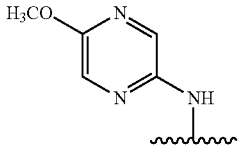,
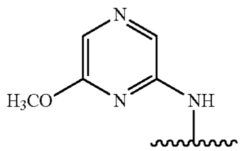,
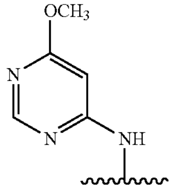,
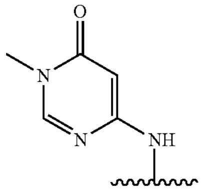,
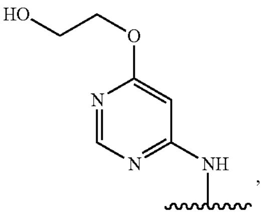,
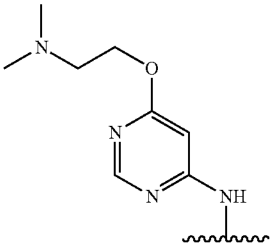,
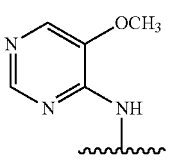,
-continued
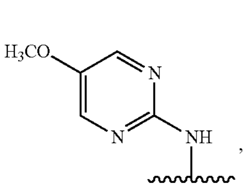,
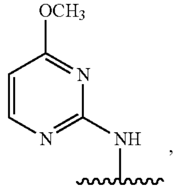,
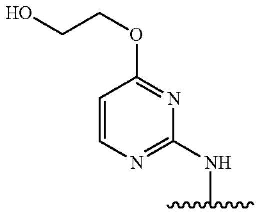,
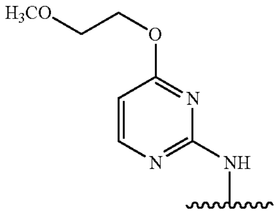,
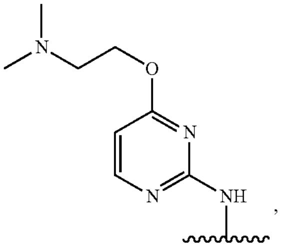,
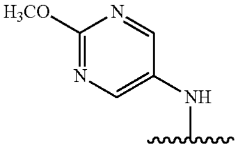,
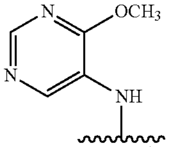,
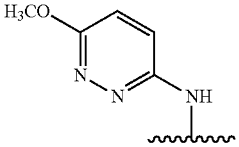,
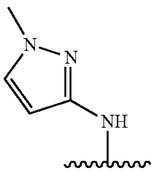,
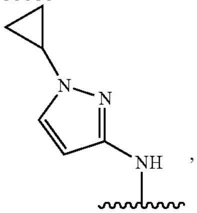,
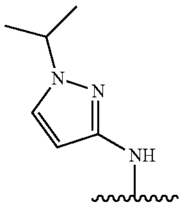,
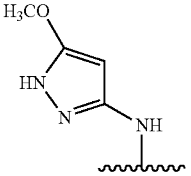,
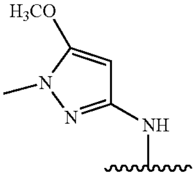,
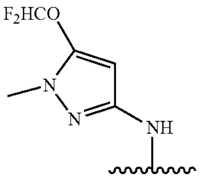,
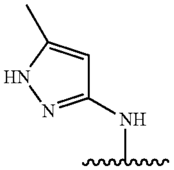,
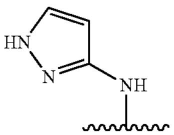,
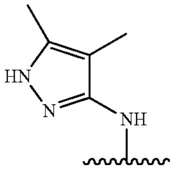,
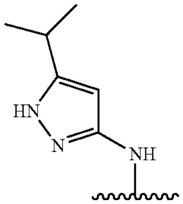,
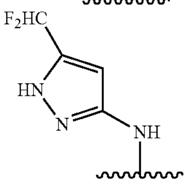,
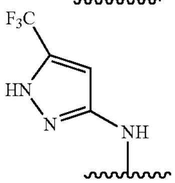,
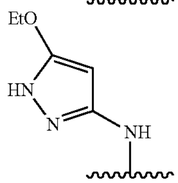, -continued
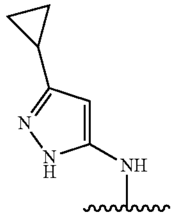, 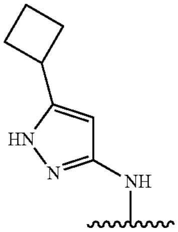,
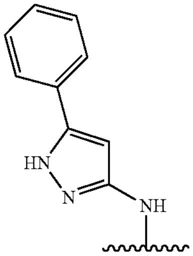, 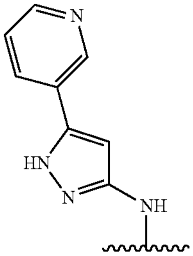,
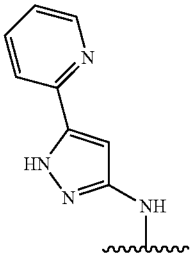, 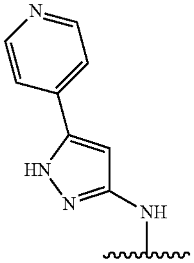,
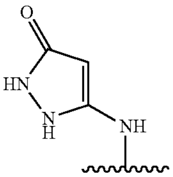, 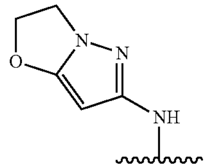,
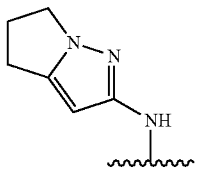, 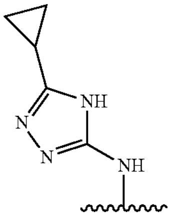,
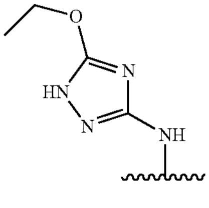, 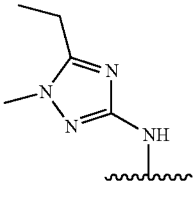,
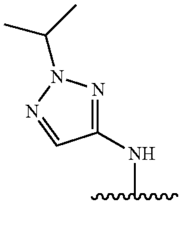, 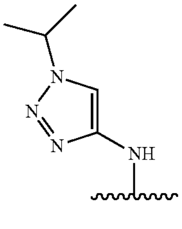, 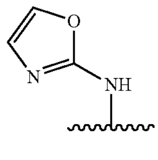,
-continued
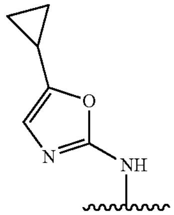, 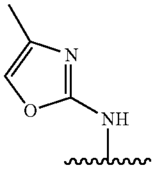, 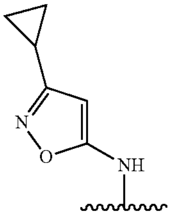,
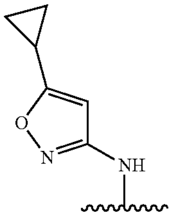, 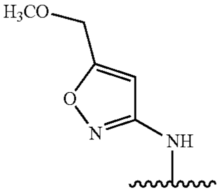,
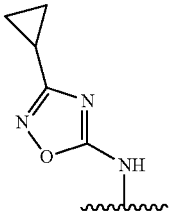, 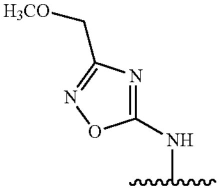,
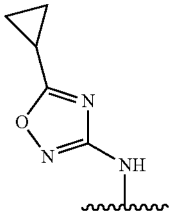, 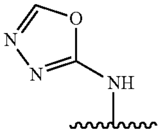, 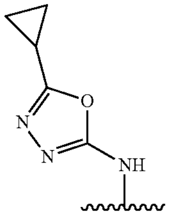,
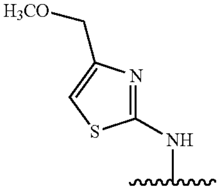, 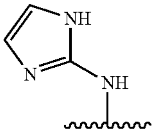, 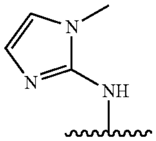,
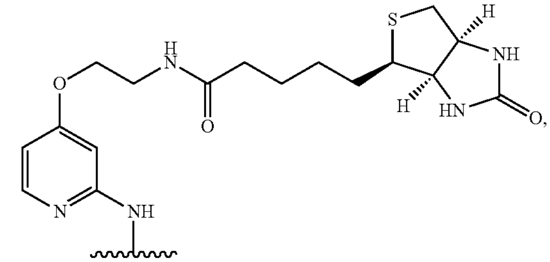
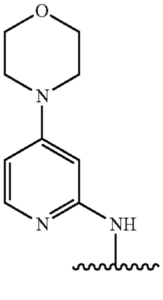, 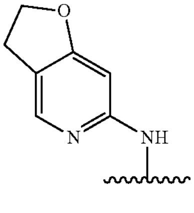, 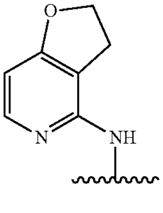, -continued
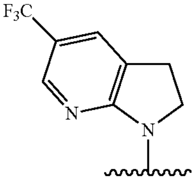
,
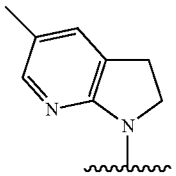
, or
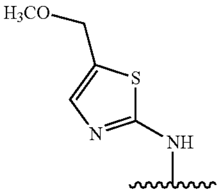
.
In some embodiments, the compound of Formula I, Formula Ia, Formula Ib, or Formula Ic is such that X is: —OH, —$NH_2$,
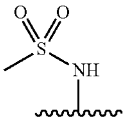
,
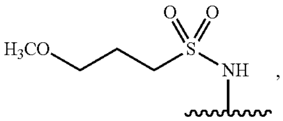
,
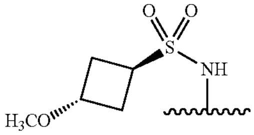
,
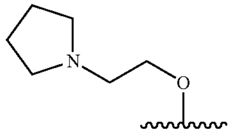
,
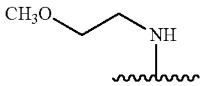
,
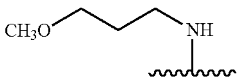
,
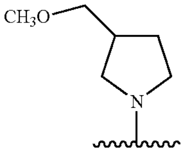
,
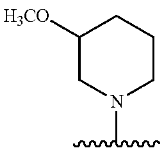
,
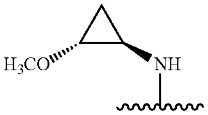
,
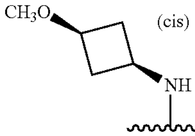
(cis)
,
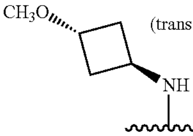
(trans)
,
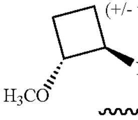
(+/- trans)
,
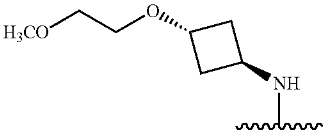
,
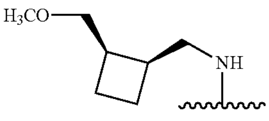
,
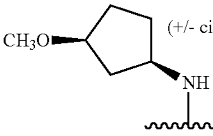
(+/- cis)
,
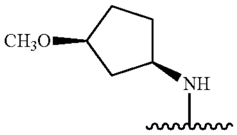
,
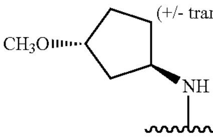
(+/- trans)
,
-continued
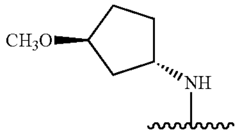
,
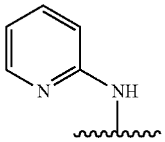
,
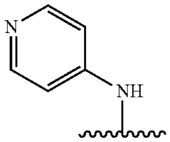
,
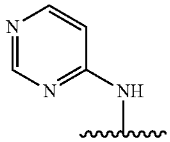
,
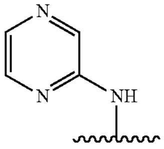
,
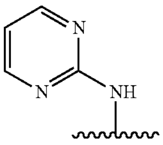
,
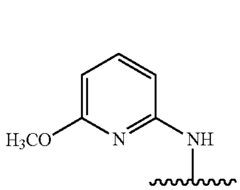
,
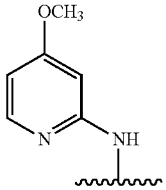
,
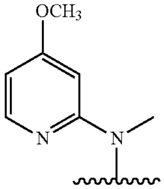
,
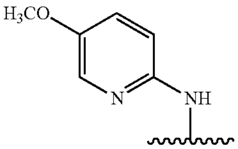
,
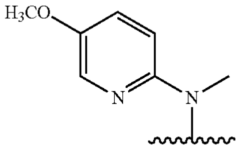
,
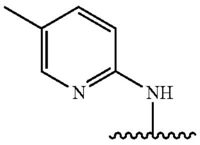
,
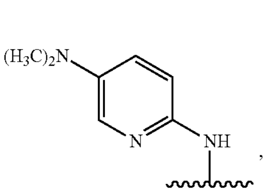
,
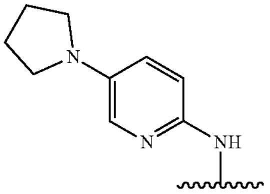
,
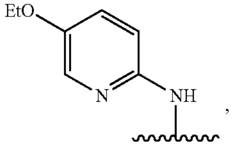
,
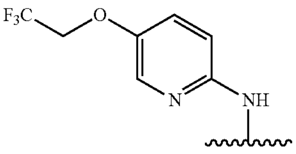
,
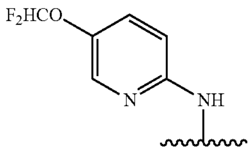
,
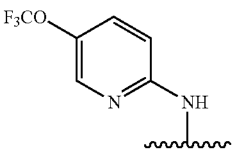
,
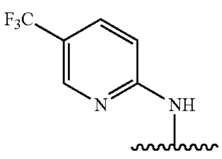
, -continued
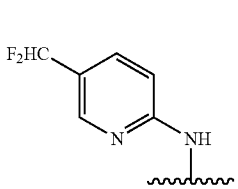,
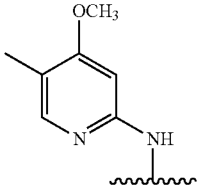,
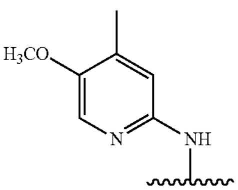,
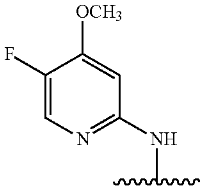,
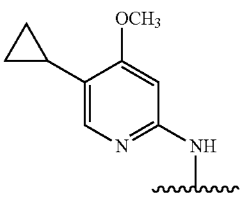,
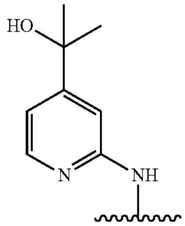,
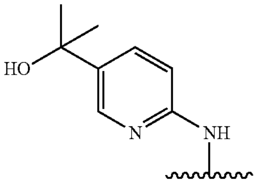,
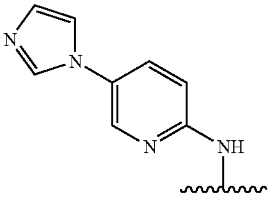,
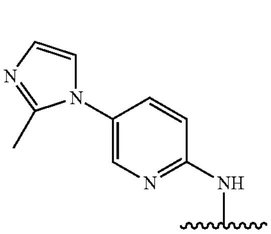,
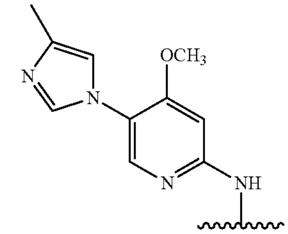,
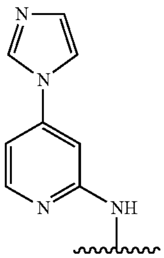,
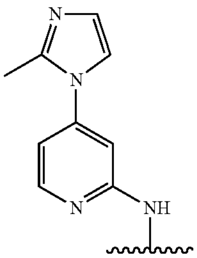,
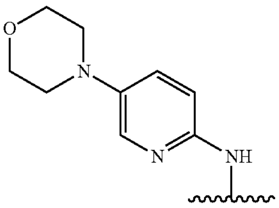,
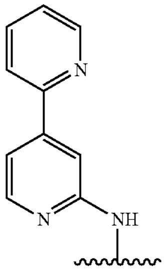,
-continued
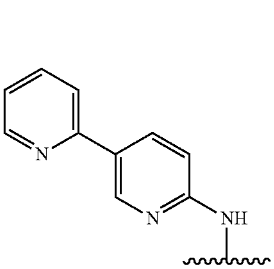,
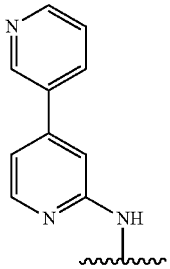,
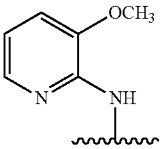,
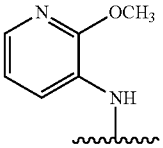,
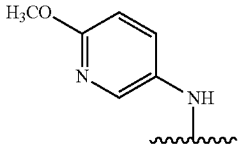,
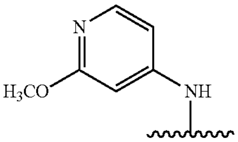,
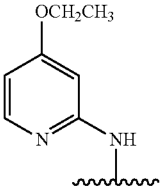,
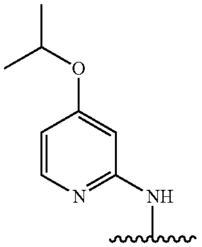,
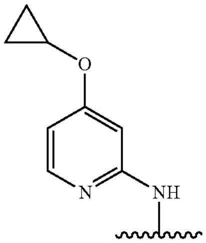,
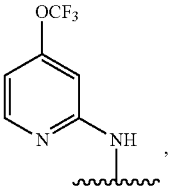,
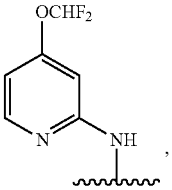,
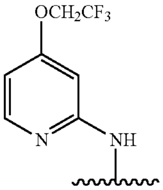,
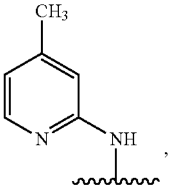,
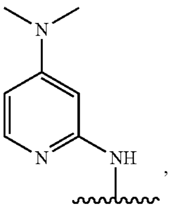,
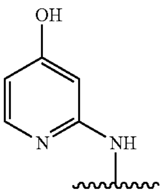,
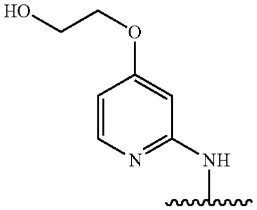,
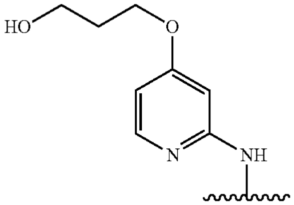, -continued
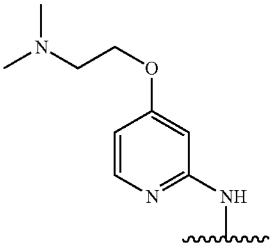,
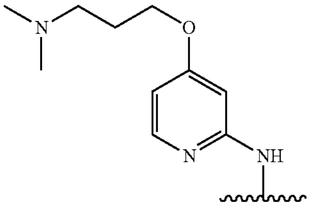, 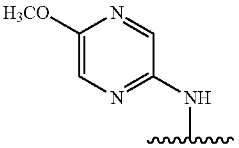,
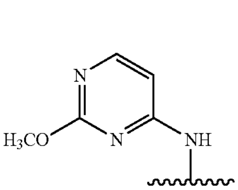, 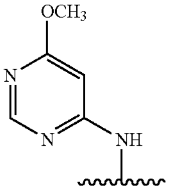,
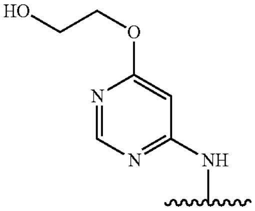, 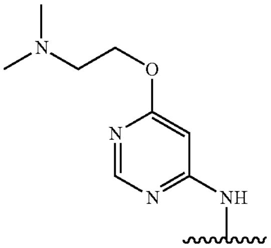,
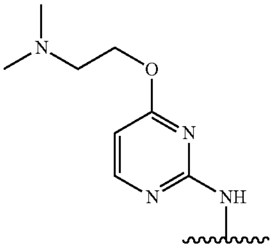, 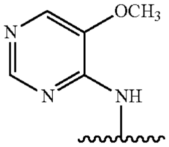,
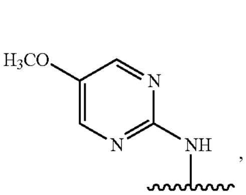, 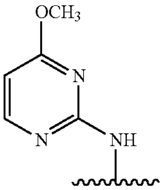,
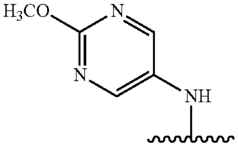,
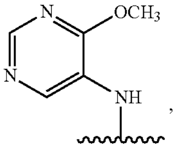, 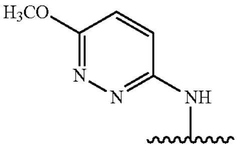,
-continued
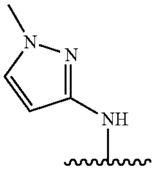, 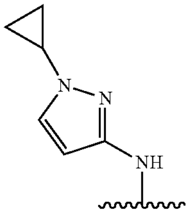, 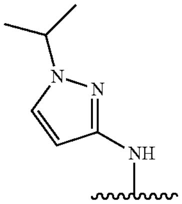,
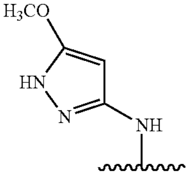, 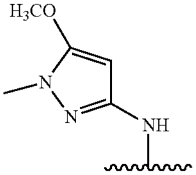,
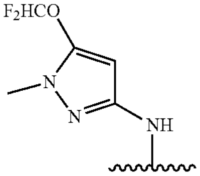, 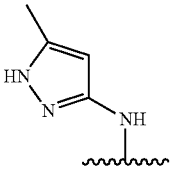,
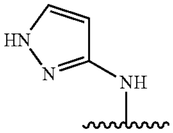, 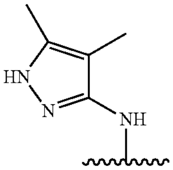, 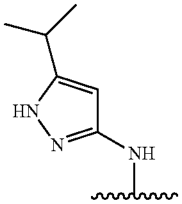,
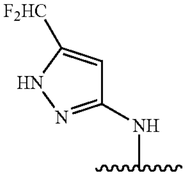, 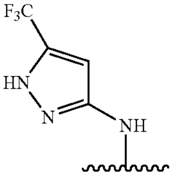, 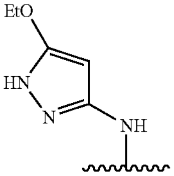,
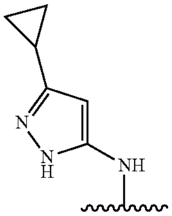, 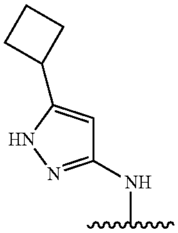,
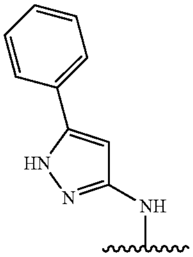, 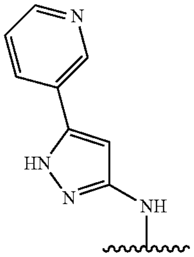,
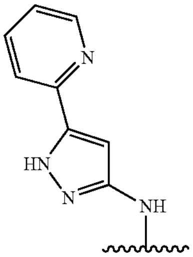, 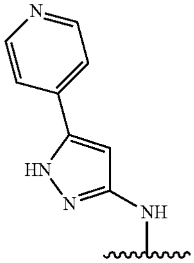, -continued

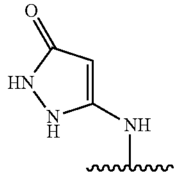 , 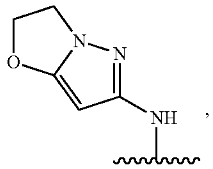 ,

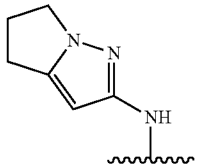 , 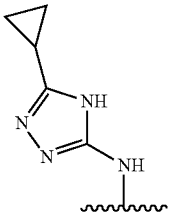 ,

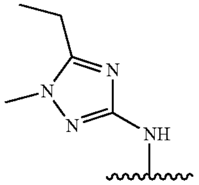 , 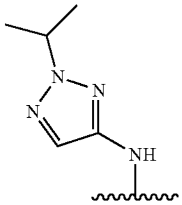 ,

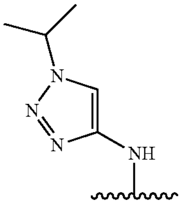 , 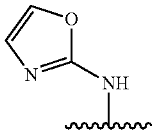 ,

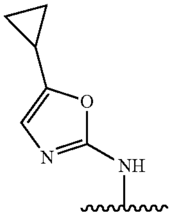 , 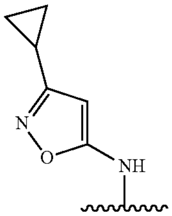 , 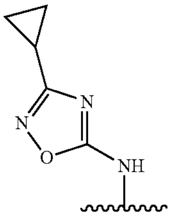 ,

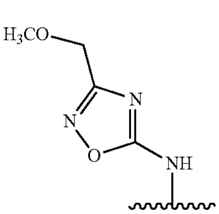 , 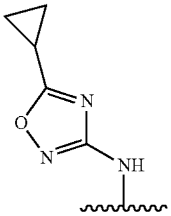 ,

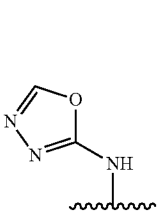 , 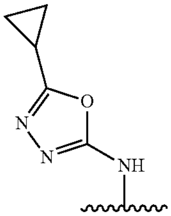 ,

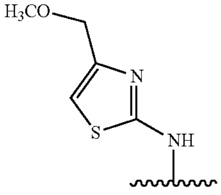 , 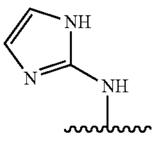 , 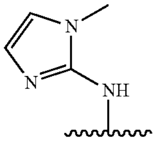 ,

-continued

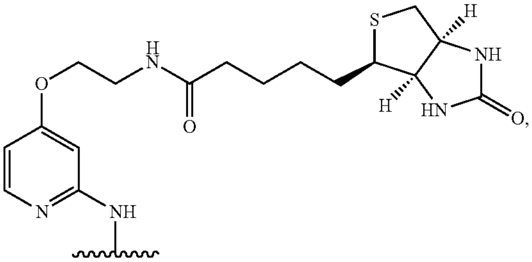

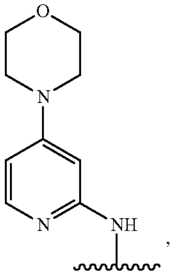 , 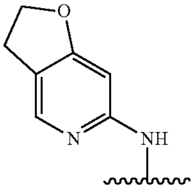 , 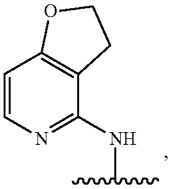 ,

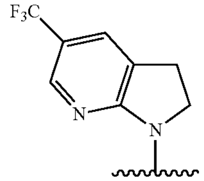 , 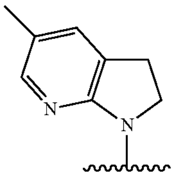 , or

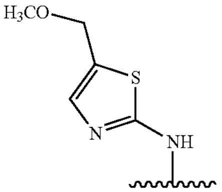 .

In some embodiments, the compound of Formula I, Formula Ia, Formula Ib, or Formula Ic is such that $R^{3A}$ is $C_{1-4}$ alkyl, $C_{3-6}$ cycloalkyl, $C_{1-4}$ heteroalkyl, phenyl, 5-6 membered heteroaryl, —(CO)$R^{11A}$, or —C(O)N$R^{12A}R^{13A}$, wherein the $C_{1-4}$ alkyl, $C_{3-6}$ cycloalkyl, $C_{1-4}$ heteroalkyl, phenyl, or 5-6 membered heteroaryl, are each independently optionally substituted with 1-3 $R^{9A}$ substituents. In some embodiments, the compound is such that $R^{9A}$ is independently selected from the group consisting of $C_{1-4}$ alkyl, $C_{3-5}$ cycloalkyl, —(CO)$R^{11A}$, $C_{1-4}$ hydroxyalkyl, $C_{1-4}$ heteroalkyl, 4-6 membered heterocycloalkyl, $C_{1-4}$ alkoxy, or $C_{3-5}$ cycloalkoxy. In some embodiments, the compound is such that $R^{9A}$ is independently selected from the group consisting of methyl, ethyl, isopropyl, cyclopropyl, cyclobutyl, —(CO)$R^{11A}$, $C_{2-3}$ hydroxyalkyl, $C_{2-4}$ heteroalkyl, methoxy, ethoxy, isopropoxy, cyclopropoxy, cyclobutoxy, imidazolyl, or piperidinyl. In some embodiments, the compound is such that $R^{3A}$ is: —$CH_3$, unsubstituted phenyl, (4-methoxy)-phenyl, ispropyl, cyclopropyl,

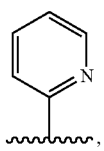, 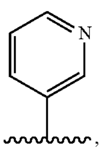, 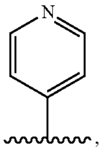, 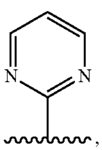,

-continued

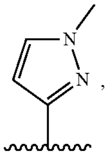 , 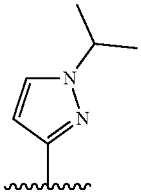 , 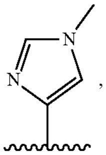 , 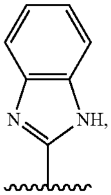

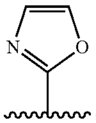 , 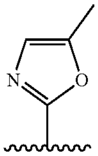 , 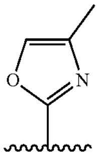 , 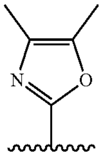 ,

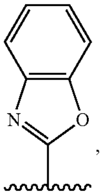 , 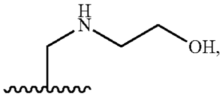

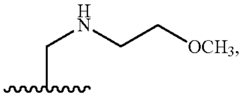 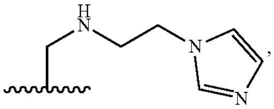 ,

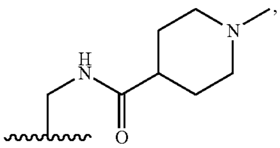 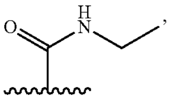

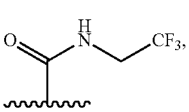 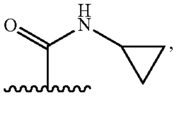 ,

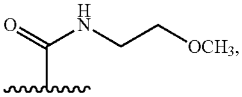 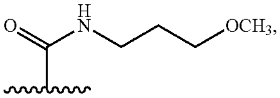

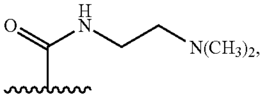 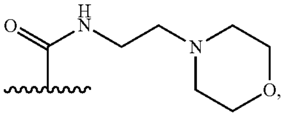

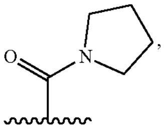 , 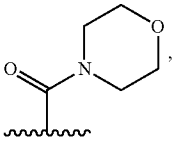 , or 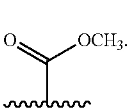

In some embodiments, the compound is such that $R^{3A}$ is: —$CH_3$, unsubstituted phenyl, isopropyl, cyclopropyl,

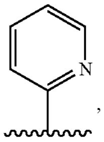 , 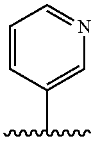 , 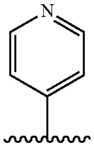 , 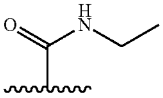 ,

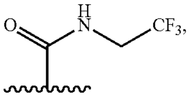 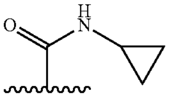 ,

-continued

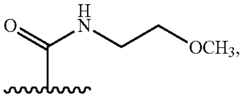 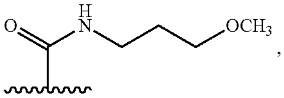 ,

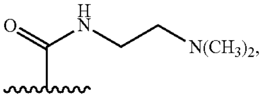 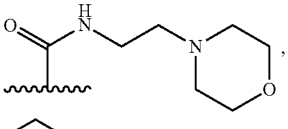 ,

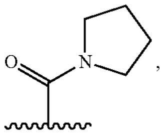 , 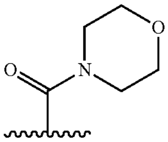 , 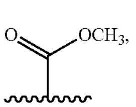 or

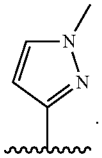 .

In some embodiments, the compound of Formula I, Formula Ia, Formula Ib, or Formula Ic is such that $R^{4A}$ is phenyl or 5-10 membered heteroaryl, wherein the phenyl or 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached. In some embodiments, the compound is such that $R^{4A}$ is phenyl optionally substituted with 1-3 $R^{10A}$ substituents. In some embodiments, the compound is such that $R^{4A}$ is 5-6 membered heteroaryl optionally substituted with 1-3 $R^{10A}$ substituents. In some embodiments, the compound is such that $R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl. In some embodiments, the compound is such that $R^{10A}$ is independently selected from the group consisting of halo, $C_1$-4 alkyl, $C_{3-5}$ cycloalkyl, $C_{1-4}$ haloalkyl, $C_{1-4}$ hydroxyalkyl, $C_{1-4}$ heteroalkyl, 3-5 membered heterocycloalkyl, —OH, $C_{1-4}$ alkoxy, $C_{3-5}$ cycloalkoxy, $C_{1-4}$ haloalkoxy, or —$NR^{12A}R^{13A}$. In some embodiments, the compound is such that $R^{10A}$ is independently selected from the group consisting of halo, methyl, ethyl, isopropyl, cyclopropyl, cyclobutyl, $C_{1-3}$ haloalkyl, $C_{2-3}$ hydroxyalkyl, $C_{2-4}$ heteroalkyl, —OH, methoxy, ethoxy, isopropoxy, cyclopropoxy, cyclobutoxy, $C_{1-4}$ haloalkoxy, or —$NR^{12A}R^{13A}$. In some embodiments, the compound is such that $R^{12A}$ and $R^{13A}$ are each independently selected from the group consisting of hydrogen, $C_{1-4}$ alkyl, $C_{3-5}$ cycloalkyl, $C_{1-4}$ hydroxyalkyl, $C_{1-4}$ heteroalkyl, —OH, or $C_{1-4}$ alkoxy. In some embodiments, the compound is such that $R^{12A}$ and $R^{13A}$ are each independently selected from the group consisting of hydrogen, methyl, ethyl, isopropyl, cyclopropyl, cyclobutyl, methoxy, or ethoxy. In some embodiments, the compound is such that $R^{12A}$ and $R^{13A}$ are each independently selected from the group consisting of hydrogen or methyl. In some embodiments, the compound is such that $R^{12A}$ and $R^{13A}$ are each hydrogen.

In some embodiments, the compound is such that $R^{4A}$ is: hydrogen, unsubstituted phenyl.

-continued
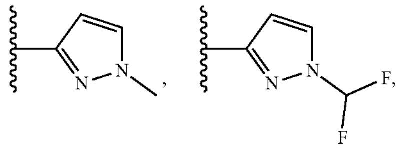
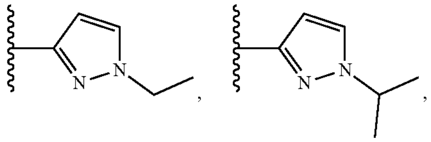
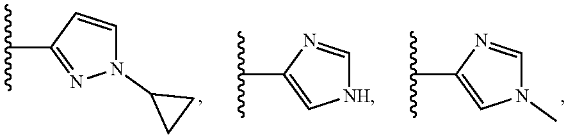
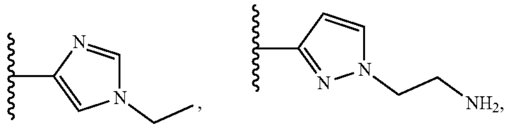
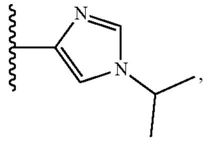
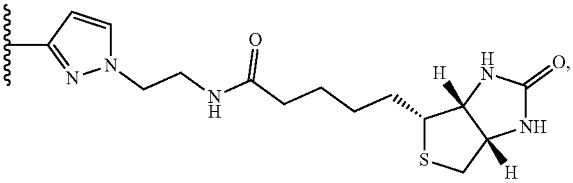
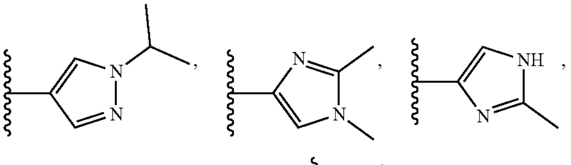
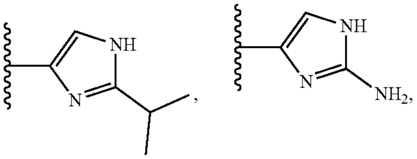
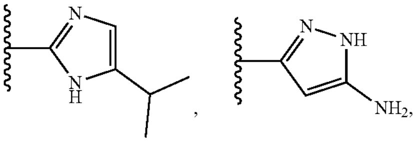
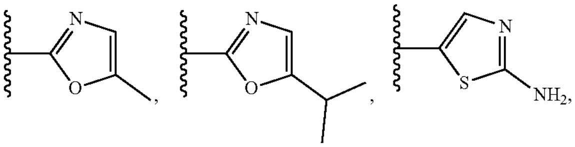
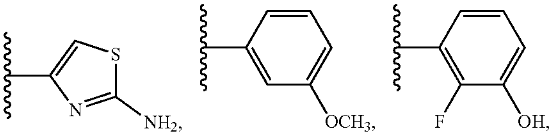
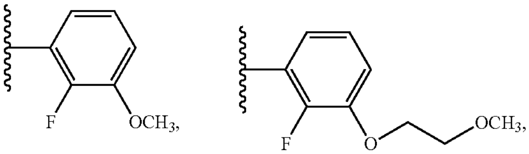
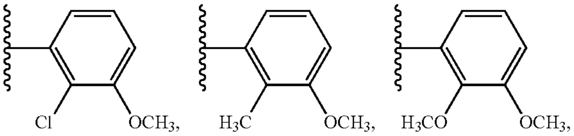
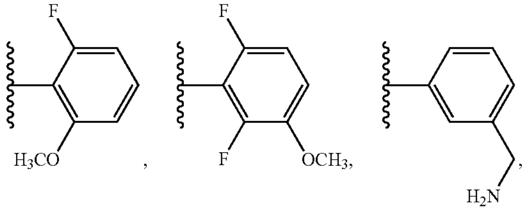
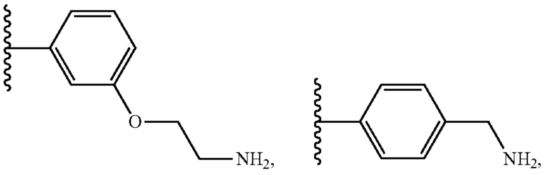
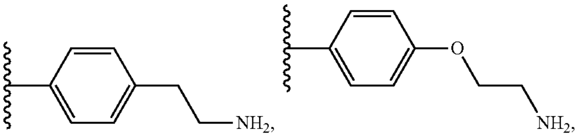
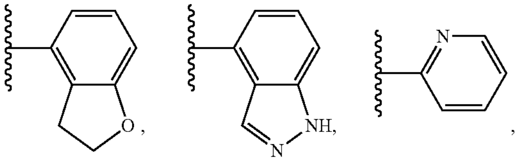
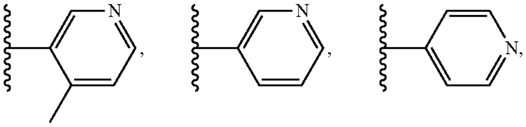
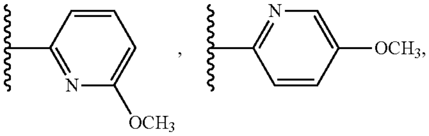
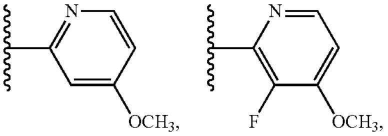
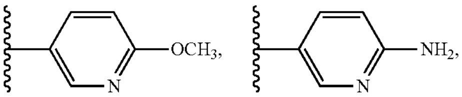
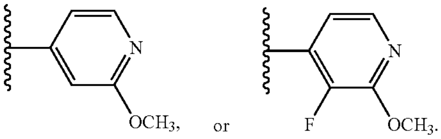
or
In some embodiments, the compound is such that $R^{4A}$ is: hydrogen, unsubstituted phenyl.

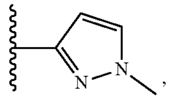, 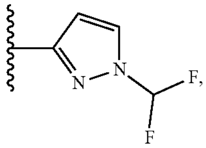

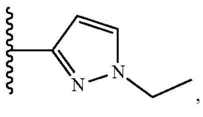, 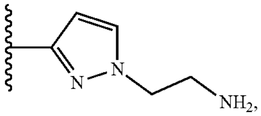

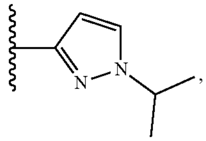

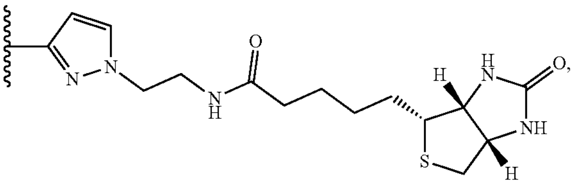

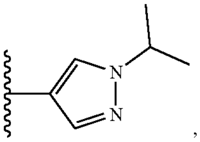, 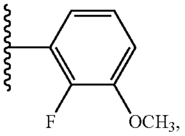 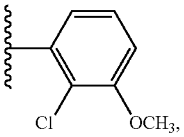

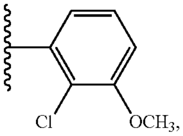 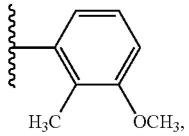 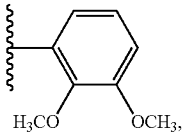

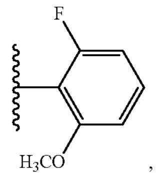, 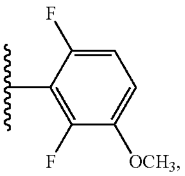 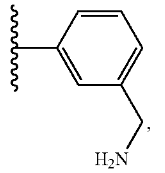

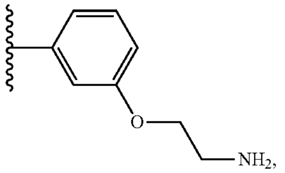 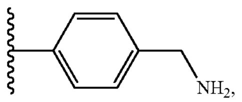

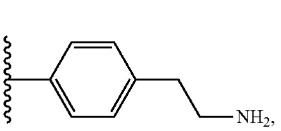 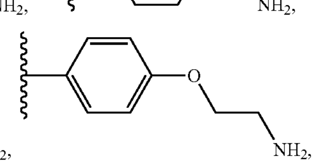

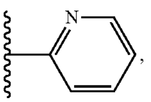, 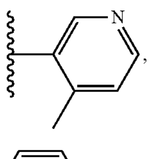, 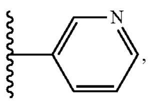

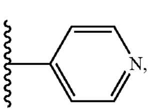 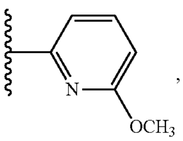, 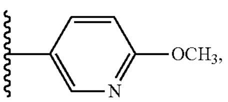

-continued

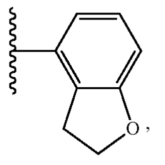, or 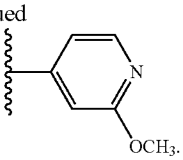

In some embodiments, the compound of Formula I is a compound of Formula II:

Formula II

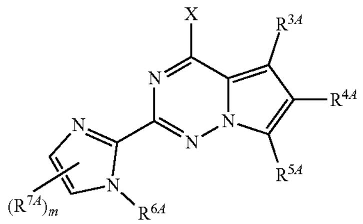

or a pharmaceutically acceptable form thereof, wherein:

X is —$NR^{1A}R^{2A}$ or —$OR^{2A}$;

$R^{1A}$ is hydrogen or $C_{1-6}$ alkyl;

$R^{2A}$ is hydrogen, $C_{1-6}$ alkyl, $C_{3-7}$ cycloalkyl, $C_{1-6}$ heteroalkyl, —$S(O)_2R^{15A}$, —$P(O)R^{16A}R^{17A}$, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached, optionally wherein the 3-6 membered heterocycloalkyl formed by $R^{1A}$ and $R^{2A}$ is fused to a 5-6 membered heteroaryl;

$R^{3A}$ is $C_{1-6}$ alkyl, $C_{3-6}$ cycloalkyl, $C_{1-6}$ heteroalkyl, phenyl, 5-10 membered heteroaryl, —$(CO)R^{11A}$, or —$C(O)NR^{12A}R^{13A}$, wherein the $C_{1-6}$ alkyl, $C_{3-6}$ cycloalkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —$(CO)R^{11A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl, wherein the $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, $C_{1-6}$ alkoxy, $C_{3-6}$ cycloalkoxy, $C_{1-6}$ haloalkoxy, or 5-6 membered heteroaryl are each independently optionally substituted with 1-3 $R^{8A}$ substituents;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-7}$ cycloalkyl, $C_{1-6}$ haloalkyl, $C_{1-6}$ hydroxyalkyl, $C_{1-6}$ heteroalkyl, —OH, $C_{1-6}$ alkoxy, or $C_{1-6}$ haloalkoxy, or $R^{12A}$ and $R^{13A}$ are combined to form a 3-6 membered heterocycloalkyl including the nitrogen atom to which they are both attached;

$R^{15A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{16A}$ and $R^{17A}$ are each independently selected from the group consisting $C_{1-6}$ alkyl, $C_{1-6}$ alkoxy, or $C_{1-6}$ heteroalkyl, wherein the $C_{1-6}$ alkyl, $C_{1-6}$ alkoxy, and $C_{1-6}$ heteroalkyl, are each independently optionally substituted with 1-3 $R^{8A}$ substituents, or $R^{16A}$ and $R^{17A}$ are combined to form a 3-7 membered heterocycloalkyl including the phorphorus atom to which they are both attached;

m is 0, 1 or 2; and wherein, when X is OH or

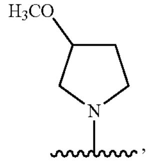

Y is N-methyl imidazoyl, and $R^{5A}$ is H, at least one of $R^{3A}$ and $R^{4A}$ is not unsubstituted phenyl.

In some embodiments, the compound of Formula I is a compound of Formula IIa:

Formula IIa

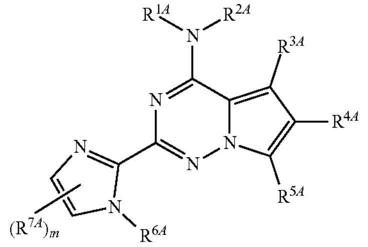

or a pharmaceutically acceptable form thereof, wherein:

$R^{1A}$ is hydrogen;

$R^{2A}$ is hydrogen, $C_{1-6}$ alkyl, $C_{3-6}$ cycloalkyl, $C_{1-6}$ heteroalkyl, —$S(O)_2R^{15A}$, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{3A}$ is $C_{1-3}$ alkyl, $C_{3-6}$ cycloalkyl, $C_{1-6}$ heteroalkyl, phenyl, 5-, 6- or 9-membered heteroaryl, —$(CO)R^{11A}$, or —$C(O)NR^{12A}R^{13A}$, wherein the $C_{1-3}$ alkyl, $C_{3-6}$ cycloalkyl, $C_{1-6}$ heteroalkyl, phenyl, and 5-, 6-, or 9-membered heteroaryl are each independently optionally substituted with 1-3 $R^{9A}$ substituents;

$R^{4A}$ is hydrogen, phenyl, or 5, 6, or 9 membered heteroaryl, wherein the phenyl and 5, 6, or 9 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is $C_{1-3}$ alkyl or $C_{1-3}$ heteroalkyl, wherein the $C_{1-3}$ alkyl or $C_{1-3}$ heteroalkyl is optionally substituted with biotinamide;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —$(CO)R^{11A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{11A}R^{12A}$, or 5-6 membered heteroaryl, wherein the $C_{1-6}$ alkyl or $C_{1-6}$ heteroalkyl is optionally substituted with biotinamide;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy, or $R^{12A}$ and $R^{13A}$ are combined to form a 5 or 6 membered heterocycloalkyl including the nitrogen atom to which they are both attached;

$R^{15A}$ is $C_{1-3}$ alkyl, $C_{3-6}$ cycloalkyl, or $C_{1-4}$ heteroalkyl;

$R^{16A}$ and $R^{17A}$ are each independently selected from the group consisting $C_{1-3}$ alkyl or $C_{1-3}$ alkoxy, or $R^{16A}$ and $R^{17A}$ are combined to form a 5 membered heterocycloalkyl including the phorphorus atom to which they are both attached; and m is 0 or 1.

In some embodiments, the compound of Formula IIa is such that:

$R^{1A}$ and $R^{2A}$ together with the nitrogen to which they are attached, have a structure of: —$NH_2$,

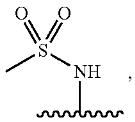

,

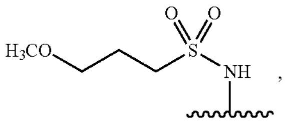

,

-continued
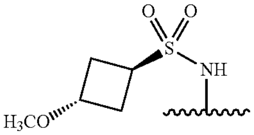, 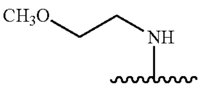,
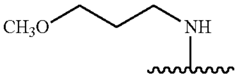, 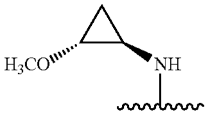,
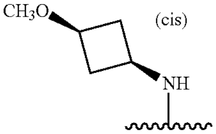, 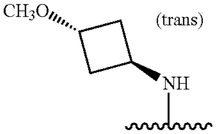,
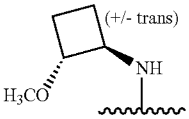, 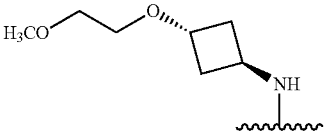,
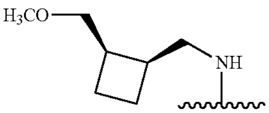, 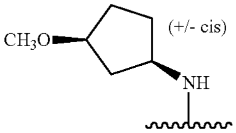,
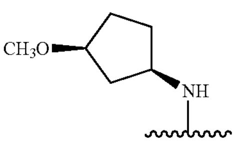, 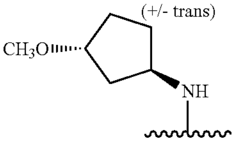,
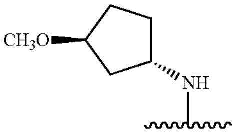, 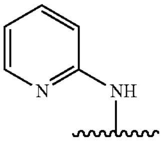,
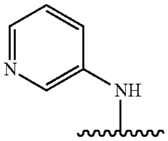, 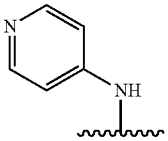, 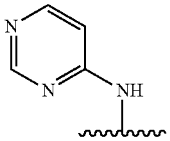,
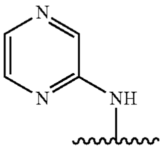, 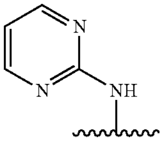, 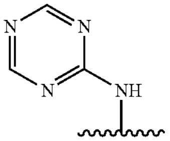,
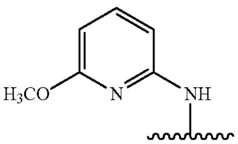, 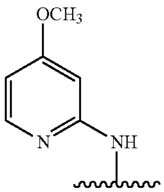,
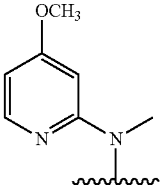, 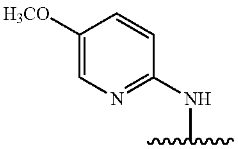,
-continued
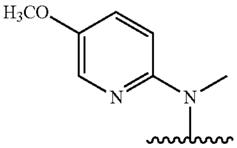, 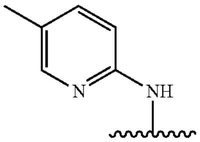,
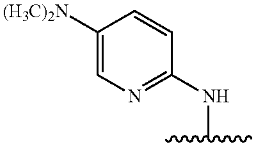, 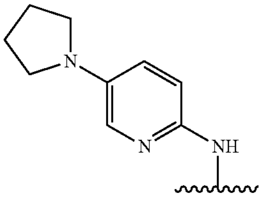,
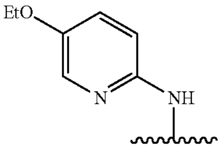,
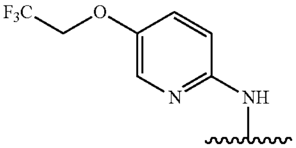, 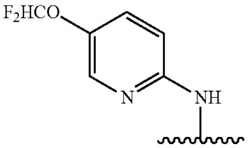,
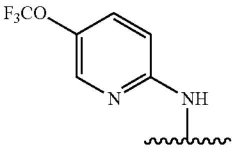, 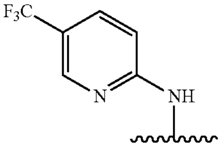,
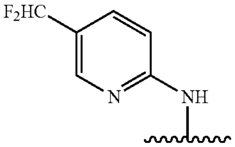, 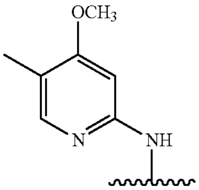,
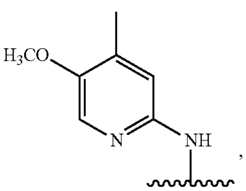, 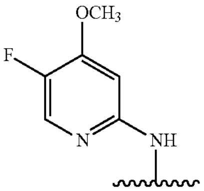,
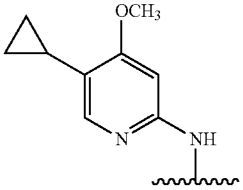, 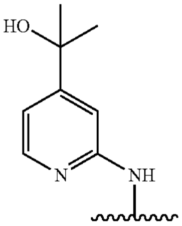,
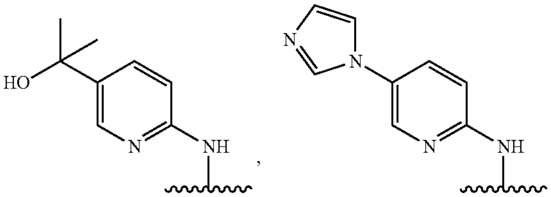, -continued
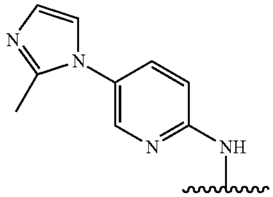,
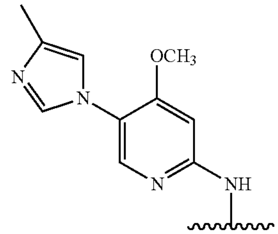,
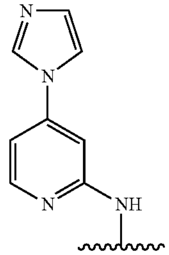,
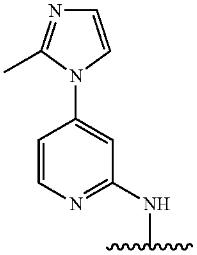,
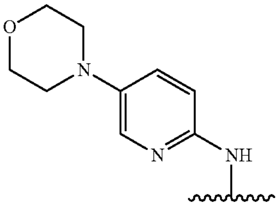,
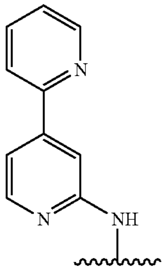,
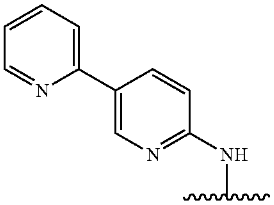,
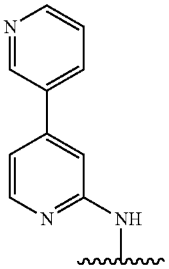,
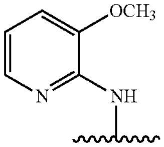,
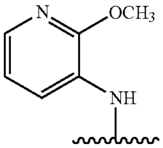,
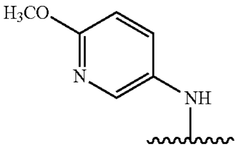,
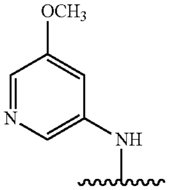,
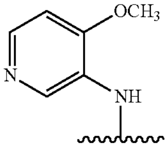,
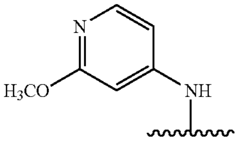,
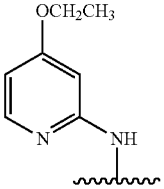,
-continued
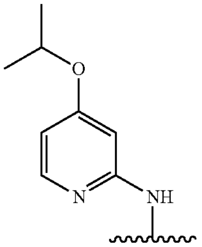,
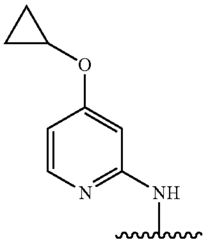,
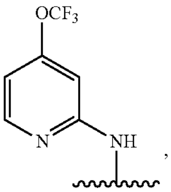,
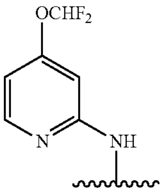,
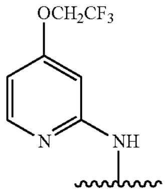,
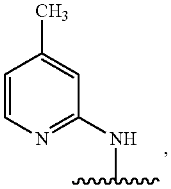,
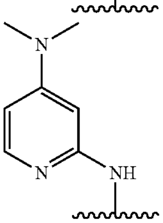,
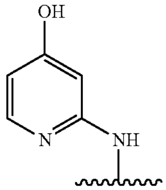,
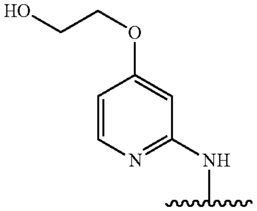,
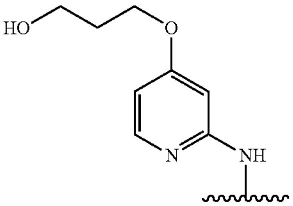,
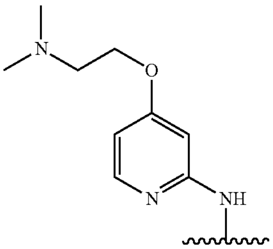,
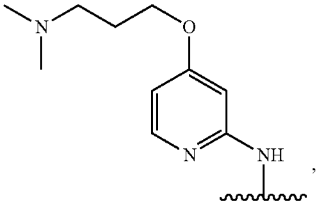,
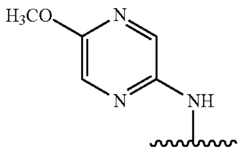,
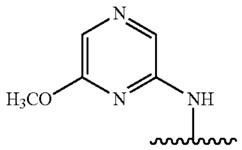,
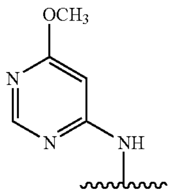,
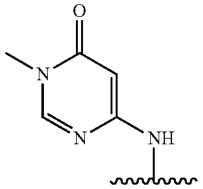,
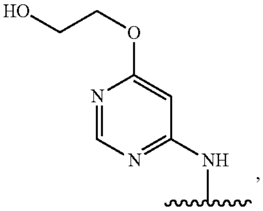, -continued
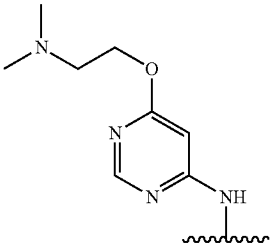,
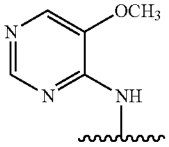,
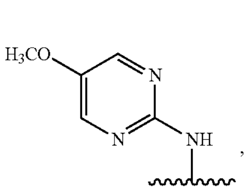,
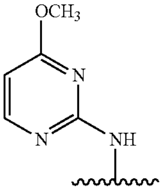,
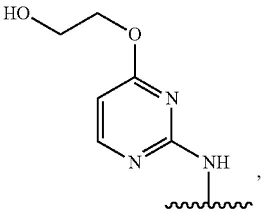,
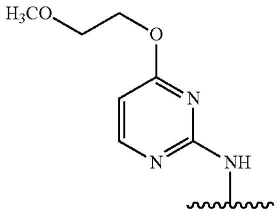,
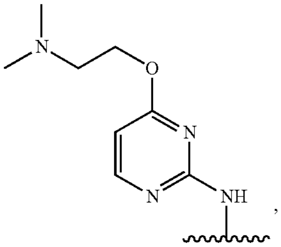,
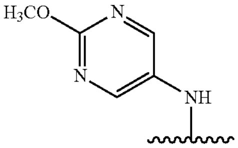,
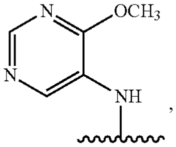,
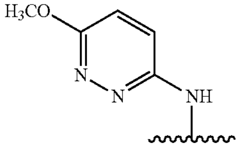,
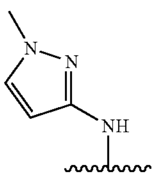,
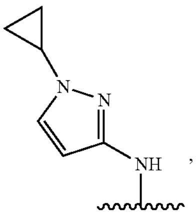,
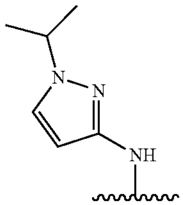,
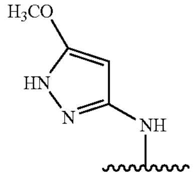,
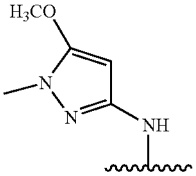,
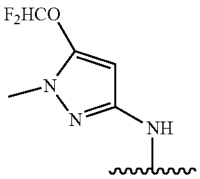,
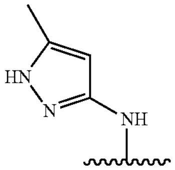,
-continued
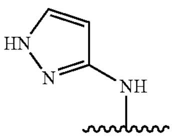,
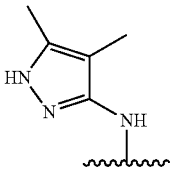,
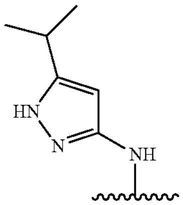,
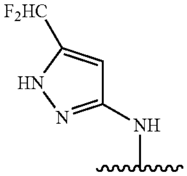,
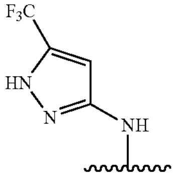,
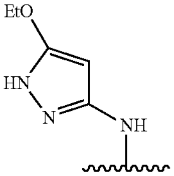,
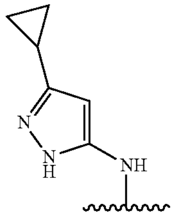,
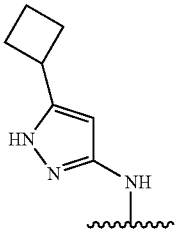,
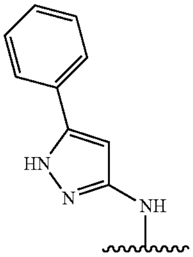,
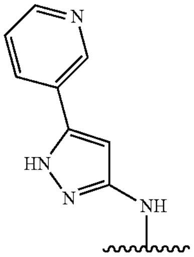,
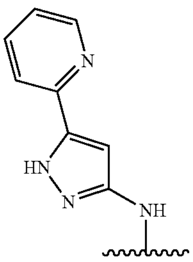,
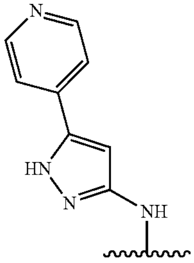,
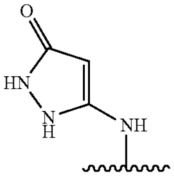,
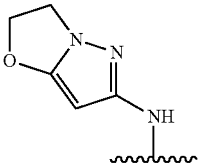,
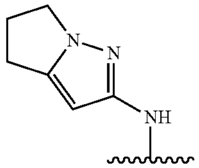,
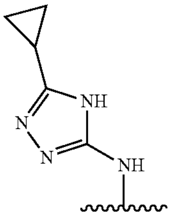,
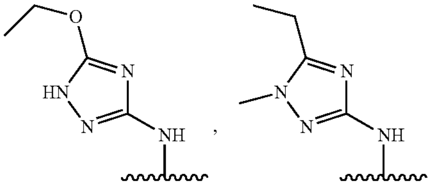, -continued
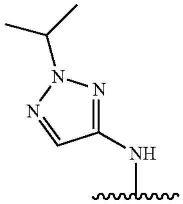, 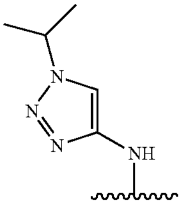, 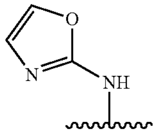,
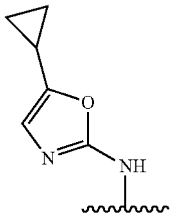, 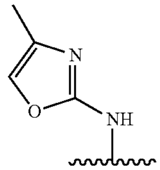, 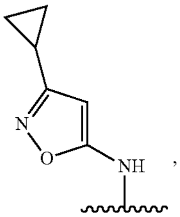,
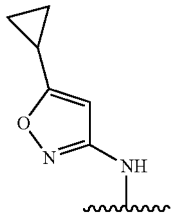, 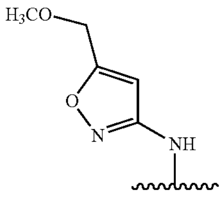,
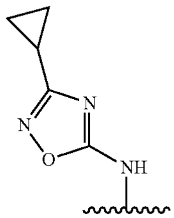, 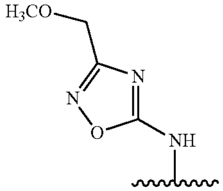,
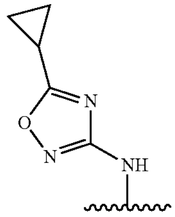, 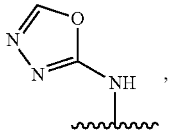, 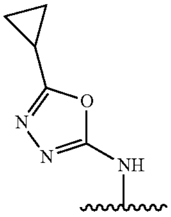,
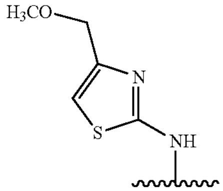, 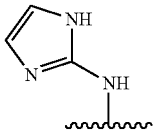, 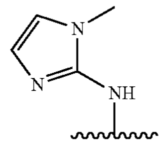,
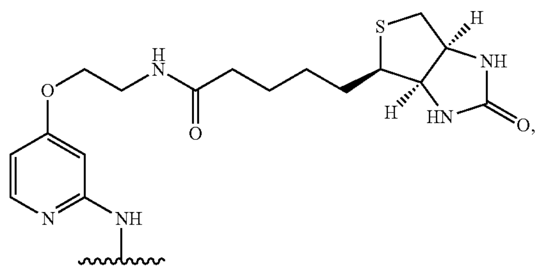
-continued
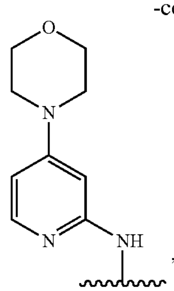, 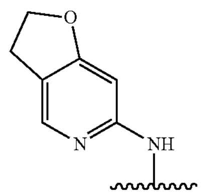,
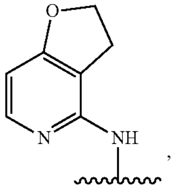, or 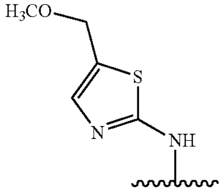;
$R^{3A}$ is —$CH_3$, unsubstituted phenyl, isopropyl, cyclopropyl,
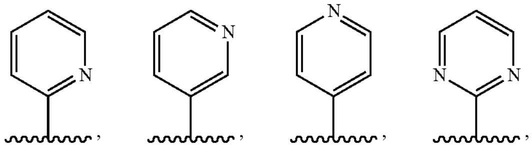
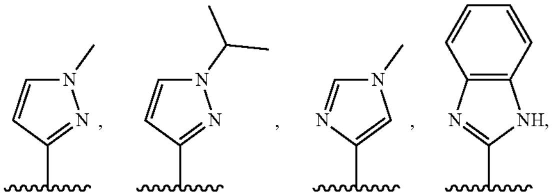
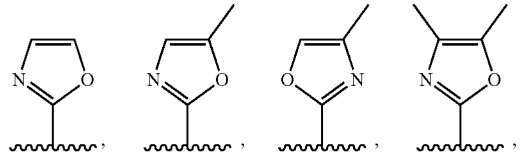
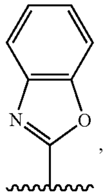, 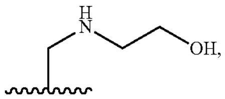
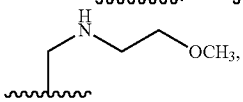 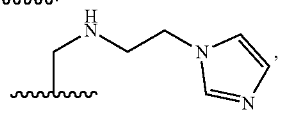
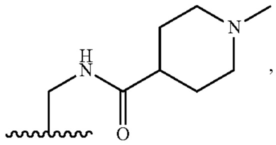, 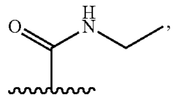
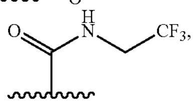 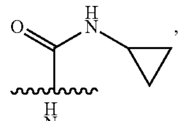,
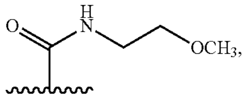 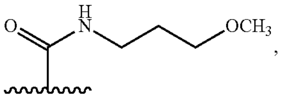, -continued
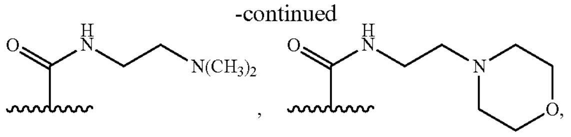
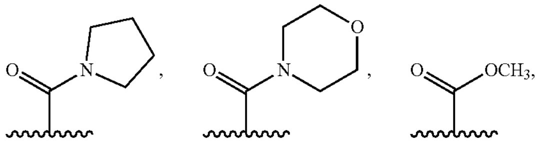
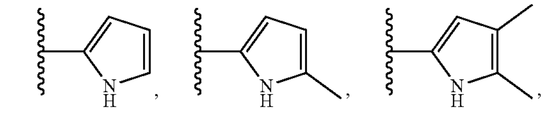
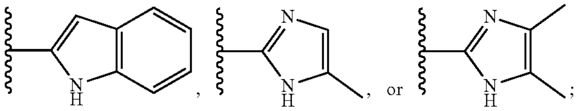
$R^{4A}$ hydrogen, unsubstituted phenyl,
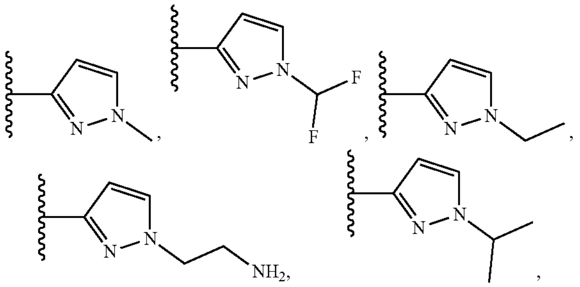
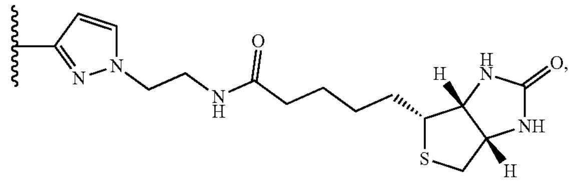
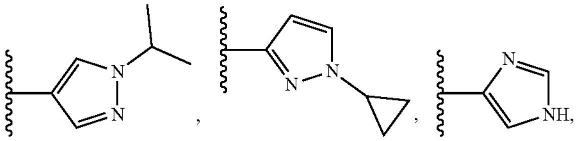
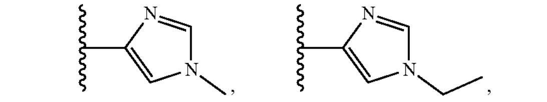
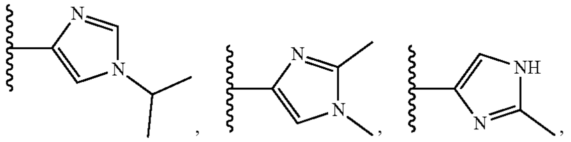
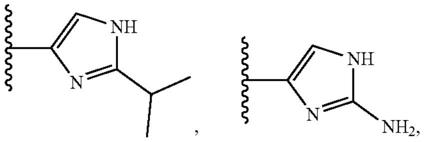
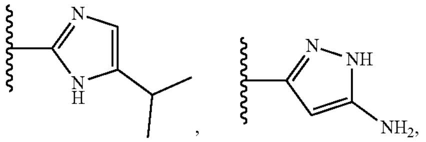
-continued
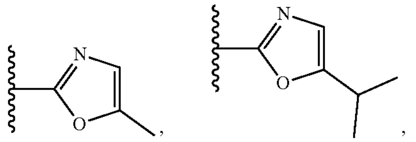
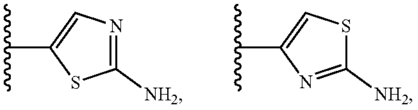
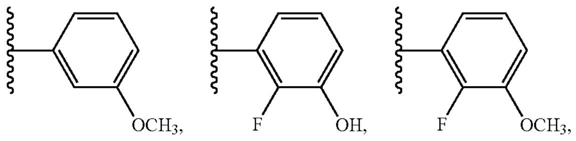
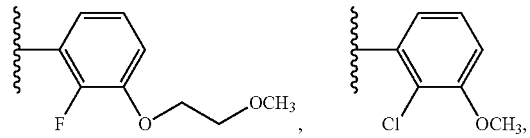
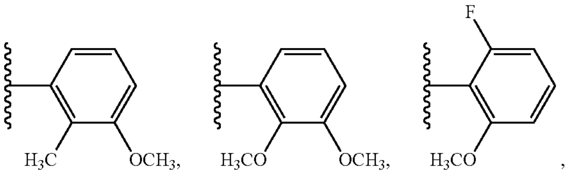
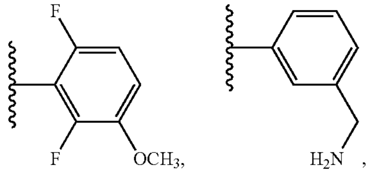
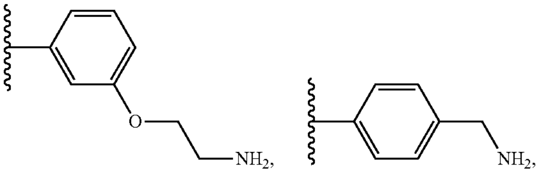
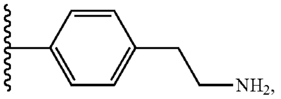
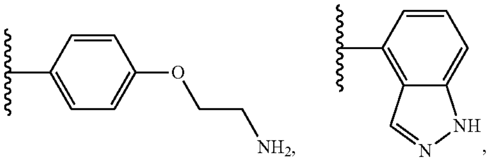
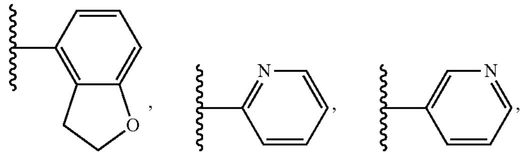
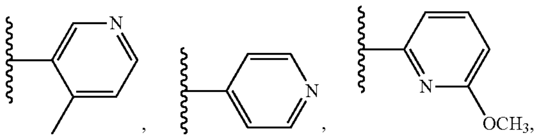

-continued
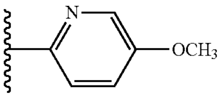,
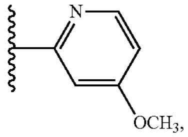
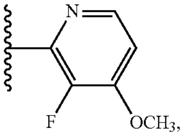
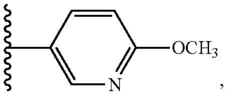,
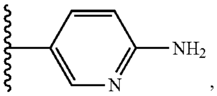,
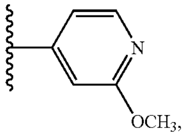
or
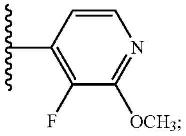
$R^{5A}$ is hydrogen;
$R^{6A}$ is methyl, $—CH_2CH_2NH_2$, or
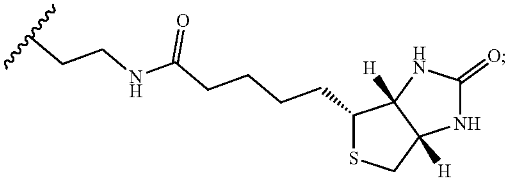 [SMILES: *CCNC(=O)CCCC[C@H]1SC[C@H]2NC(=O)N[C@H]21]
$R^{7A}$ is methyl; and
m is 0 or 1.
In some embodiments, the compound of Formula IIa is such that:
$R^{1A}$ and $R^{2A}$ together with the nitrogen to which they are attached, have a structure of: $—NH_2$,
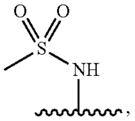
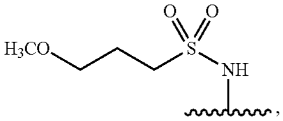
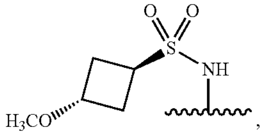
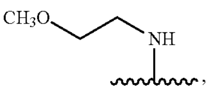
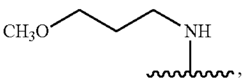
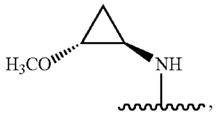
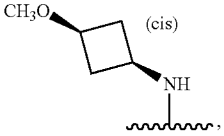
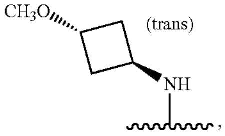
-continued
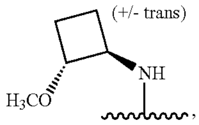
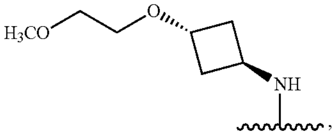
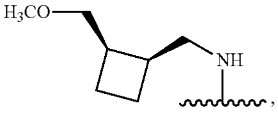
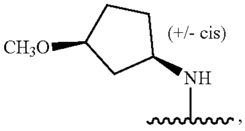
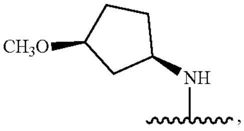
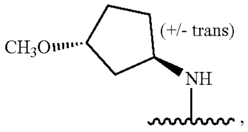
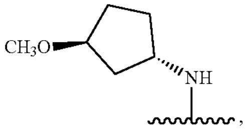
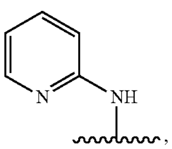
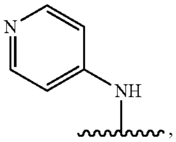
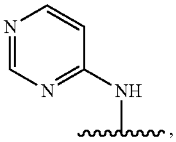
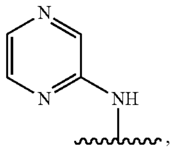
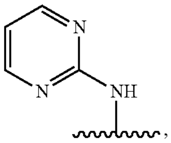
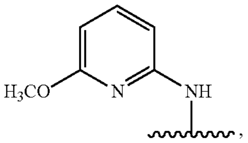
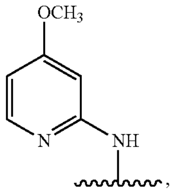
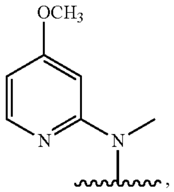
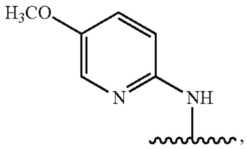
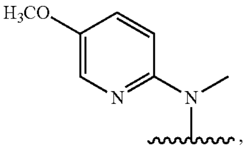
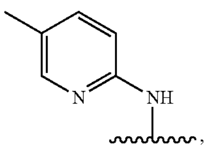
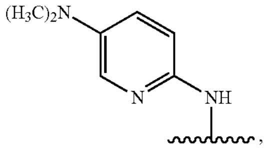
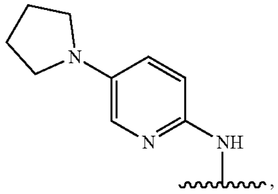
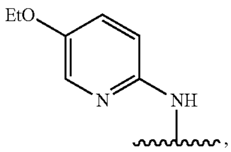
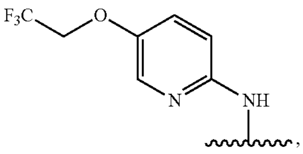
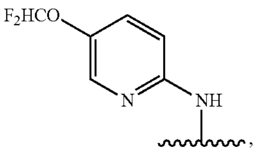

-continued
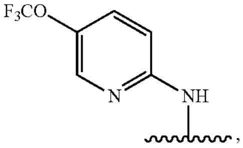,
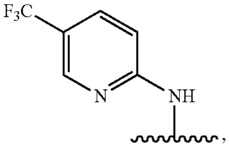,
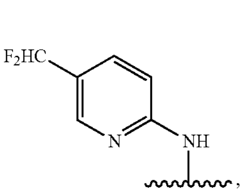,
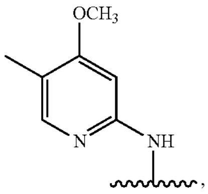,
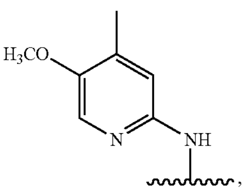,
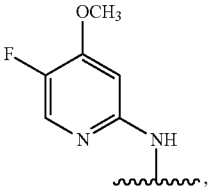,
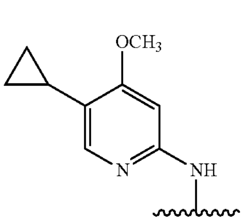,
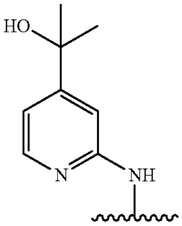,
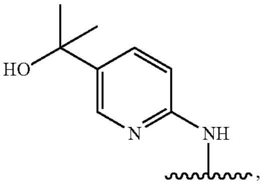,
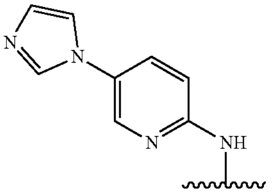,
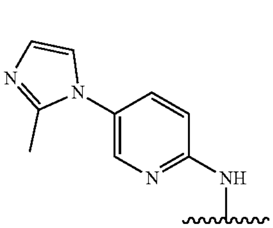,
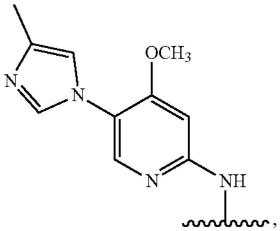,
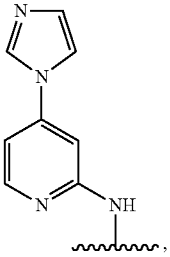,
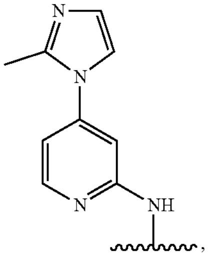,
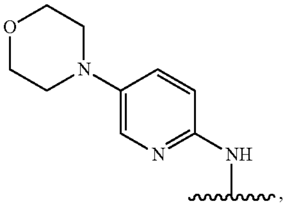,
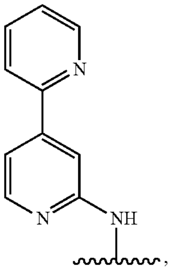,
-continued
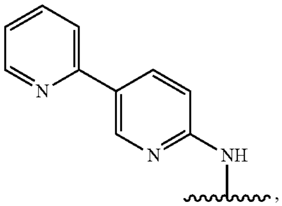,
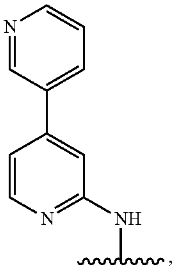,
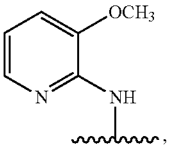,
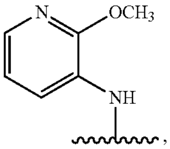,
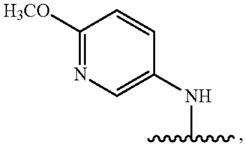,
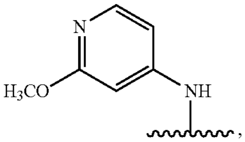,
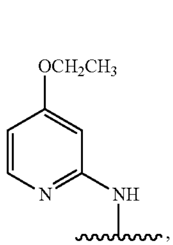,
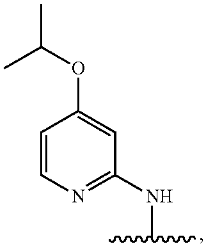,
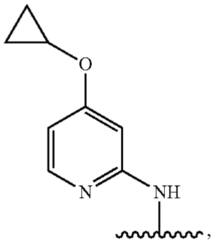,
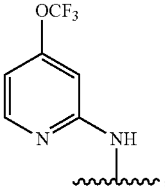,
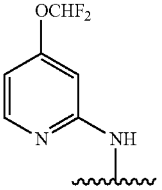,
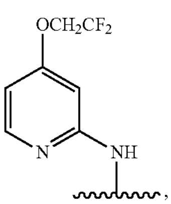,
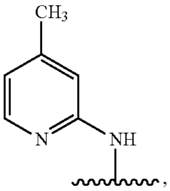,
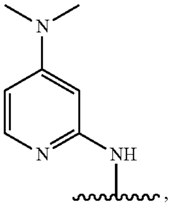,
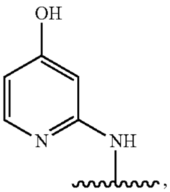,
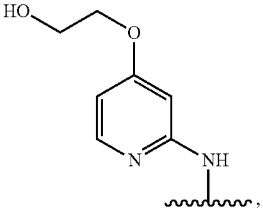,
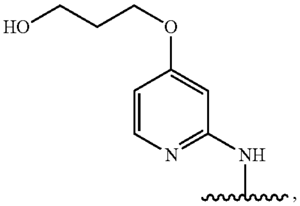, -continued
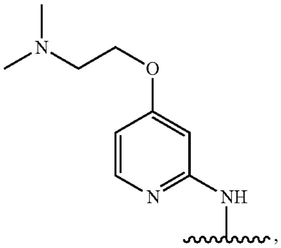,
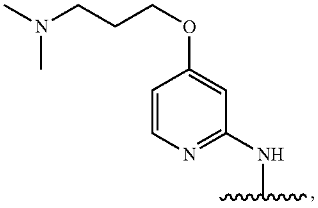,
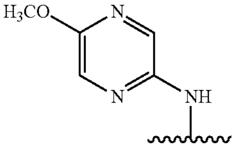,
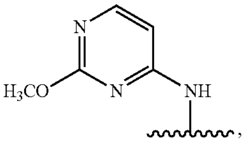,
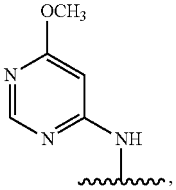,
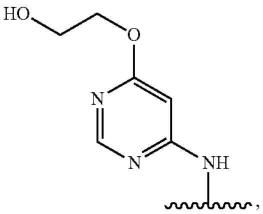,
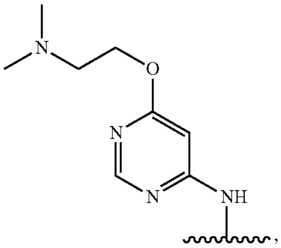,
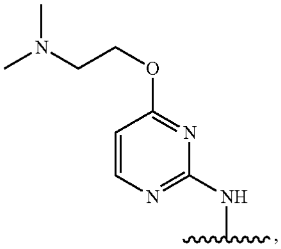,
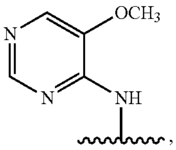,
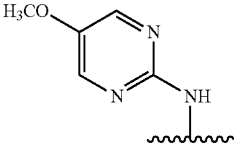,
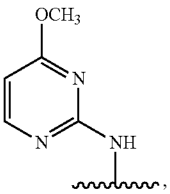,
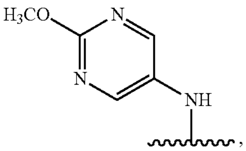,
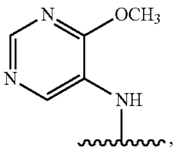,
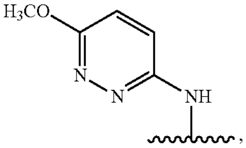,
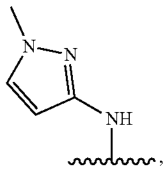,
-continued
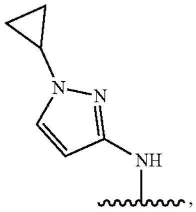,
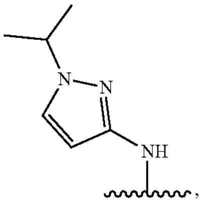,
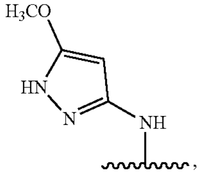,
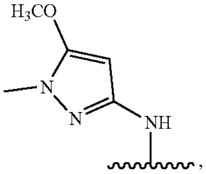,
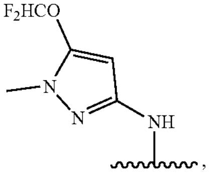,
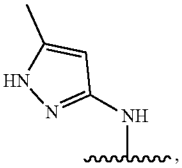,
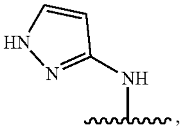,
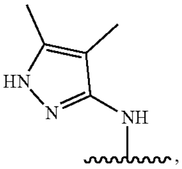,
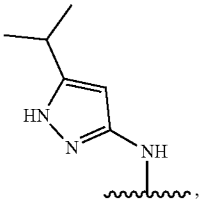,
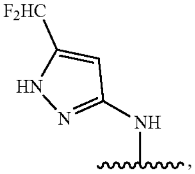,
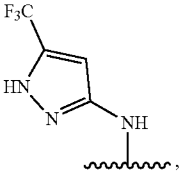,
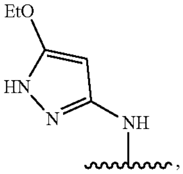,
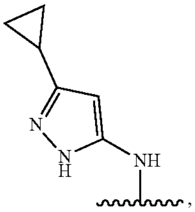,
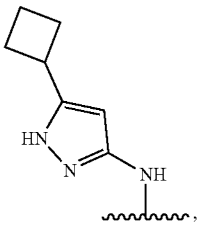,
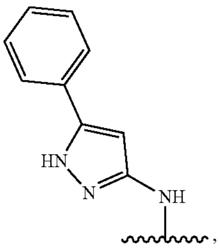,
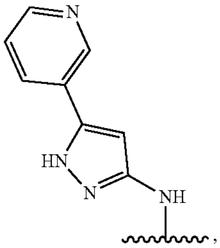, -continued
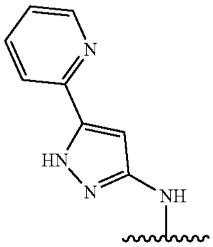,
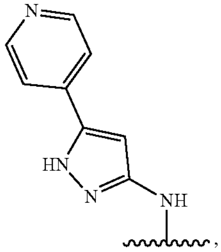,
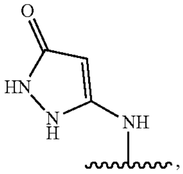,
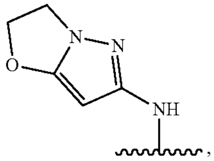,
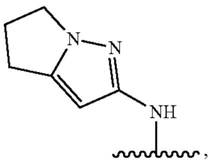,
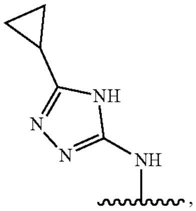,
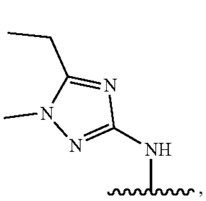,
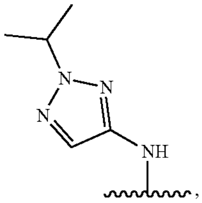,
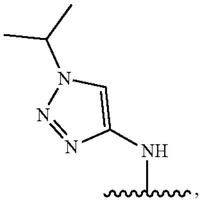,
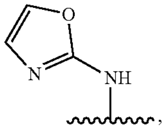,
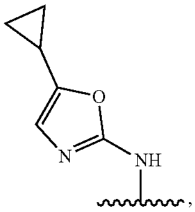,
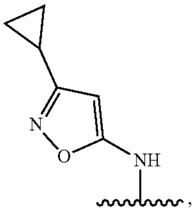,
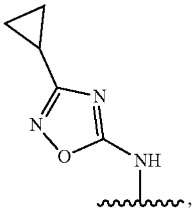,
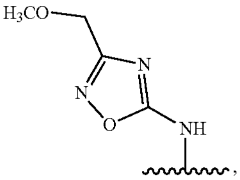,
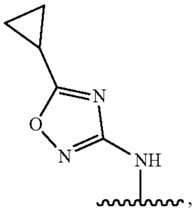,
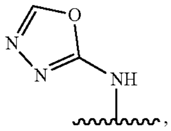,
-continued
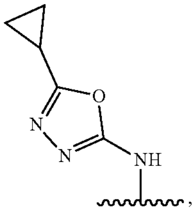,
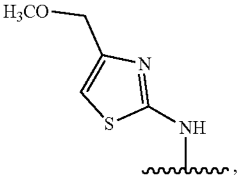,
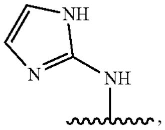,
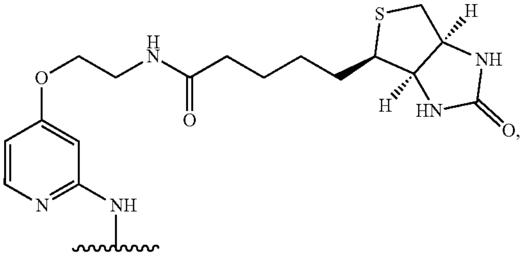,
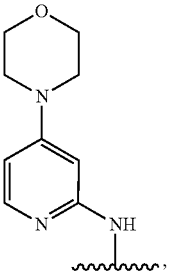,
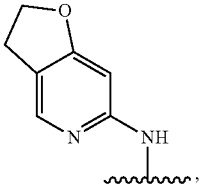,
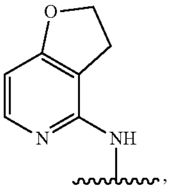, or
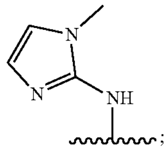;
$R^{3A}$ is —$CH_3$, unsubstituted phenyl, isopropyl, cyclopropyl,
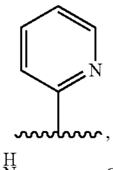,
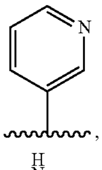,
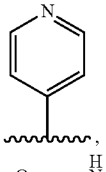,
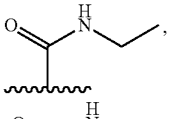,
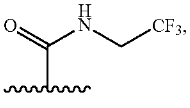,
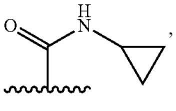,
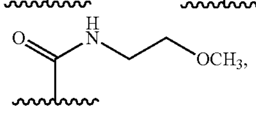,
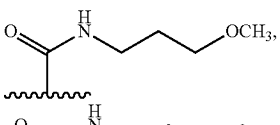,
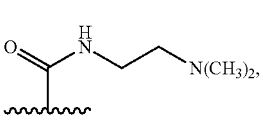,
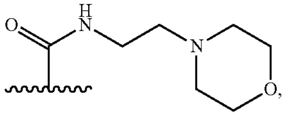, -continued

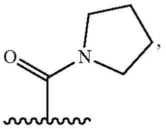, 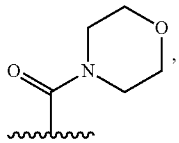, 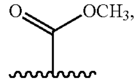 or

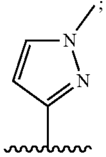;

$R^{41}$ hydrogen, unsubstituted phenyl,

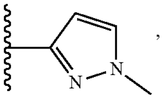, 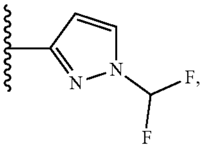 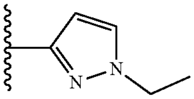,

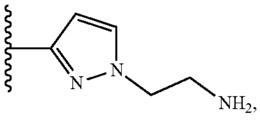 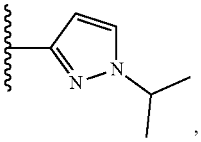,

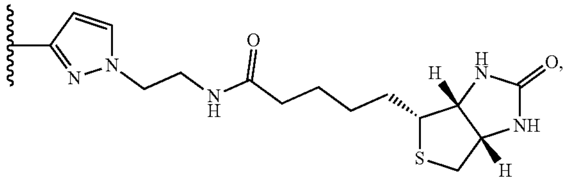

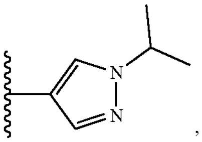, 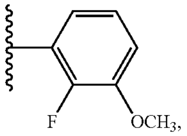

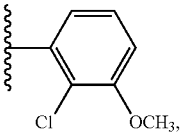 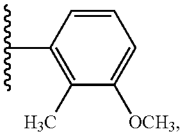 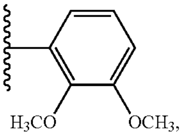

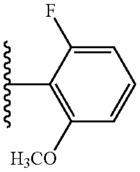, 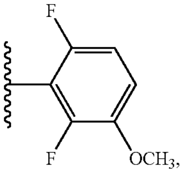 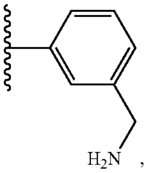,

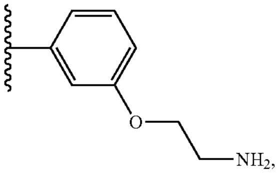 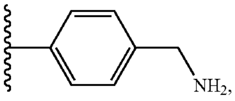

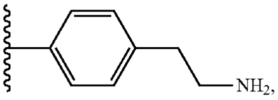

-continued

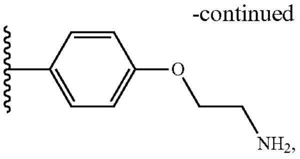 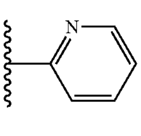,

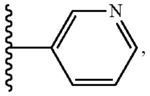, 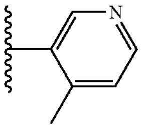, 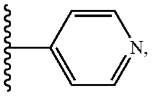

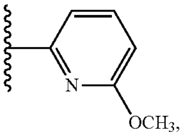 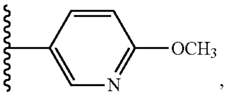,

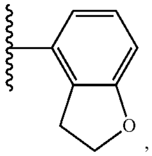, or 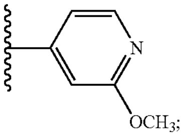

$R^{5A}$ is hydrogen;

$R^{6A}$ is methyl, $-CH_2CH_2NH_2$, or

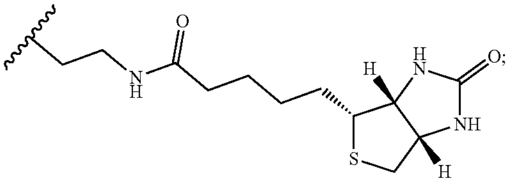 [SMILES: *CCNC(=O)CCCC[C@H]1SC[C@H]2NC(=O)N[C@H]21]

and m is 0.

In some embodiments, the compound of Formula I is a compound of Formula IIa(1):

Formula IIa(1)

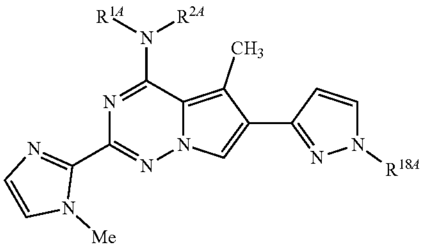

or a pharmaceutically acceptable form thereof, wherein:

$R^{1A}$ is hydrogen;

$R^{2A}$ is 5 or 6 membered heteroaryl, wherein the 5 or 6 membered heteroaryl is optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{8A}$ is selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, $-NR^{12A}R^{13A}$, $-(CO)R^{11A}$, oxo, $-OH$, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy, or $R^{12A}$ and $R^{13A}$ are combined to form a 5 or 6 membered heterocycloalkyl including the nitrogen atom to which they are both attached; and $R^{18A}$ is $C_{1-3}$ alkyl or $C_{3-6}$ cycloalkyl.

In some embodiments, the compound of Formula IIa(1) is such that $R^{18A}$ is methyl, ethyl, isopropyl, or cyclopropyl. In some embodiments, the compound of Formula IIa(1) is such that $R^{18A}$ is methyl. In some embodiments, the compound of Formula IIa(1) is such that $R^{18A}$ is ethyl. In some embodiments, the compound of Formula IIa(1) is such that $R^{18A}$ is isopropyl. In some embodiments, the compound of Formula IIa(1) is such that $R^{18A}$ is cyclopropyl.

In some embodiments, the compound of Formula IIa(1) is such that $R^{8A}$ is selected from the group consisting of $C_{1-6}$ alkyl, $C_{3-6}$ cycloalkyl, 3-6 membered heterocycloalkyl, $C_{1-6}$ alkoxy, or $C_{3-6}$ cycloalkoxy, —$NR^{12A}R^{13A}$, or 5-6 membered heteroaryl.

In some embodiments, the compound of Formula IIa(1) is such that $R^{2A}$ is pyridyl, pyrimidyl, pyrazyl, or pyrazolyl, wherein the pyridyl, pyrimidyl, pyrazyl, or pyrazolyl is optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached. In some embodiments, the compound of Formula IIa(1) is such that $R^{2A}$ is pyridyl, optionally substituted with 1-2 $R^{8A}$ substituents. In some embodiments, the compound of Formula IIa(1) is such that $R^{2A}$ is

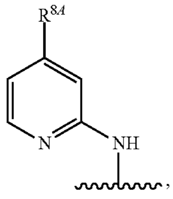,

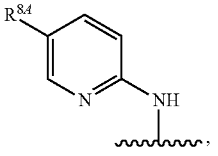,

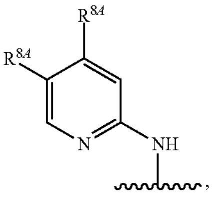, or

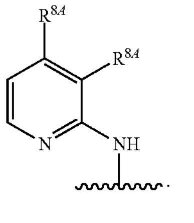.

In some embodiments, the compound of Formula IIa(1) is such that $R^{2A}$ is pyrimidyl, optionally substituted with 1-2 $R^{8A}$ substituents. In some embodiments, the compound of Formula IIa(1) is such that $R^{2A}$ is

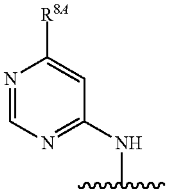

or

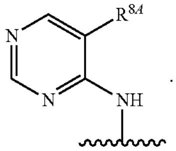.

In some embodiments, the compound of Formula IIa(1) is such that $R^{2A}$ is pyrazyl, optionally substituted with 1-2 $R^{8A}$ substituents. In some embodiments, the compound of Formula IIa(1) is such that $R^{2A}$ is pyrazolyl, optionally substituted with 1-2 $R^{8A}$ substituents. In some embodiments, the compound of Formula IIa(1) is such that $R^{2A}$ is

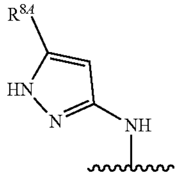,

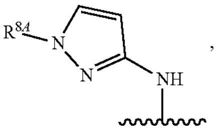,

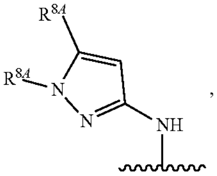, or

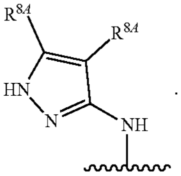.

In some embodiments, the compound of Formula IIa(1) is such that the 2 independent $R^{8A}$ substituents are combined to form a 5 membered cycloalkyl or 5 membered heterocycloalkyl including the atom or atoms to which each are attached.

In some embodiments, the compound of Formula IIa(1) is such that $R^{1A}$ and $R^{2A}$ together with the nitrogen to which they are attached have a structure of:

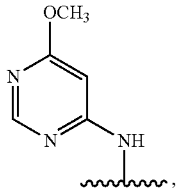,

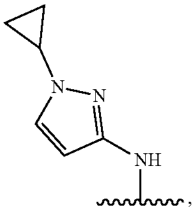,

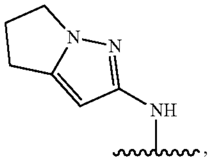,

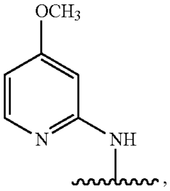,

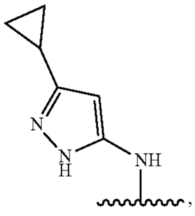,

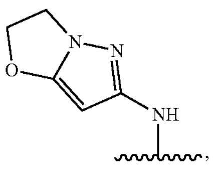,

-continued
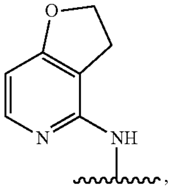,
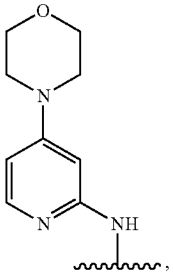,
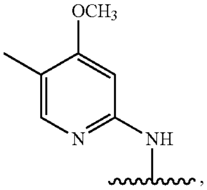,
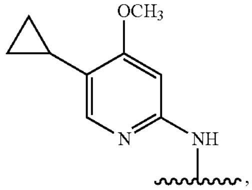,
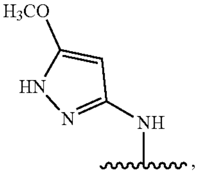,
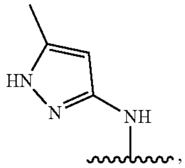,
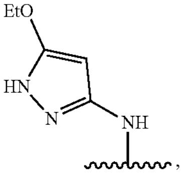,
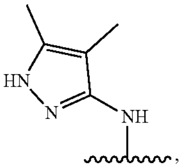,
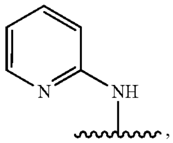,
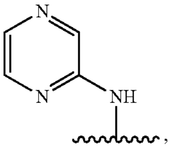,
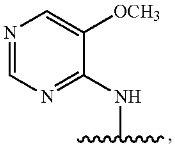,
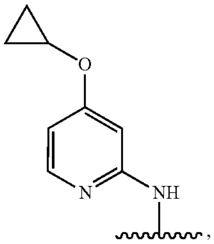,
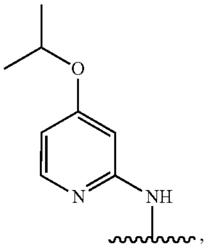,
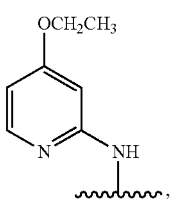,
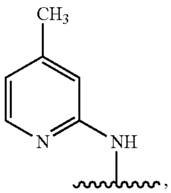,
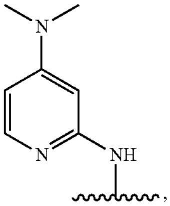,
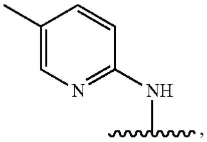,
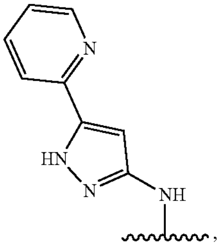, or
-continued
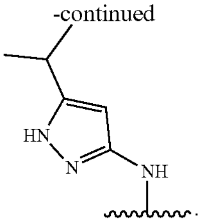.
In some embodiments, the compound of Formula IIa(1) is such that $R^{1A}$ and $R^{2A}$ together with the nitrogen to which they are attached have a structure of:
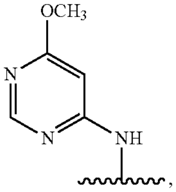,
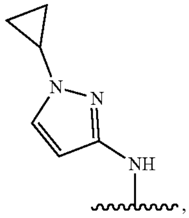,
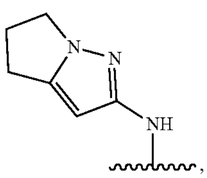,
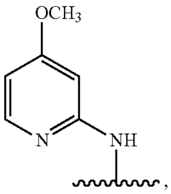,
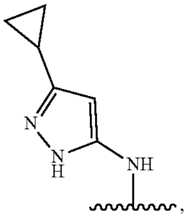,
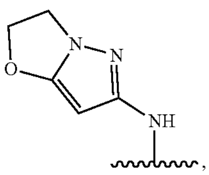,
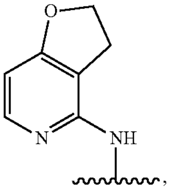,
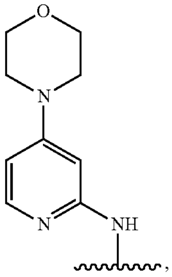,
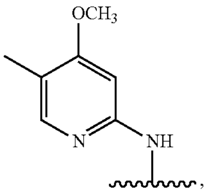,
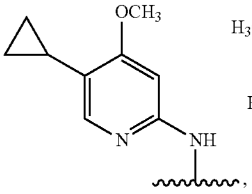,
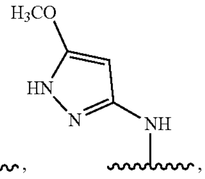,
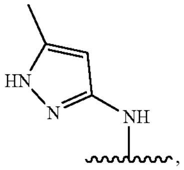,
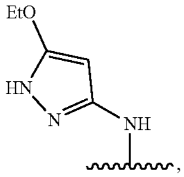, or
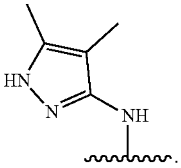.
In some embodiments, the compound of Formula IIa(1) is selected from the group consisting of Compounds 6, 57, 58, 62, 63, 64, 68, 84, 91, 100, 102, 104, 107, 124, 126, 136, 137, 141, 142, 143, 144, 145, 157, 221, 222, 226, 235, 238, 252, 255, 260, 265, 267, and 268. In some embodiments, the compound of Formula IIa(1) is selected from the group consisting of Compounds 6, 84, 100, 102, 104, 124, 221, 222, 235, 238, 252, 255, 260, and 267.

In some embodiments, the compound of Formula I is a compound of Formula IIb:

Formula IIb

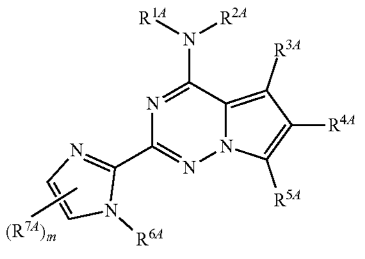

or a pharmaceutically acceptable form thereof, wherein:

$R^{1A}$ and $R^{2A}$ are combined to form a 4-6 membered heterocycloalkyl including the nitrogen atom to which they are both attached, optionally wherein the 4-6 membered heterocycloalkyl formed by RA and $R^{2A}$ is fused to a 6 membered heteroaryl;

$R^{3A}$ is $C_{1-3}$ alkyl or phenyl, wherein the $C_{1-3}$ alkyl and phenyl are each independently optionally substituted with 1-3 $R^{9A}$ substituents;

$R^{4A}$ is phenyl or 5 membered heteroaryl, wherein the phenyl and 5 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is methyl;

$R^{7A}$ is methyl;

$R^{9A}$ is each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy;

m is 0 or 1; and wherein, when $R^{1A}$ and $R^{2A}$ are combined to form

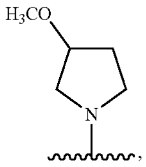

$R^{6A}$ is methyl, m is 0, and $R^{5A}$ is H, at least one of $R^{3A}$ and $R^{4A}$ is not unsubstituted phenyl.

In some embodiments, the compound of Formula IIb is such that:

$R^{1A}$ and $R^{2A}$ are combined to form

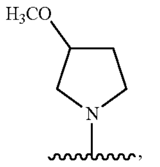 [SMILES: *N1CCC(OC)C1]

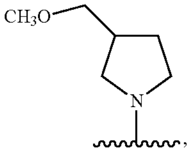

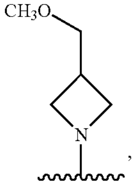

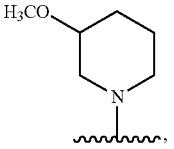

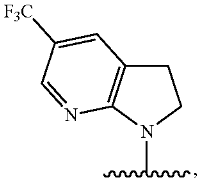

or

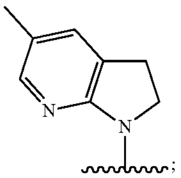

$R^{3A}$ is —$CH_3$, unsubstituted phenyl, (4-methoxy)-phenyl, or isopropyl;

$R^{4A}$ is

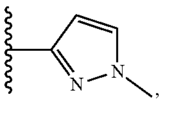

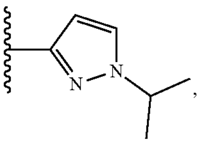

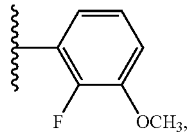

or

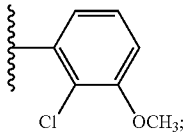

$R^{5A}$ is hydrogen;

$R^{6A}$ is methyl; and m is 0.

In some embodiments, the compound of Formula IIb is such that:

$R^{1A}$ and $R^{2A}$ are combined to form

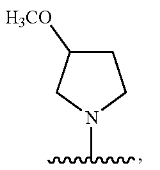, 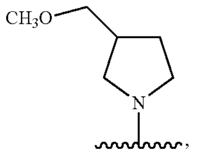, 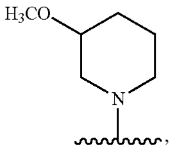, 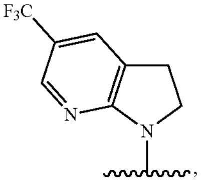, or 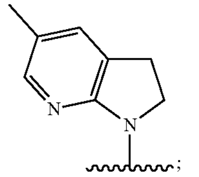;

$R^{3A}$ is —$CH_3$ or unsubstituted phenyl;

$R^{4A}$ is

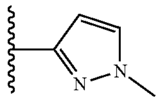 or 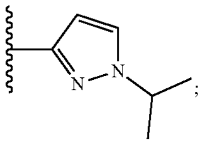;

$R^{5A}$ is hydrogen;

$R^{6A}$ is methyl; and m is 0.

In some embodiments, the compound of Formula I is a compound of Formula IIc:

Formula IIc

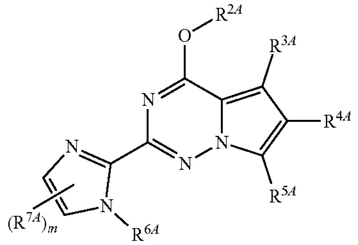

or a pharmaceutically acceptable form thereof, wherein:

$R^{2A}$ is hydrogen $C_{1-6}$ heteroalkyl, or 6 membered heteroaryl, wherein the $C_{1-6}$ heteroalkyl and 5-6 membered heteroaryl are each optionally substituted with 1-3 $R^{8A}$ substituents;

$R^{3A}$ is $C_{1-3}$ alkyl or phenyl, wherein the $C_{1-3}$ alkyl or phenyl are each independently optionally substituted with 1-3 $R^{9A}$ substituents;

$R^{4A}$ is hydrogen, phenyl, or 5 or 6 membered heteroaryl, wherein the phenyl and 5 or 6 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is methyl;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy;

m is 0 or 1; and wherein, when $R^{2A}$ is H, $R^{6A}$ is methyl, m is 0, and $R^{5A}$ is H, at least one of $R^{3A}$ and $R^{4A}$ is not unsubstituted phenyl.

In some embodiments, the compound of Formula IIc is such that:

$R^{2A}$ together with the oxygen to which it is attached have a structure of: —OH,

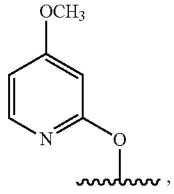, or 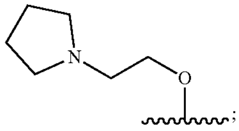;

$R^{3A}$ is —$CH_3$ or unsubstituted phenyl;

$R^{4A}$ hydrogen, unsubstituted phenyl,

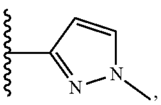, 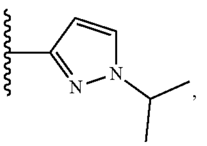,

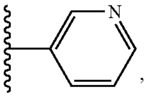, or 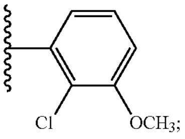;

$R^{5A}$ is hydrogen;

$R^{6A}$ is methyl; and m 0.

In some embodiments, the compound of Formula I is a compound of Formula III:

Formula III

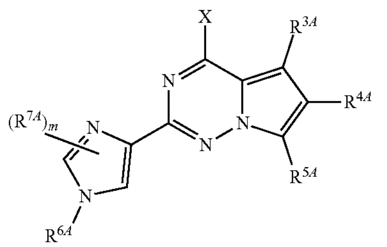

or a pharmaceutically acceptable form thereof, wherein:

X is $NR^{1A}R^{2A}$ or —$OR^{2A}$;

$R^{1A}$ is hydrogen or $C_{1-6}$ alkyl;

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

In some embodiments, the compound of Formula I is a compound of Formula IIIa:

Formula IIIa

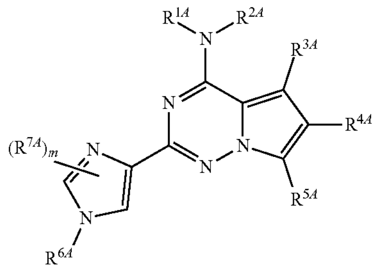

or a pharmaceutically acceptable form thereof, wherein:

$R^{1A}$ is hydrogen;

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

In some embodiments, the compound of Formula I is a compound of Formula IIIb:

Formula IIIb

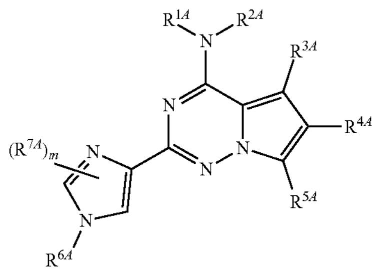

or a pharmaceutically acceptable form thereof, wherein:

$R^{1A}$ and $R^{2A}$ are combined to form a 4-6 membered heterocycloalkyl including the nitrogen atom to which they are both attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

In some embodiments, the compound of Formula I is a compound of Formula IIIc:

Formula IIIc

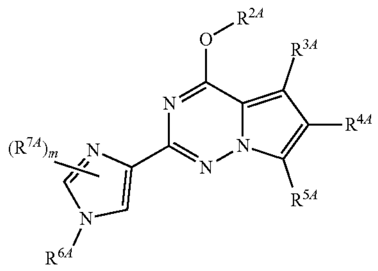

or a pharmaceutically acceptable form thereof, wherein:

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

In some embodiments, the compound of Formula I is a compound of Formula IV:

Formula IV

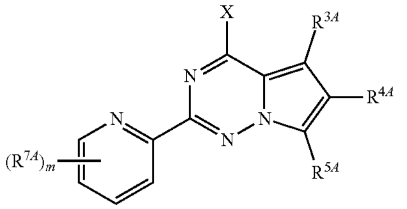

or a pharmaceutically acceptable form thereof, wherein:

X is —$NR^{1A}R^{2A}$ or —$OR^{2A}$;

$R^{1A}$ is hydrogen or $C_{1-6}$ alkyl;

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{7A}$ is $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, $C_{1-6}$ heteroalkyl, halo, —$NR^{12A}R^{13A}$, $C_{1-6}$ alkoxy, $C_{1-6}$ haloalkoxy, —$C(O)NR^{12A}R^{13A}$, —$(CO)R^{11A}$, —$C(O)OR^{14A}$, or CN, wherein the $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, and $C_{1-6}$ heteroalkyl are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$(CO)R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

In some embodiments, the compound of Formula I is a compound of Formula IVa:

Formula IVa

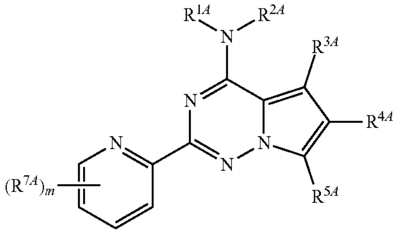

or a pharmaceutically acceptable form thereof, wherein:

$R^{1A}$ is hydrogen;

$R^{2A}$ is hydrogen, $C_{1-6}$ alkyl, $C_{3-6}$ cycloalkyl, $C_{1-6}$ heteroalkyl, or 6 membered heteroaryl, wherein the $C_{1-6}$ alkyl, $C_{3-6}$ cycloalkyl, $C_{1-6}$ heteroalkyl, and 6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{3A}$ is $C_{1-6}$ alkyl or phenyl, wherein the $C_{1-6}$ alkyl and phenyl are each independently optionally substituted with 1-3 $R^{9A}$ substituents;

$R^{4A}$ is 5 membered heteroaryl, wherein the 5 membered heteroaryl is optionally $R^{10A}$ substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$(CO)R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

In some embodiments, the compound of Formula IVa is such that:

$R^{1A}$ and $R^{2A}$ together with the nitrogen to which they are attached have a structure of:

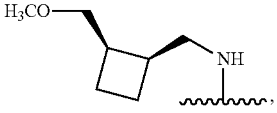, 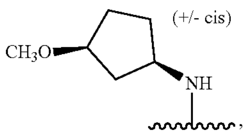,

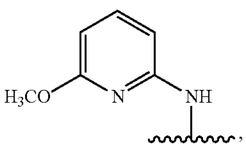, 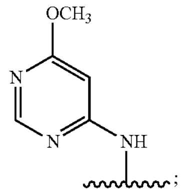;

$R^{3A}$ is —$CH_3$ or phenyl;

$R^{4A}$

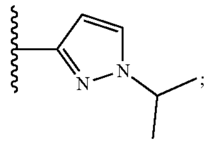 [SMILES: *c1ccn(C(C)C)n1];

$R^{5A}$ is hydrogen;

$R^{7A}$ is methyl; and m is 0.

In some embodiments, the compound of Formula I is a compound of Formula IVb:

Formula IVb

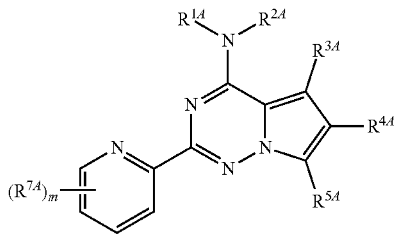

or a pharmaceutically acceptable form thereof, wherein:

$R^{1A}$ and $R^{2A}$ are combined to form a 4-6 membered heterocycloalkyl including the nitrogen atom to which they are both attached;

$R^{3A}$ is $C_{1-6}$ alkyl or phenyl, wherein the $C_{1-6}$ alkyl and phenyl are each independently optionally substituted with 1-3 $R^{9A}$ substituents;

$R^{4A}$ is 5 membered heteroaryl, wherein the 5 membered heteroaryl is optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

In some embodiments, the compound of Formula IVb is such that:

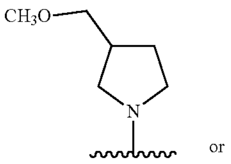 or 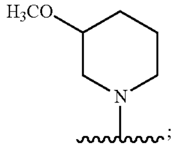;

$R^{1A}$ and $R^{2A}$ are combined to form $R^{3A}$ is —$CH_3$ or phenyl;

$R^{4A}$ is

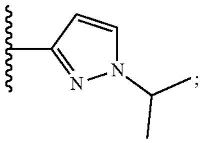 [SMILES: *c1ccn(C(C)C)n1];

$R^{5A}$ is hydrogen;

$R^{7A}$ is methyl; and m is 0.

In some embodiments, the compound of Formula I is a compound of Formula IVc:

Formula IVc

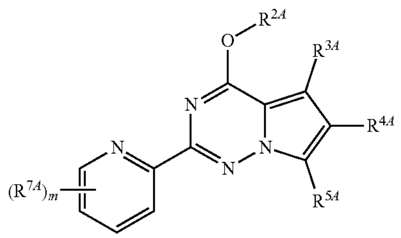

or a pharmaceutically acceptable form thereof, wherein:

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{7A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

In some embodiments, the compound of Formula IVc is such that:

$R^{2A}$ is hydrogen;

$R^{3A}$ is —$CH_3$;

$R^{4A}$ is

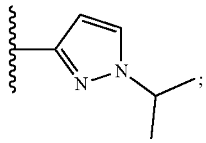 [SMILES: *c1ccn(C(C)C)n1]

;

$R^{5A}$ is hydrogen;

$R^{7A}$ is methyl;

m is 0.

In one embodiment, the compound of Formula I, Ia, II, or IIb is such that the combination of Y, X, $R^{1A}$, $R^{2A}$, $R^{3A}$, $R^{4A}$, and $R^{5A}$ substituents do not form:

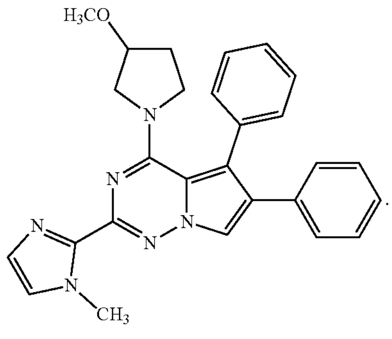 [SMILES: COC1CCN(c2nc(-c3nccn3C)nn3cc(-c4ccccc4)c(-c4ccccc4)c23)C1]

.

In one embodiment, the compound of Formula I, Ia, II, or IIb is not

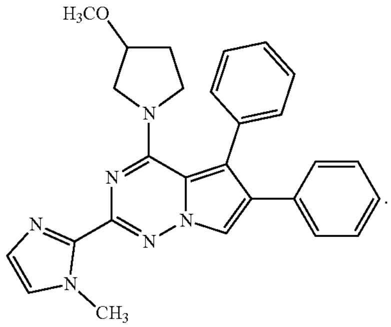 [SMILES: COC1CCN(c2nc(-c3nccn3C)nn3cc(-c4ccccc4)c(-c4ccccc4)c23)C1]

.

In one embodiment, the compound of Formula I, Ia, Ib, Ic, II, IIa, IIa(1), IIb, IIc, III, IIIa, IIIb, IIIc, IV, IVa, IVb, or IVc has a molecular weight (MW) of no more than 1000 g/mol. In one embodiment, the compound has a MW of no more than 900 g/mol, no more than 800 g/mol, no more than 700 g/mol, no more than 600 g/mol, or no more than 500 g/mol. In one embodiment, the compound has a MW of no more than 900 g/mol. In one embodiment, the compound has a MW of no more than 800 g/mol. In one embodiment, the compound has a MW of no more than 700 g/mol. In one embodiment, the compound has a MW of no more than 600 g/mol. In one embodiment, the compound has a MW of no more than 500 g/mol. In one embodiment, the compound has a MW of no more than 450 g/mol.

In one embodiment, the compound of Formula I, Ia, Ib, Ic, II, IIa, IIa(1), IIb, IIc, III, IIIa, IIIb, IIIc, IV, IVa, IVb, or IVc is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof is a modulator of Ras superfamily activity according to a Ras Superfamily Activity Assay. In one embodiment, the compound or pharmaceutically acceptable form thereof modulates Ras superfamily activity of one or more GTPase by 45% or more, 50% or more, 55% or more, 60% or more, 65% or more, 70% or more, 75% or more, 80% or more, 85% or more, 90% or more, or 95% or more at 20 μM according to a Ras Superfamily Activity Assay. In one embodiment, the compound or pharmaceutically acceptable form thereof modulates Ras superfamily activity of one or more GTPase by about 50% to about 60%, about 60% to about 70%, about 70% to about 80%, about 80% to about 90%, or about 90% to about 100% at 20 μM according to a Ras Superfamily Activity Assay. In one embodiment, the compound or pharmaceutically acceptable form thereof modulates Ras superfamily activity of one or more GTPase by 45% or more at 20 μM according to a Ras Superfamily Activity Assay. In one embodiment, the compound or pharmaceutically acceptable form thereof modulates Ras superfamily activity of one or more GTPase by 50% or more at 20 μM according to a Ras Superfamily Activity Assay. In one embodiment, the compound or pharmaceutically acceptable form thereof modulates Ras superfamily activity of one or more GTPase by 75% or more at 20 μM according to a Ras Superfamily Activity Assay. In one embodiment, the compound or pharmaceutically acceptable form thereof modulates Ras superfamily activity of one or more GTPase by 90% or more at 20 μM according to a Ras Superfamily Activity Assay. In one embodiment, the compound or pharmaceutically acceptable form thereof modulates Ras superfamily activity of one or more GTPase by 95% or more at 20 μM according to a Ras Superfamily Activity Assay. In one embodiment, the compound or pharmaceutically acceptable form thereof modulates Ras superfamily activity of one or more GTPase by about 50% to about 60% at 20 μM according to a Ras Superfamily Activity Assay. In one embodiment, the compound or pharmaceutically acceptable form thereof modulates Ras superfamily activity of one or more GTPase by about 60% to about 70% at 20 μM according to a Ras Superfamily Activity Assay. In one embodiment, the compound or pharmaceutically acceptable form thereof modulates Ras superfamily activity of one or more GTPase by about 70% to about 80% at 20 μM according to a Ras Superfamily Activity Assay. In one embodiment, the compound or pharmaceutically acceptable form thereof modulates Ras superfamily activity of one or more GTPase by about 80% to about 90% at 20 μM according to a Ras Superfamily Activity Assay. In one embodiment, the compound or pharmaceutically acceptable form thereof modulates Ras superfamily activity of one or more GTPase by about 90% to about 100% at 20 μM according to a Ras Superfamily Activity Assay. In one embodiment, the compound is selected from the group consisting of Compounds 6, 17, 22, 32, 34, 37, 42, 43, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 126, 127, 135, 136, 137, 138, 139, 140, 141, 142, 143, 144, 145, 146, 147, 148, 149, 150, 151, 152, 153, 154, 156, 157, 158, 165, 166, 167, 169, 170, 172, 173, 174, 175, 176, 177, 178, 179, 186, 187, 188, 196, 200, 202, 208, 211, 212, 213, 214, 215, 216, 217, 220, 221, 222, 223, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof. In one embodiment, the compound is selected from the group consisting of Compounds 6, 17, 22, 37, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 127, 135, 136, 137, 138, 139, 140, 141, 142, 143, 144, 145, 146, 147, 149, 150, 151, 152, 153, 154, 156, 157, 158, 165, 166, 169, 170, 173, 175, 176, 177, 178, 179, 186, 187, 188, 196, 202, 208, 211, 212, 213, 214, 215, 216, 217, 221, 222, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof inhibits phosphorylation of Erk1/2 according to Erk1/2 Phosphorylation Assay. In one embodiment, the compound or pharmaceutically acceptable form thereof inhibits phosphorylation of Erk1/2 by 50% or more, 55% or more, 60% or more, 65% or more, 70% or more, 75% or more, 80% or more, 85% or more, 90% or more, or 95% or more at 10 μM according to Erk1/2 Phosphorylation Assay. In one embodiment, the compound or pharmaceutically acceptable form thereof inhibits phosphorylation of Erk1/2 by about 50% to about 60%, about 60% to about 70%, about 70% to about 80%, about 80% to about 90%, or about 90% to about 100% at 10 μM according to Erk1/2 Phosphorylation Assay. In one embodiment, the compound or pharmaceutically acceptable form thereof inhibits phosphorylation of Erk1/2 by 50% or more at 10 μM according to Erk1/2 Phosphorylation Assay. In one embodiment, the compound or pharmaceutically acceptable form thereof inhibits phosphorylation of Erk1/2 by 75% or more at 10 μM according to Erk1/2 Phosphorylation Assay. In one embodiment, the compound or pharmaceutically acceptable form thereof inhibits phosphorylation of Erk1/2 by 80% or more at 10 μM according to Erk1/2 Phosphorylation Assay. In one embodiment, the compound or pharmaceutically acceptable form thereof inhibits phosphorylation of Erk1/2 by 85% or more at 10 μM according to Erk1/2 Phosphorylation Assay. In one embodiment, the compound or pharmaceutically acceptable form thereof inhibits phosphorylation of Erk1/2 by 90% or more at 10 μM according to Erk1/2 Phosphorylation Assay. In one embodiment, the compound or pharmaceutically acceptable form thereof inhibits phosphorylation of Erk1/2 by 95% or more at 1 μM according to Erk1/2 Phosphorylation Assay. In one embodiment, the compound or pharmaceutically acceptable form thereof inhibits phosphorylation of Erk1/2 by about 50% to about 60% at 10 μM according to Erk1/2 Phosphorylation Assay. In one embodiment, the compound or pharmaceutically acceptable form thereof inhibits phosphorylation of Erk1/2 by about 60% to about 70% at 10 μM according to Erk1/2 Phosphorylation Assay. In one embodiment, the compound or pharmaceutically acceptable form thereof inhibits phosphorylation of Erk1/2 by about 70% to about 80% at 1 μM according to Erk1/2 Phosphorylation Assay. In one embodiment, the compound or pharmaceutically acceptable form thereof inhibits phosphorylation of Erk1/2 by about 80% to about 90% at 10 μM according to Erk1/2 Phosphorylation Assay. In one embodiment, the compound or pharmaceutically acceptable form thereof inhibits phosphorylation of Erk1/2 by about 90% to about 100% at 10 μM according to Erk1/2 Phosphorylation Assay. In one embodiment, the compound is selected from the group consisting of Compounds 3, 4, 20, 23, 26, 29, 30, 31, 32, 33, 34, 36, 42, 43, 53, 58, 67, 93, 203, 209, 210, 219, 266, 269, 270, 271, 272, 273, and 274, or a pharmaceutically acceptable form thereof. In one embodiment, the compound is selected from the group consisting of Compounds 3, 4, 20, 23, 26, 29, 30, 31, 32, 33, 34, 42, 43, 53, 58, 67, 93, 203, 209, 210, 219, 266, 269, 270, 271, 272, 273, and 274, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof activates phosphorylation of Erk1/2 according to Erk1/2 Phosphorylation Assay. In one embodiment, the compound or pharmaceutically acceptable form thereof activates phosphorylation of Erk1/2 by 50% or more, 55% or more, 60% or more, 65% or more, 70% or more, 75% or more, 80% or more, 85% or more, 90% or more, 95% or more, or equal or greater than 100% at 10 μM according to Erk1/2 Phosphorylation Assay. In one embodiment, the compound or pharmaceutically acceptable form thereof activates phosphorylation of Erk1/2 by about 50% to about 60%, about 60% to about 70%, about 70% to about 80%, about 80% to about 90%, about 90% to about 100%, or about 100% or more at 10 μM according to Erk1/2 Phosphorylation Assay. In one embodiment, the compound or pharmaceutically acceptable form thereof activates phosphorylation of Erk1/2 by 50% or more at 10 μM according to Erk1/2 Phosphorylation Assay. In one embodiment, the compound or pharmaceutically acceptable form thereof activates phosphorylation of Erk1/2 by 75% or more at 10 μM according to Erk1/2 Phosphorylation Assay. In one embodiment, the compound or pharmaceutically acceptable form thereof activates phosphorylation of Erk1/2 by 85% or more at 10 μM according to Erk1/2 Phosphorylation Assay. In one embodiment, the compound or pharmaceutically acceptable form thereof activates phosphorylation of Erk1/2 by 90% or more at 10 μM according to Erk1/2 Phosphorylation Assay. In one embodiment, the compound or pharmaceutically acceptable form thereof activates phosphorylation of Erk1/2 by 95% or more at 10 μM according to Erk1/2 Phosphorylation Assay. In one embodiment, the compound or pharmaceutically acceptable form thereof activates phosphorylation of Erk1/2 by equal or greater than 100% at 10 μM according to Erk1/2 Phosphorylation Assay. In one embodiment, the compound or pharmaceutically acceptable form thereof activates phosphorylation of Erk1/2 by about 50% to about 60% at 10 μM according to Erk1/2 Phosphorylation Assay. In one embodiment, the compound or pharmaceutically acceptable form thereof activates phosphorylation of Erk1/2 by about 60% to about 70% at 10 μM according to Erk1/2 Phosphorylation Assay. In one embodiment, the compound or pharmaceutically acceptable form thereof activates phosphorylation of Erk1/2 by about 70% to about 80% at 10 μM according to Erk1/2 Phosphorylation Assay. In one embodiment, the compound or pharmaceutically acceptable form thereof activates phosphorylation of Erk1/2 by about 80% to about 90% at 10 μM according to Erk1/2 Phosphorylation Assay. In one embodiment, the compound or pharmaceutically acceptable form thereof activates phosphorylation of Erk1/2 by about 90% to about 100% at 10 μM according to Erk1/2 Phosphorylation Assay. In one embodiment, the compound or pharmaceutically acceptable form thereof activates phosphorylation of Erk1/2 by about 100% or more at 10 μM according to Erk1/2 Phosphorylation Assay. In one embodiment, the compound is selected from the group consisting of Compounds 49, 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 130, 135, 136, 138, 143, 145, 148, 149, 151, 154, 156, 157, 165, 174, 175, 176, 177, 178, 179, 183, 190, 191, 192, 193, 194, 195, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof. In one embodiment, the compound is selected from the group consisting of Compounds 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 135, 136, 138, 143, 145, 148, 149, 151, 154, 156, 157, 165, 174, 175, 176, 177, 178, 179, 183, 190, 191, 192, 193, 194, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof inhibits phosphorylation of Akt according to Akt Phosphorylation Assay. In one embodiment, the compound or pharmaceutically acceptable form thereof inhibits phosphorylation of Akt by 50% or more, 55% or more, 60% or more, 65% or more, 70% or more, 75% or more, 80% or more, 85% or more, 90% or more, or 95% or more at 10 μM according to Akt Phosphorylation Assay. In one embodiment, the compound or pharmaceutically acceptable form thereof inhibits phosphorylation of Akt by about 50% to about 60%, about 60% to about 70%, about 70% to about 80%, about 80% to about 90%, or about 90% to about 100% at 10 μM according to Akt Phosphorylation Assay. In one embodiment, the compound or pharmaceutically acceptable form thereof inhibits phosphorylation of Akt by 50% or more at 10 μM according to Akt Phosphorylation Assay. In one embodiment, the compound or pharmaceutically acceptable form thereof inhibits phosphorylation of Akt by 75% or more at 10 μM according to Akt Phosphorylation Assay. In one embodiment, the compound or pharmaceutically acceptable form thereof inhibits phosphorylation of Akt by 85% or more at 10 μM according to Akt Phosphorylation Assay. In one embodiment, the compound or pharmaceutically acceptable form thereof inhibits phosphorylation of Akt by 90% or more at 10 μM according to Akt Phosphorylation Assay. In one embodiment, the compound or pharmaceutically acceptable form thereof inhibits phosphorylation of Akt by 95% or more at 10 μM according to Akt Phosphorylation Assay. In one embodiment, the compound or pharmaceutically acceptable form thereof inhibits phosphorylation of Akt by about 50% to about 60% at 10 μM according to Akt Phosphorylation Assay. In one embodiment, the compound or pharmaceutically acceptable form thereof inhibits phosphorylation of Akt by about 60% to about 70% at 10 μM according to Akt Phosphorylation Assay. In one embodiment, the compound or pharmaceutically acceptable form thereof inhibits phosphorylation of Akt by about 70% to about 80% at 10 μM according to Akt Phosphorylation Assay. In one embodiment, the compound or pharmaceutically acceptable form thereof inhibits phosphorylation of Akt by about 80% to about 90% at 10 μM according to Akt Phosphorylation Assay. In one embodiment, the compound or pharmaceutically acceptable form thereof inhibits phosphorylation of Akt by about 90% to about 100% at 10 μM according to Akt Phosphorylation Assay. In one embodiment, the compound is selected from the group consisting of Compounds 17, 20, 23, 25, 29, 30, 31, 32, 33, 34, 42, 203, 209, 210, 219, 270, 271, 272, 273, and 274, or a pharmaceutically acceptable form thereof. In one embodiment, the compound In one embodiment, the compound of Formula I, Ia, Ib, Ic, II, IIa, IIa(1), IIb, II, III, IIIa, IIIb, IIIc, IV, IVa, IVb, or IVc, or pharmaceutically acceptable form thereof activates phosphorylation of Akt according to Akt Phosphorylation Assay. In one embodiment, the compound or pharmaceutically acceptable form thereof activates phosphorylation of Akt by 50% or more, 55% or more, 60% or more, 65% or more, 70% or more, 75% or more, 80% or more, 85% or more, 90% or more, 95% or more, or equal or greater than 100% at 10 μM according to Akt Phosphorylation Assay. In one embodiment, the compound or pharmaceutically acceptable form thereof activates phosphorylation of Akt by about 50% to about 60%, about 60% to about 70%, about 70% to about 80%, about 80% to about 90%, about 90% to about 100%, or about 100% or more at 10 μM according to Akt Phosphorylation Assay. In one embodiment, the compound or pharmaceutically acceptable form thereof activates phosphorylation of Akt by 50% or more at 10 μM according to Akt Phosphorylation Assay. In one embodiment, the compound or pharmaceutically acceptable form thereof activates phosphorylation of Akt by 75% or more at 10 μM according to Akt Phosphorylation Assay. In one embodiment, the compound or pharmaceutically acceptable form thereof activates phosphorylation of Akt by 85% or more at 10 μM according to Akt Phosphorylation Assay. In one embodiment, the compound or pharmaceutically acceptable form thereof activates phosphorylation of Akt by 90% or more at 10 μM according to Akt Phosphorylation Assay. In one embodiment, the compound or pharmaceutically acceptable form thereof activates phosphorylation of Akt by 95% or more at 10 μM according to Akt Phosphorylation Assay. In one embodiment, the compound or pharmaceutically acceptable form thereof activates phosphorylation of Akt by equal or greater than 100% at 10 μM according to Akt Phosphorylation Assay. In one embodiment, the compound or pharmaceutically acceptable form thereof activates phosphorylation of Akt by about 50% to about 60% at 10 μM according to Akt Phosphorylation Assay. In one embodiment, the compound or pharmaceutically acceptable form thereof activates phosphorylation of Akt by about 60% to about 70% at 10 μM according to Akt Phosphorylation Assay. In one embodiment, the compound or pharmaceutically acceptable form thereof activates phosphorylation of Akt by about 70% to about 80% at 10 μM according to Akt Phosphorylation Assay. In one embodiment, the compound or pharmaceutically acceptable form thereof activates phosphorylation of Akt by about 80% to about 90% at 10 μM according to Akt Phosphorylation Assay. In one embodiment, the compound or pharmaceutically acceptable form thereof activates phosphorylation of Akt by about 90% to about 100% at 10 μM according to Akt Phosphorylation Assay. In one embodiment, the compound or pharmaceutically acceptable form thereof activates phosphorylation of Akt by about 100% or more at 10 μM according to Akt Phosphorylation Assay. In one embodiment, the compound is selected from the group consisting of Compounds 1, 2, 18, 19, 21, 47, 48, 49, 50, 51, 57, 59, 60, 61, 62, 63, 64, 65, 66, 67, 68, 69, 70, 71, 72, 73, 74, 76, 77, 78, 79, 80, 81, 82, 83, 84, 85, 86, 87, 88, 89, 91, 93, 94, 95, 96, 97, 98, 100, 101, 102, 103, 104, 106, 107, 108, 109, 110, 111, 112, 113, 114, 115, 116, 118, 119, 122, 124, 125, 126, 127, 128, 129, 130, 135, 136, 137, 138, 143, 145, 149, 151, 156, 157, 158, 165, 166, 169, 170, 173, 174, 175, 176, 178, 179, 187, 190, 191, 192, 193, 194, 195, 196, 204, 205, 207, 208, 213, 217, 218, 221, 222, 224, 226, 227, 228, 229, 230, 231, 232, 233, 234, 235, 237, 238, 240, 241, 242, 243, 244, 245, 246, 247, 248, 249, 250, 252, 253, 254, 255, 256, 257, 259, 260, 263, 264, 265, 266, 267, 268, 275, and 276, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof inhibits phosphorylation of Smad2/3 according to Phospho-Smad2/3 Inhibition Assay. In one embodiment, the compound or pharmaceutically acceptable form thereof inhibits phosphorylation of Smad2/3 by 50% or more, 55% or more, 60% or more, 65% or more, 70% or more, 75% or more, 80% or more, 85% or more, 90% or more, or 95% or more at 10 μM according to Phospho-Smad2/3 Inhibition Assay. In one embodiment, the compound or pharmaceutically acceptable form thereof inhibits phosphorylation of Smad2/3 by about 50% to about 60%, about 60% to about 70%, about 70% to about 80%, about 80% to about 90%, or about 90% to about 100% at 10 μM according to Phospho-Smad2/3 Inhibition Assay. In one embodiment, the compound or pharmaceutically acceptable form thereof inhibits phosphorylation of Smad2/3 by 50% or more at 10 μM according to Phospho-Smad2/3 Inhibition Assay. In one embodiment, the compound or pharmaceutically acceptable form thereof inhibits phosphorylation of Smad2/3 by 75% or more at 10 μM according to Phospho-Smad2/3 Inhibition Assay. In one embodiment, the compound or pharmaceutically acceptable form thereof inhibits phosphorylation of Smad2/3 by 80% or more at 10 μM according to Phospho-Smad2/3 Inhibition Assay. In one embodiment, the compound or pharmaceutically acceptable form thereof inhibits phosphorylation of Smad2/3 by 85% or more at 10 μM according to Phospho-Smad2/3 Inhibition Assay. In one embodiment, the compound or pharmaceutically acceptable form thereof inhibits phosphorylation of Smad2/3 by 90% or more at 10 μM according to Phospho-Smad2/3 Inhibition Assay. In one embodiment, the compound or pharmaceutically acceptable form thereof inhibits phosphorylation of Smad2/3 by 95% or more at 10 μM according to Phospho-Smad2/3 Inhibition Assay. In one embodiment, the compound or pharmaceutically acceptable form thereof inhibits phosphorylation of Smad2/3 by about 50% to about 60% at 10 μM according to Phospho-Smad2/3 Inhibition Assay. In one embodiment, the compound or pharmaceutically acceptable form thereof inhibits phosphorylation of Smad2/3 by about 60% to about 70% at 10 μM according to Phospho-Smad2/3 Inhibition Assay. In one embodiment, the compound or pharmaceutically acceptable form thereof inhibits phosphorylation of Smad2/3 by about 70% to about 80% at 10 μM according to Phospho-Smad2/3 Inhibition Assay. In one embodiment, the compound or pharmaceutically acceptable form thereof inhibits phosphorylation of Smad2/3 by about 80% to about 90% at 10 μM according to Phospho-Smad2/3 Inhibition Assay. In one embodiment, the compound or pharmaceutically acceptable form thereof inhibits phosphorylation of Smad2/3 by about 90% to about 100% at 10 μM according to Phospho-Smad2/3 Inhibition Assay. In one embodiment, the compound is selected from the group consisting of Compounds 27, 29, 30, 31, 32, 33, 36, 43, 44, 47, 51, 52, 55, 59, 85, 96, 97, 98, 99, 116, 141, 144, 156, 203, 205, 207, 208, 209, 210, 211, 214, 219, 230, 269, 272, 273, and 274, or a pharmaceutically acceptable form thereof. In one embodiment, the compound is selected from the group consisting of Compounds 29, 30, 31, 32, 33, 36, 44, 47, 59, 85, 97, 98, 99, 116, 141, 144, 156, 203, 205, 207, 208, 209, 210, 211, 214, 219, 230, 269, 272, 273, and 274, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof activates phosphorylation of Smad2/3 according to Phospho-Smad2/3 Inhibition Assay. In one embodiment, the compound or pharmaceutically acceptable form thereof activates phosphorylation of Smad2/3 by 50% or more, 55% or more, 60% or more, 65% or more, 70% or more, 75% or more, 80% or more, 85% or more, 90% or more, 95% or more, or equal or greater than 100% at 10 μM according to Phospho-Smad2/3 Inhibition Assay. In one embodiment, the compound or pharmaceutically acceptable form thereof activates phosphorylation of Smad2/3 by about 50% to about 60%, about 60% to about 70%, about 70% to about 80%, about 80% to about 90%, about 90% to about 100%, or about 100% or more at 10 μM according to Phospho-Smad2/3 Inhibition Assay. In one embodiment, the compound or pharmaceutically acceptable form thereof activates phosphorylation of Smad2/3 by 50% or more at 10 μM according to Phospho-Smad2/3 Inhibition Assay. In one embodiment, the compound or pharmaceutically acceptable form thereof activates phosphorylation of Smad2/3 by 75% or more at 10 μM according to Phospho-Smad2/3 Inhibition Assay. In one embodiment, the compound or pharmaceutically acceptable form thereof activates phosphorylation of Smad2/3 by 85% or more at 10 μM according to Phospho-Smad2/3 Inhibition Assay. In one embodiment, the compound or pharmaceutically acceptable form thereof activates phosphorylation of Smad2/3 by 90% or more at 10 μM according to Phospho-Smad2/3 Inhibition Assay. In one embodiment, the compound or pharmaceutically acceptable form thereof activates phosphorylation of Smad2/3 by 95% or more at 10 μM according to Phospho-Smad2/3 Inhibition Assay. In one embodiment, the compound or pharmaceutically acceptable form thereof activates phosphorylation of Smad2/3 by equal or greater than 100% at 10 μM according to Phospho-Smad2/3 Inhibition Assay. In one embodiment, the compound or pharmaceutically acceptable form thereof activates phosphorylation of Smad2/3 by about 50% to about 60% at 10 μM according to Phospho-Smad2/3 Inhibition Assay. In one embodiment, the compound or pharmaceutically acceptable form thereof activates phosphorylation of Smad2/3 by about 60% to about 70% at 10 μM according to Phospho-Smad2/3 Inhibition Assay. In one embodiment, the compound or pharmaceutically acceptable form thereof activates phosphorylation of Smad2/3 by about 70% to about 80% at 10 μM according to Phospho-Smad2/3 Inhibition Assay. In one embodiment, the compound or pharmaceutically acceptable form thereof activates phosphorylation of Smad2/3 by about 80% to about 90% at 10 μM according to Phospho-Smad2/3 Inhibition Assay. In one embodiment, the compound or pharmaceutically acceptable form thereof activates phosphorylation of Smad2/3 by about 90% to about 100% at 10 μM according to Phospho-Smad2/3 Inhibition Assay. In one embodiment, the compound or pharmaceutically acceptable form thereof activates phosphorylation of Smad2/3 by about 100% or more at 10 μM according to Phospho-Smad2/3 Inhibition Assay. In one embodiment, the compound is selected from the group consisting of Compounds 56, 63, 84, 88, 89, 90, 95, 100, 101, 103, 104, 106, 108, 109, 111, 112, 113, 114, 129, 166, 173, 179, 183, 186, 216, 241, 247, 248, 250, 255, 256, 257, and 266, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof inhibits JNK according to JNK Activation Assay. In one embodiment, the compound or pharmaceutically acceptable form thereof inhibits JNK by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to JNK Activation Assay. In one embodiment, the compound or pharmaceutically acceptable form thereof inhibits JNK by about 50% to about 60%, about 60% to about 70%, about 70% to about 80%, about 80% to about 90%, or about 90% to about 100% at 10 μM according to JNK Activation Assay. In one embodiment, the compound or pharmaceutically acceptable form thereof inhibits JNK by 25% or more at 10 μM according to JNK Activation Assay. In one embodiment, the compound or pharmaceutically acceptable form thereof inhibits JNK by 30% or more at 10 μM according to JNK Activation Assay. In one embodiment, the compound or pharmaceutically acceptable form thereof inhibits JNK by 50% or more at 10 μM according to JNK Activation Assay. In one embodiment, the compound or pharmaceutically acceptable form thereof inhibits JNK by 75% or more at 10 μM according to JNK Activation Assay. In one embodiment, the compound or pharmaceutically acceptable form thereof inhibits JNK by 85% or more at 10 μM according to JNK Activation Assay. In one embodiment, the compound or pharmaceutically acceptable form thereof inhibits JNK by 90% or more at 10 μM according to JNK Activation Assay. In one embodiment, the compound or pharmaceutically acceptable form thereof inhibits JNK by 95% or more at 10 μM according to JNK Activation Assay. In one embodiment, the compound or pharmaceutically acceptable form thereof inhibits JNK by about 50% to about 60% at 10 μM according to JNK Activation Assay. In one embodiment, the compound or pharmaceutically acceptable form thereof inhibits JNK by about 60% to about 70% at 10 μM according to JNK Activation Assay. In one embodiment, the compound or pharmaceutically acceptable form thereof inhibits JNK by about 70% to about 80% at 10 μM according to JNK Activation Assay. In one embodiment, the compound or pharmaceutically acceptable form thereof inhibits JNK by about 80% to about 90% at 10 μM according to JNK Activation Assay. In one embodiment, the compound or pharmaceutically acceptable form thereof inhibits JNK by about 90% to about 100% at 10 μM according to JNK Activation Assay. In one embodiment, the compound is selected from the group consisting of Compounds 29, 30, 32, 33, and 34, or a pharmaceutically acceptable form thereof. In one embodiment, the compound is selected from the group consisting of Compounds 29, 32, 33, and 34, or a pharmaceutically acceptable form thereof. In one embodiment, the compound is selected from the group consisting of Compounds 29, 32, and 34, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof activates JNK according to JNK Activation Assay. In one embodiment, the compound or pharmaceutically acceptable form thereof activates JNK by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to JNK Activation Assay. In one embodiment, the compound or pharmaceutically acceptable form thereof activates JNK by about 50% to about 60%, about 60% to about 70%, about 70% to about 80%, about 80% to about 90%, about 90% to about 100%, or about 100% or more at 10 μM according to JNK Activation Assay. In one embodiment, the compound or pharmaceutically acceptable form thereof activates JNK by 25% or more at 10 μM according to JNK Activation Assay. In one embodiment, the compound or pharmaceutically acceptable form thereof activates JNK by 30% or more at 10 μM according to JNK Activation Assay. In one embodiment, the compound or pharmaceutically acceptable form thereof activates JNK by 50% or more at 10 μM according to JNK Activation Assay. In one embodiment, the compound or pharmaceutically acceptable form thereof activates JNK by 75% or more at 10 μM according to JNK Activation Assay. In one embodiment, the compound or pharmaceutically acceptable form thereof activates JNK by 85% or more at 10 μM according to JNK Activation Assay. In one embodiment, the compound or pharmaceutically acceptable form thereof activates JNK by 90% or more at 10 μM according to JNK Activation Assay. In one embodiment, the compound or pharmaceutically acceptable form thereof activates JNK by 95% or more at 10 μM according to JNK Activation Assay. In one embodiment, the compound or pharmaceutically acceptable form thereof activates JNK by equal or greater than 100% at 10 μM according to JNK Activation Assay. In one embodiment, the compound or pharmaceutically acceptable form thereof activates JNK by about 50% to about 60% at 10 μM according to JNK Activation Assay. In one embodiment, the compound or pharmaceutically acceptable form thereof activates JNK by about 60% to about 70% at 10 μM according to JNK Activation Assay. In one embodiment, the compound or pharmaceutically acceptable form thereof activates JNK by about 70% to about 80% at 10 μM according to JNK Activation Assay. In one embodiment, the compound or pharmaceutically acceptable form thereof activates JNK by about 80% to about 90% at 10 μM according to JNK Activation Assay. In one embodiment, the compound or pharmaceutically acceptable form thereof activates JNK by about 90% to about 100% at 10 μM according to JNK Activation Assay. In one embodiment, the compound or pharmaceutically acceptable form thereof activates JNK by about 100% or more at 10 μM according to JNK Activation Assay. In one embodiment, the compound is selected from the group consisting of Compounds 1, 2, 3, 4, 6, 7, 8, 9, 11, 13, 14, 15, 16, 18, 19, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof. In one embodiment, the compound is selected from the group consisting of Compounds 3, 4, 6, 7, 11, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof. In one embodiment, the compound is selected from the group consisting of Compounds 3, 6, 7, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof inhibits MAPK p38 according to MAPK p38 Activation Assay. In one embodiment, the compound or pharmaceutically acceptable form thereof inhibits MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to MAPK p38 Activation Assay. In one embodiment, the compound or pharmaceutically acceptable form thereof inhibits MAPK p38 by about 50% to about 60%, about 60% to about 70%, about 70% to about 80%, about 80% to about 90%, or about 90% to about 100% at 10 μM according to MAPK p38 Activation Assay. In one embodiment, the compound or pharmaceutically acceptable form thereof inhibits MAPK p38 by 25% or more at 10 μM according to MAPK p38 Activation Assay. In one embodiment, the compound or pharmaceutically acceptable form thereof inhibits MAPK p38 by 30% or more at 10 μM according to MAPK p38 Activation Assay. In one embodiment, the compound or pharmaceutically acceptable form thereof inhibits MAPK p38 by 50% or more at 10 μM according to MAPK p38 Activation Assay. In one embodiment, the compound or pharmaceutically acceptable form thereof inhibits MAPK p38 by 75% or more at 10 μM according to MAPK p38 Activation Assay. In one embodiment, the compound or pharmaceutically acceptable form thereof inhibits MAPK p38 by 85% or more at 10 μM according to MAPK p38 Activation Assay. In one embodiment, the compound or pharmaceutically acceptable form thereof inhibits MAPK p38 by 90% or more at 10 μM according to MAPK p38 Activation Assay. In one embodiment, the compound or pharmaceutically acceptable form thereof inhibits MAPK p38 by about 50% to about 60% at 10 μM according to MAPK p38 Activation Assay. In one embodiment, the compound or pharmaceutically acceptable form thereof inhibits MAPK p38 by about 60% to about 70% at 10 μM according to MAPK p38 Activation Assay. In one embodiment, the compound or pharmaceutically acceptable form thereof inhibits MAPK p38 by about 70% to about 80% at 10 μM according to MAPK p38 Activation Assay. In one embodiment, the compound or pharmaceutically acceptable form thereof inhibits MAPK p38 by about 80% to about 90% at 10 μM according to MAPK p38 Activation Assay. In one embodiment, the compound or pharmaceutically acceptable form thereof inhibits MAPK p38 by about 90% to about 100% at 10 μM according to MAPK p38 Activation Assay. In one embodiment, the compound or pharmaceutically acceptable form thereof inhibits MAPK p38 by 95% or more at 10 μM according to MAPK p38 Activation Assay. In one embodiment, the compound is selected from the group consisting of Compounds 29, 30, 32, 33, 34, 46, 47, 188, 196, 197, 203, 205, 207, 208, 209, 210, 212, 213, 214, 215, 217, and 220, or a pharmaceutically acceptable form thereof. In one embodiment, the compound is selected from the group consisting of Compounds 29, 32, 33, 34, 46, 207, and 209, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof activates MAPK p38 according to MAPK p38 Activation Assay. In one embodiment, the compound or pharmaceutically acceptable form thereof activates MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to MAPK p38 Activation Assay. In one embodiment, the compound or pharmaceutically acceptable form thereof activates MAPK p38 by about 50% to about 60%, about 60% to about 70%, about 70% to about 80%, about 80% to about 90%, about 90% to about 100%, or about 100% or more at 10 μM according to MAPK p38 Activation Assay. In one embodiment, the compound or pharmaceutically acceptable form thereof activates MAPK p38 by 25% or more at 10 μM according to MAPK p38 Activation Assay. In one embodiment, the compound or pharmaceutically acceptable form thereof activates MAPK p38 by 30% or more at 10 μM according to MAPK p38 Activation Assay. In one embodiment, the compound or pharmaceutically acceptable form thereof activates MAPK p38 by 50% or more at 10 μM according to MAPK p38 Activation Assay. In one embodiment, the compound or pharmaceutically acceptable form thereof activates MAPK p38 by 75% or more at 10 μM according to MAPK p38 Activation Assay. In one embodiment, the compound or pharmaceutically acceptable form thereof activates MAPK p38 by 85% or more at 10 μM according to MAPK p38 Activation Assay. In one embodiment, the compound or pharmaceutically acceptable form thereof activates MAPK p38 by 90% or more at 10 μM according to MAPK p38 Activation Assay. In one embodiment, the compound or pharmaceutically acceptable form thereof activates MAPK p38 by 95% or more at 10 μM according to MAPK p38 Activation Assay. In one embodiment, the compound or pharmaceutically acceptable form thereof activates MAPK p38 by equal or greater than 100% at 10 μM according to MAPK p38 Activation Assay. In one embodiment, the compound or pharmaceutically acceptable form thereof activates MAPK p38 by about 50% to about 60% at 10 μM according to MAPK p38 Activation Assay. In one embodiment, the compound or pharmaceutically acceptable form thereof activates MAPK p38 by about 60% to about 70% at 10 μM according to MAPK p38 Activation Assay. In one embodiment, the compound or pharmaceutically acceptable form thereof activates MAPK p38 by about 70% to about 80% at 10 μM according to MAPK p38 Activation Assay. In one embodiment, the compound or pharmaceutically acceptable form thereof activates MAPK p38 by about 80% to about 90% at 10 μM according to MAPK p38 Activation Assay. In one embodiment, the compound or pharmaceutically acceptable form thereof activates MAPK p38 by about 90% to about 1000% at 10 μM according to MAPK p38 Activation Assay. In one embodiment, the compound or pharmaceutically acceptable form thereof activates MAPK p38 by about 100% or more at 10 μM according to MAPK p38 Activation Assay. In one embodiment, the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 52, 53, 54, 55, 56, 57, 58, 59, 60, 61, 62, 63, 64, 65, 66, 67, 69, 70, 71, 72, 93, and 218, or a pharmaceutically acceptable form thereof. In one embodiment, the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof. In one embodiment, the compound is selected from the group consisting of Compounds 1, 2, 3, 7, 8, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof inhibits proliferation in MiaPaca2 according to Proliferation Assay. In one embodiment, the compound or pharmaceutically acceptable form thereof inhibits proliferation in MiaPaca2 with an IC50 value of 1.25 μM or less, 1.1 μM or less, 1 μM or less, 0.9 μM or less, 0.8 μM or less, 0.75 μM or less, 0.7 μM or less, 0.6 μM or less, 0.5 μM or less, 0.4 μM or less, 0.3 μM or less, 0.25 μM or less, 0.2 μM or less, 0.15 μM or less, or 0.1 μM or less according to Proliferation Assay. In one embodiment, the compound or pharmaceutically acceptable form thereof inhibits proliferation in MiaPaca2 with an IC50 value of about 1.25 μM to about 1.1 μM, about 1.1 μM to about 1 μM, about 1.0 μM to about 0.9 μM, about 0.9 μM to about 0.8 μM, about 0.8 μM to about 0.75μ, about 0.75μ M to about 0.7μ, about 0.7μ M to about 0.6μ, about 0.6μ M to about 0.5 μM, about 0.5 μM to about 0.4 μM, about 0.4 μM to about 0.3 μM, about 0.3 μM to about 0.25 μM, about 0.25 μM to about 0.2 μM, about 0.2 μM to about 0.15 μM, about 0.15 μM to about 0.1 μM, about 0.1 μM to about 0.01 μM, about 0.01 μM to about 0.001 μM, about 0.001 μM to about 0.0001 μM, or less than about 0.0001 μM according to Proliferation Assay. In one embodiment, the compound or pharmaceutically acceptable form thereof inhibits proliferation in MiaPaca2 with an IC50 value of 1.25 μM or less according to Proliferation Assay. In one embodiment, the compound or pharmaceutically acceptable form thereof inhibits proliferation in MiaPaca2 with an IC50 value of 1 μM or less according to Proliferation Assay. In one embodiment, the compound or pharmaceutically acceptable form thereof inhibits proliferation in MiaPaca2 with an IC50 value of 0.6 μM or less according to Proliferation Assay. In one embodiment, the compound or pharmaceutically acceptable form thereof inhibits proliferation in MiaPaca2 with an IC50 value of 0.5 μM or less according to Proliferation Assay. In one embodiment, the compound or pharmaceutically acceptable form thereof inhibits proliferation in MiaPaca2 with an IC50 value of 0.4 μM or less according to Proliferation Assay. In one embodiment, the compound or pharmaceutically acceptable form thereof inhibits proliferation in MiaPaca2 with an IC50 value of 0.3 μM or less according to Proliferation Assay. In one embodiment, the compound or pharmaceutically acceptable form thereof inhibits proliferation in MiaPaca2 with an IC50 value of 0.25 μM or less according to Proliferation Assay. In one embodiment, the compound or pharmaceutically acceptable form thereof inhibits proliferation in MiaPaca2 with an IC50 value of 0.20 μM or less according to Proliferation Assay. In one embodiment, the compound or pharmaceutically acceptable form thereof inhibits proliferation in MiaPaca2 with an IC50 value of 0.15 μM or less according to Proliferation Assay. In one embodiment, the compound or pharmaceutically acceptable form thereof inhibits proliferation in MiaPaca2 with an IC50 value of 0.10 μM or less according to Proliferation Assay. In one embodiment, the compound or pharmaceutically acceptable form thereof inhibits proliferation in MiaPaca2 with an IC50 value of about 1.25 μM to about 1.1 μM according to Proliferation Assay. In one embodiment, the compound or pharmaceutically acceptable form thereof inhibits proliferation in MiaPaca2 with an IC50 value of about 1.1 μM to about 1 μM according to Proliferation Assay. In one embodiment, the compound or pharmaceutically acceptable form thereof inhibits proliferation in MiaPaca2 with an IC50 value of about 1.0 μM to about 0.9 μM according to Proliferation Assay. In one embodiment, the compound or pharmaceutically acceptable form thereof inhibits proliferation in MiaPaca2 with an IC50 value of about 0.9 μM to about 0.8 μM according to Proliferation Assay. In one embodiment, the compound or pharmaceutically acceptable form thereof inhibits proliferation in MiaPaca2 with an IC50 value of about 0.8 μM to about 0.75 μM according to Proliferation Assay. In one embodiment, the compound or pharmaceutically acceptable form thereof inhibits proliferation in MiaPaca2 with an IC50 value of about 0.75 μM to about 0.7 μM according to Proliferation Assay. In one embodiment, the compound or pharmaceutically acceptable form thereof inhibits proliferation in MiaPaca2 with an IC50 value of about 0.7 μM to about 0.6 μM according to Proliferation Assay. In one embodiment, the compound or pharmaceutically acceptable form thereof inhibits proliferation in MiaPaca2 with an IC50 value of about 0.6 μM to about 0.5 μM according to Proliferation Assay. In one embodiment, the compound or pharmaceutically acceptable form thereof inhibits proliferation in MiaPaca2 with an IC50 value of about 0.5 μM to about 0.4 μM according to Proliferation Assay. In one embodiment, the compound or pharmaceutically acceptable form thereof inhibits proliferation in MiaPaca2 with an IC50 value of about 0.4 μM to about 0.3 μM according to Proliferation Assay. In one embodiment, the compound or pharmaceutically acceptable form thereof inhibits proliferation in MiaPaca2 with an IC50 value of about 0.3 μM to about 0.25 μM according to Proliferation Assay. In one embodiment, the compound or pharmaceutically acceptable form thereof inhibits proliferation in MiaPaca2 with an IC50 value of about 0.25 μM to about 0.2 μM according to Proliferation Assay. In one embodiment, the compound or pharmaceutically acceptable form thereof inhibits proliferation in MiaPaca2 with an IC50 value of about 0.2 μM to about 0.15 μM according to Proliferation Assay. In one embodiment, the compound or pharmaceutically acceptable form thereof inhibits proliferation in MiaPaca2 with an IC50 value of about 0.15 μM to about 0.1 μM according to Proliferation Assay. In one embodiment, the compound or pharmaceutically acceptable form thereof inhibits proliferation in MiaPaca2 with an IC50 value about 0.1 μM to about 0.01 μM according to Proliferation Assay. In one embodiment, the compound or pharmaceutically acceptable form thereof inhibits proliferation in MiaPaca2 with an IC50 value of about 0.01 μM to about 0.001 μM according to Proliferation Assay. In one embodiment, the compound or pharmaceutically acceptable form thereof inhibits proliferation in MiaPaca2 with an IC50 value of about 0.001 μM to about 0.0001 μM according to Proliferation Assay. In one embodiment, the compound or pharmaceutically acceptable form thereof inhibits proliferation in MiaPaca2 with an IC50 value of less than about 0.0001 μM according to Proliferation Assay. In one embodiment, the compound is selected from the group consisting of Compounds 6, 13, 22, 26, 29, 30, 32, 33, 34, 42, 45, 46, 48, 49, 50, 53, 54, 55, 56, 57, 58, 59, 61, 62, 63, 64, 65, 68, 72, 73, 74, 76, 78, 79, 81, 82, 83, 84, 86, 89, 91, 93, 94, 95, 96, 97, 98, 100, 101, 102, 104, 105, 106, 107, 108, 109, 110, 111, 112, 113, 114, 115, 116, 117, 118, 119, 120, 121, 122, 123, 124, 125, 126, 127, 128, 129, 135, 136, 137, 138, 139, 140, 141, 142, 143, 144, 145, 146, 149, 156, 157, 158, 165, 169, 170, 173, 174, 175, 176, 196, 203, 209, 210, 213, 214, 217, 219, 221, 222, 224, 226, 227, 228, 229, 230, 231, 232, 233, 234, 235, 236, 237, 238, 239, 240, 243, 244, 245, 246, 247, 248, 249, 250, 252, 253, 255, 257, 263, 264, 265, 266, 267, 268, 269, 270, 271, 274, and 276, or a pharmaceutically acceptable form thereof. In one embodiment, the compound is selected from the group consisting of Compounds 6, 13, 22, 26, 29, 30, 32, 33, 34, 42, 48, 49, 50, 53, 54, 55, 56, 57, 58, 59, 61, 62, 63, 64, 65, 68, 72, 73, 74, 76, 78, 79, 81, 82, 83, 84, 86, 89, 91, 93, 94, 95, 96, 97, 98, 100, 101, 102, 104, 105, 106, 107, 108, 109, 110, 111, 112, 113, 114, 115, 116, 117, 118, 120, 122, 123, 124, 125, 126, 127, 128, 129, 135, 136, 137, 138, 139, 140, 141, 142, 143, 144, 145, 146, 149, 156, 157, 158, 165, 169, 170, 173, 174, 175, 176, 196, 203, 209, 210, 213, 217, 219, 221, 222, 224, 226, 227, 228, 229, 230, 231, 232, 233, 234, 235, 236, 237, 238, 239, 240, 243, 244, 245, 246, 247, 248, 249, 250, 252, 253, 255, 257, 263, 264, 265, 266, 267, 268, 269, 270, 271, 274, and 276, or a pharmaceutically acceptable form thereof. In one embodiment, the compound is selected from the group consisting of Compounds 6, 13, 22, 32, 34, 48, 49, 50, 53, 54, 55, 56, 57, 58, 59, 62, 63, 64, 65, 68, 73, 74, 76, 78, 79, 81, 82, 83, 84, 86, 89, 91, 93, 94, 95, 96, 97, 98, 100, 101, 102, 104, 106, 107, 110, 111, 112, 113, 114, 115, 116, 117, 118, 120, 122, 123, 124, 125, 126, 127, 128, 129, 135, 136, 137, 138, 139, 140, 141, 142, 143, 144, 145, 146, 156, 157, 158, 165, 169, 170, 174, 175, 196, 209, 221, 222, 224, 226, 227, 228, 229, 230, 231, 232, 233, 234, 235, 236, 237, 238, 239, 240, 243, 244, 245, 246, 247, 248, 249, 250, 252, 255, 257, 263, 264, 265, 266, 267, 268, 270, 271, 274, and 276, or a pharmaceutically acceptable form thereof. In one embodiment, the compound is selected from the group consisting of Compounds 6, 48, 49, 50, 53, 54, 55, 57, 58, 62, 63, 64, 65, 68, 73, 76, 79, 82, 84, 89, 91, 94, 95, 97, 98, 100, 102, 104, 106, 107, 110, 112, 113, 114, 115, 117, 118, 120, 122, 123, 124, 126, 127, 128, 129, 135, 136, 137, 138, 139, 140, 141, 142, 143, 144, 145, 156, 157, 158, 165, 169, 170, 196, 221, 222, 224, 226, 227, 228, 230, 231, 232, 233, 234, 235, 236, 237, 238, 239, 240, 243, 244, 245, 248, 249, 250, 252, 255, 257, 263, 265, 266, 267, and 268, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof inhibits IL-6 according to IL-6 Quantification Assay. In one embodiment, the compound or pharmaceutically acceptable form thereof inhibits IL-6 by 50% or more, 55% or more, 60% or more, 65% or more, 70% or more, 75% or more, 80% or more, 85% or more, 90% or more, or 95% or more at 10 μM according to IL-6 Quantification Assay. In one embodiment, the compound or pharmaceutically acceptable form thereof inhibits IL-6 by about 50% to about 60%, about 60% to about 70%, about 70% to about 80%, about 80% to about 90%, or about 90% to about 100% at 10 μM according to IL-6 Quantification Assay. In one embodiment, the compound or pharmaceutically acceptable form thereof inhibits IL-6 by 50% or more at 10 μM according to IL-6 Quantification Assay. In one embodiment, the compound or pharmaceutically acceptable form thereof inhibits IL-6 by 75% or more at 10 μM according to IL-6 Quantification Assay. In one embodiment, the compound or pharmaceutically acceptable form thereof inhibits IL-6 by 85% or more at 10 μM according to IL-6 Quantification Assay. In one embodiment, the compound or pharmaceutically acceptable form thereof inhibits IL-6 by 90% or more at 10 μM according to IL-6 Quantification Assay. In one embodiment, the compound or pharmaceutically acceptable form thereof inhibits IL-6 by 95% or more at 10 μM according to IL-6 Quantification Assay. In one embodiment, the compound or pharmaceutically acceptable form thereof inhibits IL-6 by about 50% to about 60% at 10 μM according to IL-6 Quantification Assay. In one embodiment, the compound or pharmaceutically acceptable form thereof inhibits IL-6 by about 60% to about 70% at 10 μM according to IL-6 Quantification Assay. In one embodiment, the compound or pharmaceutically acceptable form thereof inhibits IL-6 by about 70% to about 80% at 10 μM according to IL-6 Quantification Assay. In one embodiment, the compound or pharmaceutically acceptable form thereof inhibits IL-6 by about 80% to about 90% at 10 μM according to IL-6 Quantification Assay. In one embodiment, the compound or pharmaceutically acceptable form thereof inhibits IL-6 by about 90% to about 100% at 10 μM according to IL-6 Quantification Assay. In one embodiment, the compound is selected from the group consisting of Compounds 1, 4, 6, 13, 19, 20, 22, 23, 27, 29, 30, 31, 32, 33, 34, 40, 42, 45, 46, 67, 81, 82, 85, 86, 89, 93, 99, 104, 105, 111, 113, 143, 149, 160, 161, 163, 164, 166, 173, 175, 176, 177, 192, 193, 194, 196, 199, 201, 203, 204, 206, 207, 208, 209, 210, 217, 219, 238, 247, 248, 249, 250, 257, 260, 263, 264, 265, 268, 269, 270, 271, 272, 273, and 274, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof inhibits TNF-alpha according to TNF-alpha Quantification Assay. In one embodiment, the compound or pharmaceutically acceptable form thereof inhibits TNF-alpha by 50% or more, 55% or more, 60% or more, 65% or more, 70% or more, 75% or more, 80% or more, 85% or more, 90% or more, or 95% or more at 10 μM according to TNF-alpha Quantification Assay. In one embodiment, the compound or pharmaceutically acceptable form thereof inhibits TNF-alpha by about 50% to about 60%, about 60% to about 70%, about 70% to about 80%, about 80% to about 90%, or about 90% to about 100% at 10 μM according to TNF-alpha Quantification Assay. In one embodiment, the compound or pharmaceutically acceptable form thereof inhibits TNF-alpha by 50% or more at 10 μM according to TNF-alpha Quantification Assay. In one embodiment, the compound or pharmaceutically acceptable form thereof inhibits TNF-alpha by 75% or more at 10 μM according to TNF-alpha Quantification Assay. In one embodiment, the compound or pharmaceutically acceptable form thereof inhibits TNF-alpha by 85% or more at 10 μM according to TNF-alpha Quantification Assay. In one embodiment, the compound or pharmaceutically acceptable form thereof inhibits TNF-alpha by 90% or more at 10 μM according to TNF-alpha Quantification Assay. In one embodiment, the compound or pharmaceutically acceptable form thereof inhibits TNF-alpha by 95% or more at 10 μM according to TNF-alpha Quantification Assay. In one embodiment, the compound or pharmaceutically acceptable form thereof inhibits TNF-alpha by about 50% to about 60% at 10 μM according to TNF-alpha Quantification Assay. In one embodiment, the compound or pharmaceutically acceptable form thereof inhibits TNF-alpha by about 60% to about 70% at 10 μM according to TNF-alpha Quantification Assay. In one embodiment, the compound or pharmaceutically acceptable form thereof inhibits TNF-alpha by about 70% to about 80% at 10 μM according to TNF-alpha Quantification Assay. In one embodiment, the compound or pharmaceutically acceptable form thereof inhibits TNF-alpha by about 80% to about 90% at 10 μM according to TNF-alpha Quantification Assay. In one embodiment, the compound or pharmaceutically acceptable form thereof inhibits TNF-alpha by about 90% to about 100% at 10 μM according to TNF-alpha Quantification Assay. In one embodiment, the compound is selected from the group consisting of Compounds 4, 23, 29, 30, 31, 32, 33, 42, 45, 46, 93, 99, 149, 166, 196, 203, 207, 209, 210, 219, 269, 270, 271, 272, 273, and 274, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof has a kinetic solubility of 10 μM or more, 20 μM or more, 30 μM or more, 40 μM or more, 50 μM or more, 60 μM or more, 70 μM or more, 80 μM or more, 90 μM or more, 100 μM or more, 150 μM or more, or 200 μM or more in pH 7.4 buffer comprising 2% DMSO according to Kinetic Solubility Assay. In one embodiment, the compound has a kinetic solubility of 10 μM or more in pH 7.4 buffer comprising 2% DMSO according to Kinetic Solubility Assay. In one embodiment, the compound has a kinetic solubility of 20 μM or more in pH 7.4 buffer comprising 2% DMSO according to Kinetic Solubility Assay. In one embodiment, the compound has a kinetic solubility of 30 μM or more in pH 7.4 buffer comprising 2% DMSO according to Kinetic Solubility Assay. In one embodiment, the compound has a kinetic solubility of 40 μM or more in pH 7.4 buffer comprising 2% DMSO according to Kinetic Solubility Assay. In one embodiment, the compound has a kinetic solubility of 50 μM or more in pH 7.4 buffer comprising 2% DMSO according to Kinetic Solubility Assay. In one embodiment, the compound has a kinetic solubility of 60 μM or more in pH 7.4 buffer comprising 2% DMSO according to Kinetic Solubility Assay. In one embodiment, the compound has a kinetic solubility of 70 μM or more in pH 7.4 buffer comprising 2% DMSO according to Kinetic Solubility Assay. In one embodiment, the compound has a kinetic solubility of 80 μM or more in pH 7.4 buffer comprising 2% DMSO according to Kinetic Solubility Assay. In one embodiment, the compound has a kinetic solubility of 90 μM or more in pH 7.4 buffer comprising 2% DMSO according to Kinetic Solubility Assay. In one embodiment, the compound has a kinetic solubility of 100 μM or more in pH 7.4 buffer comprising 2% DMSO according to Kinetic Solubility Assay. In one embodiment, the compound has a kinetic solubility of 150 μM or more in pH 7.4 buffer comprising 2% DMSO according to Kinetic Solubility Assay. In one embodiment, the compound has a kinetic solubility of 200 μM or more in pH 7.4 buffer comprising 2% DMSO according to Kinetic Solubility Assay. In one embodiment, the compound is selected from the group consisting of Compounds 53, 55, 57, 58, 84, 91, 100, 102, 116, 118, 124, 137, 141, 142, 145, 158, 221, 222, 255, and 267, or a pharmaceutically acceptable form thereof. In one embodiment, the compound is selected from the group consisting of Compounds 91, 102, 118, and 255, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof has a half-life of 10 minutes or more, 20 minutes or more, 30 minutes or more, 40 minutes or more, or 50 minutes or more in mouse liver microsomes according to Mouse Liver Microsome Metabolic Stability Assay. In one embodiment, the compound has a half-life of 10 minutes or more in mouse liver microsomes according to Mouse Liver Microsome Metabolic Stability Assay. In one embodiment, the compound has a half-life of 20 minutes or more in mouse liver microsomes according to Mouse Liver Microsome Metabolic Stability Assay. In one embodiment, the compound has a half-life of 30 minutes or more in mouse liver microsomes according to Mouse Liver Microsome Metabolic Stability Assay. In one embodiment, the compound has a half-life of 40 minutes or more in mouse liver microsomes according to Mouse Liver Microsome Metabolic Stability Assay. In one embodiment, the compound has a half-life of 50 minutes or more in mouse liver microsomes according to Mouse Liver Microsome Metabolic Stability Assay. In one embodiment, the compound is selected from the group consisting of Compounds 6, 102, 104, 124, 126, 128, 129, 137, 141, 142, 144, 145, 156, 157, 224, 226, 227, 235, 238, 248, 255, 265, and 267, or a pharmaceutically acceptable form thereof.

In one embodiment, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof inhibits proliferation in NCI-H358, A375, GP2d, BT549, or MM.R1 according to Proliferation Assay. In one embodiment, the compound inhibits proliferation in NCI-H358 according to Proliferation Assay. In one embodiment, the compound inhibits proliferation in A375 according to Proliferation Assay. In one embodiment, the compound inhibits proliferation in GP2d according to Proliferation Assay. In one embodiment, the compound inhibits proliferation in MM.R1 according to Proliferation Assay. In one embodiment, the compound inhibits proliferation in NCI-H358, A375, GP2d, BT549, or MM.R1 with an $IC_{50}$ value of 50 nM or less, 40 nM or less, 30 nM or less, 20 nM or less, 10 nM or less, 1 nM or less, 0.1 nM or less, or 0.01 nM or less according to Proliferation Assay. In one embodiment, the compound inhibits proliferation in NCI-H358, A375, GP2d, BT549, or MM.R1 with an $IC_{50}$ value of 50 nM or less according to Proliferation Assay. In one embodiment, the compound inhibits proliferation in NCI-H358, A375, GP2d, BT549, or MM.R1 with an $IC_{50}$ value of 40 nM or less according to Proliferation Assay. In one embodiment, the compound inhibits proliferation in NCI-H358, A375, GP2d, BT549, or MM.R1 with an IC50 value of 30 nM or less according to Proliferation Assay. In one embodiment, the compound inhibits proliferation in NCI-H358, A375, GP2d, BT549, or MM.R1 with an $IC_{50}$ value of 20 nM or less according to Proliferation Assay. In one embodiment, the compound inhibits proliferation in NCI-H358, A375, GP2d, BT549, or MM.R1 with an IC50 value of 10 nM or less according to Proliferation Assay. In one embodiment, the compound inhibits proliferation in NCI-H358, A375, GP2d, BT549, or MM.R1 with an IC50 value of 1 nM or less according to Proliferation Assay. In one embodiment, the compound inhibits proliferation in NCI-H358, A375, GP2d, BT549, or MM.R1 with an $IC_{50}$ value of 0.1 nM or less according to Proliferation Assay. In one embodiment, the compound inhibits proliferation in NCI-H358, A375, GP2d, BT549, or MM.R1 with an $IC_{50}$ value of 0.01 nM or less according to Proliferation Assay. In one embodiment, the compound inhibits proliferation in MM.R1 with an $IC_{50}$ value of 1 nM or less, 0.1 nM or less, or 0.01 nM or less according to Proliferation Assay. In one embodiment, the compound inhibits proliferation in MM.R1 with an $IC_{50}$ value of 1 nM or less according to Proliferation Assay. In one embodiment, the compound inhibits proliferation in MM.R1 with an $IC_{50}$ value of 0.1 nM or less according to Proliferation Assay. In one embodiment, the compound inhibits proliferation in MM.R1 with an $IC_{50}$ value of 0.01 nM or less according to Proliferation Assay. In one embodiment, the compound is selected from the group consisting of Compounds 6, 58, 84, 100, 102, 104, 124, 221, 222, 235, 238, 252, 255, and 267, or a pharmaceutically acceptable form thereof.

In one embodiment, the pharmaceutically acceptable form of the compound of Formula I, Ia, Ib, Ic, II, IIa, IIa(1), IIb, IIc, III, IIIa, IIIb, IIIc, IV, IVa, IVb, or IVc is an isomer, isotopic variant, pharmaceutically acceptable salt, polymorph, or solvate of said compound. In one embodiment, the pharmaceutically acceptable form of the compound is exclusive of a salt form. In one embodiment, the isomer of the compound is a diastereomer or enantiomer of the compound.

In one embodiment, the compound of Formula I, Ia, Ib, Ic, II, IIa, IIa(1), IIb, IIc, III, IIIa, IIIb, IIIc, IV, IVa, IVb, or IVc is a tautomer of the compound.

In one embodiment, the compound of Formula I, Ia, Ib, Ic, II, IIa, IIa(1), IIb, IIc, III, IIIa, IIIb, IIIc, IV, IVa, IVb, or IVc is a racemate or a mixture of diasteromers.

In one embodiment, the compound of Formula I, Ia, Ib, Ic, II, IIa, IIa(1), IIb, IIc, III, IIIa, IIIb, IIIc, IV, IVa, IVb, or IVc is a single enantiomer or a single diasteromer.

In one embodiment, the compound of Formula I, Ia, Ib, Ic, II, IIa, IIa(1), IIb, IIc, III, IIIa, IIIb, IIIc, IV, IVa, IVb, or IVc is an (R) enantiomer. In one embodiment, the compound has an enantiomeric excess of greater than 10% of the (R) enantiomer. In one embodiment, the compound has an enantiomeric excess of 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, 98% or more, or 99% or more of the (R) enantiomer. In one embodiment, the compound has an enantiomeric excess of 15% or more of the (R) enantiomer. In one embodiment, the compound has an enantiomeric excess of 25% or more of the (R) enantiomer. In one embodiment, the compound has an enantiomeric excess of 50% or more of the (R) enantiomer. In one embodiment, the compound has an enantiomeric excess of 75% or more of the (R) enantiomer. In one embodiment, the compound has an enantiomeric excess of 90% or more of the (R) enantiomer. In one embodiment, the compound has an enantiomeric excess of 95% or more of the (R) enantiomer. In one embodiment, the compound has an enantiomeric excess of 98% or more of the (R) enantiomer. In one embodiment, the compound has an enantiomeric excess of 99% or more of the (R) enantiomer. In one embodiment, the compound has an enantiomeric excess of about 90%, about 91%, about 92%, about 93%, about 94%, about 95%, about 96%, about 97%, about 98%, or about 99%, of the (R) enantiomer.

In one embodiment, the compound of Formula I, Ia, Ib, Ic, II, IIa, IIa(1), IIb, IIc, III, IIIa, IIIb, IIIc, IV, IVa, IVb, or IVc is an(S) enantiomer. In one embodiment, the compound has an enantiomeric excess of greater than 10% of the(S) enantiomer. In one embodiment, the compound has an enantiomeric excess of 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, 98% or more, or 99% or more of the(S) enantiomer. In one embodiment, the compound has an enantiomeric excess of 15% or more of the(S) enantiomer. In one embodiment, the compound has an enantiomeric excess of 25% or more of the(S) enantiomer. In one embodiment, the compound has an enantiomeric excess of 50% or more of the(S) enantiomer. In one embodiment, the compound has an enantiomeric excess of 75% or more of the(S) enantiomer. In one embodiment, the compound has an enantiomeric excess of 90% or more of the(S) enantiomer. In one embodiment, the compound has an enantiomeric excess of 95% or more of the(S) enantiomer. In one embodiment, the compound has an enantiomeric excess of 98% or more of the(S) enantiomer. In one embodiment, the compound has an enantiomeric excess of 99% or more of the(S) enantiomer. In one embodiment, the compound has an enantiomeric excess of about 90%, about 91%, about 92%, about 93%, about 94%, about 95%, about 96%, about 97%, about 98%, or about 99%, of the(S) enantiomer.

3.3. Methods of Modulating Activity of Cellular Targets

Provided herein are methods of modulating a Ras superfamily protein, comprising contacting the Ras superfamily protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof. Also provided herein are methods of modulating a Ras superfamily protein, comprising contacting the Ras superfamily protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, as disclosed herein below. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In some embodiments of the methods provided herein, the Ras superfamily protein is present in a cell.

In some embodiments, the method comprises contacting the Ras superfamily protein with a compound or pharmaceutically acceptable form thereof that modulates the activity of one or more Ras superfamily proteins by 45% or more at 20 μM according to a Ras Superfamily Activity Assay. In some embodiments, the method comprises contacting the Ras superfamily protein with a compound or pharmaceutically acceptable form thereof that modulates the activity of one or more Ras superfamily proteins by 50% or more at 20 μM according to a Ras Superfamily Activity Assay. In some embodiments, the compound is selected from the group consisting of Compounds 6, 17, 22, 32, 34, 37, 42, 43, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 126, 127, 135, 136, 137, 138, 139, 140, 141, 142, 143, 144, 145, 146, 147, 148, 149, 150, 151, 152, 153, 154, 156, 157, 158, 165, 166, 167, 169, 170, 172, 173, 174, 175, 176, 177, 178, 179, 186, 187, 188, 196, 200, 202, 208, 211, 212, 213, 214, 215, 216, 217, 220, 221, 222, 223, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof. In some embodiments, the compound is selected from the group consisting of Compounds 6, 17, 22, 37, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 127, 135, 136, 137, 138, 139, 140, 141, 142, 143, 144, 145, 146, 147, 149, 150, 151, 152, 153, 154, 156, 157, 158, 165, 166, 169, 170, 173, 175, 176, 177, 178, 179, 186, 187, 188, 196, 202, 208, 211, 212, 213, 214, 215, 216, 217, 221, 222, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof.

In some embodiments, the methods provided herein inhibit the Ras superfamily protein.

In some embodiments of the methods provided herein, the Ras superfamily protein is a Ras protein, or a mutant thereof. In some embodiments, the Ras protein is DIRAS I; DIRAS2; DIRAS3; ERAS; GEM; HRAS; KRAS; MRAS; NKIRASI; NKIRAS2; NRAS; RALA; RALB; RAP1A; RAP1B; RAP2A; RAP2B; RAP2C; RASD1; RASD2; RASLIOA; RASLIOB; RASLI IA; RASLIIB; RASL12; REMI; REM2; RERG; RERGL; RRAD; RRAS; or RRAS2. In some embodiments, the Ras protein is HRAS; KRAS; or NRAS, or a mutant thereof. In some embodiments, the Ras protein is a KRAS mutant. In some embodiments, the KRAS mutant is a KRas G12D mutant, KRas G12C mutant, or KRas Q61H mutant. In some embodiments, the Ras protein is HRAS or a mutant thereof. In some embodiments, the Ras protein is NRAS or a mutant thereof.

In some embodiments of the methods provided herein, the Ras superfamily protein is a Rac protein, or a mutant thereof. In some embodiments, the Rac protein is RAC1; RAC2; RAC3; RHOG, or a mutant thereof. In some embodiments, the Rac protein is wild-type RAC1.

In some embodiments of the methods provided herein, the Ras superfamily protein is a Rho protein, or a mutant thereof. In some embodiments, the Rho protein is RHOA; RHOB; RHOBTB1; RHOBTB2; RHOBTB3; RHOC; RHOD; RHOF; RHOH; RHOJ; RHOQ; RHOU; RHOV; RND1; RND2; RND3; CDC42, or a mutant thereof. In some embodiments, the Rho protein is wild-type RHOA.

In some embodiments of the methods provided herein, the Ras superfamily protein is a Cdc42 protein, or a mutant thereof.

In some embodiments of the methods provided herein, the Ras superfamily protein is a Rheb protein, or a mutant thereof.

In some embodiments of the methods provided herein, the contacting of the Ras superfamily protein takes place in a cell. In some embodiments, the cell is in a subject. In some embodiments, the cell is a mammalian cell. In some embodiments, the cell is a human cell. In some embodiments, the subject suffers from a cancer. In some embodiments, the subject is a human.

In some embodiments of the methods provided herein, the modulation takes place in a subject suffering from a cancer. In some embodiments, the cancer is a solid tumor. In some embodiments, the cancer is a blood borne tumor (or a hematological cancer). In some embodiments, the cancer is hepatocellular carcinoma, prostate cancer, pancreatic cancer, lung cancer, breast cancer, ovarian cancer, colon cancer, small intestine cancer, biliary tract cancer, endometrium cancer, skin cancer (melanoma), cervix cancer, urinary tract cancer, glioblastoma, or multiple myeloma. In some embodiments, the cancer is pancreatic cancer. In some embodiments, the cancer is colon cancer. In some embodiments, the cancer is triple negative breast cancer. In some embodiments, the cancer is multiple myeloma. In some embodiments, the cancer is a cancer dependent on a Ras superfamily protein.

Provided herein are methods of modulating caspase activity, comprising contacting the caspase with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof. Also provided herein are methods of modulating caspase activity, comprising contacting the caspase with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, as disclosed herein below. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In some embodiments, the methods provided herein activate the caspase. In some embodiments, the caspase is caspase 3, caspase 6, or caspase 9.

In some embodiments of the methods provided herein, the contacting of the caspase takes place in a cell. In some embodiments, the modulation of caspase activity induces apoptosis of the cell. In some embodiments, the cell is in a subject. In some embodiments, the cell is a mammalian cell. In some embodiments, the cell is a human cell. In some embodiments, the subject suffers from a cancer. In some embodiments, the modulation takes place in a subject suffering from a cancer. In some embodiments, the cancer is a solid tumor. In some embodiments, the cancer is a blood borne tumor (or a hematological cancer). In some embodiments, the cancer is hepatocellular carcinoma, prostate cancer, pancreatic cancer, lung cancer, breast cancer, ovarian cancer, colon cancer, small intestine cancer, biliary tract cancer, endometrium cancer, skin cancer (melanoma), cervix cancer, urinary tract cancer, glioblastoma, multiple myeloma. In some embodiments, the cancer is pancreatic cancer. In some embodiments, the cancer is colon cancer. In some embodiments, the cancer is triple negative breast cancer. In some embodiments, the cancer is multiple myeloma. In some embodiments, the subject is a human.

Provided herein are methods of modulating Erk1/2 activity, comprising contacting an Erk1/2 protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof. Also provided herein are methods of modulating Erk1/2 activity, comprising contacting an Erk1/2 protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, as disclosed herein below. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276 or a pharmaceutically acceptable form thereof.

In certain embodiments of the methods of of modulating Erk1/2 activity described herein, the method inhibits phosphorylation of the Erk1/2 protein. In some embodiments, the method comprises contacting the Erk1/2 protein with a compound or pharmaceutically acceptable form thereof that inhibits phosphorylation of the Erk1/2 protein by 80% or more at 10 μM according to Erk1/2 Phosphorylation Assay. In some embodiments, the method comprises contacting the Erk1/2 protein with a compound or pharmaceutically acceptable form thereof that inhibits phosphorylation of the Erk1/2 protein by 85% or more at 10 μM according to Erk1/2 Phosphorylation Assay. In some embodiments, the compound is selected from the group consisting of Compounds 3, 4, 20, 23, 26, 29, 30, 31, 32, 33, 34, 36, 42, 43, 53, 58, 67, 93, 203, 209, 210, 219, 266, 269, 270, 271, 272, 273, and 274, or a pharmaceutically acceptable form thereof. In some embodiments, the compound is selected from the group consisting of Compounds 3, 4, 20, 23, 26, 29, 30, 31, 32, 33, 34, 42, 43, 53, 58, 67, 93, 203, 209, 210, 219, 266, 269, 270, 271, 272, 273, and 274, or a pharmaceutically acceptable form thereof.

In certain embodiments of the methods of of modulating Erk1/2 activity described herein, the method activates phosphorylation of the Erk1/2 protein. In some embodiments, the method comprises contacting the Erk1/2 protein with a compound or pharmaceutically acceptable form thereof that activates phosphorylation of the Erk1/2 protein by 45% or more at 10 μM according to Erk1/2 Phosphorylation Assay. In some embodiments, the method comprises contacting the Erk1/2 protein with a compound or pharmaceutically acceptable form thereof that activates phosphorylation of the Erk1/2 protein by 50% or more at 10 μM according to Erk1/2 Phosphorylation Assay. In some embodiments, the compound is selected from the group consisting of Compounds 49, 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 130, 135, 136, 138, 143, 145, 148, 149, 151, 154, 156, 157, 165, 174, 175, 176, 177, 178, 179, 183, 190, 191, 192, 193, 194, 195, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof. In some embodiments, the compound is selected from the group consisting of Compounds 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 135, 136, 138, 143, 145, 148, 149, 151, 154, 156, 157, 165, 174, 175, 176, 177, 178, 179, 183, 190, 191, 192, 193, 194, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof.

In some embodiments of the methods provided herein, the contacting of the Erk1/2 protein takes place in a cell. In some embodiments, the cell is in a subject. In some embodiments, the cell is a mammalian cell. In some embodiments, the cell is a human cell.

Provided herein are methods of modulating Akt activity, comprising contacting an Akt protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof. Also provided herein are methods of modulating Akt activity, comprising contacting an AKT protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, as disclosed herein below. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In certain embodiments of the methods of of modulating Akt activity described herein, the method inhibits phosphorylation of the Akt protein. In some embodiments, the method comprises contacting the Akt protein with a compound or pharmaceutically acceptable form thereof that inhibits phosphorylation of the Akt protein by 85% or more at 10 μM according to Akt Phosphorylation Assay. In some embodiments, the compound is selected from the group consisting of Compounds 17, 20, 23, 25, 29, 30, 31, 32, 33, 34, 42, 203, 209, 210, 219, 270, 271, 272, 273, and 274, or a pharmaceutically acceptable form thereof.

In certain embodiments of the methods of of modulating Akt activity described herein, the method activates phosphorylation of the Akt protein. In some embodiments, the method comprises contacting the Akt protein with a compound or pharmaceutically acceptable form thereof that activates phosphorylation of the Akt protein by 50% or more at 10 μM according to Akt Phosphorylation Assay. In some embodiments, the compound is selected from the group consisting of Compounds 1, 2, 18, 19, 21, 47, 48, 49, 50, 51, 57, 59, 60, 61, 62, 63, 64, 65, 66, 67, 68, 69, 70, 71, 72, 73, 74, 76, 77, 78, 79, 80, 81, 82, 83, 84, 85, 86, 87, 88, 89, 91, 93, 94, 95, 96, 97, 98, 100, 101, 102, 103, 104, 106, 107, 108, 109, 110, 111, 112, 113, 114, 115, 116, 118, 119, 122, 124, 125, 126, 127, 128, 129, 130, 135, 136, 137, 138, 143, 145, 149, 151, 156, 157, 158, 165, 166, 169, 170, 173, 174, 175, 176, 178, 179, 187, 190, 191, 192, 193, 194, 195, 196, 204, 205, 207, 208, 213, 217, 218, 221, 222, 224, 226, 227, 228, 229, 230, 231, 232, 233, 234, 235, 237, 238, 240, 241, 242, 243, 244, 245, 246, 247, 248, 249, 250, 252, 253, 254, 255, 256, 257, 259, 260, 263, 264, 265, 266, 267, 268, 275, and 276, or a pharmaceutically acceptable form thereof.

In some embodiments of the methods provided herein, the contacting of the Akt protein takes place in a cell. In some embodiments, the cell is in a subject. In some embodiments, the cell is a mammalian cell. In some embodiments, the cell is a human cell.

Provided herein are methods of modulating Smad2/3 activity, comprising contacting a Smad2/3 protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof. Also provided herein are methods of modulating Smad2/3 activity, comprising contacting a Smad2/3 protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, as disclosed herein below. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In certain embodiments of the methods of of modulating Smad2/3 activity described herein, the method inhibits phosphorylation of the Smad2/3 protein. In some embodiments, the method comprises contacting the Smad2/3 protein with a compound or pharmaceutically acceptable form thereof that inhibits phosphorylation of the Smad2/3 protein by 80% or more at 10 μM according to Phospho-Smad2/3 Inhibition Assay. In some embodiments, the method comprises contacting the Smad2/3 protein with a compound or pharmaceutically acceptable form thereof that inhibits phosphorylation of the Smad2/3 protein by 85% or more. In some embodiments, the compound is selected from the group consisting of Compounds 27, 29, 30, 31, 32, 33, 36, 43, 44, 47, 51, 52, 55, 59, 85, 96, 97, 98, 99, 116, 141, 144, 156, 203, 205, 207, 208, 209, 210, 211, 214, 219, 230, 269, 272, 273, and 274, or a pharmaceutically acceptable form thereof. In some embodiments, the compound is selected from the group consisting of Compounds 29, 30, 31, 32, 33, 36, 44, 47, 59, 85, 97, 98, 99, 116, 141, 144, 156, 203, 205, 207, 208, 209, 210, 211, 214, 219, 230, 269, 272, 273, and 274, or a pharmaceutically acceptable form thereof.

In certain embodiments of the methods of of modulating Smad2/3 activity described herein, the method activates phosphorylation of the Smad2/3 protein. In some embodiments, the method comprises contacting the Smad2/3 protein with a compound or pharmaceutically acceptable form thereof that activates phosphorylation of the Smad2/3 protein by 50% or more at 10 μM according to Phospho- Smad2/3 Inhibition Assay. In some embodiments, the compound is selected from the group consisting of Compounds 56, 63, 84, 88, 89, 90, 95, 100, 101, 103, 104, 106, 108, 109, 111, 112, 113, 114, 129, 166, 173, 179, 183, 186, 216, 241, 247, 248, 250, 255, 256, 257, and 266, or a pharmaceutically acceptable form thereof.

In some embodiments of the methods provided herein, the contacting of the Smad2/3 protein takes place in a cell. In some embodiments, the cell is in a subject. In some embodiments, the cell is a mammalian cell. In some embodiments, the cell is a human cell.

Provided herein are methods of modulating JNK activity, comprising contacting a JNK protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof. Also provided herein are methods of modulating JNK activity, comprising contacting a JNK protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, as disclosed herein below. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In certain embodiments of the methods of of modulating JNK activity described herein, the method inhibits phosphorylation of the JNK protein. In some embodiments, the method comprises contacting the JNK protein with a compound or pharmaceutically acceptable form thereof that inhibits phosphorylation of the JNK protein by 30% or more according to JNK Activation Assay. In some embodiments, the method comprises contacting the JNK protein with a compound or pharmaceutically acceptable form thereof that inhibits phosphorylation of the JNK protein by 75% or more according to JNK Activation Assay. In some embodiments, the method comprises contacting the JNK protein with a compound or pharmaceutically acceptable form thereof that inhibits phosphorylation of the JNK protein by about 100% according to JNK Activation Assay. In some embodiments, the compound is selected from the group consisting of Compounds 29, 30, 32, 33, and 34, or a pharmaceutically acceptable form thereof. In some embodiments, the compound is selected from the group consisting of Compounds 29, 32, 33, and 34, or a pharmaceutically acceptable form thereof. In some embodiments, the compound is selected from the group consisting of Compounds 29, 32, and 34, or a pharmaceutically acceptable form thereof.

In certain embodiments of the methods of of modulating JNK activity described herein, the method activates phosphorylation of the JNK protein. In some embodiments, the method comprises contacting the JNK protein with a compound or pharmaceutically acceptable form thereof that activates phosphorylation of the JNK protein by 30% or more according to JNK Activation Assay. In some embodiments, the method comprises contacting the JNK protein with a compound or pharmaceutically acceptable form thereof that activates phosphorylation of the JNK protein by 75% or more according to JNK Activation Assay. In some embodiments, the method comprises contacting the JNK protein with a compound or pharmaceutically acceptable form thereof that activates phosphorylation of the JNK protein by about 100% or more according to JNK Activation Assay. In some embodiments, the compound is selected from the group consisting of Compounds 1, 2, 3, 4, 6, 7, 8, 9, 11, 13, 14, 15, 16, 18, 19, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof. In some embodiments, the compound is selected from the group consisting of Compounds 3, 4, 6, 7, 11, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof. In some embodiments, the compound is selected from the group consisting of Compounds 3, 6, 7, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof.

In some embodiments of the methods provided herein, the contacting of the JNK protein takes place in a cell. In some embodiments, the cell is in a subject. In some embodiments, the cell is a mammalian cell. In some embodiments, the cell is a human cell.

Provided herein are methods of modulating MAPK p38 activity, comprising contacting a MAPK p38 protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof. Also provided herein are methods of modulating MAPK p38 activity, comprising contacting a MAPK p38 protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, as disclosed herein below. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In certain embodiments of the methods of of modulating MAPK p38 described herein, the method inhibits phosphorylation of the MAPK p38 protein. In some embodiments, the method comprises contacting the MAPK p38 with a compound or pharmaceutically acceptable form thereof that inhibits phosphorylation of the MAPK p38 by 30% or more at 10 μM according to MAPK p38 Activation Assay. In some embodiments, the method comprises contacting the MAPK p38 with a compound or pharmaceutically acceptable form thereof that inhibits phosphorylation of the MAPK p38 by about 100% at 10 μM according to MAPK p38 Activation Assay. In some embodiments, the compound is selected from the group consisting of Compounds 29, 30, 32, 33, 34, 46, 47, 188, 196, 197, 203, 205, 207, 208, 209, 210, 212, 213, 214, 215, 217, and 220, or a pharmaceutically acceptable form thereof. In some embodiments, the compound is selected from the group consisting of Compounds 29, 32, 33, 34, 46, 207, and 209, or a pharmaceutically acceptable form thereof.

In certain embodiments of the methods of of modulating MAPK p38 described herein, the method activates phosphorylation of the MAPK p38 protein. In some embodiments, the method comprises contacting the MAPK p38 with a compound or pharmaceutically acceptable form thereof that activates phosphorylation of the MAPK p38 by 30% or more at 10 μM according to MAPK p38 Activation Assay. In some embodiments, the method comprises contacting the MAPK p38 with a compound or pharmaceutically acceptable form thereof that activates phosphorylation of the MAPK p38 by 75% or more at 10 μM according to MAPK p38 Activation Assay. In some embodiments, the method comprises contacting the MAPK p38 with a compound or pharmaceutically acceptable form thereof that activates phosphorylation of the MAPK p38 by about 100% or more at 10 μM according to MAPK p38 Activation Assay. In some embodiments, the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 52, 53, 54, 55, 56, 57, 58, 59, 60, 61, 62, 63, 64, 65, 66, 67, 69, 70, 71, 72, 93, and 218, or a pharmaceutically acceptable form thereof. In some embodiments, the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof. In some embodiments, the compound is selected from the group consisting of Compounds 1, 2, 3, 7, 8, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof.

In some embodiments of the methods provided herein, the contacting of the MAPK p38 protein takes place in a cell. In some embodiments, the cell is in a subject. In some embodiments, the cell is a mammalian cell. In some embodiments, the cell is a human cell.

Provided herein are methods of modulating IL-6 activity, comprising contacting a IL-6 protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof. Also provided herein are methods of modulating IL-6 activity, comprising contacting a IL-6 protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, as disclosed herein below. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In certain embodiments of the methods of of modulating IL-6 activity described herein, the method inhibits IL-6 activity. In some embodiments, the method comprises contacting the IL-6 protein with a compound or pharmaceutically acceptable form thereof that inhibits IL-6 activity by 75% or more at 10 μM according to IL-6 Quantification Assay. In some embodiments, the compound is selected from the group consisting of Compounds 1, 4, 6, 13, 19, 20, 22, 23, 27, 29, 30, 31, 32, 33, 34, 40, 42, 45, 46, 67, 81, 82, 85, 86, 89, 93, 99, 104, 105, 111, 113, 143, 149, 160, 161, 163, 164, 166, 173, 175, 176, 177, 192, 193, 194, 196, 199, 201, 203, 204, 206, 207, 208, 209, 210, 217, 219, 238, 247, 248, 249, 250, 257, 260, 263, 264, 265, 268, 269, 270, 271, 272, 273, and 274, or a pharmaceutically acceptable form thereof.

In some embodiments of the methods provided herein, the contacting of the IL-6 protein takes place in a cell. In some embodiments, the cell is in a subject. In some embodiments, the cell is a mammalian cell. In some embodiments, the cell is a human cell.

Provided herein are methods of modulating TNF-alpha activity, comprising contacting a TNF-alpha protein with an effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof. Also provided herein are methods of modulating TNF-alpha activity, comprising contacting a TNF-alpha protein with an effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, as disclosed herein below. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In certain embodiments of the methods of of modulating IL-6 activity described herein, the method inhibits TNF-alpha activity. In some embodiments, the method comprises contacting the TNF-alpha protein with a compound or pharmaceutically acceptable form thereof that inhibits TNF-alpha activity by 75% or more at 10 μM according to TNF-alpha Quantification Assay. In some embodiments, the compound is selected from the group consisting of Compounds 4, 23, 29, 30, 31, 32, 33, 42, 45, 46, 93, 99, 149, 166, 196, 203, 207, 209, 210, 219, 269, 270, 271, 272, 273, and 274, or a pharmaceutically acceptable form thereof.

In some embodiments of the methods provided herein, the contacting of the TNF-alpha protein takes place in a cell. In some embodiments, the cell is in a subject. In some embodiments, the cell is a mammalian cell. In some embodiments, the cell is a human cell.

3.4. Methods of Treating Cancer

Without being bound by theory, cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites. Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. (Roitt, I., Brostoff, J. and Kale, D., Immunology, 17.1-17.12 (3rd ed., Mosby, St. Louis, Mo., 1993))

Without being bound by theory, various stages of tumor development can be described generally as follows:

a) Tumor evolution commences when a cell within a normal population sustains a genetic mutation that expands its tendency to proliferate.

b) Such genetically altered cells and their offspring continue to appear normal, but they reproduce excessively and lead to a condition termed hyperplasia. The altered cells may also secrete signaling factors or other molecules that cause changes in their local cellular and extracellular environment, including without limitation, the response of the immune system to them. Such environmental effects may in turn affect the viability, proliferation, and further mutations of the altered cells. After some time (months or years) a very small fraction of these altered cells may sustain additional mutation with subsequent loss of control of cell growth and further potential effects on their environment.

c) The offspring of these cells not only proliferate excessively but also appear abnormal in shape and in orientation. The tissue is now said to exhibit a condition termed dysplasia. After some time, one or more additional mutations may further alter cell behavior and the effect of the cells on their environment.

d) The influenced and genetically altered cells turn still more abnormal in growth and appearance. If the tumor mass does not invade through any boundaries between tissues, it is termed an in situ tumor. This tumor may stay contained indefinitely, however, some cells may acquire still more mutations.

e) A malignant or invasive tumor results if the genetic changes allow the tumor mass to initiate invading underlying tissue and to cast off cells into the blood or lymph. The defector cells may install new tumors loci (metastases) throughout the body.

Without being bound by theory, metastases represent the end products of a multistep cell-biological process termed the invasion-metastasis cascade, which involves dissemination of cancer cells to anatomically distant organ sites and their subsequent adaptation to foreign tissue microenvironments. Each of these events is driven by the acquisition of genetic and/or epigenetic alterations within tumor cells and the co-option of non-neoplastic stromal cells, which together endow incipient metastatic cells with traits needed to generate macroscopic metastases. (Volastyan, S., et al., Cell, 2011, vol. 147, 275-292)

Without being bound by theory, an enormous variety of cancers affect different tissues throughout the body, which are described in detail in the medical literature. Over 85% of human cancers are solid tumors, including carcinomas, sarcomas and lymphomas. Different types of solid tumors are named for the type of cells that form them. Examples include cancer of the lung, colon, rectum, pancreatic, prostate, breast, brain, and intestine. Other human tumors derive from cells involved in the formation of immune cells and other blood cells, including leukemias and myelomas.

The incidence of cancer continues to climb as the general population ages, as new cancers develop, and as susceptible populations grow. A tremendous demand therefore exists for new methods and compositions that can be used to treat subjects with cancer.

Without being bound by theory, current cancer therapy may involve surgery, chemotherapy, hormonal therapy, biological therapy, targeted therapy, immunotherapy and/or radiation treatment to eradicate neoplastic cells in a patient (see, e.g., Stockdale, 1998, Medicine, vol. 3, Rubenstein and Federman, eds., Chapter 12, Section IV; and Baudino TA "Targeted Cancer Therapy: The Next Generation of Cancer Treatment", Curr Drug Discov Technol. 2015; 12 (1): 3-20).

Without being bound by theory, such therapies may be used independently or in combinations. Choices of therapy will depend on the history and nature of the cancer, the condition of the patient, and, under the circumstances, the anticipated efficacy and adverse effects of the therapeutic agents and methods considered.

Without being bound by theory, with respect to chemotherapy, there are a variety of chemotherapeutic agents and methods of delivery of such agents available for the treatment of different cancers. Most first generation chemotherapeutic agents were not tumor specific, have broad systemic effects, are toxic, and may cause significant and often dangerous side effects, including severe nausea, bone marrow depression, and immunosuppression.

Without being bound by theory, even with administration of combinations of chemotherapeutic agents, many tumor cells are or become resistant to chemotherapeutic agents. In fact, cells resistant to the particular chemotherapeutic agents used in a treatment protocol often prove to be resistant to other drugs, even if those agents act by different mechanism from those of the drugs used in the specific treatment. This phenomenon is referred to as multidrug resistance. Because of drug resistance, many cancers prove refractory to standard chemotherapeutic treatment protocols.

Thus, there exists a significant need for alternative compounds, compositions and methods for treating, preventing and managing cancer.

Without being bound by theory, whereas surgical resection and adjuvant therapy can cure well-confined primary tumors, metastatic disease is largely incurable because of its systemic nature and the resistance of disseminated tumor cells to existing therapeutic agents. This explains why greater than 90% of mortality from cancer is attributable to metastases, not the primary tumors from which these malignant lesions arise.

Provided herein are methods of treating cancer in a subject, comprising administering a therapeutically effective amount of the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, to the subject having cancer. Also provided herein are methods of treating cancer in a subject, comprising administering a therapeutically effective amount of a pharmaceutical comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, as disclosed herein below, to the subject having cancer. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In some embodiments of the methods of treating cancer provided herein, the method administering a compound or pharmaceutically acceptable form thereof that modulates the activity of one or more Ras superfamily protein. In some embodiments, the compound or pharmaceutically acceptable form thereof modulates Ras superfamily activity of one or more GTPase by 50% or more, 55% or more, 60% or more, 65% or more, 70% or more, 75% or more, 80% or more, 85% or more, 90% or more, or 95% or more at 20 μM according to a Ras Superfamily Activity Assay. In some embodiments, the compound or pharmaceutically acceptable form thereof inhibits the activity one or more Ras superfamily protein. In some embodiments, the compound or pharmaceutically acceptable form thereof modulates the activity of one or more Ras superfamily protein by 45% or more at 20 μM according to a Ras Superfamily Activity. In some embodiments, the compound or pharmaceutically acceptable form thereof modulates the activity of one or more Ras superfamily protein by 50% or more at 20 μM according to a Ras Superfamily Activity. In some embodiments, the compound is selected from the group consisting of Compounds 6, 17, 22, 32, 34, 37, 42, 43, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 126, 127, 135, 136, 137, 138, 139, 140, 141, 142, 143, 144, 145, 146, 147, 148, 149, 150, 151, 152, 153, 154, 156, 157, 158, 165, 166, 167, 169, 170, 172, 173, 174, 175, 176, 177, 178, 179, 186, 187, 188, 196, 200, 202, 208, 211, 212, 213, 214, 215, 216, 217, 220, 221, 222, 223, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof. In some embodiments, the compound is selected from the group consisting of Compounds 6, 17, 22, 37, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 127, 135, 136, 137, 138, 139, 140, 141, 142, 143, 144, 145, 146, 147, 149, 150, 151, 152, 153, 154, 156, 157, 158, 165, 166, 169, 170, 173, 175, 176, 177, 178, 179, 186, 187, 188, 196, 202, 208, 211, 212, 213, 214, 215, 216, 217, 221, 222, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof.

In some embodiments of the methods of treating cancer provided herein, the method administering a compound or pharmaceutically acceptable form thereof that modulates Erk1/2 activity. In some embodiments, the compound or pharmaceutically acceptable form thereof inhibits phosphorylation of the Erk1/2 protein. In some embodiments, the compound or pharmaceutically acceptable form thereof inhibits phosphorylation of Erk1/2 by 50% or more, 55% or more, 60% or more, 65% or more, 70% or more, 75% or more, 80% or more, 85% or more, 90% or more, or 95% or more at 10 μM according to Erk1/2 Phosphorylation Assay. In some embodiments, the compound or pharmaceutically acceptable form thereof inhibits phosphorylation of the Erk1/2 protein by 80% or more at 10 μM according to Erk1/2 Phosphorylation Assay. In some embodiments, the compound or pharmaceutically acceptable form thereof inhibits phosphorylation of the Erk1/2 protein by 85% or more at 10 μM according to Erk1/2 Phosphorylation Assay. In some embodiments, the compound is selected from the group consisting of Compounds 3, 4, 20, 23, 26, 29, 30, 31, 32, 33, 34, 36, 42, 43, 53, 58, 67, 93, 203, 209, 210, 219, 266, 269, 270, 271, 272, 273, and 274, or a pharmaceutically acceptable form thereof. In some embodiments, the compound is selected from the group consisting of Compounds 3, 4, 20, 23, 26, 29, 30, 31, 32, 33, 34, 42, 43, 53, 58, 67, 93, 203, 209, 210, 219, 266, 269, 270, 271, 272, 273, and 274, or a pharmaceutically acceptable form thereof. In some embodiments, the compound or pharmaceutically acceptable form thereof activates phosphorylation of the Erk1/2 protein. In some embodiments, the compound or pharmaceutically acceptable form thereof activates phosphorylation of Erk1/2 by 50% or more, 55% or more, 60% or more, 65% or more, 70% or more, 75% or more, 80% or more, 85% or more, 90% or more, 95% or more, or equal or greater than 100% at 10 μM according to Erk1/2 Phosphorylation Assay. In some embodiments, the compound or pharmaceutically acceptable form thereof activates phosphorylation of the Erk1/2 protein by 45% or more at 10 μM according to Erk1/2 Phosphorylation Assay. In some embodiments, the compound or pharmaceutically acceptable form thereof activates phosphorylation of the Erk1/2 protein by 50% or more at 10 μM according to Erk1/2 Phosphorylation Assay. In some embodiments, the compound is selected from the group consisting of Compounds 49, 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 130, 135, 136, 138, 143, 145, 148, 149, 151, 154, 156, 157, 165, 174, 175, 176, 177, 178, 179, 183, 190, 191, 192, 193, 194, 195, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof. In some embodiments, the compound is selected from the group consisting of Compounds 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 135, 136, 138, 143, 145, 148, 149, 151, 154, 156, 157, 165, 174, 175, 176, 177, 178, 179, 183, 190, 191, 192, 193, 194, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof.

In some embodiments of the methods of treating cancer provided herein, the method administering a compound or pharmaceutically acceptable form thereof that modulates Akt activity. In some embodiments, the compound or pharmaceutically acceptable form thereof inhibits phosphorylation of the Akt protein. In some embodiments, the compound or pharmaceutically acceptable form thereof inhibits phosphorylation of Akt by 50% or more, 55% or more, 60% or more, 65% or more, 70% or more, 75% or more, 80% or more, 85% or more, 90% or more, or 95% or more at 10 μM according to Akt Phosphorylation Assay. In some embodiments, the compound or pharmaceutically acceptable form thereof inhibits phosphorylation of the Akt protein by 85% or more at 10 μM according to Akt Phosphorylation Assay. In some embodiments, the compound is selected from the group consisting of Compounds 17, 20, 23, 25, 29, 30, 31, 32, 33, 34, 42, 203, 209, 210, 219, 270, 271, 272, 273, and 274, or a pharmaceutically acceptable form thereof. In some embodiments, the compound or pharmaceutically acceptable form thereof activates phosphorylation of the Akt protein. In some embodiments, the compound or pharmaceutically acceptable form thereof activates phosphorylation of Akt by 50% or more, 55% or more, 60% or more, 65% or more, 70% or more, 75% or more, 80% or more, 85% or more, 90% or more, 95% or more, or equal or greater than 100% at 10 μM according to Akt Phosphorylation Assay. In some embodiments, the compound or pharmaceutically acceptable form thereof activates phosphorylation of the Akt protein by 50% or more at 10 μM according to Akt Phosphorylation Assay. In some embodiments, the compound is selected from the group consisting of Compounds 1, 2, 18, 19, 21, 47, 48, 49, 50, 51, 57, 59, 60, 61, 62, 63, 64, 65, 66, 67, 68, 69, 70, 71, 72, 73, 74, 76, 77, 78, 79, 80, 81, 82, 83, 84, 85, 86, 87, 88, 89, 91, 93, 94, 95, 96, 97, 98, 100, 101, 102, 103, 104, 106, 107, 108, 109, 110, 111, 112, 113, 114, 115, 116, 118, 119, 122, 124, 125, 126, 127, 128, 129, 130, 135, 136, 137, 138, 143, 145, 149, 151, 156, 157, 158, 165, 166, 169, 170, 173, 174, 175, 176, 178, 179, 187, 190, 191, 192, 193, 194, 195, 196, 204, 205, 207, 208, 213, 217, 218, 221, 222, 224, 226, 227, 228, 229, 230, 231, 232, 233, 234, 235, 237, 238, 240, 241, 242, 243, 244, 245, 246, 247, 248, 249, 250, 252, 253, 254, 255, 256, 257, 259, 260, 263, 264, 265, 266, 267, 268, 275, and 276, or a pharmaceutically acceptable form thereof.

In some embodiments of the methods of treating cancer provided herein, the method administering a compound or pharmaceutically acceptable form thereof that modulates Smad2/3 activity. In some embodiments, the compound or pharmaceutically acceptable form thereof inhibits phosphorylation of the Smad2/3 protein. In some embodiments, the compound or pharmaceutically acceptable form thereof inhibits phosphorylation of Smad2/3 by 50% or more, 55% or more, 60% or more, 65% or more, 70% or more, 75% or more, 80% or more, 85% or more, 90% or more, or 95% or more at 10 μM according to Phospho-Smad2/3 Inhibition Assay. In some embodiments, the compound or pharmaceutically acceptable form thereof inhibits phosphorylation of the Smad2/3 protein by 80% or more at 10 μM according to Phospho-Smad2/3 Inhibition Assay. In some embodiments, the compound or pharmaceutically acceptable form thereof inhibits phosphorylation of the Smad2/3 protein by 85% or more at 10 μM according to Phospho-Smad2/3 Inhibition Assay. In some embodiments, the compound is selected from the group consisting of Compounds 27, 29, 30, 31, 32, 33, 36, 43, 44, 47, 51, 52, 55, 59, 85, 96, 97, 98, 99, 116, 141, 144, 156, 203, 205, 207, 208, 209, 210, 211, 214, 219, 230, 269, 272, 273, and 274, or a pharmaceutically acceptable form thereof. In some embodiments, the compound is selected from the group consisting of Compounds 29, 30, 31, 32, 33, 36, 44, 47, 59, 85, 97, 98, 99, 116, 141, 144, 156, 203, 205, 207, 208, 209, 210, 211, 214, 219, 230, 269, 272, 273, and 274, or a pharmaceutically acceptable form thereof. In some embodiments, the compound or pharmaceutically acceptable form thereof activates phosphorylation of the Smad2/3 protein. In some embodiments, the compound or pharmaceutically acceptable form thereof activates phosphorylation of Smad2/3 by 50% or more, 55% or more, 60% or more, 65% or more, 70% or more, 75% or more, 80% or more, 85% or more, 90% or more, 95% or more, or equal or greater than 100% at 10 μM according to Phospho-Smad2/3 Inhibition Assay. In some embodiments, the compound or pharmaceutically acceptable form thereof activates phosphorylation of the Smad2/3 protein by 50% or more at 10 μM according to Phospho-Smad2/3 Inhibition Assay. In some embodiments, the compound is selected from the group consisting of Compounds 56, 63, 84, 88, 89, 90, 95, 100, 101, 103, 104, 106, 108, 109, 111, 112, 113, 114, 129, 166, 173, 179, 183, 186, 216, 241, 247, 248, 250, 255, 256, 257, and 266, or a pharmaceutically acceptable form thereof.

In some embodiments of the methods of treating cancer provided herein, the method administering a compound or pharmaceutically acceptable form that modulates JNK activity. In some embodiments, the compound or pharmaceutically acceptable form thereof inhibits JNK by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to JNK Activation Assay. In some embodiments, the compound or pharmaceutically acceptable form thereof inhibits phosphorylation of the JNK protein. In some embodiments, the compound or pharmaceutically acceptable form thereof inhibits phosphorylation of the JNK protein by 30% or more at 10 μM according to JNK Activation Assay. In some embodiments, the compound or pharmaceutically acceptable form thereof inhibits phosphorylation of the JNK protein by 75% or more at 10 μM according to JNK Activation Assay. In some embodiments, the compound or pharmaceutically acceptable form thereof inhibits phosphorylation of the JNK protein by about 100% at 10 μM according to JNK Activation Assay. In some embodiments, the compound is selected from the group consisting of Compounds 29, 30, 32, 33, and 34, or a pharmaceutically acceptable form thereof. In some embodiments, the compound is selected from the group consisting of Compounds 29, 32, 33, and 34, or a pharmaceutically acceptable form thereof. In some embodiments, the compound is selected from the group consisting of Compounds 29, 32, and 34, or a pharmaceutically acceptable form thereof. In some embodiments, the compound or pharmaceutically acceptable form thereof activates phosphorylation of the JNK protein. In some embodiments, the compound or pharmaceutically acceptable form thereof activates JNK by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to JNK Activation Assay. In some embodiments, the compound or pharmaceutically acceptable form thereof activates phosphorylation of the JNK protein by 30% or more at 10 μM according to JNK Activation Assay. In some embodiments, the compound or pharmaceutically acceptable form thereof activates phosphorylation of the JNK protein by 75% or more at 10 μM according to JNK Activation Assay. In some embodiments, the compound or pharmaceutically acceptable form thereof activates phosphorylation of the JNK protein by about 100% or more at 10 μM according to JNK Activation Assay. In some embodiments, the compound is selected from the group consisting of Compounds 1, 2, 3, 4, 6, 7, 8, 9, 11, 13, 14, 15, 16, 18, 19, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof. In some embodiments, the compound is selected from the group consisting of Compounds 3, 4, 6, 7, 11, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof. In some embodiments, the compound is selected from the group consisting of Compounds 3, 6, 7, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof.

In some embodiments of the methods of treating cancer provided herein, the method administering a compound or pharmaceutically acceptable form thereof that modulates MAPK p38 activity. In some embodiments, the compound or pharmaceutically acceptable form thereof inhibits phosphorylation of the MAPK p38 protein. In some embodiments, the compound or pharmaceutically acceptable form thereof inhibits MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to MAPK p38 Activation Assay. In some embodiments, the compound or pharmaceutically acceptable form thereof inhibits phosphorylation of the MAPK p38 by 30% or more at 10 μM according to MAPK p38 Activation Assay. In some embodiments, the compound or pharmaceutically acceptable form thereof inhibits phosphorylation of the MAPK p38 by about 100% at 10 μM according to MAPK p38 Activation Assay. In some embodiments, the compound is selected from the group consisting of Compounds 29, 30, 32, 33, 34, 46, 47, 188, 196, 197, 203, 205, 207, 208, 209, 210, 212, 213, 214, 215, 217, and 220, or a pharmaceutically acceptable form thereof. In some embodiments, the compound is selected from the group consisting of Compounds 29, 32, 33, 34, 46, 207, and 209, or a pharmaceutically acceptable form thereof. In some embodiments, the compound or pharmaceutically acceptable form thereof activates phosphorylation of the MAPK p38 protein. In some embodiments, the compound or pharmaceutically acceptable form thereof activates MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to MAPK p38 Activation Assay. In some embodiments, the compound or pharmaceutically acceptable form thereof activates phosphorylation of the MAPK p38 by 30% or more at 10 μM according to MAPK p38 Activation Assay. In some embodiments, the compound or pharmaceutically acceptable form thereof activates phosphorylation of the MAPK p38 by 75% or more at 10 μM according to MAPK p38 Activation Assay. In some embodiments, the compound or pharmaceutically acceptable form thereof activates phosphorylation of the MAPK p38 by about 100% or more at 10 μM according to MAPK p38 Activation Assay. In some embodiments, the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 52, 53, 54, 55, 56, 57, 58, 59, 60, 61, 62, 63, 64, 65, 66, 67, 69, 70, 71, 72, 93, and 218, or a pharmaceutically acceptable form thereof. In some embodiments, the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof. In some embodiments, the compound is selected from the group consisting of Compounds 1, 2, 3, 7, 8, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof.

In some embodiments, the compounds disclosed herein inhibit cell proliferation, such as inhibit cell proliferation in a cell viability assay. In some embodiments, the anti-proliferative activity of the compounds disclosed herein are administered according to the methods of treating disclosed herein to treat cancer, including solid, soft and blood-born tumors. In some embodiments of the methods of treating cancer provided herein, the method administering a compound or pharmaceutically acceptable form thereof that inhibits proliferation in MiaPaca2. In some embodiments, the compound or pharmaceutically acceptable form thereof inhibits proliferation in MiaPaca2 with an IC50 value of 1.25 μM or less, 1.1 μM or less, 1 μM or less, 0.9 μM or less, 0.8 μM or less, 0.75 μM or less, 0.7 μM or less, 0.6 μM or less, 0.5 μM or less, 0.4 μM or less, 0.3 μM or less, 0.25 μM or less, 0.2 μM or less, 0.15 μM or less, or 0.1 μM or less according to Proliferation Assay. In some embodiments, the compound or pharmaceutically acceptable form thereof inhibits proliferation in MiaPaca2 with an IC50 value of 1.1

μM or less according to Proliferation Assay. In some embodiments, the compound or pharmaceutically acceptable form thereof inhibits proliferation in MiaPaca2 with an IC50 value of 1.0 μM or less according to Proliferation Assay. In some embodiments, the compound or pharmaceutically acceptable form thereof inhibits proliferation in MiaPaca2 with an IC50 value of 0.60 μM or less according to Proliferation Assay. In some embodiments, the compound or pharmaceutically acceptable form thereof inhibits proliferation in MiaPaca2 with an IC50 value of 0.15 μM or less according to Proliferation Assay. In some embodiments, the compound is selected from the group consisting of Compounds 6, 13, 22, 26, 29, 30, 32, 33, 34, 42, 45, 46, 48, 49, 50, 53, 54, 55, 56, 57, 58, 59, 61, 62, 63, 64, 65, 68, 72, 73, 74, 76, 78, 79, 81, 82, 83, 84, 86, 89, 91, 93, 94, 95, 96, 97, 98, 100, 101, 102, 104, 105, 106, 107, 108, 109, 110, 111, 112, 113, 114, 115, 116, 117, 118, 119, 120, 121, 122, 123, 124, 125, 126, 127, 128, 129, 135, 136, 137, 138, 139, 140, 141, 142, 143, 144, 145, 146, 149, 156, 157, 158, 165, 169, 170, 173, 174, 175, 176, 196, 203, 209, 210, 213, 214, 217, 219, 221, 222, 224, 226, 227, 228, 229, 230, 231, 232, 233, 234, 235, 236, 237, 238, 239, 240, 243, 244, 245, 246, 247, 248, 249, 250, 252, 253, 255, 257, 263, 264, 265, 266, 267, 268, 269, 270, 271, 274, and 276, or a pharmaceutically acceptable form thereof. In some embodiments, the compound is selected from the group consisting of Compounds 6, 13, 22, 26, 29, 30, 32, 33, 34, 42, 48, 49, 50, 53, 54, 55, 56, 57, 58, 59, 61, 62, 63, 64, 65, 68, 72, 73, 74, 76, 78, 79, 81, 82, 83, 84, 86, 89, 91, 93, 94, 95, 96, 97, 98, 100, 101, 102, 104, 105, 106, 107, 108, 109, 110, 111, 112, 113, 114, 115, 116, 117, 118, 120, 122, 123, 124, 125, 126, 127, 128, 129, 135, 136, 137, 138, 139, 140, 141, 142, 143, 144, 145, 146, 149, 156, 157, 158, 165, 169, 170, 173, 174, 175, 176, 196, 203, 209, 210, 213, 217, 219, 221, 222, 224, 226, 227, 228, 229, 230, 231, 232, 233, 234, 235, 236, 237, 238, 239, 240, 243, 244, 245, 246, 247, 248, 249, 250, 252, 253, 255, 257, 263, 264, 265, 266, 267, 268, 269, 270, 271, 274, and 276, or a pharmaceutically acceptable form thereof. In some embodiments, the compound is selected from the group consisting of Compounds 6, 13, 22, 32, 34, 48, 49, 50, 53, 54, 55, 56, 57, 58, 59, 62, 63, 64, 65, 68, 73, 74, 76, 78, 79, 81, 82, 83, 84, 86, 89, 91, 93, 94, 95, 96, 97, 98, 100, 101, 102, 104, 106, 107, 110, 111, 112, 113, 114, 115, 116, 117, 118, 120, 122, 123, 124, 125, 126, 127, 128, 129, 135, 136, 137, 138, 139, 140, 141, 142, 143, 144, 145, 146, 156, 157, 158, 165, 169, 170, 174, 175, 196, 209, 221, 222, 224, 226, 227, 228, 229, 230, 231, 232, 233, 234, 235, 236, 237, 238, 239, 240, 243, 244, 245, 246, 247, 248, 249, 250, 252, 255, 257, 263, 264, 265, 266, 267, 268, 270, 271, 274, and 276, or a pharmaceutically acceptable form thereof. In some embodiments, the compound is selected from the group consisting of Compounds 6, 48, 49, 50, 53, 54, 55, 57, 58, 62, 63, 64, 65, 68, 73, 76, 79, 82, 84, 89, 91, 94, 95, 97, 98, 100, 102, 104, 106, 107, 110, 112, 113, 114, 115, 117, 118, 120, 122, 123, 124, 126, 127, 128, 129, 135, 136, 137, 138, 139, 140, 141, 142, 143, 144, 145, 156, 157, 158, 165, 169, 170, 196, 221, 222, 224, 226, 227, 228, 230, 231, 232, 233, 234, 235, 236, 237, 238, 239, 240, 243, 244, 245, 248, 249, 250, 252, 255, 257, 263, 265, 266, 267, and 268, or a pharmaceutically acceptable form thereof.

In some embodiments of the methods provided herein, the cancer is a solid tumor. In some embodiments, the cancer is a blood borne tumor (or a hematological cancer). In some embodiments, the cancer is hepatocellular carcinoma, prostate cancer, pancreatic cancer, lung cancer, breast cancer, ovarian cancer, colon cancer, small intestine cancer, biliary tract cancer, endometrium cancer, skin cancer (melanoma), cervix cancer, urinary tract cancer, glioblastoma, or multiple myeloma. In some embodiments, the cancer is pancreatic cancer. In some embodiments, the cancer is colon cancer. In some embodiments, the cancer is triple negative breast cancer. In some embodiments, the cancer is multiple myeloma.

In some embodiments of the methods provided herein, the cancer is a cancer dependent on a Ras superfamily protein. In some embodiments, the Ras superfamily protein is a Ras protein, or a mutant thereof. In some embodiments, the Ras protein is DIRAS I; DIRAS2; DIRAS3; ERAS; GEM; HRAS; KRAS; MRAS; NKIRASI; NKIRAS2; NRAS; RALA; RALB; RAP1A; RAP1B; RAP2A; RAP2B; RAP2C; RASD1; RASD2; RASLIOA; RASLIOB; RASLI IA; RASLIIB; RASL 12; REMI; REM2; RERG; RERGL; RRAD; RRAS; or RRAS2. In some embodiments, the Ras protein is HRAS; KRAS; or NRAS, or a mutant thereof. In some embodiments, the Ras protein is a KRAS mutant. In some embodiments, the KRAS mutant is a KRas G12D mutant, KRas G12C mutant, or KRas Q61H mutant. In some embodiments, the Ras protein is HRAS or a mutant thereof. In some embodiments, the Ras protein is NRAS or a mutant thereof. In some embodiments, the Ras superfamily protein is a Rac protein, or a mutant thereof. In some embodiments, the Rac protein is RAC1; RAC2; RAC3; RHOG, or a mutant thereof. In some embodiments, the the Rac protein is wild-type RAC1. In some embodiments, the Ras superfamily protein is a Rho protein, or a mutant thereof. In some embodiments, the Rho protein is RHOA; RHOB; RHOBTB1; RHOBTB2; RHOBTB3; RHOC; RHOD; RHOF; RHOH; RHOJ; RHOQ; RHOU; RHOV; RND1; RND2; RND3; CDC42, or a mutant thereof. In some embodiments, the Rho protein is wild-type RHOA. In some embodiments, the Ras superfamily protein is a Cdc42 protein, or a mutant thereof. In some embodiments, the Ras superfamily protein is a Rheb protein, or a mutant thereof.

In some embodiments of the methods provided herein, the administration activates caspase activity in a cancerous cell of the subject. In some embodiments, the activation induces apoptosis of the cancerous cell. In some embodiments, the subject is a human.

Also provided herein are methods of treating subjects who have been previously treated for cancer but are non-responsive to standard therapies, as well as those who have not previously been treated. Also provided are methods of treating subjects regardless of subject's age, although some diseases or disorders are more common in certain age groups. Also provided are methods of treating subjects who have undergone surgery in an attempt to treat the disease or condition at issue, as well as those who have not. Because subjects with cancer have heterogeneous clinical manifestations and varying clinical outcomes, the treatment given to a subject may vary, depending on his/her prognosis. The skilled clinician will be able to readily determine without undue experimentation specific secondary agents, types of surgery, and types of non-drug based standard therapy that can be effectively used to treat an individual subject with cancer.

As used herein, the term "cancer" includes, but is not limited to, solid tumors and blood borne tumors. The term "cancer" refers to disease of skin tissues, organs, blood, and vessels, including, but not limited to, cancers of the bladder, bone, blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, pancreatic cancer, lung cancer, breast cancer, ovarian cancer, colon cancer, small intestine cancer, biliary tract cancer, endometrium cancer, skin cancer (melanoma), cervix cancer, urinary tract cancer, glioblastoma, or multiple myeloma.

In certain embodiments, the cancer is a blood borne tumor (or a hematological cancer). In certain embodiments, the blood borne tumor is metastatic. In certain embodiments, the blood borne tumor is drug resistant. In certain embodiments, the cancer is leukemia. In certain embodiments, the cancer is multiple myeloma.

In one embodiment, methods provided herein encompass treating, preventing or managing various types of leukemias such as chronic lymphocytic leukemia (CLL), chronic myelocytic leukemia (CML), acute lymphoblastic leukemia (ALL), acute myeloid leukemia (AML), and acute myeloblastic leukemia (AML) by administering a therapeutically effective amount of a compound provided herein or a derivative thereof.

In some embodiments, the methods provided herein encompass treating, preventing or managing acute leukemia in a subject. In some embodiments, the acute leukemia is acute myeloid leukemia (AML), which includes, but is not limited to, undifferentiated AML (M0), myeloblastic leukemia (M1), myeloblastic leukemia (M2), promyelocytic leukemia (M3 or M3 variant (M3V)), myelomonocytic leukemia (M4 or M4 variant with eosinophilia (M4E)), monocytic leukemia (M5), erythroleukemia (M6), and megakaryoblastic leukemia (M7). In one embodiment, the acute myeloid leukemia is undifferentiated AML (M0). In one embodiment, the acute myeloid leukemia is myeloblastic leukemia (M1). In one embodiment, the acute myeloid leukemia is myeloblastic leukemia (M2). In one embodiment, the acute myeloid leukemia is promyelocytic leukemia (M3 or M3 variant (M3V)). In one embodiment, the acute myeloid leukemia is myelomonocytic leukemia (M4 or M4 variant with eosinophilia (M4E)). In one embodiment, the acute myeloid leukemia is monocytic leukemia (M5). In one embodiment, the acute myeloid leukemia is erythroleukemia (M6). In one embodiment, the acute myeloid leukemia is megakaryoblastic leukemia (M7). Thus, the methods of treating, preventing or managing acute myeloid leukemia in a subject comprise the step of administering to the subject an amount of a compound provided herein or a derivative thereof effective to treat, prevent or manage acute myeloid leukemia alone or in combination. In some embodiments, the methods comprise the step of administering to the subject a compound provided herein or a derivative thereof in combination with a second active agent in amounts effective to treat, prevent or manage acute myeloid leukemia.

In some embodiments, the methods provided herein encompass treating, preventing or managing acute lymphocytic leukemia (ALL) in a subject. In some embodiments, acute lymphocytic leukemia includes leukemia that originates in the blast cells of the bone marrow (B-cells), thymus (T-cells), and lymph nodes. The acute lymphocytic leukemia can be categorized according to the French-American-British (FAB) Morphological Classification Scheme as L1—Mature-appearing lymphoblasts (T cells or pre-B-cells), L2—Immature and pleomorphic (variously shaped) lymphoblasts (T-cells or pre-B-cells), and L3—Lymphoblasts (B-cells; Burkitt's cells). In one embodiment, the acute lymphocytic leukemia originates in the blast cells of the bone marrow (B-cells). In one embodiment, the acute lymphocytic leukemia originates in the thymus (T-cells). In one embodiment, the acute lymphocytic leukemia originates in the lymph nodes. In one embodiment, the acute lymphocytic leukemia is L1 type characterized by mature-appearing lymphoblasts (T-cells or pre-B-cells). In one embodiment, the acute lymphocytic leukemia is L2 type characterized by immature and pleomorphic (variously shaped) lymphoblasts (T-cells or pre-B-cells). In one embodiment, the acute lymphocytic leukemia is L3 type characterized by lymphoblasts (B-cells; Burkitt's cells). In certain embodiments, the acute lymphocytic leukemia is T cell leukemia. In one embodiment, the T-cell leukemia is peripheral T-cell leukemia. In another embodiment, the T-cell leukemia is T-cell lymphoblastic leukemia. In another embodiment, the T-cell leukemia is cutaneous T-cell leukemia. In another embodiment, the T-cell leukemia is adult T-cell leukemia. Thus, the methods of treating, preventing or managing acute lymphocytic leukemia in a subject comprise the step of administering to the subject an amount of a compound provided herein or a derivative thereof effective to treat, prevent or manage acute lymphocytic leukemia alone or in combination with a second active agent. In some embodiments, the methods comprise the step of administering to the subject a compound provided herein or a derivative thereof in combination with a second active agent in amounts effective to treat, prevent or manage acute lymphocytic leukemia.

In some embodiments, the methods provided herein encompass treating, preventing or managing chronic myelogenous leukemia (CML) in a subject. The methods comprise the step of administering to the subject an amount of a compound provided herein or a derivative thereof effective to treat, prevent or manage chronic myelogenous leukemia. In some embodiments, the methods comprise the step of administering to the subject a compound provided herein or a derivative thereof in combination with a second active agent in amounts effective to treat, prevent or manage chronic myelogenous leukemia.

In some embodiments, the methods provided herein encompass treating, preventing or managing chronic lymphocytic leukemia (CLL) in a subject. The methods comprise the step of administering to the subject an amount of a compound provided herein or a derivative thereof effective to treat, prevent or manage chronic lymphocytic leukemia. In some embodiments, the methods comprise the step of administering to the subject a compound provided herein or a derivative thereof in combination with a second active agent in amounts effective to treat, prevent or manage chronic lymphocytic leukemia.

In certain embodiments, provided herein are methods of treating, preventing, and/or managing disease in subjects with impaired renal function. In certain embodiments, provided herein are method of treating, preventing, and/or managing cancer in subjects with impaired renal function. In certain embodiments, provided herein are methods of providing appropriate dose adjustments for subjects with impaired renal function due to, but not limited to, disease, aging, or other subject factors.

In certain embodiments, provided herein are methods of treating, preventing, and/or managing lymphoma, including non-Hodgkin's lymphoma. In some embodiments, provided herein are methods for the treatment or management of non-Hodgkin's lymphoma (NHL), including but not limited to, diffuse large B-cell lymphoma (DLBCL), using prognostic factors.

In certain embodiments, provided herein are methods of treating, preventing, and/or managing multiple myeloma, including relapsed/refractory multiple myeloma in subjects with impaired renal function or a symptom thereof, comprising administering a therapeutically effective amount of a compound provided herein, or a derivative thereof to a subject having relapsed/refractory multiple myeloma with impaired renal function.

In certain embodiments, the subject to be treated with one of the methods provided herein has not been treated with anticancer therapy prior to the administration of the compound provided herein, or a derivative thereof. In certain embodiments, the subject to be treated with one of the methods provided herein has been treated with anticancer therapy prior to the administration of the compound provided herein, or a derivative thereof. In certain embodiments, the subject to be treated with one of the methods provided herein has developed drug resistance to the anticancer therapy.

The methods provided herein encompass treating a patient regardless of subject's age, although some diseases or disorders are more common in certain age groups.

As discussed herein, Ras signaling is causally implicated in rasopathies. Thus, the compounds provided herein, which inhibit the function of one or more members of the Ras superfamily, are useful in the treatment of rasopathies including neurofibromatosis type 1, Noonan's syndrome, and Costello syndrome.

3.5. Methods of Treating Fibrosis

Fibrosis, or the accumulation of extracellular matrix molecules that constitute scar tissue, is a common result of tissue injury. Fibrosis can occur in many tissues within the body, typically as a result of inflammation or damage. Pulmonary fibrosis, renal fibrosis, and hepatic cirrhosis are among the common fibrotic diseases which altogether represent a large unmet medical need. (Friedman S L, Sheppard D, Duffield J S, Violette S. Sci Transl Med 2013 Jan. 9; 5(167): 167sr1).

Without being bound by theory, fibrosis, also known as fibrotic scarring, is a pathological wound healing process in which connective tissue replaces normal parenchymal tissue, leading to considerable tissue re-modeling and the formation of permanent scar tissue. Repeated injuries, chronic inflammation and repair are susceptible to fibrosis where excessive extracellular matrix (ECM) components, such as collagen and glycosaminoglycans, accumulate and lead to the formation of a permanent fibrotic scar which can interfere with normal organ and tissue functions. Mechanisms of fibrogenesis include inflammation as well as other pathways and generally involve reorganization of the actin cytoskeleton of affected cells, including epithelial cells, fibroblasts, endothelial cells, and macrophages.

Without being bound by theory, actin filament assembly and actomyosin contraction are directed by the Rho-associated coiled-coil forming protein kinase (ROCK) family of serine/threonine kinases (ROCK1 and ROCK2) and thus Rho is associated with fibrogenesis.

Tissue fibrosis is a leading cause of morbidity and mortality. 45% of deaths in the United States are attributable to fibrotic disorders. (Wynn TA. "Fibrotic Disease and the TH1/TH2 Paradigm." Nat Rev Immunol 2004 August: 4 (8): 583-594.) Treatments are generally palliative.

Without being bound by theory, idiopathic pulmonary fibrosis (IPF) is characterized by progressive lung scarring, short median survival, and limited therapeutic options, creating great need for new pharmacologic therapies. It is thought to result from repetitive environmental injury to the lung epithelium.

As noted above, fibrosis can occur in many tissues within the body, typically as a result of inflammation or damage. Examples include: fibrosis of kidney, fibrosis of cardiovascular system, pulmonary fibrosis, cystic fibrosis, idiopathic fibrosis, fibrosis of the lung, bridging fibrosis, fibrosis of the liver, fibrosis of the intestine, fibrosis of the muscular system, fibrosis of the brain, fibrosis of the joints, fibrosis of the skin, fibrosis of the bone marrow, fibrosis of the heart, fibrosis of the soft tissue, fibrosis of the tendons, fibrosis of the lymph nodes, fibrosis of the eyes, retroperitoneum, scleroderma and surgical scarring.

Without being bound by theory, the process of tissue repair is a complex one, with tight regulation of ECM synthesis and degradation ensuring maintenance of normal tissue architecture. However, the process can lead to a progressive irreversible fibrotic response if tissue injury is severe or repetitive, or if the wound healing response itself becomes deregulated. Fibrosis is initiated when immune cells such as macrophages and damaged tissue between surfaces called interstitium release soluble factors that stimulate fibroblasts. The best characterized pro-fibrotic mediators are the transforming growth factor-β (TGF-β ligands such as TGF-β1, —β2 and -β3, bone morphogenetic proteins (BMPs), and Activin.

Without being bound by theory, the pro-fibrotic TGF-β and its related ligands bind a heteromeric complex of type I and type II trans-membrane TGF-β receptors, each equipped with an intracellular kinase domain. Upon ligand binding the type II receptor kinases phosphorylate and thereby activate the type I receptors, which are also known as activin receptor-like kinases (ALKs). Downstream of this activated complex, a canonical signaling pathway is composed of the Smad family of transcription factors, among which Smad2 and Smad3 are phosphorylated and activated by type I TGF-β receptors. Activated Smad2/3 (RSmads) form a trimeric complex with Smad4 that translocates to the nucleus to regulate target gene expression.

Without being bound by theory, other soluble mediators of fibrosis include connective tissue growth factor (CTGF), platelet-derived growth factor (PDGF), and interleukin 10 (IL-10).

Without being bound by theory, inhibition of the TGF-β1 signaling pathway and Smad2 and 3 phosphorylation and activation represent potential therapeutic approaches for treating fibrosis.

Duchenne muscular dystrophy (DMD) is a genetic disorder characterized by progressive muscle degeneration and weakness due to the alterations of a protein called dystrophin that helps keep muscle cells intact. DMD is one of four conditions known as dystrophinopathies. Three diseases that belong to this group are Becker Muscular Dystrophy (BMD, a mild form of DMD); an intermediate clinical presentation between DMD and BMD; and DMD-associated dilated cardiomyopathy (heart-disease) with little or no clinical skeletal, or voluntary, muscle disease.

DMD primarily affects boys, but in rare cases it can affect girls. In Europe and North America, the prevalence of DMD is approximately 6 per 100,000 individuals.

Muscle weakness is the principal symptom of DMD. Symptom onset is in early childhood, usually between ages 2 and 3. The disease first affects the proximal muscles, and later the distal limb muscles. Usually, the lower external muscles are affected before the upper external muscles. Later on, the heart and respiratory muscles are affected. Progressive weakness and scoliosis result in impaired pulmonary function, which can eventually cause acute respiratory failure. Becker muscular dystrophy (BMD) is a similar to DMD, but with onset usually in the teens or early adulthood. The disease course for BMD is slower and less predictable compared to DMD.

DMD was first described by the French neurologist Guillaume Benjamin Amand Duchenne in the 1860s, but until the 1980s little was known about the cause of any kind of muscular dystrophy. In 1986, researchers identified a particular gene on the X chromosome that, when mutated, leads to DMD. In 1987, the protein associated with this gene was identified and named dystrophin. Lack of wild type dystrophin protein in muscle cells causes them to be fragile and easily damaged. DMD has an X-linked recessive inheritance pattern and is passed on by the mother, who is referred to as a carrier.

Until relatively recently, boys with DMD usually did not survive much beyond their teen years. Thanks to advances in cardiac and respiratory care, and targeted therapeutic products, life expectancy is increasing and survival into the early 30 s is becoming more common but there is still an unmet need for therapeutics to reduce morbidity and lengthen lifespans.

Without being bound by theory, when skeletal muscle is unable to regenerate due to DMD, damaged muscle is eventually replaced with fibrotic tissue. Development of this fibrosis is partially mediated by the TGF-β1 signaling pathway, which, therefore may be a therapeutic target for DMD.

Without being bound by theory, a growing number of published studies also suggest that pharmacological activation of the stress-activated MAPK proteins p-38 MAPK and c-Jun $NH_2$-terminal kinase (JNK) may also represent a therapeutic approach for the treatment of DMD related fibrosis.

Without being bound by theory, targeted therapies are a cornerstone of what is also referred to as precision medicine, a form of medicine that uses information about a person's genes and proteins to prevent, diagnose, and treat disease. Such therapeutics are sometimes called "molecularly targeted drugs," "molecularly targeted therapies," or similar names. The process of discovering them is often referred to as "rational drug design." This concept can also be referred to as "personalized medicine."

Without being bound by theory, a series of actions among molecules in a cell that leads to a certain end point or cell function is referred to as a molecular pathway.

Without being bound by theory, molecularly targeted drugs interact with a particular target molecule, or structurally related set of target molecules, in a pathway; thus modulating the endpoint effect of that pathway, such as a disease-related process; and, thus, yielding a therapeutic benefit.

Without being bound by theory, molecularly targeted drugs may be small molecules or biologics, usually antibodies. They may be useful alone or in combinations with other therapeutic agents and methods.

Without being bound by theory, because they target a particular molecule, or related set of molecules, and are usually designed to minimize their interactions with other molecules, targeted therapeutics may have fewer adverse side effects.

Without being bound by theory, some treatments for fibrotic disorders, such as idiopathic pulmonary fibrosis, hepatic fibrosis, and systemic sclerosis, target inflammatory pathways.

Provided herein are methods of treating a fibrotic disease in a subject, comprising administering a therapeutically effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, to the subject. Also provided herein are methods treating a fibrotic disease in a subject, comprising administering a therapeutically effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, to the subject. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In some embodiments of the methods of treating a fibrotic disease provided herein, the method administering a compound or pharmaceutically acceptable form thereof that modulates the activity of one or more Ras superfamily protein. In some embodiments, the compound or pharmaceutically acceptable form thereof modulates Ras superfamily activity of one or more GTPase by 50% or more, 55% or more, 60% or more, 65% or more, 70% or more, 75% or more, 80% or more, 85% or more, 90% or more, or 95% or more at 20 μM according to a Ras Superfamily Activity Assay. In some embodiments, the compound or pharmaceutically acceptable form thereof inhibits the activity one or more Ras superfamily protein. In some embodiments, the compound or pharmaceutically acceptable form thereof modulates the activity of one or more Ras superfamily protein by 45% or more at 20 μM according to a Ras Superfamily Activity. In some embodiments, the compound or pharmaceutically acceptable form thereof modulates the activity of one or more Ras superfamily protein by 50% or more at 20 μM according to a Ras Superfamily Activity. In some embodiments, the compound is selected from the group consisting of Compounds 6, 17, 22, 32, 34, 37, 42, 43, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 126, 127, 135, 136, 137, 138, 139, 140, 141, 142, 143, 144, 145, 146, 147, 148, 149, 150, 151, 152, 153, 154, 156, 157, 158, 165, 166, 167, 169, 170, 172, 173, 174, 175, 176, 177, 178, 179, 186, 187, 188, 196, 200, 202, 208, 211, 212, 213, 214, 215, 216, 217, 220, 221, 222, 223, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof. In some embodiments, the compound is selected from the group consisting of Compounds 6, 17, 22, 37, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 127, 135, 136, 137, 138, 139, 140, 141, 142, 143, 144, 145, 146, 147, 149, 150, 151, 152, 153, 154, 156, 157, 158, 165, 166, 169, 170, 173, 175, 176, 177, 178, 179, 186, 187, 188, 196, 202, 208, 211, 212, 213, 214, 215, 216, 217, 221, 222, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof.

In some embodiments of the methods of treating a fibrotic disease provided herein, the method administering a compound or pharmaceutically acceptable form thereof that modulates Erk1/2 activity. In some embodiments, the compound or pharmaceutically acceptable form thereof inhibits phosphorylation of the Erk1/2 protein. In some embodiments, the compound or pharmaceutically acceptable form thereof inhibits phosphorylation of Erk1/2 by 50% or more, 55% or more, 60% or more, 65% or more, 70% or more, 75% or more, 80% or more, 85% or more, 90% or more, or 95% or more at 10 μM according to Erk1/2 Phosphorylation Assay. In some embodiments, the compound or pharmaceutically acceptable form thereof inhibits phosphorylation of the Erk1/2 protein by 80% or more at 10 μM according to Erk1/2 Phosphorylation Assay. In some embodiments, the compound or pharmaceutically acceptable form thereof inhibits phosphorylation of the Erk1/2 protein by 85% or more at 10 μM according to Erk1/2 Phosphorylation Assay. In some embodiments, the compound is selected from the group consisting of Compounds 3, 4, 20, 23, 26, 29, 30, 31, 32, 33, 34, 36, 42, 43, 53, 58, 67, 93, 203, 209, 210, 219, 266, 269, 270, 271, 272, 273, and 274, or a pharmaceutically acceptable form thereof. In some embodiments, the compound is selected from the group consisting of Compounds 3, 4, 20, 23, 26, 29, 30, 31, 32, 33, 34, 42, 43, 53, 58, 67, 93, 203, 209, 210, 219, 266, 269, 270, 271, 272, 273, and 274, or a pharmaceutically acceptable form thereof. In some embodiments, the compound or pharmaceutically acceptable form thereof activates phosphorylation of the Erk1/2 protein. In some embodiments, the compound or pharmaceutically acceptable form thereof activates phosphorylation of Erk1/2 by 50% or more, 55% or more, 60% or more, 65% or more, 70% or more, 75% or more, 80% or more, 85% or more, 90% or more, 95% or more, or equal or greater than 100% at 10 μM according to Erk1/2 Phosphorylation Assay. In some embodiments, the compound or pharmaceutically acceptable form thereof activates phosphorylation of the Erk1/2 protein by 45% or more at 10 μM according to Erk1/2 Phosphorylation Assay. In some embodiments, the compound or pharmaceutically acceptable form thereof activates phosphorylation of the Erk1/2 protein by 50% or more at 10 μM according to Erk1/2 Phosphorylation Assay. In some embodiments, the compound is selected from the group consisting of Compounds 49, 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 130, 135, 136, 138, 143, 145, 148, 149, 151, 154, 156, 157, 165, 174, 175, 176, 177, 178, 179, 183, 190, 191, 192, 193, 194, 195, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof. In some embodiments, the compound is selected from the group consisting of Compounds 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 135, 136, 138, 143, 145, 148, 149, 151, 154, 156, 157, 165, 174, 175, 176, 177, 178, 179, 183, 190, 191, 192, 193, 194, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof.

In some embodiments of the methods of treating a fibrotic disease provided herein, the method administering a compound or pharmaceutically acceptable form thereof that modulates Akt activity. In some embodiments, the compound or pharmaceutically acceptable form thereof inhibits phosphorylation of the Akt protein. In some embodiments, the compound or pharmaceutically acceptable form thereof inhibits phosphorylation of Akt by 50% or more, 55% or more, 60% or more, 65% or more, 70% or more, 75% or more, 80% or more, 85% or more, 90% or more, or 95% or more at 10 μM according to Akt Phosphorylation Assay. In some embodiments, the compound or pharmaceutically acceptable form thereof inhibits phosphorylation of the Akt protein by 85% or more at 10 μM according to Akt Phosphorylation Assay. In some embodiments, the compound is selected from the group consisting of Compounds 17, 20, 23, 25, 29, 30, 31, 32, 33, 34, 42, 203, 209, 210, 219, 270, 271, 272, 273, and 274, or a pharmaceutically acceptable form thereof. In some embodiments, the compound or pharmaceutically acceptable form thereof activates phosphorylation of the Akt protein. In some embodiments, the compound or pharmaceutically acceptable form thereof activates phosphorylation of Akt by 50% or more, 55% or more, 60% or more, 65% or more, 70% or more, 75% or more, 80% or more, 85% or more, 90% or more, 95% or more, or equal or greater than 100% at 10 μM according to Akt Phosphorylation Assay. In some embodiments, the compound or pharmaceutically acceptable form thereof activates phosphorylation of the Akt protein by 50% or more at 10 μM according to Akt Phosphorylation Assay. In some embodiments, the compound is selected from the group consisting of Compounds 1, 2, 18, 19, 21, 47, 48, 49, 50, 51, 57, 59, 60, 61, 62, 63, 64, 65, 66, 67, 68, 69, 70, 71, 72, 73, 74, 76, 77, 78, 79, 80, 81, 82, 83, 84, 85, 86, 87, 88, 89, 91, 93, 94, 95, 96, 97, 98, 100, 101, 102, 103, 104, 106, 107, 108, 109, 110, 111, 112, 113, 114, 115, 116, 118, 119, 122, 124, 125, 126, 127, 128, 129, 130, 135, 136, 137, 138, 143, 145, 149, 151, 156, 157, 158, 165, 166, 169, 170, 173, 174, 175, 176, 178, 179, 187, 190, 191, 192, 193, 194, 195, 196, 204, 205, 207, 208, 213, 217, 218, 221, 222, 224, 226, 227, 228, 229, 230, 231, 232, 233, 234, 235, 237, 238, 240, 241, 242, 243, 244, 245, 246, 247, 248, 249, 250, 252, 253, 254, 255, 256, 257, 259, 260, 263, 264, 265, 266, 267, 268, 275, and 276, or a pharmaceutically acceptable form thereof.

In some embodiments of the methods of treating a fibrotic disease provided herein, the method administering a compound or pharmaceutically acceptable form thereof that modulates Smad2/3 activity. In some embodiments, the compound or pharmaceutically acceptable form thereof inhibits phosphorylation of the Smad2/3 protein. In some embodiments, the compound or pharmaceutically acceptable form thereof inhibits phosphorylation of Smad2/3 by 50% or more, 55% or more, 60% or more, 65% or more, 70% or more, 75% or more, 80% or more, 85% or more, 90% or more, or 95% or more at 10 μM according to Phospho-Smad2/3 Inhibition Assay. In some embodiments, the compound or pharmaceutically acceptable form thereof inhibits phosphorylation of the Smad2/3 protein by 80% or more at 10 μM according to Phospho-Smad2/3 Inhibition Assay. In some embodiments, the compound or pharmaceutically acceptable form thereof inhibits phosphorylation of the Smad2/3 protein by 85% or more at 10 μM according to Phospho-Smad2/3 Inhibition Assay. In some embodiments, the compound is selected from the group consisting of Compounds 27, 29, 30, 31, 32, 33, 36, 43, 44, 47, 51, 52, 55, 59, 85, 96, 97, 98, 99, 116, 141, 144, 156, 203, 205, 207, 208, 209, 210, 211, 214, 219, 230, 269, 272, 273, and 274, or a pharmaceutically acceptable form thereof. In some embodiments, the compound is selected from the group consisting of Compounds 29, 30, 31, 32, 33, 36, 44, 47, 59, 85, 97, 98, 99, 116, 141, 144, 156, 203, 205, 207, 208, 209, 210, 211, 214, 219, 230, 269, 272, 273, and 274, or a pharmaceutically acceptable form thereof. In some embodiments, the compound or pharmaceutically acceptable form thereof activates phosphorylation of the Smad2/3 protein. In some embodiments, the compound or pharmaceutically acceptable form thereof activates phosphorylation of Smad2/3 by 50% or more, 55% or more, 60% or more, 65% or more, 70% or more, 75% or more, 80% or more, 85% or more, 90% or more, 95% or more, or equal or greater than 100% at 10 μM according to Phospho-Smad2/3 Inhibition Assay. In some embodiments, the compound or pharmaceutically acceptable form thereof activates phosphorylation of the Smad2/3 protein by 50% or more at 10 μM according to Phospho-Smad2/3 Inhibition Assay. In some embodiments, the compound is selected from the group consisting of Compounds 56, 63, 84, 88, 89, 90, 95, 100, 101, 103, 104, 106, 108, 109, 111, 112, 113, 114, 129, 166, 173, 179, 183, 186, 216, 241, 247, 248, 250, 255, 256, 257, and 266, or a pharmaceutically acceptable form thereof.

In some embodiments of the methods of treating a fibrotic disease provided herein, the method administering a compound or pharmaceutically acceptable form that modulates JNK activity. In some embodiments, the compound or pharmaceutically acceptable form thereof inhibits JNK by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to JNK Activation Assay. In some embodiments, the compound or pharmaceutically acceptable form thereof inhibits phosphorylation of the JNK protein. In some embodiments, the compound or pharmaceutically acceptable form thereof inhibits phosphorylation of the JNK protein by 30% or more at 10 μM according to JNK Activation Assay. In some embodiments, the compound or pharmaceutically acceptable form thereof inhibits phosphorylation of the JNK protein by 75% or more at 10 μM according to JNK Activation Assay. In some embodiments, the compound or pharmaceutically acceptable form thereof inhibits phosphorylation of the JNK protein by about 100% at 10 μM according to JNK Activation Assay. In some embodiments, the compound is selected from the group consisting of Compounds 29, 30, 32, 33, and 34, or a pharmaceutically acceptable form thereof. In some embodiments, the compound is selected from the group consisting of Compounds 29, 32, 33, and 34, or a pharmaceutically acceptable form thereof. In some embodiments, the compound is selected from the group consisting of Compounds 29, 32, and 34, or a pharmaceutically acceptable form thereof. In some embodiments, the compound or pharmaceutically acceptable form thereof activates phosphorylation of the JNK protein. In some embodiments, the compound or pharmaceutically acceptable form thereof activates JNK by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to JNK Activation Assay. In some embodiments, the compound or pharmaceutically acceptable form thereof activates phosphorylation of the JNK protein by 30% or more at 10 μM according to JNK Activation Assay. In some embodiments, the compound or pharmaceutically acceptable form thereof activates phosphorylation of the JNK protein by 75% or more at 10 μM according to JNK Activation Assay. In some embodiments, the compound or pharmaceutically acceptable form thereof activates phosphorylation of the JNK protein by about 100% or more at 10 μM according to JNK Activation Assay. In some embodiments, the compound is selected from the group consisting of Compounds 1, 2, 3, 4, 6, 7, 8, 9, 11, 13, 14, 15, 16, 18, 19, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof. In some embodiments, the compound is selected from the group consisting of Compounds 3, 4, 6, 7, 11, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof. In some embodiments, the compound is selected from the group consisting of Compounds 3, 6, 7, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof.

In some embodiments of the methods of treating a fibrotic disease provided herein, the method administering a compound or pharmaceutically acceptable form thereof that modulates MAPK p38 activity. In some embodiments, the compound or pharmaceutically acceptable form thereof inhibits phosphorylation of the MAPK p38 protein. In some embodiments, the compound or pharmaceutically acceptable form thereof inhibits MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to MAPK p38 Activation Assay. In some embodiments, the compound or pharmaceutically acceptable form thereof inhibits phosphorylation of the MAPK p38 by 30% or more at 10 μM according to MAPK p38 Activation Assay. In some embodiments, the compound or pharmaceutically acceptable form thereof inhibits phosphorylation of the MAPK p38 by about 100% at 10 μM according to MAPK p38 Activation Assay. In some embodiments, the compound is selected from the group consisting of Compounds 29, 30, 32, 33, 34, 46, 47, 188, 196, 197, 203, 205, 207, 208, 209, 210, 212, 213, 214, 215, 217, and 220, or a pharmaceutically acceptable form thereof. In some embodiments, the compound is selected from the group consisting of Compounds 29, 32, 33, 34, 46, 207, and 209, or a pharmaceutically acceptable form thereof. In some embodiments, the compound or pharmaceutically acceptable form thereof activates phosphorylation of the MAPK p38 protein. In some embodiments, the compound or pharmaceutically acceptable form thereof activates MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to MAPK p38 Activation Assay. In some embodiments, the compound or pharmaceutically acceptable form thereof activates phosphorylation of the MAPK p38 by 30% or more at 10 μM according to MAPK p38 Activation Assay. In some embodiments, the compound or pharmaceutically acceptable form thereof activates phosphorylation of the MAPK p38 by 75% or more at 10 μM according to MAPK p38 Activation Assay. In some embodiments, the compound or pharmaceutically acceptable form thereof activates phosphorylation of the MAPK p38 by about 100% or more at 10 μM according to MAPK p38 Activation Assay. In some embodiments, the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 52, 53, 54, 55, 56, 57, 58, 59, 60, 61, 62, 63, 64, 65, 66, 67, 69, 70, 71, 72, 93, and 218, or a pharmaceutically acceptable form thereof. In some embodiments, the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof. In some embodiments, the compound is selected from the group consisting of Compounds 1, 2, 3, 7, 8, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof.

In some embodiments of the methods of treating a fibrotic disease provided herein, the method administering a compound or pharmaceutically acceptable form thereof that modulates IL-6 activity. In some embodiments, the compound or pharmaceutically acceptable form thereof inhibits IL-6. In some embodiments, the compound or pharmaceutically acceptable form thereof inhibits IL-6 by 50% or more, 55% or more, 60% or more, 65% or more, 70% or more, 75% or more, 80% or more, 85% or more, 90% or more, or 95% or more at 10 μM according to IL-6 Quantification Assay. In some embodiments, the compound or pharmaceutically acceptable form thereof inhibits IL-6 by 75% or more at 10 μM according to IL-6 Quantification Assay. In some embodiments, the compound is selected from the group consisting of Compounds 1, 4, 6, 13, 19, 20, 22, 23, 27, 29, 30, 31, 32, 33, 34, 40, 42, 45, 46, 67, 81, 82, 85, 86, 89, 93, 99, 104, 105, 111, 113, 143, 149, 160, 161, 163, 164, 166, 173, 175, 176, 177, 192, 193, 194, 196, 199, 201, 203, 204, 206, 207, 208, 209, 210, 217, 219, 238, 247, 248, 249, 250, 257, 260, 263, 264, 265, 268, 269, 270, 271, 272, 273, and 274, or a pharmaceutically acceptable form thereof.

In some embodiments of the methods of treating a fibrotic disease provided herein, the method administering a compound or pharmaceutically acceptable form thereof that modulates TNF-alpha activity. In some embodiments, the compound or pharmaceutically acceptable form thereof inhibits TNF-alpha. In some embodiments, the compound or pharmaceutically acceptable form thereof inhibits TNF-alpha by 50% or more, 55% or more, 60% or more, 65% or more, 70% or more, 75% or more, 80% or more, 85% or more, 90% or more, or 95% or more at 10 μM according to TNF-alpha Quantification Assay. In some embodiments, the compound or pharmaceutically acceptable form thereof inhibits TNF-alpha by 75% or more at 10 μM according to TNF-alpha Quantification Assay. In some embodiments, the compound is selected from the group consisting of Compounds 4, 23, 29, 30, 31, 32, 33, 42, 45, 46, 93, 99, 149, 166, 196, 203, 207, 209, 210, 219, 269, 270, 271, 272, 273, and 274, or a pharmaceutically acceptable form thereof.

In some embodiments, the compound of Formula I administered according to any of the methods disclosed herein treats, prevents, or inhibits fibrosis in the subject. In some embodiments, the compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, administered according to any of the methods disclosed herein inhibits fibrosis in the liver, lung, skin, soft tissue, tendons, lymph nodes, lung, kidney, heart, eye, or retroperitoneum of said subject. In some embodiments, the compound administered according to any of the methods disclosed herein treats, prevents, or ameliorates one or more symptoms of a fibrotic disease in the subject. In some embodiments, the compound administered according to any of the methods disclosed herein treats, prevents, or ameliorates the fibrotic disease in the subject. In some embodiments, the fibrotic disease is selected from the group consisting of fibrosis of kidney, fibrosis of cardiovascular system, pulmonary fibrosis, cystic fibrosis, idiopathic fibrosis, fibrosis of the lung, bridging fibrosis, fibrosis of the liver, fibrosis of the intestine, fibrosis of the muscular system, fibrosis of the brain, fibrosis of the joints, fibrosis of the skin, fibrosis of the bone marrow, fibrosis of the heart, fibrosis of the soft tissue, fibrosis of the tendons, fibrosis of the lymph nodes, fibrosis of the eyes, retroperitoneum, scleroderma and surgical scarring. In some embodiments, the fibrotic disease is fibrosis of the kidney. In some embodiments, the fibrosis of the kidney is progressive kidney disease. In some embodiments, the fibrotic disease is fibrosis of the cardiovascular system. In some embodiments, the fibrosis of the cardiovascular system is atherosclerosis or restenosis. In some embodiments, the fibrotic disease is pulmonary fibrosis. In some embodiments, the fibrotic disease is cystic fibrosis. In some embodiments, the fibrotic disease is idiopathic fibrosis. In some embodiments, the idiopathic fibrosis is idiopathic pulmonary fibrosis. In some embodiments, the fibrotic disease is fibrosis of the lung. In some embodiments, the fibrosis of the lung is progressive massive fibrosis and radiation-induced lung injury. In some embodiments, the fibrotic disease is bridging fibrosis. In some embodiments, the fibrotic disease is fibrosis of the liver. In some embodiments, the fibrosis of the liver is cirrhosis. In some embodiments, the fibrotic disease is fibrosis of the intestine. In some embodiments, the fibrosis of the intestine is Crohn's disease. In some embodiments, the fibrotic disease is fibrosis of the muscular system. In some embodiments, the fibrosis of the muscular system is Duchenne muscular dystrophy (DMD). In some embodiments, the Duchenne muscular dystrophy is Becker Muscular Dystrophy (BMD), an intermediate clinical presentation between DMD and BMD, or DMD-associated dilated cardiomyopathy. In some embodiments, the fibrotic disease is fibrosis of the brain. In some embodiments, the fibrosis of the brain is glial scar. In some embodiments, the fibrotic disease is fibrosis of the joints. In some embodiments, the fibrosis of the joints is arterial stiffness. In some embodiments, the fibrosis of the joints is fibrosis of the knee. In some embodiments, the fibrosis of the joints is fibrosis of the shoulder. In some embodiments, the fibrotic disease is fibrosis of the skin. In some embodiments, the fibrosis of the skin is Keloid. In some embodiments, the fibrotic disease is fibrosis of the bone marrow. In some embodiments, the fibrosis of the bone marrow is Myelofibrosis. In some embodiments, the fibrotic disease is fibrosis of the heart. In some embodiments, the fibrosis of the heart is Myocardial fibrosis. In some embodiments, the fibrotic disease is fibrosis of the soft tissue. In some embodiments, the fibrotic disease is fibrosis of the tendons. In some embodiments, the fibrotic disease is fibrosis of the lymph nodes. In some embodiments, the fibrotic disease is fibrosis of the eyes. In some embodiments, the fibrotic disease is retroperitoneum. In some embodiments, the fibrotic disease is scleroderma. In some embodiments, the fibrotic disease is surgical scarring.

3.6. Methods of Treating Inflammation

Inflammation is a complex protective biological response of body tissues to harmful stimuli, such as pathogens, damaged cells, or irritants, involving immune cells, blood vessels, and molecular mediators. The function of inflammation is to eliminate the initial cause of cell injury, clear out necrotic cells and tissues damaged from the original insult and the inflammatory process, and to initiate tissue repair. (Ferrero-Miliani L, Nielsen O H, Andersen P S, Girardin S E; Nielsen; Andersen; Girardin (February 2007) Clin. Exp. Immunol. 147)

Inflammation is classified as either acute or chronic. Acute inflammation is the initial response of the body to harmful stimuli and is achieved by the increased movement of plasma and leukocytes (especially granulocytes) from the blood into the injured tissues. A series of biochemical events propagates and matures the inflammatory response, involving the local vascular system, the immune system, and various cells within the injured tissue.

Prolonged inflammation, known as chronic inflammation, is characterized by simultaneous destruction and healing of the tissue from the inflammatory process. It leads to a progressive shift in the type of cells present at the site of inflammation, such as mononuclear cells, and increases in systemic concentrations of cytokines such as TNF-α, IL-6, and CRP. (Petersen, A. M.; Pedersen, B. K. (2005). J Appl Physiol. 98 (4): 1154-1162)

Many proteins are involved in inflammation. Any of them are susceptible to genetic mutation which may impair or otherwise dysregulate their normal function and expression.

Both small molecules and biologics are used to treat inflammatory diseases. Most treatments, however, are largely palliative.

A clear unmet medical need remains to find treatments that can mechanistically reduce chronic inflammatory diseases.

Provided herein are methods treating an inflammatory disease in a subject, comprising administering a therapeutically effective amount of a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, to the subject. Also provided herein are methods of treating an inflammatory disease in a subject, comprising administering a therapeutically effective amount of a pharmaceutical composition comprising a compound of Formula I, Ia, Ib, Ic, II, IIa, IIa(1), IIb, IIc, III, IIIa, IIIb, IIIc, IV, IVa, IVb, or IVc, or pharmaceutically acceptable form thereof, to the subject. In some embodiments, the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

In some embodiments of the methods of treating an inflammatory disease provided herein, the method administering a compound or pharmaceutically acceptable form thereof that modulates the activity of one or more Ras superfamily protein. In some embodiments, the compound or pharmaceutically acceptable form thereof modulates Ras superfamily activity of one or more GTPase by 50% or more, 55% or more, 60% or more, 65% or more, 70% or more, 75% or more, 80% or more, 85% or more, 90% or more, or 95% or more at 20 μM according to a Ras Superfamily Activity Assay. In some embodiments, the compound or pharmaceutically acceptable form thereof inhibits the activity one or more Ras superfamily protein. In some embodiments, the compound or pharmaceutically acceptable form thereof modulates the activity of one or more Ras superfamily protein by 45% or more at 20 μM according to a Ras Superfamily Activity. In some embodiments, the compound or pharmaceutically acceptable form thereof modulates the activity of one or more Ras superfamily protein by 50% or more at 20 μM according to a Ras Superfamily Activity. In some embodiments, the compound is selected from the group consisting of Compounds 6, 17, 22, 32, 34, 37, 42, 43, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 126, 127, 135, 136, 137, 138, 139, 140, 141, 142, 143, 144, 145, 146, 147, 148, 149, 150, 151, 152, 153, 154, 156, 157, 158, 165, 166, 167, 169, 170, 172, 173, 174, 175, 176, 177, 178, 179, 186, 187, 188, 196, 200, 202, 208, 211, 212, 213, 214, 215, 216, 217, 220, 221, 222, 223, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof. In some embodiments, the compound is selected from the group consisting of Compounds 6, 17, 22, 37, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 127, 135, 136, 137, 138, 139, 140, 141, 142, 143, 144, 145, 146, 147, 149, 150, 151, 152, 153, 154, 156, 157, 158, 165, 166, 169, 170, 173, 175, 176, 177, 178, 179, 186, 187, 188, 196, 202, 208, 211, 212, 213, 214, 215, 216, 217, 221, 222, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof.

In some embodiments of the methods of treating an inflammatory disease provided herein, the method administering a compound or pharmaceutically acceptable form thereof that modulates Erk1/2 activity. In some embodiments, the compound or pharmaceutically acceptable form thereof inhibits phosphorylation of the Erk1/2 protein. In some embodiments, the compound or pharmaceutically acceptable form thereof inhibits phosphorylation of Erk1/2 by 50% or more, 55% or more, 60% or more, 65% or more, 70% or more, 75% or more, 80% or more, 85% or more, 90% or more, or 95% or more at 10 μM according to Erk1/2 Phosphorylation Assay. In some embodiments, the compound or pharmaceutically acceptable form thereof inhibits phosphorylation of the Erk1/2 protein by 80% or more at 10 μM according to Erk1/2 Phosphorylation Assay. In some embodiments, the compound or pharmaceutically acceptable form thereof inhibits phosphorylation of the Erk1/2 protein by 85% or more at 10 μM according to Erk1/2 Phosphorylation Assay. In some embodiments, the compound is selected from the group consisting of Compounds 3, 4, 20, 23, 26, 29, 30, 31, 32, 33, 34, 36, 42, 43, 53, 58, 67, 93, 203, 209, 210, 219, 266, 269, 270, 271, 272, 273, and 274, or a pharmaceutically acceptable form thereof. In some embodiments, the compound is selected from the group consisting of Compounds 3, 4, 20, 23, 26, 29, 30, 31, 32, 33, 34, 42, 43, 53, 58, 67, 93, 203, 209, 210, 219, 266, 269, 270, 271, 272, 273, and 274, or a pharmaceutically acceptable form thereof. In some embodiments, the compound or pharmaceutically acceptable form thereof activates phosphorylation of the Erk1/2 protein. In some embodiments, the compound or pharmaceutically acceptable form thereof activates phosphorylation of Erk1/2 by 50% or more, 55% or more, 60% or more, 65% or more, 70% or more, 75% or more, 80% or more, 85% or more, 90% or more, 95% or more, or equal or greater than 100% at 10 μM according to Erk1/2 Phosphorylation Assay. In some embodiments, the compound or pharmaceutically acceptable form thereof activates phosphorylation of the Erk1/2 protein by 45% or more at 10 μM according to Erk1/2 Phosphorylation Assay. In some embodiments, the compound or pharmaceutically acceptable form thereof activates phosphorylation of the Erk1/2 protein by 50% or more at 10 μM according to Erk1/2 Phosphorylation Assay. In some embodiments, the compound is selected from the group consisting of Compounds 49, 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 130, 135, 136, 138, 143, 145, 148, 149, 151, 154, 156, 157, 165, 174, 175, 176, 177, 178, 179, 183, 190, 191, 192, 193, 194, 195, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof. In some embodiments, the compound is selected from the group consisting of Compounds 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 135, 136, 138, 143, 145, 148, 149, 151, 154, 156, 157, 165, 174, 175, 176, 177, 178, 179, 183, 190, 191, 192, 193, 194, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof.

In some embodiments of the methods of treating an inflammatory disease provided herein, the method administering a compound or pharmaceutically acceptable form thereof that modulates Akt activity. In some embodiments, the compound or pharmaceutically acceptable form thereof inhibits phosphorylation of the Akt protein. In some embodiments, the compound or pharmaceutically acceptable form thereof inhibits phosphorylation of Akt by 50% or more, 55% or more, 60% or more, 65% or more, 70% or more, 75% or more, 80% or more, 85% or more, 90% or more, or 95% or more at 10 μM according to Akt Phosphorylation Assay. In some embodiments, the compound or pharmaceutically acceptable form thereof inhibits phosphorylation of the Akt protein by 85% or more at 10 μM according to Akt Phosphorylation Assay. In some embodiments, the compound is selected from the group consisting of Compounds 17, 20, 23, 25, 29, 30, 31, 32, 33, 34, 42, 203, 209, 210, 219, 270, 271, 272, 273, and 274, or a pharmaceutically acceptable form thereof. In some embodiments, the compound or pharmaceutically acceptable form thereof activates phosphorylation of the Akt protein. In some embodiments, the compound or pharmaceutically acceptable form thereof activates phosphorylation of Akt by 50% or more, 55% or more, 60% or more, 65% or more, 70% or more, 75% or more, 80% or more, 85% or more, 90% or more, 95% or more, or equal or greater than 100% at 10 μM according to Akt Phosphorylation Assay. In some embodiments, the compound or pharmaceutically acceptable form thereof activates phosphorylation of the Akt protein by 50% or more at 10 μM according to Akt Phosphorylation Assay. In some embodiments, the compound is selected from the group consisting of Compounds 1, 2, 18, 19, 21, 47, 48, 49, 50, 51, 57, 59, 60, 61, 62, 63, 64, 65, 66, 67, 68, 69, 70, 71, 72, 73, 74, 76, 77, 78, 79, 80, 81, 82, 83, 84, 85, 86, 87, 88, 89, 91, 93, 94, 95, 96, 97, 98, 100, 101, 102, 103, 104, 106, 107, 108, 109, 110, 111, 112, 113, 114, 115, 116, 118, 119, 122, 124, 125, 126, 127, 128, 129, 130, 135, 136, 137, 138, 143, 145, 149, 151, 156, 157, 158, 165, 166, 169, 170, 173, 174, 175, 176, 178, 179, 187, 190, 191, 192, 193, 194, 195, 196, 204, 205, 207, 208, 213, 217, 218, 221, 222, 224, 226, 227, 228, 229, 230, 231, 232, 233, 234, 235, 237, 238, 240, 241, 242, 243, 244, 245, 246, 247, 248, 249, 250, 252, 253, 254, 255, 256, 257, 259, 260, 263, 264, 265, 266, 267, 268, 275, and 276, or a pharmaceutically acceptable form thereof.

In some embodiments of the methods of treating an inflammatory disease provided herein, the method administering a compound or pharmaceutically acceptable form thereof that modulates Smad2/3 activity. In some embodiments, the compound or pharmaceutically acceptable form thereof inhibits phosphorylation of the Smad2/3 protein. In some embodiments, the compound or pharmaceutically acceptable form thereof inhibits phosphorylation of Smad2/3 by 50% or more, 55% or more, 60% or more, 65% or more, 70% or more, 75% or more, 80% or more, 85% or more, 90% or more, or 95% or more at 10 μM according to Phospho-Smad2/3 Inhibition Assay. In some embodiments, the compound or pharmaceutically acceptable form thereof inhibits phosphorylation of the Smad2/3 protein by 80% or more at 10 μM according to Phospho-Smad2/3 Inhibition Assay. In some embodiments, the compound or pharmaceutically acceptable form thereof inhibits phosphorylation of the Smad2/3 protein by 85% or more at 10 μM according to Phospho-Smad2/3 Inhibition Assay. In some embodiments, the compound is selected from the group consisting of Compounds 27, 29, 30, 31, 32, 33, 36, 43, 44, 47, 51, 52, 55, 59, 85, 96, 97, 98, 99, 116, 141, 144, 156, 203, 205, 207, 208, 209, 210, 211, 214, 219, 230, 269, 272, 273, and 274, or a pharmaceutically acceptable form thereof. In some embodiments, the compound is selected from the group consisting of Compounds 29, 30, 31, 32, 33, 36, 44, 47, 59, 85, 97, 98, 99, 116, 141, 144, 156, 203, 205, 207, 208, 209, 210, 211, 214, 219, 230, 269, 272, 273, and 274, or a pharmaceutically acceptable form thereof. In some embodiments, the compound or pharmaceutically acceptable form thereof activates phosphorylation of the Smad2/3 protein. In some embodiments, the compound or pharmaceutically acceptable form thereof activates phosphorylation of Smad2/3 by 50% or more, 55% or more, 60% or more, 65% or more, 70% or more, 75% or more, 80% or more, 85% or more, 90% or more, 95% or more, or equal or greater than 100% at 10 μM according to Phospho-Smad2/3 Inhibition Assay. In some embodiments, the compound or pharmaceutically acceptable form thereof activates phosphorylation of the Smad2/3 protein by 50% or more at 10 μM according to Phospho-Smad2/3 Inhibition Assay. In some embodiments, the compound is selected from the group consisting of Compounds 56, 63, 84, 88, 89, 90, 95, 100, 101, 103, 104, 106, 108, 109, 111, 112, 113, 114, 129, 166, 173, 179, 183, 186, 216, 241, 247, 248, 250, 255, 256, 257, and 266, or a pharmaceutically acceptable form thereof.

In some embodiments of the methods of treating an inflammatory disease provided herein, the method administering a compound or pharmaceutically acceptable form that modulates JNK activity. In some embodiments, the compound or pharmaceutically acceptable form thereof inhibits JNK by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to JNK Activation Assay. In some embodiments, the compound or pharmaceutically acceptable form thereof inhibits phosphorylation of the JNK protein. In some embodiments, the compound or pharmaceutically acceptable form thereof inhibits phosphorylation of the JNK protein by 30% or more at 10 μM according to JNK Activation Assay. In some embodiments, the compound or pharmaceutically acceptable form thereof inhibits phosphorylation of the JNK protein by 75% or more at 10 μM according to JNK Activation Assay. In some embodiments, the compound or pharmaceutically acceptable form thereof inhibits phosphorylation of the JNK protein by about 100% at 10 μM according to JNK Activation Assay. In some embodiments, the compound is selected from the group consisting of Compounds 29, 30, 32, 33, and 34, or a pharmaceutically acceptable form thereof. In some embodiments, the compound is selected from the group consisting of Compounds 29, 32, 33, and 34, or a pharmaceutically acceptable form thereof. In some embodiments, the compound is selected from the group consisting of Compounds 29, 32, and 34, or a pharmaceutically acceptable form thereof. In some embodiments, the compound or pharmaceutically acceptable form thereof activates phosphorylation of the JNK protein. In some embodiments, the compound or pharmaceutically acceptable form thereof activates JNK by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to JNK Activation Assay. In some embodiments, the compound or pharmaceutically acceptable form thereof activates phosphorylation of the JNK protein by 30% or more at 10 μM according to JNK Activation Assay. In some embodiments, the compound or pharmaceutically acceptable form thereof activates phosphorylation of the JNK protein by 75% or more at 10 μM according to JNK Activation Assay. In some embodiments, the compound or pharmaceutically acceptable form thereof activates phosphorylation of the JNK protein by about 100% or more at 10 μM according to JNK Activation Assay. In some embodiments, the compound is selected from the group consisting of Compounds 1, 2, 3, 4, 6, 7, 8, 9, 11, 13, 14, 15, 16, 18, 19, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof. In some embodiments, the compound is selected from the group consisting of Compounds 3, 4, 6, 7, 11, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof. In some embodiments, the compound is selected from the group consisting of Compounds 3, 6, 7, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof.

In some embodiments of the methods of treating an inflammatory disease provided herein, the method administering a compound or pharmaceutically acceptable form thereof that modulates MAPK p38 activity. In some embodiments, the compound or pharmaceutically acceptable form thereof inhibits phosphorylation of the MAPK p38 protein. In some embodiments, the compound or pharmaceutically acceptable form thereof inhibits MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to MAPK p38 Activation Assay. In some embodiments, the compound or pharmaceutically acceptable form thereof inhibits phosphorylation of the MAPK p38 by 30% or more at 10 μM according to MAPK p38 Activation Assay. In some embodiments, the compound or pharmaceutically acceptable form thereof inhibits phosphorylation of the MAPK p38 by about 100% at 10 μM according to MAPK p38 Activation Assay. In some embodiments, the compound is selected from the group consisting of Compounds 29, 30, 32, 33, 34, 46, 47, 188, 196, 197, 203, 205, 207, 208, 209, 210, 212, 213, 214, 215, 217, and 220, or a pharmaceutically acceptable form thereof. In some embodiments, the compound is selected from the group consisting of Compounds 29, 32, 33, 34, 46, 207, and 209, or a pharmaceutically acceptable form thereof. In some embodiments, the compound or pharmaceutically acceptable form thereof activates phosphorylation of the MAPK p38 protein. In some embodiments, the compound or pharmaceutically acceptable form thereof activates MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to MAPK p38 Activation Assay. In some embodiments, the compound or pharmaceutically acceptable form thereof activates phosphorylation of the MAPK p38 by 30% or more at 10 μM according to MAPK p38 Activation Assay. In some embodiments, the compound or pharmaceutically acceptable form thereof activates phosphorylation of the MAPK p38 by 75% or more at 10 μM according to MAPK p38 Activation Assay. In some embodiments, the compound or pharmaceutically acceptable form thereof activates phosphorylation of the MAPK p38 by about 100% or more at 10 μM according to MAPK p38 Activation Assay. In some embodiments, the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 52, 53, 54, 55, 56, 57, 58, 59, 60, 61, 62, 63, 64, 65, 66, 67, 69, 70, 71, 72, 93, and 218, or a pharmaceutically acceptable form thereof. In some embodiments, the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof. In some embodiments, the compound is selected from the group consisting of Compounds 1, 2, 3, 7, 8, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof.

In some embodiments of the methods of treating an inflammatory disease provided herein, the method administering a compound or pharmaceutically acceptable form thereof that modulates IL-6 activity. In some embodiments, the compound or pharmaceutically acceptable form thereof inhibits IL-6. In some embodiments, the compound or pharmaceutically acceptable form thereof inhibits IL-6 by 50% or more, 55% or more, 60% or more, 65% or more, 70% or more, 75% or more, 80% or more, 85% or more, 90% or more, or 95% or more at 10 μM according to IL-6 Quantification Assay. In some embodiments, the compound or pharmaceutically acceptable form thereof inhibits IL-6 by 75% or more at 10 μM according to IL-6 Quantification Assay. In some embodiments, the compound is selected from the group consisting of Compounds 1, 4, 6, 13, 19, 20, 22, 23, 27, 29, 30, 31, 32, 33, 34, 40, 42, 45, 46, 67, 81, 82, 85, 86, 89, 93, 99, 104, 105, 111, 113, 143, 149, 160, 161, 163, 164, 166, 173, 175, 176, 177, 192, 193, 194, 196, 199, 201, 203, 204, 206, 207, 208, 209, 210, 217, 219, 238, 247, 248, 249, 250, 257, 260, 263, 264, 265, 268, 269, 270, 271, 272, 273, and 274, or a pharmaceutically acceptable form thereof.

In some embodiments of the methods of treating an inflammatory disease provided herein, the method administering a compound or pharmaceutically acceptable form thereof that modulates TNF-alpha activity. In some embodiments, the compound or pharmaceutically acceptable form thereof inhibits TNF-alpha. In some embodiments, the compound or pharmaceutically acceptable form thereof inhibits TNF-alpha by 50% or more, 55% or more, 60% or more, 65% or more, 70% or more, 75% or more, 80% or more, 85% or more, 90% or more, or 95% or more at 10 μM according to TNF-alpha Quantification Assay. In some embodiments, the compound or pharmaceutically acceptable form thereof inhibits TNF-alpha by 75% or more at 10 μM according to TNF-alpha Quantification Assay. In some embodiments, the compound is selected from the group consisting of 4, 23, 29, 30, 31, 32, 33, 42, 45, 46, 93, 99, 149, 166, 196, 203, 207, 209, 210, 219, 269, 270, 271, 272, 273, and 274, or a pharmaceutically acceptable form thereof.

In one embodiment, the inflammatory disease is inflammation-associated cancer development. As disclosed here, the compounds provided herein are useful in treatment of cancer. It is well recognized that the immune inflammatory state serves as a key mediator of the middle stages of tumor development. It is also well known that chronic inflammation can predispose an individual to cancer. Chronic inflammation is caused by a variety of factors, including bacterial, viral, and parasitic infections. The longer the inflammation persists, the higher the risk of associated carcinogenesis. Anti-inflammatory cancer therapy prevents premalignant cells from turning fully cancerous or impedes existing tumors from spreading to distant sites in the body. Thus, in one embodiment, the compounds provided herein are useful in treating inflammatory cancers. Such cancers, and the chronic inflammatory conditions that predispose susceptible cells to neoplastic transformation, include gastric adenocarcinoma (gastritis), mucosa-associated lymphoid tissue (MALT) lymphoma (gastritis), bladder, liver and rectal carcinomas (schistosomiasis), cholangiocarcinoma and colon carcinoma (cholangitis), gall bladder cancer (chronic cholecystitis), ovarian and cervical carcinoma (pelvic inflammatory disease, chronic cervicitis), skin carcinoma (osteomyelitis), colorectal carcinoma (inflammatory bowel disease), esophageal carcinoma (reflux esophagitis, Barrett's esophagus), bladder cancer (bladder inflammation (cystitis)), mesothelioma and lung carcinoma (asbestosis, silicosis), oral squamous cell carcinoma (gingivitis, lichen planus), pancreatic carcinoma (pancreatitis, protease mutation), vulvar squamous cell carcinoma (lichen sclerosis), salivary gland carcinoma (slaladenitis), lung carcinoma (bronchitis) and MALT lymphoma (Sjogren syndrome, Hashimoto's thyroiditis). Shacter, et al., 2002, *Oncology,* 16 (2), 217-26.

In certain embodiments, the compounds provided herein are useful in treating inflammatory diseases in the airways, such as nonspecific bronchial hyper-reactivity, chronic bronchitis, cystic fibrosis, and acute respiratory distress syndrome (ARDS).

In certain embodiments, the compounds provided herein are useful in treating asthma and idiopathic lung fibrosis or idiopathic pulmonary fibrosis (IPF), pulmonary fibrosis, and interstitial lung disease. As known to one of skill in the art, the differentiation of fibroblasts into cell types called myofibroblasts occurs during wound healing, when the cells contribute to the deposition of extracellular matrix (ECM) in the transient process of wound repair. In chronic inflammatory diseases such as asthma, pathological tissue remodeling often occurs, and is mediated by the functions of increased numbers of myofibroblasts in the diseased tissue, see Hinz, B. et al. Am J Pathol. 2007; 170:1807-1816. In certain embodiments, the compounds provided herein prevent or reduce TGF-β-induced myofibroblast differentiation, as measured by the expression of alpha smooth muscle actin (α-SMA), a hallmark of myofibroblast differentiation (Serini, G. and Gabbiani, G. 1999; Exp. Cell Res. 250:273-283).

In certain embodiments, the compounds provided herein are useful in treating psoriasis, chronic plaque psoriasis, psoriatic arthritis, acanthosis, atopic dermatitis, various forms of eczema, contact dermatitis (includes allergic dermatitis), systemic sclerosis (scleroderma), wound healing, and drug eruption.

In one embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, eczema, Sjögren's syndrome, burns, dermatitis, neuroinflammation, allergy pain, autoimmune myositis, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, acute gout, pneumonitis, myocarditis, pericarditis, myositis, eczema, alopecia, vitiligo, bullous skin diseases, atherosclerosis, depression, retinitis, uveitis, scleritis, hepatitis, pancreatitis, primary biliary cirrhosis, sclerosing cholangitis, Addison's disease, hypophysitis, thyroiditis, type I diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement, acute rejection of transplanted organs, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, postsurgical syndromes, sarcoidosis, Herxheimer reactions, encephalitis, myelitis, SIRS associated with viral infections such as influenza, herpes zoster, herpes simplex, coronavirus or dry eye syndrome (or keratoconjunctivitis sicca (KCS)).

In certain embodiments, the compounds provided herein are useful in treating neuropathic and nociceptive pain, chronic or acute, such as, without limitation, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, ocular pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain.

In certain embodiments, the compounds provided herein are useful in treating Alzheimer's disease (AD), mild cognitive impairment (MCI), age-associated memory impairment (AAMI), multiple sclerosis, Parkinson's disease, vascular dementia, senile dementia, AIDS dementia, Pick's disease, dementia caused by cerebrovascular disorders, corticobasal degeneration, amyotrophic lateral sclerosis (ALS), Huntington's disease, diminished CNS function associated with traumatic brain injury.

In one embodiment, the compounds provided herein are useful in treating Alzheimer's disease (AD), ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus, erythematous (SLE), nephritis, Parkinson's disease, ulcerative colitis.

When used for the treatment of inflammatory disease, the compounds provided herein may be administered in dosages, routes of administration and/or to achieve pK profiles as described herein for the treatment of cancer.

In one embodiment, the inflammatory disease is inflammation-associated cancer development. As disclosed here, the compounds provided herein are useful in treatment of cancer. It is well recognized that the immune inflammatory state serves as a key mediator of the middle stages of tumor development. It is also well known that chronic inflammation can predispose an individual to cancer. Chronic inflammation is caused by a variety of factors, including bacterial, viral, and parasitic infections. The longer the inflammation persists, the higher the risk of associated carcinogenesis. Anti-inflammatory cancer therapy prevents premalignant cells from turning fully cancerous or impedes existing tumors from spreading to distant sites in the body. Thus, in one embodiment, the compounds provided herein are useful in treating inflammatory cancers. Such cancers, and the chronic inflammatory conditions that predispose susceptible cells to neoplastic transformation, include gastric adenocarcinoma (gastritis), mucosa-associated lymphoid tissue (MALT) lymphoma (gastritis), bladder, liver and rectal carcinomas (schistosomiasis), cholangiocarcinoma and colon carcinoma (cholangitis), gall bladder cancer (chronic cholecystitis), ovarian and cervical carcinoma (pelvic inflammatory disease, chronic cervicitis), skin carcinoma (osteomyelitis), colorectal carcinoma (inflammatory bowel disease), esophageal carcinoma (reflux esophagitis, Barrett's esophagus), bladder cancer (bladder inflammation (cystitis)), mesothelioma and lung carcinoma (asbestosis, silicosis), oral squamous cell carcinoma (gingivitis, lichen planus), pancreatic carcinoma (pancreatitis, protease mutation), vulvar squamous cell carcinoma (lichen sclerosis), salivary gland carcinoma (slaladenitis), lung carcinoma (bronchitis) and MALT lymphoma (Sjogren syndrome, Hashimoto's thyroiditis). Shacter, et al., 2002, Oncology, 16(2), 217-26.

In certain embodiments, the compounds provided herein are useful in treating inflammatory diseases in the airways, such as nonspecific bronchial hyper-reactivity, chronic bronchitis, cystic fibrosis, and acute respiratory distress syndrome (ARDS).

In certain embodiments, the compounds provided herein are useful in treating asthma and idiopathic lung fibrosis or idiopathic pulmonary fibrosis (IPF), pulmonary fibrosis, and interstitial lung disease. As known to one of skill in the art, the differentiation of fibroblasts into cell types called myofibroblasts occurs during wound healing, when the cells contribute to the deposition of extracellular matrix (ECM) in the transient process of wound repair. In chronic inflammatory diseases such as asthma, pathological tissue remodeling often occurs, and is mediated by the functions of increased numbers of myofibroblasts in the diseased tissue, see Hinz, B. et al. Am J Pathol. 2007; 170:1807-1816. In certain embodiments, the compounds provided herein prevent or reduce TGF-β-induced myofibroblast differentiation, as measured by the expression of alpha smooth muscle actin (α-SMA), a hallmark of myofibroblast differentiation (Serini, G. and Gabbiani, G. 1999; Exp. Cell Res. 250:273-283).

In certain embodiments, the compounds provided herein are useful in treating psoriasis, chronic plaque psoriasis, psoriatic arthritis, acanthosis, atopic dermatitis, various forms of eczema, contact dermatitis (includes allergic dermatitis), systemic sclerosis (scleroderma), wound healing, and drug eruption.

In one embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, eczema, Sjögren's syndrome, burns, dermatitis, neuroinflammation, allergy pain, autoimmune myositis, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, acute gout, pneumonitis, myocarditis, pericarditis, myositis, eczema, alopecia, vitiligo, bullous skin diseases, atherosclerosis, depression, retinitis, uveitis, scleritis, hepatitis, pancreatitis, primary biliary cirrhosis, sclerosing cholangitis, Addison's disease, hypophysitis, thyroiditis, type I diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement, acute rejection of transplanted organs, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, postsurgical syndromes, sarcoidosis, Herxheimer reactions, encephalitis, myelitis, SIRS associated with viral infections such as influenza, herpes zoster, herpes simplex, coronavirus or dry eye syndrome (or keratoconjunctivitis sicca (KCS)).

In certain embodiments, the compounds provided herein are useful in treating neuropathic and nociceptive pain, chronic or acute, such as, without limitation, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, ocular pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain.

In certain embodiments, the compounds provided herein are useful in treating Alzheimer's disease (AD), mild cognitive impairment (MCI), age-associated memory impairment (AAMI), multiple sclerosis, Parkinson's disease, vascular dementia, senile dementia, AIDS dementia, Pick's disease, dementia caused by cerebrovascular disorders, corticobasal degeneration, amyotrophic lateral sclerosis (ALS), Huntington's disease, diminished CNS function associated with traumatic brain injury.

In one embodiment, the compounds provided herein are useful in treating Alzheimer's disease (AD), ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus, erythematous (SLE), nephritis, Parkinson's disease, ulcerative colitis.

3.7. Pharmaceutical Compositions

The pharmaceutical compositions provided herein contain therapeutically effective amounts of one or more of compounds provided herein (e.g. compounds of Formula I, Ia, Ib, Ic, II, IIa, IIa(1), IIb, IIc, III, IIIa, IIIb, IIIc, IV, IVa, IVb, or IVc, and a pharmaceutically acceptable carrier, diluent or excipient.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel's Pharmaceutical Dosage Forms and Drug Delivery Systems, Twelfth Edition 2021).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of a disease or disorder disclosed herein.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the subject treated. The therapeutically effective concentration may be determined empirically by testing the compounds in in vitro and in vivo systems described herein and then extrapolated therefrom for dosages for humans. In some embodiments, the active compound is administered in a method to achieve a therapeutically effective concentration of the drug. In some embodiments, a companion diagnostic (see, e.g., Olsen D and Jorgensen JT, *Front. Oncol.,* 2014 May 16, 4:105, doi: 10.3389/fonc.2014.00105) is used to determine the therapeutic concentration and safety profile of the active compound in specific subjects or subject populations.

The concentration of active compound in the pharmaceutical composition will depend on absorption, tissue distribution, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of a disease or disorder disclosed herein.

In certain embodiments, a therapeutically effective dosage should produce a serum concentration of active ingredient of from about 0.1 ng/mL to about 50-100 μg/mL. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, inactivation, excretion rates of the active compound, the dosage schedule, amount administered, particular formulation as well as other factors known to those of skill in the art.

The compositions are intended to be administered by a suitable route, including but not limited to oral, parenteral, subcutaneous, intravenous, intramuscular, intraperitoneal, intrathecal, mucosal, dermal, transdermal, buccal, rectal, topical, local, nasal or inhalation. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% to 100% active ingredient, in certain embodiments, about 0.1 85% or about 75-95%.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

Articles of Manufacture

The compounds of Formula I, Ia, Ib, Ic, II, IIa, IIa(1), IIb, IIc, III, IIIa, IIIb, IIIc, IV, IVa, IVb, or IVc, or pharmaceutically acceptable forms thereof, provided herein, and the pharmaceutical compositions comprising the same with a pharmaceutically acceptable carrier, diluent or excipient, can be contained in a pharmaceutical kit or pharmaceutical packaging (sometimes referred to as articles of manufacture). Such articles of manufacture can be used for treatment, prevention or amelioration of one or more symptoms or progression of a disease or disorder disclosed herein, and a label that indicates that the compound or pharmaceutically acceptable salt thereof is used for treatment, prevention or amelioration of one or more symptoms or progression of a disease or disorder disclosed herein.

In certain embodiments, provided herein is a a pharmaceutical kit, which, when used by the medical practitioner, can simplify the administration of appropriate amounts of active ingredients to a subject. In certain embodiments, the pharmaceutical kit provided herein includes a container and a dosage form of a compound provided herein, including a single enantiomer or a mixture of diastereomers thereof; or a pharmaceutically acceptable salt, solvate, or prodrug thereof.

In certain embodiments, the pharmaceutical kit includes a container comprising a dosage form of the compound provided herein, including a single enantiomer or a mixture of diastereomers thereof; or a pharmaceutically acceptable salt, solvate, or prodrug thereof, in a container comprising one or more other therapeutic agent(s) described herein.

Pharmaceutical kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Pharmaceutical kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

3.8. Dosing

The compounds of Formula I, Ia, Ib, Ic, II, IIa, IIa(1), IIb, IIc, III, IIIa, IIIb, IIIc, IV, IVa, IVb, or IVc, or pharmaceutically acceptable forms thereof, and pharmaceutical compositions comprising the same, provided herein may be dosed in certain therapeutically or prohylactically effective amounts, certain time intervals, certain dosage forms, and certain dosage administration methods as described below.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day.

In one embodiment, the recommended daily dose range of the compound provided herein, or a derivative thereof, for the conditions described herein lie within the range of from about 0.5 mg to about 50 mg per day, in one embodiment given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day. In a particular embodiment, the compound can be administered in an amount of about 10 mg/day. In a particular embodiment, the compound can be administered in an amount of about 5 mg/day. In a particular embodiment, the compound can be administered in an amount of about 4 mg/day. In a particular embodiment, the compound can be administered in an amount of about 3 mg/day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The administered dose can also be expressed in units other than mg/kg/day. For example, doses for parenteral administration can be expressed as $mg/m^2$/day. One of ordinary skill in the art would readily know how to convert doses from mg/kg/day to $mg/m^2$/day to given either the height or weight of a subject or both (see, e.g., Nair A B, Jacob S. A simple practice guide for dose conversion between animals and human. J Basic Clin Pharma 2016; 7:27-31). For example, a dose of 1 mg/kg/day for a 60 kg human is approximately equal to 37 $mg/m^2$/day.

In certain embodiments, the amount of the compound administered is sufficient to provide a plasma concentration of the compound at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, or a derivative thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 2 μM, from about 0.1 to about 20 μM, from about 0.5 to about 20 μM, or from about 1 to about 20 μM.

In certain embodiments, the amount of the compound administered is sufficient to provide a minimum plasma concentration (trough concentration) of the compound, ranging from about 0.001 to about 500 μM, about 0.002 to about 200 μM, about 0.005 to about 100 μM, about 0.01 to about 50 μM, from about 1 to about 50 μM, about 0.01 to about 25 μM, from about 0.01 to about 20 μM, from about 0.02 to about 20 μM, from about 0.02 to about 20 μM, or from about 0.01 to about 20 μM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

The methods provided herein encompass treating a patient regardless of subject's age, although some diseases or disorders are more common in certain age groups.

Depending on the disease to be treated and the subject's condition, the compound provided herein, or a derivative thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. The compound provided herein, or a derivative thereof, may be formulated, alone or together, in suitable dosage unit with pharmaceutically acceptable excipients, carriers, adjuvants and vehicles, appropriate for each route of administration.

In one embodiment, the compound provided herein, or a derivative thereof, is administered orally. In another embodiment, the compound provided herein, or a derivative thereof, is administered parenterally. In yet another embodiment, the compound provided herein, or a derivative thereof, is administered intravenously.

The compound provided herein, or a derivative thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the subject experiences stable disease or regression, or until the subject experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, Journal of the National Cancer Institute 92 (3): 205 216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound provided herein, or a derivative thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the compound provided herein, or a derivative thereof, is administered once or more than once each day, for example, for a period of time. The term "continuous" is intended to mean that a therapeutic compound, such as the compound provided herein or a derivative thereof, is administered daily for an uninterrupted period of at least 10 days to 52 weeks. The term "intermittent" or "intermittently" as used herein is intended to mean stopping and starting at either regular or irregular intervals. For example, intermittent administration of the compound provided herein or a derivative thereof is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound provided herein or a derivative thereof, is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound provided herein, or a derivative thereof, is administered once a day. In another embodiment, the compound provided herein, or a derivative thereof, is administered twice a day. In yet another embodiment, the compound provided herein, or a derivative thereof, is administered three times a day. In still another embodiment, the compound provided herein, or a derivative thereof, is administered four times a day.

In certain embodiments, the compound provided herein, or a derivative thereof, is administered once per day from one day to six months, from one week to three months, from one week to four weeks, from one week to three weeks, or from one week to two weeks. In certain embodiments, the compound provided herein, or a derivative thereof, is administered once per day for one week, two weeks, three weeks, or four weeks. In one embodiment, the compound provided herein, or a derivative thereof, is administered once per day for 4 days. In one embodiment, the compound provided herein, or a derivative thereof, is administered once per day for 5 days. In one embodiment, the compound provided herein, or a derivative thereof, is administered once per day for 6 days. In one embodiment, the compound provided herein, or a derivative thereof, is administered once per day for one week. In another embodiment, the compound provided herein, or a derivative thereof, is administered once per day for two weeks. In yet another embodiment, the compound provided herein, or a derivative thereof, is administered once per day for three weeks. In still another embodiment, the compound provided herein, or a derivative thereof, is administered once per day for four weeks.

Combination Therapy with a Second Active Agent

The compound provided herein, or a derivative thereof, can also be combined or used in combination with other therapeutic agents useful in the treatment and/or prevention of cancers, inflammatory diseases, rasopathies, or fibrotic disease.

In one embodiment, provided herein is a method of treating, preventing, or managing cancers, inflammatory diseases, rasopathies, and fibrotic disease, comprising administering to a subject a compound provided herein, or a derivative thereof; in combination with one or more second active agents.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein, a compound provided herein, e.g., the compound provided herein, or a derivative thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of the compound provided herein, or a derivative thereof and one or more second active agents to a subject can occur simultaneously or sequentially by the same or different routes of administration. The suitability of a particular route of administration employed for a particular active agent will depend on the active agent itself (e.g., whether it can be administered orally without decomposing prior to entering the blood stream) and the disease or disorder being treated.

The route of administration of the compound provided herein, or a derivative thereof, is independent of the route of administration of a second therapy. In one embodiment, the compound provided herein, or a derivative thereof, is administered orally. In another embodiment, the compound provided herein, or a derivative thereof, is administered intravenously. Thus, in accordance with these embodiments, the compound provided herein, or a derivative thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the compound provided herein, or a derivative thereof, and a second therapy are administered by the same mode of administration, orally or by IV. In another embodiment, the compound provided herein, or a derivative thereof, is administered by one mode of administration, e.g., by IV, whereas the second agent is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the compound provided herein, or a derivative thereof, and any optional additional active agents concurrently administered to the subject.

One or more second active ingredients or agents can be used together with the compound provided herein, or a derivative thereof, in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins.

In one embodiment, the compound provided herein, or a derivative thereof, can be administered in an amount ranging from about 0.1 to about 150 mg, from about 1 to about 25 mg, or from about 2 to about 10 mg orally and daily alone, or in combination with a second active agent, prior to, during, or after the use of conventional therapy.

4. EXAMPLES

The present disclosure will now be described with reference to specific example(s) which should not be construed as in any way limiting.

Analytical Methods:

NMR: Proton nuclear magnetic resonance spectra (NMR) were recorded at 400 MHz or 500 MHz. $^{13}C$ NMR spectra were recorded at 100 MHz or 125 MHz. Chemical shifts (δ) are given in parts per million (ppm) and are listed upfield with tetramethylsilane as a reference. Peaks are described as singlets(s), doublets (d), triplets (t), quartets (q), quintets (quint) multiplets (m) and broad (br.). All assignments of NMR spectra were based on 1D NMR data.

LCMS Specifications and Method Details:

1) SUPOR_30—Acidic_01

Application: initial purity check for all compounds with m/z up to 600

Column: Agilent Poroshell 120 SB-C18 4.6×30 mm 2.7 μm

Column Temperature: 60° C.

Mobile phase: A—water (0.1% formic acid), B—acetonitrile (0.1% formic acid)

Flow rate: 3 ml/min

Gradient: 0.01 min—1% B, 1.5 min—100% B, 1.73 min—100% B

MS Ionization mode: Electrospray ionization (ESI)

MS Scan range: 83-600 m/z

UV detection: 215 nm, 254 nm, 280 nm

2) PORIK_30—Acidic 02

Application: initial purity check for all compounds with m/z up to 1000

Column: Agilent Poroshell 120 SB-C18 4.6×30 mm 2.7 μm

Column Temperature: 60° C.

Mobile phase: A—water (0.1% formic acid), B—acetonitrile (0.1% formic acid)

Flow rate: 3 ml/min

Gradient: 0.01 min—1% B, 1.5 min—100% B, 1.73 min—100% B

MS Ionization mode: Electrospray ionization (ESI)

MS Scan range: 83-1000 m/z

UV detection: 215 nm, 254 nm, 280 nm

3) SUPOR_30F—Acidic_03

Application: strongly retained compounds with m/z up to 1000

Column: Agilent Poroshell 120 SB-C18 4.6×30 mm 2.7

Temperature: 60° C.

Mobile phase: A—water (0.1% formic acid), B—acetonitrile (0.1% formic acid)

Flow rate: 3 mL/min

Gradient: 0.01 min-1% B, 1.5 min-100% B, 2.2 min-100% B.

MS Ionization mode: Electrospray ionization (ESI)

MS Scan range: 83-1000 m/z

UV detection: 215 nm, 254 nm, 280 nm

4) N_SUPOR_30—Neutral_01

Application: unstable in acidic conditions compounds

Column: Agilent Poroshell 120 SB-C18 4.6×30 mm 2.7 μm

Column Temperature: 60° C.

Mobile phase: A—water, B—acetonitrile

Flow rate: 3 mL/min

Gradient: 0.01 min—1% B, 1.5 min—100% B, 1.73 min—100% B,

MS Ionization mode: Electrospray ionization (ESI)

MS Scan range: 83-600 m/z

UV detection: 215 nm, 254 nm, 280 nm

4) AC-GEMINI_2,3_N—Basic_01

Application: polar compounds with poor retention in acidic/neutral conditions

Column: GEMINI NX-C18 4,6×50 mm 5 Micron

Column Temperature: 25° C.

Mobile phase: A—10 mM NH4Ac in water, pH=10, B—acetonitrile

Flow rate: 2.3 ml/min

Gradient: 0.01 min—1% B, 1.5 min—100% B, 1.73 min—100% B.

MS Ionization mode: Electrospray ionization (ESI)

MS Scan range: 83-600 m/z

UV detection: 215 nm, 254 nm, 280 nm 5) 6 min_4-6×30_1-5—Acidic_04

Application: initial purity check for all compounds with m/z up to 1000

Column: Agilent Poroshell 120 SB-C18 4.6×30 mm 2.7 μm

Column Temperature: 60° C.

Mobile phase: A—water (0.1% formic acid), B—acetonitrile (0.1% formic acid)

Flow rate: 1.5 ml/min

Gradient: 0.01 min—1% B, 5.00 min—100% B, 5.99 min—100% B

MS Ionization mode: Electrospray ionization (ESI)

MS Scan range: 83-1000 m/z

UV detection: 215 nm, 254 nm, 280 nm

6) LCMS UPLC

Column: 4.6×50 mm ZORBAX SB-C18 1.8 Micron

Temperature: 50° C.

Mobile phase: Solvent A: $CH_3CN+H_2O$+FA 0.1% (900:100:2)

Solvent B: $H_2O$+FA 0.1% (1000:2)

Flow rate: 3 mL/min

Gradient:

| Time | A(%) | B(%) |
|---|---|---|
| 0.00 | 3.0 | 97.0 |
| 0.01 | 3.0 | 97.0 |
| 4.00 | 100.0 | 0.0 |
| 4.60 | 100.0 | 0.0 |
| 4.61 | 3.0 | 97.0 |
| 4.7 | 3.0 | 97.0 |

MS Ionization mode: Electrospray ionization (ESI)

MS Scan range: 83-1000 m/z

UV detection: 215 nm, 254 nm, 280 nm 4.1 Synthetic Examples

Example A1: Synthesis of Intermediate A1

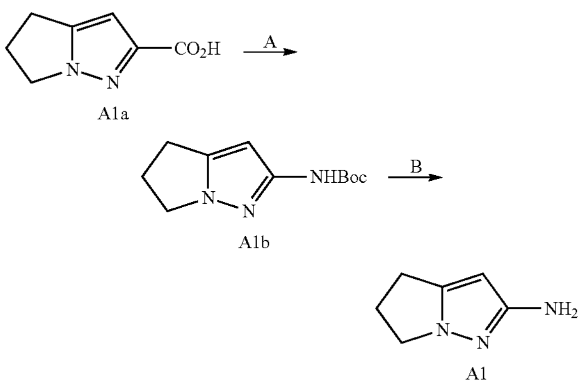

Step A: tert-Butyl (5,6-dihydro-4H-pyrrolo[1,2-b]pyrazol-2-yl)carbamate A1b

To a stirred solution of 5,6-dihydro-4H-pyrrolo[1,2-b]pyrazole-2-carboxylic acid A1a (2.00 g, 13.15 mmol) in mixture of t-BuOH (50 mL), DMF (1 mL) were added $Et_3N$ (3.64 mL, 26.3 mmol) followed by DPPA (5.42 g, 19.7 mmol) at room temperature and resulting reaction mixture slowly heated to 90° C. for 12 h. The reaction mixture was concentrated under reduced pressure to afford crude product, which was quenched with $H_2O$ (20 mL), and the aqueous layer extracted with ethyl acetate (2×20 mL), washed with brine (20 mL) and dried over anhydrous $Na_2SO_4$ and evaporated under reduced pressure afforded crude material. Obtained crude material was purified by reverse phase C-18 column chromatography (50% $CH_3CN$ in $H_2O$) afforded tert-butyl (5,6-dihydro-4H-pyrrolo[1,2-b]pyrazol-2-yl) carbamate A1b (0.80 g, 27% yield) as an off white solid. $^1$H NMR (400 MHZ, DMSO-$d_6$) δ 9.38 (s, 1H), 5.97 (s, 1H), 3.91 (t, J=7.20 Hz, 2H), 2.78 (t, J=7.60 Hz, 2H), 2.46-2.40 (m, 2H), 1.43 (s, 9H).

Step B: 5,6-Dihydro-4H-pyrrolo[1,2-b]pyrazol-2-amine A1

To a stirred solution of tert-butyl (5,6-dihydro-4H-pyrrolo[1,2-b]pyrazol-2-yl)carbamate A1b (0.8 g, 3.58 mmol) in $CF_3CH_2OH$ (8 mL) was added TMSCl (0.67 mL, 5.38 mmol) at 0° C. and slowly warmed to room temperature and stirred for 2 h. The solvent was evaporated under reduced pressure to crude which was neutralized with saturated $NaHCO_3$ solution (10 mL), extracted with $CH_2Cl_2$ (2×20 mL). The organic layer washed with brine (10 mL), dried over anhydrous $Na_2SO_4$ and the combined organic layer was evaporated under reduced pressure to afford 5,6-dihydro-4H-pyrrolo[1,2-b]pyrazol-2-amine A1 (0.35 g, 79% yield) as an off white solid. 1H-NMR (400 MHZ, $CDCl_3$) δ 5.34 (s, 1H), 3.96 (t, J=7.20 Hz, 2H), 3.17 (brs, 2H), 2.80 (t, J=8.04 Hz, 2H), 2.51-2.44 (m, 2H). MS (ESI+APCI; multimode): Calculated [M+1] 124. Found [M+1] 124.

Example A2: Synthesis of Intermediate A2

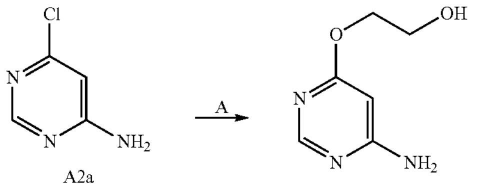

A2a

A2

Step A: 2-((6-Aminopyrimidin-4-yl)oxy)ethan-1-ol A2

To a mixture of 6-chloropyrimidin-4-amine A2a (1.00 g, 7.75 mmol) in ethane-1,2-diol (15 mL) was added 1-KOBu (1.30 g, 11.62 mmol) and resulting reaction mixture was heated to 110° C. for 16 h. The reaction mixture was quenched with $H_2O$ (10 mL), an aqueous layer extracted with $CH_2Cl_2$ (2×20 mL), washed with brine (10 mL), dried over anhydrous $Na_2SO_4$ and the combined organic layer was evaporated under reduced pressure to afford crude material. The crude material was purified using silica gel combi-flash column chromatography (10% MeOH in $CH_2Cl_2$) afforded impure material, which was re-purified using reverse phase C-18 column chromatography using (30-50% $CH_3CN$ in $H_2O$) to afford 2-((6-aminopyrimidin-4-yl)oxy)ethan-1-ol A2 (0.50 g, 41.6% yield) as white solid. $^1$H-NMR (400 MHZ, DMSO-$d_6$) δ 8.07 (d, J=0.80 Hz, 1H), 6.61 (s, 2H), 5.68 (d, J=0.80 Hz, 1H), 4.82 (t, J=5.60 Hz, 1H), 4.18 (t, J=5.20 Hz, 2H), 3.66-3.62 (m, 2H). MS (ESI+APCI; multimode): Calculated [M+1] 156. Found [M+1] 156.

Example A3: Synthesis of Intermediate A3

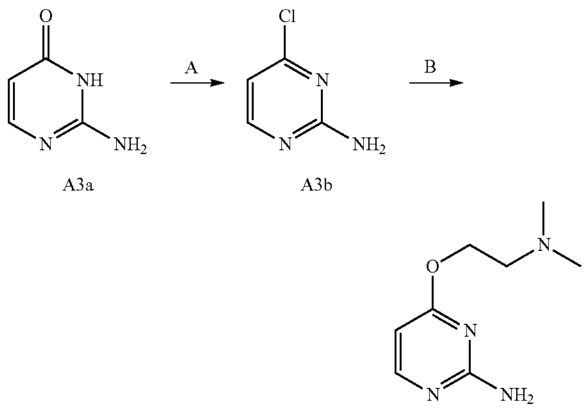

A3a

A3b

A3

Step A: 4-Chloropyrimidin-2-amine A3b

To a stirred solution of 2-aminopyrimidin-4 (3H)-one A3a (10.0 g, 90.09 mmol) in toluene (200 mL) was added $POCl_3$ at 0° C. and slowly heated to 120° C. for 5 h. The reaction mixture was concentrated under reduced pressure to afford crude residue, which was quenched with saturated $NaHCO_3$ solution (20 mL) and resulting solid was filtered and washed with $H_2O$ (30 mL) and dried under vacuum to afford 4-chloropyrimidin-2-amine A3b (4.60 g, crude) as brown solid which was directly used as such in next step without any purification.

Step B: 4-(2-(Dimethylamino)ethoxy)pyrimidin-2-amine A3

A mixture of 4-chloropyrimidin-2-amine A3b (4.60 g, 35.65 mmol) and 2-(dimethylamino) ethan-1-ol in DMF (50 mL) was added $K_2CO_3$ (9.84 g, 71.31 mmol) and heated to 80° C. for 16 h. The reaction mixture was poured into crushed ice and resulting solid was filtered, washed with $H_2O$ (30 mL) followed by MTBE (30 mL): Hexane (30 mL) and dried under vacuum to afford 4-(2-(dimethylamino) ethoxy)pyrimidin-2-amine A3 (0.90 g, 14% yield {over 2 steps}) as light brown solid. 1H-NMR (400 MHZ, DMSO-$d_6$) δ 7.94 (d, J=5.60 Hz, 1H), 6.53 (s, 2H), 5.98 (d, J=5.60 Hz, 1H), 4.28 (t, J=5.60 Hz, 2H), 2.56 (t, J=5.60 Hz, 2H), 2.20 (s, 6H).

Example A4: Synthesis of Intermediate A4

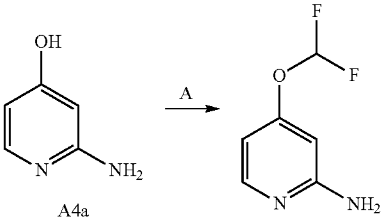

A4a

A4

Step A: 4-(Difluoromethoxy)pyridin-2-amine A4

Sodium hydroxide (18.16 g, 454.06 mmol) was added in one portion to a stirred solution of 2-aminopyridin-4-ol A4a (10.0 g, 90.82 mmol) in dioxane (150 mL) and water (50 mL) causing an exotherm to 50° C. Chlorodifluoromethane was then rapidly bubbled into the reaction over 9 minutes, causing a gradual exotherm to 70° C. After the reaction had cooled to room temperature, it was diluted with ether (150 mL) and water (150 mL) and the layers separated. The organic phase washed with water, brine and dried over $Na_2SO_4$ and concentrated in vacuo to give 4-(difluoromethoxy)pyridin-2-amine A4 (700.0 mg, 90.0% purity, 3.93 mmol, 4.3% yield) as brown solid.

Example A5: Synthesis of Intermediate A5

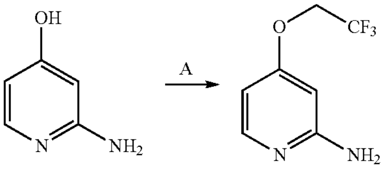

A4a

A5

Step A: 4-(2,2,2-Trifluoroethoxy)pyridin-2-amine A5

Sodium hydride (0.21 g, 5.25 mmol) (60% on mineral oil) was added portionwise to the solution of 2,2,2-trifluoroethyl trifluoromethanesulfonate (1.05 g, 4.54 mmol) and 2-aminopyridin-4-ol A4a (500.0 mg, 4.54 mmol) in DMF (5 mL). The mixture was stirred at room temperature for 16 h, then diluted with water (45 mL) and extracted 3 times by EtOAc (3*15 mL). The organic phase washed with water, brine and dried over $Na_2SO_4$ and concentrated in vacuo to give 4-(2,2,2-trifluoroethoxy)pyridin-2-amine A5 (410.0 mg, 90.0% purity, 1.92 mmol, 42.3% yield) as a brown solid.

Example A6: Synthesis of Intermediate A6

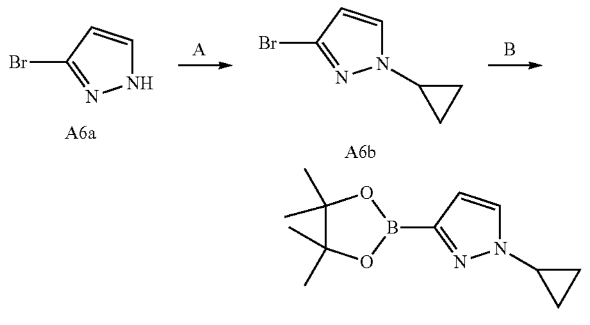

A6a

A6b

A6

Step A: 3-Bromo-1-cyclopropyl-1H-pyrazole (A6a)

A suspension of 2-(pyridin-2-yl)pyridine (21.25 g, 136.08 mmol) and copper II) acetate (24.72 g, 136.08 mmol) in DCE (320 mL) was warmed to 50° C. and stirred for 10 minutes. Then, the mixture of 3-bromo-1H-pyrazole (A6a) (20.0 g, 136.08 mmol), cyclopropylboronic acid (35.07 g, 408.24 mmol) and sodium carbonate (31.73 g, 299.38 mmol) in DCE (100 mL) was added. The reaction mixture was stirred at 65° C. for 18 hr. Then, the obtained mixture was allowed to cool to room temperature, filtered through celite frit, and rinsed with EtOAc. The filtrate was concentrated under reduced pressure. The residue was partitioned between EtOAc and $NH_4Cl$ (aqueous solution) and the organic layer was washed with $NH_4Cl$ (aqueous solution), $Na_2CO_3$ (aqueous solution) and brine and dried over $Na_2SO_4$. The residue was dried in vacuo and purified by flash column chromatography (m=30 g Interchim; 330 g $SiO_2$, hexane/methyl t-butyl ether (MtBE) with MtbE from 0~20%, flow rate 100 mL/min, Rv=6.2-8.5 CV) to give 3-bromo-1-cyclopropyl-1H-pyrazole (A6a) (10.7 g, 95.0% purity, 54.35 mmol, 39.9% yield).

Step B: 1-Cyclopropyl-3-(4,4,5,5-tetramethyl-1,3,2-dioxaborolan-2-yl)-1H-pyrazole (A6)

The mixture of 3-bromo-1-cyclopropyl-1H-pyrazole (A6a) (10.7 g, 57.21 mmol), 4,4,5,5-tetramethyl-2-(4,4,5,5-tetramethyl-1,3,2-dioxaborolan-2-yl)-1,3,2-dioxaborolane (15.25 g, 60.07 mmol), [1,1'-bis(diphenylphosphino)ferrocene]dichloropalladium(II) dichloromethane adduct (2.34 g, 2.86 mmol) and potassium acetate (11.23 g, 114.42 mmol) in dioxane (150 mL) was degassed, warmed to 100° C., and stirred for 18 h. The volatiles were removed in vacuo. The residue was suspended in EtOAc, filtered through a pad of Celite, rinsed with EtOAc. The filtrate was concentrated under reduced pressure to give 1-cyclopropyl-3-(4,4,5,5-tetramethyl-1,3,2-dioxaborolan-2-yl)-1H-pyrazole (A6) (21.0 g, 51.0% purity, 45.75 mmol, 80% yield) and used without further purification.

Example 1: Synthesis of Compound 1

(1)

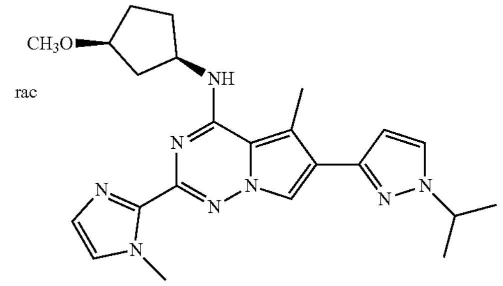

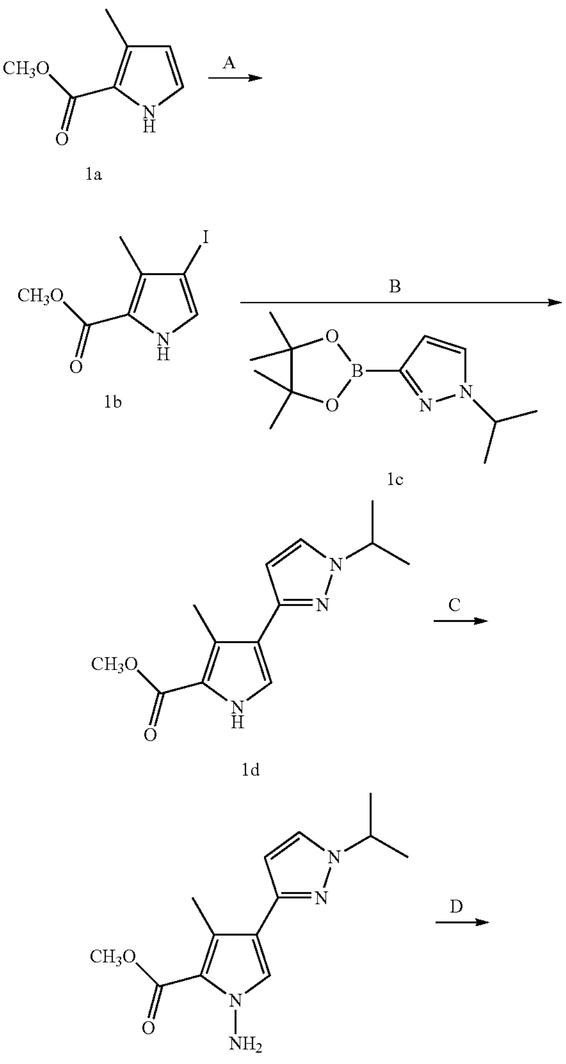

1a

1b

1c

1d

1e

-continued

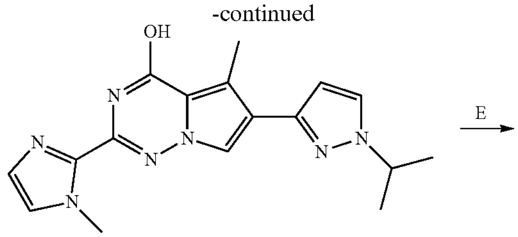

1f

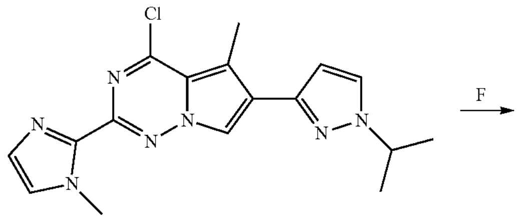

1g

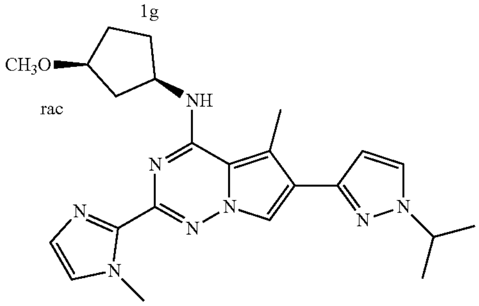

(1)

Step A: Methyl 4-iodo-3-methyl-1H-pyrrole-2-carboxylate 1b

1-Iodopyrrolidine-2,5-dione (33.95 g, 150.91 mmol) was added portionwise to the solution of methyl 3-methyl-1H-pyrrole-2-carboxylate 1a (20.0 g, 143.73 mmol) in DMF (100.0 mL) at 0° C. The reaction mixture was stirred at room temperature for 16 h. Then, the mixture was poured in ice water. The formed precipitate was collected by filtration, washed with water (2×50 mL) and dried in vacuo to afford methyl 4-iodo-3-methyl-1H-pyrrole-2-carboxylate 1b (29.0 g, 109.41 mmol, 76.1% yield) as yellow powder.

Step B: Methyl 4-(1-isopropyl-1H-pyrazol-3-yl)-3-methyl-1H-pyrrole-2-carboxylate 1d Methyl 4-iodo-3-methyl-1H-pyrrole-2-carboxylate 1b (26.94 g, 101.64 mmol), 1-isopropyl-3-(4,4,5,5-tetramethyl-1,3,2-dioxaborolan-2-yl)-1H-pyrazole 1c (24.0 g, 101.64 mmol), cesium carbonate (66.24 g, 203.29 mmol) and Pd(dppf)$Cl_2$ (8.3 g, 10.16 mmol) were dissolved in degassed dioxane (80 mL) under Ar atmosphere. 3.8 mL of water was added via syringe and the reaction mixture was stirred at 80° C. for 16 h. The mixture was cooled to room temperature, filtered through celite pad and concentrated under reduced pressure. The residue was purified by column chromatography (eluted by Hex:EtOAc 20:1 to 1:2) to afford methyl 4-(1-isopropyl-1H-pyrazol-3-yl)-3-methyl-1H-pyrrole-2-carboxylate 1d (7.5 g, 30.33 mmol, 29.8% yield) as dark-yellow powder.

Step C: Methyl 1-amino-4-(1-isopropyl-1H-pyrazol-3-yl)-3-methyl-1H-pyrrole-2-carboxylate 1e To a solution of methyl 4-(1-isopropyl-1H-pyrazol-3-yl)-3-methyl-1H-pyrrole-2-carboxylate 1d (5.8 g, 22.19 mmol) in DMF (75 mL), sodium hydride (1.15 g, 48.09 mmol) was added at 0° C. The resulting mixture was stirred for 1 h at room temperature and the solution of O-(2,4-dinitrophenyl) hydroxylamine (5.75 g, 28.85 mmol) in DMF (50 mL) was added dropwise at 0° C. The reaction mixture was stirred at RT overnight. Then, the aqueous solution of $NH_4Cl$ (20 mL) was added dropwise to reaction mixture at cooling to 0° C. The product was extracted with EtOAc (3×35 mL) and combined organic layers was washed with water (5×20 mL). The organic extracts were dried over $Na_2SO_4$ and concentrated in vacuo to afford methyl 1-amino-4-(1-isopropyl-1H-pyrazol-3-yl)-3-methyl-1H-pyrrole-2-carboxylate 1e (4.9 g, 73.5% purity, 13.03 mmol, 58.7% yield).

Step D: 6-(1-Isopropyl-1H-pyrazol-3-yl)-5-methyl-2-(1-methyl-1H-imidazol-2-yl)pyrrolo[2,1-f][1,2,4]triazin-4-ol 1f Sodium hydride (1.77 g, 73.71 mmol) (60% in mineral oil) was added portionwise (over 3 min) to the solution of methyl 1-amino-4-(1-isopropyl-1H-pyrazol-3-yl)-3-methyl-1H-pyrrole-2-carboxylate 1e (5.8 g, 22.11 mmol) and 1-methyl-1H-imidazole-2-carbonitrile (2.37 g, 22.11 mmol) in dioxane (20 mL). The reaction mixture was heated under reflux for 16 h. Then, the mixture was cooled to the room temperature, poured in ice water and neutralized by acetic acid (6.64 g, 110.56 mmol). The formed participate was collected by filtration, washed with water (2×10 mL) and purified by column chromatography (eluted Hex:EtOAc 10:1 to EtOAc 100%) to afford 6-(1-isopropyl-1H-pyrazol-3-yl)-5-methyl-2-(1-methyl-1H-imidazol-2-yl)pyrrolo[2,1-f][1,2,4]triazin-4-ol 1f (1.8 g, 5.34 mmol, 24.1% yield) as dark-yellow solid.

Step E: 4-Chloro-6-(1-isopropyl-1H-pyrazol-3-yl)-5-methyl-2-(1-methyl-1H-imidazol-2-yl)pyrrolo[2,1-f][1,2,4]triazine 1g 6-(1-Isopropyl-1H-pyrazol-3-yl)-5-methyl-2-(1-methyl-1H-imidazol-2-yl)pyrrolo[2,1-f][1,2,4]triazin-4-ol 1f (1.8 g, 5.34 mmol) was dissolved in phosphoryl trichloride (9.81 g, 64.01 mmol, 5.97 ml, 12.0 equiv). The mixture was stirred at 100° C. for 16 h. The reaction mixture was concentrated in vacuo, poured in ice water (5 mL) and neutralized by $K_2CO_3$ (pH~9!). The mixture was extracted three times with DCM, dried over $Na_2SO_4$ and concentrated under reduced pressure to afford 4-chloro-6-(1-isopropyl-1H-pyrazol-3-yl)-5-methyl-2-(1-methyl-1H-imidazol-2-yl)pyrrolo[2,1-f][1,2,4]triazine 1g (1.3 g, 3.65 mmol, 68.5% yield) as dark-brown oil.

Step G: rac 6-(1-Isopropyl-1H-pyrazol-3-yl)-N-((1R,3S)-3-methoxycyclopentyl)-5-methyl-2-(1-methyl-1H-imidazol-2-yl)pyrrolo[2,1-f][1,2,4]triazin-4-amine (1)

General Procedure: DIPEA (163.29 mg, 1.26 mmol, 220.0 µl, 3.0 equiv) was added in one portion to the solution of 4-chloro-6-(1-isopropyl-1H-pyrazol-3-yl)-5-methyl-2-(1-methyl-1H-imidazol-2-yl)pyrrolo[2,1-f][1,2,4]triazine 1g (150.0 mg, 421.56 µmol) and the appropriate corresponding amine (505.37 µmol, 1.2 eq) in DMF (2 mL). The mixture was stirred at 100° C. for 16 h. The mixture was purified by HPLC. Starting with 4-chloro-6-(1-isopropyl-1H-pyrazol-3-yl)-5-methyl-2-(1-methyl-1H-imidazol-2-yl)pyrrolo[2,1-f][1,2,4]triazine 1g (150.0 mg, 421.56 µmol) and using the General Procedure with rac (1R,3S)-3-methoxycyclopentan- 1-amine (505.37 μmol, 1.2 eq) produced rac 6-(1-isopropyl-1H-pyrazol-3-yl)-N-((1R,3S)-3-methoxycyclopentyl)-5-methyl-2-(1-methyl-1H-imidazol-2-yl)pyrrolo[2,1-f][1,2,4]triazin-4-amine (1) (16.9 mg, 9% yield, 100% purity). LCMS(ESI): Calculated [M+1] 435.3 Found [M+1] 435.2 $^{1}$H NMR (DMSO-$d_6$, 600 MHz): δ (ppm) 1.45 (m, 6H), 1.95 (m, 6H), 2.67 (s, 3H), 3.24 (s, 3H), 3.92 (m, 4H), 4.51 (m, 1H), 4.73 (m, 1H), 6.50 (d, 1H), 6.84 (m, 1H), 6.93 (d, 1H), 7.23 (d, 1H), 7.76 (d, 1H), 7.87 (s, 1H).

Example 2-Example 5: Synthesis of Compounds 2-5

Following the general procedure described in Example 1, Step G, 4-chloro-6-(1-isopropyl-1H-pyrazol-3-yl)-5-methyl-2-(1-methyl-1H-imidazol-2-yl)pyrrolo[2,1-f][1,2,4]triazine 1g (150.0 mg, 421.56 μmol) was treated with the appropriate corresponding amine (505.37 μmol, 1.2 eq) to produce the Example compounds (2)-(5) shown in Table 1. Analytical data for compounds (2)-(5) is also shown in Table 1.

Example 6: Synthesis of Compound 6

(6)

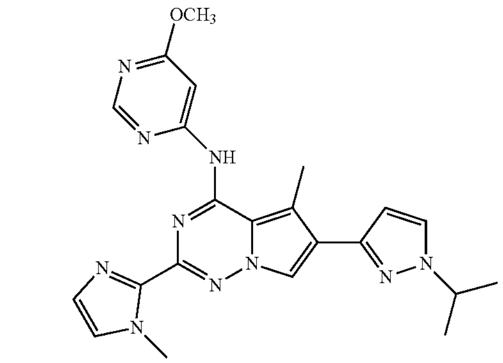

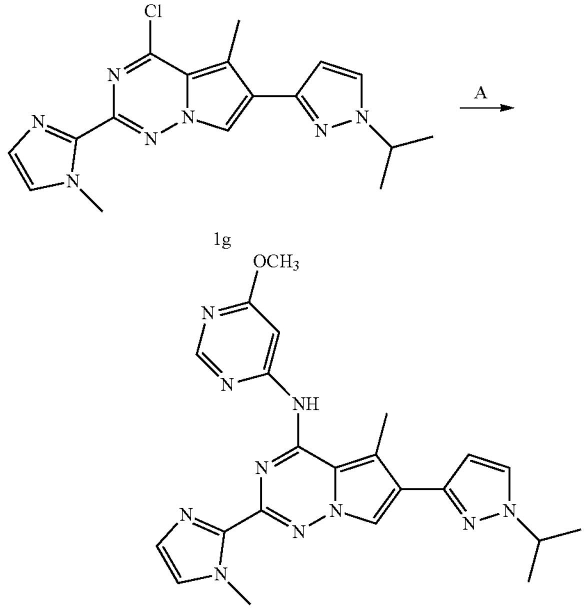

1g (6)

Step A: 6-(1-Isopropyl-1H-pyrazol-3-yl)-N-(6-methoxypyrimidin-4-yl)-5-methyl-2-(1-methyl-1H-imidazol-2-yl)pyrrolo[2,1-f][1,2,4]triazin-4-amine (6)

General Procedure: Sodium hydride (25.32 mg, 1.06 mmol, 1.5 eq) (60% in mineral oil) was added portionwise (over 3 min) to the solution of 4-chloro-6-(1-isopropyl-1H-pyrazol-3-yl)-5-methyl-2-(1-methyl-1H-imidazol-2-yl)pyrrolo[2,1-f][1,2,4]triazine 1g (prepared as described in Example 1, Step E (150.0 mg, 421.56 μmol) and the appropriate corresponding amine (633.12 μmol, 1.5 eq) in DMF (2 mL). The reaction mixture was stirred at 100° C. for 16 h. Then, the mixture was cooled to the room temperature, poured in cold solution of ammonium chloride (67.73 mg, 1.27 mmol) in water. The formed participate was collected by filtration, washed by water (2×2 mL) and purified by HPLC. Following the general procedure starting with 4-chloro-6-(1-isopropyl-1H-pyrazol-3-yl)-5-methyl-2-(1-methyl-1H-imidazol-2-yl)pyrrolo[2,1-f][1,2,4]triazine 1g (150.0 mg, 421.56 μmol) (prepared as described in Example 1, Step E) and using 6-methoxypyrimidin-4-amine (633.12 μmol, 1.5 eq), produced 6-(1-isopropyl-1H-pyrazol-3-yl)-N-(6-methoxypyrimidin-4-yl)-5-methyl-2-(1-methyl-1H-imidazol-2-yl)pyrrolo[2,1-f][1,2,4]triazin-4-amine (6) (14.6 mg, 7.20% yield, 100% purity). LCMS(ESI): Calculated [M+1] 445.2 Found [M+1] 445.2 $^{1}$H NMR (DMSO-$d_6$, 400 MHz) § 1.74 (dd, 6H), 3.06 (s, 3H), 4.28 (s, 3H), 4.50 (s, 3H), 4.76-4.85 (m, 1H), 6.82 (t, 1H), 7.74 (s, 1H), 7.89 (d, 1H), 7.91-7.98 (m, 1H), 8.02 (t, 1H), 8.54 (s, 1H), 8.89 (s, 1H).

Example 7: Synthesis of Compound 7

(7)

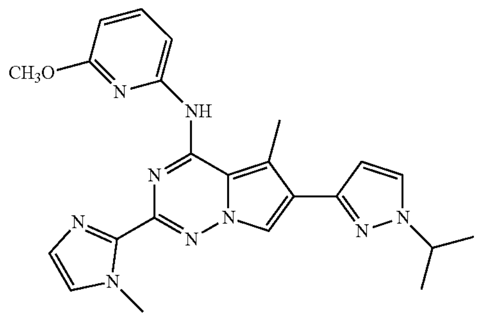

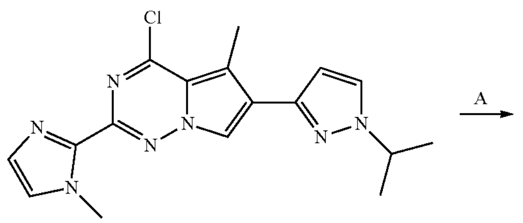

1g

-continued

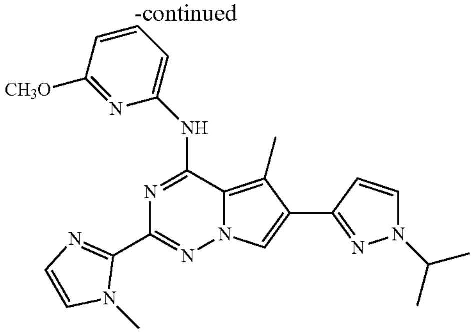

(7)

Step A: 6-(1-Isopropyl-1H-pyrazol-3-yl)-N-(6-methoxypyridin-2-yl)-5-methyl-2-(1-methyl-1H-imidazol-2-yl)pyrrolo[2,1-f][1,2,4]triazin-4-amine (7)

Using 4-chloro-6-(1-isopropyl-1H-pyrazol-3-yl)-5-methyl-2-(1-methyl-1H-imidazol-2-yl)pyrrolo[2,1-f][1,2,4]triazine 1g (prepared as described in Example 1, Step E, and 6-methoxypyridin-2-amine as the corresponding amine in the General Procedure described above in Example 6, Step A, produced 6-(1-isopropyl-1H-pyrazol-3-yl)-N-(6-methoxypyridin-2-yl)-5-methyl-2-(1-methyl-1H-imidazol-2-yl)pyrrolo[2,1-f][1,2,4]triazin-4-amine (7) (3.7 mg, 2.0% yield, 97% purity). LCMS(ESI): Calculated [M+1] 444.2 Found [M+1] 444.2.

Example 8: Synthesis of Compound 8

(8)

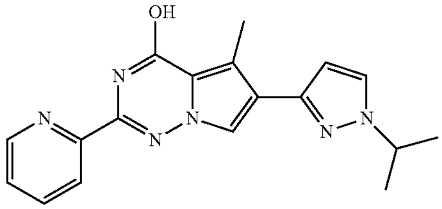

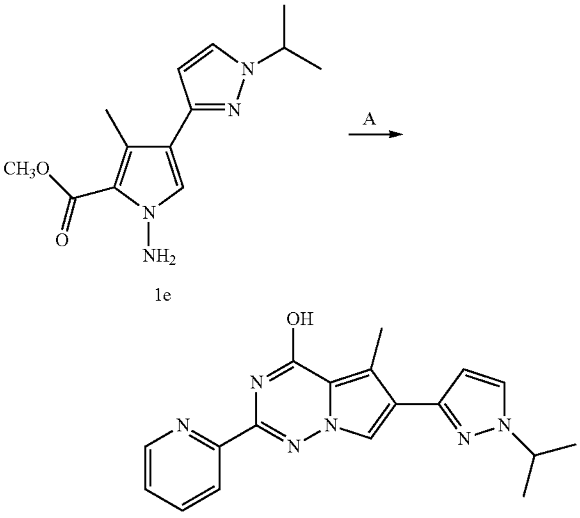

1e (8)

Step A: 6-(1-Isopropyl-1H-pyrazol-3-yl)-5-methyl-2-(pyridin-2-yl)pyrrolo[2,1-f][1,2,4]triazin-4-ol (8)

Sodium hydride (30.38 mg, 1.27 mmol) (60% in mineral oil) was added portionwise (over 3 min) to the solution of methyl 1-amino-4-(1-isopropyl-1H-pyrazol-3-yl)-3-methyl-1H-pyrrole-2-carboxylate 1e (prepared as described in Example 1, Step C (100.0 mg, 381.23 μmol) and pyridine-2-carbonitrile (39.54 mg, 379.81 μmol) in dioxane (20 mL). The reaction mixture was heated under reflux for 16 h. Then, the mixture was cooled to the room temperature, poured in ice water and neutralized by acetic acid. The obtained precipitate was collected by filtration, washed with water (2×10 mL) and purified by column chromatography (eluted hexane: EtOAc 10:1 to EtOAc 100%) to afford 6-(1-isopropyl-1H-pyrazol-3-yl)-5-methyl-2-(pyridin-2-yl)pyrrolo[2,1-f][1,2,4]triazin-4-ol (8) (13.0 mg, 38.88 μmol, 10.2% yield, 100% purity) as dark-yellow solid. LCMS(ESI): Calculated [M+1] 335.2 Found [M+1] 335.2 $^1$H NMR (DMSO-d6, 400 MHz) δ1.43 (m, 6H), 2.67 (s, 3H), 4.49 (m, 1H), 6.51 (d, 1H), 7.62 (m, 1H), 7.78 (m, 1H), 7.91 (s, 1H), 8.04 (dd, 1H), 8.20 (m, 1H), 8.80 (m, 1H), 11.02 (br s, 1H).

Example 9: Synthesis of Compound 9

(9)

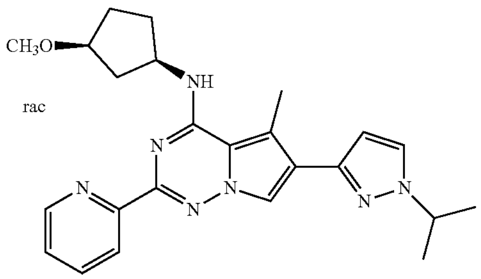

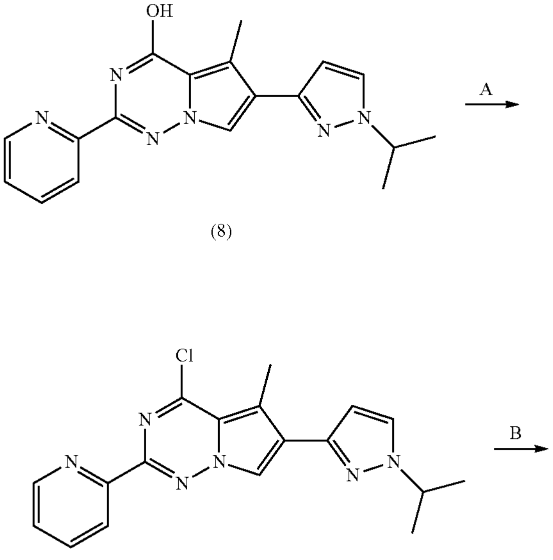

(8)

9a

-continued

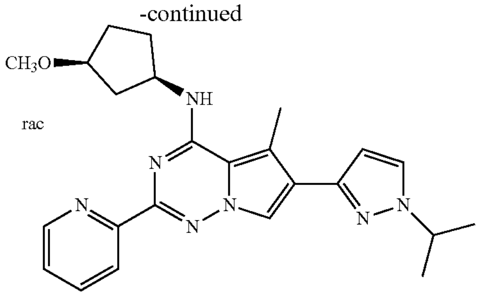

rac (9)

Step A: 4-Chloro-6-(1-isopropyl-1H-pyrazol-3-yl)-5-methyl-2-(pyridin-2-yl)pyrrolo[2,1-f][1,2,4]triazine 9a 6-(1-Isopropyl-1H-pyrazol-3-yl)-5-methyl-2-(pyridin-2-yl)pyrrolo[2,1-f][1,2,4]triazin-4-ol (8) (prepared as described in Example 8, Step A (2.99 g, 8.96 mmol) was dissolved in phosphoryl trichloride (16.48 g, 107.48 mmol, 10.02 mL, 12.0 equiv). The mixture was heated to 100° C. and stirred at this temperature for 16 h. The reaction mixture was concentrated in vacuo, poured in ice water (5 mL) and neutralized by $K_2CO_3$ (pH~9!). The mixture was extracted three times with DCM, dried over $Na_2SO_4$ and concentrated under reduced pressure to afford 4-chloro-6-(1-isopropyl-1H-pyrazol-3-yl)-5-methyl-2-(pyridin-2-yl)pyrrolo[2,1-f][1,2,4]triazine 9a (2.5 g, 7.09 mmol, 79.1% yield) as dark-brown oil. The obtained material was used in next step without further purification.

Step B: rac 6-(1-Isopropyl-1H-pyrazol-3-yl)-N-((1R,3S)-3-methoxycyclopentyl)-5-methyl-2-(pyridin-2-yl)pyrrolo[2,1-f][1,2,4]triazin-4-amine (9)

General Procedure: DIPEA (148.4 mg, 1.15 mmol, 200.0 μl, 4.0 equiv) was added in one portion to the solution of 4-chloro-6-(1-isopropyl-1H-pyrazol-3-yl)-5-methyl-2-(pyridin-2-yl)pyrrolo[2,1-f][1,2,4]triazine 9a (101.38 mg, 287.35 μmol) and the appropriate corresponding amine (431.02 μmol, 1.5 eq) in DMF (2 mL). The mixture was heated to 100° C. and stirred at this temperature for 16 h. The mixture was purified by HPLC. Following the General Procedure with 4-chloro-6-(1-isopropyl-1H-pyrazol-3-yl)-5-methyl-2-(pyridin-2-yl)pyrrolo[2,1-f][1,2,4]triazine 9a (101.38 mg, 287.35 μmol) and using rac (1R,3S)-3-methoxycyclopentan-1-amine (431.02 μmol, 1.5 eq) as the corresponding amine, produced rac 6-(1-isopropyl-1H-pyrazol-3-yl)-N-((1R,3S)-3-methoxycyclopentyl)-5-methyl-2-(pyridin-2-yl)pyrrolo[2,1-f][1,2,4]triazin-4-amine (9) (15.8 mg, 12.7% yield, 100% purity). LCMS(ESI): Calculated [M+1] 432.3 Found [M+1] 432.2 $^1H$ NMR (DMSO-$d_6$, 400 MHz) δ 1.46 (d, 6H), 1.83-2.00 (m, 4H), 2.02-2.13 (m, 2H), 2.71 (s, 3H), 3.29 (s, 3H), 3.93-4.01 (m, 1H), 4.53 (p, 1H), 4.84-4.95 (m, 1H), 6.52 (d, 1H), 6.88 (d, 1H), 7.43-7.51 (m, 1H), 7.80 (d, 1H), 7.88-7.98 (m, 2H), 8.27 (d, 1H), 8.68 (d, 1H).

Example 10-Example 12: Synthesis of Compounds 10-12

Following the general procedure described in Example 9, Step B, 4-chloro-6-(1-isopropyl-1H-pyrazol-3-yl)-5-methyl-2-(pyridin-2-yl)pyrrolo[2,1-f][1,2,4]triazine 9a (101.38 mg, 287.35 μmol) and the appropriate corresponding amine (431.02 μmol, 1.5 eq) to produce the Example compounds (10)-(12) shown in Table 1. Analytical data for compounds 10-12 is also presented in Table 1.

Example 13: Synthesis of Compound 13

(13)

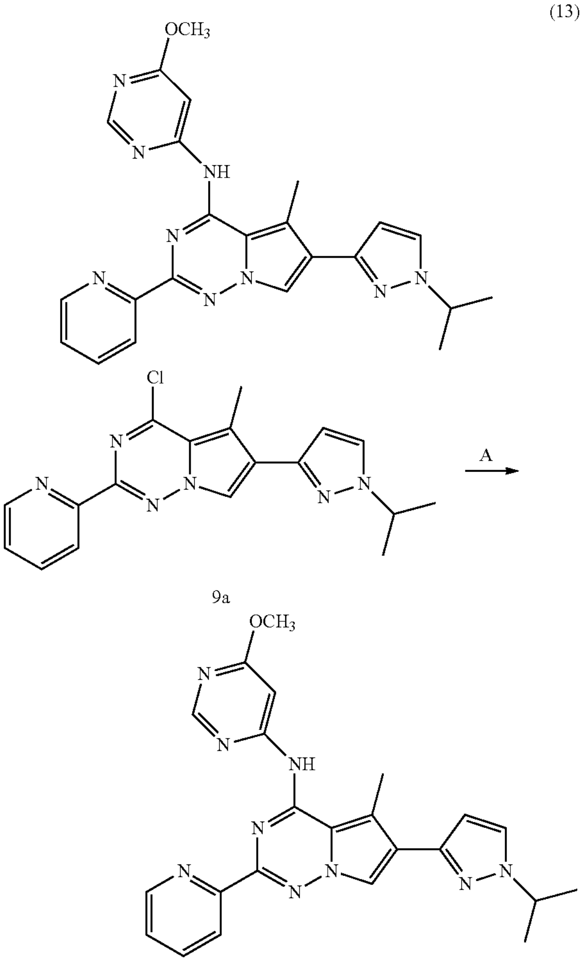

9a (13)

Step A: 6-(1-Isopropyl-1H-pyrazol-3-yl)-N-(6-methoxypyrimidin-4-yl)-5-methyl-2-(pyridin-2-yl)pyrrolo[2,1-f][1,2,4]triazin-4-amine (13)

General Procedure: Sodium hydride (25.55 mg, 1.06 mmol) (60% in mineral oil) was added portionwise (over 3 min) to the solution of 4-chloro-6-(1-isopropyl-1H-pyrazol-3-yl)-5-methyl-2-(pyridin-2-yl)pyrrolo[2,1-f][1,2,4]triazine 9a (prepared as described in Example 9, Step A) (150.0 mg, 425.15 μmol) and the appropriate corresponding amine (638.75 μmol, 1.5 eq) in DMF (2 mL). The reaction mixture was heated 100° C. and stirred at this temperature for 16 h. Then the mixture was cooled to the room temperature, poured in cold solution of ammonium chloride (68.34 mg, 1.28 mmol) in water. The formed participate was collected by filtration, washed by water (2×10 mL) and purified by HPLC. Following the General Procedure with 4-chloro-6-(1-isopropyl-1H-pyrazol-3-yl)-5-methyl-2-(pyridin-2-yl)

pyrrolo[2,1-f][1,2,4]triazine 9a (150.0 mg, 425.15 μmol) and 6-methoxypyrimidin-4-amine (638.75 μmol, 1.5 eq) as the corresponding amine, produced 6-(1-isopropyl-1H-pyrazol-3-yl)-N-(6-methoxypyrimidin-4-yl)-5-methyl-2-(pyridin-2-yl)pyrrolo[2,1-f][1,2,4]triazin-4-amine (13) (30.8 mg, 16.4% yield, 100% purity). LCMS(ESI): Calculated [M+1] 442.2 Found [M+1] 442.2 $^1$H NMR (DMSO-$d_6$, 400 MHz) § 1.47 (d, 6H), 2.86 (s, 3H), 3.94 (s, 3H), 4.47-4.65 (m, 1H), 6.47 (s, 1H), 6.56 (s, 1H), 7.63 (s, 1H), 7.81 (d, 1H), 7.89-8.11 (m, 2H), 8.21 (d, 1H), 8.52-8.85 (m, 2H), 14.85 (s, 1H).

Example 14: Synthesis of Compound 14

(14)

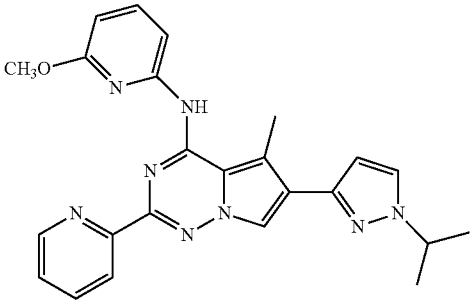

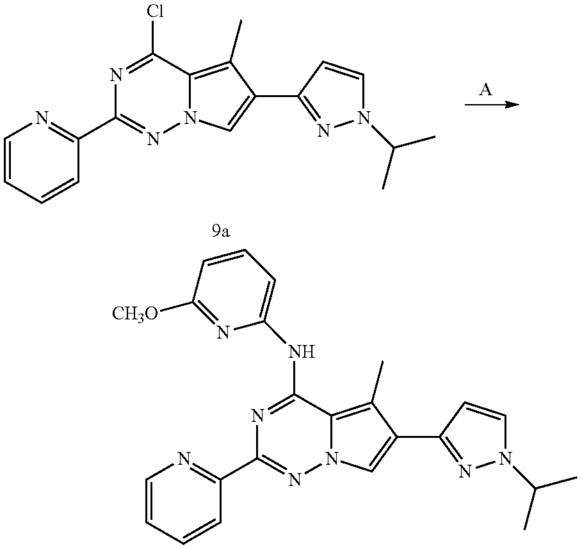

9a (14)

Step A: 6-(1-Isopropyl-1H-pyrazol-3-yl)-N-(6-methoxypyridin-2-yl)-5-methyl-2-(pyridin-2-yl)pyrrolo[2,1-f][1,2,4]triazin-4-amine (14)

Following the in the General Procedure described above in Example 13, Step A, 4-chloro-6-(1-isopropyl-1H-pyrazol-3-yl)-5-methyl-2-(pyridin-2-yl)pyrrolo[2,1-f][1,2,4]triazine 9a (prepared as described in Example 9, Step A) (150.0 mg, 425.15 μmol) and 6-methoxypyridin-2-amine (638.75 μmol, 1.5 eq) as the corresponding amine, produced 6-(1-Isopropyl-1H-pyrazol-3-yl)-N-(6-methoxypyridin-2-yl)-5-methyl-2-(pyridin-2-yl)pyrrolo[2,1-f][1,2,4]triazin-4-amine (14) (30.8 mg, 16.4% yield, 100% purity). LCMS(ESI): Calculated [M+1] 441.2 Found [M+1] 441.2 $^1$H NMR (DMSO-$d_6$, 400 MHz) § 1.47 (d, 6H), 2.86 (s, 3H), 3.94 (s, 3H), 4.47-4.65 (m, 1H), 6.47 (s, 1H), 6.56 (s, 1H), 7.63 (s, 1H), 7.81 (d, 1H), 7.89-8.11 (m, 2H), 8.21 (d, 1H), 8.52-8.85 (m, 2H), 14.85 (s, 1H).

Example 15: Synthesis of Compound 15

(15)

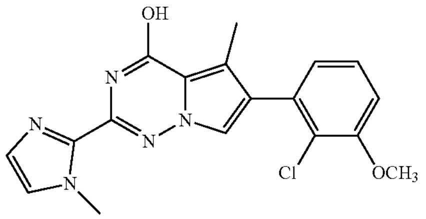

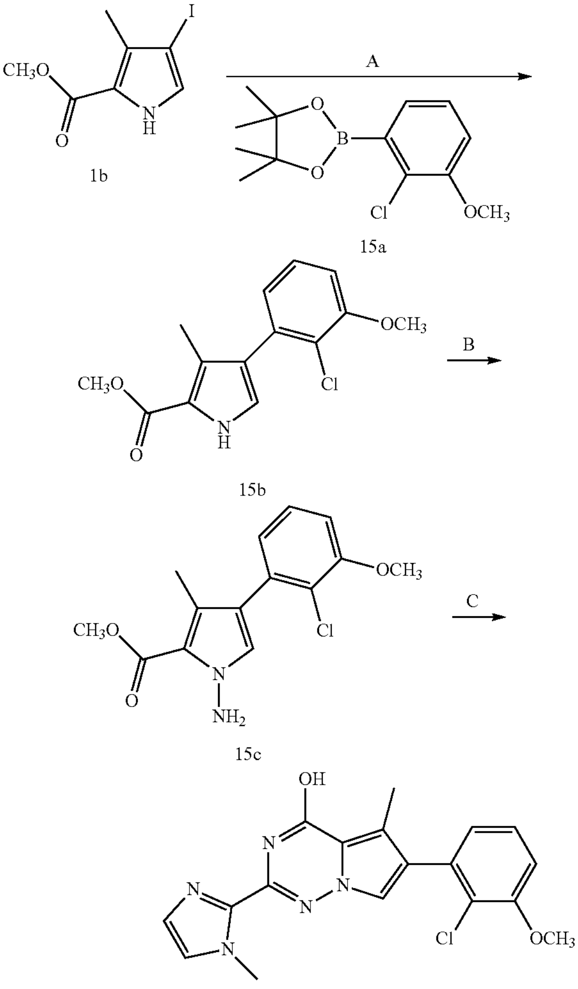

1b

15a

15b

15c (15)

Step A: Methyl 4-(2-chloro-3-methoxyphenyl)-3-methyl-1H-pyrrole-2-carboxylate 15b A mixture of methyl 4-iodo-3-methyl-1H-pyrrole-2-carboxylate 1b (prepared as described in Example 1, Step A (5.0 g, 18.86 mmol), 2-(2-chloro-3-methoxyphenyl)-4,4,5,5-tetramethyl-1,3,2-dioxaborolane 15a (6.08 g, 22.64 mmol), cesium carbonate (12.29 g, 37.73 mmol) and [1,1'-bis(diphenylphosphino)ferrocene]dichloropalladium(II) dichloromethane adduct (1.54 g, 1.89 mmol) in dioxane/$H_2O$ (100/5 mL) was heated at 100° C. overnight under Argon atmosphere. The reaction mixture was concentrated, and crude compound was purified by flash chromatography to give methyl 4-(2-chloro-3-methoxyphenyl)-3-methyl-1H-pyrrole-2-carboxylate 15b (3.05 g, 57.8% yield).

Step B: Methyl 1-amino-4-(2-chloro-3-methoxyphenyl)-3-methyl-1H-pyrrole-2-carboxylate 15c To solution of methyl 4-(2-chloro-3-methoxyphenyl)-3-methyl-1H-pyrrole-2-carboxylate 15b (2.4 g, 8.58 mmol) in DMF (70 mL), sodium hydride (686.39 mg, 28.6 mmol) was added at 0° C. After 30 min, O-(diphenylphosphinyl) hydroxylamine (4.0 g, 17.16 mmol) was added portionwise at 0° C. Reaction mixture was stirred at 60° C. overnight. Then, the mixture was cooled, filtered and filtrate was evaporated under reduce pressure to give methyl 1-amino-4-(2-chloro-3-methoxyphenyl)-3-methyl-1H-pyrrole-2-carboxylate 15c (1.7 g, 65.4% yield).

Step C: 6-(2-Chloro-3-methoxyphenyl)-5-methyl-2-(1-methyl-1H-imidazol-2-yl)pyrrolo[2,1-f][1,2,4]triazin-4-ol (15)

To solution of methyl 1-amino-4-(2-chloro-3-methoxyphenyl)-3-methyl-1H-pyrrole-2-carboxylate 15c (499.72 mg, 1.7 mmol) and 1-methyl-1H-imidazole-2-carbonitrile (217.93 mg, 2.03 mmol) in dioxane (20 mL), sodium hydride (169.53 mg, 7.06 mmol) was added at 0° C. Reaction mixture was heated at 100° C. overnight. Solution of $NH_4Cl$ (5 mL) was added dropwise to reaction mixture after cooling to 0° C., then extracted with EtOAc (3×15 mL). The organic extracts were dried over $Na_2SO_4$, concentrated in vacuo to give 6-(2-chloro-3-methoxyphenyl)-5-methyl-2-(1-methyl-1H-imidazol-2-yl)pyrrolo[2,1-f][1,2,4]triazin-4-ol (15) (610.0 mg, 64% purity, 1.06 mmol, 62.3% yield). A small amount was purified by HPLC for bioassay (100% purity). LCMS(ESI): Calculated [M+1] 370.1 Found [M+1] 370.0 $^1H$ NMR (DMSO-$d_6$, 400 MHz) § 2.30 (s, 1H), 3.87 (s, 3H), 3.98 (s, 3H), 6.95 (d, 1H), 7.10 (s, 1H), 7.29 (d, 1H), 7.35 (dd, 1H), 7.45 (s, 1H), 7.58 (s, 1H), 11.05 (br s, 1H).

Example 16: Synthesis of Compound 16

(16)

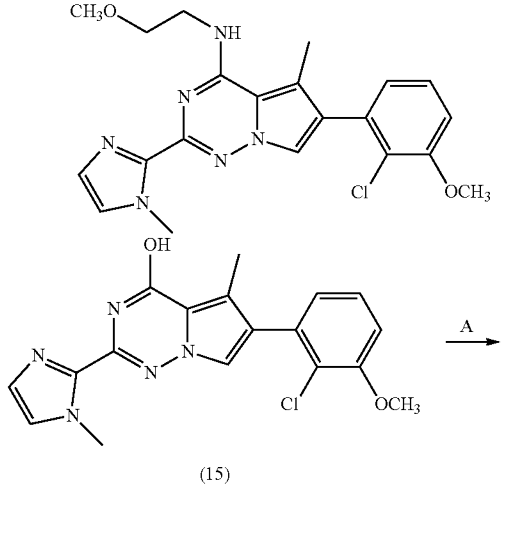

(15)

-continued

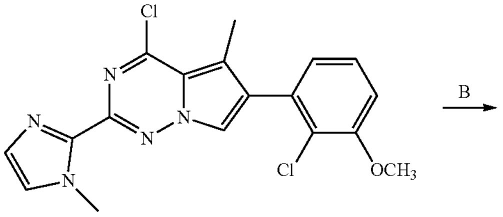

16a

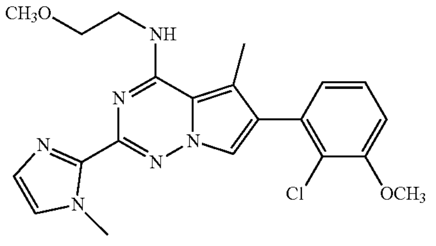

(16)

Step A: 4-Chloro-6-(2-chloro-3-methoxyphenyl)-5-methyl-2-(1-methyl-1H-imidazol-2-yl)pyrrolo[2,1-f][1,2,4]triazine 16a To solution of 6-(2-chloro-3-methoxyphenyl)-5-methyl-2-(1-methyl-1H-imidazol-2-yl)pyrrolo[2,1-f][1,2,4]triazin-4-ol (15) (prepared as described in Example 15, Step C, used without purification) (926.77 mg, 2.51 mmol) in phosphoryl trichloride (3.84 g, 25.06 mmol, 2.34 ml, 10.0 equiv) DIPEA (972.02 mg, 7.52 mmol, 1.31 mL, 3.0 equiv) was added. Reaction mixture was stirred at 100° C. overnight then concentrated in vacuo, washed with aqueous solution of $NaHCO_3$ to pH 7 and extracted with $CHCl_3$ (3×15 mL). The combined organic layers were dried over $Na_2SO_4$ and concentrated in vacuo to give 4-chloro-6-(2-chloro-3-methoxyphenyl)-5-methyl-2-(1-methyl-1H-imidazol-2-yl)pyrrolo[2,1-f][1,2,4]triazine 16a (1.1 g, 50.0% purity, 1.42 mmol, 56.5% yield).

Step B: 6-(2-Chloro-3-methoxyphenyl)-N-(2-methoxyethyl)-5-methyl-2-(1-methyl-1H-imidazol-2-yl)pyrrolo[2,1-f][1,2,4]triazin-4-amine (16)

The 4-chloro-6-(2-chloro-3-methoxyphenyl)-5-methyl-2-(1-methyl-1H-imidazol-2-yl)pyrrolo[2,1-f][1,2,4]triazine 16a (355.6 mg, 915.91 µmol) was dissolved in DMSO (7 mL) and 2-methoxyethylamine (137.6 mg, 1.83 mmol, 160.0 µL, 2.0 equiv) followed by DIPEA (355.12 mg, 2.75 mmol, 480.0 µL, 3.0 equiv) were added at room temperature. The mixture was heated at 100° C. overnight. Then, the mixture was cooled and purified by HPLC (20-80% 0-6 min $H_2O$/MeOH, flow: 30 mL/min; column: SunFire C18) to afford 6-(2-chloro-3-methoxyphenyl)-N-(2-methoxyethyl)-5-methyl-2-(1-methyl-1H-imidazol-2-yl)pyrrolo[2,1-f][1,2,4]triazin-4-amine (16) (34.0 mg, 8.7% yield, 100% purity) as yellow gum. LCMS(ESI): Calculated [M+1] 427.2 Found [M+1] 427.0 $^1H$ NMR (DMSO-$d_6$, 400 MHz) § 2.32 (s, 3H), 3.30 (s, 3H), 3.59 (t, 2H), 3.74-3.80 (m, 2H), 3.90 (s, 3H), 3.96 (s, 3H), 6.94-7.00 (m, 2H), 7.16-7.21 (m, 2H), 7.28 (s, 1H), 7.37 (t, 1H), 7.72 (s, 1H).

Example 17: Synthesis of Compound 17

(17)

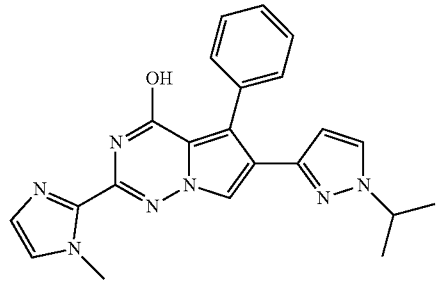

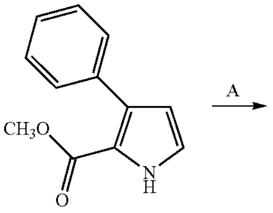

17a

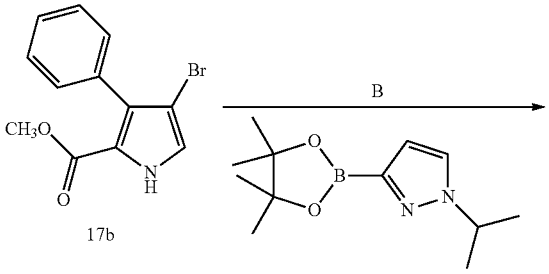

17b

1c

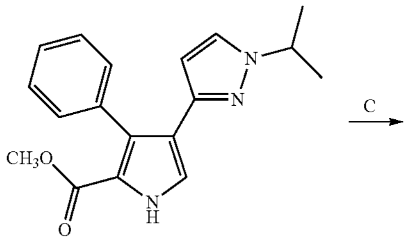

17c

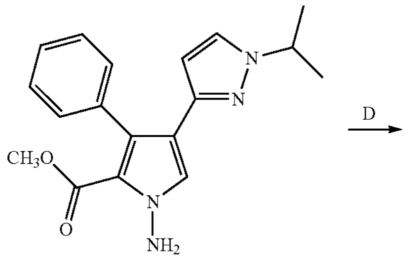

17d

-continued

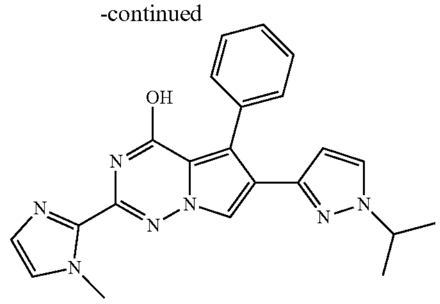

(17)

Step A: Methyl 4-bromo-3-phenyl-1H-pyrrole-2-carboxylate 17b

To a solution of methyl 3-phenyl-1H-pyrrole-2-carboxylate 17a (5.0 g, 24.85 mmol) in THF/$H_2O$ 4:1 (100 mL) was added N-bromosuccinimide (4.42 g, 24.85 mmol). The reaction mixture was stirred vigorously at room temperature for 15 min following by the addition of water (50 mL) and EtOAc (200 mL). The reaction mixture was extracted with two portions of EtOAc (100 mL). The organic layers were combined, dried over anhydrous sodium sulfate and concentrated under reduced pressure. Methyl 4-bromo-3-phenyl-1H-pyrrole-2-carboxylate 17b (5.0 g, 70.0% purity, 12.49 mmol, 50.3% yield) was used in next step without purification.

Step B: Methyl 4-(1-isopropyl-1H-pyrazol-3-yl)-3-phenyl-1H-pyrrole-2-carboxylate 17c Methyl 4-bromo-3-phenyl-1H-pyrrole-2-carboxylate 17b (5.0 g, 17.85 mmol), 1-isopropyl-3-(4,4,5,5-tetramethyl-1,3,2-dioxaborolan-2-yl)-1H-pyrazole 1c (5.06 g, 21.42 mmol), [1,1'-bis(diphenylphosphino)ferrocene]dichloropalladium(II) dichloromethane adduct (1.46 g, 1.78 mmol), cesium carbonate (11.63 g, 35.7 mmol) were suspended in degassed dioxane: water (50 mL: 10 mL). The mixture was heated under argon at 100° C. overnight. After cooling to room temperature, the mixture was diluted with ethyl acetate (100 mL), the organic layer was washed with water (100 mL) and saturated brine (100 mL), dried over magnesium sulfate, filtered, and concentrated in vacuo to afford the methyl 4-(1-isopropyl-1H-pyrazol-3-yl)-3-phenyl-1H-pyrrole-2-carboxylate 17c (5.7 g, 56.0% purity, 10.32 mmol, 57.8% yield).

Step C: Methyl 1-amino-4-(1-isopropyl-1H-pyrazol-3-yl)-3-phenyl-1H-pyrrole-2-carboxylate 17d The mixture of methyl 4-(1-isopropyl-1H-pyrazol-3-yl)-3-phenyl-1H-pyrrole-2-carboxylate 17c (3.2 g, 10.34 mmol) sodium hydride (620.52 mg, 25.86 mmol) in DMF (50 mL) was cooled to 0° C. and O-(diphenylphosphinyl) hydroxylamine (2.89 g, 12.41 mmol) was added. The mixture was allowed to warm up to 60° C. and stirred for 16 h. The mixture was poured into the ice-cold water (150 mL) and extracted with EtOAc (100 mL). The organic layer was washed with water (100 mL), dried over $Na_2SO_4$ and evaporated under reduced pressure to obtain methyl 1-amino-4-(1-isopropyl-1H-pyrazol-3-yl)-3-phenyl-1H-pyrrole-2-carboxylate 17d after crystallization in methyl tert-butyl ether and hexane (10/3) (3.1 g, 90.0% purity, 6.69 mmol, 64.7% yield).

Step D: 6-(1-Isopropyl-1H-pyrazol-3-yl)-2-(1-methyl-1H-imidazol-2-yl)-5-phenylpyrrolo[2,1-f][1,2,4]triazin-4-ol (17)

1-Methyl-1H-imidazole-2-carbonitrile (990.77 mg, 9.25 mmol) and 1-amino-4-(1-isopropyl-1H-pyrazol-3-yl)-3-phenyl-1H-pyrrole-2-carboxylate 17d (2.5 g, 7.71 mmol) was dissolved in DMF (50 mL) and sodium hydride (616.59 mg, 25.69 mmol) was added. The mixture was stirred at 80° C. 16 h. Then mixture was evaporated, and the residue was diluted with water (80 mL). The product was extracted with EtOAc (80 mL). Organic layer was dried over $Na_2SO_4$ and evaporated to give 6-(1-isopropyl-1H-pyrazol-3-yl)-2-(1-methyl-1H-imidazol-2-yl)-5-phenylpyrrolo[2,1-f][1,2,4]triazin-4-ol (17) (2.6 g, 60.0% purity, 3.91 mmol, 50.7% yield). A small amount of material was purified by HPLC for bioassay (100% purity). LCMS(ESI): Calculated [M+1] 400.2 Found [M+1] 400.2 $^1$H NMR (DMSO-$d_6$, 400 MHz) § 1.32 (m, 6H), 4.00 (s, 3H), 4.32 (m, 1H), 5.65 (s, 1H), 7.08 (s, 1H), 7.30 (m, 5H), 7.42 (s, 1H), 7.51 (s, 1H), 7.88 (s, 1H), 11.22 (br s, 1H).

Example 18: Synthesis of Compound 18

(18)

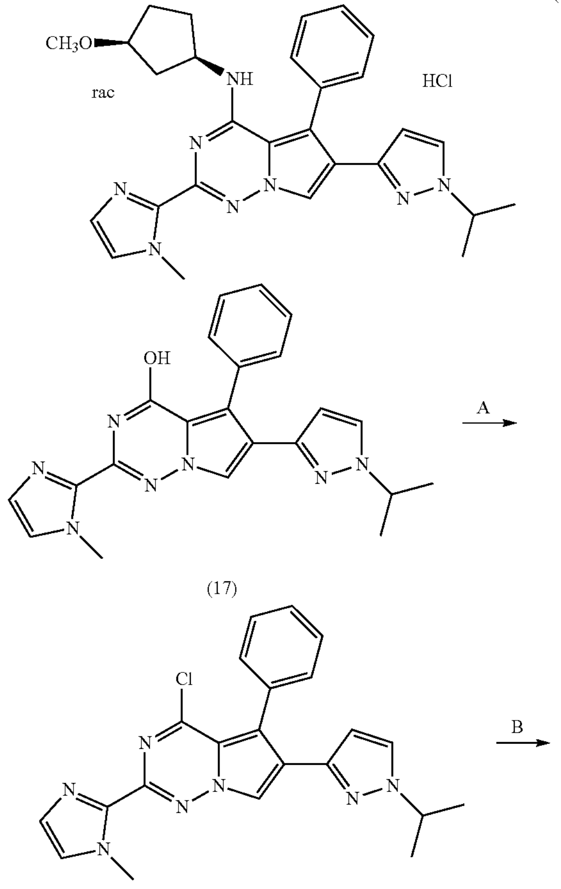

(17)

18a

-continued

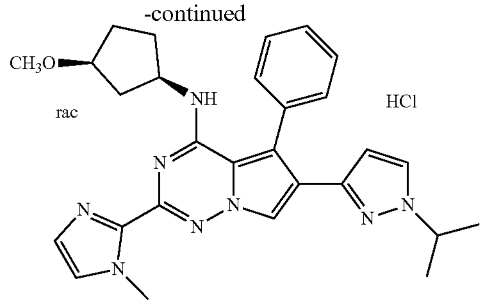

(18)

Step A: 4-Chloro-6-(1-isopropyl-1H-pyrazol-3-yl)-2-(1-methyl-1H-imidazol-2-yl)-5-phenylpyrrolo[2,1-f][1,2,4]triazine 18a The starting material 6-(1-isopropyl-1H-pyrazol-3-yl)-2-(1-methyl-1H-imidazol-2-yl)-5-phenylpyrrolo[2,1-f][1,2,4]triazin-4-ol (17) (crude product prepared as described in Example 17, Step D (2.5 g, 6.26 mmol) was suspended in phosphoryl trichloride (9.59 g, 62.58 mmol, 5.83 mL, 10.0 equiv) and DIPEA (2.43 g, 18.77 mmol, 3.27 mL, 3.0 equiv) was added at RT. The reaction mixture was heated at 100° C. for 16 h. The solution was cooled to RT, evaporated under reduced pressure, poured in ice (25 mL) and diluted with ice-cold ammonia (20 mL, 20-25% of ammonia), the product was extracted with chloroform (2×50 mL) and evaporated. 4-Chloro-6-(1-isopropyl-1H-pyrazol-3-yl)-2-(1-methyl-1H-imidazol-2-yl)-5-phenylpyrrolo[2,1-f][1,2,4]triazine 18a (2.8 g, 52.0% purity, 3.48 mmol, 55.7% yield) was obtained as brown slurry.

Step B: rac 6-(1-Isopropyl-1H-pyrazol-3-yl)-N-((1R,3S)-3-methoxycyclopentyl)-2-(1-methyl-1H-imidazol-2-yl)-5-phenylpyrrolo[2,1-f][1,2,4]triazin-4-amine hydrochloride (18)

General Procedure: The 4-chloro-6-(1-isopropyl-1H-pyrazol-3-yl)-2-(1-methyl-1H-imidazol-2-yl)-5-phenylpyrrolo[2,1-f][1,2,4]triazine 18a (202.8 mg, 485.29 μmol) was dissolved in DMSO (2 mL) and triethylamine (196.02 mg, 1.94 mmol, 270.0 μl, 4.0 equiv) and the appropriate corresponding amine (1.5 equiv) was added at room temperature. The mixture was heated at 100° C. overnight (16 hours), cooled and purified by HPLC.

Following the General Procedure using 4-chloro-6-(1-isopropyl-1H-pyrazol-3-yl)-2-(1-methyl-1H-imidazol-2-yl)-5-phenylpyrrolo[2,1-f][1,2,4]triazine 18a (202.8 mg, 485.29 μmol) and rac (1R,3S)-3-methoxycyclopentan-1-amine (1.5 equiv) as the corresponding amine, produced (after conversion to the HCl salt) rac 6-(1-isopropyl-1H-pyrazol-3-yl)-N-((1R,3S)-3-methoxycyclopentyl)-2-(1-methyl-1H-imidazol-2-yl)-5-phenylpyrrolo[2,1-f][1,2,4]triazin-4-amine hydrochloride salt (18) (7.00 mg, 1.70% yield, 97% purity). LCMS(ESI): Calculated [M+1] 497.3 Found [M+1] 497.2 $^1$H NMR (cd$_3$od, 400 MHZ,) δ 1.46-1.53 (m, 7H), 1.60-1.79 (m, 3H), 1.92-2.01 (m, 1H), 2.03-2.16 (m, 1H), 3.01 (s, 3H), 3.73-3.80 (m, 1H), 4.39 (s, 3H), 4.55 (p, 1H), 4.81-4.86 (m, 1H), 5.65 (d, 1H), 7.42-7.49 (m, 2H), 7.54-7.60 (m, 4H), 7.68 (d, 1H), 7.75 (d, 1H), 8.17 (s, 1H).

Example 19-Example 21: Synthesis of Compounds 19-21

Following the General Procedure described in Example 18, Step B, chloro-6-(1-isopropyl-1H-pyrazol-3-yl)-2-(1-methyl-1H-imidazol-2-yl)-5-phenylpyrrolo[2,1-f][1,2,4]triazine 18a (202.8 mg, 485.29 μmol) and the appropriate corresponding amine (1.5 equiv) produced the Example compounds (19)-(21) shown in Table 1. Analytical data for compounds (19)-(21) is also presented in Table 1.

Example 22: Synthesis of Compound 22

(22)

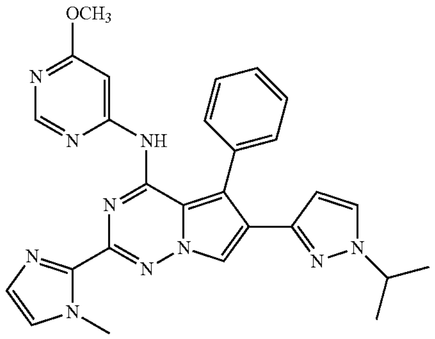

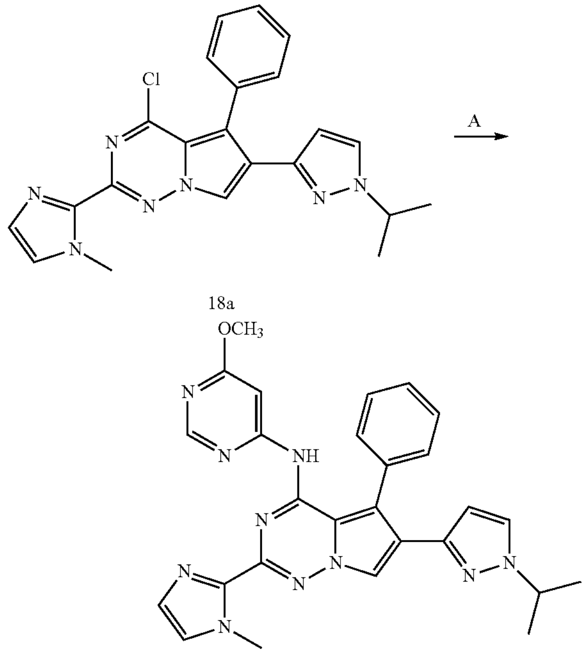

18a (22)

Step A: 6-(1-Isopropyl-1H-pyrazol-3-yl)-N-(6-methoxypyrimidin-4-yl)-2-(1-methyl-1H-imidazol-2-yl)-5-phenylpyrrolo[2,1-f][1,2,4]triazin-4-amine (22)

General Procedure: To a solution of 4-chloro-6-(1-isopropyl-1H-pyrazol-3-yl)-2-(1-methyl-1H-imidazol-2-yl)-5-phenylpyrrolo[2,1-f][1,2,4]triazine 18a (prepared as described in Example 18, (259.87 mg, 621.87 μmol) and the appropriate corresponding amine (518.22 μmol, 1 equiv) in dry DMF (5.0 mL), sodium hydride (31.09 mg, 1.3 mmol) was added under Ar atmosphere. The reaction mixture was stirred at 80° C. for 15 h. The mixture was cooled, diluted with water (20 mL) and concentrated to dryness. The residue was purified by HPLC (20-80% 0-6 min $H_2O$/MeOH, flow: 30 mL/min; column: SunFire C18) to afford product. Following the General Procedure using 4-chloro-6-(1isopropyl-1H-pyrazol-3-yl)-2-(1-methyl-1H-imidazol-2-yl)-5-phenylpyrrolo[2,1-f][1,2,4]triazine 18a (259.87 mg, 621.87 μmol) and 6-methoxypyrimidin-4-amine amine (518.22 μmol, 1 equiv) as the corresponding amine, produced 6-(1-isopropyl-1H-pyrazol-3-yl)-N-(6-methoxypyrimidin-4-yl)-2-(1-methyl-1H-imidazol-2-yl)-5-phenylpyrrolo[2,1-f][1,2,4]triazin-4-amine (22) (4.60 mg, 2.30% yield, 99% purity). LCMS(ESI): Calculated [M+1] 507.3 Found [M+1] 507.2 $^1$H NMR ($cd_3od$, 400 MHz) § 1.49 (d, 6H), 3.95 (s, 3H), 4.12 (s, 3H), 4.44-4.57 (m, 1H), 5.66 (d, 1H), 7.19 (s, 1H), 7.32 (s, 1H), 7.48 (d, 1H), 7.52-7.65 (m, 5H), 8.12 (s, 1H), 8.25 (s, 2H).

Example 23: Synthesis of Compound 23

(23)

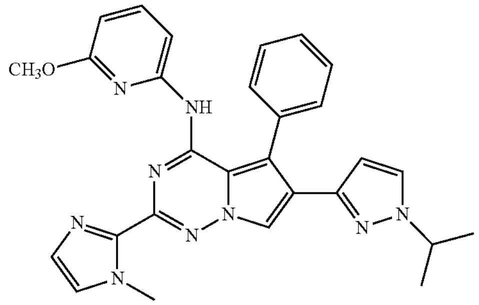

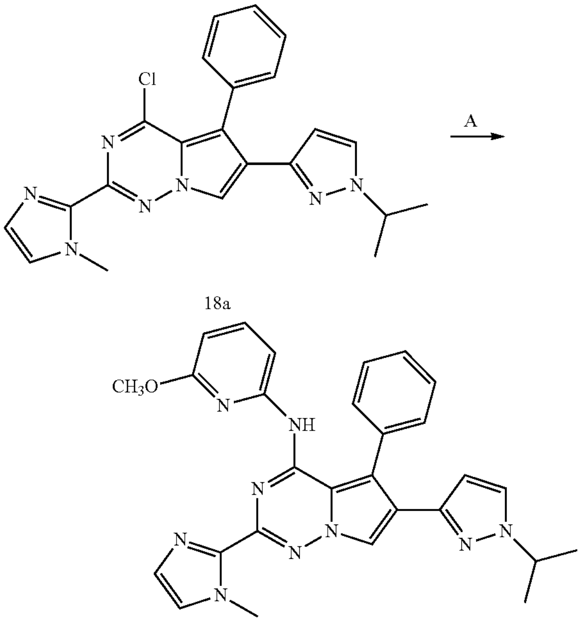

18a (23)

Step A: 6-(1-Isopropyl-1H-pyrazol-3-yl)-N-(6-methoxypyridin-2-yl)-2-(1-methyl-1H-imidazol-2-yl)-5-phenylpyrrolo[2,1-f][1,2,4]triazin-4-amine (23)

Following the General Procedure described in Example 22, Step A, using 4-chloro-6-(1-isopropyl-1H-pyrazol-3-yl)-

2-(1-methyl-1H-imidazol-2-yl)-5-phenylpyrrolo[2,1-f][1,2,4]triazine 18a (prepared as described in Example 18, Step A) (259.87 mg, 621.87 μmol) and 6-methoxypyridin-2-amine (518.22 μmol, 1 equiv) as the corresponding amine, produced 6-(1-isopropyl-1H-pyrazol-3-yl)-N-(6-methoxypyridin-2-yl)-2-(1-methyl-1H-imidazol-2-yl)-5-phenylpyrrolo[2,1-f][1,2,4]triazin-4-amine (23) (6.00 mg, 2.30% yield, 100% purity). LCMS(ESI): Calculated [M+1] 506.3 Found [M+1] 506.2.

Example 24: Synthesis of Compound 24

(24)

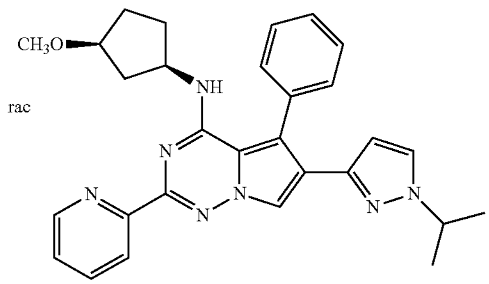

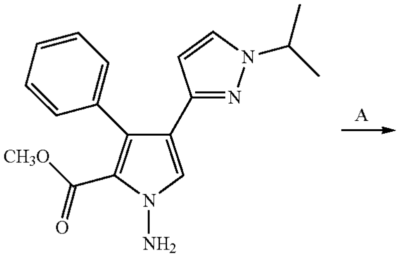

17d

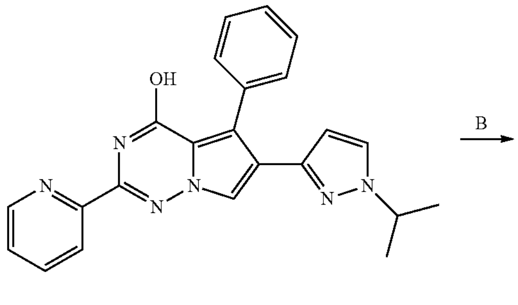

24a

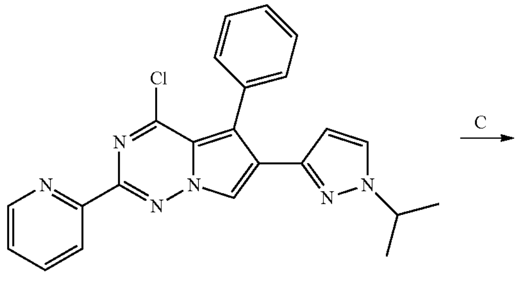

24b

-continued

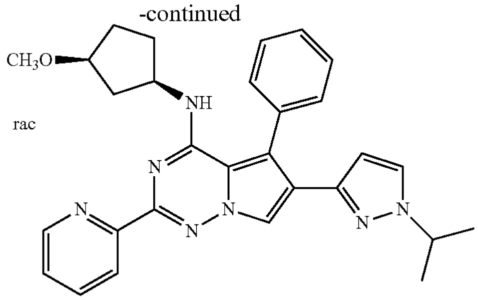

(24)

Step A: 6-(1-Isopropyl-1H-pyrazol-3-yl)-5-phenyl-2-(pyridin-2-yl)pyrrolo[2,1-f][1,2,4]triazin-4-ol 24a Pyridine-2-carbonitrile (1.44 g, 13.87 mmol) and methyl 1-amino-4-(1-isopropyl-1H-pyrazol-3-yl)-3-phenyl-1H-pyrrole-2-carboxylate 17b (prepared as described in Example 17, Step A (3.75 g, 11.56 mmol) was dissolved in DMF (15 mL) and sodium hydride (1.16 g, 48.17 mmol) was added. The mixture was stirred and heated at 80° C. for 16 h. Then mixture was diluted with water (40 mL) and extracted with EtOAc (3×50 mL). Organic layer dried and evaporated to give 6-(1-isopropyl-1H-pyrazol-3-yl)-5-phenyl-2-(pyridin-2-yl)pyrrolo[2,1-f][1,2,4]triazin-4-ol 24a (5.0 g, 34.0% purity, 4.29 mmol, 37.1% yield).

Step B: 4-Chloro-6-(1-isopropyl-1H-pyrazol-3-yl)-5-phenyl-2-(pyridin-2-yl)pyrrolo[2,1-f][1,2,4]triazine 24b The starting material 6-(1-isopropyl-1H-pyrazol-3-yl)-5-phenyl-2-(pyridin-2-yl)pyrrolo[2,1-f][1,2,4]triazin-4-ol 24a (5.0 g, 12.61 mmol) was suspended in phosphoryl trichloride (19.34 g, 126.13 mmol, 11.76 ml, 10.0 equiv) and DIPEA (4.89 g, 37.84 mmol, 6.59 mL, 3.0 equiv) was added at room temperature. The reaction mixture was heated at 100° C. for 16 h. The solution was cooled to RT, evaporated under reduced pressure, poured in ice (100 mL) and diluted with ice-cold ammonia (20 mL, 20-25% of ammonia). The product was extracted with chloroform (2×100 mL) and evaporated under reduced pressure to afford 4-chloro-6-(1-isopropyl-1H-pyrazol-3-yl)-5-phenyl-2-(pyridin-2-yl)pyrrolo[2,1-f][1,2,4]triazine 24b (6.0 g, 48.0% purity, 6.94 mmol, 55% yield) as brown slurry.

Step C: rac 6-(1-Isopropyl-1H-pyrazol-3-yl)-N-((1R,3S)-3-methoxycyclopentyl)-5-phenyl-2-(pyridin-2-yl)pyrrolo[2,1-f][1,2,4]triazin-4-amine (24)

General Procedure: The 4-chloro-6-(1-isopropyl-1H-pyrazol-3-yl)-5-phenyl-2-(pyridin-2-yl)pyrrolo[2,1-f][1,2,4]triazine 24b (400.0 mg, 964.11 μmol) was dissolved in DMSO (7 mL) and DIPEA (415.8 mg, 3.22 mmol, 560.0 μL, 4.0 equiv) with the appropriate corresponding amine (1.0 equiv) were added at room temperature. The mixture was heated at 100° C. overnight, cooled and purified by HPLC to produce product.

Following the General Procedure using 4-chloro-6-(1-isopropyl-1H-pyrazol-3-yl)-5-phenyl-2-(pyridin-2-yl)pyrrolo[2,1-f][1,2,4]triazine 24b and rac (1R,3S)-3-methoxycyclopentan-1-amine (1.0 equiv) as the corresponding amine, produced rac 6-(1-isopropyl-1H-pyrazol-3-yl)-N-((1R,3S)-

3-methoxycyclopentyl)-5-phenyl-2-(pyridin-2-yl)pyrrolo[2,1-f][1,2,4]triazin-4-amine (24) (7.30 mg, 1.80% yield, 98% purity). LCMS(ESI): Calculated [M+1] 494.3 Found [M+1] 494.4 $^1$H NMR ($cd_3od$, 400 MHz) δ 1.40-1.51 (m, 7H), 1.56 (d, 1H), 1.66-1.74 (m, 2H), 1.99-2.13 (m, 2H), 3.04 (s, 3H), 3.72-3.81 (m, 1H), 4.49 (hept, 1H), 4.85-4.86 (m, 1H), 5.61 (d, 1H), 7.37-7.48 (m, 3H), 7.48-7.58 (m, 4H), 7.97 (td, 1H), 8.07 (s, 1H), 8.44 (d, 1H), 8.65-8.70 (m, 1H).

Example 25-Example 27: Synthesis of Compounds 25-27

Following the general procedure described in Example 24, Step C, 4-chloro-6-(1-isopropyl-1H-pyrazol-3-yl)-5-phenyl-2-(pyridin-2-yl)pyrrolo[2,1-f][1,2,4]triazine 24b (400.0 mg, 964.11 μmol) and the appropriate corresponding amine (1.0 equiv) produced the Example compounds (25)-(27) shown in Table 1. Analytical data for compounds (25)-(27) is shown is also presented in Table 1.

Example 28: Synthesis of Compound 28

(28)

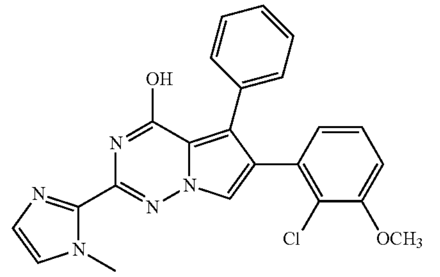

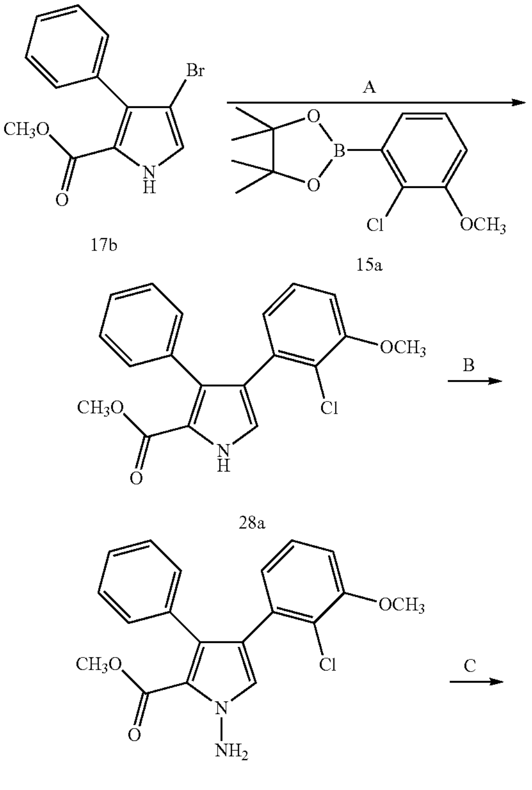

17b
15a
28a
28b

-continued

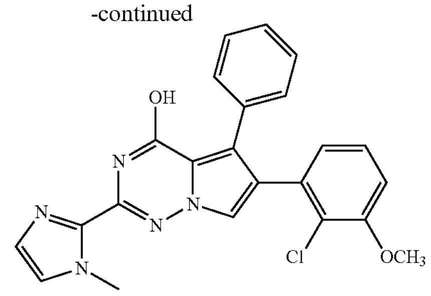

(28)

Step A: Methyl 4-(2-chloro-3-methoxyphenyl)-3-phenyl-1H-pyrrole-2-carboxylate 28a A mixture of methyl 4-bromo-3-phenyl-1H-pyrrole-2-carboxylate 17b (prepared as described in Example 17, Step A) (8.5 g, 30.34 mmol), 2-(2-chloro-3-methoxyphenyl)-4,4,5,5-tetramethyl-1,3,2-dioxaborolane 15a (9.78 g, 36.41 mmol), cesium carbonate (19.77 g, 60.69 mmol) and [1,1'-bis(diphenylphosphino)ferrocene]dichloropalladium(II) dichloromethane adduct (2.48 g, 3.03 mmol) in Dioxane/$H_2O$ (170/10 mL) was heated at 100° C. under Argon atmosphere overnight. Reaction mixture was evaporated, and crude compound was purified by flash chromatography (Hexane-EtOAc as a solvent mixture) to give methyl 4-(2-chloro-3-methoxyphenyl)-3-phenyl-1H-pyrrole-2-carboxylate 28a (7.7 g, 85.56% purity, 19.28 mmol, 63.5% yield).

Step B: Methyl 1-amino-4-(2-chloro-3-methoxyphenyl)-3-phenyl-1H-pyrrole-2-carboxylate 28b To solution of methyl 4-(2-chloro-3-methoxyphenyl)-3-phenyl-1H-pyrrole-2-carboxylate 28a (7.7 g, 22.53 mmol) in DMF (70 mL) sodium hydride (1.8 g, 75.09 mmol) was added at 0° C. After 30 min, amino diphenylphosphinate (10.51 g, 45.06 mmol) was added portionwise at 0° C. Reaction mixture was stirred at 60° C. overnight then cooled, filtered and filtrate was evaporated under reduce pressure to give methyl 1-amino-4-(2-chloro-3-methoxyphenyl)-3-phenyl-1H-pyrrole-2-carboxylate 28b (6.5 g, 80.22% purity, 14.61 mmol, 64.9% yield).

Step C: 6-(2-Chloro-3-methoxyphenyl)-2-(1-methyl-1H-imidazol-2-yl)-5-phenylpyrrolo[2,1-f][1,2,4]triazin-4-ol (28)

1-Methyl-1H-imidazole-2-carbonitrile (3.24 g, 30.27 mmol) and methyl 1-amino-4-(2-chloro-3-methoxyphenyl)-3-phenyl-1H-pyrrole-2-carboxylate 28b (9.0 g, 25.22 mmol) was dissolved in DMF (40 mL) and sodium hydride (2.52 g, 105.1 mmol) was added. The mixture was stirred heated at 80° C. 16 h. Then mixture was evaporated, diluted with water (100 mL) and extracted with EtOAc (3×150 mL). Organic layer dried and evaporated to give a 6-(2-chloro-3-methoxyphenyl)-2-(1-methyl-1H-imidazol-2-yl)-5-phenylpyrrolo[2,1-f][1,2,4]triazin-4-ol (28) (13.0 g, 50% purity, 15.05 mmol, 59.7% yield). A small amount was purified by HPLC for bioassay (100% purity). LCMS(ESI): Calculated [M+1] 432.1 Found [M+1] 432.5 $^1$H NMR (DMSO-$d_6$, 400 MHz) δ 3.82 (s, 3H), 4.00 (s, 3H), 6.77 (m, 1H), 7.07 (m, 1H), 7.20 (m, 7H), 7.52 (m, 1H), 7.88 (s, 1H), 11.30 (br s, 1H).

Example 29: Synthesis of Compound 29

(29)

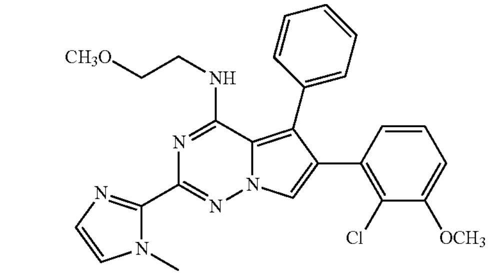

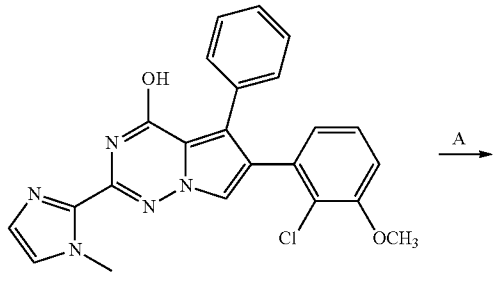

(28)

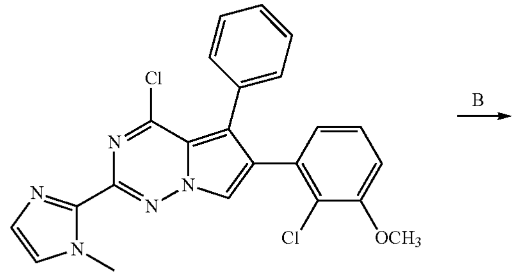

29a

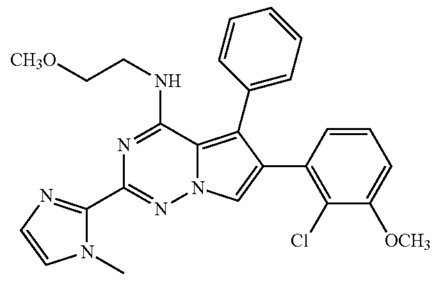

(29)

Step A: 4-Chloro-6-(2-chloro-3-methoxyphenyl)-2-(1-methyl-1H-imidazol-2-yl)-5-phenylpyrrolo[2,1-f][1,2,4]triazine 29a The 6-(2-chloro-3-methoxyphenyl)-2-(1-methyl-1H-imidazol-2-yl)-5-phenylpyrrolo[2,1-f][1,2,4]triazin-4-ol (28) (prepared as described in Example 28, Step C; crude product) (13.0 g, 30.1 mmol) was suspended in phosphoryl trichloride (46.15 g, 301.01 mmol, 28.06 mL, 10.0 equiv) and DIPEA (11.67 g, 90.3 mmol, 15.73 ml, 3.0 equiv) was added at room temperature. The reaction mixture was heated at 100° C. for 16 h. Then, the solution was cooled to room temperature, evaporated under reduced pressure, poured in ice (200 mL) and diluted with ice-cold ammonia (200 mL, 20-25% of ammonia). The product was extracted with chloroform (2×200 mL) and evaporated under reduced pressure to afford 4-chloro-6-(2-chloro-3-methoxyphenyl)-2-(1-methyl-1H-imidazol-2-yl)-5-phenylpyrrolo[2,1-f][1,2,4]triazine 29a (17.0 g, 36.42% purity, 13.75 mmol, 45.7% yield) as brown slurry.

Step B: 6-(2-Chloro-3-methoxyphenyl)-N-(2-methoxyethyl)-2-(1-methyl-1H-imidazol-2-yl)-5-phenylpyrrolo[2,1-f][1,2,4]triazin-4-amine (29)

General Procedure: The 4-chloro-6-(2-chloro-3-methoxyphenyl)-2-(1-methyl-1H-imidazol-2-yl)-5-phenylpyrrolo[2,1-f][1,2,4]triazine 29a (500.08 mg, 1.11 mmol) was dissolved in DMSO (7 mL) and DIPEA (430.36 mg, 3.33 mmol, 580.0 μL, 3.0 equiv) with the appropriate corresponding amine (1.33 mmol) was added at room temperature. The mixture was heated at 100° C. overnight, cooled and purified by HPLC ((20-80% 0-6 min $H_2O$/MeOH, flow: 30 mL/min; column: SunFire C18) to afford pure product. Following the general procedure, 6-(2-chloro-3-methoxyphenyl)-N-(2-methoxyethyl)-2-(1-methyl-1H-imidazol-2-yl)-5-phenylpyrrolo[2,1-f][1,2,4]triazin-4-amine (29) was prepared (30.00 mg, 5.50% yield, 97% purity). LCMS(ESI): Calculated [M+1] 489.2 Found [M+1] 489.2 $^1$H NMR (DMSO-$d_6$, 400 MHz) δ 3.14 (s, 3H), 3.37-3.43 (m, 2H), 3.59-3.64 (m, 2H), 3.83 (s, 3H), 3.98 (s, 3H), 5.83-5.90 (m, 1H), 6.81 (d, 1H), 7.01 (s, 1H), 7.05 (d, 1H), 7.19 (t, 1H), 7.26 (d, 2H), 7.31 (s, 1H), 7.34-7.42 (m, 3H), 7.93 (s, 1H).

Example 30-Example 34: Synthesis of Compounds 30-34

Following the general procedure described in Example 29, Step B, 4-chloro-6-(2-chloro-3-methoxyphenyl)-2-(1-methyl-1H-imidazol-2-yl)-5-phenylpyrrolo[2,1-f][1,2,4]triazine 29a (500.08 mg, 1.11 mmol) and the appropriate corresponding amine (1.33 mmol) produced the Example compounds (30)-(34) shown in Table 1. Analytical data for compounds (30)-(34) is also presented in Table 1.

Example 35: Synthesis of Compound 35

(35)

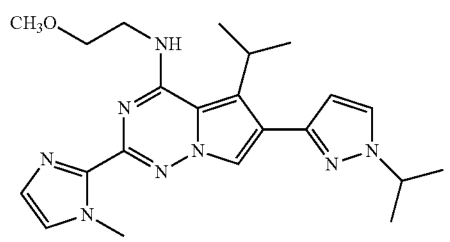

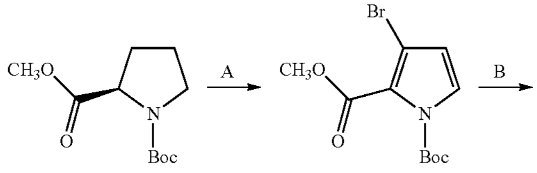

35a 35b

-continued

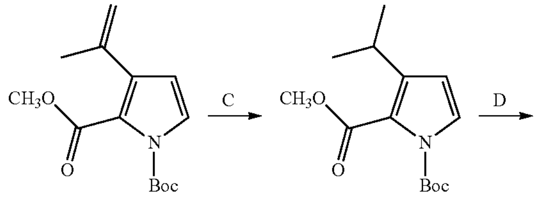

35c 35d

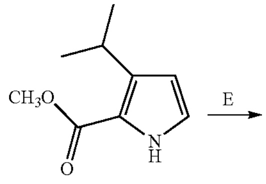

35e

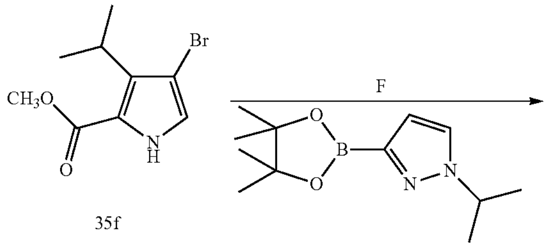

35f

1c

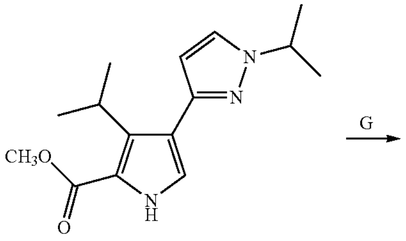

35g

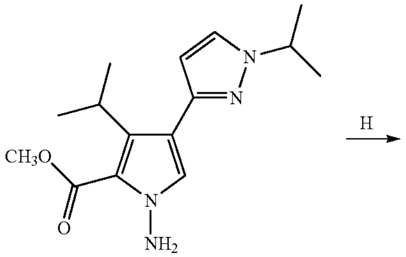

35h

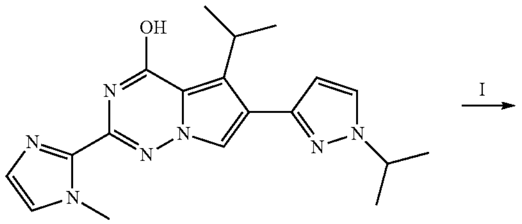

35i

-continued

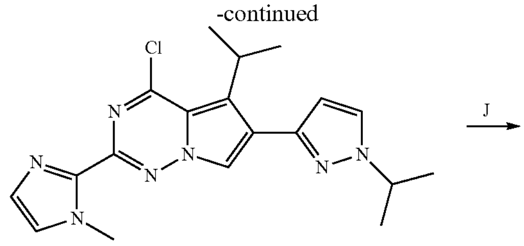

35j

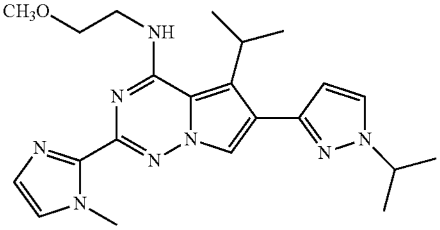

(35)

Step A: 1-(tert-Butyl) 2-methyl 3-bromo-1H-pyrrole-1,2-dicarboxylate 35b

To solution of 1-tert-butyl 2-methyl (R)-pyrrolidine-1,2-dicarboxylate (40.0 g, 174.46 mmol) in $CCl_4$ (500 mL) N-bromosuccinimide (108.68 g, 610.62 mmol) was added in one portion. Reaction mixture was refluxed for 1 h, then cooled and filtered. Filtrate was evaporated and crude compound was purified by flash chromatography to give 1-(tert-butyl) 2-methyl 3-bromo-1H-pyrrole-1,2-dicarboxylate 35b (6.37 g, 20.94 mmol, 12% yield).

Step B: 1-(tert-Butyl) 2-methyl 3-(prop-1-en-2-yl)-1H-pyrrole-1,2-dicarboxylate 35c A mixture of 1-(tert-butyl) 2-methyl 3-bromo-1H-pyrrole-1,2-dicarboxylate 35b (6.37 g, 20.96 mmol), 4,4,5,5-tetramethyl-2-(prop-1-en-2-yl)-1,3,2-dioxaborolane (5.28 g, 31.44 mmol, 5.91 mL, 1.5 equiv), sodium carbonate (4.44 g, 41.92 mmol) and [1,1'-bis(diphenylphosphino)ferrocene]dichloropalladium(II) dichloromethane adduct (855.87 mg, 1.05 mmol) in Dioxane/$H_2O$ (120/10 mL) was heated at 100° C. under Argon atmosphere overnight. Reaction mixture was evaporated, and crude compound was purified by flash chromatography to give 1-(tert-butyl) 2-methyl 3-(prop-1-en-2-yl)-1H-pyrrole-1,2-dicarboxylate 35c (4.2 g, 80.0% purity, 12.66 mmol, 60.4% yield).

Step C: 1-(ter-Butyl) 2-methyl 3-isopropyl-1H-pyrrole-1,2-dicarboxylate 35d 1-(tert-butyl) 2-methyl 3-(prop-1-en-2-yl)-1H-pyrrole-1,2-dicarboxylate 35c (2.1 g, 7.92 mmol) was dissolved in MeOH (30 mL) and stirred with 10% Pd/C (0.42 g) under $H_2$ atmosphere at room temperature for 3 h. Reaction mixture was degassed and filtered. Filtrate was concentrated under reduced pressure to give 1-(tert-butyl) 2-methyl 3-isopropyl-1H-pyrrole-1,2-dicarboxylate 35d (2.05 g, 78.6% purity, 6.03 mmol, 76.1% yield).

Step D: Methyl 3-isopropyl-1H-pyrrole-2-carboxylate 35e

To solution of 1-(ter-butyl) 2-methyl 3-isopropyl-1H-pyrrole-1,2-dicarboxylate 35d (5.0 g, 18.7 mmol) in DCM (40 mL) 2,2,2-trifluoroacetic acid (31.99 g, 280.52 mmol, 21.66 mL, 15.0 equiv) was added at 0° C. Reaction mixture was stirred at room temperature overnight and then concentrated under reduced pressure to give methyl 3-isopropyl-1H-pyrrole-2-carboxylate 35e (2.9 g, 44.3% purity, 7.68 mmol, 41.1% yield).

Step E: Methyl 4-bromo-3-isopropyl-1H-pyrrole-2-carboxylate 35f

To solution of methyl 3-isopropyl-1H-pyrrole-2-carboxylate 35e (2.9 g, 17.34 mmol) in DMF (25 mL) N-bromosuccinimide (3.09 g, 17.34 mmol) was added at 0° C. Reaction mixture was stirred at room temperature overnight then poured into water, extracted with EtOAc three times. Combined EtOAc was washed with water and brine, dried over $Na_2SO_4$, and concentrated in vacuo to give methyl 4-bromo-3-isopropyl-1H-pyrrole-2-carboxylate 35f (1.26 g, 73.0% purity, 3.74 mmol, 21.6% yield).

Step F: Methyl 3-isopropyl-4-(1-isopropyl-1H-pyrazol-3-yl)-1H-pyrrole-2-carboxylate 35g A mixture of methyl 4-bromo-3-isopropyl-1H-pyrrole-2-carboxylate 35f (1.26 g, 5.12 mmol), 1-isopropyl-3-(4,4,5,5-tetramethyl-1,3,2-dioxaborolan-2-yl)-1H-pyrazole 1c (1.21 g, 5.12 mmol), cesium carbonate (3.34 g, 10.24 mmol) and [1,1'-bis(diphenylphosphino)ferrocene]dichloropalladium(II) dichloromethane adduct (418.19 mg, 512.08 μmol) in Dioxane/$H_2O$ (25/3 mL) was heated at 100° C. under Argon atmosphere overnight. Reaction mixture was evaporated and crude compound was purified by flash chromatography (Hexane-EtOAc as a solvent mixture) to give methyl 3-isopropyl-4-(1-isopropyl-1H-pyrazol-3-yl)-1H-pyrrole-2-carboxylate 35g (1.28 g, 68.1% purity, 3.17 mmol, 61.8% yield).

Step G: Methyl 1-amino-3-isopropyl-4-(1-isopropyl-1H-pyrazol-3-yl)-1H-pyrrole-2-carboxylate 35h To solution of methyl 3-isopropyl-4-(1-isopropyl-1H-pyrazol-3-yl)-1H-pyrrole-2-carboxylate 35g (513.97 mg, 1.87 mmol) in DMF (20 mL) sodium hydride (149.32 mg, 6.22 mmol) was added at 0° C. After 30 min amino diphenylphosphinate (870.61 mg, 3.73 mmol) was added portionwise at 0° C. Reaction mixture was stirred at 60° C. overnight then cooled, filtered and filtrate was evaporated under reduce pressure to give methyl 1-amino-3-isopropyl-4-(1-isopropyl-1H-pyrazol-3-yl)-1H-pyrrole-2-carboxylate 35h (550.0 mg, 63.31% purity, 1.2 mmol, 64.2% yield).

Step H: 5-Isopropyl-6-(1-isopropyl-1H-pyrazol-3-yl)-2-(1-methyl-1H-imidazol-2-yl)pyrrolo[2,1-f][1,2,4]triazin-4-ol 35i Methyl 1-amino-3-isopropyl-4-(1-isopropyl-1H-pyrazol-3-yl)-1H-pyrrole-2-carboxylate 35h (549.84 mg, 1.89 mmol) and 1-methyl-1H-imidazole-2-carbonitrile (243.4 mg, 2.27 mmol) were dissolved in Dioxane (20 mL) and sodium hydride (189.35 mg, 7.89 mmol) was added at 0° C. Reaction mixture was heated at 80° C. overnight. Solution of $NH_4Cl$ (5 mL) was added dropwise to reaction mixture after cooling to 0° C., then extracted with EtOAc (3×15 mL). The organic extracts were dried over $Na_2SO_4$, concentrated in vacuo to give 5-isopropyl-6-(1-isopropyl-1H-pyrazol-3-yl)-2-(1-methyl-1H-imidazol-2-yl)pyrrolo[2,1-f][1,2,4]triazin-4-ol 35i (620.0 mg, 58.7% purity, 995.92 μmol, 52.6% yield).

Step I: 4-Chloro-5-isopropyl-6-(1-isopropyl-1H-pyrazol-3-yl)-2-(1-methyl-1H-imidazol-2-yl)pyrrolo[2,1-f][1,2,4]triazine 35j To 5-isopropyl-6-(1-isopropyl-1H-pyrazol-3-yl)-2-(1-methyl-1H-imidazol-2-yl)pyrrolo[2,1-f][1,2,4]triazin-4-ol 35i (622.57 mg, 1.7 mmol) in phosphoroyl trichloride (2.61 g, 17.04 mmol, 1.59 mL, 10.0 equiv) DIPEA (660.38 mg, 5.11 mmol, 890.0 μL, 3.0 equiv) was added. Reaction mixture was stirred at 100° C. overnight then concentrated in vacuo, washed with solution of $NaHCO_3$ to pH 7 and extracted with $CHCl_3$ (3×15 mL). Combined $CHCl_3$ was dried over $Na_2SO_4$, and concentrated in vacuo to give 4-chloro-5-isopropyl-6-(1-isopropyl-1H-pyrazol-3-yl)-2-(1-methyl-1H-imidazol-2-yl)pyrrolo[2,1-f][1,2,4]triazine 35j (800.0 mg, 43.7% purity, 910.71 μmol, 53.5% yield).

Step J: 5-Isopropyl-6-(1-isopropyl-1H-pyrazol-3-yl)-N-(2-methoxyethyl)-2-(1-methyl-1H-imidazol-2-yl)pyrrolo[2,1-f][1,2,4]triazin-4-amine (35)

General Procedure: To a solution of 4-chloro-5-isopropyl-6-(1-isopropyl-1H-pyrazol-3-yl)-2-(1-methyl-1H-imidazol-2-yl)pyrrolo[2,1-f][1,2,4]triazine 35j (411.56 mg, 1.07 mmol) and the appropriate corresponding amine (1.5 equiv) in DMSO (5 mL) DIPEA (415.52 mg, 3.22 mmol, 560.0 μl, 3.0 equiv) was added. Reaction mixture was stirred at 90° C. overnight. Product was purified by HPLC (2-10 min 60-75% methanol flow 30 mL/min (loading pump 4 mL/min methanol), Column Sun Fire C18 100×19 mm) to give product. Following the general procedure, 5-isopropyl-6-(1-isopropyl-1H-pyrazol-3-yl)-N-(2-methoxyethyl)-2-(1-methyl-1H-imidazol-2-yl)pyrrolo[2,1-f][1,2,4]triazin-4-amine (35) was prepared (13.20 mg, 2.80% yield, 100% purity). LCMS (ESI): Calculated [M+1] 423.3 Found [M+1] 423.4 $^1H$ NMR (DMSO-$d_6$, 400 MHz) δ 1.30-1.39 (m, 6H), 1.46 (d, 6H), 3.31 (s, 3H), 3.61 (t, 2H), 3.70-3.83 (m, 3H), 3.94-4.01 (m, 3H), 4.46-4.60 (m, 1H), 6.40 (d, 1H), 6.97 (s, 1H), 7.27 (s, 1H), 7.77 (d, 1H), 7.82 (s, 1H).

Example 36: Synthesis of Compound 36

(36)

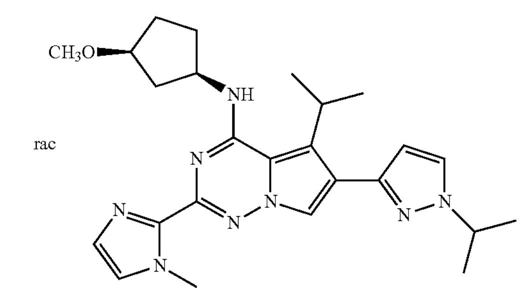

35j

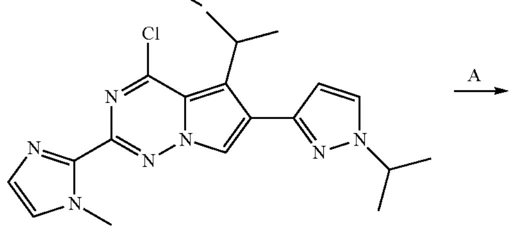

-continued rac

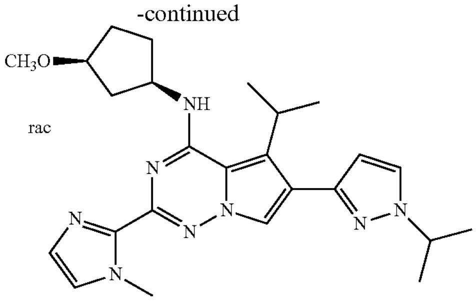

(36)

Step A: rac 5-Isopropyl-6-(1-isopropyl-1H-pyrazol-3-yl)-N-((1R,3S)-3-methoxycyclopentyl)-2-(1-methyl-1H-imidazol-2-yl)pyrrolo[2,1-f][1,2,4]triazin-4-amine (36)

Following the General Procedure described in Example 35, Step J, 5-isopropyl-6-(1-isopropyl-1H-pyrazol-3-yl)-2-(1-methyl-1H-imidazol-2-yl)pyrrolo[2,1-f][1,2,4]triazine 35j (prepared as described in Example 35, Step I) was converted to rac 5-isopropyl-6-(1-isopropyl-1H-pyrazol-3-yl)-N-((1R,3S)-3-methoxycyclopentyl)-2-(1-methyl-1H-imidazol-2-yl)pyrrolo[2,1-f][1,2,4]triazin-4-amine (36) (12.70 mg, 2.60% yield, 100% purity). LCMS(ESI): Calculated [M+1] 463.3 Found [M+1] 463.4 $^1H$ NMR (DMSO-$d_6$, 400 MHz) δ 1.33-1.40 (m, 6H), 1.46 (d, 6H), 1.80-2.03 (m, 6H), 3.29 (s, 3H), 3.61-3.74 (m, 1H), 3.94-4.00 (m, 4H), 4.46-4.61 (m, 1H), 4.84-4.92 (m, 1H), 6.40 (d, 1H), 6.98 (s, 1H), 7.28 (s, 1H), 7.77 (d, 1H), 7.81 (s, 1H).

Example 37: Synthesis of Compound 37

(37)

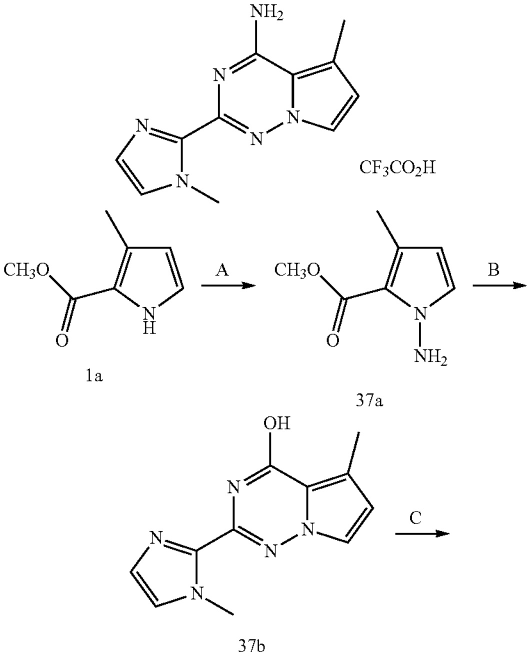

$CF_3CO_2H$

1a

37a

37b

-continued

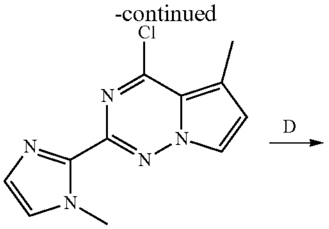

37c

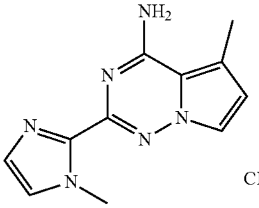

$CF_3CO_2H$ (37)

Step A: Methyl 1-amino-3-methyl-1H-pyrrole-2-carboxylate 37a

To solution of methyl 3-methyl-1H-pyrrole-2-carboxylate (15.0 g, 107.8 mmol) in DMF (200 mL) sodium hydride (8.62 g, 359.33 mmol) was added at 0° C. After 1 h, amino diphenylphosphinate (50.28 g, 215.6 mmol) was added. Reaction mixture was stirred at 60° C. overnight then cooled, filtered and filtrate was evaporated under reduce pressure to give methyl 1-amino-3-methyl-1H-pyrrole-2-carboxylate 37a (12.9 g, 80.0% purity, 66.94 mmol, 62.1% yield).

Step B: 5-Methyl-2-(1-methyl-1H-imidazol-2-yl) pyrrolo[2,1-f][1,2,4]triazin-4-ol 37b Sodium hydride (6.23 g, 259.45 mmol) (60% on mineral oil) was added portionwise (during 3 min) to the solution of methyl 1-amino-3-methyl-1H-pyrrole-2-carboxylate 37a (12.0 g, 77.84 mmol) and 1-methyl-1H-imidazole-2-carbonitrile (8.34 g, 77.84 mmol, 8.34 mL, 1.0 equiv) in dioxane (20 mL). The reaction mixture was heated to reflux and stirred at this temperature for 16 h. Then the mixture was cooled to the room temperature, poured in ice water and neutralized by acetic acid. The formed participate was collected by filtration, washed by water (2×10 mL) and dried in vacuo. 5-Methyl-2-(1-methyl-1H-imidazol-2-yl)pyrrolo [2,1-f][1,2,4]triazin-4-ol 37b (9.5 g, 41.44 mmol, 53.2% yield) was obtained.

Step C: 4-Chloro-5-methyl-2-(1-methyl-1H-imidazol-2-yl)pyrrolo[2,1-f][1,2,4]triazine 37c 5-Methyl-2-(1-methyl-1H-imidazol-2-yl)pyrrolo[2,1-f][1,2,4]triazin-4-ol 37b (1.0 g, 4.36 mmol) was dissolved in phosphoroyl trichloride (8.02 g, 52.32 mmol, 4.88 mL, 12.0 equiv). The mixture was heated to 100° C. and stirred at this temperature for 16 h. The reaction mixture was concentrated in vacuo, poured in ice water (5 mL) and neutralized by aqueous solution of $K_2CO_3$. The formed participate was collected by filtration, washed by water (2×5 mL) and dried in vacuo. 4-Chloro-5-methyl-2-(1-methyl-1H-imidazol-2-yl)pyrrolo[2,1-f][1,2,4]triazine 37c (450.0 mg, 1.82 mmol, 41.7% yield) was obtained.

Step D: 5-Methyl-2-(1-methyl-1H-imidazol-2-yl) pyrrolo[2,1-f][1,2,4]triazin-4-amine trifluoroacetic acid salt (37)

4-Chloro-5-methyl-2-(1-methyl-1H-imidazol-2-yl)pyrrolo[2,1-f][1,2,4]triazine 37c (250.0 mg, 1.01 mmol) was dissolved in 20 mL 10% solution $NH_3$ in iPA. The mixture was heated in sealed tube for 48 h, then evaporated and the residue was triturated in water. The solid was filtered and purified on HPLC (2-10 min 10-50% MeOH+TFA flow 30 mL/min (loading pump 4 mL/min water), Column Sun Fire C18 100×19 mm). 5-Methyl-2-(1-methyl-1H-imidazol-2-yl) pyrrolo[2,1-f][1,2,4]triazin-4-amine trifluoroacetic acid salt (37) (5.4 mg, 23.66 μmol, 2.3% yield, 100% purity) was obtained. LCMS(ESI): Calculated [M+1] 229.1 Found [M+1] 229.1 $^1$H NMR (DMSO-$d_6$, 400 MHz) § 2.55 (s, 3H), 4.31 (s, 3H), 6.61 (s, 1H), 7.62 (m, 3H).

Example 38: Synthesis of Compound 38

(38)

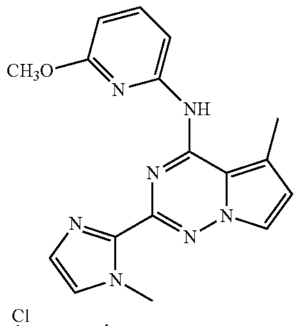

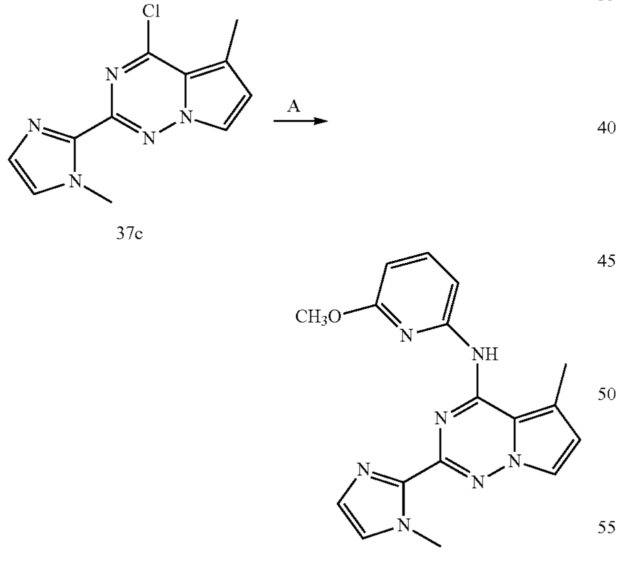

37c (38)

Step A: N-(6-Methoxypyridin-2-yl)-5-methyl-2-(1-methyl-1H-imidazol-2-yl)pyrrolo[2,1-f][1,2,4]triazin-4-amine (38)

Sodium hydride (24.15 mg, 1.01 mmol) (60% on mineral oil) was added portionwise (over 3 min) to the solution of 4-chloro-5-methyl-2-(1-methyl-1H-imidazol-2-yl)pyrrolo

[2,1-f][1,2,4]triazine 37c (prepared as described in Example 37, Step C) (99.7 mg, 402.55 μmol) and 6-methoxypyridin-2-amine (74.96 mg, 603.82 μmol) in DMF (2 mL). The reaction mixture was heated 100° C. and stirred at this temperature for 16 h. Then, the mixture was cooled to the room temperature, poured in clod solution of ammonium chloride (64.6 mg, 1.21 mmol) in water. The formed participate was collected by filtration, washed by water (2×10 mL) and purified by HPLC (2-10 min 55-80% methanol+ $NH_3$ flow 30 mL/min (loading pump 4 mL/min methanol), Column Sun Fire C18 100×19 mm). N-(6-Methoxypyridin-2-yl)-5-methyl-2-(1-methyl-1H-imidazol-2-yl)pyrrolo[2,1-f][1,2,4]triazin-4-amine (38) (15.8 mg, 47.11 μmol, 11.7% yield) was obtained (15.80 mg, 11.70% yield, 100% purity). LCMS(ESI): Calculated [M+1] 336.2 Found [M+1] 336.2 $^1$H NMR (DMSO-$d_6$, 400 MHz): δ (ppm) 2.56 (s, 3H), 4.00 (s, 3H), 4.12 (s, 3H), 6.40 (m, 1H), 6.50 (d, 1H), 6.75 (d, 1H), 7.08 (m, 1H), 7.50 (m, 2H), 7.68 (dd, 1H), 13.10 (m, 1H).

Example 39: Synthesis of Compound 39

(39)

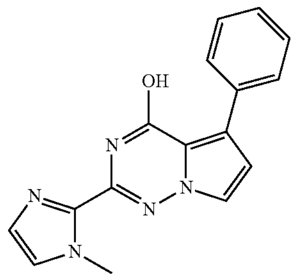

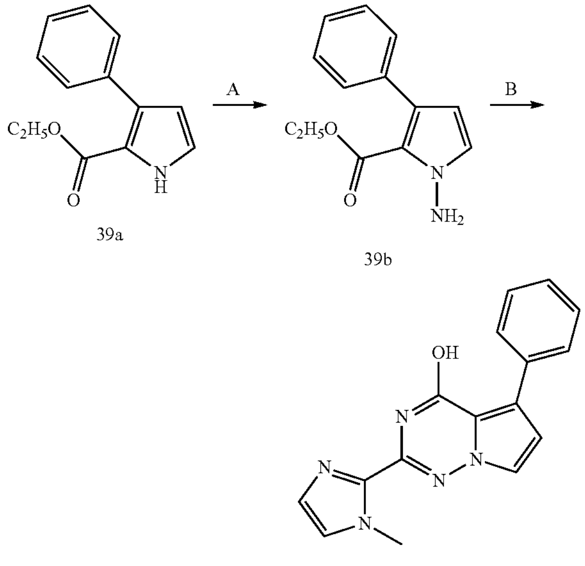

39a

39b (39)

Step A: Ethyl 1-amino-3-phenyl-1H-pyrrole-2-carboxylate 39b

To solution of ethyl 1-amino-3-phenyl-1H-pyrrole-2-carboxylate 39a (12.0 g, 55.75 mmol) in DMF (150 mL) sodium hydride (4.46 g, 185.82 mmol) was added at 0° C. After 30 min, amino diphenylphosphinate (26.0 g, 111.49 mmol) was added portionwise at 0° C. Reaction mixture was stirred at 60° C. overnight then cooled, filtered and filtrate was evaporated under reduce pressure to give ethyl 1-amino-3-phenyl-1H-pyrrole-2-carboxylate 39b (15.9 g, 45.28% purity, 31.27 mmol, 56.1% yield).

Step B: 2-(1-Methyl-1H-imidazol-2-yl)-5-phenylpyrrolo[2,1-f][1,2,4]triazin-4-ol (39)

Ethyl 1-amino-3-phenyl-1H-pyrrole-2-carboxylate 39b (15.0 g, 65.14 mmol) and 1-methyl-1H-imidazole-2-carbonitrile (8.37 g, 78.17 mmol) were dissolved in Dioxane (150 mL) and sodium hydride (6.51 g, 271.43 mmol) was added at 0° C. Reaction mixture was heated at 100° C. overnight. Solution of $NH_4Cl$ (25 mL) was added dropwise to reaction mixture after cooling to 0° C., then extracted with EtOAc (3×75 mL). The organic extracts were dried over $Na_2SO_4$, concentrated in vacuo. Product was recrystallized from MTBE to give 2-(1-methyl-1H-imidazol-2-yl)-5-phenylpyrrolo[2,1-f][1,2,4]triazin-4-ol (39) (7.9 g, 85% purity, 23.14 mmol, 35.5% yield). A small amount was purified by HPLC for bioassay (100% purity). Calculated [M+1] 292.1 Found [M+1] 292.0 $^1$H NMR (DMSO-$d_6$, 400 MHz): δ (ppm) 4.03 (s, 3H), 6.83 (d, 1H), 7.14 (d, 1H), 7.32 (m, 1H), 7.39 (m, 2H), 7.50 (d, 1H), 7.72 (m, 1H), 7.82 (m, 2H).

Example 40: Synthesis of Compound 40

(40)

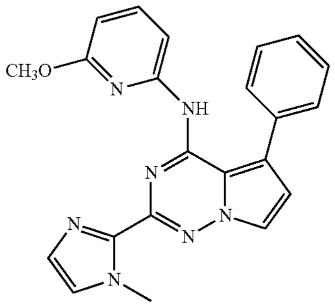

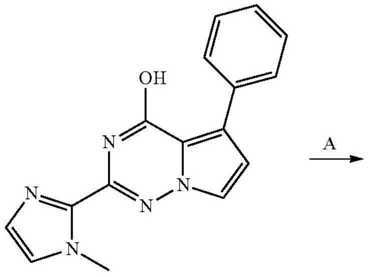

(39)

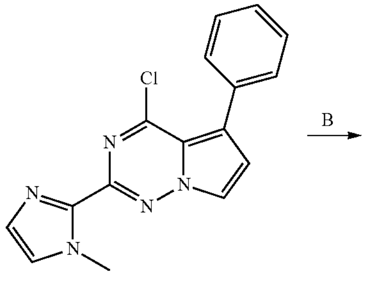

40a

-continued

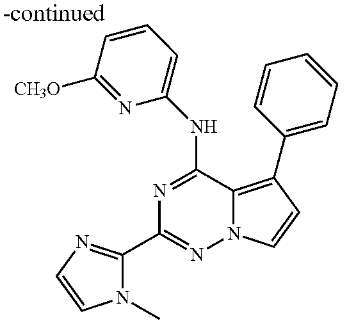

(40)

Step A: 4-Chloro-2-(1-methyl-1H-imidazol-2-yl)-5-phenylpyrrolo[2,1-f][1,2,4]triazine 40a To 2-(1-methyl-1H-imidazol-2-yl)-5-phenylpyrrolo[2,1-f][1,2,4]triazin-4-ol (39) (prepared as described in Example 39, Step B; crude product) (500.32 mg, 1.72 mmol) phosphoroyl trichloride (2.63 g, 17.17 mmol, 1.6 mL, 10.0 equiv) was added. Reaction mixture was stirred at 100° C. overnight then concentrated in vacuo, washed with aqueous solution of $NaHCO_3$ to pH 7 and extracted with $CHCl_3$ (3×15 mL). Combined $CHCl_3$ was dried over $Na_2SO_4$, and concentrated in vacuo to give 4-chloro-2-(1-methyl-1H-imidazol-2-yl)-5-phenylpyrrolo[2,1-f][1,2,4]triazine 40a (500.0 mg, 92.0% purity, 1.49 mmol, 86.5% yield).

Step B: N-(6-Methoxypyridin-2-yl)-2-(1-methyl-1H-imidazol-2-yl)-5-phenylpyrrolo[2,1-f][1,2,4]triazin-4-amine (40)

General Procedure: To the appropriate corresponding amine (1.1 equiv) in DMF (10 mL) sodium hydride (52.23 mg, 2.18 mmol) was added at 0° C. After 30 min, 4-chloro-2-(1-methyl-1H-imidazol-2-yl)-5-phenylpyrrolo[2,1-f][1,2,4]triazine 40a (269.67 mg, 870.59 μmol) was added. Reaction mixture was stirred at 50° C. overnight. Product was purified by HPLC (2-10 min 60-85% methanol+$NH_3$ flow 30 mL/min (loading pump 4 mL/min methanol), Column Sun Fire C18 100×19 mm) to give pure product. Following the general procedure, N-(6-methoxypyridin-2-yl)-2-(1-methyl-1H-imidazol-2-yl)-5-phenylpyrrolo[2,1-f][1,2,4]triazin-4-amine (40) was obtained (32.90 mg, 9.00% yield, 100% purity). LCMS(ESI): Calculated [M+1] 398.2 Found [M+1] 398.2 $^1$H NMR (DMSO-$d_6$, 400 MHz): δ (ppm) 3.68 (s, 3H), 4.00 (s, 3H), 6.53 (d, 1H), 6.95 (m, 1H), 7.12 (m, 1H), 7.41 (m, 1H), 7.52 (m, 1H), 7.65 (m, 4H), 7.75 (dd, 1H), 8.03 (m, 2H), 8.33 (d, 1H).

Example 41: Synthesis of Compound 41

(41)

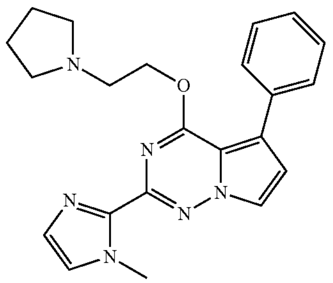

-continued

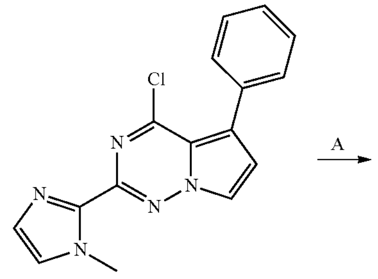

40a

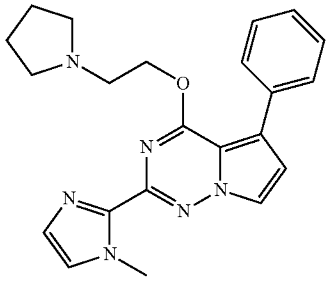

(41)

Step A: 2-(1-Methyl-1H-imidazol-2-yl)-5-phenyl-4-(2-(pyrrolidin-1-yl)ethoxy)pyrrolo[2,1-f][1,2,4]triazine (41)

Following the general procedure described in Example 40, Step B, except using 2-(pyrrolidin-1-yl) ethan-1-ol in place of an amine, 4-chloro-2-(1-methyl-1H-imidazol-2-yl)-5-phenylpyrrolo[2,1-f][1,2,4]triazine 40a (prepared as described in Example 40, Step A) produced 2-(1-methyl-1H-imidazol-2-yl)-5-phenyl-4-(2-(pyrrolidin-1-yl)ethoxy) pyrrolo[2,1-f][1,2,4]triazine (41) (12.90 mg, 4.90% yield, 97% purity). LCMS(ESI): Calculated [M+2]/2=195.1 Found [M+2]/2=195.2 $^{1}$H NMR (DMSO-$d_6$, 400 MHz) δ 1.60-1.66 (m, 4H), 2.39-2.44 (m, 4H), 2.81 (t, 2H), 4.02 (s, 3H), 4.65 (t, 2H), 7.05 (d, 1H), 7.06 (d, 1H), 7.32 (t, 1H), 7.37 (s, 1H), 7.40 (t, 2H), 7.69 (s, 1H), 7.71 (d, 1H), 8.08 (d, 1H).

Example 42: Synthesis of Compound 42

(42)

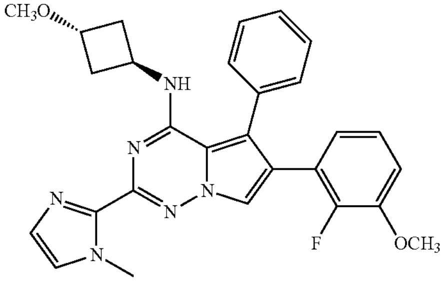

-continued

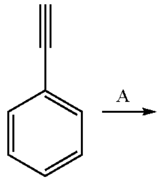

42a

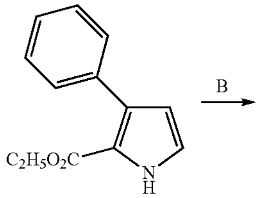

42b

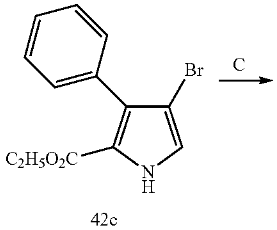

42c

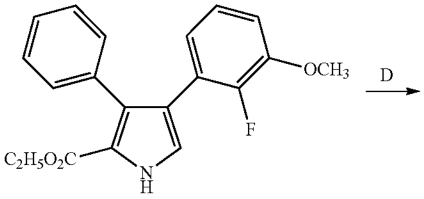

42d

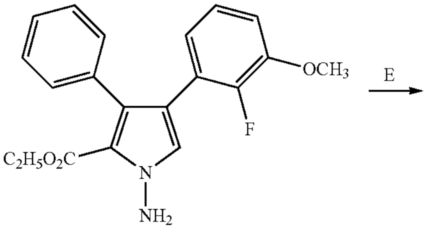

42e

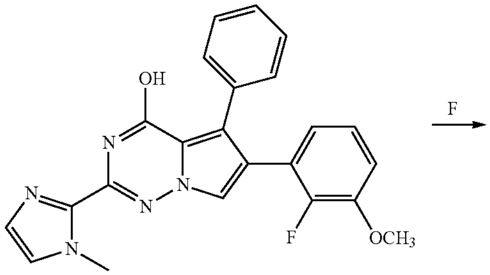

42f

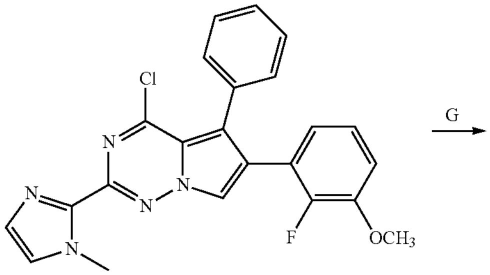

42g

-continued

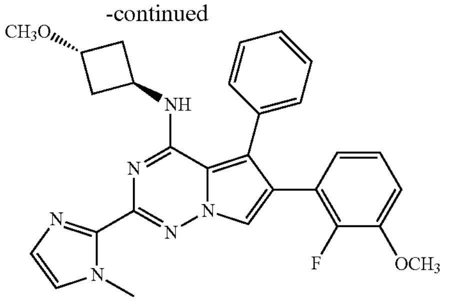

(42)

Step A: Ethyl 3-phenyl-1H-pyrrole-2-carboxylate 42b

To a solution of ethynylbenzene 42a (40.0 g, 391.65 mmol) in NMP (400 mL), silver carbonate (10.8 g, 39.16 mmol) and ethyl 2-isocyanoacetate (66.45 g, 587.47 mmol) were added under Ar. The reaction mixture was stirred at 80° C. overnight, then cooled and filtered. Water (400 mL) was added to filtrate and extracted with DCM once (400 mL). DCM was washed with water (10*150 mL). The organic layer dried and evaporated under reduce pressure. Crude compound was purified by flash chromatography ($SiO_2$, Hexane-MtBE as a solvent mixture) to give ethyl 3-phenyl-1H-pyrrole-2-carboxylate 42b (5.4 g, 89.0% purity, 22.33 mmol, 5.7% yield).

Step B: Ethyl 4-bromo-3-phenyl-1H-pyrrole-2-carboxylate 42c

To a solution of ethyl 3-phenyl-1H-pyrrole-2-carboxylate 42b (5.4 g, 25.09 mmol) in DMF (50 mL) N-bromosuccinimide (4.46 g, 25.09 mmol) was added cooling with ice. The reaction mixture was stirred at RT overnight and then poured into water (150 mL). The product was extracted with TBME (3*75 mL). Combined TBME was washed with water (5*50 mL), dried and evaporated under reduce pressure to give ethyl 4-bromo-3-phenyl-1H-pyrrole-2-carboxylate 42c (5.8 g, 70.9% purity, 13.98 mmol, 55.7% yield).

Step C: Ethyl 4-(2-fluoro-3-methoxyphenyl)-3-phenyl-1H-pyrrole-2-carboxylate 42d A mixture of 4-bromo-3-phenyl-1H-pyrrole-2-carboxylate 42c (5.7 g, 19.38 mmol), 2-fluoro-3-methoxyphenylboronic acid (3.29 g, 19.38 mmol), cesium carbonate (12.63 g, 38.76 mmol) and [1,1'-bis(diphenylphosphino)ferrocene]dichloropalladium(II) dichloromethane adduct (1.58 g, 1.94 mmol) was heated at 100° C. under Argon atmosphere overnight. The reaction mixture was evaporated and crude compound was purified by flash chromatography ($SiO_2$, Hexane-MtBE as a solvent mixture) to give ethyl 4-(2-fluoro-3-methoxyphenyl)-3-phenyl-1H-pyrrole-2-carboxylate 42d (3.3 g, 82.5% purity, 8.02 mmol, 41.4% yield).

Step D: Ethyl 1-amino-4-(2-fluoro-3-methoxyphenyl)-3-phenyl-1H-pyrrole-2-carboxylate 42e To a solution of ethyl 4-(2-fluoro-3-methoxyphenyl)-3-phenyl-1H-pyrrole-2-carboxylate 42d (2.2 g, 6.48 mmol) in DMF (30 mL) sodium hydride (337.02 mg, 14.04 mmol) was added at 0° C. After 1 hour, O-(2,4-dinitrophenyl) hydroxylamine (1.68 g, 8.43 mmol) in DMF was added dropwise. The reaction mixture was stirred at RT overnight. An aqueous solution of $NH_4Cl$ was added to reaction mixture, extracted with EtOAc (3*25 mL), combined EtOAc was washed with water (7*15 mL), dried and evaporated under reduce pressure to give ethyl 1-amino-4-(2-fluoro-3-methoxyphenyl)-3-phenyl-1H-pyrrole-2-carboxylate 42e (2.3 g, 78.1% purity, 5.07 mmol, 78.2% yield).

Step E: 6-(2-Fluoro-3-methoxyphenyl)-2-(1-methyl-1H-imidazol-2-yl)-5-phenylpyrrolo[2,1-f][1,2,4]triazin-4-ol 42f To a mixture of ethyl 1-amino-4-(2-fluoro-3-methoxyphenyl)-3-phenyl-1H-pyrrole-2-carboxylate 42e (3.3 g, 9.31 mmol) and 1-methyl-1H-imidazole-2-carbonitrile (997.34 mg, 9.31 mmol) in dioxane (35 mL), sodium hydride (744.81 mg, 31.04 mmol) was added at cooling with ice. The reaction mixture was stirred at 80° C. overnight. An aqueous solution of $NH_4Cl$ was added to reaction mixture, extracted with EtOAc (3*20 mL), dried and evaporated under reduce pressure to give 6-(2-fluoro-3-methoxyphenyl)-2-(1-methyl-1H-imidazol-2-yl)-5-phenylpyrrolo[2,1-f][1,2,4]triazin-4-ol 42f (4.0 g, 51.6% purity, 4.97 mmol, 53.4% yield).

Step F: 4-Chloro-6-(2-fluoro-3-methoxyphenyl)-2-(1-methyl-1H-imidazol-2-yl)-5-phenylpyrrolo[2,1-f][1,2,4]triazine 42g The starting material 6-(2-fluoro-3-methoxyphenyl)-2-(1-methyl-1H-imidazol-2-yl)-5-phenylpyrrolo[2,1-f][1,2,4]triazin-4-ol 42f (4.0 g, 9.62 mmol) was suspended in phosphoroyl trichloride (14.76 g, 96.23 mmol, 8.97 mL, 10.0 equiv) and ethylbis(propan-2-yl)amine (3.73 g, 28.87 mmol, 5.03 ml, 3.0 equiv) was added at RT. The reaction mixture was heated at 100° C. overnight. The solution was cooled to RT, evaporated under reduced pressure, poured into aqueous solution of $NaHCO_3$ and the product was extracted with chloroform (3*50 mL), evaporated to give 4-chloro-6-(2-fluoro-3-methoxyphenyl)-2-(1-methyl-1H-imidazol-2-yl)-5-phenylpyrrolo[2,1-f][1,2,4]triazine 42g (3.1 g, 53.5% purity, 3.82 mmol, 39.7% yield).

Step H: 6-(2-Fluoro-3-methoxyphenyl)-N-((1r,3r)-3-methoxycyclobutyl)-2-(1-methyl-1H-imidazol-2-yl)-5-phenylpyrrolo[2,1-f][1,2,4]triazin-4-amine (42)

A mixture of 4-chloro-6-(2-fluoro-3-methoxyphenyl)-2-(1-methyl-1H-imidazol-2-yl)-5-phenylpyrrolo[2,1-f][1,2,4]triazine 42g (248.89 mg, 573.66 μmol), (1r,3r)-3-methoxycyclobutan-1-amine hydrochloride (78.94 mg, 573.66 μmol) and ethylbis(propan-2-yl)amine (222.6 mg, 1.72 mmol, 300.0 μL, 3.0 equiv) in DMSO (5 mL) was heated at 100° C. 18h then cooled and purified by HPLC (2-10 min 30-60$H_2O$-MeOH+$NH_3$; Flow 30 mL/min; (loading pump 4.0 mL methanol), column: sun fire C18) to give 6-(2-fluoro-3-methoxyphenyl)-N-((1r,3r)-3-methoxycyclobutyl)-2-(1-methyl-1H-imidazol-2-yl)-5-phenylpyrrolo[2,1-f][1,2,4]triazin-4-amine (42) (20.3 mg, 95.0% purity, 38.68 μmol, 6.7% yield) as yellow gum. LCMS(ESI): Calculated [M+1] 499.3 Found [M+1] 499.2.

Example 43: Synthesis of Compound 43

(43)

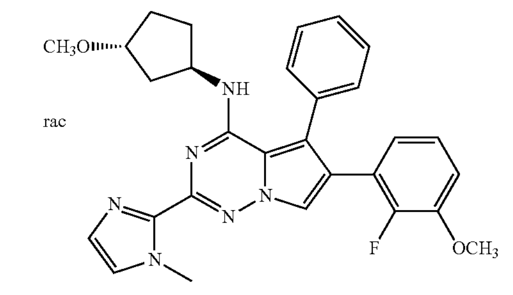

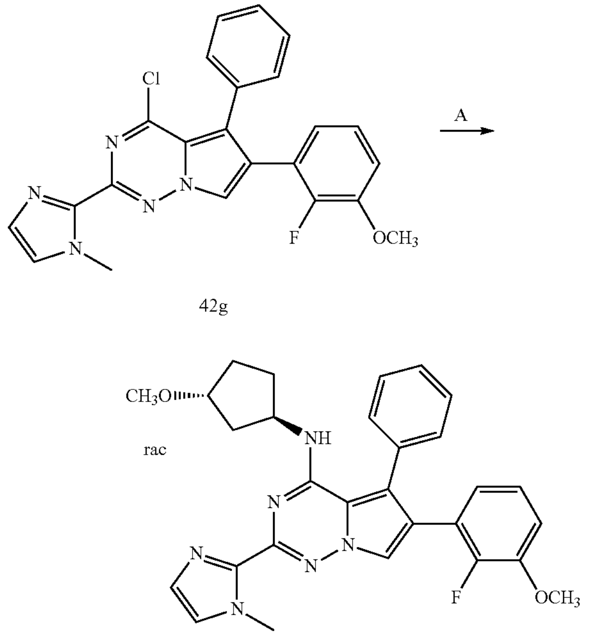

42g (43)

Step A: rac 6-(2-Fluoro-3-methoxyphenyl)-N-((1R, 3R)-3-methoxycyclopentyl)-2-(1-methyl-1H-imidazol-2-yl)-5-phenylpyrrolo[2,1-f][1,2,4]triazin-4-amine (43)

A mixture of 4-chloro-6-(2-fluoro-3-methoxyphenyl)-2-(1-methyl-1H-imidazol-2-yl)-5-phenylpyrrolo[2,1-f][1,2,4] triazine 42g (prepared as described in Example 42, Step F) (198.91 mg, 458.47 μmol), rac (1R,3R)-3-methoxycyclopentan-1-amine hydrochloride (69.52 mg, 458.47 μmol) and ethylbis(propan-2-yl)amine (178.08 mg, 1.38 mmol, 240.0 μL, 3.0 equiv) in DMSO (5.0 mL) was heated at 100° C. for 18 h, then cooled and purified by HPLC (2-10 min 30-60$H_2O$-MeOH+$NH_3$; Flow 30 mL/min; (loading pump 4.0 mL methanol), column: sun fire C18) to give rac 6-(2-Fluoro-3-methoxyphenyl)-N-((1R,3R)-3-methoxycyclopentyl)-2-(1-methyl-1H-imidazol-2-yl)-5-phenylpyrrolo [2,1-f][1,2,4]triazin-4-amine (43) (16.6 mg, 95.0% purity, 30.77 μmol, 6.7% yield) as yellow gum. LCMS(ESI): Calculated [M+1] 513.3 Found [M+1] 513.2.

Example 44: Synthesis of Compound 44

(44)

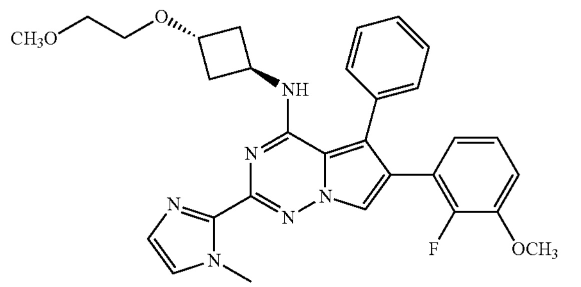

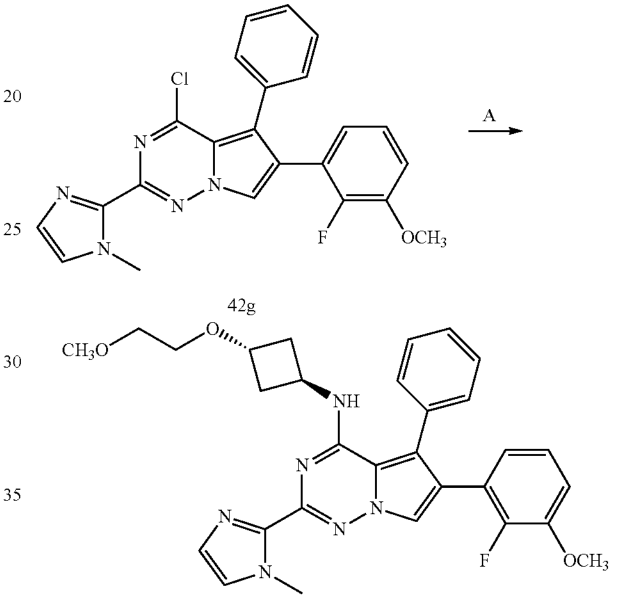

42g (44)

Step A: 6-(2-Fluoro-3-methoxyphenyl)-N-((1r,3r)-3-(2-methoxyethoxy)cyclobutyl)-2-(1-methyl-1H-imidazol-2-yl)-5-phenylpyrrolo[2,1-f][1,2,4]triazin-4-amine (44)

A mixture of 4-chloro-6-(2-fluoro-3-methoxyphenyl)-2-(1-methyl-1H-imidazol-2-yl)-5-phenylpyrrolo[2,1-f][1,2,4] triazine 42g (250.0 mg, 576.22 μmol), (1r,3r)-3-(2-methoxyethoxy)cyclobutan-1-amine (83.76 mg, 576.85 μmol) and ethylbis(propan-2-yl)amine (223.66 mg, 1.73 mmol) in DMSO (5 mL) was heated at 100° C. for 18h then cooled and purified by HPLC (2-10 min 40-70% $H_2O$-acetonitrile+ $NH_3$; loading pump 4.0 mL methanol), column: sun fire C18) to give 6-(2-fluoro-3-methoxyphenyl)-N-((1r,3r)-3-(2-methoxyethoxy)cyclobutyl)-2-(1-methyl-1H-imidazol-2-yl)-5-phenylpyrrolo[2,1-f][1,2,4]triazin-4-amine (44) (20.8 mg, 95.0% purity, 36.42 μmol, 6.3% yield) as light-brown gum. LCMS(ESI): Calculated [M+1] 433.2 Found [M+1] 433.2 $^1H$ NMR (400 MHz, $CD_3OD$) δ 1.85 (m, 2H), 2.37 (m, 2H), 3.35 (s, 3H), 3.45 (m, 2H), 3.51 (m, 2H), 3.86 (s, 3H), 3.99 (quin, 1H), 4.10 (s, 3H), 4.65 (quin, 1H), 6.67 (dd, 1H), 6.90 (m, 2H), 7.09 (d, 1H), 7.20 (m, 1H), 7.45 (m, 5H), 7.89 (d, 1H).

Example 45: Synthesis of Compound 45

(45)

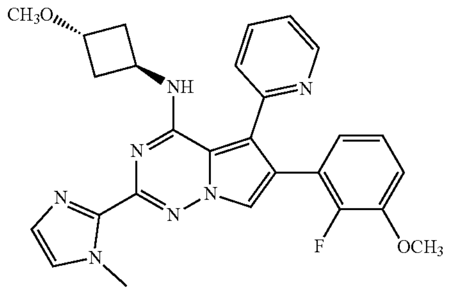

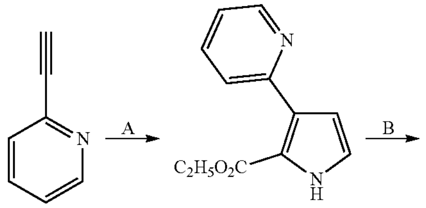

45a

45b

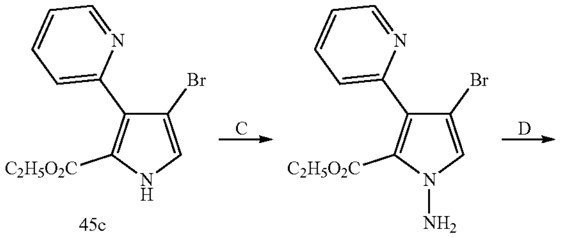

45c

45d

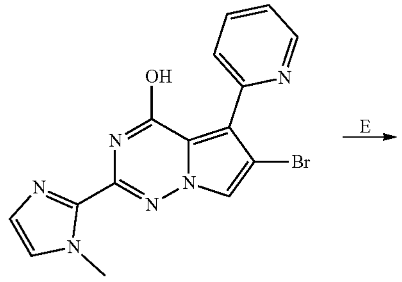

45e

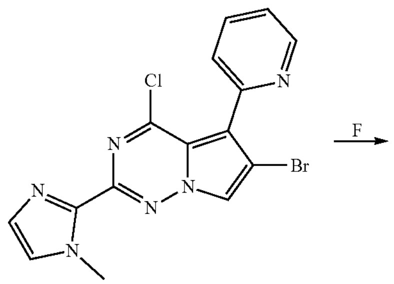

45f

-continued

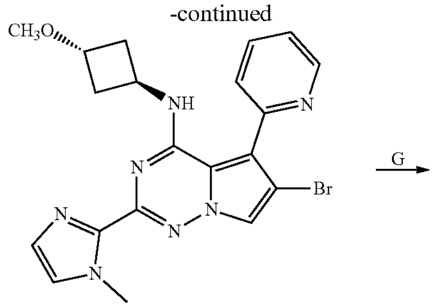

45g

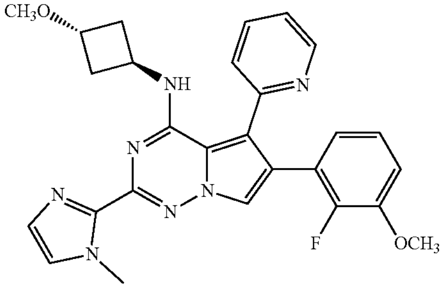

(45)

Step A: Ethyl 3-(pyridin-2-yl)-1H-pyrrole-2-carboxylate 45b

To a solution of 2-ethynylpyridine 45a (38.0 g, 368.5 mmol) in NMP (400 mL), silver carbonate (10.16 g, 36.85 mmol) and ethyl 2-isocyanoacetate (50.02 g, 442.2 mmol) were added under Ar. The reaction mixture was stirred at 80° C. overnight, then cooled and filtered. Water (300 mL) was added to filtrate and extracted with DCM once (400 mL). DCM was washed with water (10*150 mL). Organic layer dried and evaporated under reduce pressure. Crude compound was purified by flash chromatography ($SiO_2$, Hexane-MtBE as a solvent mixture) to give ethyl 3-(pyridin-2-yl)-1H-pyrrole-2-carboxylate 45b (53.0 g, 92.9% purity, 227.7 mmol, 61.8% yield).

Step B: Ethyl 4-bromo-3-(pyridin-2-yl)-1H-pyrrole-2-carboxylate 45c

To solution of ethyl 3-(pyridin-2-yl)-1H-pyrrole-2-carboxylate 45b (11.5 g, 53.18 mmol) in DMF (100 mL), N-bromosuccinimide (8.52 g, 47.86 mmol) was added under cooling with ice. The reaction mixture was stirred at RT overnight and then poured into water (200 mL). The product was extracted with TBME (3*100 mL), combined TBME was washed with water (5*50 mL), dried and evaporated under reduce pressure to give ethyl 4-bromo-3-(pyridin-2-yl)-1H-pyrrole-2-carboxylate 45c (11.3 g, 68.4% purity, 26.19 mmol, 49.2% yield).

Step C: Ethyl 1-amino-4-bromo-3-(pyridin-2-yl)-1H-pyrrole-2-carboxylate 45d

To a solution of ethyl 4-bromo-3-(pyridin-2-yl)-1H-pyrrole-2-carboxylate 45c (15.7 g, 53.2 mmol) in DMF (150 mL) sodium hydride (2.77 g, 115.26 mmol) was added at 0° C. After 1 hour, O-(2,4-dinitrophenyl) hydroxylamine (13.77 g, 69.16 mmol) in DMF was added dropwise. The reaction mixture was stirred at RT overnight. An aqueous solution of $NH_4Cl$ was added to reaction mixture, extracted with EtOAc (3*75 mL), combined EtOAc was washed with water (7*30 mL), dried and evaporated under reduce pressure to give ethyl 1-amino-4-bromo-3-(pyridin-2-yl)-1H-pyrrole-2-carboxylate 45d (16.0 g, 49.6% purity, 25.59 mmol, 48.1% yield).

Step D: 6-Bromo-2-(1-methyl-1H-imidazol-2-yl)-5-(pyridin-2-yl)pyrrolo[2,1-f][1,2,4]triazin-4-ol 45e To mixture of ethyl 1-amino-4-bromo-3-(pyridin-2-yl)-1H-pyrrole-2-carboxylate 45d (16.0 g, 51.59 mmol) and 1-methyl-1H-imidazole-2-carbonitrile (5.53 g, 51.59 mmol) in dioxane (200 mL) sodium hydride (4.13 g, 171.96 mmol) was added cooling with ice. The reaction mixture was stirred at 80° C. overnight. An aqueous solution of $NH_4Cl$ was added to reaction mixture, extracted with EtOAc (3*100 mL), dried and evaporated under reduce pressure to give 6-bromo-2-(1-methyl-1H-imidazol-2-yl)-5-(pyridin-2-yl)pyrrolo[2,1-f][1,2,4]triazin-4-ol 45e (14.5 g, 49.3% purity, 19.26 mmol, 37.3% yield).

Step E: 6-Bromo-4-chloro-2-(1-methyl-1H-imidazol-2-yl)-5-(pyridin-2-yl)pyrrolo[2,1-f][1,2,4]triazine 45f The starting material 6-bromo-2-(1-methyl-1H-imidazol-2-yl)-5-(pyridin-2-yl)pyrrolo[2,1-f][1,2,4]triazin-4-ol 45e (14.5 g, 39.06 mmol) was suspended in phosphoroyl trichloride (59.89 g, 390.62 mmol, 36.41 mL, 10.0 equiv) and the reaction mixture was heated at 100° C. overnight. The solution was cooled to RT, evaporated under reduced pressure, poured into aqueous solution of $NaHCO_3$, the product was extracted with chloroform (3*50 mL) and evaporated to give 6-bromo-4-chloro-2-(1-methyl-1H-imidazol-2-yl)-5-(pyridin-2-yl)pyrrolo[2,1-f][1,2,4]triazine 45f (8.0 g, 51.2% purity, 10.51 mmol, 26.9% yield).

Step F: 6-Bromo-N-((1r,3r)-3-methoxycyclobutyl)-2-(1-methyl-1H-imidazol-2-yl)-5-(pyridin-2-yl)pyrrolo[2,1-f][1,2,4]triazin-4-amine 45g A mixture of 6-bromo-4-chloro-2-(1-methyl-1H-imidazol-2-yl)-5-(pyridin-2-yl)pyrrolo[2,1-f][1,2,4]triazine 45f (298.45 mg, 765.97 μmol), (1r,3r)-3-methoxycyclobutan-1-amine hydrochloride (105.4 mg, 765.98 μmol) and ethylbis(propan-2-yl)amine (296.8 mg, 2.3 mmol, 400.0 μL, 3.0 equiv) in DMSO (5 mL) was heated at 100° C. for 18 h. Then, the mixture was cooled and purified by HPLC (2-10 min 50-85% $H_2O$-methanol+$NH_3$; flow 30 mL/min; (loading pump 4.0 mL methanol), column: sun fire C18) to give 6-bromo-N-((1r,3r)-3-methoxycyclobutyl)-2-(1-methyl-1H-imidazol-2-yl)-5-(pyridin-2-yl)pyrrolo[2,1-f][1,2,4]triazin-4-amine 45g (29.5 mg, 98.0% purity, 63.63 μmol, 8.3% yield).

Step G: 6-(2-Fluoro-3-methoxyphenyl)-N-((1r,3r)-3-methoxycyclobutyl)-2-(1-methyl-1H-imidazol-2-yl)-5-(pyridin-2-yl)pyrrolo[2,1-f][1,2,4]triazin-4-amine (45)

6-Bromo-N-((1r,3r)-3-methoxycyclobutyl)-2-(1-methyl-1H-imidazol-2-yl)-5-(pyridin-2-yl)pyrrolo[2,1-f][1,2,4]triazin-4-amine 45g (30.0 mg, 66.03 μmol), 2-fluoro-3-methoxyphenylboronic acid (13.47 mg, 79.27 μmol), cesium carbonate (43.05 mg, 132.12 μmol) and Pd(dppf)$Cl_2$ (5.39 mg, 6.61 μmol) was dissolved in degassed dioxane (1.0 mL)

under Ar. 0.05 mL of water was added via syringe. The reaction mixture was heated to 80° C. and stirred at this temperature for 16 h. The mixture was cooled to room temperature, filtered through celite and concentrated. The residue was purified by HPLC (2-10 min 10-70% $H_2O$-methanol+FA; Flow 30 mL/min; (loading pump 4.0 mL methanol), column: sun fire C18). 6-(2-Fluoro-3-methoxyphenyl)-N-((1r,3r)-3-methoxycyclobutyl)-2-(1-methyl-1H-imidazol-2-yl)-5-(pyridin-2-yl)pyrrolo[2,1-f][1,2,4]triazin-4-amine (45) (2.4 mg, 4.8 μmol, 7.3% yield) was obtained as light-brown solid. LCMS(ESI): Calculated [M+1] 500.2 Found [M+1] 500.0.

Example 46: Synthesis of Compound 46

(46)

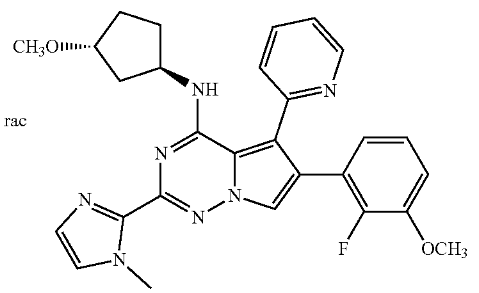

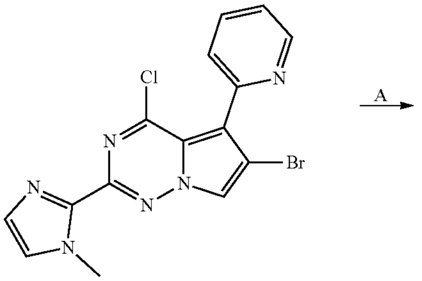

45f

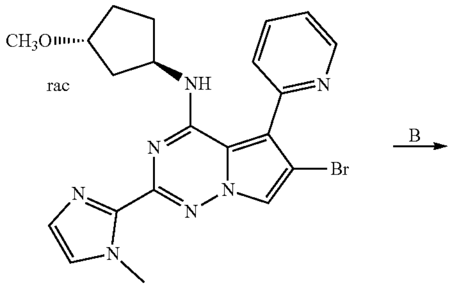

46a

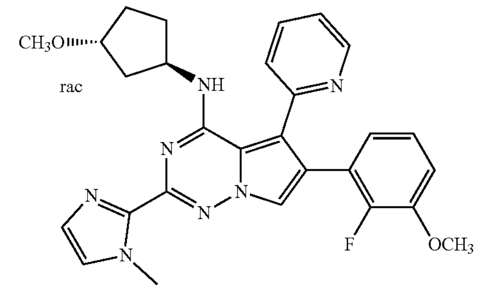

(46)

Step A: rac 6-Bromo-N-((1R,3R)-3-methoxycyclopentyl)-2-(1-methyl-1H-imidazol-2-yl)-5-(pyridin-2-yl)pyrrolo[2,1-f][1,2,4]triazin-4-amine 46a A mixture of 6-bromo-4-chloro-2-(1-methyl-1H-imidazol-2-yl)-5-(pyridin-2-yl)pyrrolo[2,1-f][1,2,4]triazine 45f (prepared as described in Example 45, Step E) (300.0 mg, 769.95 μmol), rac (1R,3R)-3-methoxycyclopentan-1-amine (88.77 mg, 770.79 μmol) and ethylbis(propan-2-yl)amine (298.86 mg, 2.31 mmol) in DMSO (5 mL) was heated at 100° C. 18h then cooled and purified by HPLC (2-10 min 50-85% $H_2O$-methanol+$NH_3$; Flow 30 mL/min; (loading pump 4.0 mL methanol), column: sun fire C18) to give rac 6-bromo-N-((1R,3R)-3-methoxycyclopentyl)-2-(1-methyl-1H-imidazol-2-yl)-5-(pyridin-2-yl)pyrrolo[2,1-f][1,2,4]triazin-4-amine 46a (46.7 mg, 97.7% purity, 97.42 μmol, 12.6% yield).

Step B: rac 6-(2-Fluoro-3-methoxyphenyl)-N-((1R,3R)-3-methoxycyclopentyl)-2-(1-methyl-1H-imidazol-2-yl)-5-(pyridin-2-yl)pyrrolo[2,1-f][1,2,4]triazin-4-amine (46)

rac 6-bromo-N-((1R,3R)-3-methoxycyclopentyl)-2-(1-methyl-1H-imidazol-2-yl)-5-(pyridin-2-yl)pyrrolo[2,1-f][1,2,4]triazin-4-amine 46a (47.0 mg, 100.35 μmol), 2-fluoro-3-methoxyphenylboronic acid (20.45 mg, 120.36 μmol), cesium carbonate (65.36 mg, 200.59 μmol) and Pd(dppf)$Cl_2$ (8.19 mg, 10.03 μmol) were dissolved in degassed dioxane (1.0 mL) under Ar. 0.05 mL of water was added via syringe. The reaction mixture was heated to 80° C. and stirred at this temperature for 16 h. The mixture was cooled to room temperature, filtered through celite and concentrated. The residue was purified by HPLC (2-10 min 55-85% $H_2O$-methanol+$NH_3$; Flow 30 mL/min; (loading pump 4.0 mL methanol), column: sun fire C18), rac 6-(2-Fluoro-3-methoxyphenyl)-N-((1R,3R)-3-methoxycyclopentyl)-2-(1-methyl-1H-imidazol-2-yl)-5-(pyridin-2-yl)pyrrolo[2,1-f][1,2,4]triazin-4-amine (46) (0.017 g, 34.84 μmol, 36.5% yield was obtained as beige solid. LCMS(ESI): Calculated [M+1] 514.3 Found [M+1] 514.2.

Example 47: Synthesis of Compound 47

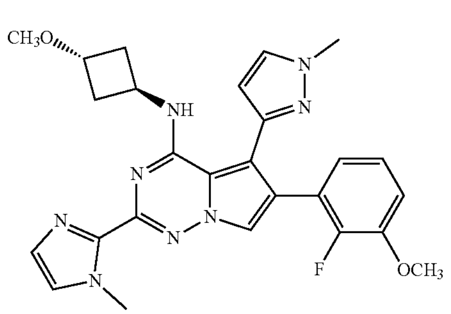

(47)

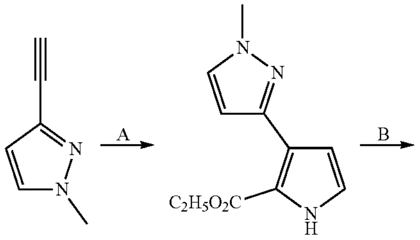

47a 47b

-continued

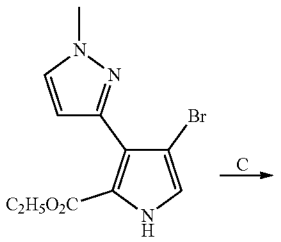

47c

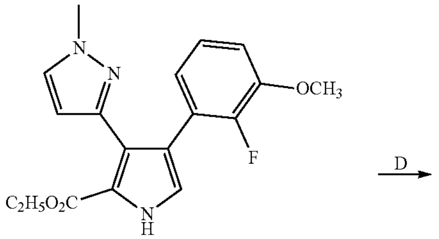

47d

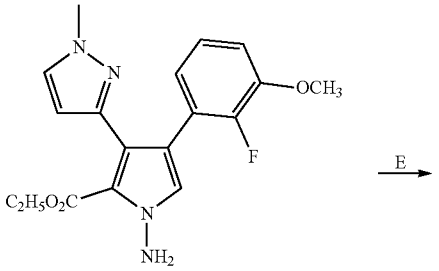

47e

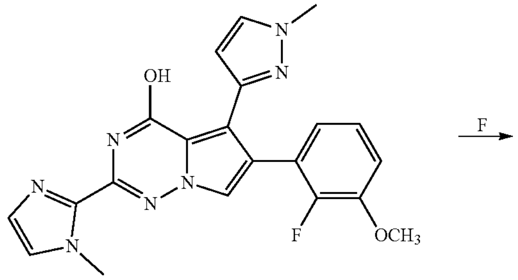

47f

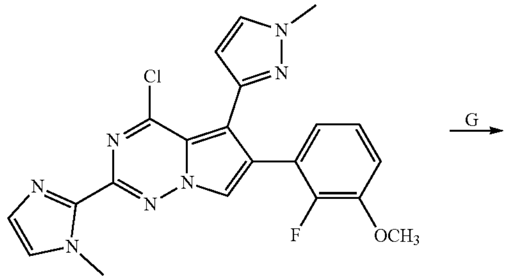

47g

-continued

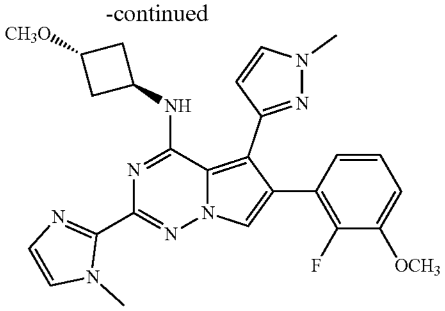

(47)

Step A: Ethyl 3-(1-methyl-1H-pyrazol-3-yl)-1H-pyrrole-2-carboxylate 47b

To a solution of 3-ethynyl-1-methyl-1H-pyrazole 47a (15.0 g, 141.34 mmol) in NMP (200 mL), silver carbonate (3.9 g, 14.13 mmol) and ethyl 2-isocyanoacetate (20.78 g, 183.75 mmol) were added under Argon. The reaction mixture was stirred at 80° C. overnight, then cooled and filtered. Water (200 mL) was added to filtrate and extracted with DCM once (200 mL). DCM was washed with water (10*75 mL). Organic layer dried and evaporated under reduce pressure. Crude compound was purified by flash chromatography ($SiO_2$, Hexane-MtBE as a solvent mixture) to give ethyl 3-(1-methyl-1H-pyrazol-3-yl)-1H-pyrrole-2-carboxylate 47b (7.3 g, 91.7% purity, 30.53 mmol, 21.6% yield).

Step B: Ethyl 4-bromo-3-(1-methyl-1H-pyrazol-3-yl)-1H-pyrrole-2-carboxylate ethyl 4-bromo-3-(1-methyl-1H-pyrazol-3-yl)-1H-pyrrole-2-carboxylate 47c To a solution of ethyl 3-(1-methyl-1H-pyrazol-3-yl)-1H-pyrrole-2-carboxylate 47b (7.3 g, 33.3 mmol) in DMF (80 mL) N-bromosuccinimide (5.93 g, 33.3 mmol) was added portionwise under cooling with ice. The reaction mixture was stirred at RT overnight and then poured into water (40 mL), extracted with TBME (3*50 mL). Combined TBME was washed with water (5*20 mL), dried and evaporated under reduce pressure to give ethyl 4-bromo-3-(1-methyl-1H-pyrazol-3-yl)-1H-pyrrole-2-carboxylate ethyl 4-bromo-3-(1-methyl-1H-pyrazol-3-yl)-1H-pyrrole-2-carboxylate 47c (8.1 g, 72.0% purity, 19.56 mmol, 58.7% yield).

Step C: Ethyl 4-(2-fluoro-3-methoxyphenyl)-3-(1-methyl-1H-pyrazol-3-yl)-1H-pyrrole-2-carboxylate 47d A mixture of ethyl 4-bromo-3-(1-methyl-1H-pyrazol-3-yl)-1H-pyrrole-2-carboxylate ethyl 4-bromo-3-(1-methyl-1H-pyrazol-3-yl)-1H-pyrrole-2-carboxylate 47c (8.1 g, 27.17 mmol), 2-fluoro-3-methoxyphenylboronic acid (5.08 g, 29.88 mmol), potassium fluoride (4.74 g, 81.5 mmol), palladium(II) acetate (452.26 mg, 2.72 mmol) and bis(adamantan-1-yl) (butyl)phosphane (1.95 g, 5.43 mmol) in dioxane/$H_2O$ (160 mL/10 mL) was heated at 100° C. under Argon atmosphere overnight. The reaction mixture was evaporated and crude compound was purified by flash chromatography ($SiO_2$, Hexane-MtBE as a solvent mixture) to give ethyl 4-(2-fluoro-3-methoxyphenyl)-3-(1-methyl-1H-pyrazol-3-yl)-1H-pyrrole-2-carboxylate 47d (5.5 g, 76.2% purity, 12.21 mmol, 44.9% yield).

Step D: Ethyl 1-amino-4-(2-fluoro-3-methoxyphenyl)-3-(1-methyl-1H-pyrazol-3-yl)-1H-pyrrole-2-carboxylate 47e To solution of ethyl 4-(2-fluoro-3-methoxyphenyl)-3-(1-methyl-1H-pyrazol-3-yl)-1H-pyrrole-2-carboxylate 47d (5.5 g, 16.02 mmol) in DMF (75 mL) sodium hydride (832.96 mg, 34.71 mmol) was added at 0° C. After 1 hour, O-(2,4-dinitrophenyl) hydroxylamine (4.15 g, 20.83 mmol) in DMF was added dropwise. Reaction mixture was stirred at RT overnight. An aqueous solution of $NH_4Cl$ was added to reaction mixture, extracted with EtOAc (3*50 mL), combined EtOAc was washed with water (7*20 mL), dried and evaporated under reduce pressure to give ethyl 1-amino-4-(2-fluoro-3-methoxyphenyl)-3-(1-methyl-1H-pyrazol-3-yl)-1H-pyrrole-2-carboxylate 47e (5.6 g, 60.1% purity, 9.39 mmol, 58.6% yield).

Step E: 6-(2-Fluoro-3-methoxyphenyl)-2-(1-methyl-1H-imidazol-2-yl)-5-(1-methyl-1H-pyrazol-3-yl) pyrrolo[2,1-f][1,2,4]triazin-4-ol 47f To a mixture of ethyl 1-amino-4-(2-fluoro-3-methoxyphenyl)-3-(1-methyl-1H-pyrazol-3-yl)-1H-pyrrole-2-carboxylate 47e (5.6 g, 15.63 mmol) and 1-methyl-1H-imidazole-2-carbonitrile (1.67 g, 15.63 mmol) in dioxane (75 mL) sodium hydride (1.25 g, 52.09 mmol) was added cooling with ice. The reaction mixture was stirred at 100° C. overnight. An aqueous solution of $NH_4Cl$ was added to reaction mixture, extracted with EtOAc (3*50 mL), dried and evaporated under reduce pressure to give 6-(2-fluoro-3-methoxyphenyl)-2-(1-methyl-1H-imidazol-2-yl)-5-(1-methyl-1H-pyrazol-3-yl)pyrrolo[2,1-f][1,2,4]triazin-4-ol 47f (4.5 g, 40.8% purity, 4.38 mmol, 28% yield).

Step F: 4-Chloro-6-(2-fluoro-3-methoxyphenyl)-2-(1-methyl-1H-imidazol-2-yl)-5-(1-methyl-1H-pyrazol-3-yl)pyrrolo[2,1-f][1,2,4]triazine 47g The starting material 6-(2-fluoro-3-methoxyphenyl)-2-(1-methyl-1H-imidazol-2-yl)-5-(1-methyl-1H-pyrazol-3-yl) pyrrolo[2,1-f][1,2,4]triazin-4-ol 47f (1.0 g, 2.38 mmol) was suspended in phosphoroyl trichloride (3.66 g, 23.84 mmol) and ethylbis(propan-2-yl)amine (924.48 mg, 7.15 mmol) was added at RT. The reaction mixture was heated at 100° C. overnight. The solution was cooled to RT, evaporated under reduced pressure, poured into solution of $NaHCO_3$, the product was extracted with chloroform (3*20 mL) and evaporated to give 4-chloro-6-(2-fluoro-3-methoxyphenyl)-2-(1-methyl-1H-imidazol-2-yl)-5-(1-methyl-1H-pyrazol-3-yl)pyrrolo[2,1-f][1,2,4]triazine 47g (500.0 mg, 40.5% purity, 462.48 μmol, 19.4% yield).

Step G: 6-(2-Fluoro-3-methoxyphenyl)-N-((1r,3r)-3-methoxycyclobutyl)-2-(1-methyl-1H-imidazol-2-yl)-5-(1-methyl-1H-pyrazol-3-yl)pyrrolo[2,1-f][1,2,4]triazin-4-amine (47)

A mixture of 4-chloro-6-(2-fluoro-3-methoxyphenyl)-2-(1-methyl-1H-imidazol-2-yl)-5-(1-methyl-1H-pyrazol-3-yl) pyrrolo[2,1-f][1,2,4]triazine 47g (500.0 mg, 1.14 mmol), (1r,3r)-3-methoxycyclobutan-1-amine hydrochloride (157.17 mg, 1.14 mmol) and ethylbis(propan-2-yl)amine (442.86 mg, 3.43 mmol) in DMSO (5 mL) was stirred at 100° C. overnight. Crude product was purified by HPLC (2-10 min 30-50% $H_2O$-MeCN+$NH_3$; flow 30 mL/min ((loading pump 4 mL MeCN); column: SunFire C18 100*19

5 microM) to give 6-(2-fluoro-3-methoxyphenyl)-N-((1r,3r)-3-methoxycyclobutyl)-2-(1-methyl-1H-imidazol-2-yl)-5-(1-methyl-1H-pyrazol-3-yl)pyrrolo[2,1-f][1,2,4]triazin-4-amine (47) (34.9 mg, 95.0% purity, 65.97 μmol, 5.8% yield) as light-brown solid. LCMS(ESI): Calculated [M+1] 503.2 Found [M+1] 503.2. $^1$H NMR (DMSO-$d_6$, 400 MHz) δ 2.40 (m, 4H), 3.18 (s, 3H), 3.87 (s, 3H), 3.95 (m, 6H), 4.15 (m, 1H), 4.65 (m, 1H), 5.51 (m, 1H), 6.93 (dd, 1H), 7.00 (s, 1H), 7.19 (m, 2H), 7.30 (d, 1H), 7.65 (d, 1H), 7.85 (d, 1H), 11.15 (d, 1H).

Example 48: Synthesis of Compound 48

(48)

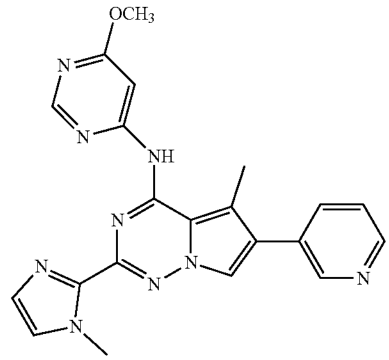

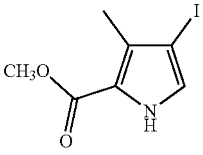

1b

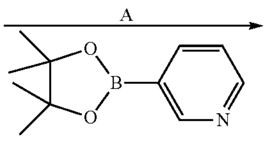

48a

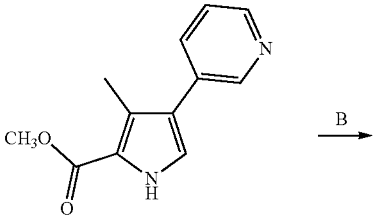

48b

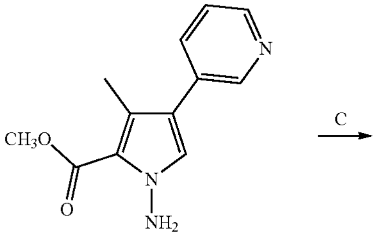

48c

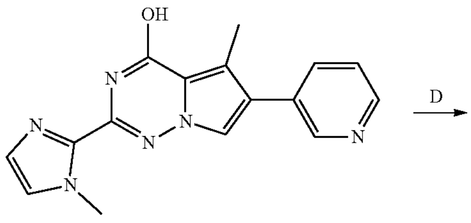

48d

-continued

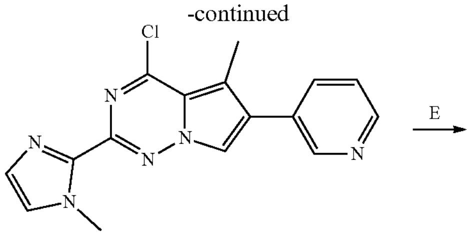

48e

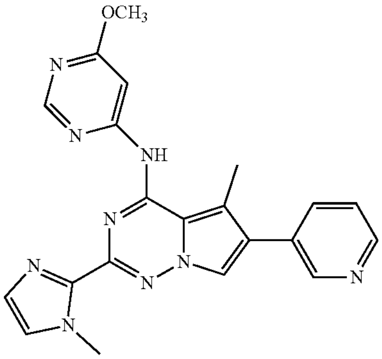

(48)

Step A: Methyl 3-methyl-4-(pyridin-3-yl)-1H-pyrrole-2-carboxylate 48b

A mixture of methyl 4-iodo-3-methyl-1H-pyrrole-2-carboxylate 1b (prepared as described in Example 1, Step A) (2.35 g, 8.87 mmol), 3-(4,4,5,5-tetramethyl-1,3,2-dioxaborolan-2-yl)pyridine 48a (2.0 g, 9.75 mmol), cesium carbonate (5.78 g, 17.73 mmol) and [1,1'-bis(diphenylphosphino)ferrocene]dichloropalladium(II) dichloromethane adduct (723.97 mg, 886.53 μmol) in dioxane/$H_2O$ (20 mL/3 mL) was heated at 100° C. under Argon atmosphere overnight. The reaction mixture was evaporated, and crude compound was purified by flash chromatography ($SiO_2$, Hexane-AtOAc as a solvent mixture) to give methyl 3-methyl-4-(pyridin-3-yl)-1H-pyrrole-2-carboxylate 48b (1.0 g, 84.5% purity, 3.91 mmol, 44.1% yield).

Step B: Methyl 1-amino-3-methyl-4-(pyridin-3-yl)-1H-pyrrole-2-carboxylate 48c

To a solution of methyl 3-methyl-4-(pyridin-3-yl)-1H-pyrrole-2-carboxylate 48b (1 g, 4.62 mmol) in DMF (20 mL) sodium hydride (240.36 mg, 10.02 mmol) was added at 0° C. After 1 hour, O-(2,4-dinitrophenyl) hydroxylamine (1.2 g, 6.01 mmol) in DMF was added dropwise. Reaction mixture was stirred at RT overnight. An aqueous solution of $NH_4Cl$ was added to reaction mixture, extracted with EtOAc (3*20 mL), combined EtOAc was washed with water (7*10 mL), dried and evaporated under reduce pressure to give methyl 1-amino-3-methyl-4-(pyridin-3-yl)-1H-pyrrole-2-carboxylate 48c (1.05 g, 96.8% purity, 4.4 mmol, 95.1% yield).

Step C: 5-Methyl-2-(1-methyl-1H-imidazol-2-yl)-6-(pyridin-3-yl)pyrrolo[2,1-f][1,2,4]triazin-4-ol 48d To mixture of methyl 1-amino-3-methyl-4-(pyridin-3-yl)-1H-pyrrole-2-carboxylate 48c (1.05 g, 4.54 mmol) and 1-methyl-1H-imidazole-2-carbonitrile (486.4 mg, 4.54 mmol) in dioxane (30 mL) sodium hydride (363.24 mg, 15.14 mmol) was added cooling with ice. The reaction mixture was stirred at 100° C. overnight. An aqueous solution of $NH_4Cl$ was added to reaction mixture, extracted with EtOAc (3*20 mL), dried and evaporated under reduce pressure to give 5-methyl-2-(1-methyl-1H-imidazol-2-yl)-6-(pyridin-3-yl)pyrrolo[2,1-f][1,2,4]triazin-4-ol 48d (1.0 g, 57.5% purity, 1.88 mmol, 41.3% yield).

Step D: 4-Chloro-5-methyl-2-(1-methyl-1H-imidazol-2-yl)-6-(pyridin-3-yl)pyrrolo[2,1-f][1,2,4]triazine 48e The starting material 5-methyl-2-(1-methyl-1H-imidazol-2-yl)-6-(pyridin-3-yl)pyrrolo[2,1-f][1,2,4]triazin-4-ol 48d (998.85 mg, 3.26 mmol) was suspended in phosphoroyl trichloride (5.0 g, 32.61 mmol, 3.04 ml, 10.0 equiv) and the reaction mixture was heated at 100° C. overnight. The solution was cooled to RT, evaporated under reduced pressure, poured into solution of $NaHCO_3$, the product was extracted with chloroform (3*20 mL) and evaporated to give 4-chloro-5-methyl-2-(1-methyl-1H-imidazol-2-yl)-6-(pyridin-3-yl)pyrrolo[2,1-f][1,2,4]triazine 48e (600.0 mg, 79.7% purity, 1.47 mmol, 45.2% yield).

Step E: N-(6-Methoxypyrimidin-4-yl)-5-methyl-2-(1-methyl-1H-imidazol-2-yl)-6-(pyridin-3-yl)pyrrolo[2,1-f][1,2,4]triazin-4-amine (48)

To the mixture of 4-chloro-5-methyl-2-(1-methyl-1H-imidazol-2-yl)-6-(pyridin-3-yl)pyrrolo[2,1-f][1,2,4]triazine 48e (600.0 mg, 1.85 mmol) and 6-methoxypyrimidin-4-amine (231.23 mg, 1.85 mmol) in DMF (15 mL) sodium hydride (147.82 mg, 6.16 mmol) was added under cooling with ice. Reaction mixture was stirred at RT overnight then poured into water, extracted with EtOAc (3*15 mL), dried under $Na_2SO_4$ and evaporated. The crude product was purified by HPLC (2-10 min 30-80% $H_2O$-MeCN; flow 30 mL/min (loading pump 4 mL MeCN), column: SunFire 100*19 mm, 5 microM) to give N-(6-methoxypyrimidin-4-yl)-5-methyl-2-(1-methyl-1H-imidazol-2-yl)-6-(pyridin-3-yl)pyrrolo[2,1-f][1,2,4]triazin-4-amine (48) (27.1 mg, 95.0% purity, 62.27 μmol, 3.4% yield) as pink solid. LCMS(ESI): Calculated [M+1] 414.2 Found [M+1] 414.2.

Example 49: Synthesis of Compound 49

(49)

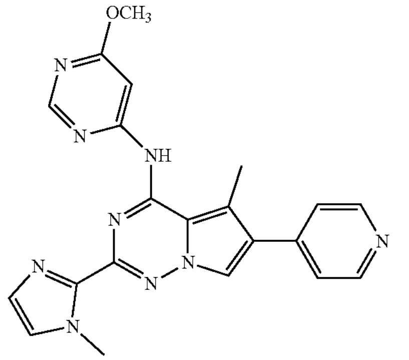

-continued

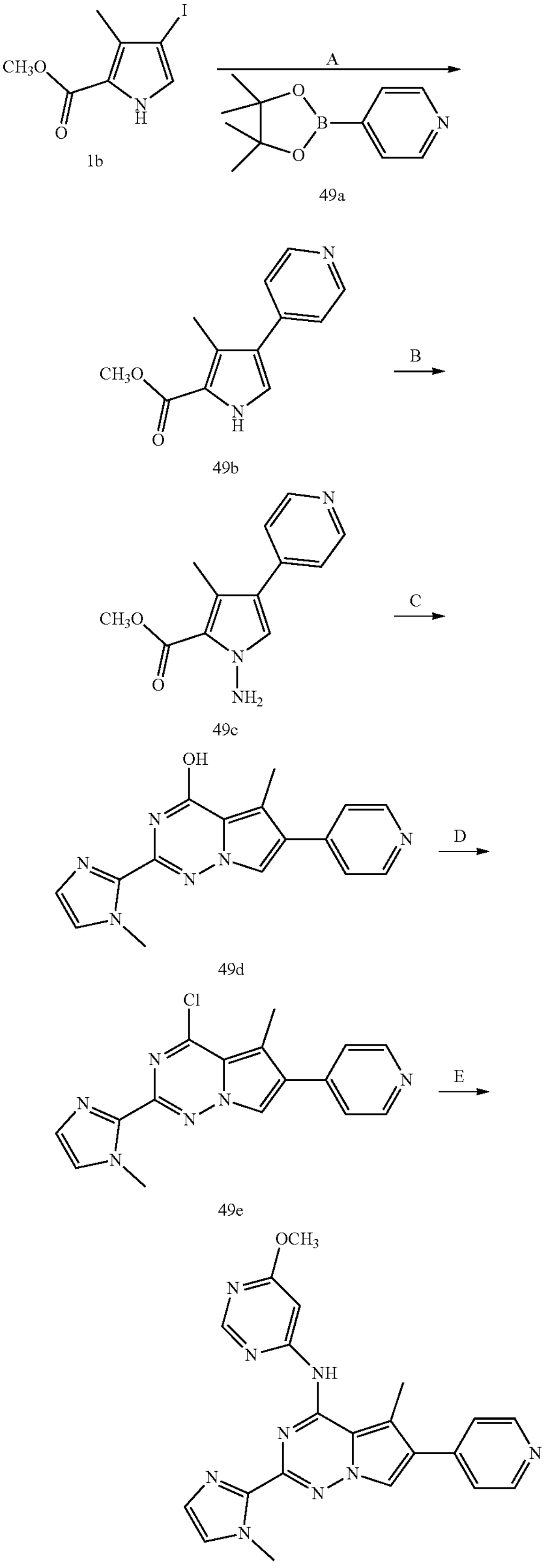

1b

49a

49b

49c

49d

49e (49)

Step A: Methyl 3-methyl-4-(pyridin-4-yl)-1H-pyrrole-2-carboxylate 49b

A mixture of methyl 4-iodo-3-methyl-1H-pyrrole-2-carboxylate 1b (prepared as described in Example 1, Step A) (3.0 g, 11.32 mmol), 4-(4,4,5,5-tetramethyl-1,3,2-dioxaborolan-2-yl)pyridine 49a (2.55 g, 12.45 mmol), cesium carbonate (7.38 g, 22.64 mmol) and [1,1'-bis(diphenylphosphino)ferrocene]dichloropalladium(II) dichloromethane adduct (924.51 mg, 1.13 mmol) in dioxane/$H_2O$ (20 mL/3 mL) was heated at 100° C. under Argon atmosphere overnight. Reaction mixture was evaporated, and crude compound was purified by flash chromatography to give methyl methyl 3-methyl-4-(pyridin-4-yl)-1H-pyrrole-2-carboxylate 49b (850.0 mg, 83.8% purity, 3.29 mmol, 29.1% yield).

Step B: Methyl 1-amino-3-methyl-4-(pyridin-4-yl)-1H-pyrrole-2-carboxylate 49c

To a solution of methyl 3-methyl-4-(pyridin-4-yl)-1H-pyrrole-2-carboxylate 49b (849.98 mg, 3.93 mmol) in DMF (20 mL) sodium hydride (204.38 mg, 8.52 mmol) was added at 0° C. After 1 hour, O-(2,4-dinitrophenyl) hydroxylamine (1.02 g, 5.11 mmol) in DMF was added dropwise. Reaction mixture was stirred at RT overnight. An aqueous solution of $NH_4Cl$ was added to reaction mixture, extracted with EtOAc (3*25 mL), combined EtOAc was washed with water (7*15 mL), dried and evaporated under reduce pressure to give methyl 1-amino-3-methyl-4-(pyridin-4-yl)-1H-pyrrole-2-carboxylate 49c (760.0 mg, 68.8% purity, 2.26 mmol, 57.5% yield).

Step C: 5-Methyl-2-(1-methyl-1H-imidazol-2-yl)-6-(pyridin-4-yl)pyrrolo[2,1-f][1,2,4]triazin-4-ol 49d To a mixture of methyl 1-amino-3-methyl-4-(pyridin-4-yl)-1H-pyrrole-2-carboxylate 49c (760.21 mg, 3.29 mmol) and 1-methyl-1H-imidazole-2-carbonitrile (352.12 mg, 3.29 mmol) in dioxane (20 mL) sodium hydride (262.97 mg, 10.96 mmol) was added cooling with ice. Reaction mixture was stirred at 100° C. overnight. An aqueous solution of $NH_4Cl$ was added to reaction mixture, extracted with EtOAc (3*20 mL), dried and evaporated under reduce pressure to give 5-methyl-2-(1-methyl-1H-imidazol-2-yl)-6-(pyridin-4-yl)pyrrolo[2,1-f][1,2,4]triazin-4-ol 49d (720.0 mg, 82.2% purity, 1.93 mmol, 58.8% yield).

Step D: 4-Chloro-5-methyl-2-(1-methyl-1H-imidazol-2-yl)-6-(pyridin-4-yl)pyrrolo[2,1-f][1,2,4]triazine 49e The starting material 5-methyl-2-(1-methyl-1H-imidazol-2-yl)-6-(pyridin-4-yl)pyrrolo[2,1-f][1,2,4]triazin-4-ol 49d (719.66 mg, 2.35 mmol) was suspended in phosphoroyl trichloride (3.6 g, 23.5 mmol, 2.19 ml, 10.0 equiv) and the reaction mixture was heated at 100° C. overnight. The solution was cooled to RT, evaporated under reduced pressure, poured into solution of $NaHCO_3$, the product was extracted with chloroform (3*20 mL) and evaporated to give 4-chloro-5-methyl-2-(1-methyl-1H-imidazol-2-yl)-6-(pyridin-4-yl)pyrrolo[2,1-f][1,2,4]triazine 49e (60.0 mg, 53.7% purity, 99.21 μmol, 4.2% yield).

Step E: N-(6-Methoxypyrimidin-4-yl)-5-methyl-2-(1-methyl-1H-imidazol-2-yl)-6-(pyridin-4-yl)pyrrolo[2,1-f][1,2,4]triazin-4-amine (49)

To the mixture of 4-chloro-5-methyl-2-(1-methyl-1H-imidazol-2-yl)-6-(pyridin-4-yl)pyrrolo[2,1-f][1,2,4]triazine 49e (60.01 mg, 184.79 μmol) and 6-methoxypyrimidin-4-amine (23.12 mg, 184.79 μmol) in DMF (5 mL) sodium hydride (14.78 mg, 615.98 μmol) was added under cooling with ice. Reaction mixture was stirred at RT overnight then poured into water, extracted with EtOAc (3*10 mL), dried under $Na_2SO_4$ and evaporated. The crude product was purified by HPLC (2-10 min 50-85% $H_2O$-methanol+$NH_3$; flow 30 mL/min (loading pump 4 mL MeCN), column: SunFire 100*19 mm, 5 microM) to give N-(6-methoxypyrimidin-4-yl)-5-methyl-2-(1-methyl-1H-imidazol-2-yl)-6-(pyridin-4-yl)pyrrolo[2,1-f][1,2,4]triazin-4-amine (49) (4.3 mg, 95.0% purity, 9.88 μmol, 5.3% yield) as light-brown gum. LCMS (ESI): Calculated [M+1] 414.2 Found [M+1] 414.2.

Example 50: Synthesis of Compound 50

(50)

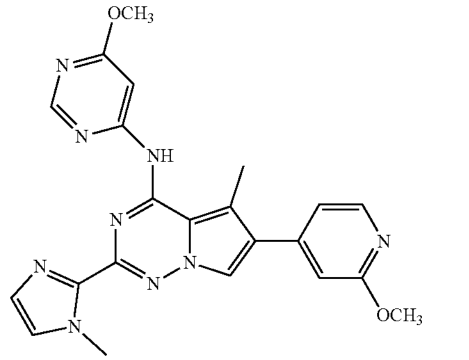

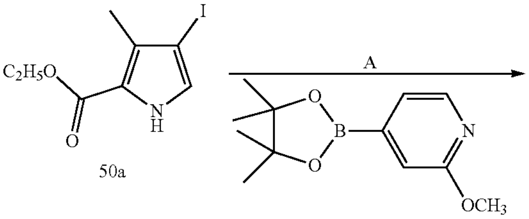

50a

50b

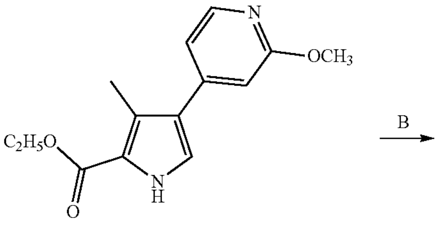

50c

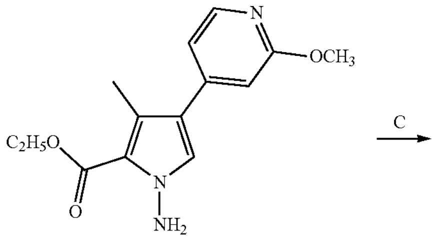

50d

-continued

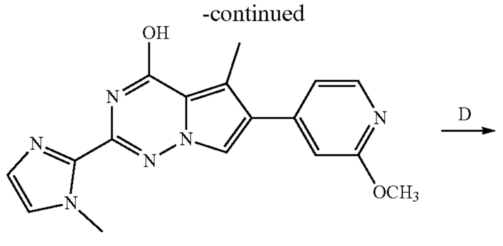

50e

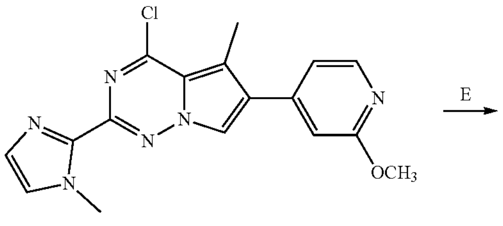

50f

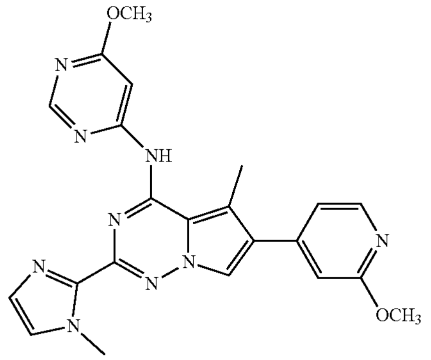

(50)

Step A: Ethyl 4-(2-methoxypyridin-4-yl)-3-methyl-1H-pyrrole-2-carboxylate 50c

Ethyl 4-iodo-3-methyl-1H-pyrrole-2-carboxylate 50a (prepared like methyl 4-iodo-3-methyl-1H-pyrrole-2-carboxylate 1b in Example 1, Step A, except starting with ethyl 3-methyl-1H-pyrrole-2-carboxylate in place of methyl 3-methyl-1H-pyrrole-2-carboxylate 1a) (4.5 g, 16.12 mmol), 2-methoxy-4-(4,4,5,5-tetramethyl-1,3,2-dioxaborolan-2-yl) pyridine 50b (4.55 g, 19.35 mmol), Pd(dppf)$Cl_2$ (1.32 g, 1.61 mmol) and cesium carbonate (10.51 g, 32.25 mmol) were suspended in degassed dioxane (90 mL) under Ar. 4.5 mL of water was added via syringe. The reaction mixture was heated to 80° C. and stirred at this temperature for 16 h. The mixture was cooled to room temperature, filtered through celite and concentrated. The residue was purified by column chromatography ($SiO_2$, Eluted by Hex:EtOAc 20:1 to 1:2). Ethyl 4-(2-methoxypyridin-4-yl)-3-methyl-1H-pyrrole-2-carboxylate 50c (1.0 g, 3.84 mmol, 23.8% yield) was obtained as light-yellow powder.

Step B: Ethyl 1-amino-4-(2-methoxypyridin-4-yl)-3-methyl-1H-pyrrole-2-carboxylate 50d To a solution of ethyl 4-(2-methoxypyridin-4-yl)-3-methyl-1H-pyrrole-2-carboxylate 50c (1.0 g, 3.84 mmol) in DMF (20 mL) sodium hydride (199.82 mg, 8.33 mmol) was added at 0° C. After 1 hour, O-(2,4-dinitrophenyl) hydroxylamine (994.8 mg, 5.0 mmol) in DMF was added dropwise. The reaction mixture was stirred at RT overnight. An aqueous solution of $NH_4Cl$ was added to reaction mixture, extracted with EtOAc (3*25 mL), combined EtOAc was washed with water (7*15 mL), dried and evaporated under reduce pressure to give ethyl 1-amino-4-(2-methoxypyridin-4-yl)-3-methyl-1H-pyrrole-2-carboxylate 50d (1.1 g, 80.9% purity, 3.23 mmol, 84.1% yield).

Step C: 6-(2-Methoxypyridin-4-yl)-5-methyl-2-(1-methyl-1H-imidazol-2-yl)pyrrolo[2,1-f][1,2,4]triazin-4-ol 50e Sodium hydride (319.64 mg, 13.32 mmol) (60% on mineral oil) was added portionwise (during 3 min) to the solution of ethyl 1-amino-4-(2-methoxypyridin-4-yl)-3-methyl-1H-pyrrole-2-carboxylate 50d (1.1 g, 4.0 mmol) and 1-methyl-1H-imidazole-2-carbonitrile (428.01 mg, 4.0 mmol) in dioxane (5 mL). The reaction mixture was heated to reflux and stirred at this temperature for 16 h. Then the mixture was cooled to the room temperature, poured in ice water and neutralized by acetic acid. The formed participate was collected by filtration, washed by water (2*10 mL) and dried in vacuo. 6-(2-Methoxypyridin-4-yl)-5-methyl-2-(1-methyl-1H-imidazol-2-yl)pyrrolo[2,1-f][1,2,4]triazin-4-ol 50e (400.0 mg, 1.19 mmol, 29.8% yield) was obtained.

Step D: 4-Chloro-6-(2-methoxypyridin-4-yl)-5-methyl-2-(1-methyl-1H-imidazol-2-yl)pyrrolo[2,1-f][1,2,4]triazine 50f 6-(2-Methoxypyridin-4-yl)-5-methyl-2-(1-methyl-1H-imidazol-2-yl)pyrrolo[2,1-f][1,2,4]triazin-4-ol 50e (150.0 mg, 445.97 μmol) was dissolved in phosphoroyl trichloride (819.4 mg, 5.34 mmol, 500.0 μL, 12.0 equiv). The mixture was heated to 100° C. and stirred at this temperature for 16 h. The reaction mixture was concentrated in vacuo, poured in ice water (5 mL) and neutralized by $K_2CO_3$. The formed participate was collected by filtration, washed by water (2*5 mL) and dried on vacuo. 4-Chloro-6-(2-methoxypyridin-4-yl)-5-methyl-2-(1-methyl-1H-imidazol-2-yl)pyrrolo[2,1-f][1,2,4]triazine 50f (100.0 mg, 80.0% purity, 225.48 μmol, 50.6% yield) was obtained.

Step E: 6-(2-Methoxypyridin-4-yl)-N-(6-methoxypyrimidin-4-yl)-5-methyl-2-(1-methyl-1H-imidazol-2-yl)pyrrolo[2,1-f][1,2,4]triazin-4-amine (50)

Sodium hydride (18.04 mg, 751.66 μmol) (60% on mineral oil) was added in portionwise to the solution of 4-chloro-6-(2-methoxypyridin-4-yl)-5-methyl-2-(1-methyl-1H-imidazol-2-yl)pyrrolo[2,1-f][1,2,4]triazine 50f (100.0 mg, 281.85 μmol) and 6-methoxypyrimidin-4-amine (28.22 mg, 225.5 μmol) in DMF (1 mL). The mixture was stirred at room temperature for 16 h. The mixture was quenched by concentrated aq. $NH_4Cl$. The formed participate was collected by filtration, washed with water (2*3 mL) and purified by HPLC (2-10 min 40-55% $H_2O$-MeCN+$NH_3$; flow 30 mL/min (loading pump 4.0 mL MeCN+$NH_3$); column: SunFire 100*19 mm, 5 microM). 6-(2-Methoxypyridin-4-yl)-N-(6-methoxypyrimidin-4-yl)-5-methyl-2-(1-methyl-1H-imidazol-2-yl)pyrrolo[2,1-f][1,2,4]triazin-4-amine (50) (16.0 mg, 36.08 μmol, 16% yield) was obtained as yellow solid. LCMS(ESI): Calculated [M+1] 444.2 Found [M+1] 444.2. $^1H$ NMR (DMSO-$d_6$, 400 MHz) § 2.76 (s, 3H), 3.14 (s, 3H), 3.80-3.85 (m, 6H), 6.72 (d, 1H), 6.90 (m, 2H), 7.12 (m, 2H), 7.72 (s, 1H), 8.13 (d, 1H), 8.32 (s, 1H).

Example 51-Example 61: Synthesis of Compounds 51-61

Following the general procedure described in Example 1, Step G, 4-chloro-6-(1-isopropyl-1H-pyrazol-3-yl)-5-methyl-2-(1-methyl-1H-imidazol-2-yl)pyrrolo[2,1-f][1,2,4]triazine 1 g (150.0 mg, 421.56 μmol) was treated with the appropriate corresponding amine (505.37 μmol, 1.2 eq) to produce the Example compounds (51)-(62) shown in Table 1. Analytical data for compounds (51)-(62) is also presented in Table 1.

Example 63: Synthesis of Compound 63

(63)

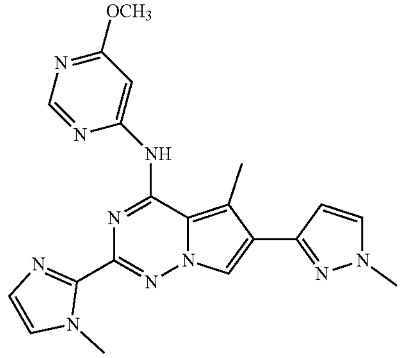

N-(6-Methoxypyrimidin-4-yl)-5-methyl-2-(1-methyl-1H-imidazol-2-yl)-6-(1-methyl-1H-pyrazol-3-yl)pyrrolo[2,1-f][1,2,4]triazin-4-amine (63)

Compound 63 was prepared according to analogous to those described herein above. (100% purity) LCMS(ESI): Calculated [M+1] 417.2 Found [M+1] 417.2

Example 64: Synthesis of Compound 64

(64)

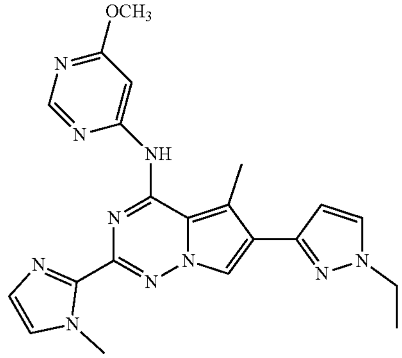

6-(1-Ethyl-1H-pyrazol-3-yl)-N-(6-methoxypyrimidin-4-yl)-5-methyl-2-(1-methyl-1H-imidazol-2-yl)pyrrolo[2,1-f][1,2,4]triazin-4-amine (64)

Compound 64 was prepared according to analogous to those described herein above. (97% purity) LCMS(ESI): Calculated [M+1] 431.2 Found [M+1] 431.2

Example 65: Synthesis of Compound 65

(65)

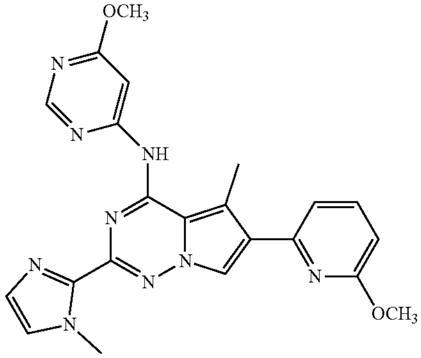

6-(6-Methoxypyridin-2-yl)-N-(6-methoxypyrimidin-4-yl)-5-methyl-2-(1-methyl-1H-imidazol-2-yl)pyrrolo[2,1-f][1,2,4]triazin-4-amine (65)

Compound 65 was prepared according to analogous to those described herein above. (100% purity) LCMS(ESI): Calculated [M+1] 444.2 Found [M+1] 444.0

Example 66: Synthesis of Compound 66

(66)

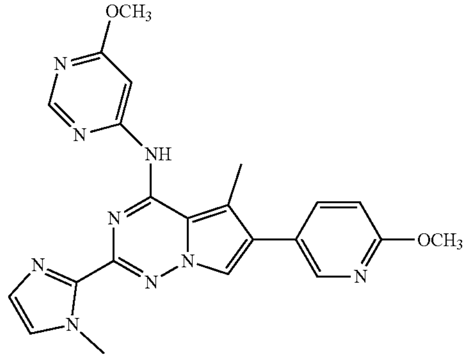

6-(6-Methoxypyridin-3-yl)-N-(6-methoxypyrimidin-4-yl)-5-methyl-2-(1-methyl-1H-imidazol-2-yl)pyrrolo[2,1-f][1,2,4]triazin-4-amine (66)

Compound 66 was prepared according to analogous to those described herein above. (94% purity) LCMS(ESI): Calculated [M+1] 444.2 Found [M+1] 444.2.

Example 67-Example 93: Synthesis of Compounds 67-93

Following the general procedure described in Example 1, Step G, 4-chloro-6-(1-isopropyl-1H-pyrazol-3-yl)-5-methyl-2-(1-methyl-1H-imidazol-2-yl)pyrrolo[2,1-f][1,2,4]triazine 1g (150.0 mg, 421.56 μmol) was treated with the appropriate corresponding amine (505.37 μmol, 1.2 eq) to produce the Example compounds (67)-(93) shown in Table 1. Analytical data for compound (67)-(93) is also shown in Table 1.

Example 94: Synthesis of Compound 94

(94)

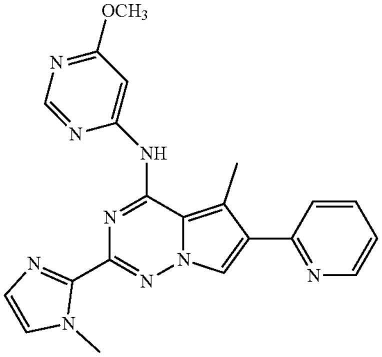

N-(6-Methoxypyrimidin-4-yl)-5-methyl-2-(1-methyl-1H-imidazol-2-yl)-6-(pyridin-2-yl)pyrrolo[2,1-f][1,2,4]triazin-4-amine (94)

Compound 94 was prepared using procedures similar to those described in Example 1, Example 48, Example 49 and Example 50. (100% purity) LCMS(ESI): Calculated [M+1] 414.1 Found [M+1] 414.2

Example 95: Synthesis of Compound 95

(95)

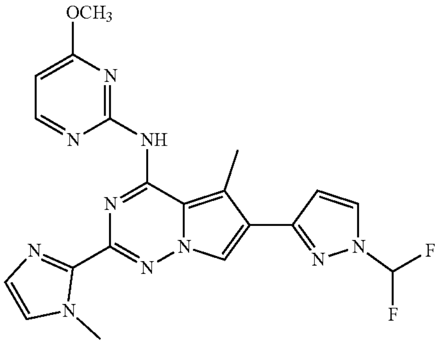

6-(1-(Difluoromethyl)-1H-pyrazol-3-yl)-N-(4-methoxypyrimidin-2-yl)-5-methyl-2-(1-methyl-1H-imidazol-2-yl)pyrrolo[2,1-f][1,2,4]triazin-4-amine (95)

Compound 95 was prepared using procedures similar to those described in Example 1, Example 48, Example 49 and Example 50. (95% purity) LCMS(ESI): Calculated [M+1] 453.1 Found [M+1] 453.2.

Example 96: Synthesis of Compound 96

(96)

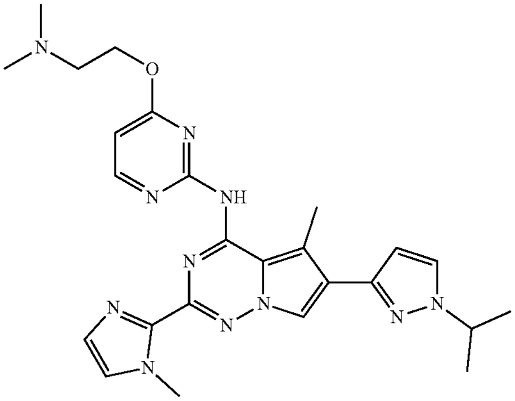

N-(4-(2-(Dimethylamino) ethoxy)pyrimidin-2-yl)-6-(1-isopropyl-1H-pyrazol-3-yl)-5-methyl-2-(1-methyl-1H-imidazol-2-yl)pyrrolo[2,1-f][1,2,4]triazin-4-amine (96)

Compound 96 was prepared using procedures similar to those described in the foregoing Examples.

Example 97: Synthesis of Compound 97

(97)

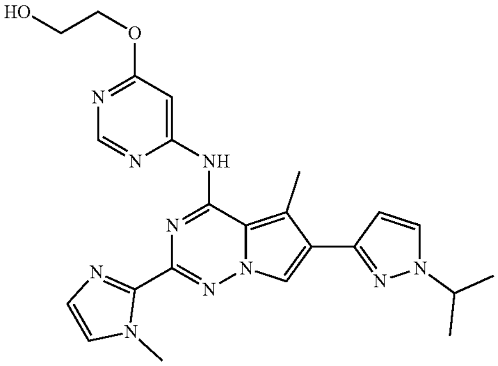

2-((6-((6-(1-Isopropyl-1H-pyrazol-3-yl)-5-methyl-2-(1-methyl-1H-imidazol-2-yl)pyrrolo[2,1-f][1,2,4]triazin-4-yl)amino) pyrimidin-4-yl)oxy) ethan-1-ol (97)

Compound 97 was prepared using procedures similar to those described in the foregoing Examples.

Example 98: Synthesis of Compound 98
(98)
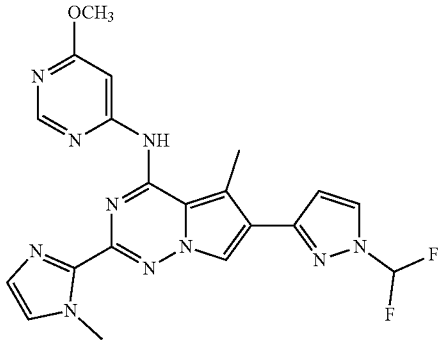
6-(1-(Difluoromethyl)-1H-pyrazol-3-yl)-N-(6-methoxypyrimidin-4-yl)-5-methyl-2-(1-methyl-1H-imidazol-2-yl)pyrrolo[2,1-f][1,2,4]triazin-4-amine (98)
Compound 98 was prepared using procedures similar to those described in the foregoing Examples.
Example 99: Synthesis of Compound 99
(99)
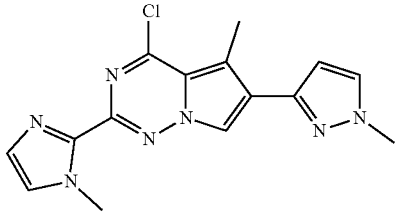
Procedure A:
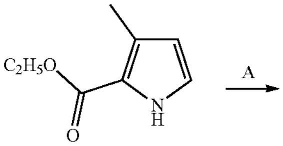
99a
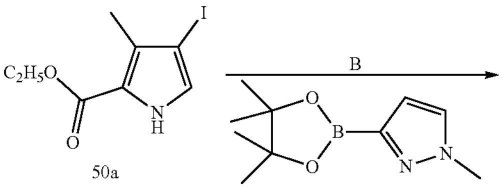
50a
99b
-continued
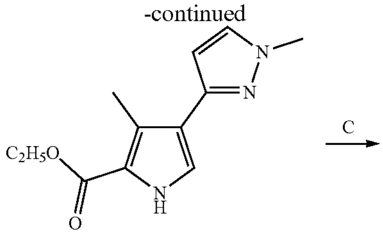
99c
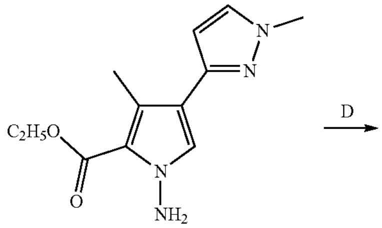
99d
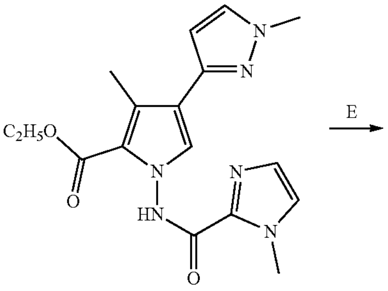
99e
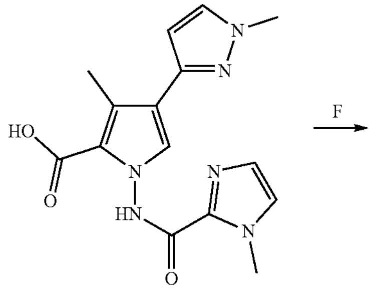
99f
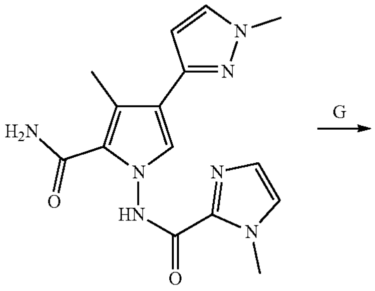
99g
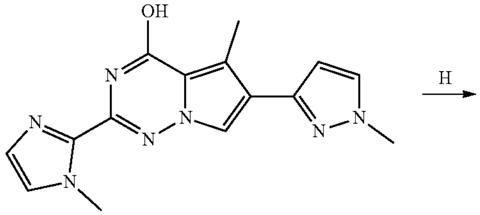
99h -continued

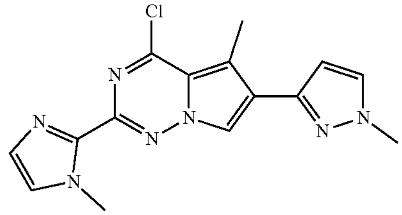

(99)

Step A: Ethyl 4-iodo-3-methyl-1H-pyrrole-2-carboxylate 50a

To a stirred solution of ethyl 3-methyl-1H-pyrrole-2-carboxylate 99a (5.00 g, 32.67 mmol) in DMF (50 mL), NIS (6.98 g, 31.04 mmol) was added portion wise at 0° C. After addition of NIS completed, resulting reaction mixture was stirred at room temperature under dark condition for 4 h. After 4 h, reaction mixture was poured on ice cold water with good stirring. Solid precipitate out, was filtered, washed with $H_2O$ (2×50 mL) followed by hexanes (2×50 mL) and dried in vacuo to afford ethyl 4-iodo-3-methyl-1H-pyrrole-2-carboxylate 50a (7.50 g, 82% yield) as an off white solid. $^1H$ NMR (400 MHZ, DMSO-$d_6$) δ 11.90 (brs, 1H), 7.10 (s, 1H), 4.20 (m, 2H), 2.20 (s, 3H), 1.30 (t, 3H).

Step B: Ethyl 3-methyl-4-(1-methyl-1H-pyrazol-3-yl)-1H-pyrrole-2-carboxylate 99c To a stirred solution of ethyl 4-iodo-3-methyl-1H-pyrrole-2-carboxylate 50a (10.00 g, 35.98 mmol) in 1,4-dioxane: $H_2O$ (5:1, 200 mL) $Cs_2CO_3$ (29.23 g, 89.92 mmol) was added, resulting reaction mixture was degassed with Argon for 5 min, followed by addition of Pd(dppf)$Cl_2$ (1.30 g, 0.05 mmol) and resulting reaction mixture was stirred at 60° C. for 1 h. To above reaction mixture a solution of 1-methyl-3-(4,4,5,5-tetramethyl-1,3,2-dioxaborolan-2-yl)-1H-pyrazole 99b (9.73 g, 46.76 mmol) in 1,4-dioxane (50 mL) was added dropwise over a period of 2 h and resulting reaction mixture and heated to 80° C. for 16 h. After completion of reaction, all volatiles were removed under reduced pressure left behind crude material, which was purified by combi flash column chromatography (50% ethyl acetate in hexanes) to afford ethyl 3-methyl-4-(1-methyl-1H-pyrazol-3-yl)-1H-pyrrole-2-carboxylate 99c (5.00 g, 48% yield) as an off white solid. $^1H$ NMR (400 MHZ, DMSO-$d_6$) δ 11.55 (brs, 1H), 7.62 (d, J=2.0 Hz, 1H), 7.16 (d, J=3.2 Hz, 1H), 6.35 (s, 1H), 4.26 (m, 2H), 3.80 (s, 3H), 2.47 (s, 3H), 1.31 (t, 3H). MS (ESI+APCI; multimode): Calculated [M+1] 234. Found [M+1] 234.

Step C: Ethyl 1-amino-3-methyl-4-(1-methyl-1H-pyrazol-3-yl)-1H-pyrrole-2-carboxylate 99d To a stirred solution of ethyl 3-methyl-4-(1-methyl-1H-pyrazol-3-yl)-1H-pyrrole-2-carboxylate 99c (10.00 g, 42.91 mmol) in DMF (100 mL), 1-BuOK (1M solution in THF) (5.76 g, 51.48 mmol) was added at 0° C. (over a period of 5 min.) and stirred at 30 min (at same temperature) followed by addition of (aminooxy)diphenyl phosphine oxide (11.99 g, 51.50 mmol) at same temperature. After addition completed, resulting reaction mixture was allowed to come at room temperature and stirred for 6 h at room temperature. The reaction mixture was quenched with saturated $NH_4Cl$ solution (100 mL), an aqueous layer extracted with ethyl acetate (2×100 mL). The combined organic layer washed with brine solution (100 mL), dried over anhydrous $Na_2SO_4$ and distilled off under reduced pressure to afford crude ethyl 1-amino-3-methyl-4-(1-methyl-1H-pyrazol-3-yl)-1H-pyrrole-2-carboxylate 99d (7.00 g, crude) which was used taken for next step without any purification. MS (ESI+APCI; multimode): Calculated [M+1] 249. Found [M+1] 249.

Step D: Ethyl 3-methyl-1-(1-methyl-1H-imidazole-2-carboxamido)-4-(1-methyl-1H-pyrazol-3-yl)-1H-pyrrole-2-carboxylate 99e To a stirred solution of crude ethyl 1-amino-3-methyl-4-(1-methyl-1H-pyrazol-3-yl)-1H-pyrrole-2-carboxylate 99d (7.00 g, 28.22 mmol) in $CH_2Cl_2$ (140 mL) were added DIPEA (12.30 mL, 70.56 mmol), 1-methyl-1H-imidazole-2-carboxylic acid (3.91 g, 31.04 mmol) followed by $T_3P$ (50% in EtOAc) (44.87 mL, 70.56 mmol) at 0° C. After addition completed, resulting reaction mixture was allowed to come at room temperature and stirred for 12 h. The reaction mixture was quenched with $H_2O$ (100 mL), an aqueous layer extracted with $CH_2Cl_2$ (2×100 mL). The combined organic layers washed with brine solution (100 mL), dried over anhydrous $Na_2SO_4$ and distilled off under reduced pressure to afford crude material. Obtained crude material was purified by combi flash column chromatography using 50% ethyl acetate in hexanes as eluent to afford ethyl 3-methyl-1-(1-methyl-1H-imidazole-2-carboxamido)-4-(1-methyl-1H-pyrazol-3-yl)-1H-pyrrole-2-carboxylate 99e (6.00 g, 39% {over 2 steps} yield) as an off white solid. $^1H$ NMR (400 MHz, DMSO-$d_6$) δ 11.60 (s, 1H), 7.70 (d, J=2.0 Hz, 1H), 7.50 (s, 1H), 7.30 (s, 1H), 7.10 (s, 1H), 6.40 (s, 1H), 4.10 (m, 2H), 3.90 (s, 3H), 3.80 (s, 3H), 2.47 (s, 3H), 1.00 (t, 3H). MS (ESI+APCI; multimode): Calculated [M+1] 357. Found [M+1] 357.

Step E: 3-Methyl-1-(1-methyl-1H-imidazole-2-carboxamido)-4-(1-methyl-1H-pyrazol-3-yl)-1H-pyrrole-2-carboxylic acid 99f To a stirred solution of ethyl 3-methyl-1-(1-methyl-1H-imidazole-2-carboxamido)-4-(1-methyl-1H-pyrazol-3-yl)-1H-pyrrole-2-carboxylate 99e (6.00 g, 16.85 mmol) in mixture of EtOH:THF:$H_2O$ (1:1:1 {180 mL}) was added NaOH (2.69 g, 67.4 mmol) and heated to 65° C. for 24 h. The excess of solvent was evaporated under reduced pressure left behind viscous mass, which was neutralized with dilute HCl, solid precipitated out, was filtered, washed with water and dried in vacuo to afford crude 3-methyl-1-(1-methyl-1H-imidazole-2-carboxamido)-4-(1-methyl-1H-pyrazol-3-yl)-1H-pyrrole-2-carboxylic acid 99f (5.50 g crude) as an off white solid. MS (ESI+APCI; multimode): Calculated [M−1] 327. Found [M−1] 327.

Step F: N-(2-Carbamoyl-3-methyl-4-(1-methyl-1H-pyrazol-3-yl)-1H-pyrrol-1-yl)-1-methyl-1H-imidazole-2-carboxamide 99g To a stirred solution of crude 3-methyl-1-(1-methyl-1H-imidazole-2-carboxamido)-4-(1-methyl-1H-pyrazol-3-yl)-1H-pyrrole-2-carboxylic acid 99f (5.50 g, 16.7 mmol) in DMF (100 mL) were added HATU (7.64 g, 20.12 mmol), $NH_4$+Cl (2.68 g, 50.3 mmol) followed by DIPEA (6.48 g, 50.3 mmol) at room temperature and stirred for 12 h. The reaction mixture was quenched with $H_2O$ (100 mL), an aqueous layer extracted with ethyl acetate (2×100 mL). The combined organic layer washed with brine solution (100 mL), dried over anhydrous $Na_2SO_4$ and distilled off under reduced pressure to afford crude N-(2-carbamoyl-3-methyl-4-(1-methyl-1H-pyrazol-3-yl)-1H-pyrrol-1-yl)-1-methyl-1H-imidazole-2-carboxamide 99g (10) (7.70 g crude) as a brown color viscous mass, which was taken for next step without any further purification. MS (ESI+APCI; multimode): Calculated [M−1] 326. Found [M+1] 326.

Step G: 5-Methyl-2-(1-methyl-1H-imidazol-2-yl)-6-(1-methyl-1H-pyrazol-3-yl)pyrrolo[2,1-f][1,2,4]triazin-4-ol 99h To a stirred solution of crude N-(2-carbamoyl-3-methyl-4-(1-methyl-1H-pyrazol-3-yl)-1H-pyrrol-1-yl)-1-methyl-1H-imidazole-2-carboxamide 99f (7.70 g, 23.54 mmol) in mixture of EtOH: $H_2O$ (1:1; 200 mL), KOH (3.95 g, 70.64 mmol) was added and resulting mixture was heated to 100° C. for 16 h. Excess of EtOH was distilled off under reduced pressure, left behind aqueous layer; pH of an aqueous layer was adjusted to neutral with dilute HCl, solid principiated out was filtered, washed with water (25 mL) gave a crude material. Obtained crude material was purified by combi flash column chromatography (50%-100% ethyl acetate in hexanes) to afford 5-methyl-2-(1-methyl-1H-imidazol-2-yl)-6-(1-methyl-1H-pyrazol-3-yl)pyrrolo[2,1-f][1,2,4]triazin-4-ol 99h (2.50 g, 48% {over 3 steps} yield) as a pale-yellow solid. $^1H$ NMR (400 MHz, DMSO-$d_6$) δ 11.10 (s, 1H), 7.90 (d, J=2.0 Hz, 1H), 7.70 (s, 1H), 7.50 (s, 1H), 7.10 (s, 1H), 5.60 (s, 1H), 4.00 (s, 3H), 3.80 (s, 3H), 2.60 (s, 3H). MS (ESI+APCI; multimode): Calculated [M+1] 310. Found [M+1] 310.

Step H: 4-Chloro-5-methyl-2-(1-methyl-1H-imidazol-2-yl)-6-(1-methyl-1H-pyrazol-3-yl)pyrrolo[2,1-f][1,2,4]triazine (99)

A mixture of 5-methyl-2-(1-methyl-1H-imidazol-2-yl)-6-(1-methyl-1H-pyrazol-3-yl)pyrrolo[2,1-f][1,2,4]triazin-4-ol 99h (2.00 g, 6.451 mmol) and $POCl_3$ (20 mL) was heated at 100-110° C. for 18 h. The excess $POCl_3$ was distilled off under reduced pressure, left behind viscous dark brown mass, which was diluted in $CH_2Cl_2$ (20 mL) and basified with aq. $NaHCO_3$ solution (50 mL) up to pH=8-9. The obtained crude material was again extracted with $CH_2Cl_2$ (2×100 mL), the combined organic layer, were washed with brine solution (100 mL), dried over anhydrous $Na_2SO_4$, and concentrated under reduced pressure affording crude material, which was triturated with MTBE (20 mL) followed by hexane (20 mL) to give 4-chloro-5-methyl-2-(1-methyl-1H-imidazol-2-yl)-6-(1-methyl-1H-pyrazol-3-yl)pyrrolo[2,1-f][1,2,4]triazine Compound (99) (1.50 g, 71% yield) as yellow brownish solid. $^1H$ NMR (400 MHZ, DMSO-$d_6$) δ 8.53 (s, 1H), 7.79 (d, J=2.4 Hz, 1H), 7.40 (s, 1H), 7.09 (s, 1H), 6.70 (s, 1H), 3.99 (s, 3H), 3.92 (s, 3H), 2.83 (s, 3H). MS (ESI+APCI; multimode): Calculated [M+1] 328. Found [M+1] 328.

Procedure B:

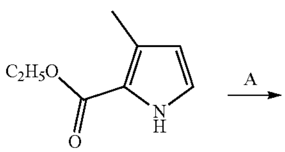

99a

-continued

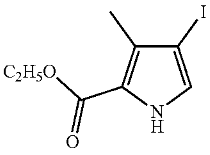

50a

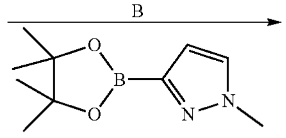

99b

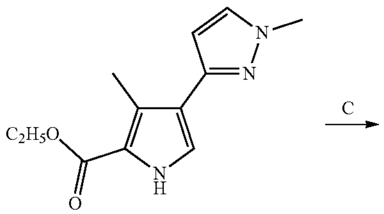

99c

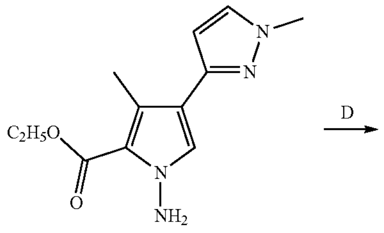

99d

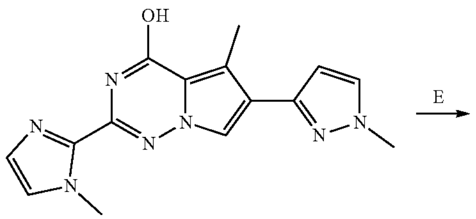

99h

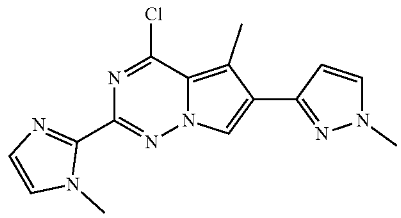

99i

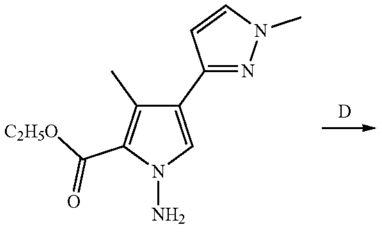

99d

-continued

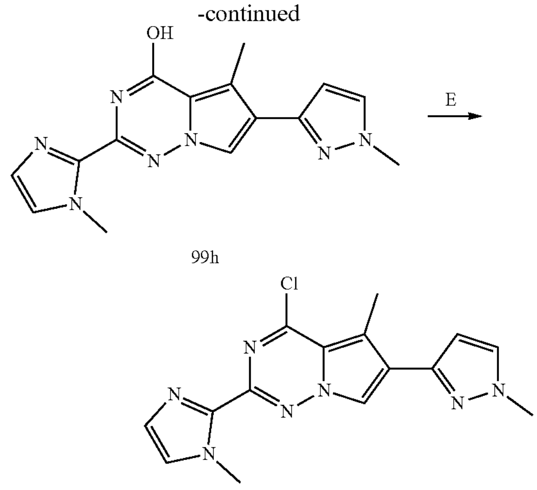

99h (99)

Step A: Ethyl 4-iodo-3-methyl-1H-pyrrole-2-carboxylate 50a

N-iodosuccinimde (35.62 g, 158.31 mmol) was added portionwise to the solution of ethyl 3-methyl-1H-pyrrole-2-carboxylate (1) (25.0 g, 163.21 mmol) in DMF (600 mL). The mixture was stirred at ambient temperature for 16 h. The mixture was poured into ice water. The formed precipitate was filtered through celite and dried in vacuo. Ethyl 4-iodo-3-methyl-1H-pyrrole-2-carboxylate 50a (33.0 g, 118.25 mmol, 72.5% yield) was obtained.

Step B: Ethyl 3-methyl-4-(1-methyl-1H-pyrazol-3-yl)-1H-pyrrole-2-carboxylate 99c Ethyl 4-iodo-3-methyl-1H-pyrrole-2-carboxylate 50a (21.24 g, 76.1 mmol), 1-methyl-3-(4,4,5,5-tetramethyl-1,3,2-dioxaborolan-2-yl)-1H-pyrazole 99c (19.0 g, 91.32 mmol), Pd(dppf)$Cl_2$·2DCM (6.21 g, 7.61 mmol) and cesium carbonate (49.59 g, 152.2 mmol) was dissolved in degassed dioxane (600 mL) under Ar atmosphere. 30 mL of water was added via syringe. The reaction mixture was heated to 100° C. and stirred at this temperature for 48 h. The mixture was cooled to room temperature, filtered through celite and concentrated. The residue was purified by column chromatography (SiO2, Eluted by Hex:EtOAc 20:1 to 1:4). Ethyl 3-methyl-4-(1-methyl-1H-pyrazol-3-yl)-1H-pyrrole-2-carboxylate 99c (7.0 g, 30.01 mmol, 39.4% yield) was obtained.

Step C: Ethyl 1-amino-3-methyl-4-(1-methyl-1H-pyrazol-3-yl)-1H-pyrrole-2-carboxylate 99d Sodium hydride (913.91 mg, 38.08 mmol) (60% in mineral oil) was added portionwise to a solution of Ethyl 3-methyl-4-(1-methyl-1H-pyrazol-3-yl)-1H-pyrrole-2-carboxylate 99c (4.1 g, 17.58 mmol) in DMF (10 mL) at 0° C. The mixture was stirred for 1 h at room temperature. Then the mixture was cooled to 0° C. and O-(2,4-dinitrophenyl) hydroxylamine (4.55 g, 22.85 mmol) was added portionwise. The mixture was stirred for 16 h at room temperature. Then the mixture was poured in ice water, diluted with EtOAc (10 mL), washed with water (5*5 mL), dried in vacuo and purified by HPLC (0-2-10 min 30-50% $H_2O$/MeOH/0.1$NH_4$+OH, flow 30 mL/min ((loading pump 4 mL MeOH); column: Chromatorex C18 SMB100-5T 100*19 mm, 5 microM). Ethyl 1-amino-3-methyl-4-(1-methyl-1H-pyrazol-3-yl)-1H-pyrrole-2-carboxylate 99d (3.8 g, 15.31 mmol, 87.1% yield) was obtained.

Step D: 5-Methyl-2-(1-methyl-1H-imidazol-2-yl)-6-(1-methyl-1H-pyrazol-3-yl)pyrrolo[2,1-f][1,2,4]triazin-4-ol 99h Sodium hydride (1.48 g, 61.76 mmol) (60% in mineral oil) was added portionwise (during 3 min) to the solution of ethyl 1-amino-3-methyl-4-(1-methyl-1H-pyrazol-3-yl)-1H-pyrrole-2-carboxylate 99d (4.6 g, 18.53 mmol) and 1-methyl-1H-imidazole-2-carbonitrile (2.38 g, 22.23 mmol, 2.38 mL) in dioxane (20 mL). The reaction mixture was heated under reflux for 16 h. Then, the mixture was cooled to room temperature, poured in ice water and neutralized by acetic acid. The formed precipitate was collected by filtration, washed by water (2*10 mL) and dried in vacuo and purified by flash chromatography ($SiO_2$, Hexane-EtOAc). 5-Methyl-2-(1-methyl-1H-imidazol-2-yl)-6-(1-methyl-1H-pyrazol-3-yl)pyrrolo[2,1-f][1,2,4]triazin-4-ol 99h (1.85 g, 5.98 mmol, 32.3% yield) was obtained. $^1H$ NMR (500 MHz, DMSO-$d_6$) δ (ppm) 2.65 (s, 3H), 3.82 (S, 3H), 3.97 (s, 3H), 6.50 (d, 1H), 7.12 (s, 1H), 7.47 (d, 1H), 7.58 (d, 1H), 7.87 (d, 1H), 11.04 (br s, 1H). LCMS(ESI): MS Calculated [M+1] 310.2. Found [M+1] 310.2; Rt=1.112 min.

Step E: 4-Chloro-5-methyl-2-(1-methyl-1H-imidazol-2-yl)-6-(1-methyl-1H-pyrazol-3-yl)pyrrolo[2,1-f][1,2,4]triazine (99)

5-Methyl-2-(1-methyl-1H-imidazol-2-yl)-6-(1-methyl-1H-pyrazol-3-yl)pyrrolo[2,1-f][1,2,4]triazin-4-ol 99h (1.85 g, 5.98 mmol) was dissolved in phosphoroyl trichloride (9.17 g, 59.8 mmol, 5.57 mL). The mixture was heated to 100° C. and stirred at this temperature for 16 h. The reaction mixture was concentrated in vacuo, poured in ice water (5 mL) and neutralized by $K_2CO_3$. The formed precipitate was collected by filtration, washed by water (2*20 mL) and dried in vacuo. 4-Chloro-5-methyl-2-(1-methyl-1H-imidazol-2-yl)-6-(1-methyl-1H-pyrazol-3-yl)pyrrolo[2,1-f][1,2,4]triazine Compound (99) (1.7 g, 5.19 mmol, 86.7% yield) was obtained.

LCMS(ESI): MS Calculated [M+1] 328.0. Found [M+1] 328.0; Rt=1.014 min.

Example 100: Synthesis of Compound 100

(100)

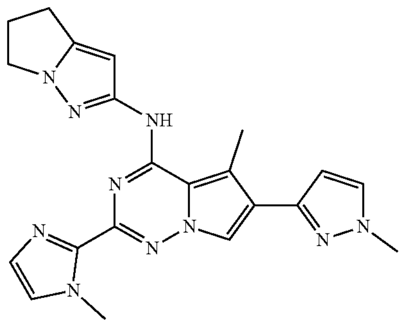

-continued

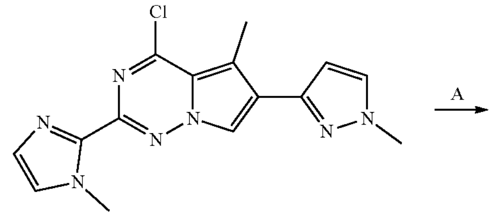

99

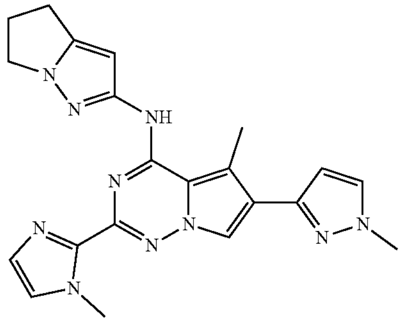

(100)

Step A: N-(5,6-Dihydro-4H-pyrrolo[1,2-b]pyrazol-2-yl)-5-methyl-2-(1-methyl-1H-imidazol-2-yl)-6-(1-methyl-1H-pyrazol-3-yl)pyrrolo[2,1-f][1,2,4]triazin-4-amine (100)

To a stirred solution of 5,6-dihydro-4H-pyrrolo[1,2-b]pyrazol-2-amine A1 (0.033 g, 0.274 mmol, 1.50 equiv.) in dry THF (1 mL) at 0° C., NaHMDS (2.0 M in THF) (0.2 mL, 0.366 mmol, 2.0 equiv.) was added and resulting mixture was stirred at room temperature for 15 minutes. In another round bottomed flask 4-chloro-5-methyl-2-(1-methyl-1H-imidazol-2-yl)-6-(1-methyl-1H-pyrazol-3-yl)pyrrolo[2,1-f][1,2,4]triazine Compound 99 (0.06 g, 0.183 mmol, 1.0 equiv.) was dissolved in dry DMF (1 mL) and then was added dropwise to above reaction mixture and stirred for 2 h at room temperature. Excess of THF was distilled off, diluted with 10% ammonium chloride solution (2 mL), solid precipitated out, was filtered, washed with water (2×5 mL). Obtained solid was stirred in acetonitrile (15 mL) for 10 min, filtered and then lyophilized to afford N-(5,6-Dihydro-4H-pyrrolo[1,2-b]pyrazol-2-yl)-5-methyl-2-(1-methyl-1H-imidazol-2-yl)-6-(1-methyl-1H-pyrazol-3-yl)pyrrolo[2,1-f][1,2,4]triazin-4-amine (100) (0.038 g, 42% yield, 99% purity) as an off-white solid. $^1$H NMR (400 MHZ, DMSO-d6) δ 2.24-2.14 (m, 2H), 2.52-2.55 (m, 1H), 2.64-2.60 (m, 1H), 2.75 (s, 1H), 2.88 (s, 3H), 3.52-3.32 (m, 1H), 3.87-3.86 (s, 3H), 4.04 (m, 3H), 4.11-4.09 (m, 1H), 5.84-5.64 (m, 1H), 6.42-6.40 (m, 2H), 7.12-7.06 (m, 1H), 7.42 (s, 1H), 7.60-7.59 (m, 1H), 12.63 (brs, 1H). MS (ESI+APCI; multimode): Calculated [M+1] 415. Found [M+1] 415.

Example 101: Synthesis of Compound 101

(101)

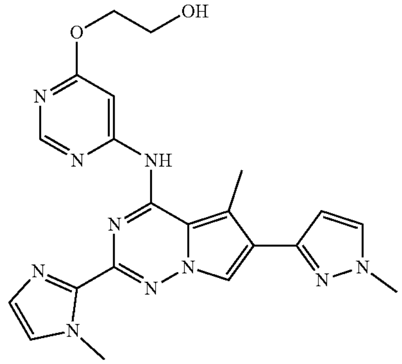

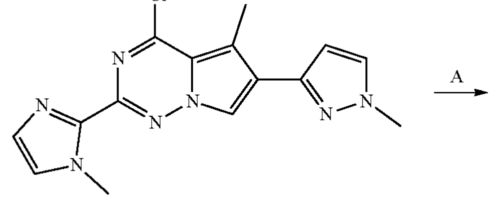

(99)

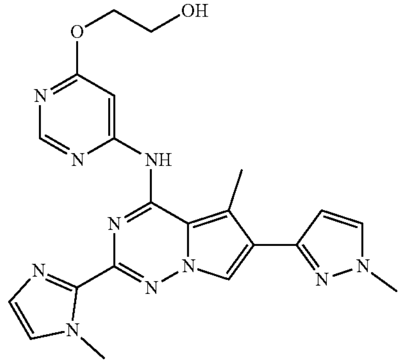

(101)

Step A: 2-((6-((5-Methyl-2-(1-methyl-1H-imidazol-2-yl)-6-(1-methyl-1H-pyrazol-3-yl)pyrrolo[2,1-f][1,2,4]triazin-4-yl)amino) pyrimidin-4-yl)oxy) ethan-1-ol (101)

To a stirred solution of 2-((6-aminopyrimidin-4-yl)oxy) ethan-1-ol A2 (0.043 g, 0.278 mmole, 1.30 equiv.) in dry DMF (1 mL) at 0° C. was added NaH (60% in mineral oil) (0.017 g, 0.428 mmole, 2.0 equiv.), stirred for 15 min at room temperature then Compound (99) (0.07 g, 0.214 mmole, 1.0 equiv.) in dry DMF (1 mL), was added dropwise to above reaction mixture under nitrogen atmosphere. After addition completed, resulting reaction mixture was stirred at room temperature for 2 h. After 2 h, reaction mixture was quenched with saturated $NH_4Cl$ solution (5 mL), solid precipitated out, was filtered. Obtained solid was stirred in mixture of MeOH: ACN (1:1; 10 mL) for 30 min. Solid was filtered and subjected to lyophilization to afford 2-((6-((5-methyl-2-(1-methyl-1H-imidazol-2-yl)-6-(1-methyl-1H-pyrazol-3-yl)pyrrolo[2,1-f][1,2,4]triazin-4-yl)amino) pyrimidin-4-yl)oxy) ethan-1-ol Compound (101) (0.037 g, 32% yield, purity 98%) as an off-white solid. $^1$H NMR (400

MHZ, DMSO-d6) δ 2.84 (s, 3H), 3.74 (d, J=8.00 Hz, 2H), 3.88 (s, 3H), 4.06 (s, 3H), 4.39 (s, 2H), 4.53 (s, 1H), 6.46-6.51 (m, 1H), 7.10-7.17 (m, 1H), 7.28-7.42 (m, 1H), 7.66 (s, 1H), 7.79-8.15 (m, 2H), 8.51-8.58 (m, 1H), 14.16 (bs, 1H). MS (ESI+APCI; multimode): Calculated [M+1] 447. Found [M+1] 447.

Example 102: Synthesis of Compound 102

(102)

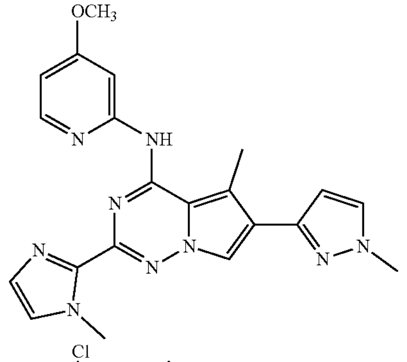

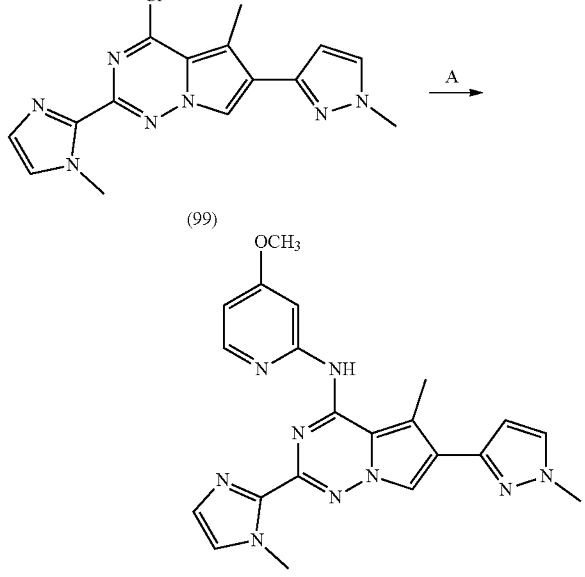

(99)

(102)

Step A: N-(4-Methoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine (102)

Sodium hydride (40.3 mg, 1.68 mmol) (60% on mineral oil) was added in one portion to the solution of 4-chloro-5-methyl-2-(1-methyl-1H-imidazol-2-yl)-6-(1-methyl-1H-pyrazol-3-yl)pyrrolo[2,1-f][1,2,4]triazine (99) (113.73 mg, 916.11 μmol) (prepared as described in Example 99, Procedure B, Step E) in DMF (1.0 mL). The mixture was stirred at ambient temperature for 0.30 min. 4-Methoxypyridin-2-amine (113.73 mg, 916.11 μmol) in DMF (2.0 mL) was added in one portion and stirred 16 h, then quenched with conc. $NH_4Cl$ and purified by HPLC (0-2-9 min 48-55-75% $MeOH/H_2O+NH_4OH$; flow 30 mL/min (loading pump 4 mL/min MeOH); column: Cromatorex C18 SMB100-5T 100*19, 5 microM). N-(4-Methoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine (102) (36.0 mg, 79.66 μmol, 17.4% yield) was obtained as yellow solid. $^1H$ NMR (500 MHZ, $CD_3OD$) δ (ppm) 2.81 (s, 3H), 3.98 (s, 3H), 4.16 (s, 3H), 4.26 (s, 3H), 6.68 (s, 1H), 7.23 (d, 1H), 7.51 (s, 1H), 7.70 (s, 1H), 7.75 (m, 2H), 8.41 (m, 2H), NH is not observed. LCMS(ESI): MS Calculated [M+1] 416.2. Found [M+1] 416.2.

Example 103: Synthesis of Compound 103

(103)

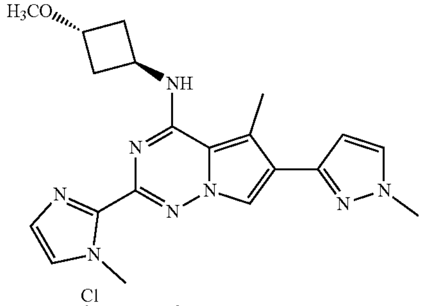

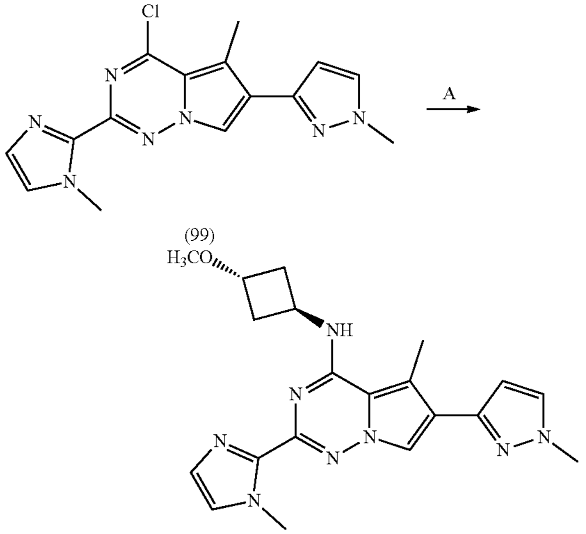

(99)

(103)

Step A: N-((1r,3r)-3-Methoxycyclobutyl)-5-methyl-2-(1-methyl-1H-imidazol-2-yl)-6-(1-methyl-1H-pyrazol-3-yl)pyrrolo[2,1-f][1,2,4]triazin-4-amine hydrochloride salt (103)

DIEA (155.82 mg, 1.21 mmol, 210.0 μL) was added in one portion to the solution of 4-chloro-5-methyl-2-(1-methyl-1H-imidazol-2-yl)-6-(1-methyl-1H-pyrazol-3-yl) pyrrolo[2,1-f][1,2,4]triazine 99 (98.55 mg, 300.67 μmol) and (1r,3r)-3-methoxycyclobutan-1-amine hydrochloride (82.75 mg, 601.34 μmol) in DMF (1 mL). The mixture was heated to 100° C. and stirred at this temperature for 16 h. The mixture was purified by HPLC (0-2-10 min 10-60% $H_2O$/ACN/0.1HCl, flow 30 mL/min ((loading pump 4 mL ACN); column: Chromatorex C18 SMB100-5T 100*19 mm, 5 microM). N-((1r,3r)-3-Methoxycyclobutyl)-5-methyl-2-(1-methyl-1H-imidazol-2-yl)-6-(1-methyl-1H-pyrazol-3-yl)

pyrrolo[2,1-f][1,2,4]triazin-4-amine hydrochloride salt, Compound (103) (28.7 mg, 73.13 μmol, 24.3% yield, 97% purity) was obtained as an light-beige gum. $^1$H NMR (500 MHZ, DMSO-$d_6$) δ 2.39 (m, 4H), 1.78 (s, 3H), 3.19 (s, 3H), 3.88 (s, 3H), 4.05 (m, 1H), 4.23 (s, 3H), 4.99 (quin, 1H), 6.63 (d, 1H), 7.50 (m, 1H), 7.74 (d, 1H), 7.77 (m, 1H), 7.83 (s, 1H), 8.04 (s, 1H). LCMS(ESI): MS Calculated [M+1] 393.2. Found [M+1] 393.0.

Example 104-Example 111 in Table 1 were prepared using procedures similar to those described in Example 100.

Example 112-Example 113 in Table 1 were prepared using procedures similar to those described in Example 101.

Example 114-Example 129 in Table 1 were prepared using procedures similar to those described in Example 102.

Example 130-Example 133 in Table 1 were prepared using procedures similar to those described in Example 103.

Example 134: Synthesis of Compound 134

(134)

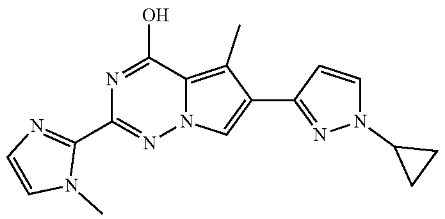

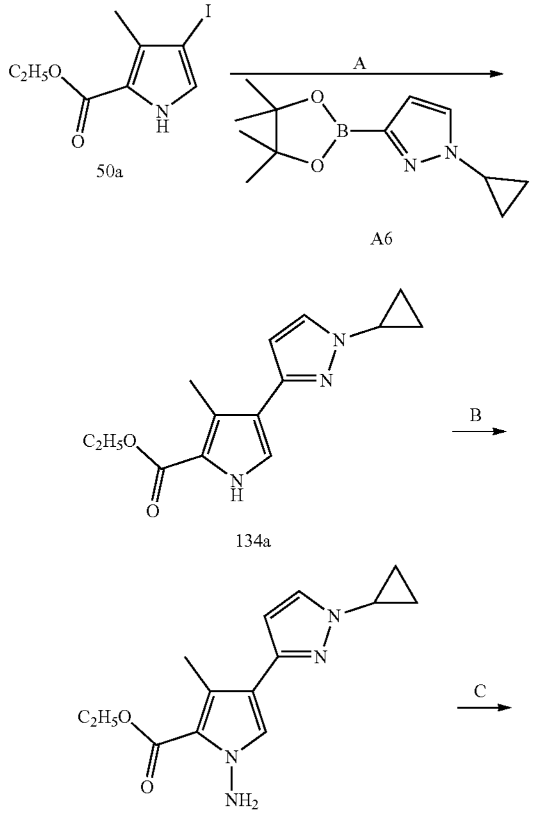

50a

A6

134a

134b

-continued

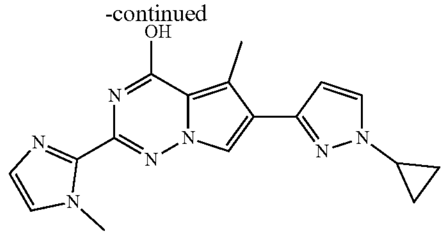

(134)

Step A: Ethyl 4-(1-cyclopropyl-1H-pyrazol-3-yl)-3-methyl-1H-pyrrole-2-carboxylate 134a Ethyl 4-iodo-3-methyl-1H-pyrrole-2-carboxylate (50a) (prepared as described in Example 99, Procedure B, Step A) (4.0 g, 14.33 mmol), 1-cyclopropyl-3-(4,4,5,5-tetramethyl-1,3,2-dioxaborolan-2-yl)-1H-pyrazole A6 (3.69 g, 15.77 mmol), cesium carbonate (9.34 g, 28.67 mmol) and Pd(dppf) $Cl_2$·2 DCM (1.17 g, 1.43 mmol) was dissolved in degassed dioxane (80 mL) under Ar. 3.8 mL of water was added via syringe. The reaction mixture was heated to 80° C. and stirred at this temperature for 16 h. The mixture was cooled to room temperature, filtered through celite and concentrated. The residue was purified by column chromatography (eluted by Hex:EtOAc 20:1 to 1:3). Ethyl 4-(1-cyclopropyl-1H-pyrazol-3-yl)-3-methyl-1H-pyrrole-2-carboxylate 134a (2.5 g, 9.64 mmol, 67.3% yield) was obtained as dark yellow oil.

Step B: Ethyl 1-amino-4-(1-cyclopropyl-1H-pyrazol-3-yl)-3-methyl-1H-pyrrole-2-carboxylate 134b Sodium hydride (98.71 mg, 4.11 mmol) (60% on mineral oil) was added portionwise (during 3 min) to the solution of ethyl 4-(1-cyclopropyl-1H-pyrazol-3-yl)-3-methyl-1H-pyrrole-2-carboxylate 134a (640.0 mg, 2.47 mmol) DMF (10 mL) at 0° C. The mixture was stirred for 30 min at this temperature, then O-(2,4-dinitrophenyl) hydroxylamine (491.42 mg, 2.47 mmol) was added in one portion. The reaction mixture was stirred at room temperature for 16 h. Then the mixture was cooled to the room temperature, poured in ice water and extracted 3 times by EtOAc (3*20 mL). Organic phase was washed with brine for 5 times, then dried. The solvents were evaporated in vacuo. The crude ethyl 1-amino-4-(1-cyclopropyl-1H-pyrazol-3-yl)-3-methyl-1H-pyrrole-2-carboxylate 134b (700.0 mg) was obtained and used in next step without further purification.

Step C: 6-(1-Cyclopropyl-1H-pyrazol-3-yl)-5-methyl-2-(1-methyl-1H-imidazol-2-yl)pyrrolo[2,1-f][1,2,4]triazin-4-ol (134)

Sodium hydride (204.18 mg, 8.51 mmol) (60% on mineral oil) was added portionwise (during 3 min) to the solution of ethyl 1-amino-4-(1-cyclopropyl-1H-pyrazol-3-yl)-3-methyl-1H-pyrrole-2-carboxylate 134b (700.0 mg, 2.55 mmol) and 1-methyl-1H-imidazole-2-carbonitrile (328.08 mg, 3.06 mmol) in dioxane (10 mL). The reaction mixture was heated under reflux for 16 h. Then the mixture was cooled to room temperature, poured in ice water and neutralized by acetic acid. The formed precipitate was collected by filtration, washed by water (2*10 mL) and dried in vacuo and purified by flash chromatography ($SiO_2$, Hexane-EtOAc). 6-(1-Cyclopropyl-1H-pyrazol-3-yl)-5-methyl-2-(1-methyl-1H-imidazol-2-yl)pyrrolo[2,1-f][1,2,4]triazin-4-ol (134) (100.0 mg, 298.18 μmol, 12% yield over two steps) was obtained.

Example 135: The Synthesis of Compound 135

(135)

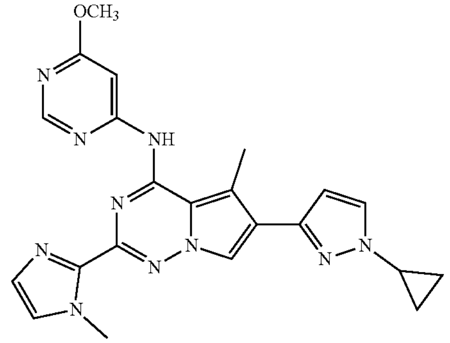

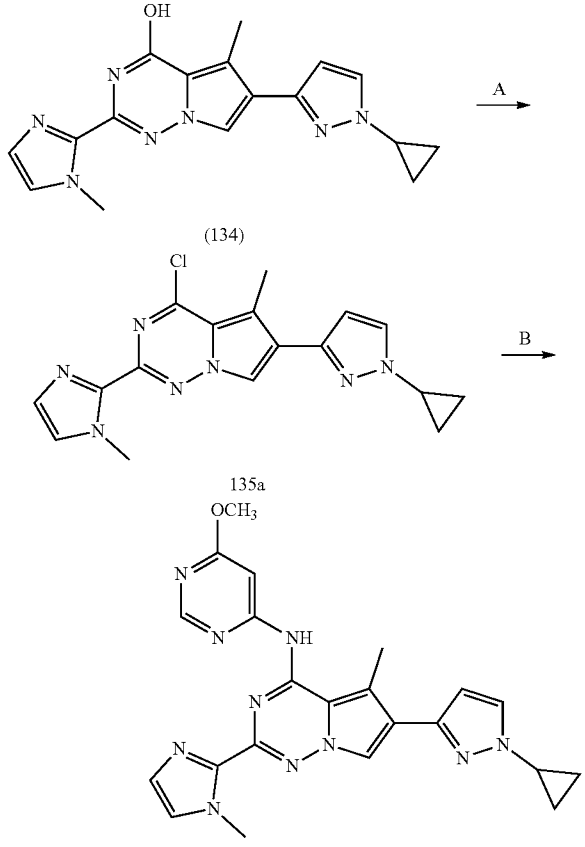

(134)

135a (135)

Step A: 4-Chloro-6-(1-cyclopropyl-1H-pyrazol-3-yl)-5-methyl-2-(1-methyl-1H-imidazol-2-yl)pyrrolo[2,1-f][1,2,4]triazine 135a 6-(1-Cyclopropyl-1H-pyrazol-3-yl)-5-methyl-2-(1-methyl-1H-imidazol-2-yl)pyrrolo[2,1-f][1,2,4]triazin-4-ol (134) (100.0 mg, 298.18 μmol) was dissolved in phosphoroyl trichloride (551.25 mg, 3.6 mmol). The mixture was heated to 100° C. and stirred at this temperature for 16 h. The reaction mixture was concentrated in vacuo, poured in ice water (5 mL) and neutralized by $K_2CO_3$. The formed precipitate was collected by filtration, washed by water (2*5 mL) and dried in vacuo. 4-Chloro-6-(1-cyclopropyl-1H-pyrazol-3-yl)-5-methyl-2-(1-methyl-1H-imidazol-2-yl)pyrrolo[2,1-f][1,2,4]triazine 135a (100.0 mg, 282.64 μmol, 94.3% yield) was obtained and used in next step without further purification.

Step B: 6-(1-Cyclopropyl-1H-pyrazol-3-yl)-N-(6-methoxypyrimidin-4-yl)-5-methyl-2-(1-methyl-1H-imidazol-2-yl)pyrrolo[2,1-f][1,2,4]triazin-4-amine (135)

Sodium hydride (24.86 mg, 1.04 mmol) (60% in mineral oil) was added in portion wise to the solution of 4-chloro-6-(1-cyclopropyl-1H-pyrazol-3-yl)-5-methyl-2-(1-methyl-1H-imidazol-2-yl)pyrrolo[2,1-f][1,2,4]triazine 135a and 6-methoxypyrimidin-4-amine (70.7 mg, 565.0 μmol) in DMF (1 mL). The mixture was stirred at room temperature for 16 h, then quenched by concentrated aq. $NH_4Cl$. The formed precipitate was collected by filtration, washed by water (2*3 mL) and purified by HPLC (0-2-9 min 53-60-85% water—MeOH/$H_2O$+$NH_4OH$; flow 30 mL/min (loading pump 4 mL MeOH); column: Chromatorex C18 SMB100-5T 100*19 mm, 5 μM). 6-(1-Cyclopropyl-1H-pyrazol-3-yl)-N-(6-methoxypyrimidin-4-yl)-5-methyl-2-(1-methyl-1H-imidazol-2-yl)pyrrolo[2,1-f][1,2,4]triazin-4-amine (135) (30.0 mg, 67.8 μmol, 22.7% yield by two steps) was obtained as an yellow solid. $^1H$ NMR (500 MHZ, DMSO-$d_6$) δ (ppm) 1.01 (m, 4H), 2.77 (s, 3H), 3.90 (m, 7H), 6.45 (m, 1H), 7.02 (m, 3H), 7.59 (m, 1H), 7.72 (m, 1H), 8.30 (m, 1H). LCMS(ESI): MS Calculated [M+1] 443.0. Found [M+1]. 443.0. Rt=1.134 min.

General Procedure for library compounds: To the suspension of sodium hydride (22 mg, 0.55 mmol) (60% dispersion in mineral oil) in dry DMF (1.5 mL), the solution of the appropriate corresponding amine (0.45 mmol) in DMF (1.0 mL) was added at room temperature. The obtained mixture was stirred for 30 min at room temperature followed by the addition of 4-chloro-6-(1-cyclopropyl-1H-pyrazol-3-yl)-5-methyl-2-(1-methyl-1H-imidazol-2-yl)pyrrolo[2,1-f][1,2,4]triazine 135a (80.0 mg, 226.11 μmol) in one portion. The resulting mixture was stirred at 40° C. for 18 h. Then, the resulting mixture was quenched with MeOH (0.5 mL) and subjected to HPLC purification.

Example 136-Example 150 in Table 1 were prepared using the General Procedure described in Example 135, Step B.

TABLE 1

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 2 | rac 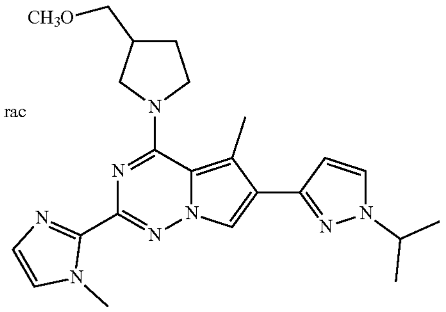 (2) | rac 6-(1-Isopropyl-1H-pyrazol-3-yl)-4-(3-(methoxymethyl)pyrrolidin-1-yl)-5-methyl-2-(1-methyl-1H-imidazol-2-yl)pyrrolo[2,1-f][1,2,4]triazine | 16.0 mg (8.7%) | 100% | 435.3 | 435.4 | (DMSO-$d_6$, 600 MHz) δ 1.45 (d, 6H), 1.65-1.73 (m, 1H), 2.00-2.07 (m, 1H), 2.51-2.55 (m, 1H), 2.62 (s, 3H), 3.25 (s, 3H), 3.34-3.41 (m, 2H), 3.60 (dd, 1H), 3.82-3.88 (m, 3H), 3.94 (s, 3H), 4.52 (hept, 1H), 6.51 (d, 1H), 6.95 (s, 1H), 7.24 (s, 1H), 7.78 (d, 1H), 7.98 (s, 1H). |
| 3 | rac 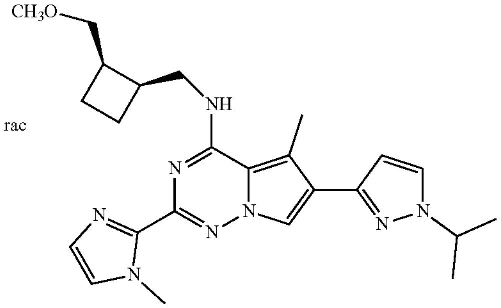 (3) | rac 6-(1-Isopropyl-1H-pyrazol-3-yl)-N-(((1S,2R)-2-(methoxymethyl)cyclobutyl)methyl)-5-methyl-2-(1-methyl-1H-imidazol-2-yl)pyrrolo[2,1-f][1,2,4]triazin-4-amine | 28.8 mg (15.2%) | 97% | 449.3 | 449.2 | (DMSO-d6, 400 MHz) δ 1.46 (d, 6H), 1.53-1.60 (m, 1H), 1.76-1.86 (m, 1H), 1.92-2.02 (m, 2H), 2.60-2.65 (m, 1H), 2.71 (s, 3H), 2.74-2.82 (m, 1H), 3.32 (s, 3H), 3.39 (dd, 1H), 3.48-3.57 (m, 1H), 3.71 (t, 1H), 3.84-3.94 (m, 1H), 3.96 (s, 3H), 4.48-4.57 (m, 1H), 6.52 (d, 1H), 6.97 (s, 1H), 7.27 (s, 1H), 7.79 (d, 1H), 7.89 (s, 1H). |

TABLE 1-continued

Compounds and Analytical Data

| Example | Structure | Name | (Amount Yield)* | Purity | Calc'd [M + 1] | [Found M + 1] | $^1$H NMR |
|---|---|---|---|---|---|---|---|
| 4 | rac 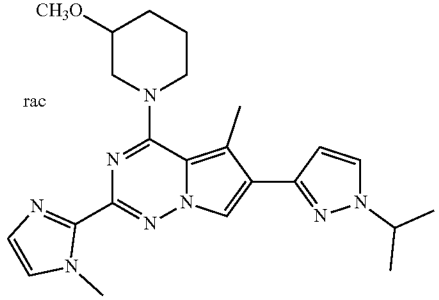 (4) | rac 6-(1-Isopropyl-1H-pyrazol-3-yl)-5-methyl-2-(1-methyl-1H-imidazol-2-yl)-4-(3-(oxo-γ6-methyl)piperidin-1-yl)pyrrolo[2,1-f][1,2,4]triazine | 21.5 mg (11.5%) | 100% | 435.3 | 435.1 | ($CD_3OD$, 400 MHz) δ 1.55 (d, 6H), 1.58-1.77 (m, 2H), 1.98-2.07 (m, 1H), 2.07-2.15 (m, 1H), 2.63 (s, 3H), 3.36 (s, 3H), 3.43-3.58 (m, 2H), 3.77-3.86 (m, 1H), 4.06-4.10 (m, 1H), 4.58 (hept, 1H), 4.89 (s, 3H), 6.51 (d, 1H), 7.09 (s, 1H), 7.22 (s, 1H), 7.71 (d, 1H), 8.01 (s, 1H). |
| 5 | 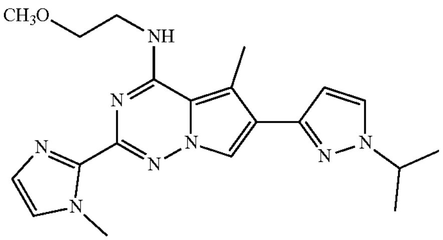 (5) | 6-(1-Isopropyl-1H-pyrazol-3-yl)-N-(2-methoxyethyl)-5-methyl-2-(1-methyl-1H-imidazol-2-yl)pyrrolo[2,1-f][1,2,4]triazin-4-amine | 24.0 mg (14.5%) | 100% | 435.3 | 435.1 | ($CD_3OD$, 400 MHz) δ 1.55 (d, 6H), 1.58-1.77 (m, 2H), 1.98-2.07 (m, 1H), 2.07-2.15 (m, 1H), 2.63 (s, 3H), 3.36 (s, 3H), 3.43-3.58 (m, 2H), 3.77-3.86 (m, 1H), 4.06-4.10 (m, 1H), 4.58 (hept, 1H), 4.89 (s, 3H), 6.51 (d, 1H), 7.09 (s, 1H), 7.22 (s, 1H), 7.71 (d, 1H), 8.01 (s, 1H). |
| 10 | rac 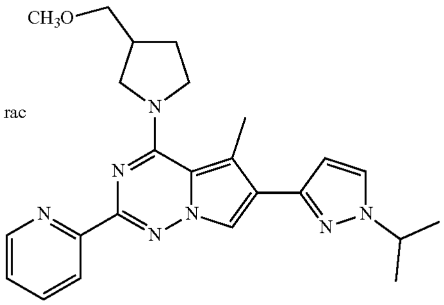 (10) | rac 6-(1-Isopropyl-1H-pyrazol-3-yl)-4-(3-(methoxymethyl)pyrrolidin-1-yl)-5-methyl-2-(pyridin-2-yl)pyrrolo[2,1-f][1,2,4]triazine | 17.6 mg (14.4%) | 100% | 432.3 | 432.2 | (DMSO-$d_6$, 400 MHz) δ 1.47 (d, 6H), 1.67-1.79 (m, 1H), 2.02-2.11 (m, 1H), 2.55-2.59 (m, 1H), 2.65 (s, 3H), 3.28 (s, 3H), 3.36-3.46 (m, 2H), 3.67 (dd, 1H), 3.86-3.96 (m, 3H), 4.54 (p, 1H), 6.53 (d, 1H), 7.46 (dd, 1H), 7.81 (d, 1H), 7.93 (td, 1H), 8.05 (s, 1H), 8.25 (d, 1H), 8.68 (d, 1H). |

TABLE 1-continued

Compounds and Analytical Data

| Example | Structure | Name | (Amount Yield)* | Purity | Calc'd [M + 1] | [Found M + 1] | $^1$H NMR |
|---|---|---|---|---|---|---|---|
| 11 | 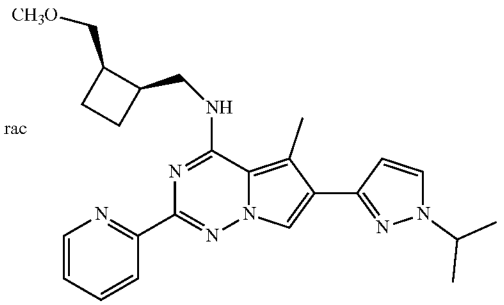 rac (11) | rac 6-(1-Isopropyl-1H-pyrazol-3-yl)-N-(((1S,2R)-2-(methoxymethyl)cyclo-butyl)methyl)-5-methyl-2-(pyridin-2-yl)pyrrolo[2,1-f][1,2,4]triazin-4-amine | 16.0 mg (12.7%) | 100% | 446.3 | 446.2 | DMSO-$d_6$, (400 MHz) δ 1.46 (d, 6H), 1.55-1.62 (m, 1H), 1.79-1.91 (m, 1H), 1.94-2.04 (m, 2H), 2.72 (s, 3H), 2.76-2.88 (m, 1H), 3.31-3.31 (m, 1H), 3.33 (s, 3H), 3.42 (dd, 1H), 3.54-3.62 (m, 1H), 3.74 (t, 1H), 3.98-4.07 (m, 1H), 4.50-4.58 (m, 1H), 6.52 (d, 1H), 6.93-6.99 (m, 1H), 7.43-7.49 (m, 1H), 7.79 (d, 1H), 7.90-7.96 (m, 2H), 8.25 (d, 1H), 8.68 (d, 1H). |
| 12 | 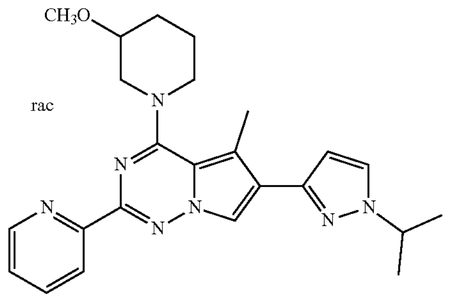 rac (12) | rac 6-(1-Isopropyl-1H-pyrazol-3-yl)-4-(3-methoxypiperidin-1-yl)-5-methyl-2-(pyridin-2-yl)pyrrolo[2,1-f][1,2,4]triazine | 11.1 mg (9.0%) | 98% | 432.3 | 432.2 | (DMSO-d6, 400 MHz) δ 1.47 (d, 6H), 1.52-1.68 (m, 2H), 1.88-1.95 (m, 1H), 2.00-2.08 (m, 1H), 2.62 (s, 3H), 3.21-3.28 (m, 4H), 3.37-3.54 (m, 2H), 3.74-3.82 (m, 1H), 4.05-4.14 (m, 1H), 4.50-4.60 (m, 1H), 6.59 (d, 1H), 7.44-7.50 (m, 1H), 7.82 (d, 1H), 7.95 (t, 1H), 8.15 (s, 1H), 8.27 (d, 1H), 8.70 (d, 1H). |

TABLE 1-continued

Compounds and Analytical Data

| Example | Structure | Name | (Amount Yield)* | Purity | Calc'd [M + 1] | [Found M + 1] | $^1H$ NMR |
| --- | --- | --- | --- | --- | --- | --- | --- |
| 19 | rac 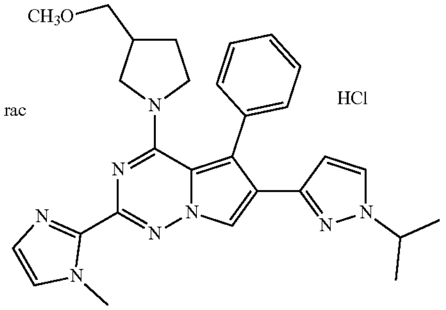 HCl (19) | rac 6-(1-Isopropyl-1H-pyrazol-3-yl)-4-(3-(methoxymethyl)pyrrolidin-1-yl)-2-(1-methyl-1H-imidazol-2-yl)-5-phenylpyrrolo[2,1-f][1,2,4]triazine hydrochloride salt | 10.00 mg (1.40%) | 100% | 497.3 | 497.4 | ($CD_3OD$, 400 MHz,) δ 1.45-1.59 (m, 7H), 1.78-1.92 (m, 1H), 2.26-2.38 (m, 1H), 2.75-2.98 (m, 1H), 3.07-3.17 (m, 1H), 3.20-3.31 (m, 5H), 3.40-3.55 (m, 2H), 4.39 (s, 3H), 4.54 (p, 1H), 5.55 (d, 1H), 7.30-7.41 (m, 2H), 7.43-7.49 (m, 3H), 7.52 (d, 1H), 7.67 (d, 1H), 7.73 (d, 1H), 8.18 (s, 1H). |
| 20 | rac 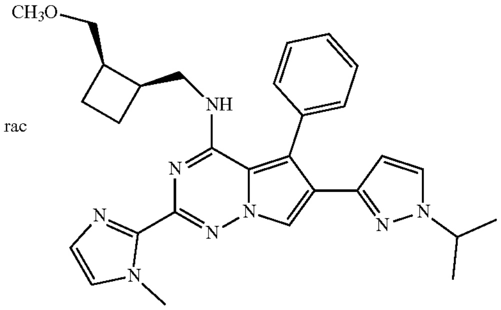 (20) | rac 6-(1-Isopropyl-1H-pyrazol-3-yl)-N-(((1S,2R)-2-(methoxymethyl)cyclobutyl)methyl)-2-(1-methyl-1H-imidazol-2-yl)-5-phenylpyrrolo[2,1-f][1,2,4]triazin-4-amine | 23.00 mg (3.00%) | 100% | 511.3 | 511.2 | (DMSO-$d_6$, 400 MHz) δ 1.36 (d, 6H), 1.43-1.57 (m, 2H), 1.73-1.83 (m, 1H), 1.85-1.92 (m, 1H), 2.37-2.44 (m, 2H), 3.05 (s, 3H), 3.15-3.20 (m, 1H), 3.38-3.44 (m, 1H), 3.52-3.59 (m, 1H), 3.97 (s, 3H), 4.39-4.46 (m, 1H), 5.31-5.35 (m, 1H), 5.61 (s, 1H), 7.00 (s, 1H), 7.30 (s, 1H), 7.44-7.48 (m, 2H), 7.49-7.53 (m, 3H), 7.57 (s, 1H), 7.98 (d, 1H). |

TABLE 1-continued

Compounds and Analytical Data

| Example | Structure | Name | (Amount Yield)* | Purity | Calc'd [M + 1] | [Found M + 1] | $^1$H NMR |
|---|---|---|---|---|---|---|---|
| 21 | rac 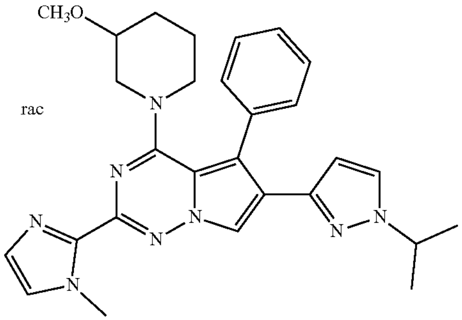 (21) | rac 6-(1-Isopropyl-1H-pyrazol-3-yl)-4-(3-methoxypiperidin-1-yl)-2-(1-methyl-1H-imidazol-2-yl)-5-phenylpyrrolo[2,1-f][1,2,4]triazine | 6.40 mg (1.80%) | 96% | 497.3 | 497.2 | ($cd_3od$, 400 MHz) δ 1.09-1.20 (m, 1H), 1.28-1.46 (m, 2H), 1.50 (dd, 6H), 1.78-1.87 (m, 1H), 2.88 (dd, 1H), 2.93-3.00 (m, 1H), 3.08-3.18 (m, 4H), 3.55-3.63 (m, 1H), 3.65-3.72 (m, 1H), 4.14 (s, 3H), 4.51 (p, 1H), 5.67 (d, 1H), 7.11 (d, 1H), 7.24 (d, 1H), 7.34-7.38 (m, 2H), 7.39-7.45 (m, 3H), 7.49 (d, 1H), 8.08 (s, 1H). |
| 25 | rac 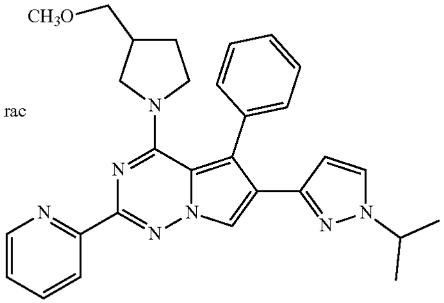 (25) | rac 6-(1-Isopropyl-1H-pyrazol-3-yl)-4-(3-(methoxymethyl)pyrrolidin-1-yl)-5-phenyl-2-(pyridin-2-yl)pyrrolo[2,1-f][1,2,4]triazine | 20.0 mg (2.80%) | 100% | 494.3 | 494.2 | (400 MHz, DMSO-d6) δ 1.38 (d, 6H), 1.65-1.78 (m, 1H), 2.18-2.28 (m, 1H), 2.78-2.92 (m, 1H), 3.01-3.14 (m, 3H), 3.16 (s, 3H), 3.26-3.31 (m, 2H), 3.37-3.41 (m, 1H), 4.40-4.49 (m, 1H), 5.56 (d, 1H), 7.35-7.45 (m, 5H), 7.46-7.51 (m, 1H), 7.57 (d, 1H), 7.92-7.98 (m, 1H), 8.06 (s, 1H), 8.28 (d, 1H), 8.68-8.73 (m, 1H). |

TABLE 1-continued

Compounds and Analytical Data

| Example | Structure | Name | (Amount Yield)* | Purity | Calc'd [M + 1] | [Found M + 1] | $^1$H NMR |
|---|---|---|---|---|---|---|---|
| 26 | rac 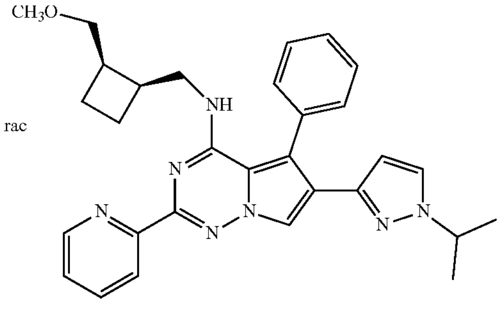 (26) | rac 6-(1-Isopropyl-1H-pyrazol-3-yl)-N-(((1S,2R)-2-(methoxymethyl)cyclo-butyl)methyl)-5-phenyl-2-(pyridin-2-yl)pyrrolo[2,1-f][1,2,4]triazin-4-amine | 10.90 mg (1.40%) | 98% | 508.3 | 508.5 | ($CD_3OD$, 400 MHz,) δ 1.48 (d, 6H), 1.52-1.69 (m, 2H), 1.86-2.08 (m, 2H), 2.44-2.56 (m, 2H), 3.13 (s, 3H), 3.26 (dd, 1H), 3.45 (t, 1H), 3.53 (dd, 1H), 3.80 (dd, 1H), 4.49 (hept, 1H), 5.60 (d, 1H), 7.41-7.47 (m, 3H), 7.49-7.53 (m, 4H), 7.98 (t, 1H), 8.07 (s, 1H), 8.43 (d, 1H), 8.69 (d, 1H). |
| 27 | rac 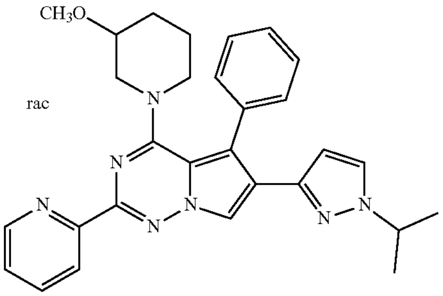 (27) | rac 6-(1-Isopropyl-1H-pyrazol-3-yl)-4-(3-methoxypiperidin-1-yl)-5-phenyl-2-(pyridin-2-yl)pyrrolo[2,1-f][1,2,4]triazine | 20.70 mg (3.50%) | 100% | 494.3 | 494.4 | (DMSO-$d_6$, 400 MHz) δ 1.02-1.12 (m, 1H), 1.20-1.28 (m, 1H), 1.40 (d, 6H), 1.42-1.52 (m, 1H), 1.75-1.84 (m, 1H), 2.72-2.81 (m, 1H), 2.89-2.96 (m, 1H), 2.99-3.08 (m, 4H), 3.51-3.59 (m, 1H), 3.63-3.71 (m, 1H), 4.41-4.49 (m, 1H), 5.77 (d, 1H), 7.36-7.45 (m, 5H), 7.48-7.53 (m, 1H), 7.62 (d, 1H), 7.97 (t, 1H), 8.12 (s, 1H), 8.30 (d, 1H), 8.72 (d, 1H). |
| 30 | 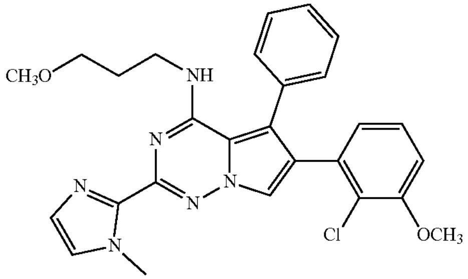 (30) | 6-(2-Chloro-3-methoxyphenyl)-N-(3-methoxypropyl)-2-(1-methyl-1H-imidazol-2-yl)-5-phenylpyrrolo[2,1-f][1,2,4]triazin-4-amine | 20.40 mg (3.70%) | 100% | 503.2 | 503.2 | (DMSO-d6, 500 MHz) δ (ppm) 1.68 (t, 2H), 3.01 (s, 3H), 3.22 (t, 2H), 3.52 (m, 2H), 3.79 (s, 3H), 3.98 (s, 3H), 5.80 (m, 1H), 6.77 (d, 1H), 7.00 (m, 2H), 7.13 (m, 1H), 7.53 (m, 6H), 7.89 (s, 1H). |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1H$ NMR |
| 31 | 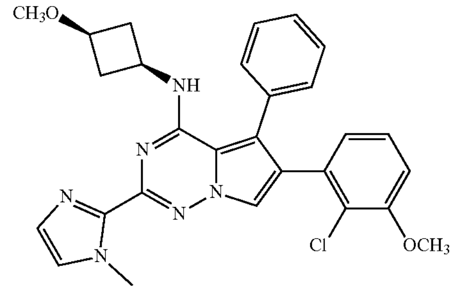 (31) | 6-(2-Chloro-3-methoxyphenyl)-N-((1s,3s)-3-methoxycyclobutyl)-2-(1-methyl-1H-imidazol-2-yl)-5-phenylpyrrolo[2,1-f][1,2,4]triazin-4-amine | 11.00 mg (3.80%) | 88% | 515.2 | 515.2 | ($CD_3OD$, 400 MHz) δ 1.46-1.56 (m, 2H), 2.73-2.81 (m, 2H), 3.19 (s, 3H), 3.68 (p, 1H), 3.86 (s, 3H), 4.12 (s, 3H), 4.46 (p, 1H), 6.79 (dd, 1H), 6.98 (dd, 1H), 7.08-7.16 (m, 2H), 7.24 (d, 1H), 7.31-7.35 (m, 2H), 7.38-7.44 (m, 3H), 7.79 (s, 1H). |
| 32 | 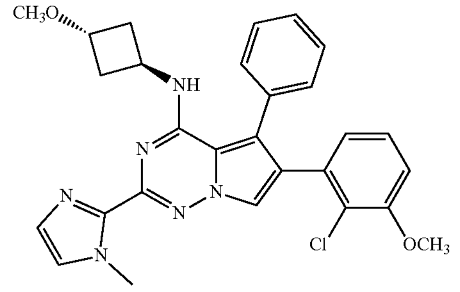 (32) | 6-(2-Chloro-3-methoxyphenyl)-N-((1r,3r)-3-methoxycyclobutyl)-2-(1-methyl-1H-imidazol-2-yl)-5-phenylpyrrolo[2,1-f][1,2,4]triazin-4-amine | 4.70 mg (1.60%) | 97% | 515.2 | 515.2 | ($CD_3OD$, 400 MHz) δ 1.92-2.02 (m, 2H), 2.33-2.45 (m, 2H), 3.22 (s, 3H), 3.87 (s, 3H), 3.88-3.94 (m, 1H), 4.11 (s, 3H), 4.66-4.75 (m, 1H), 6.80 (dd, 1H), 6.98 (dd, 1H), 7.08-7.17 (m, 2H), 7.24 (s, 1H), 7.32-7.37 (m, 2H), 7.39-7.46 (m, 3H), 7.80 (s, 1H). |
| 33 | rac 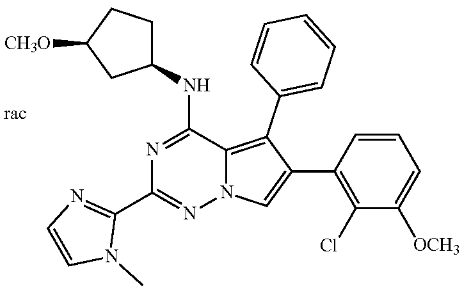 (33) | rac 6-(2-Chloro-3-methoxyphenyl)-N-((1R,3S)-3-methoxycyclopentyl)-2-(1-methyl-1H-imidazol-2-yl)-5-phenylpyrrolo[2,1-f][1,2,4]triazin-4-amine | 26.00 mg (6.30%) | 100% | 529.2 | 529.2 | (DMSO-$d_6$, 500 MHz) δ (ppm) 1.56 (m, 4H), 1.92 (m, 2H), 2.83 (s, 3H), 3.76 (m, 1H), 3.80 (s, 3H), 3.98 (s, 3H), 4.65 (m, 1H), 5.82 (d, 1H), 6.74 (d, 1H), 6.97 (m, 2H), 7.10 (m, 1H), 7.20 (m, 2H), 7.31 (m, 4H), 7.88 (s, 1H). |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 34 | 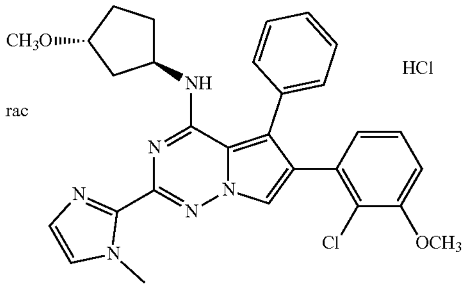 (34) | rac 6-(2-Chloro-3-methoxyphenyl)-N-((1R,3R)-3-methoxycyclopentyl)-2-(1-methyl-1H-imidazol-2-yl)-5-phenylpyrrolo[2,1-f][1,2,4]triazin-4-amine hydrochloride | 12.60 mg (3.00%) | 100% | 529.2 | 529.2 | (DMSO-$d_6$, 400 MHz) δ 1.16-1.28 (m, 1H), 1.38-1.47 (m, 1H), 1.52-1.62 (m, 1H), 1.64-1.75 (m, 1H), 1.97-2.06 (m, 2H), 3.13 (s, 3H), 3.65-3.72 (m, 1H), 3.83 (s, 3H), 3.99 (s, 3H), 4.53 (q, 1H), 5.45 (d, 1H), 6.82 (d, 1H), 7.01 (s, 1H), 7.06 (d, 1H), 7.20 (t, 1H), 7.30 (d, 3H), 7.37-7.44 (m, 3H), 7.93 (s, 1H). |
| 51 | 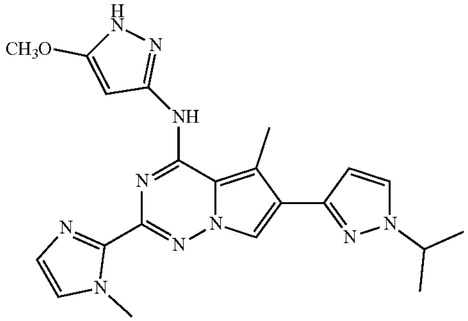 (51) | 6-(1-Isopropyl-1H-pyrazol-3-yl)-N-(5-methoxy-1H-pyrazol-3-yl)-5-methyl-2-(1-methyl-1H-imidazol-2-yl)pyrrolo[2,1-f][1,2,4]triazin-4-amine | 5.5 mg (4.5%) | 100% | 433.2 | 433.2 | ($CD_3OD$, 400 MHz) δ 1.85 (m, 2H), 2.37 (m, 2H), 3.35 (s, 3H), 3.45 (m, 2H), 3.51 (m, 2H), 3.86 (s, 3H), 3.99 (quin, 1H), 4.10 (s, 3H), 4.65 (quin, 1H), 6.67 (dd, 1H), 6.90 (m, 2H), 7.09 (d, 1H), 7.20 (m, 1H), 7.45 (m, 5H), 7.89 (d, 1H). |
| 52 | 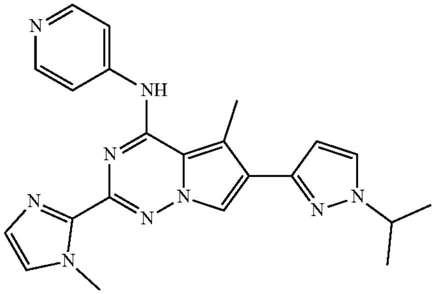 (52) | 6-(1-Isopropyl-1H-pyrazol-3-yl)-5-methyl-2-(1-methyl-1H-imidazol-2-yl)-N-(pyridin-4-yl)pyrrolo[2,1-f][1,2,4]triazin-4-amine | 7.0 mg (6.0%) | 91% | 414.2 | 414.2 | ($CD_3OD$, 400 MHz) δ 1.53 (d, 6H), 2.82 (s, 3H), 3.88 (s, 3H), 4.03 (s, 3H), 4.60 (sept., 1H), 6.50 (d, 1H), 7.11 (d, 1H), 7.24 (s, 1H), 7.74 (d, 1H), 8.02 (s, 1H), NH is not observed. |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 53 | 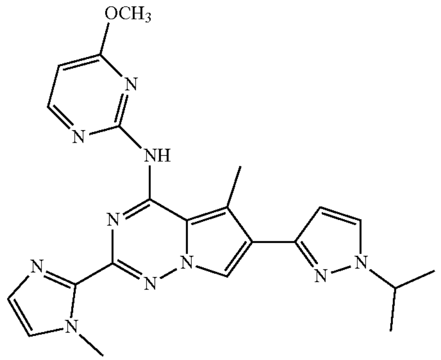 (53) | 6-(1-Isopropyl-1H-pyrazol-3-yl)-N-(4-methoxypyrimidin-2-yl)-5-methyl-2-(1-methyl-1H-imidazol-2-yl)pyrrolo[2,1-f][1,2,4]triazin-4-amine | 53.0 mg (42.4%) | 100% | 445.2 | 445.2 | (DMSO-$d_6$, 400 MHz) δ 1.40 (d, 6H), 2.89 (s, 3H), 4.00 (s, 3H), 4.05 (s, 3H), 4.51 (sept, 1H), 6.55 (m, 2H), 7.18 (d, 1H), 7.53 (d, 1H), 7.77 (d, 1H), 7.95 (d, 1H), 8.45 (d, 1H), 14.22 (s, 1H). |
| 54 | 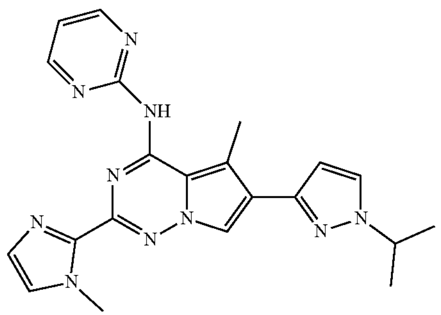 (54) | 6-(1-Isopropyl-1H-pyrazol-3-yl)-5-methyl-2-(1-methyl-1H-imidazol-2-yl)-N-(pyrimidin-2-yl)pyrrolo[2,1-f][1,2,4]triazin-4-amine | 27.0 mg (23.3%) | 100% | 415.2 | 415.2 | (DMSO-$d_6$, 400 MHz) δ 1.42 (d, 6H), 2.85 (s, 3H), 4.05 (s, 3H), 4.51 (sept, 1H), 6.56 (m, 1H), 7.15 (m, 2H), 7.53 (d, 1H), 7.80 (dd, 1H), 7.96 (d, 1H), 8.75 (m, 2H), 14.39 (m, 1H). |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 55 | 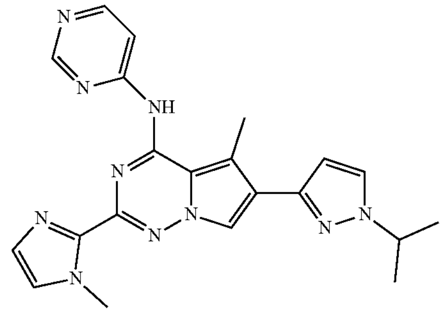 (55) | 6-(1-Isopropyl-1H-pyrazol-3-yl)-5-methyl-2-(1-methyl-1H-imidazol-2-yl)-N-(pyrimidin-4-yl)pyrrolo[2,1-f][1,2,4]triazin-4-amine | 3.0 mg (2.6%) | 97% | 415.2 | 415.2 | NA |
| 56 | 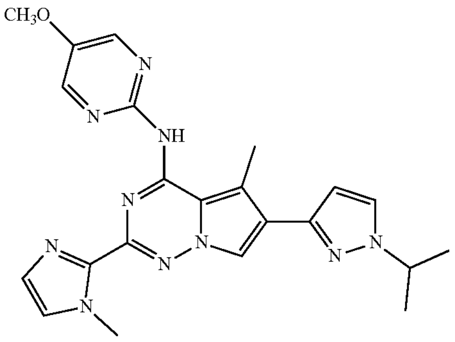 (56) | 6-(1-Isopropyl-1H-pyrazol-3-yl)-N-(5-methoxypyrimidin-2-yl)-5-methyl-2-(1-methyl-1H-imidazol-2-yl)pyrrolo[2,1-f][1,2,4]triazin-4-amine | 11.0 mg (8.8%) | 100% | 445.2 | 445.2 | (DMSO-d6, 400 MHz) δ 1.45 (d, 6H), 2.80 (s, 3H), 3.90 (s, 3H), 4.07 (s, 3H), 4.51 (sept, 1H), 6.51 (d, 1H), 7.20 (d, 1H), 7.51 (s, 1H), 7.76 (d, 1H), 7.85 (s, 1H), 8.50 (m, 2H). |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 57 | 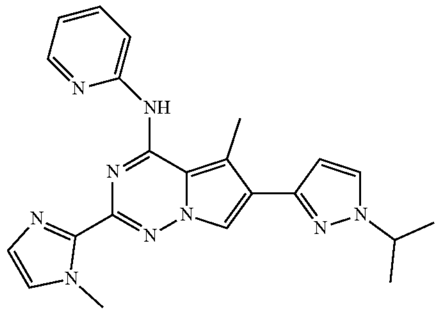 (57) | 6-(1-Isopropyl-1H-pyrazol-3-yl)-5-methyl-2-(1-methyl-1H-imidazol-2-yl)-N-(pyridin-2-yl)pyrrolo[2,1-f][1,2,4]triazin-4-amine | 6.9 mg (5.9%) | 100% | 414.2 | 414.2 | NA |
| 58 | 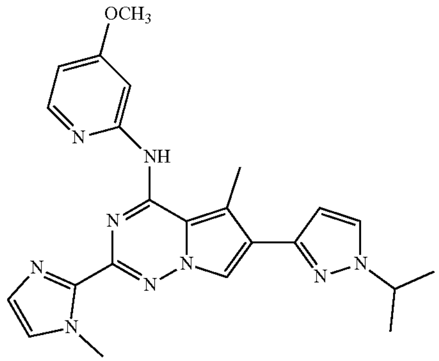 (58) | 6-(1-Isopropyl-1H-pyrazol-3-yl)-N-(4-methoxypyridin-2-yl)-5-methyl-2-(1-methyl-1H-imidazol-2-yl)pyrrolo[2,1-f][1,2,4]triazin-4-amine | 8.8 mg (7.0%) | 92% | 444.2 | 444.2 | ($CD_3OD$, 400 MHz) δ 1.51 (d, 7H), 2.74 (s, 3H), 3.85 (s, 3H), 3.99 (s, 3H), 4.57 (sept, 1H), 6.40 (s, 1H), 6.64 (d, 1H), 1.78 (m, 2H), 7.68 (s, 1H), 7.80 (m, 2H), 8.06 (d, 1H). |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 59 | 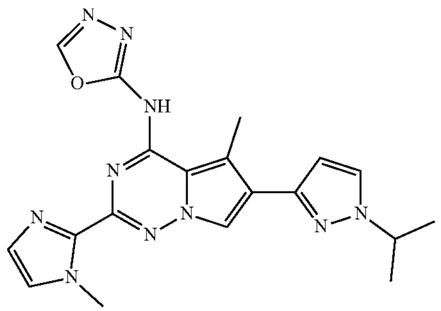 (59) | N-(6-(1-Isopropyl-1H-pyrazol-3-yl)-5-methyl-2-(1-methyl-1H-imidazol-2-yl)pyrrolo[2,1-f][1,2,4]triazin-4-yl)-1,3,4-oxadiazol-2-amine | 11.1 mg (9.7%) | 100% | 405.2 | 405.2 | (DMSO-$d_6$, 400 MHz) δ 1.45 (d, 6H), 2.82 (s, 3H), 4.08 (s, 3H), 4.55 (sept., 1H), 6.55 (d, 1H), 7.20 (s, 1H), 7.55 (d, 1H), 7.83 (d, 1H), 8.11 (d, 1H), 8.95 (s, 1H), 13.03 (s, 1H). |
| 60 | 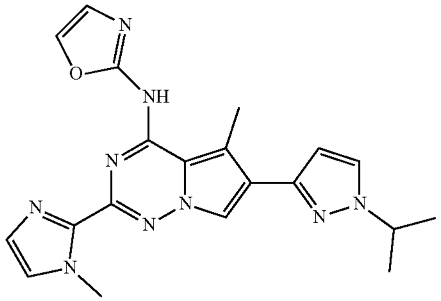 (60) | N-(6-(1-Isopropyl-1H-pyrazol-3-yl)-5-methyl-2-(1-methyl-1H-imidazol-2-yl)pyrrolo[2,1-f][1,2,4]triazin-4-yl)oxazol-2-amine | 3.8 mg (3.4%) | 97% | 404.2 | 404.2 | NA |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^{1}$H NMR |
| 61 | 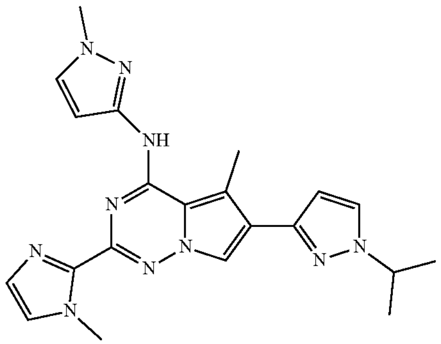 (61) | 6-(1-Isopropyl-1H-pyrazol-3-yl)-5-methyl-2-(1-methyl-1H-imidazol-2-yl)-N-(1-methyl-1H-pyrazol-3-yl)pyrrolo[2,1-f][1,2,4]triazin-4-amine | 7.2 mg (6.2%) | 90% | 417.2 | 417.2 | ($CD_3OD$, 400 MHz) δ 1.58 (d, 6H), 2.78 (s, 3H), 3.81 (s, 3H), 3.99 (s, 3H), 4.61 (sept., 1H), 6.58 (d, 1H), 6.64 (s, 1H), 7.22 (m, 2H), 7.49 (d, 1H), 7.72 (d, 1H), 7.89 (d, 1H). |
| 62 | 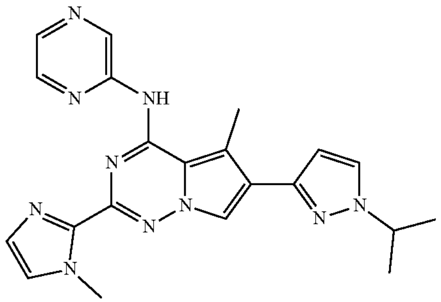 (62) | 6-(1-Isopropyl-1H-pyrazol-3-yl)-5-methyl-2-(1-methyl-1H-imidazol-2-yl)-N-(pyrazin-2-yl)pyrrolo[2,1-f][1,2,4]triazin-4-amine | 16.8 mg (14.5%) | 100% | 415.2 | 415.2 | (DMSO-$d_6$, 400 MHz) δ 1.48 (d, 6H), 2.89 (s, 3H), 4.08 (s, 3H), 4.52 (Sept., 1H), 6.57 (d, 1H), 7.16 (s, 1H), 7.52 (s, 1H), 7.79 (d, 1H), 7.94 (d, 1H), 8.24 (d, 1H), 8.40 (d, 1H), 8.52 (d, 1H), 14.11 (s, 1H). |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 67 | 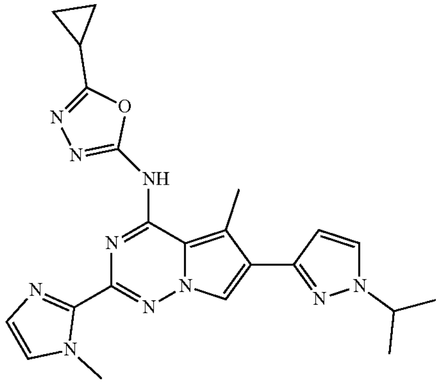 (67) | 5-Cyclopropyl-N-(6-(1-isopropyl-1H-pyrazol-3-yl)-5-methyl-2-(1-methyl-1H-imidazol-2-yl)pyrrolo[2,1-f][1,2,4]triazin-4-yl)-1,3,4-oxadiazol-2-amine | NA | 100% | 445.2 | 445.2 | NA |
| 68 | 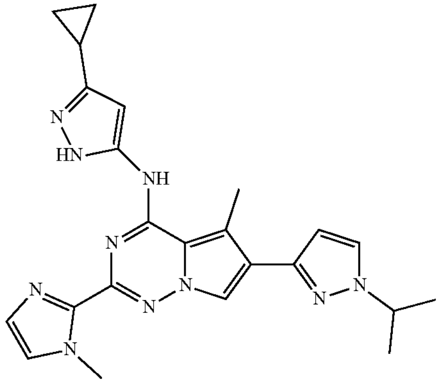 (68) | N-(3-Cyclopropyl-1H-pyrazol-5-yl)-6-(1-isopropyl-1H-pyrazol-3-yl)-5-methyl-2-(1-methyl-1H-imidazol-2-yl)pyrrolo[2,1-f][1,2,4]triazin-4-amine | NA | 99% | 443.2 | 443.1 | NA |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^{1}$H NMR |
| 69 | 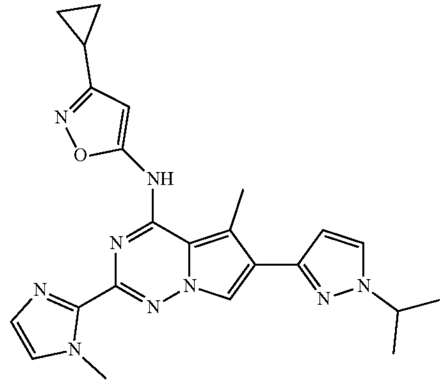 (69) | 3-Cyclopropyl-N-(6-(1-isopropyl-1H-pyrazol-3-yl)-5-methyl-2-(1-methyl-1H-imidazol-2-yl)pyrrolo[2,1-f][1,2,4]triazin-4-yl)isoxazol-5-amine | NA | 100% | 444.2 | 444.2 | NA |
| 70 | 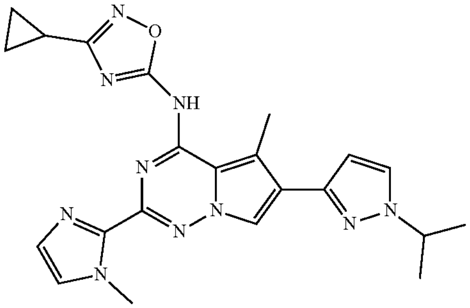 (70) | 3-Cyclopropyl-N-(6-(1-isopropyl-1H-pyrazol-3-yl)-5-methyl-2-(1-methyl-1H-imidazol-2-yl)pyrrolo[2,1-f][1,2,4]triazin-4-yl)-1,2,4-oxadiazol-5-amine | NA | 100% | 445.2 | 445.2 | NA |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 71 | 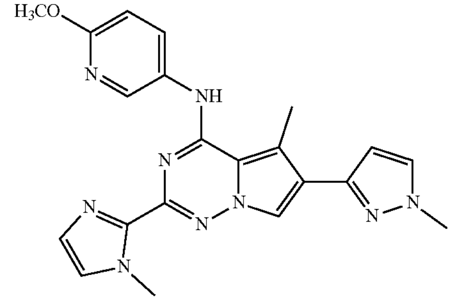 (71) | 6-(1-Isopropyl-1H-pyrazol-3-yl)-N-(6-methoxypyridin-3-yl)-5-methyl-2-(1-methyl-1H-imidazol-2-yl)pyrrolo[2,1-f][1,2,4]triazin-4-amine | NA | 100% | 444.2 | 444.2 | NA |
| 72 | 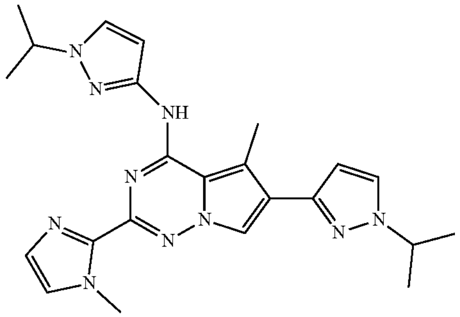 (72) | N,6-bis(1-Isopropyl-1H-pyrazol-3-yl)-5-methyl-2-(1-methyl-1H-imidazol-2-yl)pyrrolo[2,1-f][1,2,4]triazin-4-amine | NA | 91% | 445.2 | 445.4 | NA |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 73 | 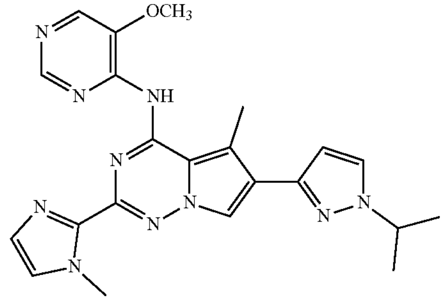 (73) | 6-(1-Isopropyl-1H-pyrazol-3-yl)-N-(5-methoxypyrimidin-4-yl)-5-methyl-2-(1-methyl-1H-imidazol-2-yl)pyrrolo[2,1-f][1,2,4]triazin-4-amine | NA | 100% | 445.2 | 445.2 | NA |
| 74 | 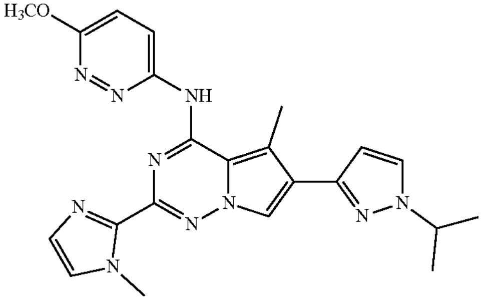 (74) | 6-(1-Isopropyl-1H-pyrazol-3-yl)-N-(6-methoxypyridazin-3-yl)-5-methyl-2-(1-methyl-1H-imidazol-2-yl)pyrrolo[2,1-f][1,2,4]triazin-4-amine | NA | 100% | 414.2 | 414.2 | NA |
| 75 | 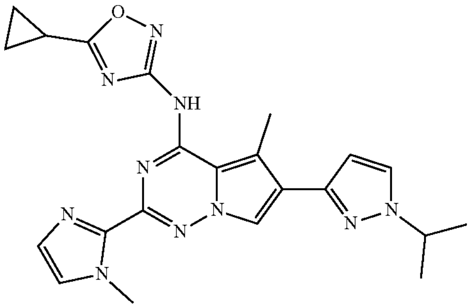 (75) | 5-Cyclopropyl-N-(6-(1-isopropyl-1H-pyrazol-3-yl)-5-methyl-2-(1-methyl-1H-imidazol-2-yl)pyrrolo[2,1-f][1,2,4]triazin-4-yl)-1,2,4-oxadiazol-3-amine | NA | 99% | 445.2 | 445.0 | NA |

TABLE 1-continued
Compounds and Analytical Data
| Example | Structure | Name | (Amount Yield)* | Purity | Calc'd [M + 1] | [Found M + 1] | $^1$H NMR |
|---|---|---|---|---|---|---|---|
| 76 | 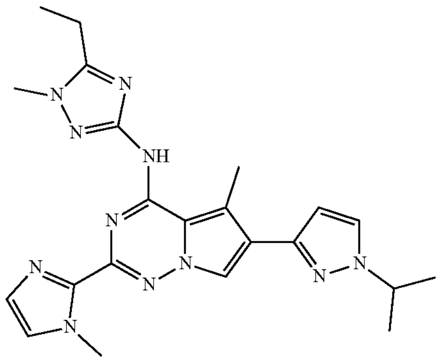 (76) | N-(5-Ethyl-1-methyl-1H-1,2,4-triazol-3-yl)-6-(1-isopropyl-1H-pyrazol-3-yl)-5-methyl-2-(1-methyl-1H-imidazol-2-yl)pyrrolo[2,1-f][1,2,4]triazin-4-amine | NA | 95% | 446.2 | 446.2 | NA |
| 77 | 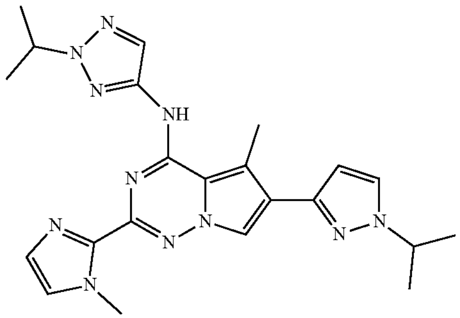 (77) | 6-(1-Isopropyl-1H-pyrazol-3-yl)-N-(2-isopropyl-2H-1,2,3-triazol-4-yl)-5-methyl-2-(1-methyl-1H-imidazol-2-yl)pyrrolo[2,1-f][1,2,4]triazin-4-amine | NA | 100% | 446.2 | 446.2 | NA |

TABLE 1-continued
Compounds and Analytical Data
| Example | Structure | Name | (Amount Yield)* | Purity | Calc'd [M + 1] | [Found M + 1] | $^1$H NMR |
|---|---|---|---|---|---|---|---|
| 78 | 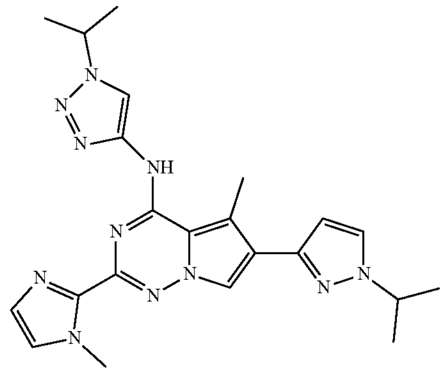 (78) | N-(1-Isopropyl-1H-1,2,3-triazol-4-yl)-6-(1-isopropyl-1H-pyrazol-3-yl)-5-methyl-2-(1-methyl-1H-imidazol-2-yl)pyrrolo[2,1-f][1,2,4]triazin-4-amine | NA | 89% | 446.2 | 446.2 | NA |
| 79 | 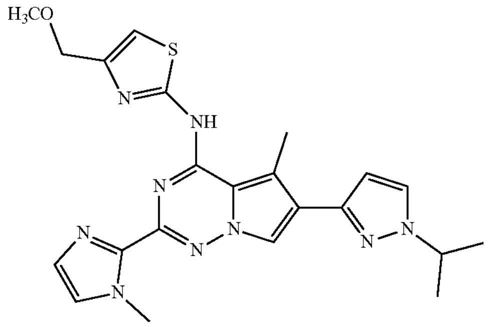 (79) | N-(6-(1-Isopropyl-1H-pyrazol-3-yl)-5-methyl-2-(1-methyl-1H-imidazol-2-yl)pyrrolo[2,1-f][1,2,4]triazin-4-yl)-4-(methoxymethyl)thiazol-2-amine | NA | 100% | 464.2 | 464.2 | NA |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 80 | 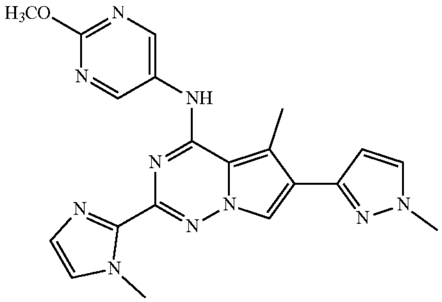 (80) | 6-(1-Isopropyl-1H-pyrazol-3-yl)-N-(2-methoxypyrimidin-5-yl)-5-methyl-2-(1-methyl-1H-imidazol-2-yl)pyrrolo[2,1-f][1,2,4]triazin-4-amine | NA | 100% | 445.2 | 445.2 | NA |
| 81 | 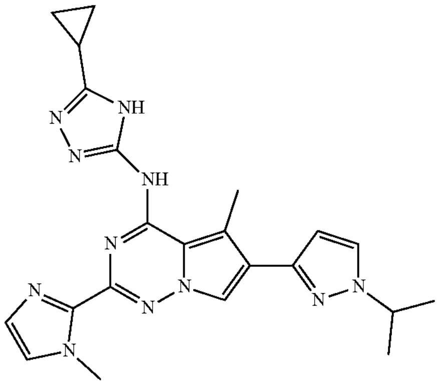 (81) | N-(5-Cyclopropyl-4H-1,2,4-triazol-3-yl)-6-(1-isopropyl-1H-pyrazol-3-yl)-5-methyl-2-(1-methyl-1H-imidazol-2-yl)pyrrolo[2,1-f][1,2,4]triazin-4-amine | NA | 97% | 444.2 | 444.1 | NA |

TABLE 1-continued
Compounds and Analytical Data
| Example | Structure | Name | (Amount Yield)* | Purity | Calc'd [M + 1] | [Found M + 1] | $^1$H NMR |
|---|---|---|---|---|---|---|---|
| 82 | 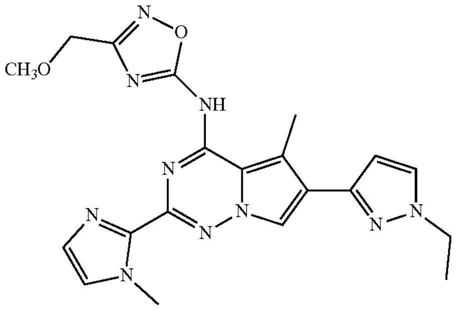 (82) | N-(6-(1-Isopropyl-1H-pyrazol-3-yl)-5-methyl-2-(1-methyl-1H-imidazol-2-yl)pyrrolo[2,1-f][1,2,4]triazin-4-yl)-3-(methoxymethyl)-1,2,4-oxadiazol-5-amine | NA | 100% | 449.2 | 449.2 | NA |
| 83 | 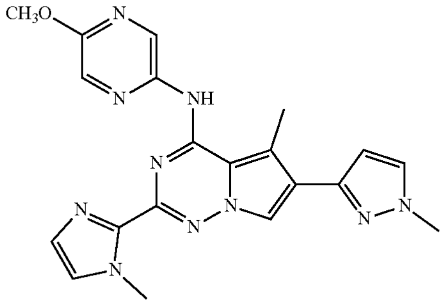 (83) | 6-(1-Isopropyl-1H-pyrazol-3-yl)-N-(5-methoxypyrazin-2-yl)-5-methyl-2-(1-methyl-1H-imidazol-2-yl)pyrrolo[2,1-f][1,2,4]triazin-4-amine | NA | 100% | 445.2 | 445.2 | NA |

TABLE 1-continued

Compounds and Analytical Data

| Example | Structure | Name | (Amount Yield)* | Purity | Calc'd [M + 1] | [Found M + 1] | $^1$H NMR |
|---|---|---|---|---|---|---|---|
| 84 | 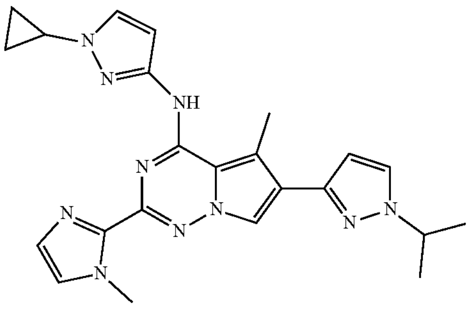 (84) | N-(1-Cyclopropyl-1H-pyrazol-3-yl)-6-(1-isopropyl-1H-pyrazol-3-yl)-5-methyl-2-(1-methyl-1H-imidazol-2-yl)pyrrolo[2,1-f][1,2,4]triazin-4-amine | NA | 100% | 444.2 | 444.2 | NA |
| 85 | 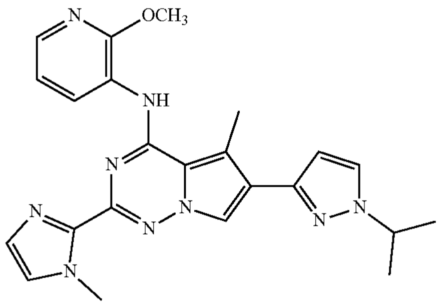 (85) | 6-(1-Isopropyl-1H-pyrazol-3-yl)-N-(2-methoxypyridin-3-yl)-5-methyl-2-(1-methyl-1H-imidazol-2-yl)pyrrolo[2,1-f][1,2,4]triazin-4-amine | NA | 100% | 444.2 | 444.2 | NA |
| 86 | 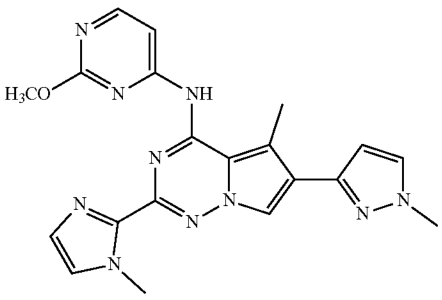 (86) | 6-(1-Isopropyl-1H-pyrazol-3-yl)-N-(2-methoxypyrimidin-4-yl)-5-methyl-2-(1-methyl-1H-imidazol-2-yl)pyrrolo[2,1-f][1,2,4]triazin-4-amine | NA | 100% | 445.2 | 445.2 | NA |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^{1}$H NMR |
| 87 | 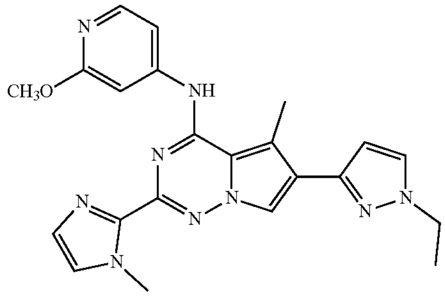 (87) | 6-(1-Isopropyl-1H-pyrazol-3-yl)-N-(2-methoxypyridin-4-yl)-5-methyl-2-(1-methyl-1H-imidazol-2-yl)pyrrolo[2,1-f][1,2,4]triazin-4-amine | NA | 100% | 444.2 | 444.2 | NA |
| 88 | 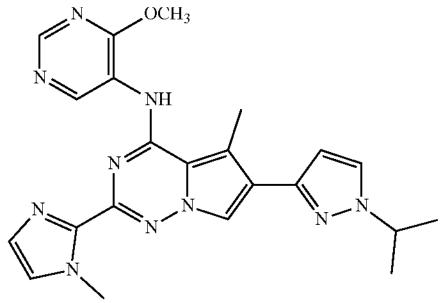 (88) | 6-(1-Isopropyl-1H-pyrazol-3-yl)-N-(4-methoxypyrimidin-5-yl)-5-methyl-2-(1-methyl-1H-imidazol-2-yl)pyrrolo[2,1-f][1,2,4]triazin-4-amine | NA | 100% | 445.2 | 445.2 | NA |

TABLE 1-continued
Compounds and Analytical Data
| Example | Structure | Name | (Amount Yield)* | Purity | Calc'd [M + 1] | [Found M + 1] | $^1$H NMR |
|---|---|---|---|---|---|---|---|
| 89 | 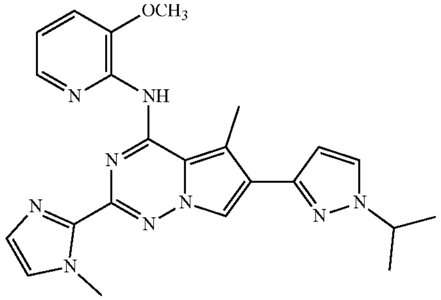 (89) | 6-(1-Isopropyl-1H-pyrazol-3-yl)-N-(3-methoxypyridin-2-yl)-5-methyl-2-(1-methyl-1H-imidazol-2-yl)pyrrolo[2,1-f][1,2,4]triazin-4-amine | NA | 100% | 444.2 | 444.2 | NA |
| 90 | 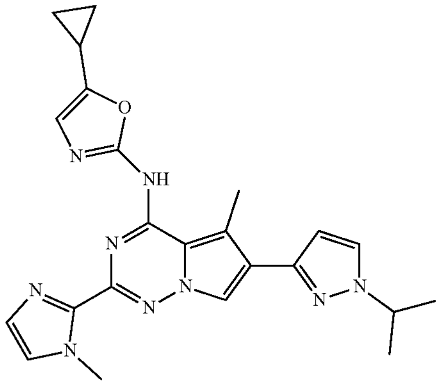 (90) | 5-Cyclopropyl-N-(6-(1-isopropyl-1H-pyrazol-3-yl)-5-methyl-2-(1-methyl-1H-imidazol-2-yl)pyrrolo[2,1-f][1,2,4]triazin-4-yl)oxazol-2-amine | NA | 100% | 444.2 | 444.2 | NA |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^{1}$H NMR |
| 91 | 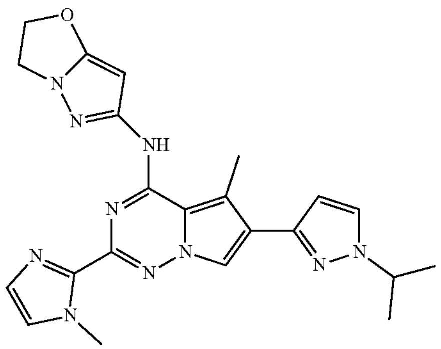 (91) | N-(6-(1-Isopropyl-1H-pyrazol-3-yl)-5-methyl-2-(1-methyl-1H-imidazol-2-yl)pyrrolo[2,1-f][1,2,4]triazin-4-yl)-2,3-dihydropyrazolo[5,1-b]oxazol-6-amine | NA | 96% | 445.2 | 445.2 | NA |
| 92 | 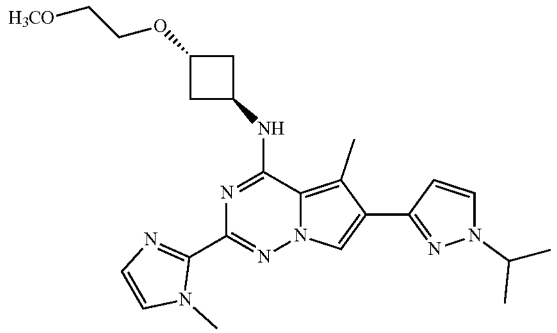 (92) | 6-(1-Isopropyl-1H-pyrazol-3-yl)-N-((1r,3r)-3-(2-methoxyethoxy)cyclobutyl)-5-methyl-2-(1-methyl-1H-imidazol-2-yl)pyrrolo[2,1-f][1,2,4]triazin-4-amine | NA | 100% | 465.3 | 465.2 | NA |

TABLE 1-continued
Compounds and Analytical Data
| Example | Structure | Name | (Amount Yield)* | Purity | Calc'd [M + 1] | [Found M + 1] | $^1$H NMR |
|---|---|---|---|---|---|---|---|
| 93 | 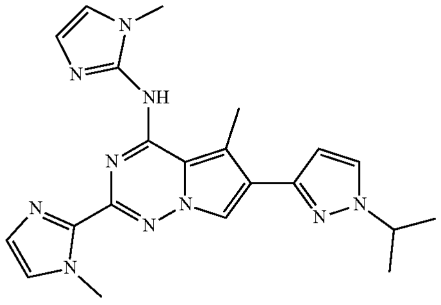 (93) | 6-(1-Isopropyl-1H-pyrazol-3-yl)-5-methyl-N,2-bis(1-methyl-1H-imidazol-2-yl)pyrrolo[2,1-f][1,2,4]triazin-4-amine | NA | 100% | 417.2 | 417.1 | NA |
| 104 | 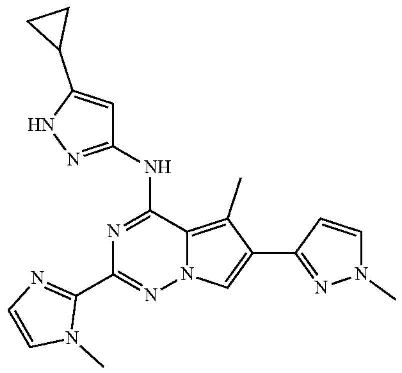 (104) | N-(5-Cyclopropyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 25 mg (15%) | 99% | 415 | 415 | (400 MHz, DMSO-$d_6$) δ 0.76-0.69 (m, 2H), 0.94-0.90 (m, 2H), 1.92-1.88 (m, 1H), 2.75 (s, 3H), 3.87 (s, 3H), 4.05 (s, 3H), 5.79 (s, 1H), 6.44 (s, 1H), 7.11 (s, 1H), 7.39 (s, 1H), 7.62-7.59 (m, 2H), 12.16 (brs, 1H), 12.78 (brs, 1H) |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 105 | 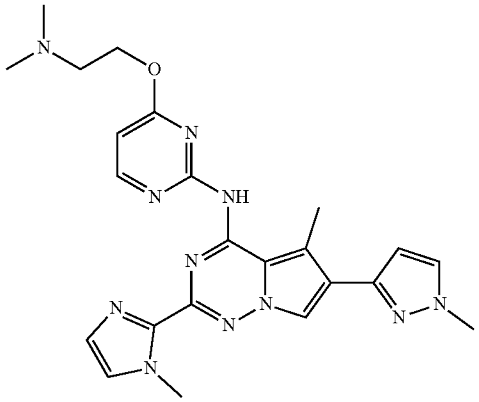 (105) | N-(4-(2-(Dimethylamino)ethoxy)pyrimidin-2-yl)-5-methyl-2-(1-methyl-1H-imidazol-2-yl)-6-(1-methyl-1H-pyrazol-3-yl)pyrrolo[2,1-f][1,2,4]triazin-4-amine | 24 mg (29%) | 95% | 474 | 474 | (400 MHz, DMSO-$d_6$) δ 2.23 (s, 6H), 2.67 (s, 2H), 2.82-0.00 (m, 3H), 3.88 (s, 3H), 4.06 (s, 3H), 4.57-4.54 (m, 2H), 6.49 (s, 1H), 6.51-6.50 (m, 1H), 7.12 (s, 1H), 7.41 (s, 1H), 7.65 (d, J = 2.00 Hz, 1H), 7.85 (s, 1H), 8.39 (d, J = 8.40 Hz, 1H) |
| 106 | 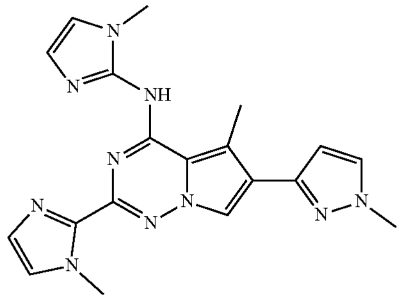 (106) | 5-Methyl-N,2-bis(1-methyl-1H-imidazol-2-yl)-6-(1-methyl-1H-pyrazol-3-yl)pyrrolo[2,1-f][1,2,4]triazin-4-amine | 9 mg (15%) | 99% | 389 | 389 | (400 MHz, DMSO-$d_6$) δ 2.82 (s, 3H), 3.65 (s, 3H), 3.87 (s, 3H), 4.05 (s, 3H), 6.47 (d, J = 4.00 Hz, 1H), 6.97 (d, J = 12.00 Hz, 2H), 7.14 (s, 1H), 7.37 (s, 1H), 7.63 (d, J = 2.00 Hz, 1H), 7.70 (s, 1H), 13.85 (bs, 1H) |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 107 | 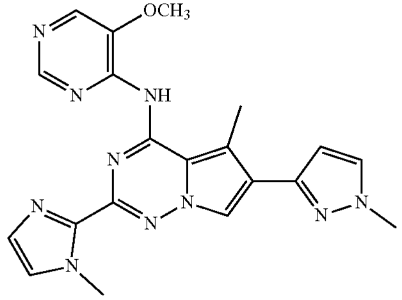 (107) | N-(5-Methoxypyrimidin-4-yl)-5-methyl-2-(1-methyl-1H-imidazol-2-yl)-6-(1-methyl-1H-pyrazol-3-yl)pyrrolo[2,1-f][1,2,4]triazin-4-amine | 37 mg (52%) | 99% | 417 | 417 | (400 MHz, DMSO-$d_6$) δ 2.96 (s, 3H), 3.88 (s, 3H), 3.95 (s, 3H), 4.07 (s, 3H), 6.51 (d, J = 2.00 Hz, 1H), 7.17 (s, 1H), 7.43 (d, J = Hz, 1H), 7.66 (d, J = 2.00 Hz, 1H), 7.86 (s, 1H), 8.32 (s, 1H), 8.55 (s, 1H) |
| 108 | 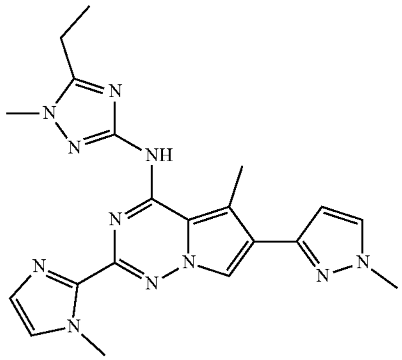 (108) | N-(5-Ethyl-1-methyl-1H-1,2,4-triazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 30 mg (41%) | 99% | 418 | 418 | (400 MHz, DMSO-$d_6$) δ 1.40 (t, J = 8.00 Hz, 3H), 2.79-0.00 (m, 4H), 2.90 (s, 1H), 3.53 (s, 1H), 3.75 (s, 2H), 3.88 (d, J = 4.00 Hz, 3H), 4.03 (d, J = 16.00 Hz, 3H), 6.40-6.46 (m, 1H), 7.10 (s, 1H), 7.39-7.54 (m, 1H), 7.63 (d, J = 4.00 Hz, 1H), 7.66 (s, 1H), 13.40 (brs, 1H) |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^{1}$H NMR |
| 109 | 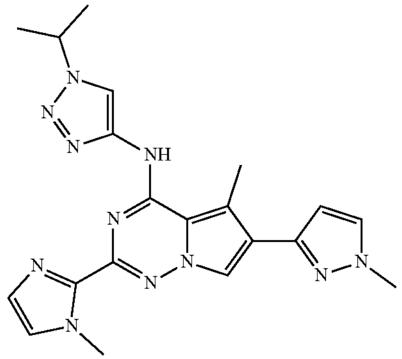 (109) | N-(1-Isopropyl-1H-1,2,3-triazol-4-yl)-5-methyl-2-(1-methyl-1H-imidazol-2-yl)-6-(1-methyl-1H-pyrazol-3-yl)pyrrolo[2,1-f][1,2,4]triazin-4-amine | 19 mg (27%) | 99% | 418 | 418 | (400 MHz, DMSO-$d_6$) δ 1.57 (s, 6H), 2.77 (s, 2H), 2.84 (s, 1H), 3.88-3.87 (m, 3H), 4.06 (s, 3H), 4.84-4.76 (m, 1H), 6.45 (d, J = 2.00 Hz, 1H), 7.17 (s, 1H), 7.41 (s, 1H), 7.62-7.64 (m, 2H), 7.98 (s, 1H), 12.8 (brs, 1H). |
| 110 | 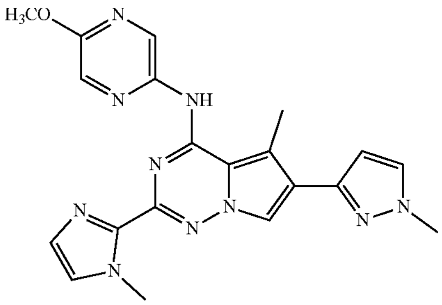 (110) | N-(5-Methoxypyrazin-2-yl)-5-methyl-2-(1-methyl-1H-imidazol-2-yl)-6-(1-methyl-1H-pyrazol-3-yl)pyrrolo[2,1-f][1,2,4]triazin-4-amine | 24 mg (17%) | 99% | 417 | 417 | (400 MHz, DMSO-$d_6$) δ 2.83 (s, 3H), 3.88-3.95 (m, 9H), 6.48 (s, 1H), 7.14 (s, 1H), 7.40 (d, J = 12.00 Hz, 1H), 7.64-7.71 (m, 2H), 8.07-8.14 (m, 2H), 13.44 (brs, 1H) |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 111 | 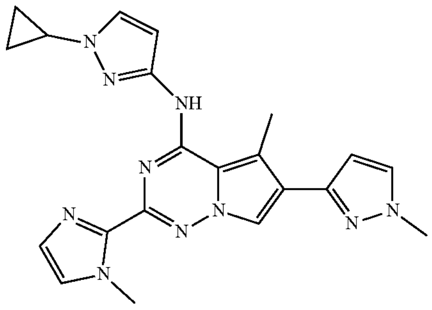 (111) | N-(1-Cyclopropyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 8 mg (13%) | 97% | 415 | 415 | (400 MHz, DMSO-$d_6$) δ 0.97-0.96 (m, 2H), 1.42 (s, 2H), 2.76 (s, 3H), 3.77 (s, 1H), 3.87 (s, 3H), 4.06 (s, 3H), 6.09 (s, 1H), 6.44 (s, 1H), 7.14 (s, 1H), 7.41 (s, 1H), 7.62 (s, 2H), 7.72 (s, 1H), 12.95 (brs, 1H) |
| 112 | 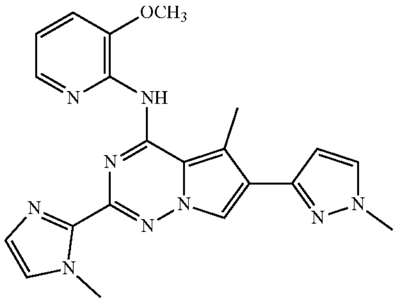 (112) | N-(3-Methoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 8 mg (8%) | 99% | 416 | 416 | (400 MHz, DMSO-$d_6$) δ 2.97 (s, 3H), 3.90 (s, 6H), 4.07 (s, 3H), 6.53 (s, 1H), 7.12 (m, 2H), 7.41(m, 2H), 7.67(m, 1H), 8.03 (m, 2H) |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 113 | 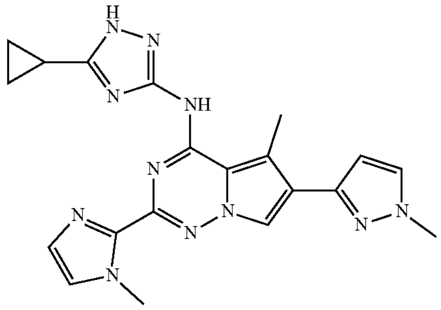 (113) | N-(5-Cyclopropyl-1H-1,2,4-triazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 7 mg (5.5%) | 92% | 416 | 416 | (400 MHz, DMSO-$d_6$) δ 0.95 (dd, J = 4.00 Hz, 2H), 1.11 (dd, J = 16.00 Hz, 2H), 1.94-1.98 (m, 1H), 2.78 (s, 3H), 3.87 (s, 3H), 4.06 (s, 3H), 6.48 (d, J = 4.00 Hz, 1H), 7.14 (s, 1H), 7.42 (s, 1H), 7.64 (d, J = 2.00 Hz, 1H), 7.74 (s, 1H), 12.81 (brs, 1H), 13.85 (brs, 1H) |
| 114 | 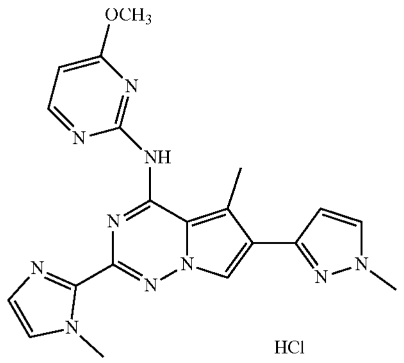 (114) | N-(4-Methoxypyrimidin-2-yl)-5-methyl-2-(1-methyl-1H-imidazol-2-yl)-6-(1-methyl-1H-pyrazol-3-yl)pyrrolo[2,1-f][1,2,4]triazin-4-amine hydrochloride salt | 5.5 mg (4.3%) | 100% | 417.2 | 417.0 | (500 MHz, DMSO-$d_6$) δ 2.87 (s, 3H), 3.85 (s, 3H), 4.07 (m, 6H), 6.53 (m, 2H), 7.14 (m, 1H), 7.51 (m, 1H), 7.71 (m, 1H), 7.95 (m, 1H), 8.43 (m, 1H), 14.27 (br s, 1H) |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 115 | 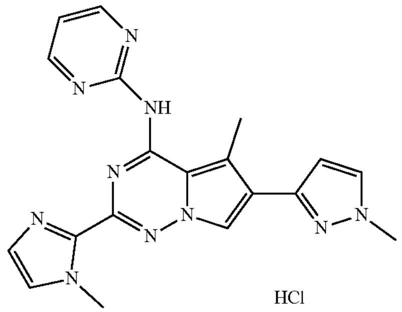 (115) | 5-Methyl-2-(1-methyl-1H-imidazol-2-yl)-6-(1-methyl-1H-pyrazol-3-yl)-N-(pyrimidin-2-yl)pyrrolo[2,1-f][1,2,4]triazin-4-amine hydrochloride salt | 18.5 mg (15.7) | 100% | 387.2 | 387.2 | (500 MHz, DMSO-$d_6$) δ 2.73 (s, 3H), 3.90 (s, 3H), 4.16 (s, 3H), 6.65 (d, 1H), 7.23 (dd, 1H), 7.69 (s, 1H), 7.78 (d, 1H), 7.85 (d, 1H), 8.31 (d, 1H), 8.75 (m, 2H) |
| 116 | 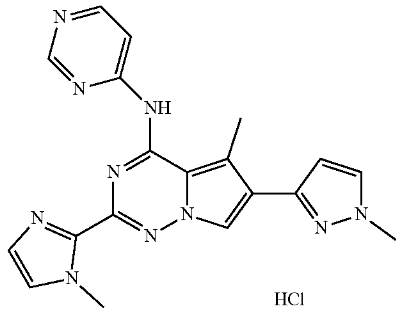 (116) | 5-Methyl-2-(1-methyl-1H-imidazol-2-yl)-6-(1-methyl-1H-pyrazol-3-yl)-N-(pyrimidin-4-yl)pyrrolo[2,1-f][1,2,4]triazin-4-amine hydrochloride salt | 29.1 mg (24.7%) | 97% | 387.2 | 387.2 | (500 MHz, DMSO-$d_6$) δ 2.82 (s, 3H), 3.90 (s, 3H), 4.12 (s, 3H), 6.65 (d, 1H), 7.75 (m, 3H), 8.34 (m, 1H), 8.50 (m, 1H), 8.66 (m, 1H), 8.95 (m, 2H) |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 117 | 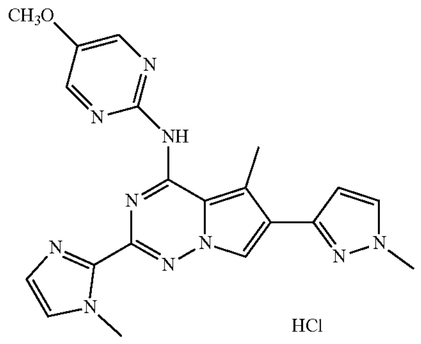 (117) | N-(5-Methoxypyrimidin-2-yl)-5-methyl-2-(1-methyl-1H-imidazol-2-yl)-6-(1-methyl-1H-pyrazol-3-yl)pyrrolo[2,1-f][1,2,4]triazin-4-amine hydrochloride salt | 11.5 mg (9.1%) | 100% | 417.2 | 417.0 | (500 MHz, DMSO-$d_6$) δ 2.75 (s, 3H), 3.94 (m, 6H), 4.12 (s, 3H), 6.51 (d, 1H), 7.63 (m, 1H), 7.80 (m, 2H), 8.33 (m, 2H), 8.52 (m, 2H), 8.90 (m, 1H) |
| 118 | 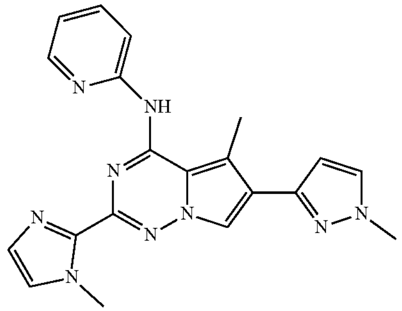 (118) | 5-Methyl-2-(1-methyl-1H-imidazol-2-yl)-6-(1-methyl-1H-pyrazol-3-yl)-N-(pyridin-2-yl)pyrrolo[2,1-f][1,2,4]triazin-4-amine | 2.7 mg (2.3%) | 95% | 386.2 | 386.2 | NA |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 119 | 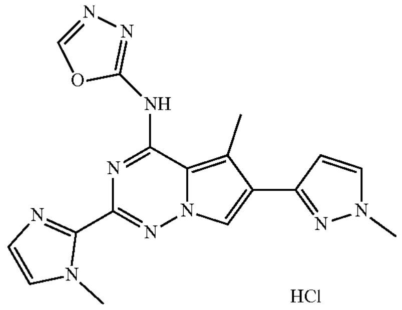 HCl (119) | N-(5-Methyl-2-(1-methyl-1H-imidazol-2-yl)-6-(1-methyl-1H-pyrazol-3-yl)pyrrolo[2,1-f][1,2,4]triazin-4-yl)-1,3,4-oxadiazol-2-amine hydrochloride salt | 6.3 mg (5.5%) | 100% | 377.2 | 377.0 | (500 MHz, DMSO-$d_6$) δ 2.83 (s, 3H), 3.89 (s, 3H), 4.10 (s, 3H), 6.56 (d, 1H), 7.25 (d, 1H), 7.55 (d, 1H), 7.70 (d, 1H), 8.08 (s, 1H), 8.95 (s, 1H), 13.05 (br s, 1H) |
| 120 | 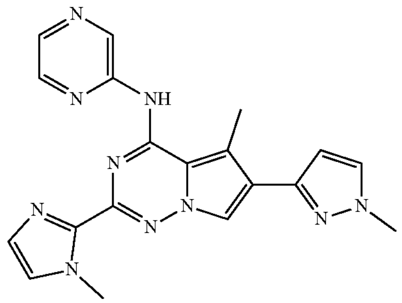 (120) | 5-Methyl-2-(1-methyl-1H-imidazol-2-yl)-6-(1-methyl-1H-pyrazol-3-yl)-N-(pyrazin-2-yl)pyrrolo[2,1-f][1,2,4]triazin-4-amine | 10.3 mg (8.7%) | 100% | 387.2 | 387.2 | (500 MHz, DMSO-$d_6$) δ 2.85 (s, 3H), 3.82 (s, 3H), 4.03 (s, 3H), 6.53 (d, 1H), 7.20 (m, 1H), 7.51 (m, 1H), 7.70 (m, 1H), 7.80 (m, 1H), 8.25 (m, 1H), 8.40 (m, 1H), 8.52 (s, 1H), 14.10 (br s, 1H) |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 121 | 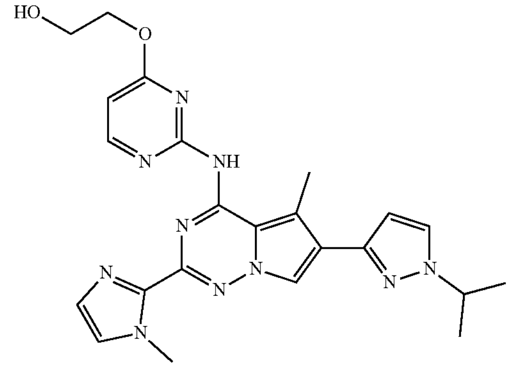 (121) | 2-((2-((6-(1-Isopropyl-1H-pyrazol-3-yl)-5-methyl-2-(1-methyl-1H-imidazol-2-yl)pyrrolo[2,1-f][1,2,4]triazin-4-yl)amino)pyrimidin-4-yl)oxy)ethan-1-ol | 17.0 mg (12.8%) | 96% | 475.2 | 475.2 | NA |
| 122 | 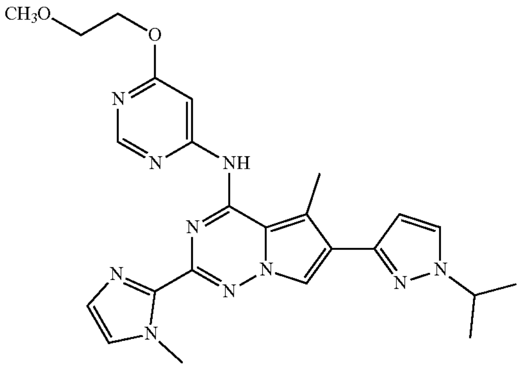 (122) | 6-(1-Isopropyl-1H-pyrazol-3-yl)-N-(6-(2-methoxyethoxy)pyrimidin-4-yl)-5-methyl-2-(1-methyl-1H-imidazol-2-yl)pyrrolo[2,1-f][1,2,4]triazin-4-amine | 8.0 mg (5.8%) | 96% | 489.2 | 489.2 | NA |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 123 | 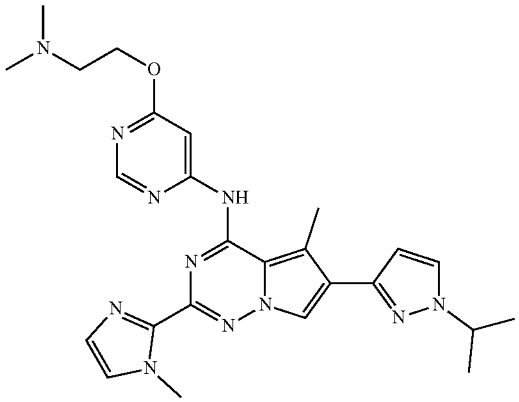 (123) | N-(6-(2-(Dimethylamino)ethoxy)pyrimidin-4-yl)-6-(1-isopropyl-1H-pyrazol-3-yl)-5-methyl-2-(1-methyl-1H-imidazol-2-yl)pyrrolo[2,1-f][1,2,4]triazin-4-amine | 17.5 mg (12.4%) | 100% | 502.3 | 502.2 | (500 MHz, DMSO-$d_6$) δ 1.42 (d, 6H), 2.19 (m, 6H), 2.59 (t, 2H), 2.82 (m, 3H), 3.98 (m, 3H), 4.39 (m, 2H), 4.52 (quin, 1H), 6.50 (m, 1H), 7.05 (m, 1H), 7.35 (m, 1H), 7.76 (s, 1H), 7.90 (m, 1H), 8.50 (m, 1H) |
| 124 | 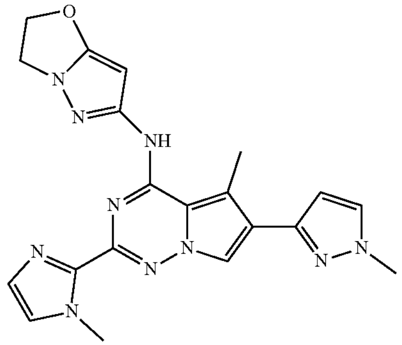 (124) | N-(5-Methyl-2-(1-methyl-1H-imidazol-2-yl)-6-(1-methyl-1H-pyrazol-3-yl)pyrrolo[2,1-f][1,2,4]triazin-4-yl)-2,3-dihydropyrazolo[5,1-b]oxazol-6-amine | 18.1 mg (14.3%) | 100% | 417.2 | 417.2 | (500 MHz, DMSO-$d_6$) δ 3.26 (s, 3H), 4.00 (m, 7H), 4.22 (m, 1H), 5.00 (m, 2H), 5.32 (m, 1H), 6.50 (m, 1H), 7.15 (m, 1H), 7.47 (m, 1H), 7070 (m, 2H), 12.73 (m, 1H). |

TABLE 1-continued
Compounds and Analytical Data
| Example | Structure | Name | (Amount Yield)* | Purity | Calc'd [M + 1] | [Found M + 1] | $^1$H NMR |
|---|---|---|---|---|---|---|---|
| 125 | 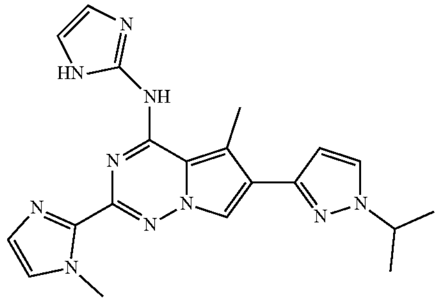 (125) | N-(1H-Imidazol-2-yl)-6-(1-isopropyl-1H-pyrazol-3-yl)-5-methyl-2-(1-methyl-1H-imidazol-2-yl)pyrrolo[2,1-f][1,2,4]triazin-4-amine | 5.0 mg (4.4%) | 99% | 403.2 | 403.2 | (500 MHz, $CD_3OD$) δ 1.53 (d, 6H), 2.20 (m, 1H), 2.80 (s, 3H), 4.10 (s, 3H), 4.57 (quin, 1H), 6.45 (d, 1H), 6.89 (m, 2H), 7.21 (m, 1H), 7.26 (m, 1H), 7.70 (m, 2H), 8.40 (s, 1H). |
| 126 | 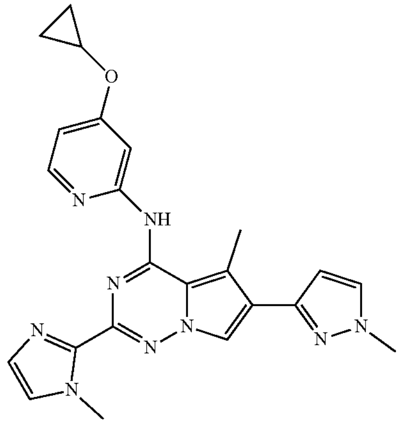 (126) | N-(4-Cyclopropoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 29.6 mg (21.9%) | 100% | 442.2 | 442.2 | NA |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 127 | 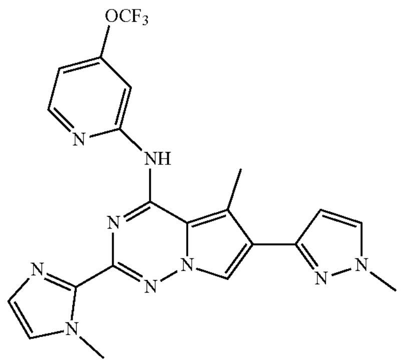 (127) | 5-Methyl-2-(1-methyl-1H-imidazol-2-yl)-6-(1-methyl-1H-pyrazol-3-yl)-N-(4-(trifluorometh-oxy)pyridin-2-yl)pyrrolo[2,1-f][1,2,4]triazin-4-amine | 7.8 mg (5.5%) | 100% | 470.2 | 470.2 | NA |
| 128 | 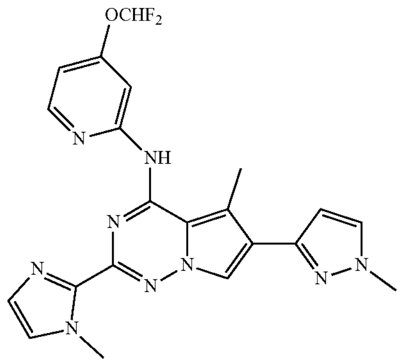 (128) | N-(4-(Difluoromethoxy)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 3.2 mg (2.2%) | 99% | 452.2 | 452.2 | NA |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 129 | 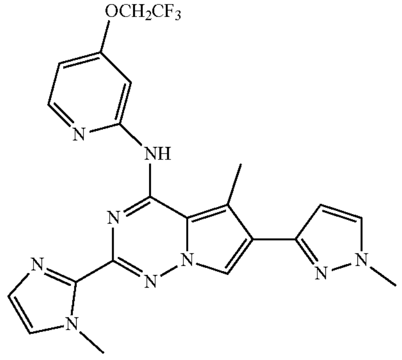 (129) | 5-Methyl-2-(1-methyl-1H-imidazol-2-yl)-6-(1-methyl-1H-pyrazol-3-yl)-N-(4-(2,2,2-trifluoroethoxy)pyridin-2-yl)pyrrolo[2,1-f][1,2,4]triazin-4-amine | 10.2 mg (11.5%) | 100% | 484.2 | 484.0 | NA |
| 130 | 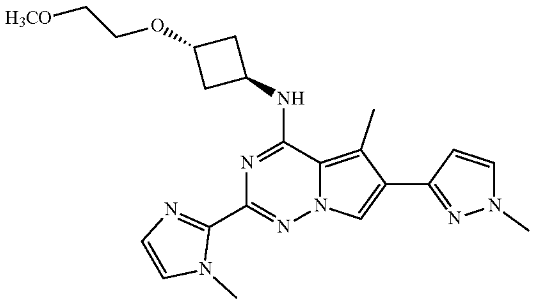 (130) | N-((1r,3r)-3-(2-Methoxyethoxy)cyclobutyl)-5-methyl-2-(1-methyl-1H-imidazol-2-yl)-6-(1-methyl-1H-pyrazol-3-yl)pyrrolo[2,1-f][1,2,4]triazin-4-amine | 30.3 mg (22.8%) | 100% | 437.3 | 437.3 | (500 MHz, DMSO-$d_6$) δ 2.24 (m, 2H), 2.45 (m, 1H), 2.71 (s, 3H), 3.23 (s, 3H), 3.42 (m, 4H), 3.86 (s, 3H), 3.94 (s, 3H), 4.18 (m, 1H), 4.76 (m, 2H), 6.51 (d, 1H), 6.90 (d, 1H), 7.07 (br s, 1H), 7.25 (d, 1H), 7.70 (s, 1H), 7.91 (d, 1H) |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 131 | 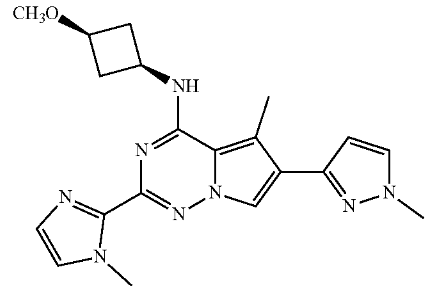 (131) | N-((1s,3s)-3-Methoxycyclobutyl)-5-methyl-2-(1-methyl-1H-imidazol-2-yl)-6-(1-methyl-1H-pyrazol-3-yl)pyrrolo[2,1-f][1,2,4]triazin-4-amine | 38.5 mg (31.6%) | 100% | 393.2 | 393.2 | (500 MHz, DMSO-$d_6$) δ 2.10 (m, 2H), 2.62 (m, 2H), 2.73 (s, 3H), 3.14 (s, 3H), 3.45 (quin, 1H), 3.88 (s, 3H), 3.95 (s, 3H), 4.36 (m, 1H), 6.53 (d, 1H), 6.95 (d, 1H), 7.08 (br s, 1H), 7.25 (s, 1H), 7.68 (d, 1H), 7.90 (d, 1H) |
| 132 | rac 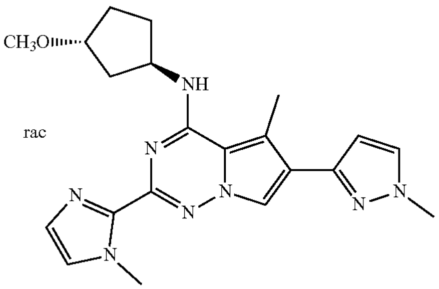 (132) | rac N-((1R,3R)-3-Methoxycyclopentyl)-5-methyl-2-(1-methyl-1H-imidazol-2-yl)-6-(1-methyl-1H-pyrazol-3-yl)pyrrolo[2,1-f][1,2,4]triazin-4-amine | 39.7 mg (31.5%) | 100% | 407.2 | 407.2 | (500 MHz, DMSO-$d_6$) δ 1.90 (m, 6H), 2.70 (s, 3H), 3.19 (s, 3H), 3.95 (m, 7H), 4.72 (m, 1H), 6.51 (d, 1H), 6.75 (m, 1H), 6.91 (d, 1H), 7.27 (d, 1H), 7.71 (s, 1H), 7.90 (d, 1H) |
| 133 | rac 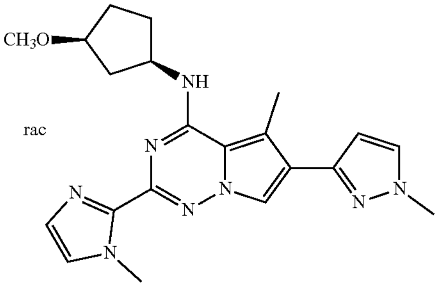 (133) | rac N-((1R,3S)-3-Methoxycyclopentyl)-5-methyl-2-(1-methyl-1H-imidazol-2-yl)-6-(1-methyl-1H-pyrazol-3-yl)pyrrolo[2,1-f][1,2,4]triazin-4-amine | 8.2 mg (6.5%) | 100% | 407.2 | 407.2 | (500 MHz, CD3OD) δ 2.00 (m, 7H), 2.60 (s, 3H), 3.29 (m, 2H), 3.92 (s, 3H), 4.04 (m, 4H), 5.01 (m, 1H), 6.48 (d, 1H), 7.10 (m, 2H), 7.60 (m, 1H), 7.75 (m, 1H) |

TABLE 1-continued

Compounds and Analytical Data

| Example | Structure | Name | (Amount Yield)* | Purity | Calc'd [M + 1] | [Found M + 1] | $^1$H NMR |
|---|---|---|---|---|---|---|---|
| 136 | 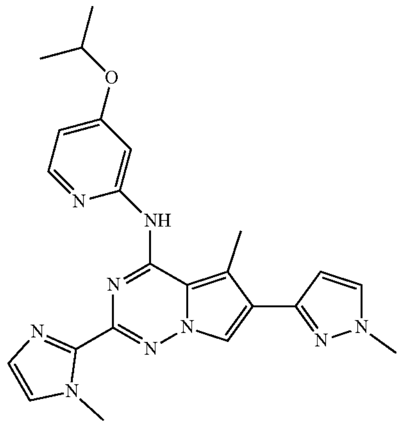 (136) | N-(4-Isopropoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 26 mg | 100% | 444.2 | 444.2 | NA |
| 137 | 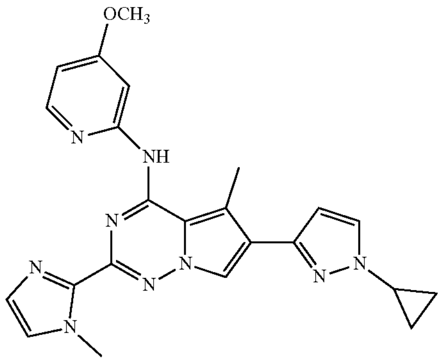 (137) | 6-(1-Cyclopropyl-1H-pyrazol-3-yl)-N-(4-methoxypyridin-2-yl)-5-methyl-2-(1-methyl-1H-imidazol-2-yl)pyrrolo[2,1-f][1,2,4]triazin-4-amine | 31.9 mg (24.0%) | 100% | 442.2 | 442.2 | (500 MHz, DMSO-$d_6$) δ 0.99 (m, 4H), 2.84 (s, 3H), 3.69 (quin, 1H), 3.90 (s, 3H), 4.01 (s, 3H), 6.53 (s, 1H), 6.70 (m, 2H), 7.14 (m, 1H), 7.45 (m, 1H), 8.00 (m, 3H), 14.98 (br s, 1H). |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 138 | 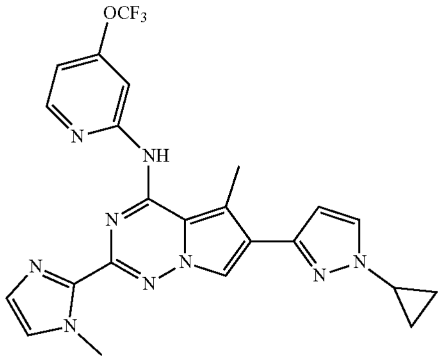 (138) | 6-(1-Cyclopropyl-1H-pyrazol-3-yl)-5-methyl-2-(1-methyl-1H-imidazol-2-yl)-N-(4-(trifluoromethoxy)pyridin-2-yl)pyrrolo[2,1-f][1,2,4]triazin-4-amine | 46.3 mg (45.0%) | 100% | 496.2 | 496.0 | (500 MHz, DMSO-$d_6$) δ 1.00 (m, 4H), 2.88 (s, 3H), 3.90 (m, 4H), 6.52 (m, 1H), 7.02 (m, 3H), 7.50 (s, 1H), 7.78 (m, 1H), 7.89 (m, 1H), 8.50 (d, 1H), 14.52 (br s, 1H). |
| 139 | 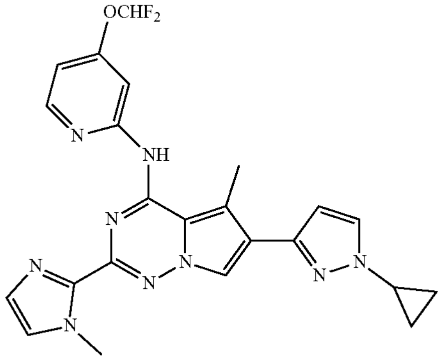 (139) | 6-(1-Cyclopropyl-1H-pyrazol-3-yl)-N-(4-(difluoromethoxy)pyridin-2-yl)-5-methyl-2-(1-methyl-1H-imidazol-2-yl)pyrrolo[2,1-f][1,2,4]triazin-4-amine | 10.2 mg (10.0%) | 94% | 478.2 | 478.2 | NA |

TABLE 1-continued
Compounds and Analytical Data
| Example | Structure | Name | (Amount Yield)* | Purity | Calc'd [M + 1] | [Found M + 1] | $^1$H NMR |
|---|---|---|---|---|---|---|---|
| 140 | 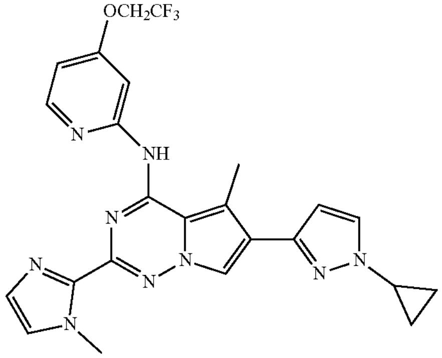 (140) | 6-(1-Cyclopropyl-1H-pyrazol-3-yl)-5-methyl-2-(1-methyl-1H-imidazol-2-yl)-N-(4-(2,2,2-trifluoroethoxy)pyridin-2-yl)pyrrolo[2,1-f][1,2,4]triazin-4-amine | 24.4 mg (22.0%) | 100% | 510.2 | 510.2 | NA |
| 141 | 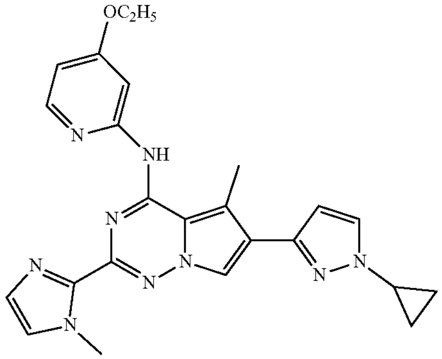 (141) | 6-(1-Cyclopropyl-1H-pyrazol-3-yl)-N-(4-ethoxypyridin-2-yl)-5-methyl-2-(1-methyl-1H-imidazol-2-yl)pyrrolo[2,1-f][1,2,4]triazin-4-amine | 22.1 mg (18.0%) | 100% | 456.2 | 456.2 | NA |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 142 | 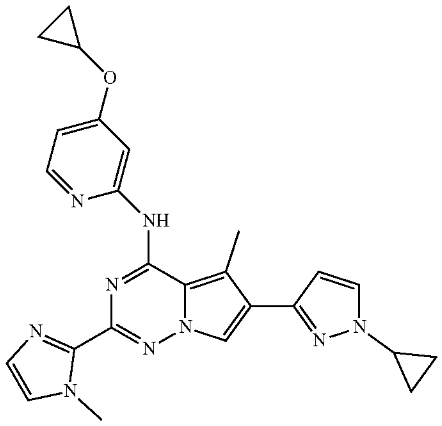 (142) | N-(4-Cyclopropoxypyridin-2-yl)-6-(1-cyclopropyl-1H-pyrazol-3-yl)-5-methyl-2-(1-methyl-1H-imidazol-2-yl)pyrrolo[2,1-f][1,2,4]triazin-4-amine | 18.3 mg (14.0%) | 100% | 468.2 | 468.2 | NA |
| 143 | 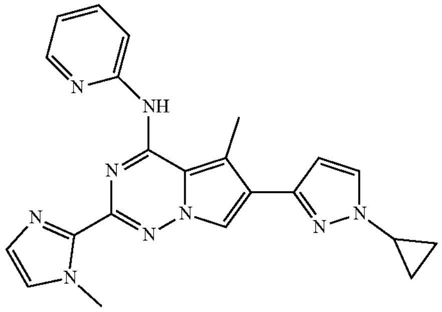 (143) | 6-(1-Cyclopropyl-1H-pyrazol-3-yl)-5-methyl-2-(1-methyl-1H-imidazol-2-yl)-N-(pyridin-2-yl)pyrrolo[2,1-f][1,2,4]triazin-4-amine | 25.6 mg (29.9%) | 100% | 412.2 | 412.2 | (500 MHz, DMSO-$d_6$) δ 1.00 (m, 4H), 2.88 (s, 3H), 3.78 (quin, 1H), 4.02 (s, 3H), 6.51 (s, 1H), 7.18 (m, 3H), 7.49 (s, 1H), 7.80 (m, 3H), 8.37 (d, 1H), 14.80 (br s, 1H) |

TABLE 1-continued
| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 144 | 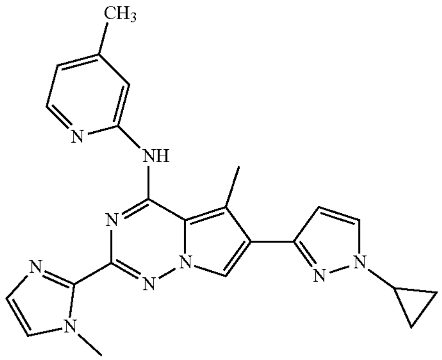 (144) | 6-(1-Cyclopropyl-1H-pyrazol-3-yl)-5-methyl-2-(1-methyl-1H-imidazol-2-yl)-N-(4-methylpyridin-2-yl)pyrrolo[2,1-f][1,2,4]triazin-4-amine | 13.5 mg (14.0%) | 100% | 426.2 | 426.2 | NA |
| 145 | 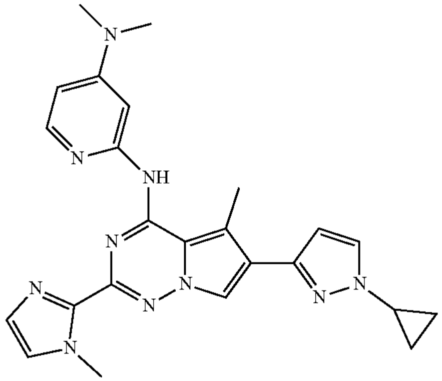 (145) | $N^2$-(6-(1-Cyclopropyl-1H-pyrazol-3-yl)-5-methyl-2-(1-methyl-1H-imidazol-2-yl)pyrrolo[2,1-f][1,2,4]triazin-4-yl)-$N^4$,$N^4$-dimethylpyridine-2,4-diamine | 20.6 mg (16.0%) | 100% | 455.2 | 455.2 | NA |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 146 | 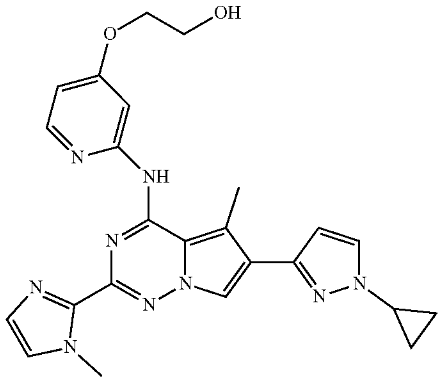 (146) | 2-((2-((6-(1-Cyclopropyl-1H-pyrazol-3-yl)-5-methyl-2-(1-methyl-1H-imidazol-2-yl)pyrrolo[2,1-f][1,2,4]triazin-4-yl)amino)pyridin-4-yl)oxy)ethan-1-ol | 9.2 mg (9.0%) | 95% | 472.2 | 472.2 | NA |
| 147 | 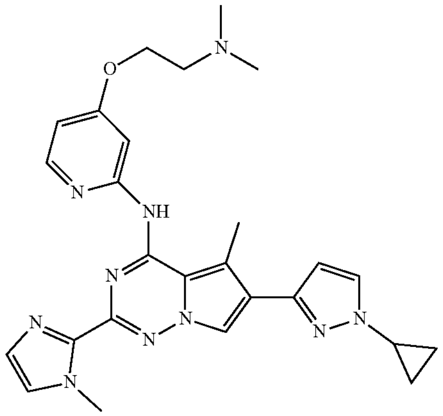 (147) | 6-(1-Cyclopropyl-1H-pyrazol-3-yl)-N-(4-(2-(dimethylamino)ethoxy)pyridin-2-yl)-5-methyl-2-(1-methyl-1H-imidazol-2-yl)pyrrolo[2,1-f][1,2,4]triazin-4-amine | 27.0 mg (25.0%) | 100% | Calc'd m/z [M + 2]/2 = 250.0 | Calc'd m/z [M + 2]/2 = 250.0 | (500 MHz, $CD_3OD$) δ 1.10 (m, 4H), 2.20 (s, 6H), 2.68 (t, 2H), 2.78 (s, 3H), 3.69 (quin, 1H), 4.08 (s, 3H), 4.21 (t, 2H), 6.34 (m, 2H), 6.47 (d, 1H), 7.11 (s, 1H), 7.28 (s, 1H), 7.69 (d, 1H), 7.80 (m, 2H), NH is not observed. |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1H$ NMR |
| 148 | 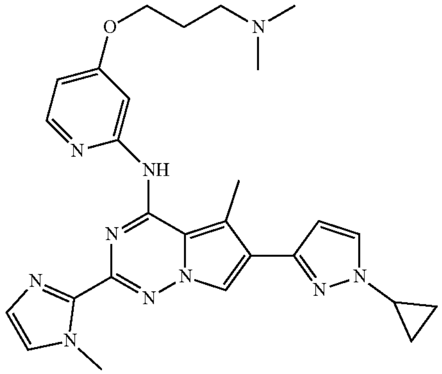 (148) | 6-(1-Cyclopropyl-1H-pyrazol-3-yl)-N-(4-(3-(dimethylamino)propoxy)pyridin-2-yl)-5-methyl-2-(1-methyl-1H-imidazol-2-yl)pyrrolo[2,1-f][1,2,4]triazin-4-amine | 28.3 (25.0%) | 99% | Calc'd m/z [M + 2]/2 = 257.2 | Calc'd m/z [M + 2]/2 = 257.2 | (500 MHz, DMSO-$d_6$) δ 1.00 (m, 2H), 1.87 (t, 2H), 2.10 (s, 6H), 2.24 (t, 2H), 2.79 (s, 3H), 3.74 (quin, 1H), 3.89 (s, 3H), 4.19 (t, 2H), 6.18 (d, 1H), 6.49 (d, 1H), 6.96 (s, 1H), 7.25 (m, 2H), 7.75 (m, 2H), 7.85 (d, 1H). |
| 149 | 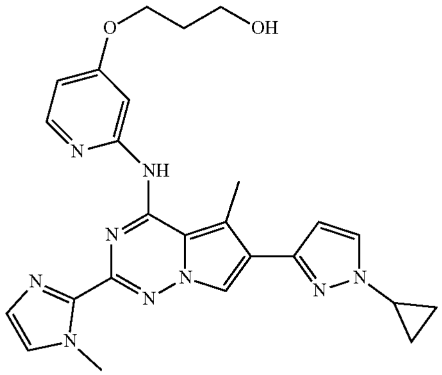 (149) | 3-((2-((6-(1-Cyclopropyl-1H-pyrazol-3-yl)-5-methyl-2-(1-methyl-1H-imidazol-2-yl)pyrrolo[2,1-f][1,2,4]triazin-4-yl)amino)pyridin-4-yl)oxy)propan-1-ol | 19.3 mg (18.0%) | 95% | 486.2 | 486.4 | NA |

TABLE 1-continued

| Compounds and Analytical Data | | | | | | | |
|---|---|---|---|---|---|---|---|
| Example | Structure | Name | (Amount Yield)* | Purity | Calc'd [M + 1] | [Found M + 1] | $^1$H NMR |
| 150 | 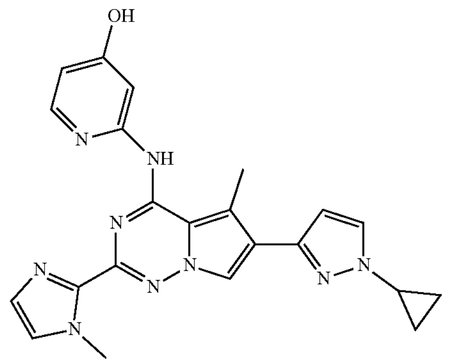 (150) | 2-((6-(1-Cyclopropyl-1H-pyrazol-3-yl)-5-methyl-2-(1-methyl-1H-imidazol-2-yl)pyrrolo[2,1-f][1,2,4]triazin-4-yl)amino)pyridin-4-ol | 11.3 mg (12.0%) | 100% | 428.2 | 428.2 | (500 MHz, DMSO-$d_6$) δ 1.00 (m. 4H), 2.88 (s, 3H), 3.78 (quin, 1H), 4.00 (s, 3H), 6.50 (m, 2H), 7.12 (m, 1H), 7.49 (m, 1H), 8.00 (m, 4H). |

Table note:
*Amount and yield refer to the final total amount obtained and yield in the last step of the synthesis of the respective compound, respectively.

Example 151: Synthesis of Compound 151

(151)

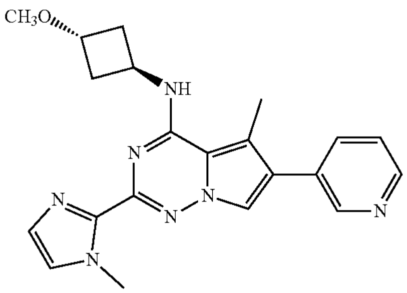

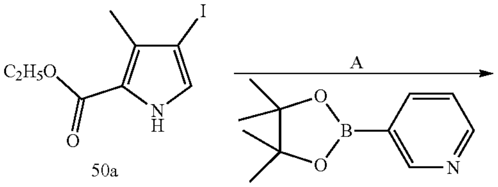

50a

151a

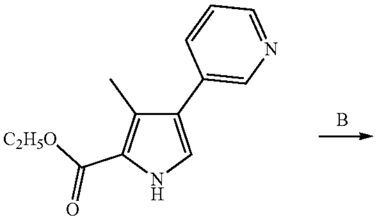

151b

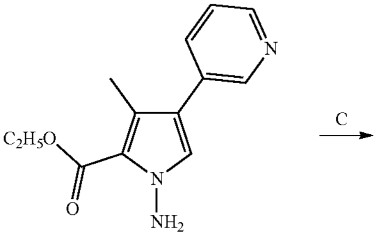

151c

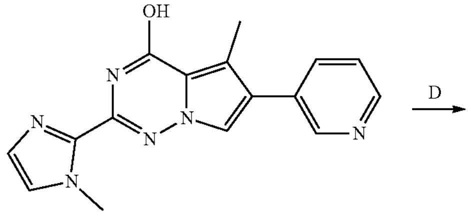

151d

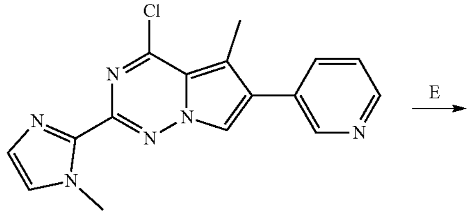

151e

-continued

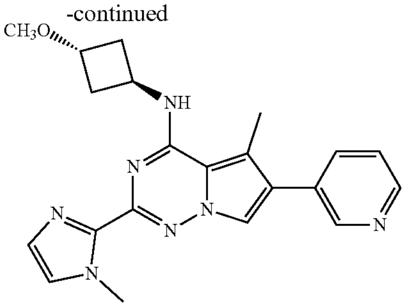

(151)

Step A: Ethyl 3-methyl-4-(pyridin-3-yl)-1H-pyrrole-2-carboxylate 151b

Ethyl 4-iodo-3-methyl-1H-pyrrole-2-carboxylate 50a (preparation described in Example 99, Procedure A, Step A) (20.0 g, 76.1 mmol), 3-(4,4,5,5-tetramethyl-1,3,2-dioxaborolan-2-yl)pyridine 151a (17.64 g, 86 mmol), [1,1'-bis (diphenylphosphino)ferrocene]dichloropalladium(II) dichloromethane adduct (5.85 g, 7.17 mmol) and cesium carbonate (49.59 g, 143.3 mmol) was dissolved in degassed dioxane (400 mL) under Ar. 20 mL of water was added via syringe. The reaction mixture was heated to 80° C. and stirred at this temperature for 16 h. The mixture was cooled to room temperature, filtered through celite and concentrated. The residue was purified by column chromatography (eluted by Hex:EtOAc 20:1 to 1:5) to give ethyl 3-methyl-4-(pyridin-3-yl)-1H-pyrrole-2-carboxylate 151b (9.5 g, 41.26 mmol, 57.6% yield).

Step B: Ethyl 1-amino-3-methyl-4-(pyridin-3-yl)-1H-pyrrole-2-carboxylate 151c

Sodium hydride (0.158 g, 6.58 mmmol) (60% in mineral oil) was added portionwise to a solution of ethyl 3-methyl-4-(pyridin-3-yl)-1H-pyrrole-2-carboxylate 151b (0.7 g, 3.04 mmol) in DMF (5 mL) at 0° C. The mixture was stirred for 1 h at room temperature. Then the mixture was cooled to 0° C. and O-(2,4-dinitrophenyl) hydroxylamine (0.787 g, 3.95 mmol) was added portionwise. The mixture was stirred for 16 h at room temperature. Then the mixture poured in ice water, diluted with EtOAc (10 mL), washed with water (5*5 mL), dried in vacuo and purified by flash chromatography ($SiO_2$, Hexane-EtOAc) to give ethyl 1-amino-3-methyl-4-(pyridin-3-yl)-1H-pyrrole-2-carboxylate 151c (0.6 g, 2.45 mmol, 57.6% yield).

Step C: 5-Methyl-2-(1-methyl-1H-imidazol-2-yl)-6-(pyridin-3-yl)pyrrolo[2,1-f][1,2,4]triazin-4-ol 151d Sodium hydride (521.75 mg, 21.74 mmol) (60% in mineral oil) was added portionwise (during 3 min) to the solution of ethyl 1-amino-3-methyl-4-(pyridin-3-yl)-1H-pyrrole-2-carboxylate 151c (1.6 g, 6.52 mmol) and 1-methyl-1H-imidazole-2-carbonitrile (838.00 mg, 7.83 mmol) in dioxane (20 mL). The reaction mixture was heated under reflux for 16 h. Then the mixture was cooled to room temperature, poured in ice water and neutralized by acetic acid. The formed precipitate was collected by filtration, washed with water (2*10 mL) and dried in vacuo to give 5-methyl-2-(1-methyl-1H-imidazol-2-yl)-6-(pyridin-3-yl)pyrrolo[2,1-f][1,2,4]triazin-4-ol 151d (900.0 mg, 2.94 mmol, 45% yield).

Step D: 4-Chloro-5-methyl-2-(1-methyl-1H-imidazol-2-yl)-6-(pyridin-3-yl)pyrrolo[2,1-f][1,2,4]triazine 151e 5-Methyl-2-(1-methyl-1H-imidazol-2-yl)-6-(pyridin-3-yl)pyrrolo[2,1-f][1,2,4]triazin-4-ol 151d (800.0 mg, 2.61 mmol) was in phosphoroyl trichloride (16.01 g, 104.44 mmol, 9.74 mL). The mixture was heated to 100° C. and stirred at this temperature for 36 h. The reaction mixture was concentrated in vacuo, poured in ice water (5 mL) and neutralized by $K_2CO_3$. The formed precipitate was collected by filtration, washed with water (2*5 mL) and dried in vacuo to give 4-chloro-5-methyl-2-(1-methyl-1H-imidazol-2-yl)-6-(pyridin-3-yl)pyrrolo[2,1-f][1,2,4]triazine 151e (700.0 mg, 2.16 mmol, 82.5% yield).

Step E: N-((1r,3r)-3-Methoxycyclobutyl)-5-methyl-2-(1-methyl-1H-imidazol-2-yl)-6-(pyridin-3-yl)pyrrolo[2,1-f][1,2,4]triazin-4-amine (151)

Using the procedure described in Example 103, Step A, (1r,3r)-3-methoxycyclobutan-1-amine hydrochloric acid salt (84.8 mg, 616.25 μmol), 4-chloro-5-methyl-2-(1-methyl-1H-imidazol-2-yl)-6-(pyridin-3-yl)pyrrolo[2,1-f][1,2,4]triazine 151e (100.0 mg, 307.91 μmol) and DIEA (199.11 mg, 1.54 mmol), gave N-((1r,3r)-3-methoxycyclobutyl)-5-methyl-2-(1-methyl-1H-imidazol-2-yl)-6-(pyridin-3-yl)pyrrolo[2,1-f][1,2,4]triazin-4-amine (151) as a yellow solid (39.6 mg, 33% yield) (100% purity). LCMS(ESI): Calculated [M+1] 390.2. Found [M+1] 390.2.

Example 152-Example 158

4-Chloro-5-methyl-2-(1-methyl-1H-imidazol-2-yl)-6-(pyridin-3-yl)pyrrolo[2,1-f][1,2,4]triazine 151e (100.0 mg, 307.91 μmol) was treated with the appropriate corresponding amine (1.2 eq) to produce the Example compounds (152)-(158) shown in Table C. Examples 152-155 used the procedure described in Example 103. Examples 156-158 used the procedure described in Example 102.

Example 159: Synthesis of Compound 159

(159)

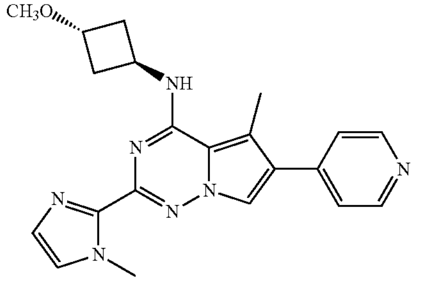

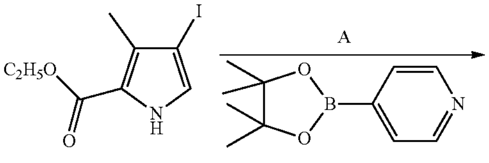

50a

159a

-continued

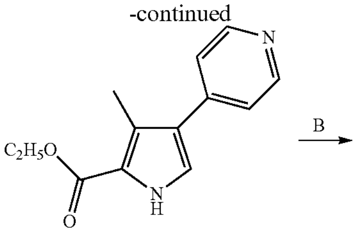

159b

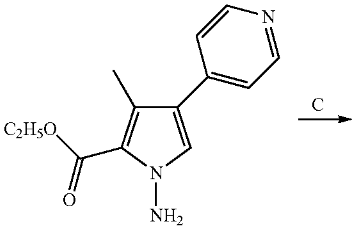

159c

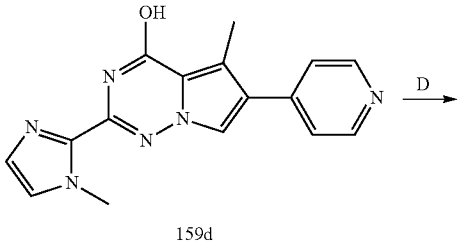

159d

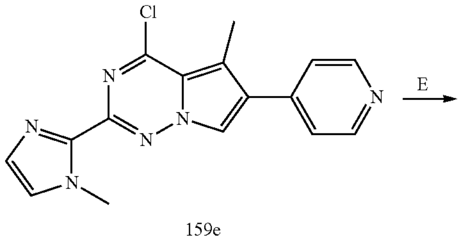

159e

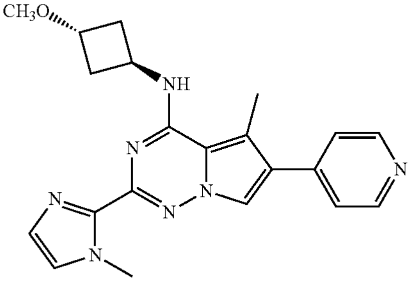

(159)

Step A: Ethyl 3-methyl-4-(pyridin-4-yl)-1H-pyrrole-2-carboxylate 159b

Ethyl 4-iodo-3-methyl-1H-pyrrole-2-carboxylate 50a (preparation described in Example 99, Procedure A, Step A) (30 g, 0,107 mol) and pyridin-4-ylboronic acid 159a (15.86 g, 0,129 mol) were dissolved in degassed mixture of dioxane/water (9/1 by vol.). [1,1'-Bis(diphenylphosphino)ferrocene]dichloropalladium(II) dichloromethane adduct (9.4 g 0.0129 mol) and cesium carbonate (84.1 g, 0.258 mol) were added in Ar flow. The mixture was stirred at 100° C. overnight, then diluted with EtOAc, washed with brine and evaporated. Crude product was purified by FCC (Hex:

EtOAc 4:1) to give ethyl 3-methyl-4-(pyridin-4-yl)-1H-pyrrole-2-carboxylate 159b. (1 g 4.3 mmol).

Step B: Ethyl 1-amino-3-methyl-4-(pyridin-4-yl)-1H-pyrrole-2-carboxylate 159c

Ethyl 3-methyl-4-(pyridin-4-yl)-1H-pyrrole-2-carboxylate 159b (1 g, 4.3 mmol) was dissolved in DMF and the mixture was cooled to 0° C. Sodium hydride (160 mg, 5.2 mmol) was added in portions and the mixture was stirred at room temperature until the evolution of gas stopped (20 min), then it was cooled again and the solution of O-(2,4-dinitrophenyl) hydroxylamine (0.8546 mg, 4.3 mmol) in DMF was added dropwise at 0–+5 C. The mixture was stirred at room temperature overnight, then poured in a saturated solution of ammonium chloride, extracted with EtOAc, washed with water, brine and evaporated. Crude product ethyl 1-amino-3-methyl-4-(pyridin-4-yl)-1H-pyrrole-2-carboxylate 159c was used without further purification.

Step C: 5-Methyl-2-(1-methyl-1H-imidazol-2-yl)-6-(pyridin-4-yl)pyrrolo[2,1-f][1,2,4]triazin-4-ol 159d Ethyl 1-amino-3-methyl-4-(pyridin-4-yl)-1H-pyrrole-2-carboxylate 159c (1 g, 4.08 mmol) and 1-methyl-1H-imidazole-2-carbonitrile (518.1 mg, 4.83 mmol) were dissolved in dioxane. Sodium hydride (212.8 mg, 8.866 mmol) was added in portions and the mixture was heated at 100° C. overnight. Crude product was purified by FCC ($CHCl_3$: MeOH, gradient elution (TLC 20:1 Rf=0.6, first flake)) to give 5-Methyl-2-(1-methyl-1H-imidazol-2-yl)-6-(pyridin-4-yl)pyrrolo[2,1-f][1,2,4]triazin-4-ol 159d (400.0 mg, 95.0% purity, 1.307 mmol).

Step D: 4-Chloro-5-methyl-2-(1-methyl-1H-imidazol-2-yl)-6-(pyridin-4-yl)pyrrolo[2,1-f][1,2,4]triazine 159e 5-Methyl-2-(1-methyl-1H-imidazol-2-yl)-6-(pyridin-4-yl)pyrrolo[2,1-f][1,2,4]triazin-4-ol 159d (800.0 mg, 2.61 mmol) was in phosphoroyl trichloride (16.01 g, 104.44 mmol, 9.74 mL). The mixture was heated to 100° C. and stirred at this temperature for 16 h. The reaction mixture was concentrated in vacuo, poured in ice water (5 mL) and neutralized by $K_2CO_3$. The formed precipitate was collected by filtration, washed with water (2*5 mL) and dried in vacuo to give 4-chloro-5-methyl-2-(1-methyl-1H-imidazol-2-yl)-6-(pyridin-4-yl)pyrrolo[2,1-f][1,2,4]triazine 159e (700.0 mg, 2.16 mmol, 82.5% yield).

Step E: N-((1r,3r)-3-Methoxycyclobutyl)-5-methyl-2-(1-methyl-1H-imidazol-2-yl)-6-(pyridin-4-yl)pyrrolo[2,1-f][1,2,4]triazin-4-amine (159)

DIEA (155.82 mg, 1.21 mmol, 210.0 μL) was added in one portion to the solution of 4-chloro-5-methyl-2-(1-methyl-1H-imidazol-2-yl)-6-(pyridin-4-yl)pyrrolo[2,1-f][1,2,4]triazine 159e (97.57 mg, 300.42 μmol) and (1r,3r)-3-methoxycyclobutan-1-amine hydrochloride (82.68 mg, 600.84 μmol) in DMF (1 mL). The mixture was heated to 100° C. and stirred at this temperature for 16 h. The mixture was purified by HPLC to give N-((1r,3r)-3-methoxycyclobutyl)-5-methyl-2-(1-methyl-1H-imidazol-2-yl)-6-(pyridin-4-yl)pyrrolo[2,1-f][1,2,4]triazin-4-amine (159) (20.0 mg, 51.35 μmol, 17.1% yield) (purity 100%). LCMS(ESI): Calculated [M+1] 390.2. Found [M+1] 390.2. $^1H$ NMR (500 MHZ, DMSO-$d_6$) δ (ppm) 2.29 (m, 2H), 2.41 (m, 2H), 2.64 (s, 3H), 3.11 (s, 3H), 4.00 (m, 4H), 4.80 (m, 1H), 6.96 (d, 1H), 7.23 (m, 2H), 7.49 (m, 2H), 8.05 (d, 1H), 8.58 (m, 2H).

Example 160: Synthesis of Compound 160

(160)

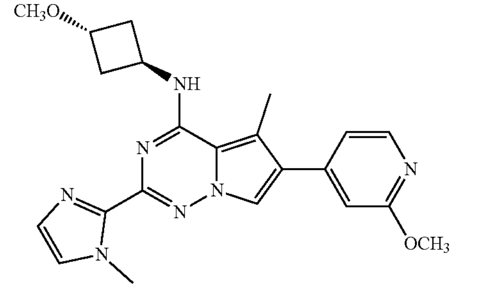

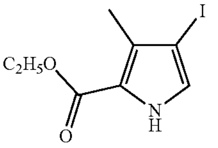

50a

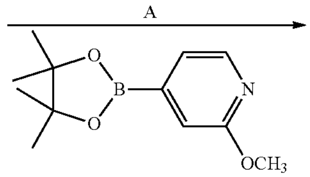

160a

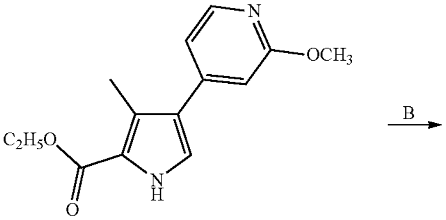

160b

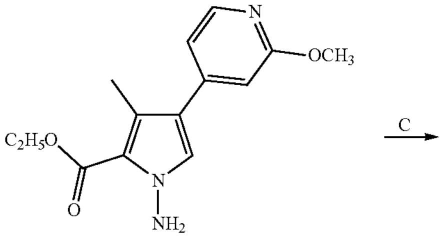

160c

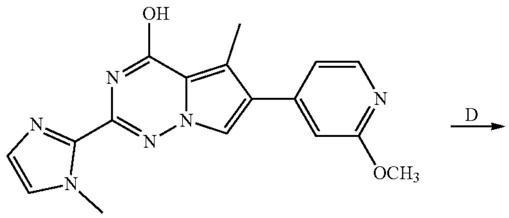

160d

-continued

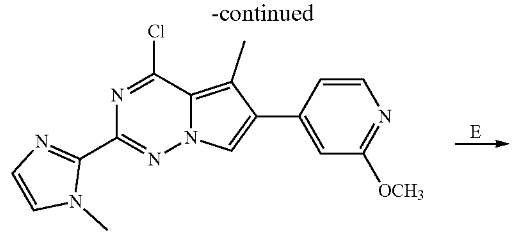

160e

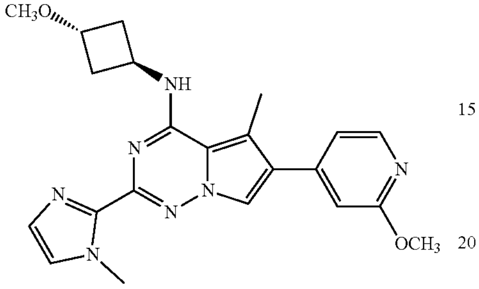

(160)

Step A: Ethyl 4-(2-methoxypyridin-4-yl)-3-methyl-1H-pyrrole-2-carboxylate 160b

Ethyl 4-iodo-3-methyl-1H-pyrrole-2-carboxylate 50a (preparation described in Example 99, Procedure A, Step A) (4.5 g, 16.12 mmol), 2-methoxy-4-(4,4,5,5-tetramethyl-1,3,2-dioxaborolan-2-yl)pyridine 160a (4.55 g, 19.35 mmol), $Pd(dppf)Cl_2 \cdot 2DCM$ (1.32 g, 1.61 mmol) and cesium carbonate (10.51 g, 32.25 mmol) was dissolved in degassed dioxane (90 mL) under Ar. 4.5 mL of water was added via syringe. The reaction mixture was heated to 80° C. and stirred at this temperature for 16 h. The mixture was cooled to room temperature, filtered through celite and concentrated. The residue was purified by column chromatography (eluted by Hexane: EtOAc 20:1 to 1:2). Ethyl 4-(2-methoxypyridin-4-yl)-3-methyl-1H-pyrrole-2-carboxylate 160b (1.0 g, 3.84 mmol, 23.8% yield) was obtained as light-yellow powder.

Step B: Ethyl 1-amino-4-(2-methoxypyridin-4-yl)-3-methyl-1H-pyrrole-2-carboxylate 160c To solution of Ethyl 4-(2-methoxypyridin-4-yl)-3-methyl-1H-pyrrole-2-carboxylate 160b (1.0 g, 3.84 mmol) in DMF (20 mL) sodium hydride (199.82 mg, 8.33 mmol) was added at 0° C. After 1 hour O-(2,4-dinitrophenyl) hydroxylamine (994.8 mg, 5.0 mmol) in DMF was added dropwise. Reaction mixture was stirred at room temperature overnight. An aqueous solution of $NH_4Cl$ was added to reaction mixture, extracted with EtOAc (3*25 mL), combined EtOAc was washed with water (7*15 mL), dried and evaporated under reduce pressure to give ethyl 1-amino-4-(2-methoxypyridin-4-yl)-3-methyl-1H-pyrrole-2-carboxylate 160c (1.1 g, 80.9% purity, 3.23 mmol, 84.1% yield).

Step C: 6-(2-Methoxypyridin-4-yl)-5-methyl-2-(1-methyl-1H-imidazol-2-yl)pyrrolo[2,1-f][1,2,4]triazin-4-ol 160d Sodium hydride (319.64 mg, 13.32 mmol) (60% in mineral oil) was added portionwise (during 3 min) to the solution of ethyl 1-amino-4-(2-methoxypyridin-4-yl)-3-methyl-1H-pyrrole-2-carboxylate 160c (1.1 g, 4.0 mmol) and 1-methyl-1I-imidazole-2-carbonitrile (428.01 mg, 4.0 mmol) in dioxane (20 mL). The reaction mixture was heated under reflux for 16 h. Then the mixture was cooled to room temperature, poured in ice water and neutralized by acetic acid. The formed precipitate was collected by filtration, washed by water (2*10 mL) and dried in vacuo to give 6-(2-methoxypyridin-4-yl)-5-methyl-2-(1-methyl-1H-imidazol-2-yl)pyrrolo[2,1-f][1,2,4]triazin-4-ol 160d (400.0 mg, 1.19 mmol, 29.8% yield).

Step D: 4-Chloro-6-(2-methoxypyridin-4-yl)-5-methyl-2-(1-methyl-1H-imidazol-2-yl)pyrrolo[2,1-f][1,2,4]triazine 160e 6-(2-Methoxypyridin-4-yl)-5-methyl-2-(1-methyl-1H-imidazol-2-yl)pyrrolo[2,1-f][1,2,4]triazin-4-ol 160d (3.0 g, 8.92 mmol) was dissolved in phosphoroyl trichloride (54.71 g, 356.82 mmol, 33.26 mL). The mixture was heated to 100° C. and stirred at this temperature for 16 h. The reaction mixture was concentrated in vacuo, poured in ice water (5 mL) and neutralized by $K_2CO_3$. The formed precipitate was collected by filtration, washed by water (2*5 mL) and dried in vacuo to give 4-chloro-6-(2-methoxypyridin-4-yl)-5-methyl-2-(1-methyl-1H-imidazol-2-yl)pyrrolo[2,1-f][1,2,4]triazine 160e (2.2 g, 6.12 mmol, 69.5% yield).

Step E: N-((1r,3r)-3-Methoxycyclobutyl)-6-(2-methoxypyridin-4-yl)-5-methyl-2-(1-methyl-1H-imidazol-2-yl)pyrrolo[2,1-f][1,2,4]triazin-4-amine (160)

Using arylation procedure A, DIEA (288.04 mg, 2.23 mmol), 4-chloro-6-(2-methoxypyridin-4-yl)-5-methyl-2-(1-methyl-1H-imidazol-2-yl)pyrrolo[2,1-f][1,2,4]triazine 160e (200.0 mg, 556.77 μmol) and (1r,3r)-3-methoxycyclobutan-1-amine (77.01 mg, 668.61 μmol) gave N-((1r,3r)-3-Methoxycyclobutyl)-6-(2-methoxypyridin-4-yl)-5-methyl-2-(1-methyl-1H-imidazol-2-yl)pyrrolo[2,1-f][1,2,4]triazin-4-amine (160) as a yellow solid (11.4 mg, 4.8% yield) (purity 99%). LCMS(ESI) Calculated [M+1] 420.2. Found [M+1] 420.2. $^1H$ NMR (500 MHZ, DMSO-$d_6$) δ (ppm) 2.38 (m, 2H), 2.41 (m, 2H), 2.60 (s, 3H), 3.12 (s, 3H), 3.88 (s, 3H), 3.91 (s, 3H), 4.80 (m, 1H), 6.92 (m, 2H), 7.11 (d, 1H), 7.25 (m, 2H), 8.02 (m, 2H), 8.15 (d, 1H).

Examples 161-164

4-Chloro-6-(2-methoxypyridin-4-yl)-5-methyl-2-(1-methyl-1H-imidazol-2-yl)pyrrolo[2,1-f][1,2,4]triazine 160e (200.0 mg, 556.77 μmol) was treated with the appropriate corresponding amine (1.2 eq) using the procedure described in Example 103 to produce the Example compounds (161)-(164) shown in Table C.

Example 165: Synthesis of Compound 165

(165)

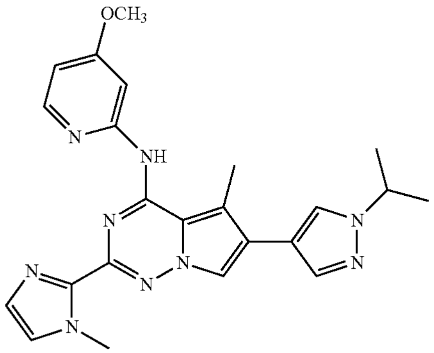

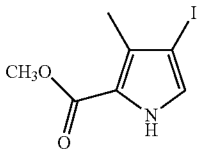

1b

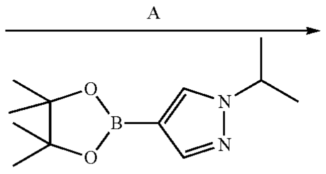

165a

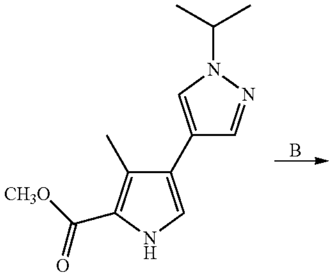

165b

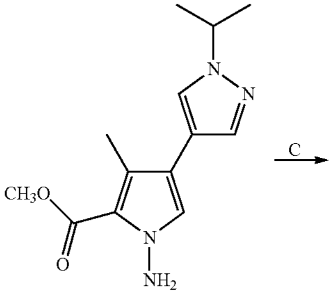

165c

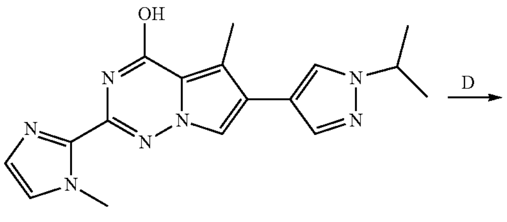

165d

-continued

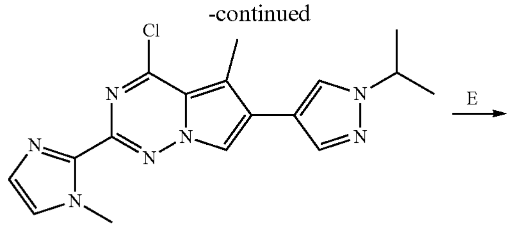

165d

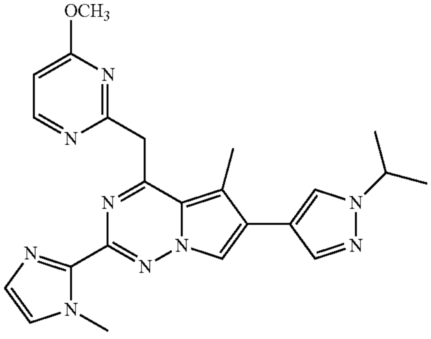

(165)

Step A: Methyl 4-(1-isopropyl-1H-pyrazol-4-yl)-3-methyl-1H-pyrrole-2-carboxylate 165b Under Ar atmosphere methyl 4-iodo-3-methyl-1H-pyrrole-2-carboxylate (6.0 g, 22.6 mmol), 1-isopropyl-4-(4,4,5,5-tetramethyl-1,3,2-dioxaborolan-2-yl)-1H-pyrazole 165a (5.4 g, 22.6 mmol), $Cs_2CO_3$ (14.7 g, 45.2 mmol) and Pd (dppf) $C_{12}$ (1.7 g, 2.26 mmol) were suspended in degassed dioxane (18.0 mL). After stirring for 2 min degassed $H_2O$ (0.9 mL) was added. The reaction mixture was stirred at 80° C. for 4 days. The mixture was cooled to room temperature, filtered thought Celite and concentrated under reduced pressure to give 6.88 g of black oil. This product was purified by column chromatography on silica gel (255 g): toluene: acetone 9:1 fraction 1 (500 mL); toluene: acetone 9:1 fractions 2-20 (100 mL each). Fractions 7-19 were combined and evaporated to give 1.83 g (32.7%) of methyl 4-(1-isopropyl-1H-pyrazol-4-yl)-3-methyl-1H-pyrrole-2-carboxylate 165b as a dark oil.

Step B: Methyl 1-amino-4-(1-isopropyl-1H-pyrazol-4-yl)-3-methyl-1H-pyrrole-2-carboxylate 165c 60% NaH (437 mg, 10.9 mmol) was washed with pentane (2×4 mL), dried under argon and suspended in dry DMF (40 mL). The solution of methyl 4-(1-isopropyl-1H-pyrazol-4-yl)-3-methyl-1H-pyrrole-2-carboxylate 165b (1.8 g; 7.28 mmol) in DMF (9 mL) was then added dropwise at 0° C. The resulting mixture was stirred at room temperature for 1 h. Reaction mixture was cooled to 0° C. and $Ph_2(O)PONH_2$ (2.2 g; 9.46 mmol) was added in one portion. Reaction mixture was stirred at 60° C. for 18 h. After cooling to room temperature water (100 mL) was added and the mixture was extracted with ether (3×100 mL). Combined organic layers were dried over $Na_2SO_4$ and concentrated to obtain 826 mg of methyl 1-amino-4-(1-isopropyl-1H-pyrazol-4-yl)-3-methyl-1H-pyrrole-2-carboxylate 165c as an orange oil. $^1H$ NMR ($CDCl_3$, 400 MHz) δ 7.52 (d, J=0.8 Hz, 1H), 7.41 (d, J=0.8 Hz, 1H), 6.98 (s, 1H), 5.54 (s, 2H), 4.51 (p, J=6.72 Hz, 1H), 3.37 (s, 3H), 2.35 (s, 3H), 1.53 (d, J=6.66 Hz, 6H).

Step C: 6-(1-Isopropyl-1H-pyrazol-4-yl)-5-methyl-2-(1-methyl-1H-imidazol-2-yl)pyrrolo[2,1-f][1,2,4]triazin-4-ol 165d 60% NaH (396 mg, 9.9 mmol) was washed with pentane (2×5 mL), dried under argon and suspended in dry 1,4-dioxane (2.0 mL) and then solution of methyl 1-amino-4-(1-isopropyl-1H-pyrazol-4-yl)-3-methyl-1H-pyrrole-2-carboxylate 165c (800 mg; 3.0 mmol) in dry 1,4-dioxane (6.0 mL) was added. The resulting mixture was stirred at room temperature for 0.5 h and solution of 1-methyl-1I-imidazole-2-carbonitrile (321 mg; 3.0 mmol) in dry 1,4-dioxane (4.0 mL) was added. Reaction mixture was stirred under reflux for 20 h. After cooling to RT, water (10 mL) was added, the mixture was neutralized with AcOH (0.5 mL) and extracted with $CHCl_3$ (3× 25 mL). Combined organic layers were dried over $Na_2SO_4$ and concentrated to obtain 833 mg of dark oil. This product was purified by column chromatography on silica gel (45 g): toluene: acetone 7:3 fraction 1-2 (100 mL each); toluene: acetone 1:1 fractions 3-4 (25 mL each). Pure fraction 3 was evaporated to give 17 mg of 6-(1-isopropyl-1H-pyrazol-4-yl)-5-methyl-2-(1-methyl-1H-imidazol-2-yl)pyrrolo[2,1-f][1,2,4]triazin-4-ol 165d as a precipitate. Impure fraction 2 was evaporated too, to give 290 mg of the orange oil. To this product $Et_2O$ was added and 99 mg of 6-(1-isopropyl-1H-pyrazol-4-yl)-5-methyl-2-(1-methyl-1H-imidazol-2-yl)pyrrolo[2,1-f][1,2,4]triazin-4-ol 165d as a white precipitate was obtained. $^1H$ NMR ($CDCl_3$, 400 MHz) δ 7.67 (d, J=0.8 Hz, 1H), 7.58 (d, J=0.8 Hz, 1H), 7.43 (s, 3H), 7.12 (d, J=1.07 Hz, 1H), 7.04 (d, J=1.1 Hz, 1H), 7.55 (p, J=6.7 Hz, 1H), 4.07 (s, 3H), 2.63 (s, 3H), 1.56 (d, J=6.74 Hz, 2H).

Step D: 4-Chloro-6-(1-isopropyl-1H-pyrazol-4-yl)-5-methyl-2-(1-methyl-1H-imidazol-2-yl)pyrrolo[2,1-f][1,2,4]triazine 165e 6-(1-Isopropyl-1H-pyrazol-4-yl)-5-methyl-2-(1-methyl-1H-imidazol-2-yl)pyrrolo[2,1-f][1,2,4]triazin-4-ol 165d (37 mg, 0.11 mmol) was dissolved in phosphoryl trichloride (800 mg, 5.28 mmol, 48.0 equiv). The mixture was stirred at 100° C. for 16 h. The reaction mixture was poured into ice water (5 mL) and neutralized with $K_2CO_3$ (pH~9!). The mixture was extracted three times with dichloromethane, dried over $Na_2SO_4$ and concentrated under reduced pressure to afford 4-chloro-6-(1-isopropyl-1H-pyrazol-4-yl)-5-methyl-2-(1-methyl-1H-imidazol-2-yl)pyrrolo[2,1-f][1,2,4]triazine 165e 40 mg (100% yield) as an orange oil.

Step E: 6-(1-Isopropyl-1H-pyrazol-4-yl)-N-(4-methoxypyridin-2-yl)-5-methyl-2-(1-methyl-1H-imidazol-2-yl)pyrrolo[2,1-f][1,2,4]triazin-4-amine (165)

A solution of 4-methoxypyridin-2-amine (35 mg, 0.25 mmol) in anhydrous DMF (1.0 mL) was added to a suspension of sodium hydride (13 mg, 0.54 mmol) in anhydrous DMF (1.5 mL). The mixture was stirred at room temperature in an argon atmosphere for 1 h. Then a solution of 4-chloro-6-(1-isopropyl-1H-pyrazol-4-yl)-5-methyl-2-(1-methyl-1H-imidazol-2-yl)pyrrolo[2,1-f][1,2,4]triazine 165e (50 mg, 0.14 mmol) in anhydrous DMF (1.5 mL) was added to the mixture. The mixture was heated at 70° C. for 2 h and then at 60° C. for 16 h. Then the reaction mixture was poured into water (20 mL) and extracted three times with ethyl ether (15 mL-15 mL-10 mL). The combined organic layers were washed with water (5×5 mL), dried over $Na_2SO_4$ and evaporated to dryness to afford 31 mg (48%) of dark yellow solid of crude 6-(1-isopropyl-1H-pyrazol-4-yl)-N-(4-methoxypyridin-2-yl)-5-methyl-2-(1-methyl-1H-imidazol-2-yl)pyrrolo[2,1-f][1,2,4]triazin-4-amine (165). The material (ca. 30 mg of crude) was dissolved in hot methyl 1-butyl ether (10 mL) and the solution was concentrated in a stream of argon to 5 mL. The concentrated solution was left overnight for crystallization in a refrigerator. The crystals formed were filtered off, washed with MTBE and dried in a stream of argon to afford a yellow solid of 6-(1-isopropyl-1H-pyrazol-4-yl)-N-(4-methoxypyridin-2-yl)-5-methyl-2-(1-methyl-1H-imidazol-2-yl)pyrrolo[2,1-f][1,2,4]triazin-4-amine (165) (17 mg, 27% yield, 93% purity). MS Calculated [M+1] 444.2. Found [M+1] 444.2. $^1H$ NMR ($CDCl_3$, 600 MHz) δ 7.67 (s, 1H), 7.57 (s, 1H), 7.18 (s, 1H), 7.01 (s, 1H), 6.56 (s, 1H), 4.55 (p, J=6.7 Hz, 1H), 4.08 (s, 3H), 3.95 (s, 3H), 2.79 (s, 3H), 1.67 (d, J=6.7 Hz, 6H).

Example 166: Synthesis of Compound 166

(166)

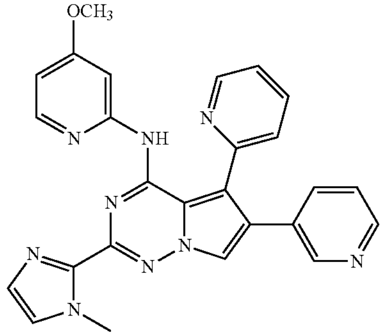

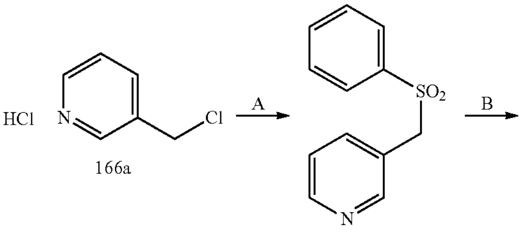

166a

166b

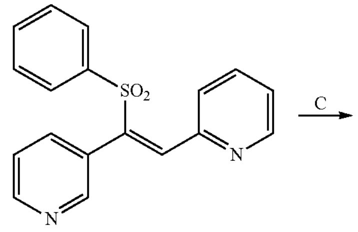

166c

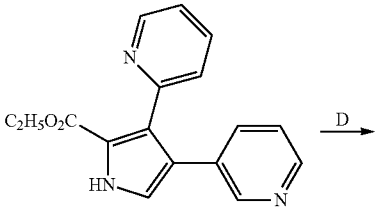

166d

-continued

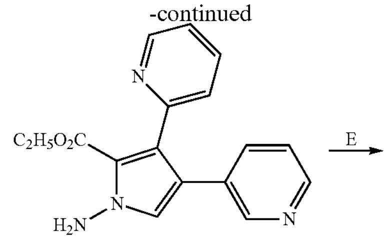

166e

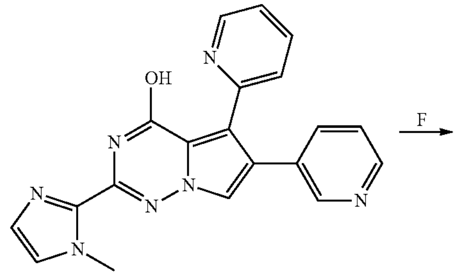

166f

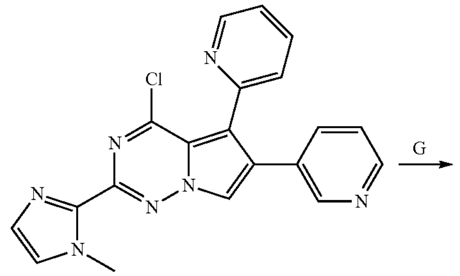

166g

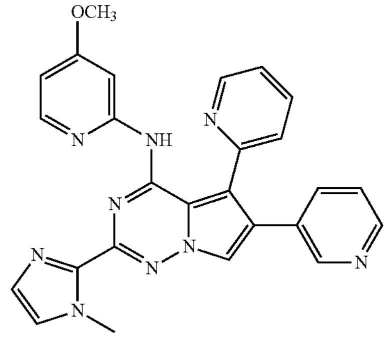

(166)

Step A: 3-((Phenylsulfonyl)methyl)pyridine 166b

Potassium acetate (13.22 g, 134.97 mmol) was added in one portion to a stirred solution of 3-(chloromethyl)pyridine hydrochloride salt (20.0 g, 122.7 mmol) and sodium benzenesulfinate (22.13 g, 134.97 mmol) in IPA (300 ml). The mixture was heated to 80° C. and stirred at this temperature overnight. Then reaction mixture was concentrated in vacuo, diluted with ice water (150 ml) and extracted 3 times by EtOAc (3*150 ml). The organic phase washed with water, brine, dried over $Na_2SO_4$ and concentrated in vacuo to give 3-((phenylsulfonyl)methyl)pyridine 166b (19.9 g, 95.0% purity, 81.04 mmol, 66% yield) as yellow solid.

LCMS(ESI) Rt=1.567 min. Calculated [M+1] 234.2. Found [M+1] 234.0. $[M+H]^+$ m/z: calcd 234.2; found 234.0; Rt=1.567 min.

Step B: (Z)-2-(2-(Phenylsulfonyl)-2-(pyridin-3-yl)vinyl)pyridine 166c

To 3-((phenylsulfonyl)methyl)pyridine 166b (17.5 g, 75.09 mmol) in THF (600 mL) was added LiHMDS (1.1 M in THF/Ethylbenzene, 150 mL), at −78° C. and the mixture was stirred for 45 min. To the solution was added pyridine-2-carbaldehyde (12.06 g, 112.64 mmol), and the mixture was stirred for 1 h. Diethyl chlorophosphonate (15.5 g, 90.11 mmol) was added, and the mixture was stirred for 1 h. Then LiHMDS (1.1 M in THF/ethylbenzene, 150 ml) was added at −78° C., and the mixture was stirred to ambient temperature. The resulting mixture was poured into sat. aq $NH_4Cl$ (400 mL) and extracted with EtOAc (3*300 mL). The organic phase was washed with water, brine, and dried over $Na_2SO_4$, then concentrated in vacuo and purified by FCC (Interchim; 330g $SiO_2$, chloroform/acetonitrile with acetonitrile from 0~30%, flow rate=127 mL/min, Rv=8.5-12 CV) to (Z)-2-(2-(phenylsulfonyl)-2-(pyridin-3-yl)vinyl)pyridine 166c (6.7 g, 95.0% purity, 19.74 mmol, 26.3% yield). LCMS(ESI) Rt=0.955 min.

Calculated [M+1] 322.2. Found [M+1] 322.2.

Step C: Ethyl 3-(pyridin-2-yl)-4-(pyridin-3-yl)-1H-pyrrole-2-carboxylate 166d

Potassium 1-butoxide (3.49 g, 31.17 mmol) was added portionwise to the solution of (Z)-2-(2-(phenylsulfonyl)-2-(pyridin-3-yl)vinyl)pyridine 166c (6.7 g, 20.78 mmol) and ethyl 2-isocyanoacetate (3.52 g, 31.17 mmol) in dry THF (140 mL) at (−10° C.), and stirred at room temperature overnight. Then the reaction mixture was diluted with ice water (100 mL) and extracted 3 times by EtOAc (3*1000 mL). The organic phase washed with water, brine, dried over $Na_2SO_4$, concentrated in vacuo to give ethyl 3-(pyridin-2-yl)-4-(pyridin-3-yl)-1H-pyrrole-2-carboxylate 166d (6.7 g, 75.0% purity, 17.13 mmol, 82.4% yield)

LCMS(ESI) Rt=1.285 min. Calculated [M+1] 294.2. Found [M+1] 294.2.

Step D: Ethyl 1-amino-3-(pyridin-2-yl)-4-(pyridin-3-yl)-1H-pyrrole-2-carboxylate 166e Sodium hydride (1.3 g, 32.5 mmol) (60% in mineral oil), was added portionwise to a solution of ethyl 3-(pyridin-2-yl)-4-(pyridin-3-yl)-1H-pyrrole-2-carboxylate 166d (6.7 g, 22.84 mmol) in DMF (70 mL) at 0° C. The mixture was stirred for 1 h at room temperature. Then the mixture was cooled to 0° C. and O-(2,4-dinitrophenyl) hydroxylamine (4.43 g, 22.27 mmol) was added portionwise. The mixture was stirred for 16 h at room temperature. Then the mixture poured in ice water, and extracted with EtOAc (3*20 mL). The organic phase washed with water, brine, dried over $Na_2SO_4$, concentrated in vacuo to give ethyl 1-amino-3-(pyridin-2-yl)-4-(pyridin-3-yl)-1H-pyrrole-2-carboxylate 166e (7.3 g, 70.0% purity, 16.57 mmol, 96.7% yield) as dark oil.

LCMS(ESI) Rt=1.298 min. Calculated [M+1] 309.2. Found [M+1] 309.2.

Step E: 2-(1-Methyl-1H-imidazol-2-yl)-5-(pyridin-2-yl)-6-(pyridin-3-yl)pyrrolo[2,1-f][1,2,4]triazin-4-ol 166f Sodium hydride (1.94 g, 0.04 mmol) (60% in mineral oil) was added portionwise to the solution of ethyl 1-amino-3-(pyridin-2-yl)-4-(pyridin-3-yl)-1H-pyrrole-2-carboxylate 166e (7.47 g, 24.23 mmol) and 1-methyl-1H-imidazole-2-carbonitrile (2.72 g, 25.44 mmol) in dry dioxane (80 mL). Then reaction mixture was heated 80° C. and stirred at this temperature for 16 h. Then the mixture was cooled to room temperature, poured in ice water, neutralized with acetic acid and extracted with EtOAc (3*50 mL). The organic phase washed with water, brine, dried over $Na_2SO_4$, concentrated in vacuo to give 2-(1-methyl-1H-imidazol-2-yl)-5-(pyridin-2-yl)-6-(pyridin-3-yl)pyrrolo[2,1-f][1,2,4]triazin-4-ol 166f (1.2 g, 90.0% purity, 2.92 mmol, 17.2% yield) and used for the next step without further purification.

Step F: 4-Chloro-2-(1-methyl-1H-imidazol-2-yl)-5-(pyridin-2-yl)-6-(pyridin-3-yl)pyrrolo[2,1-f][1,2,4]triazine 166g To the solution of 2-(1-methyl-1H-imidazol-2-yl)-5-(pyridin-2-yl)-6-(pyridin-3-yl)pyrrolo[2,1-f][1,2,4]triazin-4-ol 166f (1.2 g, 3.25 mmol) in $CH_3CN$ (45 mL), phosphoroyl trichloride (5.33 g, 35.09 mmol) was added dropwise. The mixture was heated to 80° C. and stirred at this temperature for 16 h and then concentrated in vacuo, poured in ice water (25 mL) and neutralized with $NaHCO_3$. The formed precipitate was collected by filtration, washed by water (2*20 mL) and dried in vacuo, to give 4-chloro-2-(1-methyl-1H-imidazol-2-yl)-5-(pyridin-2-yl)-6-(pyridin-3-yl)pyrrolo[2,1-f][1,2,4]triazine 166g (500.0 mg, 75.0% purity, 966.93 μmol, 33.1% yield) as a yellow solid. LCMS(ESI) Rt=1.528 min. Calculated [M+1] 388.2. Found [M+1] 388.2.

Step G: N-(4-Methoxypyridin-2-yl)-2-(1-methyl-1H-imidazol-2-yl)-5-(pyridin-2-yl)-6-(pyridin-3-yl)pyrrolo[2,1-f][1,2,4]triazin-4-amine (166)

Sodium hydride (43 mg, 1.07 mmol) (60% in mineral oil) was added in portionwise to the solution of 4-methoxypyridin-2-amine (108.54 mg, 874.86 μmol) in DMF (1 mL). The mixture was stirred at room temperature for 30 min, then 4-chloro-2-(1-methyl-1H-imidazol-2-yl)-5-(pyridin-2-yl)-6-(pyridin-3-yl)pyrrolo[2,1-f][1,2,4]triazine 166g (170.0 mg, 438.34 μmol) was added in one portion, and stirred overnight. After this time the resulting mixture was quenched by saturated $NH_4Cl$. The formed precipitate was collected by filtration, washed with water (2*1 mL) and purified by HPLC (column: XBridge BEH C18 100*19 mm, 5 microM (SYSTEM 0-2-10 min; 33-40-75% $H_2O$/MeOH/0.1$NH_4OH$; flow 30 mL/min ((loading pump 4 mL MeOH))) to give N-(4-methoxypyridin-2-yl)-2-(1-methyl-1H-imidazol-2-yl)-5-(pyridin-2-yl)-6-(pyridin-3-yl)pyrrolo[2,1-f][1,2,4]triazin-4-amine (166) (6.5 mg, 95.0% purity, 12.99 μmol, 3% yield). LCMS(ESI) Rt=0.929 min. Calculated [M+1] 476.2. Found [M+1] 476.0. $^1H$ NMR (500 MHZ, $CD_3OD$) δ (ppm) 3.89 (s, 3H), 4.01 (s, 3H), 6.59 (d, 1H), 6.91 (m, 1H), 7.10 (m, 3H), 7.39 (m, 2H), 7.69 (m, 1H), 7.82 (s, 1H), 8.02 (d, 1H), 8.40 (m, 3H), 8.74 (s, 1H).

Examples 167-168

4-Chloro-2-(1-methyl-1H-imidazol-2-yl)-5-(pyridin-2-yl)-6-(pyridin-3-yl)pyrrolo[2,1-f][1,2,4]triazine 166g was treated with the appropriate corresponding amine (1.2 eq) according to the procedure described in Example 102 to produce Example compound (167), and the procedure described in Example 103 to produce Example compound (168). Example compound (167) and Example compound (168) are shown in Table C along with analytical data.

Example 169: The Synthesis of Compound 169

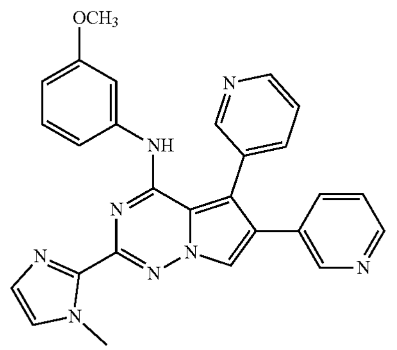

(169)

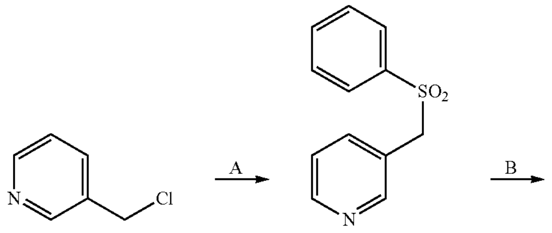

169a 169b

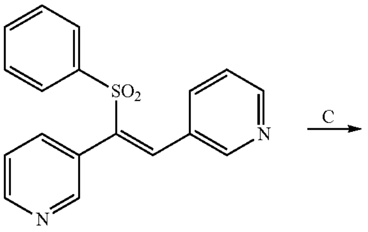

169c

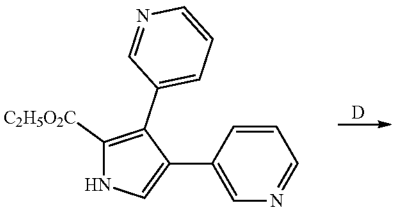

169d

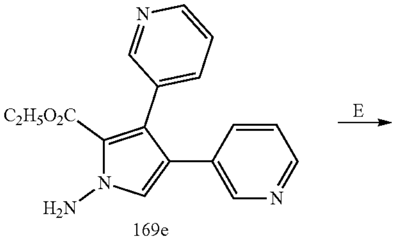

169e

-continued

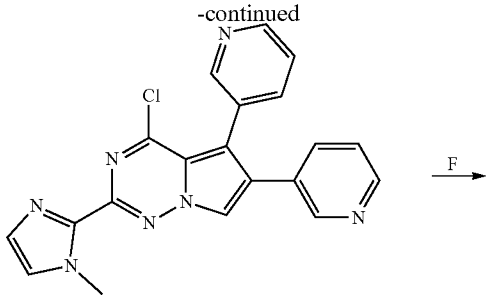

169f

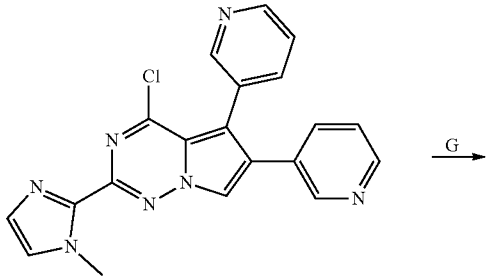

169g

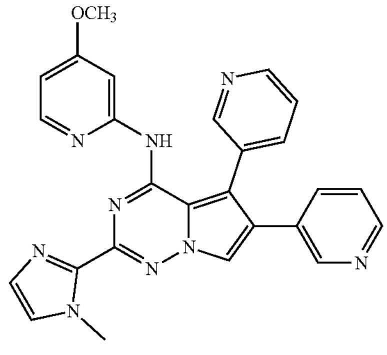

(169)

Step A: 3-((Phenylsulfonyl)methyl)pyridine 169b

Potassium acetate (6.58 g, 67.06 mmol) was added in one portion to a stirred solution of 3-(chloromethyl)pyridine hydrochloride 169a (10.0 g, 60.96 mmol) and sodium benzenesulfinate (11.01 g, 67.06 mmol) in isopropyl alcohol (150 mL). The mixture was heated to 80° C. and stirred at this temperature overnight. Then reaction mixture was concentrated in vacuo, diluted with ice water (150 mL) and extracted 3 times by EtOAc (3*150 mL). The organic phase washed with water, brine, dried over $Na_2SO_4$ and concentrated in vacuo to give 3-((phenylsulfonyl)methyl)pyridine 169b (9.8 g, 95.0% purity, 39.91 mmol, 65.5% yield) as yellow solid.

Step B: (Z)-3,3'-(1-(Phenylsulfonyl) ethene-1,2-diyl)dipyridine 169c

The mixture of 3-((phenylsulfonyl)methyl)pyridine 169b (8.3 g, 35.58 mmol) and pyridine-3-carbaldehyde (7.62 g, 71.16 mmol) in dry MeOH (100 mL) was added dropwise to the solution of sodium methanolate (2.5 g, 46.25 mmol) in MeOH (200 mL) at room temperature, and stirred overnight. Then reaction mixture was concentrated in vacuo, diluted with ice water (150 mL). Water was acidified to pH 5 and extracted 3 times by EtOAc (3*150 mL). The organic phase washed with water, brine, dried over $Na_2SO_4$, concentrated in vacuo and purified by FCC (Interchim, 220 g $SiO_2$, chloroform/acetonitrile (30-100%), flow rate=100 mL/min, 4.9-12.5 CV.) to give (Z)-3,3'-(1-(phenylsulfonyl) ethene-1,2-diyl)dipyridine 169c (4.8 g, 95.0% purity, 14.14 mmol, 39.8% yield) as white solid.

Step C: Ethyl 3,4-di(pyridin-3-yl)-1H-pyrrole-2-carboxylate 169d

Ethyl 2-isocyanoacetate (1.8 g, 15.91 mmol, 1.74 ml, 1.0 equiv) was added dropwise to the solution of (Z)-3,3'-(1-(phenylsulfonyl) ethene-1,2-diyl)dipyridine 169c (5.13 g, 15.91 mmol) and 2-methylpropan-2-ol (1.18 g, 15.91 mmol) in dry THF (100 mL) at 0° C., and stirred at room temperature overnight. Then reaction mixture was diluted with ice water (100 mL) and extracted 3 times by EtOAc (3*100 mL). The organic phase washed with water, brine, dried over $Na_2SO_4$, concentrated in vacuo and purified by FCC (A: Interchim; 80 g $SiO_2$ methyl t-butyl ether/methanol with methanol from 0~20%, flow rate=65 mL/min, Rv=8-12 CV) to give ethyl 3,4-di(pyridin-3-yl)-1H-pyrrole-2-carboxylate 169d (940.0 mg, 95.0% purity, 3.04 mmol, 19.1% yield) as yellow solid.

Step D: ethyl 1-amino-3,4-di(pyridin-3-yl)-1H-pyrrole-2-carboxylate 169e

Sodium hydride (165 mg, 4.125 mmol) (60% on mineral oil), was added portionwise to a solution of ethyl 3,4-di (pyridin-3-yl)-1H-pyrrole-2-carboxylate 169d (940.0 mg, 3.2 mmol) in DMF (30 mL) at 0° C. The mixture was stirred for 1 h at room temperature. Then the mixture was cooled to 0° C. and O-(2,4-dinitrophenyl) hydroxylamine (829.46 mg, 4.17 mmol) was added portionwise. The mixture was stirred for 16 h at room temperature. Then the mixture poured in ice water, to give ethyl 1-amino-3,4-di(pyridin-3-yl)-1H-pyrrole-2-carboxylate 169e (1.2 g, 66.0% purity, 2.57 mmol, 80.2% yield) as a dark oil.

Step E: 2-(1-methyl-1H-imidazol-2-yl)-5,6-di(pyridin-3-yl)pyrrolo[2,1-f][1,2,4]triazin-4-ol 169f Sodium hydride (0.311 g, 7.75 mmol) (60% in mineral oil) was added portionwise to the solution of ethyl 1-amino-3,4-di(pyridin-3-yl)-1H-pyrrole-2-carboxylate 169e (1.2 g, 3.89 mmol) and 1-methyl-1H-imidazole-2-carbonitrile (330.23 mg, 3.08 mmol) in dry dioxane (12 mL). Then reaction mixture was heated 80° C. and stirred at this temperature for 16 h. Then the mixture was cooled to room temperature, poured into ice water, neutralized with acetic acid and extracted with EtOAc (3*15 mL). The organic phase washed with water, brine, dried over $Na_2SO_4$, concentrated in vacuo and purified by HPLC ((column: Chromatorex C18 SMB100-5T 100*19 mm, 5 microM) SYSTEM 0-2-10 min; 23-30-55$H_2O$/MeOH, flow 30 mL/min (loading pump 4 mL MeOH)) to give 2-(1-methyl-1H-imidazol-2-yl)-5,6-di(pyridin-3-yl)pyrrolo[2,1-f][1,2,4]triazin-4-ol 169f (121.6 mg, 329.2 μmol, 12.8% yield).

Step F: 4-chloro-2-(1-methyl-1H-imidazol-2-yl)-5,6-di(pyridin-3-yl)pyrrolo[2,1-f][1,2,4]triazine 169g To the solution of 2-(1-methyl-1H-imidazol-2-yl)-5,6-di (pyridin-3-yl)pyrrolo[2,1-f][1,2,4]triazin-4-ol 169f (840.0 mg, 2.27 mmol) in $CH_3CN$ (20 mL), phosphoroyl trichloride (1.39 g, 9.1 mmol) was added dropwise. The mixture was heated to 80° C. and stirred at this temperature for 16 h and then concentrated in vacuo, poured into ice water (5 mL) and neutralized by $NaHCO_3$. The formed precipitate was collected by filtration, washed by water (2*20 mL) and dried in vacuo, to give 4-chloro-2-(1-methyl-1H-imidazol-2-yl)-5,6-di(pyridin-3-yl)pyrrolo[2,1-f][1,2,4]triazine 169g (700.0 mg, 73.0% purity, 1.32 mmol, 57.9% yield) as a black solid.

Step G: N-(4-methoxypyridin-2-yl)-2-(1-methyl-1H-imidazol-2-yl)-5,6-di(pyridin-3-yl)pyrrolo[2,1-f][1,2,4]triazin-4-amine (169)

The procedure described in Example 102 was implemented with sodium hydride (34 mg, 0.85 mmol) (60% in mineral oil), 4-chloro-2-(1-methyl-1H-imidazol-2-yl)-5,6-di(pyridin-3-yl)pyrrolo[2,1-f][1,2,4]triazine 169g (101.14 mg, 260.78 μmol) and 4-methoxypyridin-2-amine (178.08 mg, 1.38 mmol) to give N-(4-methoxypyridin-2-yl)-2-(1-methyl-1H-imidazol-2-yl)-5,6-di(pyridin-3-yl)pyrrolo[2,1-f][1,2,4]triazin-4-amine (169) as a beige solid (2.9 mg, 2.2% yield) (92% purity). LCMS(ESI) Rt=0.691 min. MS Calculated [M+1] 476.2. Found [M+1] 476.2.

Examples 170-171

4-Chloro-2-(1-methyl-1H-imidazol-2-yl)-5,6-di(pyridin-3-yl)pyrrolo[2,1-f][1,2,4]triazine 169g (101.14 mg, 260.78 μmol) was treated with the appropriate corresponding amine (1.2 eq) according to the procedure described in Example 102 to produce Example compound (170), and the procedure described in Example 103 to produce Example compound (171). Example compound (170) and Example compound (171) are shown in Table C.

Example 172: The Synthesis of Compound 172

(172)

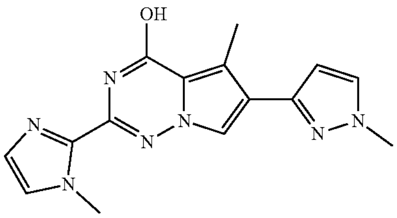

99h

5-Methyl-2-(1-methyl-1H-imidazol-2-yl)-6-(1-methyl-1H-pyrazol-3-yl)pyrrolo[2,1-f][1,2,4]triazin-4-ol 99h from Example 99, Procedure B, Step D was purified as Example Compound (172) (100% purity) LCMS(ESI) Calculated [M+1] 310.2 Found [M+1] 310.2. $^1$H NMR (500 MHz, DMSO-$d_6$) δ (ppm) 2.65 (s, 3H), 3.82 (S, 3H), 3.97 (s, 3H), 6.50 (d, 1H), 7.12 (s, 1H), 7.47 (d, 1H), 7.58 (d, 1H), 7.87 (d, 1H), 11.04 (br s, 1H).

Example 173: The Synthesis of Compound 173

(173)

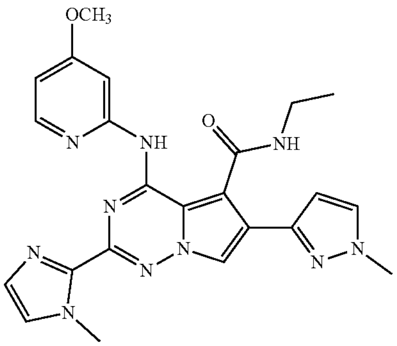

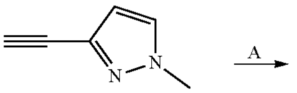

173a

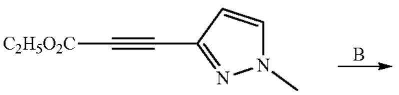

173b

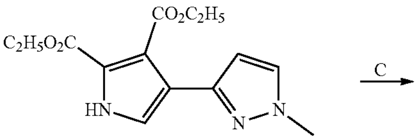

173c

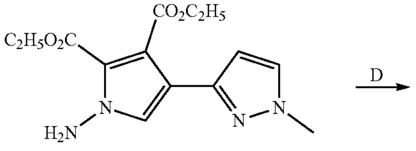

173d

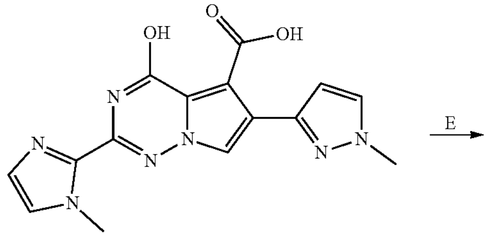

173e

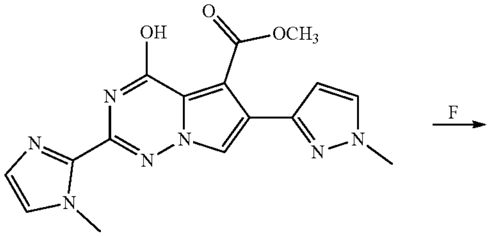

173f

-continued

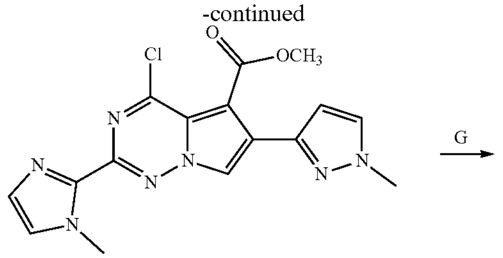

173g

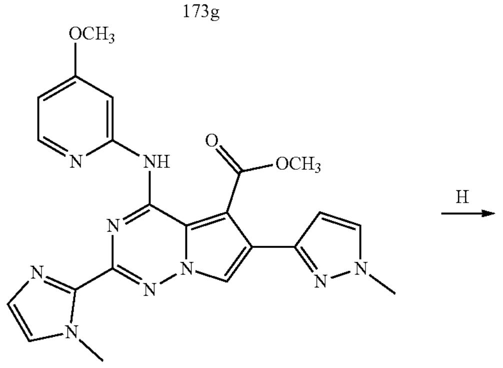

173h

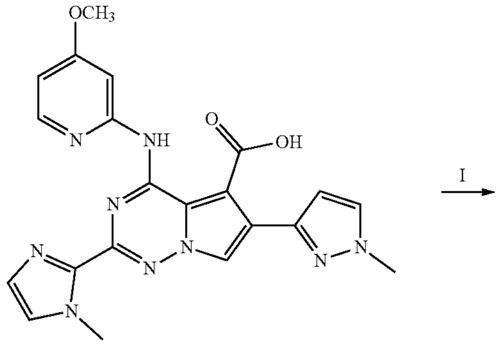

173i

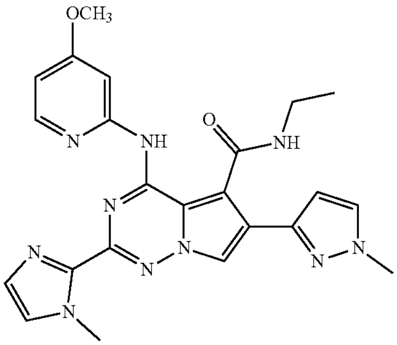

(173)

Step A: Ethyl 3-(1-methyl-1H-pyrazol-3-yl) propiolate 173b

To a solution of 3-ethynyl-1-methyl-1H-pyrazole 173a (5.0 g, 47.14 mmol) in THF at −78° C. n-BuLi (2.5M, 20.7 mL) was added dropwise and the solution was stirred at −78° C. for 15 min, followed by the addition of ethyl carbonochloridate (7.67 g, 70.7 mmol, 6.76 mL). The mixture was allowed to warm to 0° C. for 30 min. Then, the mixture was quenched with $H_2O$, diluted with EtOAc (50 mL), washed with $H_2O$ (2×20 mL), dried over $Na_2SO_4$ and evaporated under reduce pressure to give ethyl 3-(1-methyl-1H-pyrazol-3-yl) propiolate 173b (7.2 g, 82.0% purity, 33.13 mmol, 70.3% yield). LCMS Calculated [M+1] 179.0. Found [M+1] 179.0. Rt=1.121 min.

Step B: Diethyl 4-(1-methyl-1H-pyrazol-3-yl)-1H-pyrrole-2,3-dicarboxylate 173c

To the solution of ethyl 3-(1-methyl-1H-pyrazol-3-yl) propiolate 173b (2.0 g, 11.23 mmol) in dioxane (30 mL), 1,3-bis(diphenylphosphino) propane (694.48 mg, 1.68 mmol) and ethyl 2-isocyanoacetate (1.9 g, 16.84 mmol, 1.84 mL) were added under Ar atmosphere. The reaction mixture was stirred at 100° C. overnight and then cooled to room temperature. The volatiles were evaporated under reduce pressure. The residue was diluted with EtOAc (50 mL) and washed with water (3×15 mL). EtOAc was dried under $Na_2SO_4$, evaporated under reduce pressure to give crude compound which was purified by flash chromatography to give diethyl 4-(1-methyl-1H-pyrazol-3-yl)-1H-pyrrole-2,3-dicarboxylate 173c (1.4 g, 95% purity, 42.8% yield). $^1H$ NMR (500 MHZ, $CDCl_3$) δ (ppm) 1.38 (m, 6H), 3.81 (s, 3H), 4.32 (m, 4H), 6.27 (s, 1H), 7.11 (d, 1H), 7.27 (d, 1H), 9.36 (br s, 1H).

Step C: Diethyl 1-amino-4-(1-methyl-1H-pyrazol-3-yl)-1H-pyrrole-2,3-dicarboxylate 173d To solution of diethyl 4-(1-methyl-1H-pyrazol-3-yl)-1H-pyrrole-2,3-dicarboxylate 173c (17.5 g, 60.07 mmol) in DMF (170 mL) sodium hydride (3.12 g, 130.16 mmol) was added at 0° C. After 1 hour, O-(2,4-dinitrophenyl) hydroxylamine (15.55 g, 78.1 mmol) was added portionwise. The reaction mixture was stirred at room temperature overnight. An aqueous solution of $NH_4Cl$ was added to reaction mixture, extracted with EtOAc (3*50 mL), combined EtOAc was washed with water (7*20 mL), dried and evaporated under reduce pressure to diethyl 1-amino-4-(1-methyl-1H-pyrazol-3-yl)-1H-pyrrole-2,3-dicarboxylate 173d (16.7 g, 86.3% purity, 78.3% yield).

LCMS(ESI) Rt=1.067 min. MS Calculated [M+1] 307.0. Found [M+1] 307.0.

Step D: 4-Hydroxy-2-(1-methyl-1H-imidazol-2-yl)-6-(1-methyl-1H-pyrazol-3-yl)pyrrolo[2,1-f][1,2,4] triazine-5-carboxylic acid 173e Diethyl 1-amino-4-(1-methyl-1H-pyrazol-3-yl)-1H-pyrrole-2,3-dicarboxylate 173d (10.41 g, 33.98 mmol) and 1-methyl-1H-imidazole-2-carbonitrile (3.64 g, 33.98 mmol, 3.64 mL) was dissolved in dioxane (150 mL) and sodium hydride (2.72 g, 113.28 mmol) was added. The reaction mixture was stirred at 100° C. for 16 h. Then, the mixture was cooled to room temperature and an aqueous solution of $NH_4Cl$ was added. The product was extracted with EtOAc (70 mL*3). Aqueous layer was concentrated in vacuo to give 4-hydroxy-2-(1-methyl-1H-imidazol-2-yl)-6-(1-methyl-1H-pyrazol-3-yl)pyrrolo[2,1-f][1,2,4]triazine-5-carboxylic acid 173e (6.3 g, 31.8% purity, 17.3% yield). LCMS(ESI): Rt=0.864 min. MS Calculated [M+1] 340.0. Found [M+1] 340.0.

Step E: Methyl 4-hydroxy-2-(1-methyl-1H-imidazol-2-yl)-6-(1-methyl-1H-pyrazol-3-yl)pyrrolo[2,1-f][1,2,4]triazine-5-carboxylate 173f To the solution of 4-hydroxy-2-(1-methyl-1H-imidazol-2-yl)-6-(1-methyl-1H-pyrazol-3-yl)pyrrolo[2,1-f][1,2,4]triazine-5-carboxylic acid 173e (6.39 g, 18.84 mmol) in MeOH (70 mL), thionyl chloride (3.36 g, 28.26 mmol, 2.05 mL) was added dropwise under cooling with ice. The reaction mixture was stirred at 65° C. overnight. Then, the volatiles were evaporated under reduce pressure. 100 mL of $CH_3CN$ was added to a crude compound, filtered from solids and filtrate was concentrated in vacuo to give methyl 4-hydroxy-2-(1-methyl-1H-imidazol-2-yl)-6-(1-methyl-1H-pyrazol-3-yl)pyrrolo[2,1-f][1,2,4]triazine-5-carboxylate 173f (4.5 g, 62.5% purity, 44.1% yield). LCMS(ESI) Rt=1.001 min. MS Calculated [M+1] 354.0. Found [M+1] 354.0.

Step F: Methyl 4-chloro-2-(1-methyl-1H-imidazol-2-yl)-6-(1-methyl-1H-pyrazol-3-yl)pyrrolo[2,1-f][1,2,4]triazine-5-carboxylate 173g Methyl 4-hydroxy-2-(1-methyl-1H-imidazol-2-yl)-6-(1-methyl-1H-pyrazol-3-yl)pyrrolo[2,1-f][1,2,4]triazine-5-carboxylate 173f (3.8 g, 10.75 mmol) was suspended in phosphoroyl trichloride (16.48 g, 107.5 mmol, 10.02 mL) and the reaction mixture was heated at 100° C. for 16 h. The solution was cooled to room temperature. The volatiles were evaporated under reduced pressure. The residue was poured into ice and $K_2CO_3$ was added until pH 5. The product was extracted with chloroform (3×50 mL) and evaporated under reduced pressure to give methyl 4-chloro-2-(1-methyl-1H-imidazol-2-yl)-6-(1-methyl-1H-pyrazol-3-yl)pyrrolo[2,1-f][1,2,4]triazine-5-carboxylate 173g (3.7 g, 38.5% purity, 30.2% yield).LCMS(ESI) Rt=0.930 min. MS Calculated [M+1] 372.2. Found [M+1] 372.2.

Step G: methyl 4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxylate 173h To the solution of methyl 4-chloro-2-(1-methyl-1H-imidazol-2-yl)-6-(1-methyl-1H-pyrazol-3-yl)pyrrolo[2,1-f][1,2,4]triazine-5-carboxylate 173g (2.16 g, 5.82 mmol) and 4-methoxypyridin-2-amine (865.36 mg, 6.98 mmol) in dry DMF (25 mL), sodium hydride (464.67 mg, 19.36 mmol) was added under cooling with ice. The reaction mixture was stirred at room temperature 3 h. Then, the mixture was poured into saturated solution of $NH_4Cl$ (20 mL) and evaporated under reduced pressure. 30 mL of ethanol was added to crude compound and precipitate was filtered, dried on air to give methyl 4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxylate 173h (2.5 g, 56.6% purity, 53.2% yield). LCMS(ESI) Rt=0.859 min. Calculated [M+1] 460.0. Found [M+1] 460.0.

Step H: 4-((4-Methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxylic acid 173i To the solution of methyl 4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxylate 173h (2.5 g, 5.44 mmol) in MeOH (15 mL), the solution of sodium hydroxide (435.32 mg, 10.89 mmol) in water (15 mL) was added. The reaction mixture was stirred at room temperature overnight. After the completion of reaction, MeOH was evaporated under reduced pressure and water solution was acidified with 5M HCl to pH 5. Then, the product was extracted with dichloromethane (3×10 mL). Water was evaporated to give 4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxylic acid 173i (1.95 g, 93.4%, 75.2% yield). LCMS(ESI) Rt=0.766 min. MS Calculated [M+1] 446.2. Found [M+1] 446.2.

Step I: N-Ethyl-4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxamide (173)

General Procedure: To a suspension of 4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxylic acid 173i (120.67 mg, 271.06 μmol) in $CH_3CN$ (15 mL), 1-methyl-1H-imidazole (55.62 mg, 677.85 μmol, 50.0 μL) and TCFH (chloro-N,N,N',N'-tetramethylformamidinium hexafluorophosphate) (114.01 mg, 407.14 μmol) were added at room temperature. The resulting mixture was stirred for 10 min and the appropriate amine added (580.83 μmol) was added under cooling with ice. The reaction mixture was stirred at room temperature overnight. Then, $CH_3CN$ was removed under reduced pressure and the crude compound was purified with HPLC (column: Chromatorex C18 SMB100-5T 100*19 mm, 5 microM; Mar. 10, 1955% 0-2-10 min $H_2O$/MeOH, flow 30 mL/min ((loading pump 4 mL MeOH). Using the general procedure with ethyl amine (26.17 mg, 580.83 μmol, 40.0 μL) gave N-ethyl-4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxamide (173) (3.6 mg, 95% purity, 2.8% yield) (100% purity). LCMS(ESI) Rt=0.831 min. Calculated [M+1] 473.2. Found [M+1] 473.2.

Example 174-Example 179

According to the general procedure described in Example 173, Step I, to a suspension of 4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxylic acid 173i in $CH_3CN$, 1-methyl-1H-imidazole and TCFH (chloro-N,N,N',N'-tetramethylformamidinium hexafluorophosphate) were added at room temperature. The resulting mixture was stirred for 10 min and the appropriate amine added was added under cooling with ice. Reaction amounts are shown in Table A, and analytical data and structures for Example compound (174)-Example compound (179) are shown in Table C.

TABLE A

| Example | 173i | $CH_3CN$ | 1-methyl-1H-imidazole | TCFH | Amine |
|---|---|---|---|---|---|
| 174 | 148.06 mg, 332.6 μmol | 20 mL | 100.98 mg, 1.23 mmol | 139.9 mg, 499.57 μmol | 42.91 mg, 433.28 μmol 30.0 μL |

TABLE A-continued

| Example | 173i | $CH_3CN$ | 1-methyl-1H-imidazole | TCFH | Amine |
|---|---|---|---|---|---|
| 175 | 201.34 mg, 452.28 μmol | 20 mL | 92.7 mg, 1.13 mmol | 190.23 mg, 679.32 μmol | 38.71 mg, 678.43 μmol 50.0 μL |
| 176 | 148.91 mg, 334.51 μmol | 20 mL | 68.62 mg, 836.29 μmol | 140.7 mg, 502.44 μmol | 32.68 mg, 435.34 μmol 40.0 μL |
| 177 | 150.0 mg, 336.96 μmol | 20 mL | 69.27 mg, 844.25 μmol | 142.04 mg, 507.22 μmol | 38.68 mg, 438.99 μmol |
| 178 | 151.89 mg, 341.21 μmol | 15 mL | 70.04 mg, 853.59 μmol | 143.51 mg, 512.49 μmol | 29.1 mg, 409.47 μmol 30.0 μL |
| 179 | 149.77 mg, 336.43 μmol | 15 mL | 69.01 mg, 841.04 μmol | 141.51 mg, 505.32 μmol | 35.15 mg, 403.71 μmol 40.0 μL |

Example 180: Synthesis of Compound 180

(180)

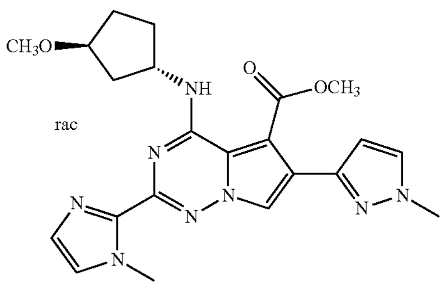

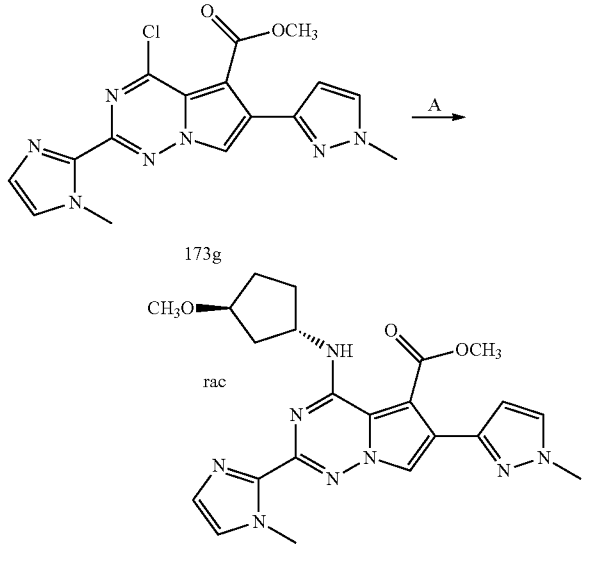

173g (180)

Step A: rac Methyl 4-(((1S,3S)-3-methoxycyclopentyl)amino)-2-(1-methyl-1H-imidazol-2-yl)-6-(1-methyl-1H-pyrazol-3-yl)pyrrolo[2,1-f][1,2,4]triazine-5-carboxylate (180)

To suspension of methyl 4-chloro-2-(1-methyl-1H-imidazol-2-yl)-6-(1-methyl-1H-pyrazol-3-yl)pyrrolo[2,1-f][1,2,4]triazine-5-carboxylate 173g (2.3 g, 6.18 mmol) in $CH_3CN$, DIEA (2.4 g, 18.54 mmol, 3.23 mL) and rac (1S,3S)-3-methoxycyclopentan-1-amine (712.02 mg, 6.18 mmol) was added. Reaction mixture was stirred at 80° C. overnight and then evaporated under reduced pressure. $CH_2Cl_2$ (70 mL) was added and washed with water (3×15 mL). Organic layer was dried under $Na_2SO_4$ and evaporated to give the desired product (2.55 g, 19.4% purity, 17.8% yield). Purification of a small amount by HPLC gave 11.7 mg (98% purity) of rac methyl 4-(((1S,3S)-3-methoxycyclopentyl)amino)-2-(1-methyl-1H-imidazol-2-yl)-6-(1-methyl-1H-pyrazol-3-yl)pyrrolo[2,1-f][1,2,4]triazine-5-carboxylate (180). LCMS (ESI) Calculated [M+1] 451.2. Found [M+1] 451.2.

Example 181: Synthesis of Compound 181

(181)

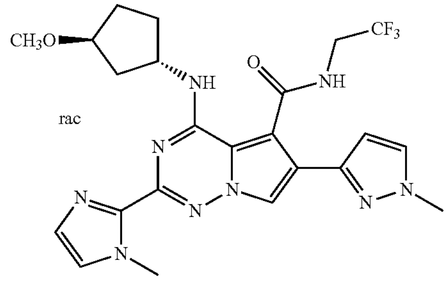

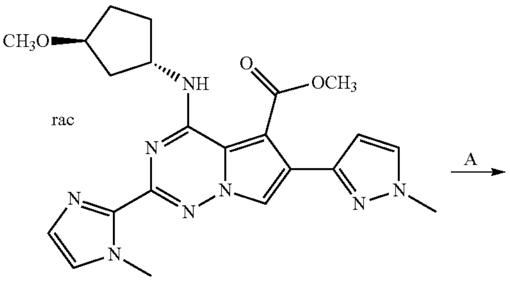

180

-continued

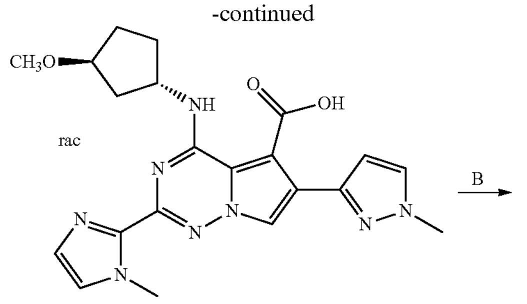

181a

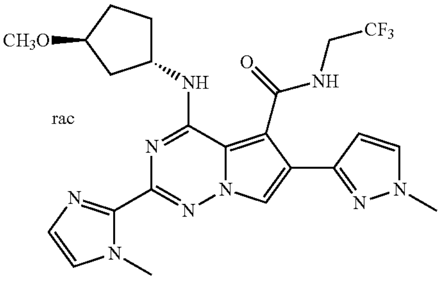

(181)

Step A: rac 4-(((1S,3S)-3-Methoxycyclopentyl)amino)-2-(1-methyl-1H-imidazol-2-yl)-6-(1-methyl-1H-pyrazol-3-yl)pyrrolo[2,1-f][1,2,4]triazine-5-carboxylic acid 181a To solution of rac methyl 4-(((1S,3S)-3-methoxycyclopentyl)amino)-2-(1-methyl-1H-imidazol-2-yl)-6-(1-methyl-1H-pyrazol-3-yl)pyrrolo[2,1-f][1,2,4]triazine-5-carboxylate (180) (2.55 g, 5.66 mmol) in MeOH (20 mL), sodium hydroxide (452.88 mg, 11.32 mmol) in 20 mL of water was added. Reaction mixture was stirred at room temperature overnight and then MeOH was evaporated. Water was extracted with EtOAc (3x15 mL) and then water was acidified by 2N HCl to pH 5, extracted with dichloromethane (3x15 mL) and aqueous layer was evaporated to give crude compound which was purified by flash chromatography ($SiO_2$, hexane-EtOAc) to give rac 4-(((1S,3S)-3-methoxycyclopentyl)amino)-2-(1-methyl-1H-imidazol-2-yl)-6-(1-methyl-1H-pyrazol-3-yl)pyrrolo[2,1-f][1,2,4]triazine-5-carboxylic acid 181a (0.7 g, 100% purity, 28.3% yield).

Step B: rac 4-(((1S,3S)-3-Methoxycyclopentyl)amino)-2-(1-methyl-1H-imidazol-2-yl)-6-(1-methyl-1H-pyrazol-3-yl)-N-(2,2,2-trifluoroethyl)pyrrolo[2,1-f][1,2,4]triazine-5-carboxamide (181)

To suspension of rac 4-(((1S,3S)-3-methoxycyclopentyl)amino)-2-(1-methyl-1H-imidazol-2-yl)-6-(1-methyl-1H-pyrazol-3-yl)pyrrolo[2,1-f][1,2,4]triazine-5-carboxylic acid 181a (220.0 mg, 504.05 μmol) in $CH_3CN$ (20 mL), 1-methyl-1H-imidazole (165.63 mg, 2.02 mmol) and TCFH (chloro-N,N,N',N'-tetramethylformamidinium hexafluorophosphate) (212.26 mg, 756.51 μmol) was added at room temperature. After 10 min, 2,2,2-trifluoroethan-1-amine hydrochloride (102.52 mg, 756.51 μmol) was added under cooling with ice. Reaction mixture was stirred at room temperature overnight and then $CH_3CN$ was evaporated under reduced pressure and crude compound was purified by HPLC (0-2-10 min; 48-55-80% $H_2O$/MeCN/0.1% $NH_4OH$, flow 30 mL/min ((loading pump 4 mL MeCN); column: XBridge BEH C18 100*19 mm, 5 microM) to give rac 4-(((1S,3S)-3-Methoxycyclopentyl)amino)-2-(1-methyl-1H-imidazol-2-yl)-6-(1-methyl-1H-pyrazol-3-yl)-N-(2,2,2-trifluoroethyl)pyrrolo[2,1-f][1,2,4]triazine-5-carboxamide (181) (3.3 mg, 95% purity, 1.3% yield) as beige solid (purity 100%). LCMS(ESI) Rt=1.103 min. Calculated [M+1] 518.2. Found [M+1] 518.2.

Example 182-Example 185

According to the general procedure described in Example 181, Step B, to a suspension of rac 4-(((1S,3S)-3-methoxycyclopentyl)amino)-2-(1-methyl-1H-imidazol-2-yl)-6-(1-methyl-1H-pyrazol-3-yl)pyrrolo[2,1-f][1,2,4]triazine-5-carboxylic acid 181a in $CH_3CN$, 1-methyl-1H-imidazole and TCFH (chloro-N,N,N',N'-tetramethylformamidinium hexafluorophosphate) were added at room temperature. The resulting mixture was stirred for 10 min and the appropriate amine added was added under cooling with ice. Reaction amounts are shown in Table B, and analytical data and structures for Example compound (182)-Example compound (185) are shown in Table C.

TABLE B

| Example | 181a | 1-methyl-1H-imidazole | TCFH | Amine |
|---|---|---|---|---|
| 182 | 87.65 mg, 200.82 μmol | 41.2 mg, 501.8 μmol | 84.52 mg, 301.23 μmol | 17.2 mg, 301.23 μmol 20.0 μL |
| 183 | 7.91 mg, 18.13 μmol | 3.72 mg, 45.33 μmol | 7.63 mg, 27.2 μmol | 1.63 mg, 21.75 μmol |
| 184 | 220.0 mg, 504.05 μmol | 103.52 mg, 1.26 mmol | 212.26 mg, 756.52 μmol | 67.43 mg, 756.52 μmol |
| 185 | 89.9 mg, 205.96 μmol | 42.28 mg, 514.91 μmol | 86.68 mg, 308.95 μmol | 35.0 mg, 268.84 μmol, 40.0 μL |

Example 186: Synthesis of Compound 186

(186)

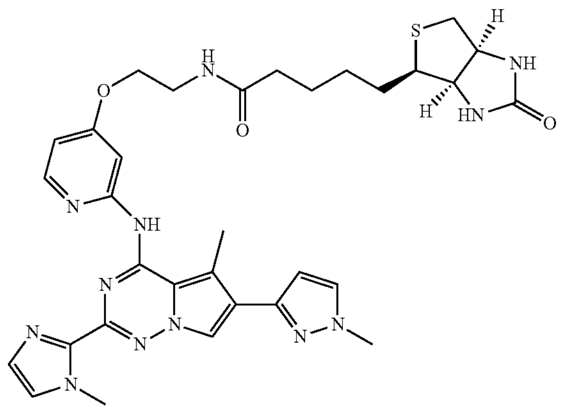

-continued

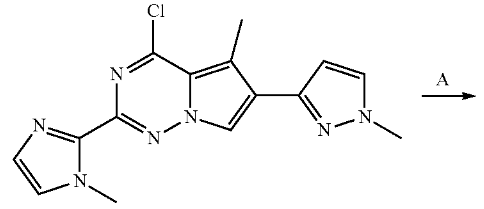

99

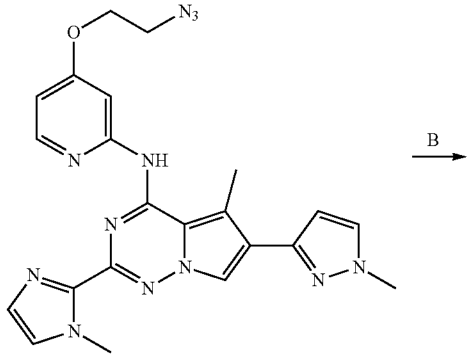

186a

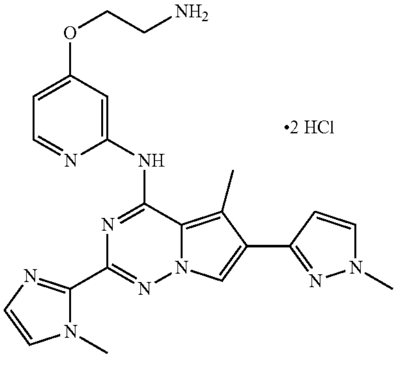

186b

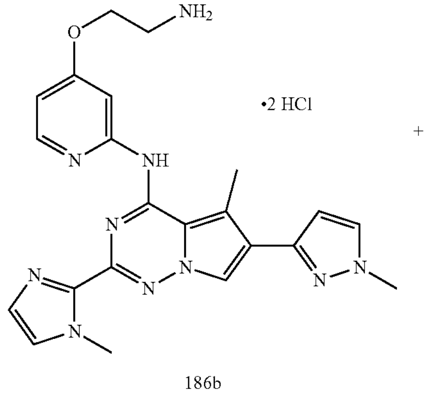

186b

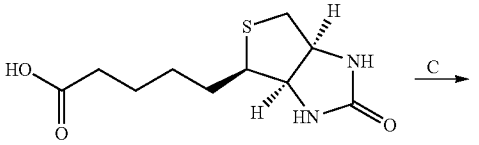

186c

-continued

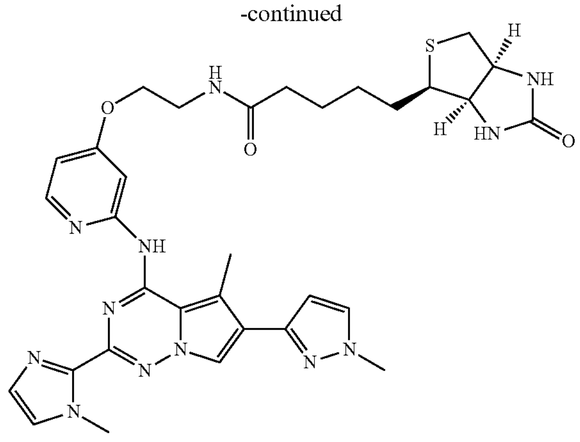

(186)

Step A: N-(4-(2-Azidoethoxy)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine 186a Sodium hydride (50.36 mg, 2.1 mmol) (60% on mineral oil) was added in portionwise to the solution of 4-chloro-5-methyl-2-(1-methyl-1H-imidazol-2-yl)-6-(1-methyl-1H-pyrazol-3-yl)pyrrolo[2,1-f][1,2,4]triazine 99 (prepared as described in Example 99, Procedure B, Step E) (250.0 mg, 762.73 μmol) and 4-(2-azidoethoxy)pyridin-2-amine (205.08 mg, 1.14 mmol) in DMF (5 mL). The mixture was stirred at room temperature for 16 h. The mixture was quenched by concentrated aq. $NH_4Cl$. The formed precipitate was collected by filtration, triturated by MeCN and dried in vacuo. N-(4-(2-Azidoethoxy)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine 186a (120.0 mg, 255.05 μmol, 33.4% yield) was obtained.

Step B: N-(4-(2-Aminoethoxy)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine dihydrochloride salt 186b To the solution of N-(4-(2-azidoethoxy)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine 186a (120.0 mg, 255.05 μmol) was dissolved in 3 mL of THF, and triphenylphosphane (80.01 mg, 305.07 μmol) was added portionwise at room temperature. The mixture was stirred for 30 min and water (45.8 mg, 2.54 mmol) was added in one portion. The mixture was stirred for 16 h at room temperature, then concentrated and diluted with 0.5M aq HCl (10 mL). Solution was extracted 3 times with EtOAc (5 mL). Water phase was dried in vacuo. N-(4-(2-Aminoethoxy)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine dihydrochloride salt 186b was obtained and used in next step without further purification.

Step C: N-(2-((2-((5-Methyl-2-(1-methyl-1H-imidazol-2-yl)-6-(1-methyl-1H-pyrazol-3-yl)pyrrolo[2,1-f][1,2,4]triazin-4-yl)amino) pyridin-4-yl)oxy) ethyl)-5-((3aR,4R,6aS)-2-oxohexahydro-1H-thieno[3,4-d]imidazol-4-yl)pentanamide (186)

To a solution of biotin (5-((3aR,4R,6aS)-2-oxohexahydro-1H-thieno[3,4-d]imidazol-4-yl)pentanoic acid) 186c (47.71 mg, 195.29 μmol) in DMF (2 mL), TCFH (chloro-N,N,N',N'-tetramethylformamidinium hexafluorophosphate) (89.11 mg, 234.35 μmol) was added in one portion. Then DIEA (126.14 mg, 975.99 μmol, 170.0 μL) was added in one portion and the mixture was stirred for 15 min. N-(4-(2-Aminoethoxy)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine dihydrochloride salt 186b (101.05 mg, 195.29 μmol) was added and the mixture was stirred for 16 h at room temperature. After HPLC purification (0-2-10 min 13-20-45% $H_2O$/MeCN/0.1% $NH_4OH$, flow 30 mL/min ((loading pump 4 mL MeCN/0.1% $NH_4OH$); column: XBridge BEH C18 100*19 mm, 5 microM)N-(2-((2-((5-Methyl-2-(1-methyl-1H-imidazol-2-yl)-6-(1-methyl-1H-pyrazol-3-yl)pyrrolo[2,1-f][1,2,4]triazin-4-yl)amino) pyridin-4-yl)oxy) ethyl)-5-((3aR,4R,6aS)-2-oxohexahydro-1H-thieno[3,4-d]imidazol-4-yl)pentanamide (186) was obtained as an olive solid (60.0 mg, 89.45 μmol, 35% yield over two steps) (98% purity). LCMS(ESI) Rt=0.777 min. MS Calculated [M+1] 671.2. Found [M+1] 671.2.

Example 187: Synthesis of Compound 187

(187)

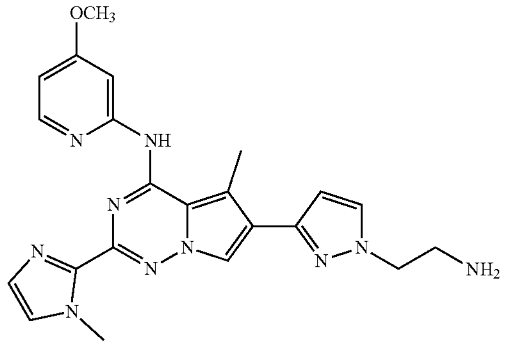

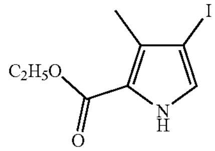

50a

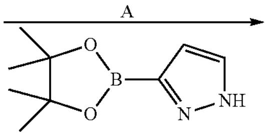

187a

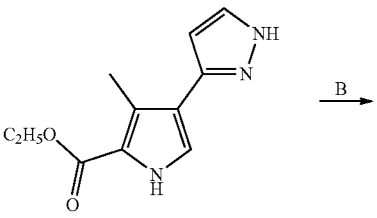

187b

-continued

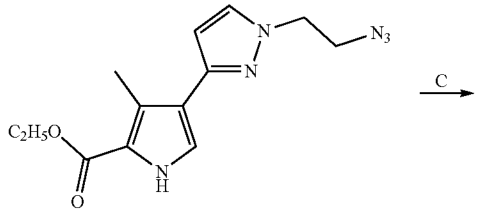

187c

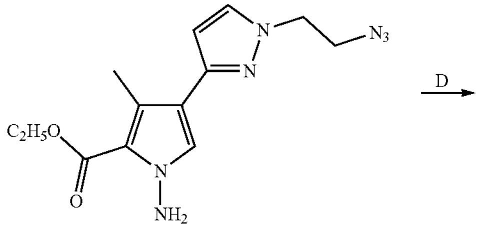

187d

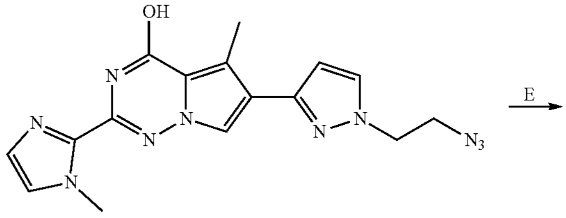

187e

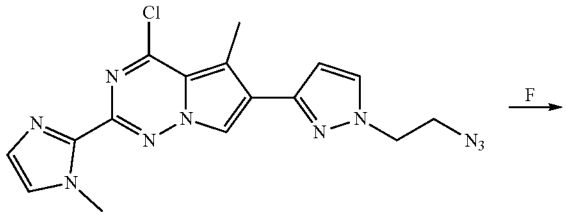

187f

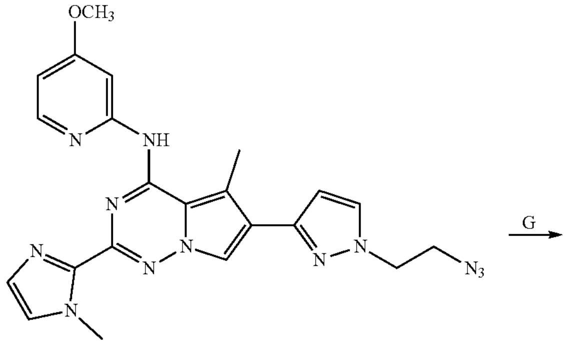

187g

-continued

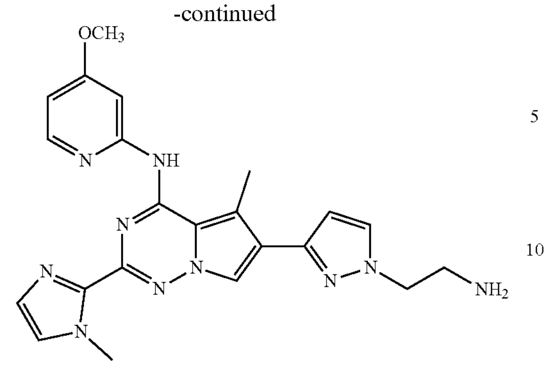

(187)

Step A: Ethyl 3-methyl-4-(1H-pyrazol-3-yl)-1H-pyrrole-2-carboxylate 187b 3-(4,4,5,5-tetramethyl-1,3,2-dioxaborolan-2-yl)-1H-pyrazole 187a (34.79 g, 179.23 mmol), ethyl 4-iodo-3-methyl-1H-pyrrole-2-carboxylate 50a (prepared as described in Example 50, Step A) (25.0 g, 89.61 mmol), disodium carbonate (18.99 g, 179.23 mmol) and bis(4-(di-tert-butylphosphanyl)-N,N-dimethylaniline); dichloropalladium (1.27 g, 1.79 mmol) were dissolved in degassed $CH_3CN$ (700 mL) under Ar atmosphere. Then, 70 mL of water was added via syringe. The reaction mixture was heated to 70° C. and stirred at this temperature for 18 h. The mixture was cooled to room temperature, filtered through celite pad and the filtrate was concentrated under reduced pressure. The residue was purified by FCC (Interchim; 80 g, C18, water/acetonitrile with acetonitrile from 0~60%, flow rate=60 mL/min, Rv=11-13 CV) to give ethyl 3-methyl-4-(1H-pyrazol-3-yl)-1H-pyrrole-2-carboxylate 187b (970.0 mg, 90.0% purity, 3.98 mmol, 4.4% yield). LCMS(ESI) Rt=1.024 min. Calculated [M+1] 220.2. Found [M+1] 220.2.

Step B: Ethyl 4-(1-(2-azidoethyl)-1H-pyrazol-3-yl)-3-methyl-1H-pyrrole-2-carboxylate 187c 1-Azido-2-bromoethane (492.59 mg, 3.31 mmol) was added in one portion to a stirred solution of ethyl 3-methyl-4-(1H-pyrazol-3-yl)-1H-pyrrole-2-carboxylate 187b (690.0 mg, 3.15 mmol) and DIEA (610.13 mg, 4.72 mmol) in $CH_3CN$ (15 mL). The mixture was heated to 80° C. and stirred at this temperature overnight. Then reaction mixture was concentrated in vacuo, diluted with ice water (150 mL) and extracted 3 times by EtOAc (3*150 mL). The organic phase washed with water, brine, dried over $Na_2SO_4$, concentrated in vacuo and purified by FCC (Interchim, 80 g $SiO_2$, hexane/MTBE (20-84%), flow rate=60 mL/min, RV=17.2-23.1 CV) to give ethyl 4-(1-(2-azidoethyl)-1H-pyrazol-3-yl)-3-methyl-1H-pyrrole-2-carboxylate 187c (290.0 mg, 95.0% purity, 955.58 μmol, 30.3% yield). LCMS (ESI) Rt=1.035 min. MS Calculated [M+1] 289.2. Found [M+1] 289.2.

Step C: Ethyl 1-amino-4-(1-(2-azidoethyl)-1H-pyrazol-3-yl)-3-methyl-1H-pyrrole-2-carboxylate 187d Sodium hydride (0.06 g, 1.5 mmol) (60% in mineral oil), was added portionwise to a solution of ethyl 4-(1-(2-azidoethyl)-1H-pyrazol-3-yl)-3-methyl-1H-pyrrole-2-carboxylate 187c (290.0 mg, 1.01 mmol) in DMF (8 mL) at 0° C.

The mixture was stirred for 1 h at room temperature. Then, the mixture was cooled to 0° C. and O-(2,4-dinitrophenyl) hydroxylamine (300.19 mg, 1.51 mmol) was added portionwise. The mixture was stirred for 16 h at room temperature. Then the mixture poured in ice water and extracted with EtOAc (3*100 mL). The organic phase washed with water, brine, dried over $Na_2SO_4$, concentrated in vacuo to give ethyl 1-amino-4-(1-(2-azidoethyl)-1H-pyrazol-3-yl)-3-methyl-1H-pyrrole-2-carboxylate 187d. (570.0 mg, 50.0% purity, 939.6 μmol, 93.4% yield) as dark oil. LCMS(ESI) Rt=2.871 min. MS Calculated [M+1] 304.2. Found [M+1] 304.2.

Step D: 6-(1-(2-Azidoethyl)-1H-pyrazol-3-yl)-5-methyl-2-(1-methyl-1H-imidazol-2-yl)pyrrolo[2,1-f][1,2,4]triazin-4-ol 187e Sodium hydride (0.15 g, 3.75 mmol) (60% in mineral oil) was added portionwise to the solution of ethyl 1-amino-4-(1-(2-azidoethyl)-1H-pyrazol-3-yl)-3-methyl-1H-pyrrole-2-carboxylate 187d (570.0 mg, 1.88 mmol) and 1-methyl-1H-imidazole-2-carbonitrile (151.16 mg, 1.41 mmol) in dry dioxane (8 mL). Then, the reaction mixture was heated 80° C. and stirred at this temperature for 16 h. The mixture was cooled to room temperature, poured in ice water, neutralized with acetic acid and extracted with EtOAc (3*30 mL). The organic phase washed with water, brine, dried over $Na_2SO_4$, concentrated in vacuo and purified by FCC (Interchim; 40 g $SiO_2$, chloroform/acetonitrile with acetonitrile from 0~60%, flow rate=40 mL/min, 11.9-14.5) to give 6-(1-(2-azidoethyl)-1H-pyrazol-3-yl)-5-methyl-2-(1-methyl-1H-imidazol-2-yl)pyrrolo[2,1-f][1,2,4]triazin-4-ol 187e (210.0 mg, 85.0% purity, 489.89 μmol, 52% yield). LCMS(ESI) Rt=1.208 min. MS Calculated [M+1] 365.2. Found [M+1] 365.2. [

Step E: 6-(1-(2-Azidoethyl)-1H-pyrazol-3-yl)-4-chloro-5-methyl-2-(1-methyl-1H-imidazol-2-yl)pyrrolo[2,1-f][1,2,4]triazine 187f To the solution of 6-(1-(2-azidoethyl)-1H-pyrazol-3-yl)-5-methyl-2-(1-methyl-1H-imidazol-2-yl)pyrrolo[2,1-f][1,2,4]triazin-4-ol 187e (220.0 mg, 604.15 μmol) in $CH_3CN$ (15 mL), phosphoroyl trichloride (4.58 g, 30.17 mmol) was added dropwise. The mixture was heated to 80° C. and stirred at this temperature for 16 h and then concentrated in vacuo, poured in ice water (15 mL) and neutralized by $NaHCO_3$ (aqueous solution), and extracted with EtOAc (3*15 mL). The organic phase washed with water, brine, dried over $Na_2SO_4$, concentrated in vacuo to give 6-(1-(2-azidoethyl)-1H-pyrazol-3-yl)-4-chloro-5-methyl-2-(1-methyl-1H-imidazol-2-yl)pyrrolo[2,1-f][1,2,4]triazine 187f (220.0 mg, 70.0% purity, 402.29 μmol, 66.7% yield) as yellow solid. LCMS(ESI) Rt=2.807 min.: MS Calculated [M+1] 383.2. Found [M+1] 383.2.

Step F: 6-(1-(2-Azidoethyl)-1H-pyrazol-3-yl)-N-(4-methoxypyridin-2-yl)-5-methyl-2-(1-methyl-1H-imidazol-2-yl)pyrrolo[2,1-f][1,2,4]triazin-4-amine 187g Sodium hydride (57 mg, 1.425 mmol) (60% in mineral oil) was added in portionwise to the solution of 4-methoxypyridin-2-amine (100.2 mg, 807.67 μmol) in DMF (1 mL). The mixture was stirred at room temperature for 30 min, then 6-(1-(2-azidoethyl)-1H-pyrazol-3-yl)-4-chloro-5-methyl-2-(1-methyl-1H-imidazol-2-yl)pyrrolo[2,1-f][1,2,4]

triazine 187f (220.0 mg, 575.74 μmol) was added in one portion, and stirred overnight. After this time resulting mixture quenched by saturated $NH_4Cl$. The formed precipitate was collected by filtration, washed by water (2*1 mL) and purified by HPLC (0-2-10 min 43-50-85% $H_2O$/MeOH; flow 30 mL/min ((loading pump 4 mL MEOH) column: Chromatorex C18 SMB100-5T 100*19 mm, 5 microM) to give 6-(1-(2-azidoethyl)-1H-pyrazol-3-yl)-N-(4-methoxypyridin-2-yl)-5-methyl-2-(1-methyl-1H-imidazol-2-yl)pyrrolo[2,1-f][1,2,4]triazin-4-amine 187g (77.9 mg, 95.0% purity, 157.29 μmol, 39% yield). LCMS(ESI) Rt=0.892 min. MS Calculated [M+1] 471.2. Found [M+1] 471.0.

Step G: 6-(1-(2-Aminoethyl)-1H-pyrazol-3-yl)-N-(4-methoxypyridin-2-yl)-5-methyl-2-(1-methyl-1H-imidazol-2-yl)pyrrolo[2,1-f][1,2,4]triazin-4-amine (187)

To the solution of 6-(1-(2-azidoethyl)-1H-pyrazol-3-yl)-N-(4-methoxypyridin-2-yl)-5-methyl-2-(1-methyl-1H-imidazol-2-yl)pyrrolo[2,1-f][1,2,4]triazin-4-amine 187g (77.9 mg, 165.67 μmol) in THF (5 mL), triphenylphosphane (45.57 mg, 173.86 μmol) was added in one portion. The mixture was stirred at room temperature overnight. After 1N HCl (1 mL) was added dropwise and stirred over 2 hr. The resulting mixture was washed by $CH_2Cl_2$ (2×5 mL), adjusted to pH 8 with $NaHCO_3$ (aqueous solution) and extracted with EtOAc (3×5 mL). The organic phase washed with water, brine, dried over $Na_2SO_4$, concentrated in vacuo and purified by HPLC (0-2-12 min 0-55$H_2O$/MeOH/0.1FA; flow 30 mL/min ((loading pump 4 mL MeOH) column: XBridge BEH C18 100*19 mm, 5 microM)) to give 6-(1-(2-Aminoethyl)-1H-pyrazol-3-yl)-N-(4-methoxypyridin-2-yl)-5-methyl-2-(1-methyl-1H-imidazol-2-yl)pyrrolo[2,1-f][1,2,4]triazin-4-amine (187) (2.9 mg, 93.0% purity, 6.07 μmol, 3.7% yield). LCMS(ESI) Rt=0.775 min. Calculated [M+1] 445.2. Found [M+1] 445.2.

Example 188: Synthesis of Compound 188

(188)

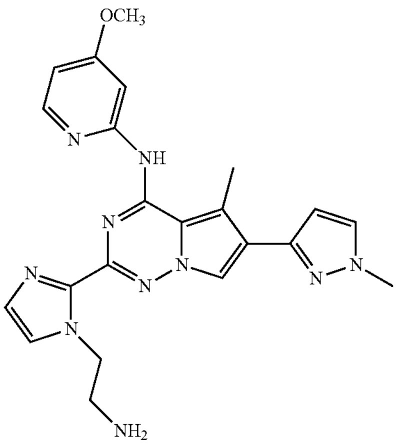

-continued

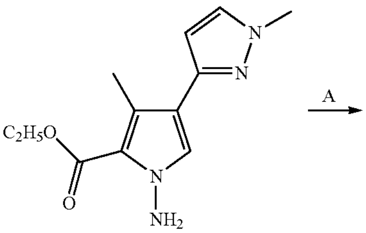

99d

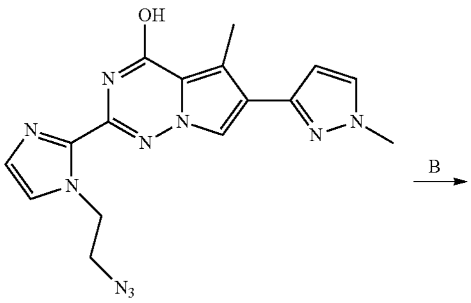

188a

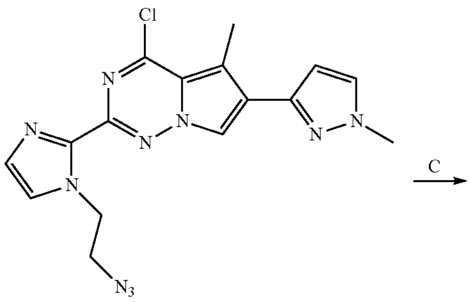

188b

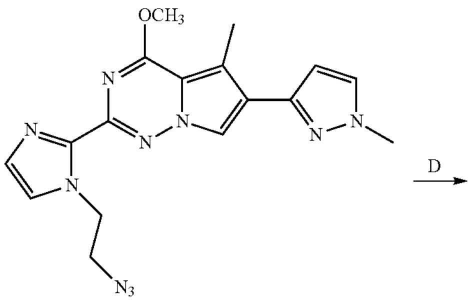

188c

-continued

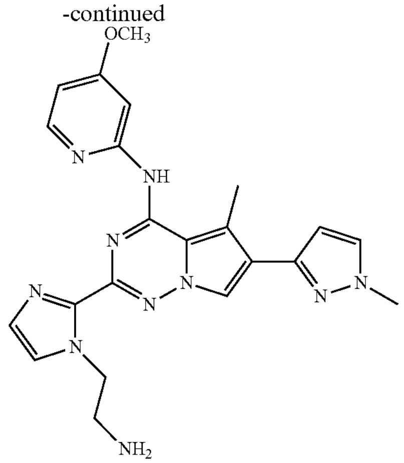

(188)

Step A: 2-(1-(2-Azidoethyl)-1H-imidazol-2-yl)-5-methyl-6-(1-methyl-1H-pyrazol-3-yl)pyrrolo[2,1-f][1,2,4]triazin-4-ol 188a Sodium hydride (934.36 mg, 38.94 mmol) (60% in mineral oil) was added portionwise (during 3 min) to the solution of ethyl 1-amino-3-methyl-4-(1-methyl-1H-pyrazol-3-yl)-1H-pyrrole-2-carboxylate 99d (2.9 g, 11.68 mmol) (prepared as described in Example 99, Procedure B, Step C) and 1-(2-azidoethyl)-1I-imidazole-2-carbonitrile (2.27 g, 14.02 mmol) in dioxane (20 mL). The reaction mixture was heated under reflux for 16 h. Then the mixture was cooled to room temperature, poured in ice water and neutralized by acetic acid. The formed precipitate was collected by filtration, washed by water (2*10 mL) and dried in vacuo. 2-(1-(2-Azidoethyl)-1H-imidazol-2-yl)-5-methyl-6-(1-methyl-1H-pyrazol-3-yl)pyrrolo[2,1-f][1,2,4]triazin-4-ol 188a (1.0 g, 2.74 mmol, 23.5% yield) was obtained.

Step B: 2-(1-(2-Azidoethyl)-1H-imidazol-2-yl)-4-chloro-5-methyl-6-(1-methyl-1H-pyrazol-3-yl)pyrrolo[2,1-f][1,2,4]triazine 188b 2-(1-(2-Azidoethyl)-1H-imidazol-2-yl)-5-methyl-6-(1-methyl-1H-pyrazol-3-yl)pyrrolo[2,1-f][1,2,4]triazin-4-ol 188a (1.0 g, 2.74 mmol) was dissolved in phosphoryl trichloride (8.42 g, 54.91 mmol, 5.12 mL). The mixture was heated to 100° C. and stirred at this temperature for 16 h. The reaction mixture was concentrated in vacuo, poured in ice water (5 mL) and neutralized by $K_2CO_3$. The formed precipitate was collected by filtration, washed by water (2*5 mL) and dried in vacuo. 2-(1-(2-Azidoethyl)-1H-imidazol-2-yl)-4-chloro-5-methyl-6-(1-methyl-1H-pyrazol-3-yl)pyrrolo[2,1-f][1,2,4]triazine 188b (740.0 mg, 1.93 mmol, 70.4% yield) was obtained.

Step C: 2-(1-(2-Azidoethyl)-1H-imidazol-2-yl)-N-(4-methoxypyridin-2-yl)-5-methyl-6-(1-methyl-1H-pyrazol-3-yl)pyrrolo[2,1-f][1,2,4]triazin-4-amine 188c Sodium hydride (135.23 mg, 5.64 mmol) (60% in mineral oil) was added portionwise to the solution of-(1-(2-azidoethyl)-1H-imidazol-2-yl)-4-chloro-5-methyl-6-(1-methyl-1H-pyrazol-3-yl)pyrrolo[2,1-f][1,2,4]triazine 188b (740.0 mg, 1.93 mmol) and 4-methoxypyridin-2-amine (359.76 mg, 2.9 mmol) in DMF (10 mL). The mixture was stirred at room temperature for 16 h. The mixture was quenched by concentrated aq. $NH_4Cl$. The formed precipitate was collected by filtration, triturated by MeCN and dried in vacuo. 2-(1-(2-Azidoethyl)-1H-imidazol-2-yl)-N-(4-methoxypyridin-2-yl)-5-methyl-6-(1-methyl-1H-pyrazol-3-yl)pyrrolo[2,1-f][1,2,4]triazin-4-amine 188c (400.0 mg, 850.18 μmol, 44% yield) was obtained Step D: 2-(1-(2-Aminoethyl)-1H-imidazol-2-yl)-N-(4-methoxypyridin-2-yl)-5-methyl-6-(1-methyl-1H-pyrazol-3-yl)pyrrolo[2,1-f][1,2,4]triazin-4-amine (188)

To the solution of 2-(1-(2-azidoethyl)-1H-imidazol-2-yl)-N-(4-methoxypyridin-2-yl)-5-methyl-6-(1-methyl-1H-pyrazol-3-yl)pyrrolo[2,1-f][1,2,4]triazin-4-amine 188c (400.0 mg, 850.18 μmol) in 10 mL of THF, triphenylphosphane (267.66 mg, 1.02 mmol) was added portionwise at room temperature. The mixture was stirred for 30 min and water (15.32 mg, 850.41 μmol, 20.0 μL) was added in one portion. The mixture was stirred for 16 h at room temperature, then concentrated and diluted with 0.5M aq HCl (10 mL). Solution was extracted 3 times with EtOAc (5 mL). Water phase was dried in vacuo. 2-(1-(2-aminoethyl)-1H-imidazol-2-yl)-N-(4-methoxypyridin-2-yl)-5-methyl-6-(1-methyl-1H-pyrazol-3-yl)pyrrolo[2,1-f][1,2,4]triazin-4-amine (188) (350.0 mg, 676.44 μmol, 92.6% yield) was obtained. An analytical sample was purified by HPLC (0-2-10 min 40-60-85% $H_2O$/MeOH; flow 30 mL/min ((loading pump 4 mL MeOH); column: XBridge BEH C18 100*19 mm, 5 microM) to give 2-(1-(2-aminoethyl)-1H-imidazol-2-yl)-N-(4-methoxypyridin-2-yl)-5-methyl-6-(1-methyl-1H-pyrazol-3-yl)pyrrolo[2,1-f][1,2,4]triazin-4-amine (188) (6.0 mg, 11.6 μmol) (purity 95%). LCMS (ESI) Rt=0.638 min. Calculated [M+1] 445.2. Found [M+1] 445.2.

Example 189: Synthesis of Compound 189

(189)

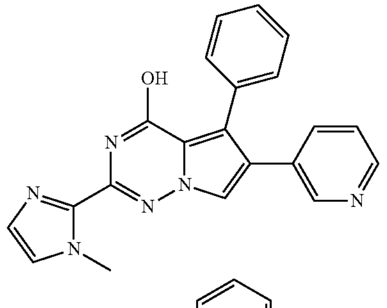

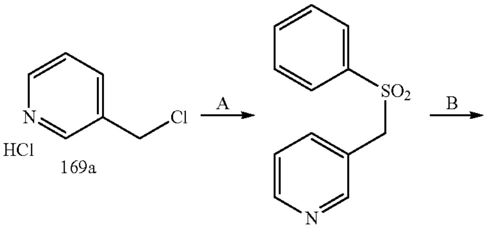

169a

169b

-continued

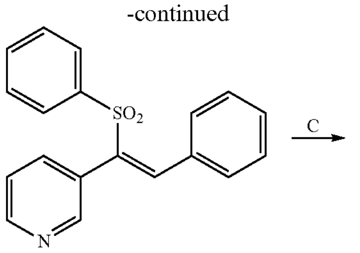

189a

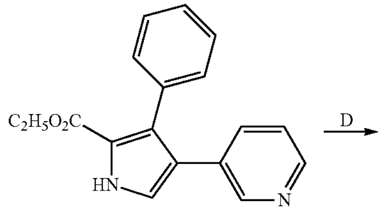

189b

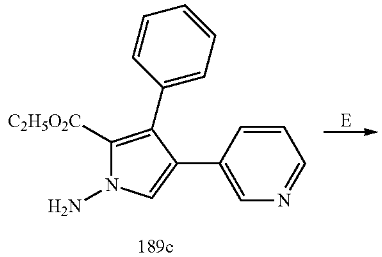

189c

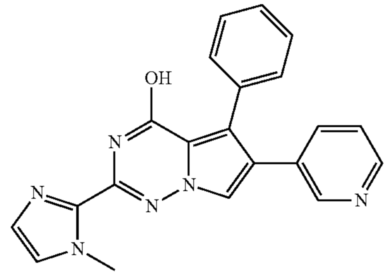

(189)

Step A: 3-((Phenylsulfonyl)methyl)pyridine 169b 3-(Chloromethyl)pyridine hydrochloride 169a (60.0 g, 368.11 mmol), sodium benzenesulfinate (90.07 g, 549.23 mmol) and sodium acetate (60.01 g, 731.84 mmol) were dissolved in 600 mL iPA. The mixture was stirred at 80° C. for 16 hours. Then, the mixture was cooled to room temperature and the formed precipitate was collected by filtration, and then washed by 300 mL MTBE. The precipitate was dissolved in 500 mL dichloromethane and extracted 4 times with 0.5 M $K_2CO_3$ (4*300 mL). The organic phase was dried over sodium sulfate, filtered off and the solvent was evaporated in vacuo. 3-((Phenylsulfonyl)methyl)pyridine 169b (27.7 g, 118.74 mmol, 32.5% yield) was obtained as yellow solid. LCMS(ESI) Rt=0.819 min. MS Calculated [M+1] 234.2. Found [M+1] 234.2.

Step B: (Z)-3-(2-Phenyl-1-(phenylsulfonyl)vinyl) pyridine 189a

Sodium (3.33 g, 145.03 mmol) was added in one portion to a 300 mL MeOH at 0° C. The mixture was stirred for 1 h until the gas formation was stopped. 3-((Phenylsulfonyl) methyl)pyridine 169b (26.0 g, 111.56 mmol) was added to the mixture, followed by benzaldehyde (11.83 g, 111.56 mmol). The mixture was heated to 60° C. and stirred for 16 hours at this temperature. 45% conversion (LCMS control) was observed and benzaldehyde (11.83 g, 111.56 mmol) was added. The mixture was stirred for 16 h at 60° C. and the procedure was repeated until >90% conversion was obtained (LCMS control). The mixture was concentrated and diluted with 500 mL of water and 500 mL of DCM. The organic phase was separated, washed with brine, dried over sodium sulfate and evaporated in vacuo. The residue was triturated in hexane: MTBE (2:1) and the formed precipitate was collected by filtration and purified by flash chromatography. (Z)-3-(2-Phenyl-1-(phenylsulfonyl)vinyl)pyridine 189a (8.0 g, 24.89 mmol, 22.3% yield) was obtained. LCMS(ESI) Rt=1.300 min. MS Calculated [M+1] 322.2. Found [M+1] 322.0.

Step C: Ethyl 3-phenyl-4-(pyridin-3-yl)-1H-pyrrole-2-carboxylate 189b (Z)-3-(2-Phenyl-1-(phenylsulfonyl)vinyl)pyridine 189a (27.7 g, 86.28 mmol) was added in one portion to a solution of potassium t-butoxide (9.67 g, 86.33 mmol) in 300 mL THF at 0° C. Ethyl 2-isocyanoacetate (9.75 g, 86.24 mmol, 9.42 mL) was added dropwise and the mixture was stirred for 3 h at room temperature. The mixture was concentrated in vacuo, diluted with 300 mL water and 300 mL EtOAc. The organic phase was separated and washed 3 times with 0.5 M $K_2CO_3$ (300 mL), dried over $Na_2SO_4$ and concentrated in vacuo. The residue was triturated in MTBE and the formed precipitate was collected by filtration. Ethyl 3-phenyl-4-(pyridin-3-yl)-1H-pyrrole-2-carboxylate 189b (15.0 g, 51.31 mmol, 59.5% yield) was obtained. LCMS(ESI) Rt=0.816 min. MS Calculated [M+1] 293.2. Found [M+1] 293.2.

Step D: Ethyl 1-amino-3-phenyl-4-(pyridin-3-yl)-1H-pyrrole-2-carboxylate 189c

Ethyl 3-phenyl-4-(pyridin-3-yl)-1H-pyrrole-2-carboxylate 189b (15.0 g, 51.35 mmol) was added portionwise to a suspension of (60% in mineral oil) sodium hydride (2.67 g, 111.17 mmol) in 200 mL DMF at 0° C. The mixture was stirred for 1 hour and O-(2,4-dinitrophenyl) hydroxylamine (13.28 g, 66.74 mmol) was added in one portion. The mixture was stirred for 16 hours at room temperature, then quenched with 400 mL water. The mixture was extracted 3 times with EtOAc (3*300 mL). Organic phase was washed 5 times with brine (5*300 mL), dried over sodium sulfate and concentrated in vacuo. Ethyl 1-amino-3-phenyl-4-(pyridin-3-yl)-1H-pyrrole-2-carboxylate 189c (15.0 g, 48.8 mmol, 95.1% yield) was obtained and used in next step without further purification. LCMS(ESI) Rt=1.022 min. MS Calculated [M+1] 308.2. Found [M+1] 451.2.

Step E: 2-(1-Methyl-1H-imidazol-2-yl)-5-phenyl-6-(pyridin-3-yl)pyrrolo[2,1-f][1,2,4]triazin-4-ol (189)

Sodium hydride (3.91 g, 162.8 mmol) (60% in mineral oil) was added portionwise (during 3 min) to the solution of ethyl 1-amino-3-phenyl-4-(pyridin-3-yl)-1H-pyrrole-2-carboxylate 189c (15.0 g, 48.84 mmol) and 1-methyl-1H-imidazole-2-carbonitrile (6.27 g, 58.61 mmol) in dioxane (300 mL). The reaction mixture was heated to reflux and stirred at this temperature for 16 h. Then the mixture was cooled to room temperature, poured into ice water and neutralized by acetic acid. The formed precipitate was collected by filtration, washed with water (2*50 mL), dried in vacuo to give 2-(1-methyl-1H-imidazol-2-yl)-5-phenyl-6-(pyridin-3-yl)pyrrolo[2,1-f][1,2,4]triazin-4-ol (189) (6.0 g, 16.29 mmol, 33.3% yield) (100% purity). LCMS (ESI) Rt=1.043 min. MS Calculated [M+1] 369.0. Found [M+1] 369.0. $^1$H NMR (400 MHZ, $CDCl_3$) δ (ppm) 4.20 (s, 3H), 7.11 (m, 3H), 7.27 (m, 6H), 7.63 (s, 1H), 8.42 (s, 1H), 8.56 (s, 1H), 9.63 (br s, 1H).

Example 190: Synthesis of Compound 190

(190)

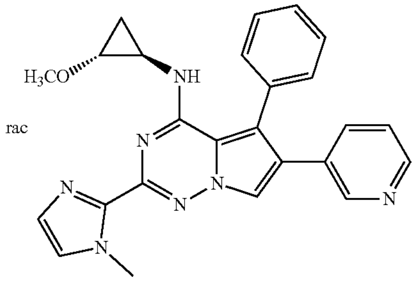

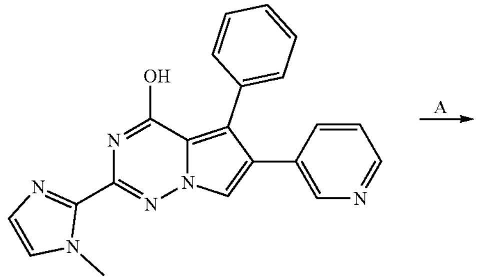

(189)

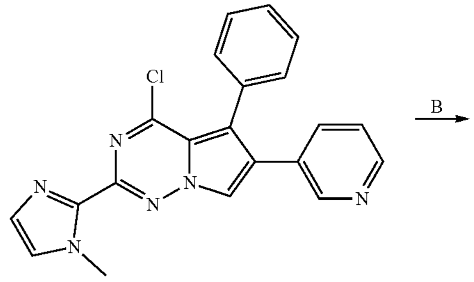

190a

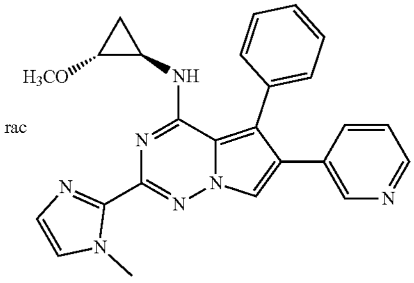

(190)

Step A: 4-Chloro-2-(1-methyl-1H-imidazol-2-yl)-5-phenyl-6-(pyridin-3-yl)pyrrolo[2,1-f][1,2,4]triazine 190a 2-(1-Methyl-1H-imidazol-2-yl)-5-phenyl-6-(pyridin-3-yl)pyrrolo[2,1-f][1,2,4]triazin-4-ol (189) (prepared as described in Example 189, Step E) (6.0 g, 16.3 mmol) was suspended in 100 mL $POCl_3$. The mixture was heated to 100° C. and stirred at this temperature for 16 h. The reaction mixture was concentrated in vacuo, poured in ice water (50 mL) and neutralized with $K_2CO_3$. The formed precipitate was collected by filtration, washed with water (2*50 mL) and dried in vacuo. The residue was purified by flash chromatography (eluted with DCM:IPA 100:1 to 1:100). 4-Chloro-2-(1-methyl-1H-imidazol-2-yl)-5-phenyl-6-(pyridin-3-yl)pyrrolo[2,1-f][1,2,4]triazine 190a (1.5 g, 3.88 mmol, 23.8% yield) was obtained and used in next step without further purification. LCMS(ESI) Rt=0.808 min. MS Calculated [M+1] 387.0. Found [M+1] 387.0.

Step B: rac N-((1R,2R)-2-Methoxycyclopropyl)-2-(1-methyl-1H-imidazol-2-yl)-5-phenyl-6-(pyridin-3-yl)pyrrolo[2,1-f][1,2,4]triazin-4-amine (190)

Using the procedure described in Example 103, Step A, DIEA (150.8 mg, 1.31 mmol, 200.0 μL), 4-chloro-2-(1-methyl-1H-imidazol-2-yl)-5-phenyl-6-(pyridin-3-yl)pyrrolo[2,1-f][1,2,4]triazine 190a (101.49 mg, 262.86 μmol) and rac ((1R,2R)-2-methoxycyclopropan-1-amine hydrochloride salt (64.69 mg, 525.72 μmol) in DMF (1 mL) afforded rac N-((1R,2R)-2-Methoxycyclopropyl)-2-(1-methyl-1H-imidazol-2-yl)-5-phenyl-6-(pyridin-3-yl)pyrrolo[2,1-f][1,2,4]triazin-4-amine (190) (8.5 mg, 95.0% purity, 18.46 μmol, 7% yield) as a yellow solid. LCMS(ESI) Rt=0.834 min. MS Calculated [M+1] 438.2. Found [M+1] 438.2. $^1$H NMR (500 MHz, DMSO-$d_6$) δ (ppm) 0.50 (m, 1H), 1.01 (m, 1H), 2.82 (m, 2H), 3.01 (m, 2H), 4.00 (s, 3H), 5.28 (m, 2H), 6.98 (s, 1H), 7.23 (m, 2H), 7.35 (m, 2H), 7.52 (m, 4H), 8.17 (s, 1H), 8.39 (m, 2H).

Example 191-Example 196

Following the procedure described in Example 190, Step B, 4-chloro-2-(1-methyl-1H-imidazol-2-yl)-5-phenyl-6-(pyridin-3-yl)pyrrolo[2,1-f][1,2,4]triazine 190a was treated with the appropriate corresponding amine to produce the compounds of Examples 191-195. Following the procedure described in Example 102, Step A, 4-chloro-2-(1-methyl-1H-imidazol-2-yl)-5-phenyl-6-(pyridin-3-yl)pyrrolo[2,1-f][1,2,4]triazine 190a was treated with the appropriate corresponding amine to produce the compound of Example 196. Example compounds (191)-(196) are shown in Table C along with their analytical data.

Example 197-Example 202

Example compound (197)-(202) were prepared using a procedure similar to that described in Examples 189 and Example 190, using the appropriate starting materials. Example compounds (197)-(202) are shown in Table C along with their analytical data.

Example 203: Synthesis of Compound 203

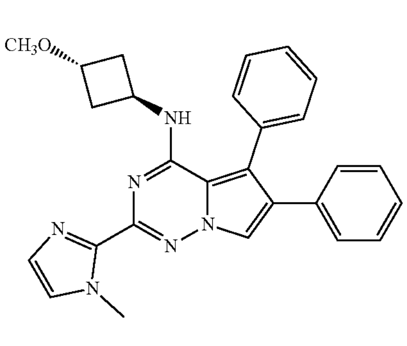

(203)

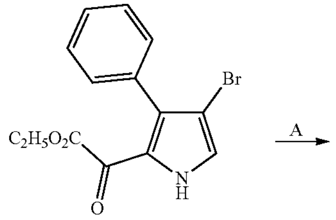

42c

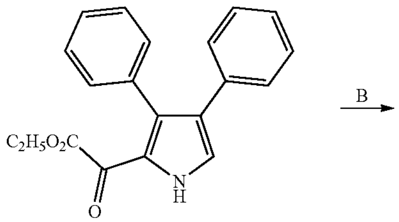

203a

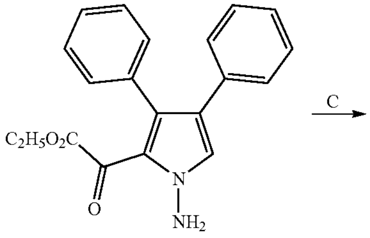

203b

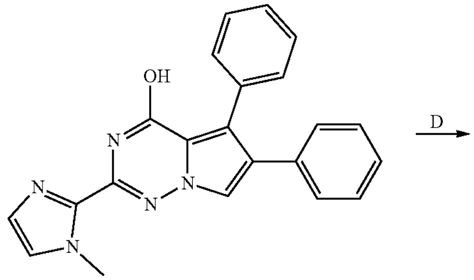

203c

-continued

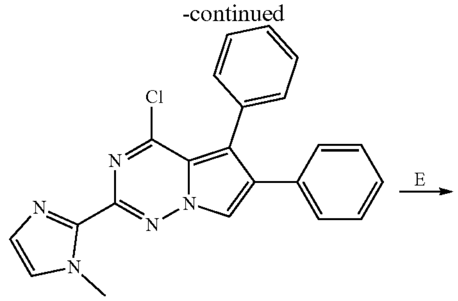

203d

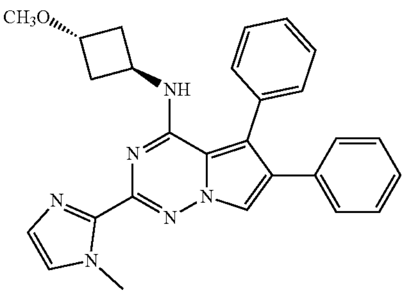

(203)

Step A: Ethyl 2-(3,4-diphenyl-1H-pyrrol-2-yl)-2-oxoacetate 203a

A mixture of ethyl 4-bromo-3-phenyl-1H-pyrrole-2-carboxylate ethyl 4-bromo-3-phenyl-1H-pyrrole-2-carboxylate 42c (prepared as described in Example 42, Step B) (1.0 g, 3.41 mmol), phenylboronic acid (414.32 mg, 3.39 mmol), cesium carbonate (2.21 g, 6.8 mmol), Pd(dppf)$Cl_2$·2DCM (277.5 mg, 340.95 μmol) in dioxane/$H_2O$ (20 mL/1 mL) was heated at 100° C. under Argon atmosphere overnight. The reaction mixture was evaporated, and crude compound was purified by flash chromatography to give ethyl 2-(3,4-diphenyl-1H-pyrrol-2-yl)-2-oxoacetate 203a (0.5 g, 91.9% purity, 46.4% yield). LCMS(ESI) Rt=1.317 min. MS Calculated [M+1] 292.2. Found [M+1] 292.2.

Step B: Ethyl 2-(1-amino-3,4-diphenyl-1H-pyrrol-2-yl)-2-oxoacetate 203b

To solution of ethyl 2-(3,4-diphenyl-1H-pyrrol-2-yl)-2-oxoacetate 203a (500.22 mg, 1.72 mmol) in DMF (15 mL) sodium hydride (60% in mineral oil) (89.27 mg, 3.72 mmol) was added at 0° C. After 1 h, O-(2,4-dinitrophenyl) hydroxylamine (444.44 mg, 2.23 mmol) was added portionwise at 0° C. Reaction mixture was stirred at room temperature overnight. An aqueous solution of $NH_4Cl$ was added to reaction mixture, extracted with EtOAc (3*15 mL), combined EtOAc was washed with water (7*10 mL), dried and evaporated under reduce pressure to give ethyl 2-(1-amino-3,4-diphenyl-1H-pyrrol-2-yl)-2-oxoacetate 203b (0.5 g, 82.9% purity, 87.7% yield).

LCMS(ESI) Rt=1.331 min. MS Calculated [M+1] 307.2. Found [M+1] 307.2.

Step C: 2-(1-methyl-1H-imidazol-2-yl)-5,6-diphenylpyrrolo[2,1-f][1,2,4]triazin-4-ol 203c To mixture of give ethyl 2-(1-amino-3,4-diphenyl-1H-pyrrol-2-yl)-2-oxoacetate 203b (500.31 mg, 1.63 mmol) and 1-methyl-1I-imidazole-2-carbonitrile (192.42 mg, 1.8 mmol) in dioxane (20 mL) sodium hydride (60% in mineral oil) (130.63 mg, 5.44 mmol) was added under cooling with ice. Reaction mixture was stirred at 100° C. overnight. An aqueous solution of $NH_4Cl$ was added to reaction mixture, extracted with EtOAc (3*40 mL), dried and evaporated under reduce pressure to give 2-(1-methyl-1H-imidazol-2-yl)-5,6-diphenylpyrrolo[2,1-f][1,2,4]triazin-4-ol 203c (0.52 g, 64.7% purity, 56.1% yield). LCMS(ESI) Rt=1.447 min. MS Calculated [M+1] 368.2. Found [M+1] 368.0.

Step D: 4-Chloro-2-(1-methyl-1H-imidazol-2-yl)-5,6-diphenylpyrrolo[2,1-f][1,2,4]triazine 203d The starting material 2-(1-methyl-1H-imidazol-2-yl)-5,6-diphenylpyrrolo[2,1-f][1,2,4]triazin-4-ol 203c (520.0 mg, 1.42 mmol) was suspended in phosphoryl trichloride (2.17 g, 14.29 mmol) and the reaction mixture was heated at 100° C. overnight. The solution was cooled to room temperature, evaporated under reduced pressure, poured into aqueous solution of $NaHCO_3$ and the product was extracted with chloroform (3*20 mL), evaporated to give 4-chloro-2-(1-methyl-1H-imidazol-2-yl)-5,6-diphenylpyrrolo[2,1-f][1,2,4]triazine 203d (0.6 g, 71.2% purity, 78% yield). LCMS (ESI) Rt=1.264 min. MS Calculated [M+1] 386.2. Found [M+1] 386.2.

Step E: N-((1r,3r)-3-Methoxycyclobutyl)-2-(1-methyl-1H-imidazol-2-yl)-5,6-diphenylpyrrolo[2,1-f][1,2,4]triazin-4-amine (203)

To suspension of 4-chloro-2-(1-methyl-1H-imidazol-2-yl)-5,6-diphenylpyrrolo[2,1-f][1,2,4]triazine 203d (600.0 mg, 1.56 mmol) and (1r,3r)-3-methoxycyclobutan-1-amine hydrochloride salt (321.16 mg, 2.34 mmol) in $CH_3CN$ (20 mL) DIEA (603.28 mg, 4.67 mmol) was added at room temperature. Reaction mixture was stirred at 80° C. overnight. After completion of reaction $CH_3CN$ was evaporated and crude material was purified by HPLC to give N-((1r,3r)-3-Methoxycyclobutyl)-2-(1-methyl-1H-imidazol-2-yl)-5,6-diphenylpyrrolo[2,1-f][1,2,4]triazin-4-amine (203) (18.4 mg, 95% purity, 2.6% yield) as an yellow solid. LCMS(ESI) Rt=1.159 min. MS Calculated [M+1] 451.2. Found [M+1] 451.2. $^1H$ NMR (500 MHZ, DMSO-$d_6$) δ (ppm) 1.80 (m, 2H), 2.22 (m, 2H), 3.08 (s, 3H), 3.79 (m, 1H), 3.94 (s, 3H), 4.47 (m, 1H), 5.41 (d, 1H), 7.98 (d, 1H), 7.17 (m, 1H), 7.28 (m, 5H), 7.50 (m, 5H), 8.13 (m, 1H).

Example 204: Synthesis of Compound 204

204

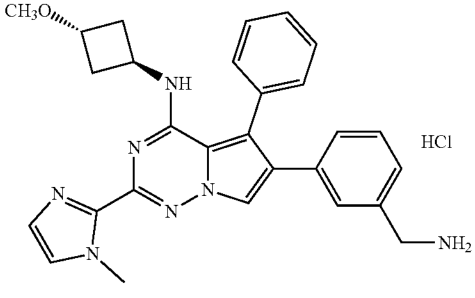

-continued

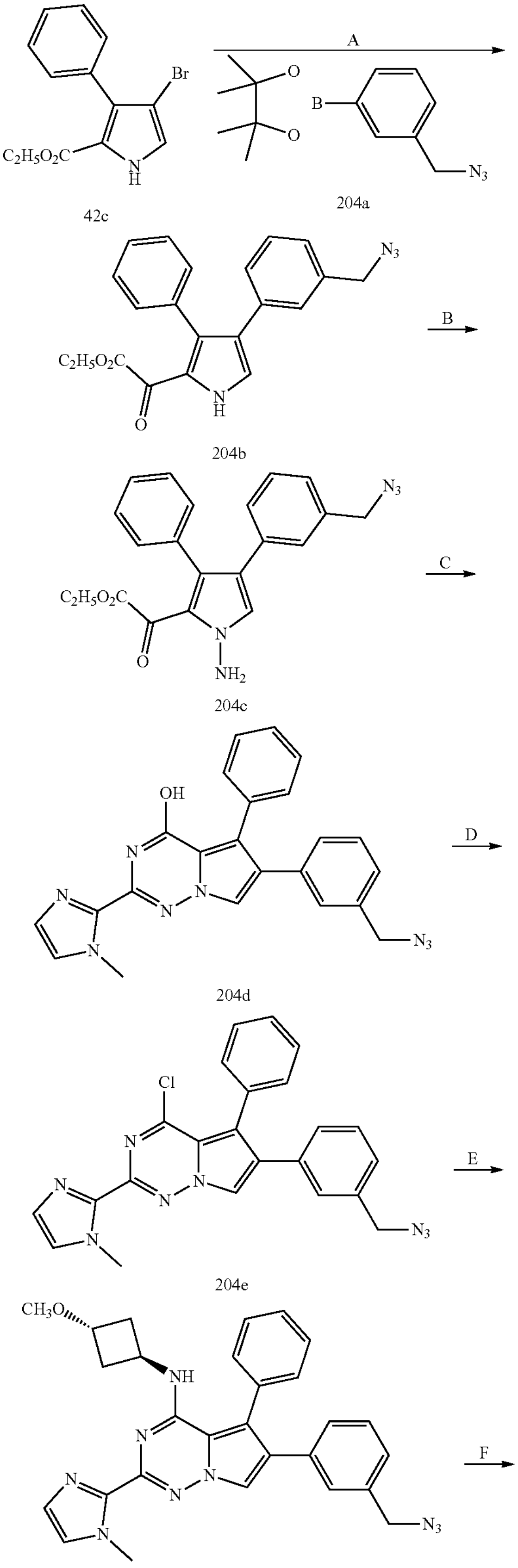

42c

204a

204b

204c

204d

204e

204f

-continued

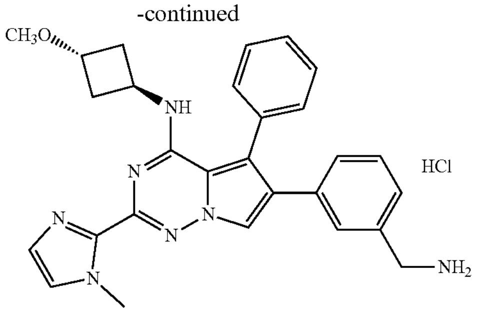

(204)

Step A: Ethyl 2-(4-(3-(azidomethyl)phenyl)-3-phenyl-1H-pyrrol-2-yl)-2-oxoacetate 204b A mixture of 2-(3-(azidomethyl)phenyl)-4,4,5,5-tetramethyl-1,3,2-dioxaborolane 204a (1.0 g, 3.86 mmol), ethyl 4-bromo-3-phenyl-1H-pyrrole-2-carboxylate 42c (prepared as described in Example 42, Step B) (1.14 g, 3.87 mmol), cesium carbonate (2.52 g, 7.72 mmol) and [1,1-bis(diphenylphosphino)ferrocene]dichloropalladium(II) dichloromethane complex (315.21 mg, 387.29 μmol) in dioxane/$H_2O$ (20 mL/1 mL) was heated at 100° C. under Argon atmosphere overnight. The reaction mixture was evaporated under reduced pressure and the crude compound was purified by flash chromatography ($SiO_2$, Hexane-EtOAc) to give ethyl 2-(4-(3-(azidomethyl)phenyl)-3-phenyl-1H-pyrrol-2-yl)-2-oxoacetate 204b (0.32 g, 92% purity, 22.1% yield). LCMS(ESI) Rt=1.569 min. MS Calculated [M+1] 347.2. Found [M+1] 347.2.

Step B: Ethyl 2-(1-amino-3,4-diphenyl-1H-pyrrol-2-yl)-2-oxoacetate 203b

To the solution of ethyl 2-(4-(3-(azidomethyl)phenyl)-3-phenyl-1H-pyrrol-2-yl)-2-oxoacetate 204b (320.12 mg, 924.83 μmol) in DMF (15 mL), sodium hydride (48.05 mg, 2.0 mmol) was added at 0° C. After 1 h, O-(2,4-dinitrophenyl) hydroxylamine (239.23 mg, 1.2 mmol) was added portionwise at 0° C. The reaction mixture was stirred at room temperature overnight. An aqueous solution of $NH_4Cl$ was added to reaction mixture and the product was extracted with EtOAc (3*20 mL). The combined EtOAc layer was washed with water (7*10 mL), dried over $Na_2SO_4$ and evaporated under reduce pressure to give ethyl 2-(1-amino-3,4-diphenyl-1H-pyrrol-2-yl)-2-oxoacetate 203b (132 mg, 93.2% purity, 36.7% yield). LCMS(ESI) Rt=1.416 min. MS Calculated [M+1] 362.2. Found [M+1] 362.2.

Step C: 6-(3-(Azidomethyl)phenyl)-2-(1-methyl-1H-imidazol-2-yl)-5-phenylpyrrolo[2,1-f][1,2,4]triazin-4-ol 204d To mixture of ethyl 2-(1-amino-3,4-diphenyl-1H-pyrrol-2-yl)-2-oxoacetate 203b (131.75 mg, 364.79 μmol) and 1-methyl-1H-imidazole-2-carbonitrile (39.0 mg, 364.32 μmol, 40.0 μL) in dioxane (15 mL), sodium hydride (29.16 mg, 1.22 mmol) was added under cooling with ice. The reaction mixture was stirred at 100° C. overnight. An aqueous solution of $NH_4Cl$ was added to reaction mixture. The product was extracted with EtOAc (3*20 mL), dried and evaporated under reduce pressure to give 6-(3-(azidomethyl) phenyl)-2-(1-methyl-1H-imidazol-2-yl)-5-phenylpyrrolo[2,1-f][1,2,4]triazin-4-ol 204d (141 mg, 78.5% purity, 71.4% yield). LCMS (ESI) Rt=1.382 min. MS Calculated [M+1] 423.2. Found [M+1] 423.0.

Step D: 6-(3-(Azidomethyl)phenyl)-4-chloro-2-(1-methyl-1H-imidazol-2-yl)-5-phenylpyrrolo[2,1-f][1,2,4]triazine 204e The starting material 6-(3-(azidomethyl)phenyl)-2-(1-methyl-1H-imidazol-2-yl)-5-phenylpyrrolo[2,1-f][1,2,4]triazin-4-ol 204d (140.85 mg, 333.64 μmol) was suspended in phosphoryl trichloride (509.95 mg, 3.36 mmol, 310.0 μL). The reaction mixture was heated at 100° C. overnight. The solution was cooled to room temperature. The volatiles were removed under reduced pressure and the residue was poured into aqueous solution of $NaHCO_3$. The product was extracted with chloroform (3*20 mL). The solvent was removed in vacuo to afford 6-(3-(azidomethyl)phenyl)-4-chloro-2-(1-methyl-1H-imidazol-2-yl)-5-phenylpyrrolo[2,1-f][1,2,4]triazine 204e (126 mg, 44.5% purity, 38.1% yield).

LCMS(ESI) Rt=1.204 min. MS Calculated [M+1] 441.2. Found [M+1] 441.2.

Step E: 6-(3-(Azidomethyl)phenyl)-N-((1r,3r)-3-methoxycyclobutyl)-2-(1-methyl-1H-imidazol-2-yl)-5-phenylpyrrolo[2,1-f][1,2,4]triazin-4-amine 204f To the suspension of 6-(3-(azidomethyl)phenyl)-4-chloro-2-(1-methyl-1H-imidazol-2-yl)-5-phenylpyrrolo[2,1-f][1,2,4]triazine 204e (126.45 mg, 287.3 μmol) and (1r,3r)-3-methoxycyclobutan-1-amine hydrochloride salt (47.36 mg, 345.54 μmol) in $CH_3CN$, DIEA (111.3 mg, 861.78 μmol, 150.0 μl, 3.0 equiv) was added at room temperature. The reaction mixture was stirred at 80° C. overnight. After completion, the reaction mixture was filtered and filtrate was evaporated to give 6-(3-(azidomethyl)phenyl)-N-((1r,3r)-3-methoxycyclobutyl)-2-(1-methyl-1H-imidazol-2-yl)-5-phenylpyrrolo[2,1-f][1,2,4]triazin-4-amine 204f (203 mg, 68.5% purity, 95.9% yield). LCMS(ESI) Rt=1.217 min. MS Calculated [M+1] 506.2. Found [M+1] 506.2.

Step F: 6-(3-(aminomethyl)phenyl)-N-((1r,3r)-3-methoxycyclobutyl)-2-(1-methyl-1H-imidazol-2-yl)-5-phenylpyrrolo[2,1-f][1,2,4]triazin-4-amine hydrochloride salt (204)

To the solution of 6-(3-(azidomethyl)phenyl)-N-((1r,3r)-3-methoxycyclobutyl)-2-(1-methyl-1H-imidazol-2-yl)-5-phenylpyrrolo[2,1-f][1,2,4]triazin-4-amine 204f (203.01 mg, 500.78 μmol) in THF (30 mL), water (18.0 mg, 999.41 μmol, 20.0 μL) and triphenylphosphane (157.51 mg, 600.98 μmol) were added. The reaction mixture was stirred at room temperature overnight. After completion of the reaction, THF was evaporated. 15 mL of 5M HCl was added to crude compound and heated to 80° C. for 5 h. Then, the reaction mixture was cooled and extracted with DCM (3*10 mL) and then water was evaporated. The crude compound was purified by HPLC (0-2-9 min 0-O-40% MeCN/$H_2O$+HCl, flow 30 mL/min (loading pump 4 mL MeCN); column: Chromatorex C18 SMB100-5T 100*19, 5 microM) to give 6-(3-(aminomethyl)phenyl)-N-((1r,3r)-3-methoxycyclobutyl)-2-(1-methyl-1H-imidazol-2-yl)-5-phenylpyrrolo[2,1-f][1,2,4]triazin-4-amine hydrochloride salt (204) (5.2 mg, 95% purity, 2.4% yield).

LCMS(ESI) Rt=0.779 min. MS Calculated [M+1] 480.2. Found [M+1] 480.2.

Example 205: Synthesis of Compound 205

(205)

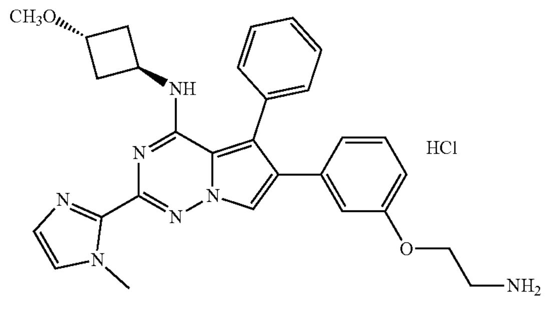

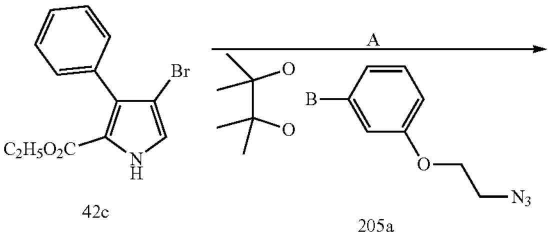

42c 205a

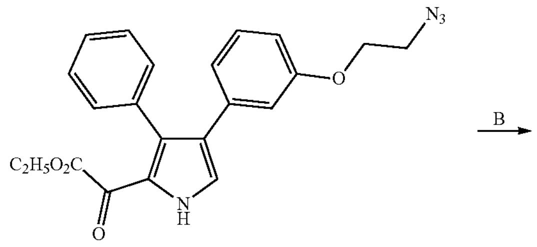

205b

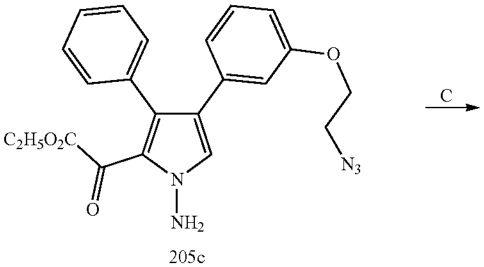

205c

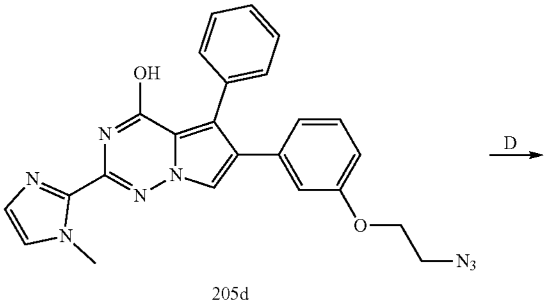

205d

-continued

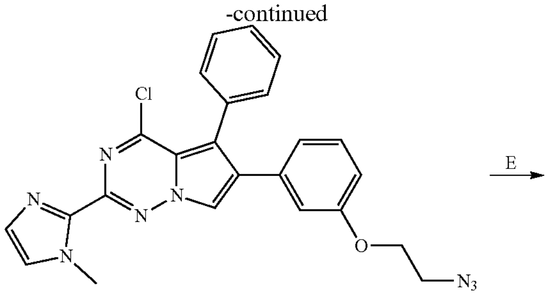

205e

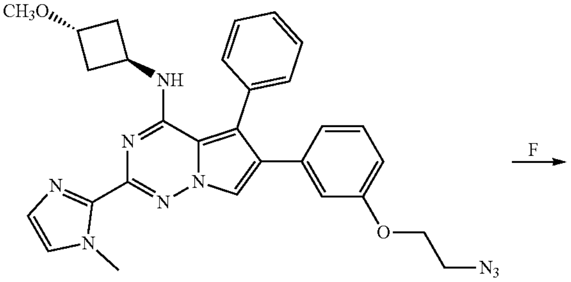

205f

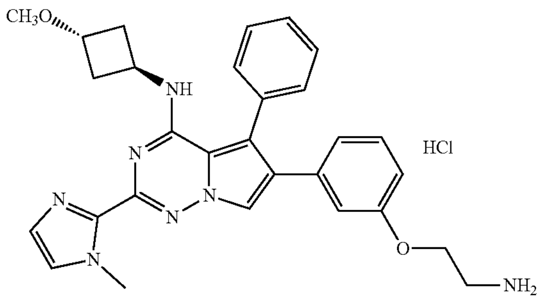

(205)

Step A: Ethyl 2-(4-(3-(2-azidoethoxy)phenyl)-3-phenyl-1H-pyrrol-2-yl)-2-oxoacetate 205b A mixture of 2-(3-(2-azidoethoxy)phenyl)-4,4,5,5-tetramethyl-1,3,2-dioxaborolane 205a (1.0 g, 3.46 mmol), ethyl 4-bromo-3-phenyl-1H-pyrrole-2-carboxylate 42c (prepared as described in Example 42, Step B) (915.7 mg, 3.13 mmol), cesium carbonate (2.25 g, 6.92 mmol) and [1,1'-bis(diphenylphosphino)ferrocene]dichloropalladium(II) dichloromethane complex (282.48 mg, 347.07 μmol) in dioxane/$H_2O$ (20 mL/1 mL) was heated at 100° C. under Argon atmosphere overnight. The reaction mixture was evaporated under reduced pressure and the crude compound was purified by flash chromatography to give ethyl 2-(4-(3-(2-azidoethoxy)phenyl)-3-phenyl-1H-pyrrol-2-yl)-2-oxoacetate 205b (0.5 g, 70.5% purity, 27.1% yield).

LCMS(ESI) Rt=1.403 min. MS Calculated [M+1] 377.2. Found [M+1] 377.2.

Step B: Ethyl 2-(1-amino-4-(3-(2-azidoethoxy)phenyl)-3-phenyl-1H-pyrrol-2-yl)-2-oxoacetate 205c To solution of ethyl 2-(4-(3-(2-azidoethoxy)phenyl)-3-phenyl-1H-pyrrol-2-yl)-2-oxoacetate 205b (500.05 mg, 1.33 mmol) in DMF (20 mL), sodium hydride (69.07 mg, 2.88 mmol) was added at 0° C. After 1 h, O-(2,4-dinitrophenyl) hydroxylamine (343.89 mg, 1.73 mmol) was added portionwise at 0° C. The reaction mixture was stirred at room temperature overnight. An aqueous solution of $NH_4Cl$ was added to reaction mixture. The product was extracted with EtOAc (3*75 mL). The combined EtOAc layer was washed with water (7*10 mL), dried and evaporated under reduce pressure to give ethyl 2-(1-amino-4-(3-(2-azidoethoxy)phenyl)-3-phenyl-1H-pyrrol-2-yl)-2-oxoacetate 205c (0.38 g, 59.1% purity, 43.1% yield).

LCMS(ESI); Rt=1.507 min. MS Calculated [M+1] 392.2. Found [M+1] 392.2.

Step C: 6-(3-(2-Azidoethoxy)phenyl)-2-(1-methyl-1H-imidazol-2-yl)-5-phenylpyrrolo[2,1-f][1,2,4]triazin-4-ol 205d To the mixture of ethyl 2-(1-amino-4-(3-(2-azidoethoxy)phenyl)-3-phenyl-1H-pyrrol-2-yl)-2-oxoacetate 205c (379.77 mg, 970.88 μmol) and 1-methyl-1H-imidazole-2-carbonitrile (114.32 mg, 1.07 mmol) in dioxane (20 mL), sodium hydride (77.61 mg, 3.23 mmol) was added under cooling with ice. The reaction mixture was stirred at 100° C. overnight. An aqueous solution of $NH_4Cl$ was added to reaction mixture. The product was extracted with EtOAc (3*20 mL), dried and evaporated under reduce pressure to give 6-(3-(2-azidoethoxy)phenyl)-2-(1-methyl-1H-imidazol-2-yl)-5-phenylpyrrolo[2,1-f][1,2,4]triazin-4-ol 205d (0.42 g, 61.7% purity, 60.5% yield).

LCMS(ESI) Rt=1.510 min. MS Calculated [M+1] 453.2. Found [M+1] 453.2.

Step D: 6-(3-(2-Azidoethoxy)phenyl)-4-chloro-2-(1-methyl-1H-imidazol-2-yl)-5-phenylpyrrolo[2,1-f][1,2,4]triazine 205e 6-(3-(2-Azidoethoxy)phenyl)-2-(1-methyl-1H-imidazol-2-yl)-5-phenylpyrrolo[2,1-f][1,2,4]triazin-4-ol 205d (417.0 mg, 922.22 μmol) was suspended in phosphoroyl trichloride (1.41 g, 9.31 mmol, 860.0 μL) and the reaction mixture was heated at 100° C. overnight. The solution was cooled to room temperature. The volatiles were removed under reduced pressure. The residue was poured into aqueous solution of $NaHCO_3$ and the product was extracted with chloroform (3*15 mL). The solvent was evaporated under reduced pressure to give 6-(3-(2-azidoethoxy)phenyl)-4-chloro-2-(1-methyl-1H-imidazol-2-yl)-5-phenylpyrrolo[2,1-f][1,2,4]triazine 205e (0.33 g, 72.7% purity, 55.2% yield).

LCMS(ESI) Rt=1.340 min. MS Calculated [M+1] 471.2. Found [M+1] 471.0.

Step E: 6-(3-(2-Azidoethoxy)phenyl)-N-((1r,3r)-3-methoxycyclobutyl)-2-(1-methyl-1H-imidazol-2-yl)-5-phenylpyrrolo[2,1-f][1,2,4]triazin-4-amine 205f To the suspension of 6-(3-(2-azidoethoxy)phenyl)-4-chloro-2-(1-methyl-1H-imidazol-2-yl)-5-phenylpyrrolo[2,1-f][1,2,4]triazine 205e (333.23 mg, 708.79 μmol) and (1r,3r)-3-methoxycyclobutan-1-amine hydrochloride salt (116.85 mg, 852.53 μmol) in $CH_3CN$, DIEA (274.54 mg, 2.13 mmol, 370.0 μL) was added at RT. The reaction mixture was stirred at 80° C. overnight. Then, the mixture was cooled and filtered. The filtrate was evaporated under reduced pressure to give 6-(3-(2-azidoethoxy)phenyl)-N-((1r,3r)-3-methoxycyclobutyl)-2-(1-methyl-1H-imidazol-2-yl)-5-phenylpyrrolo[2,1-f][1,2,4]triazin-4-amine 205f (0.5 g, 54.8% purity, 74.3% yield). LCMS(ESI) Rt=1.191 min. MS Calculated [M+1] 53.2. Found [M+1] 53.2.

Step F: 6-(3-(2-Aminoethoxy)phenyl)-N-((1r,3r)-3-methoxycyclobutyl)-2-(1-methyl-1H-imidazol-2-yl)-5-phenylpyrrolo[2,1-f][1,2,4]triazin-4-amine (205)

To the solution of 6-(3-(2-azidoethoxy)phenyl)-N-((1r,3r)-3-methoxycyclobutyl)-2-(1-methyl-1H-imidazol-2-yl)-5-phenylpyrrolo[2,1-f][1,2,4]triazin-4-amine 205f (505.54 mg, 944.5 μmol) in THF (30 mL), water (34.0 mg, 1.89 mmol, 30.0 μL) and triphenylphosphane (272.32 mg, 1.04 mmol) were added. The reaction mixture was stirred at room temperature overnight. After completion, THF was evaporated. Then, 15 mL of 5M HCl was added to crude compound and heated to 80° C. for 5 h. The reaction mixture was cooled and extracted with DCM (3*10 mL) and then water was evaporated. The crude compound was purified with HPLC (0-2-9 min Mar. 10, 1970% MeOH/$H_2O$+HCl, flow 30 mL/min (loading pump 4 mL MeOH), column: Chromatorex C18 SMB100-5T 100*19, 5 microM) to give 6-(3-(2-aminoethoxy)phenyl)-N-((1r,3r)-3-methoxycyclobutyl)-2-(1-methyl-1H-imidazol-2-yl)-5-phenylpyrrolo[2,1-f][1,2,4]triazin-4-amine (205) (47.4 mg, 93.01 μmol, 96% purity, 9.9% yield). LCMS(ESI) Rt=0.783 min. MS Calculated [M+1] 510.2. Found [M+1] 510.2. $^1H$ NMR (500 MHZ, DMSO-$d_6$) δ (ppm) 1.81 (m, 2H), 2.30 (m, 2H), 3.10 (m, 5H), 3.76 (m, 1H), 4.05 (m, 2H), 4.24 (s, 3H), 4.70 (m, 1H), 5.70 (d, 1H), 6.81 (m, 2H), 6.88 (s, 1H), 7.17 (dd, 1H), 7.45 (m, 2H), 7.56 (m, 3H), 7.80 (d, 1H), 7.92 (d, 1H), 8.28 (m, 4H).

Example 206-Example 210

Example compound (206) and Example compound (207) were prepared using a procedure similar to that described for Example compound (204), using the appropriate azide-substituted boronic acid in Step A. Example compound (208) was prepared using a procedure similar to that described for Example compound (205), using the appropriate azide-substituted boronic acid in Step A. Example compounds (206)-(208) are shown in Table C along with their analytical data.

Example 209: Synthesis of Compound 209

(209)

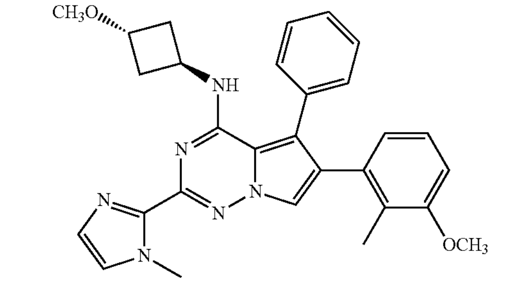

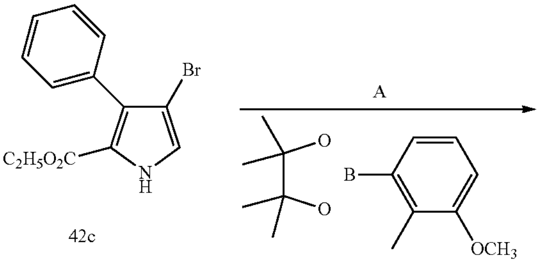

42c

209a

-continued

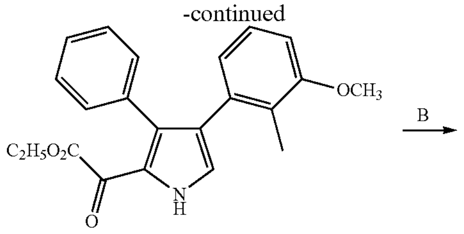

209b

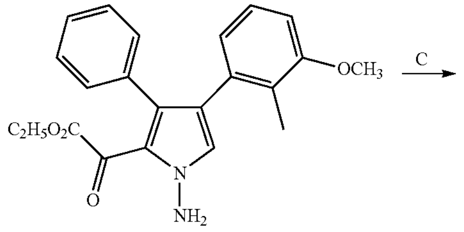

209c

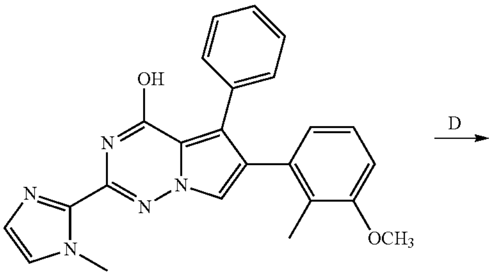

209d

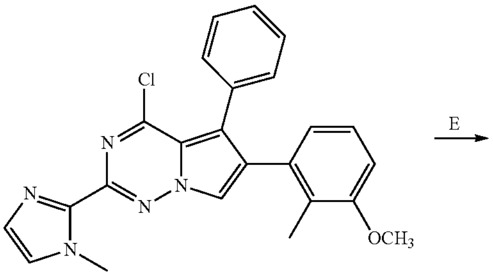

209e

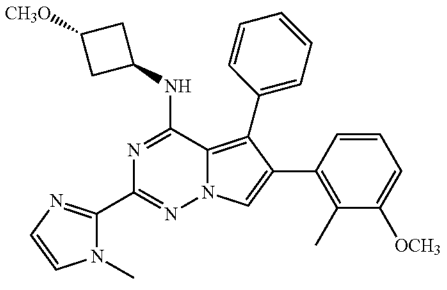

(209)

Step A: Ethyl 2-(4-(3-methoxy-2-methylphenyl)-3-phenyl-1H-pyrrol-2-yl)-2-oxoacetate 209b A mixture of ethyl 4-bromo-3-phenyl-1H-pyrrole-2-carboxylate 42 (prepared as described in Example 42, Step B) (1.0 g, 3.41 mmol), 2-(3-methoxy-2-methylphenyl)-4,4,5,5-tetramethyl-1,3,2-dioxaborolane 209a (843.37 mg, 3.4 mmol), cesium carbonate (2.21 g, 6.8 mmol) and [1,1'-bis(diphenylphosphino)ferrocene]dichloropalladium(II) dichloromethane complex (84.72 mg, 340.15 μmol) in dioxane/$H_2O$ (20 mL/1 mL) was heated at 100° C. under Argon atmosphere overnight. The reaction mixture was evaporated, and crude compound was purified by flash chromatography to give ethyl 2-(4-(3-methoxy-2-methylphenyl)-3-phenyl-1H-pyrrol-2-yl)-2-oxoacetate 209b (670 mg, 75% purity, 44% yield). LCMS(ESI) Rt=1.442 min. MS Calculated [M+1] 336.2. Found [M+1] 336.0.

Step B: Ethyl 2-(1-amino-4-(3-methoxy-2-methylphenyl)-3-phenyl-1H-pyrrol-2-yl)-2-oxoacetate 209c To solution of ethyl 2-(4-(3-methoxy-2-methylphenyl)-3-phenyl-1H-pyrrol-2-yl)-2-oxoacetate 209b (670.01 mg, 2.0 mmol) in DMF (20 mL), sodium hydride (103.87 mg, 4.33 mmol) was added at 0° C. After 1 h, O-(2,4-dinitrophenyl) hydroxylamine (517.11 mg, 2.6 mmol) was added portion-wise at 0° C. The reaction mixture was stirred at room temperature overnight. An aqueous solution of $NH_4Cl$ was added to reaction mixture. The product was extracted with EtOAc (3*30 mL). The combined EtOAc layer was washed with water (7*10 mL), dried and evaporated under reduce pressure to give ethyl 2-(1-amino-4-(3-methoxy-2-methylphenyl)-3-phenyl-1H-pyrrol-2-yl)-2-oxoacetate 209c (620 mg, 71.1% purity, 62.9% yield). LCMS(ESI) Rt=1.453 min. MS Calculated [M+1] 351.2. Found [M+1] 351.0.

Step C: 6-(3-Methoxy-2-methylphenyl)-2-(1-methyl-1H-imidazol-2-yl)-5-phenylpyrrolo[2,1-f][1,2,4]triazin-4-ol 209d To mixture of ethyl 2-(1-amino-4-(3-methoxy-2-methylphenyl)-3-phenyl-1H-pyrrol-2-yl)-2-oxoacetate 209c (620 mg, 1.77 mmol) and 1-methyl-1H-imidazole-2-carbonitrile (208.47 mg, 1.95 mmol) in dioxane (20 mL) sodium hydride (141.53 mg, 5.9 mmol) was added under cooling with ice. The reaction mixture was stirred at 100° C. overnight. An aqueous solution of $NH_4Cl$ was added to reaction mixture. The product was extracted with EtOAc (3*15 mL), dried and evaporated under reduce pressure to give 6-(3-methoxy-2-methylphenyl)-2-(1-methyl-1H-imidazol-2-yl)-5-phenylpyrrolo[2,1-f][1,2,4]triazin-4-ol 209d (750 mg, 56% purity, 57.5% yield). LCMS(ESI) Rt=1.338 min. MS Calculated [M+1] 412.2. Found [M+1] 412.2.

Step D: 4-Chloro-6-(3-methoxy-2-methylphenyl)-2-(1-methyl-1H-imidazol-2-yl)-5-phenylpyrrolo[2,1-f][1,2,4]triazine 209e 6-(3-Methoxy-2-methylphenyl)-2-(1-methyl-1H-imidazol-2-yl)-5-phenylpyrrolo[2,1-f][1,2,4]triazin-4-ol 209d (750.36 mg, 1.82 mmol) was suspended in phosphoroyl trichloride (2.8 g, 18.41 mmol, 1.7 mL) and the reaction mixture was heated at 100° C. overnight. The solution was cooled to room temperature, evaporated under reduced pressure, poured into aqueous solution of $NaHCO_3$ and the product was extracted with chloroform (3*20 mL), evaporated to give 4-chloro-6-(3-methoxy-2-methylphenyl)-2-(1-methyl-1H-imidazol-2-yl)-5-phenylpyrrolo[2,1-f][1,2,4]triazine 209e (715 mg, 58% purity, 53.2% yield).

LCMS(ESI) Rt=1.140 min. MS Calculated [M+1] 430.2. Found [M+1] 430.0.

Step E: 6-(3-methoxy-2-methylphenyl)-N-((1r,3r)-3-methoxycyclobutyl)-2-(1-methyl-1H-imidazol-2-yl)-5-phenylpyrrolo[2,1-f][1,2,4]triazin-4-amine (209)

To the suspension of 4-chloro-6-(3-methoxy-2-methylphenyl)-2-(1-methyl-1H-imidazol-2-yl)-5-phenylpyrrolo [2,1-f][1,2,4]triazine 209e (715.36 mg, 1.67 mmol) and (1r,3r)-3-methoxycyclobutan-1-amine hydrochloride salt (343.47 mg, 2.51 mmol) in $CH_3CN$ DIEA (645.54 mg, 5.0 mmol, 870.0 μL) was added at room temperature. Reaction mixture was stirred at 80° C. overnight. After completion, $CH_3CN$ was evaporated and crude material was purified by HPLC (0-2-10 min 48-55-85% $H_2O$/MeOH/0.1$NH_4OH$, flow 30 mL/min ((loading pump 4 mL MeOH); column: XBridge BEH C18 100*19 mm, 5 microM) to give 6-(3-methoxy-2-methylphenyl)-N-((1r,3r)-3-methoxycyclobutyl)-2-(1-methyl-1H-imidazol-2-yl)-5-phenylpyrrolo [2,1-f][1,2,4]triazin-4-amine (209) (59.5 mg, 96% purity, 7.2% yield). LCMS (ESI) Rt=1.181 min. MS Calculated [M+1] 496.2. Found [M+1] 496.2.

$^1$H NMR (500 MHZ, DMSO-$d_6$) δ (ppm) 1.72 (s, 3H), 1.89 (m, 2H), 2.25 (m, 2H), 3.10 (s, 3H), 3.71 (s, 3H), 3.82 (m, 1H), 3.94 (s, 3H), 4.49 (m, 1H), 6.75 (d, 1H), 6.69 (dd, 1H), 6.80 (m, 1H), 6.96 (s, 1H), 7.05 (dd, 1H), 7.26 (m, 3H), 7.42 (m, 3H), 7.85 (s, 1H).

Example 210: Synthesis of Compound 210

Example compound (210) was prepared using the method described in Example 209, using the appropriately substituted 4,4,5,5-tetramethyl-2-phenyl-1,3,2-dioxaborolane in Step A. Example compound (210) is shown in Table C along with analytical data.

Example 211: Synthesis of Compound 211

(211)

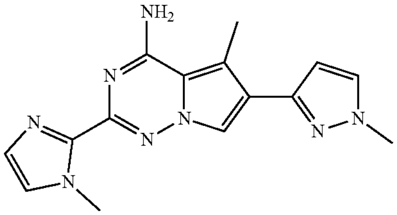

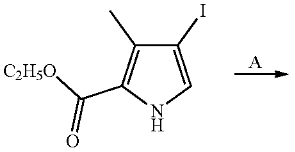

50a

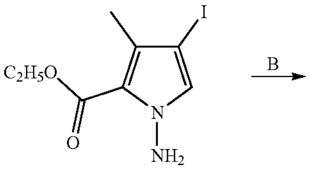

211a

-continued

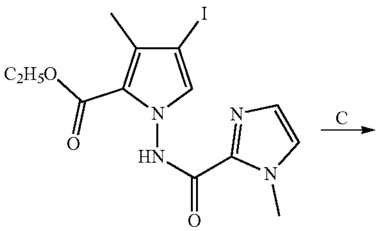

211b

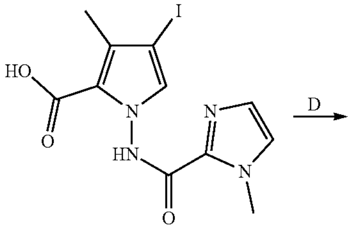

211c

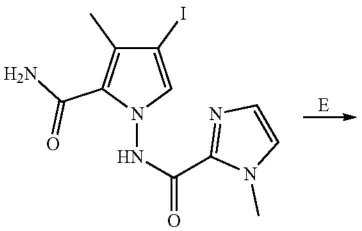

211d

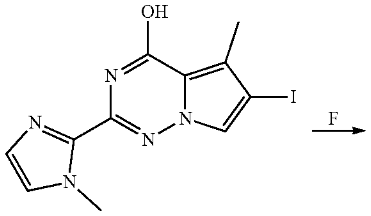

211e

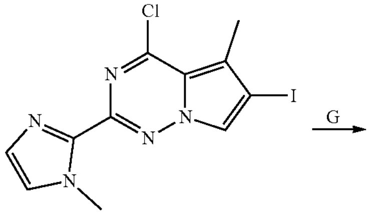

211f

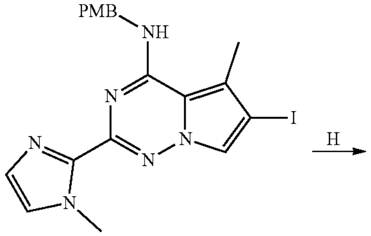

211g

-continued

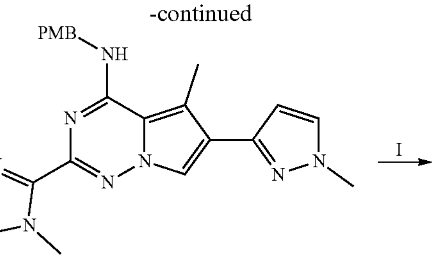

211h

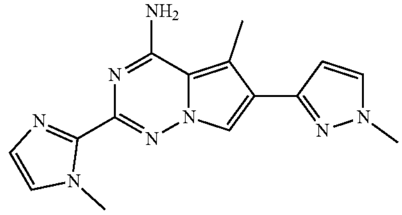

(211)

Step A: ethyl 1-amino-4-iodo-3-methyl-1H-pyrrole-2-carboxylate 211a

To a stirred solution of ethyl 4-iodo-3-methyl-1H-pyrrole-2-carboxylate 50a (prepared as described in Example 50, Step A) (8.00 g, 28.77 mmol) in DMF (80 mL), t-BuOK (3.22 g, 28.77 mmol) was added at 0° C. (over a period of 5 min.) and stirred at 30 min (at same temperature) followed by addition of O-diphenylphosphinylhydroxylamine (3) (8.04 g, 34.53 mmol). After addition completed, resulting reaction mixture was allowed to come at room temperature and stirred for 4 h at room temperature. The reaction mixture was quenched with saturated $NH_4Cl$ solution (50 mL), an aqueous layer extracted with ethyl acetate (3×100 mL). The combined organic layer washed with brine solution (100 mL), dried over anhydrous $Na_2SO_4$ and distilled off under reduced pressure to afford crude ethyl 1-amino-4-iodo-3-methyl-1H-pyrrole-2-carboxylate 211a (7.50 g) which was used taken for next step without any purification. MS (ESI+APCI; multimode): MS Calculated [M+1] 294 Found [M+1] 294.

Step B: Ethyl 4-iodo-3-methyl-1-(1-methyl-1H-imidazole-2-carboxamido)-1H-pyrrole-2-carboxylate 211b To a stirred solution of crude ethyl 1-amino-4-iodo-3-methyl-1H-pyrrole-2-carboxylate 211a (7.50 g, 25.59 mmol) in $CH_2Cl_2$ (150 mL) were added DIEA (8.25 g, 63.97 mmol), 1-methyl-1H-imidazole-2-carboxylic acid (3.54 g, 28.14 mmol) followed by $T_3P$ (propanephosphonic acid anhydride) (50% in EtOAc) (20.34 g, 63.97 mmol) at 0° C. After addition completed, resulting reaction mixture was allowed to come at room temperature and stirred for 12 h. The reaction mixture was quenched with $H_2O$ (400 mL), an aqueous layer extracted with $CH_2Cl_2$ (3×100 mL). The combined organic layers washed with brine solution (100 mL), dried over anhydrous $Na_2SO_4$ and distilled off under reduced pressure to afford crude material. Obtained crude material was purified by combi flash column chromatography (50% ethyl acetate in hexanes) to afford ethyl 4-iodo-3-methyl-1-(1-methyl-1H-imidazole-2-carboxamido)-1H-pyrrole-2-carboxylate 211b (5.50 g, 44% {over 2 steps} yield) as an off white solid. MS (ESI+APCI; multimode): Calculated [M+1] 403. Found [M+1] 403.

Step C: 4-Iodo-3-methyl-1-(1-methyl-1H-imidazole-2-carboxamido)-1H-pyrrole-2-carboxylic acid 211c To a stirred solution of ethyl 4-iodo-3-methyl-1-(1-methyl-1H-imidazole-2-carboxamido)-1H-pyrrole-2-carboxylate 211b (5.50 g, 13.68 mmol) in mixture of EtOH: $H_2O$ (1:11 {100 mL}) was added NaOH (2.73 g, 68.4 mmol) and heated to 80° C. for 5 h. The excess of solvent was evaporated under reduced pressure left behind viscous mass, which was neutralized with dilute HCl, solid precipitated out, was filtered, washed with water and dried in vacuo to afford 4-iodo-3-methyl-1-(1-methyl-1H-imidazole-2-carboxamido)-1H-pyrrole-2-carboxylic acid 211c (5.50 g crude) as an off white solid. MS (ESI+APCI; multimode): Calculated [M+1] 375. Found [M+1] 375.

Step D: N-(2-Carbamoyl-4-iodo-3-methyl-1H-pyrrol-1-yl)-1-methyl-1H-imidazole-2-carboxamide 211d To a stirred solution of 4-iodo-3-methyl-1-(1-methyl-1H-imidazole-2-carboxamido)-1H-pyrrole-2-carboxylic acid 211c (4.00 g, 10.72 mmol) in DMF (80 mL) was added HATU (4.90 g, 12.88 mmol), $NH_4Cl$ (3.44 g, 64.34 mmol) followed by DIEA (8.30 g, 64.3 mmol) at room temperature and stirred for 12 h. The reaction mixture was quenched with $H_2O$ (100 mL), an aqueous layer extracted with ethyl acetate (3×100 mL). The combined organic layer washed with brine solution (100 mL), dried over anhydrous $Na_2SO_4$ and distilled off under reduced pressure to afford crude N-(2-carbamoyl-4-iodo-3-methyl-1H-pyrrol-1-yl)-1-methyl-1H-imidazole-2-carboxamide 211d (5.50 g, crude) as a brown color viscous mass, which was taken for next step without any further purification. MS (ESI+APCI; multimode): Calculated [M+1] 374. Found [M+1] 374.

Step E: 6-iodo-5-methyl-2-(1-methyl-1H-imidazol-2-yl)pyrrolo[2,1-f][1,2,4]triazin-4-ol 211e To a stirred solution of N-(2-carbamoyl-4-iodo-3-methyl-1H-pyrrol-1-yl)-1-methyl-1H-imidazole-2-carboxamide 211d (5.50 g, 14.74 mmol) in mixture of EtOH: $H_2O$ (1:1 {160 mL}), KOH (2.48 g, 44.23 mmol) was added and resulting mixture was heated to 100° C. for 16 h. Excess of EtOH was distilled off under reduced pressure, left behind aqueous layer; pH of an aqueous layer was adjusted to neutral with dilute HCl, solid precipitated out was filtered, washed with water (25 mL) gave a crude material. Obtained crude material was purified by combi flash column chromatography (50%-100% ethyl acetate in hexanes) to afford 6-iodo-5-methyl-2-(1-methyl-1H-imidazol-2-yl)pyrrolo[2,1-f][1,2,4]triazin-4-ol 211e (2.50 g, 51% {over 3 steps} yield) as an off white solid. MS (ESI+APCI; multimode): Calculated [M+1] 356. Found [M+1] 356. $^1H$ NMR (400 MHZ, DMSO-$d_6$) δ 2.35 (s, 3H), 3.85 (s, 3H), 6.89 (s, 1H), 7.10 (s, 1H), 7.35 (s, 1H).

Step F: 4-Chloro-6-iodo-5-methyl-2-(1-methyl-1H-imidazol-2-yl)pyrrolo[2,1-f][1,2,4]triazine 211f A mixture of 6-iodo-5-methyl-2-(1-methyl-1H-imidazol-2-yl)pyrrolo[2,1-f][1,2,4]triazin-4-ol 211e (1.50 g, 4.23 mmol) in $POCl_3$ (20 mL) was heated at 100-110° C. for 18 h. The excess $POCl_3$ was stilled off under reduced pressure, left behind viscous dark brown mass, which was diluted in $CH_2Cl_2$ (20 mL) and basified with aq. $NaHCO_3$ solution (50 mL) up to pH=8-9. The obtained crude material was again extracted with $CH_2Cl_2$ (2×100 mL), the combined organic layer, were washed with brine solution (100 mL), dried over anhydrous $Na_2SO_4$, and concentrated under reduced pressure to afford crude material, which was triturated with MTBE (20 mL) followed by hexane (20 mL) to give crude 4-chloro-6-iodo-5-methyl-2-(1-methyl-1H-imidazol-2-yl) pyrrolo[2,1-f][1,2,4]triazine 211f (0.80 g, crude) as yellow brownish solid. MS (ESI+APCI; multimode): Calculated [M+1] 374. Found 374.

Step G: 6-Iodo-N-(4-methoxybenzyl)-5-methyl-2-(1-methyl-1H-imidazol-2-yl)pyrrolo[2,1-f][1,2,4]triazin-4-amine 211g To a stirred solution of 4-chloro-6-iodo-5-methyl-2-(1-methyl-1H-imidazol-2-yl)pyrrolo[2,1-f][1,2,4]triazine 211f (0.40 g, 1.07 mmol) in DMSO (8 mL), 4-methoxybenzyl amine (176.2 mg, 1.28 mmol), DIEA (0.35 mL, 2.14 mmol) were added at room temperature then resulting reaction mixture was heated to 90° C. for 16 h. After 16 h, reaction mixture was poured on ice cold water (50 mL), solid precipitate out, was filtered, washed with $H_2O$ (2×50 mL) followed by hexanes (2×50 mL) and dried in vacuo to afford crude 6-iodo-N-(4-methoxybenzyl)-5-methyl-2-(1-methyl-1H-imidazol-2-yl)pyrrolo[2,1-f][1,2,4]triazin-4-amine 211g (0.40 g, crude) as an off white solid. MS (ESI+APCI; multimode): Calculated [M+1] 475. Found 475.

Step H: N-(4-Methoxybenzyl)-5-methyl-2-(1-methyl-1H-imidazol-2-yl)-6-(1-methyl-1H-pyrazol-3-yl)pyrrolo[2,1-f][1,2,4]triazin-4-amine 211h To a stirred solution of 6-iodo-N-(4-methoxybenzyl)-5-methyl-2-(1-methyl-1H-imidazol-2-yl)pyrrolo[2,1-f][1,2,4]triazin-4-amine 211g (0.40 g, 0.84 mmol) in 1,4-dioxane: $H_2O$ (5:1, 20 mL), $Cs_2CO_3$ (685 mg, 2.10 mmol) was added, resulting reaction mixture was degassed with Argon for 5 min, followed by addition of Pd(dppf)$Cl_2$ (0.030 g, 0.04 mmol) and resulting reaction mixture was stirred at 60° C. for 1 h. To above reaction mixture a solution of 1-methyl-3-(4,4,5,5-tetramethyl-1,3,2-dioxaborolan-2-yl)-1H-pyrazole (0.35 g, 1.68 mmol) in 1,4-dioxane (50 mL) was added dropwise over a period of 1 h and resulting reaction mixture and heated to 90° C. for 16 h. After completion of reaction, all volatiles were removed under reduced pressure left behind crude material, which was purified by combi flash column chromatography (5-10% MeOH in $CH_2Cl_2$) to afford impure N-(4-methoxybenzyl)-5-methyl-2-(1-methyl-1H-imidazol-2-yl)-6-(1-methyl-1H-pyrazol-3-yl)pyrrolo[2,1-f][1,2,4]triazin-4-amine 211h (0.30 g, impure) as brown solid. MS (ESI+APCI; multimode): Calculated [M+1] 429. Found 429.

Step I: 5-Methyl-2-(1-methyl-1H-imidazol-2-yl)-6-(1-methyl-1H-pyrazol-3-yl)pyrrolo[2,1-f][1,2,4]triazin-4-amine (211)

To crude N-(4-methoxybenzyl)-5-methyl-2-(1-methyl-1H-imidazol-2-yl)-6-(1-methyl-1H-pyrazol-3-yl)pyrrolo[2,1-f][1,2,4]triazin-4-amine 211h (0.30 g, 0.70 mmol) was added TFA (3 mL) and heated to 80° C. for 4 h. After completion of the reaction, all volatiles were removed under reduced pressure. Obtained residue was quenched with 30 mL water and then extracted with $CH_2Cl_2$ (2×60 mL). Separated aqueous layer was basified by using saturated $NaHCO_3$ solution and then extracted by $CH_2Cl_2$ (2×80 mL). The combined organic layer washed with brine solution (50 mL), dried over anhydrous $Na_2SO_4$ and distilled off under reduced pressure to afford 5-methyl-2-(1-methyl-1H-imidazol-2-yl)-6-(1-methyl-1H-pyrazol-3-yl)pyrrolo[2,1-f][1,2,4]triazin-4-amine (211) (120 mg, crude, 18% (over 4 steps) yield). MS (ESI+APCI; multimode): Calculated [M+1] 309. Found [M+1] 309. $^1$H NMR (400 MHZ, DMSO-$d_6$) δ 7.92 (s, 1H), 7.72 (s, 1H), 7.26 (s, 1H), 6.96 (s, 1H), 6.54 (s, 1H), 3.95 (s, 3H), 3.88 (s, 3H), 2.71 (s, 3H).

Example 212: Synthesis of Compound 212

(212)

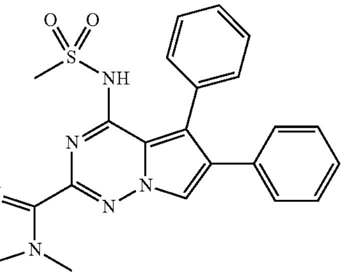

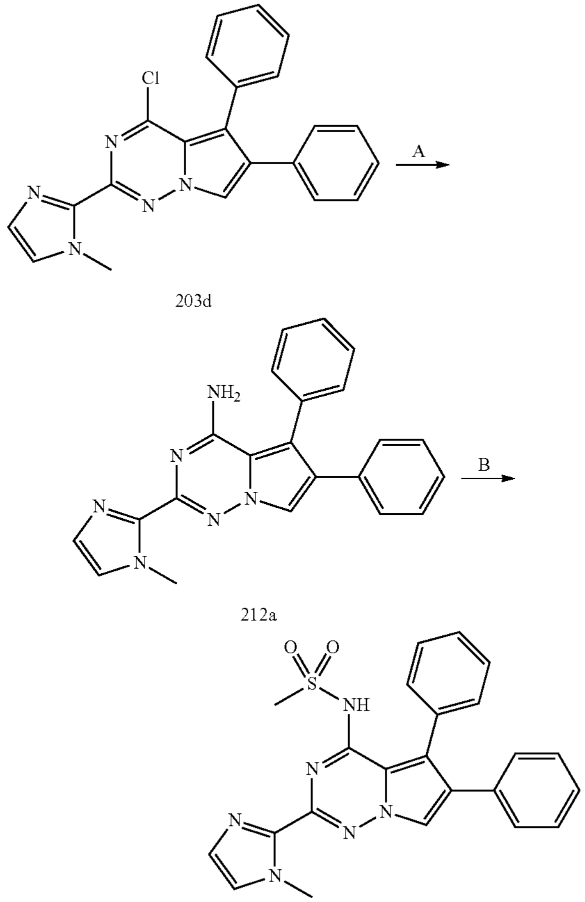

203d

212a (212)

Step A: 2-(1-Methyl-1H-imidazol-2-yl)-5,6-diphenylpyrrolo[2,1-f][1,2,4]triazin-4-amine 212a 4-Chloro-2-(1-methyl-1H-imidazol-2-yl)-5,6-diphenylpyrrolo[2,1-f][1,2,4]triazine 203d (prepared as described in Example 203, Step D) (2.0 g, 5.19 mmol) was dissolved in 30 mL MeCN. 25% aq. $NH_4OH$ was added in one portion.

The mixture was heated to 60° C. and stirred at this temperature for 36 h. The mixture was cooled and the formed precipitate was collected by filtration, washed 2 times with 20 mL water, 20 mL MeCN and dried in vacuo. 2-(1-Methyl-1H-imidazol-2-yl)-5,6-diphenylpyrrolo[2,1-f][1,2,4]triazin-4-amine 212a (1.1 g, 3.0 mmol, 57.8% yield) was obtained as pale-brown powder.

Step B: N-(2-(1-Methyl-1H-imidazol-2-yl)-5,6-diphenylpyrrolo[2,1-f][1,2,4]triazin-4-yl) methanesulfonamide (212)

Using the method described in Example 102, Step A, 2-(1-methyl-1H-imidazol-2-yl)-5,6-diphenylpyrrolo[2,1-f][1,2,4]triazin-4-amine 212a (50.0 mg, 129.87 mmol), methanesulfonamide (24.7 mg, 260.0 mmol), sodium hydride (11.4 mg, 475.13 μmol) (60% in mineral oil) in DMF (2 mL) afforded N-(2-(1-methyl-1H-imidazol-2-yl)-5,6-diphenylpyrrolo[2,1-f][1,2,4]triazin-4-yl) methanesulfonamide (212) as a yellow solid (8.5 mg, 14.8% yield) (purity 100%). LCMS(ESI) Rt=1.277 min. Calculated [M+1] 445.2. Found [M+1] 455.0.

Example 213-Example 214

Using the method described in Example 212, 2-(1-methyl-1H-imidazol-2-yl)-5,6-diphenylpyrrolo[2,1-f][1,2,4]triazin-4-amine 212a (100.0 mg, 0.273 mmol), 3-methoxypropane-1-sulfonamide, sodium hydride (22.76 mg, 0.948 mmol) (60% in mineral oil) in DMF (1 mL) gave Example compound (213). Using the method described in Example 212, 2-(1-methyl-1H-imidazol-2-yl)-5,6-diphenylpyrrolo[2,1-f][1,2,4]triazin-4-amine 212a (100.0 mg, 0.259 mmol), (1r,3r)-3-methoxycyclobutane-1-sulfonyl chloride (100.47 mg, 0.546 mmol), sodium hydride (22.76 mg, 0.948 mmol) (60% in mineral oil) in DMF (1 mL) gave Example compound (213). Example compound (213) and Example compound (214) are shown in Table C along with analytical data.

Example 215: Synthesis of Compound 215

(215)

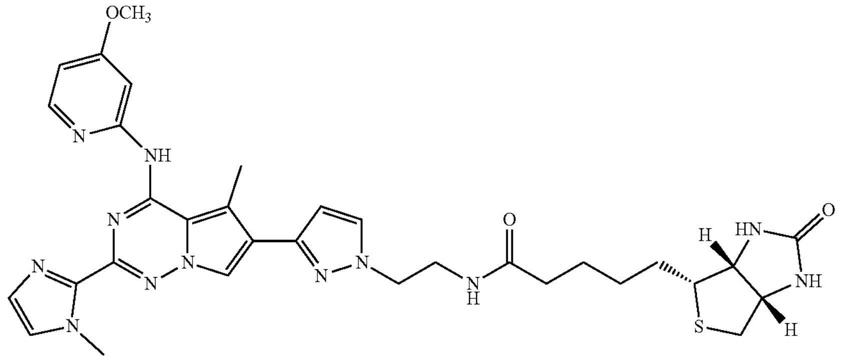

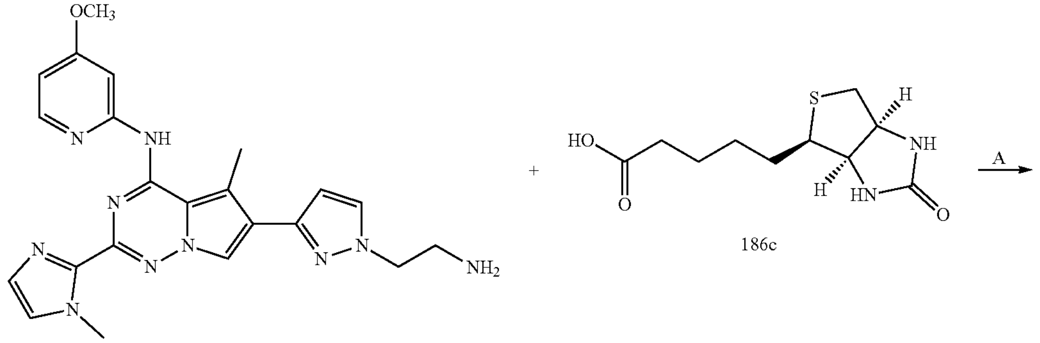

(187)

186c

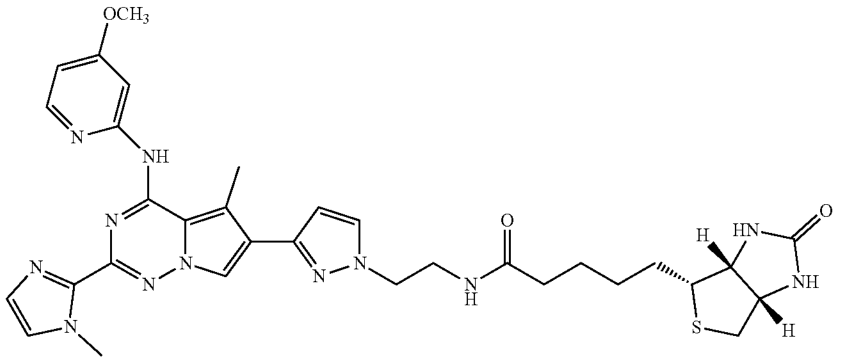

(215)

Step A: N-(2-(3-(4-((4-methoxypyridin-2-yl)amino)-5-methyl-2-(1-methyl-1H-imidazol-2-yl)pyrrolo[2,1-f][1,2,4]triazin-6-yl)-1H-pyrazol-1-yl)ethyl)-5-((3aR,4R,6aS)-2-oxohexahydro-1H-thieno[3,4-d]imidazol-4-yl)pentanamide (215)

To the solution of biotin 186c (19.8 mg, 81.1 μmol) in DMF (2 mL), TCFH (chloro-N,N,N',N'-tetramethylformamidinium hexafluorophosphate) (36.99 mg, 97.32 μmol) was added in one portion followed by the dropwise addition of ethylbis(propan-2-yl)amine (52.37 mg, 405.49 μmol). The mixture was stirred at room temperature for 15 min and the solution of N-((1r,3r)-3-Methoxycyclobutyl)-2-(1-methyl-1H-imidazol-2-yl)-5,6-diphenylpyrrolo[2,1-f][1,2,4]triazin-4-amine (203) (prepared as described in Example 187, Step G) (90.0 mg, 202.61 μmol) in DMF (0.5 mL) was added. The mixture was stirred for 1 h (reaction has been completed) and then purified by HPLC (0-2-12 min 0-55$H_2O$/MeOH/0.1FA; flow 30 mL/min ((loading pump 4 mL MeOH) column: XBridge BEH C18 100*19 mm, 5 microM)), to give N-(2-(3-(4-((4-methoxypyridin-2-yl)amino)-5-methyl-2-(1-methyl-1H-imidazol-2-yl)pyrrolo[2,1-f][1,2,4]triazin-6-yl)-1H-pyrazol-1-yl)ethyl)-5-((3aR,4R,6aS)-2-oxohexahydro-1H-thieno[3,4-d]imidazol-4-yl)pentanamide (215) (7.5 mg, 95.0% purity, 10.62 μmol, 13.1% yield). LCMS(ESI) Rt=0.773 min. Calculated [M+1] 671.2. Found [M+1] 671.4. $^1$H NMR (500 MHz, DMSO-$d_6$) δ (ppm) 1.20 (m, 3H), 1.50 (m, 5H), 1.99 (t, 2H), 2.71 (m, 1H), 2.83 (s, 3H), 3.01 (m, 1H), 3.43 (m, 2H), 3.88 (s, 3H), 4.02 (m, 4H), 4.21 (m, 3H), 6.33 (m, 2H), 6.51 (s, 1H), 6.70 (m, 1H), 7.35 (m, 2H), 7.70 (s, 1H), 7.96 (m, 2H), 8.20 (m, 1H).

Example 216: Synthesis of Compound 216

(216)

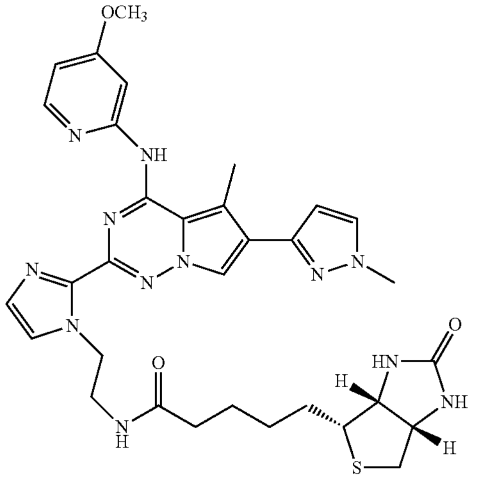

-continued

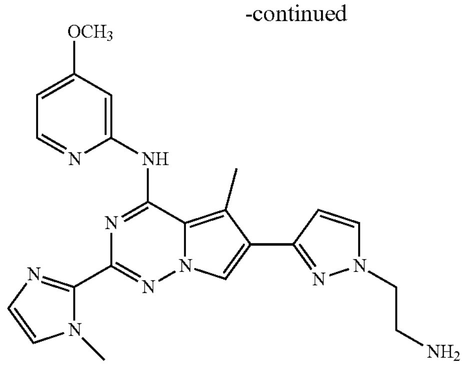

+

(188)

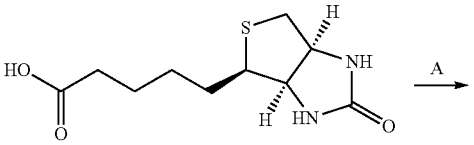

186c

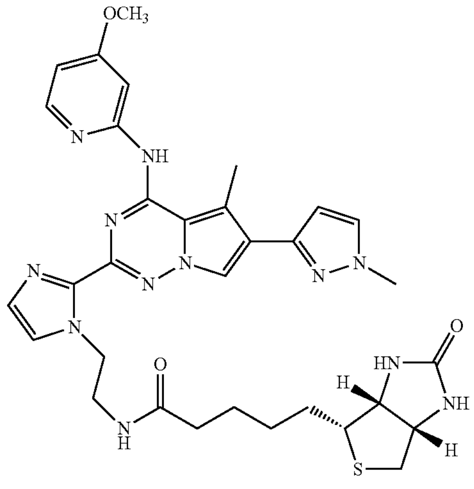

(216)

Step E: N-(2-(2-(4-((4-methoxypyridin-2-yl)amino)-5-methyl-6-(1-methyl-1H-pyrazol-3-yl)pyrrolo[2,1-f][1,2,4]triazin-2-yl)-1H-imidazol-1-yl)ethyl)-5-((3aR,4R,6aS)-2-oxohexahydro-1H-thieno[3,4-d]imidazol-4-yl)pentanamide (216)

To a solution of biotin 186c (165.35 mg, 676.82 μmol) in DMF (2 mL), HATU (308.81 mg, 812.18 μmol) was added in one portion. Then DIEA (437.78 mg, 3.39 mmol, 590.0 μL) was added in one portion and the mixture was stirred for 15 min. 2-(1-(2-Aminoethyl)-1H-imidazol-2-yl)-N-(4-methoxypyridin-2-yl)-5-methyl-6-(1-methyl-1H-pyrazol-3-yl)pyrrolo[2,1-f][1,2,4]triazin-4-amine (188) (prepared as described in Example 188, Step D) (350.19 mg, 676.82 μmol) was added and the mixture was stirred for 16 h at room temperature. After HPLC (0-2-9 min 0-0-50% MeOH/$H_2O$+HCl, flow: 30 mL/min (loading pump 4 mL MeOH); column: Chromatorex C18 SMB100-5T 100*19 mm, 5 microM) purification N-(2-(2-(4-((4-methoxypyridin-2-yl)amino)-5-methyl-6-(1-methyl-1H-pyrazol-3-yl)pyrrolo[2,1-f][1,2,4]triazin-2-yl)-1H-imidazol-1-yl)ethyl)-5-((3aR,4R,6aS)-2-oxohexahydro-1H-thieno[3,4-d]imidazol-4-yl)pentanamide (216) (60.0 mg, 89.45 μmol, 13.2% yield) (purity 97%) was obtained as brown solid. LCMS(ESI) Rt=0.774 min. Calculated [M+1] 671.2. Found [M+1] 671.2.

$^1$H NMR (500 MHZ, DMSO-$d_6$) δ (ppm) 1.15 (m, 2H), 1.26 (m, 3H), 1.50 (m, 1H), 1.99 (m, 2H), 2.77 (m, 1H), 2.81 (m, 3H), 3.01 (m, 1H), 3.20 (m, 1H), 3.50 (m, 2H), 3.80 (m, 7H), 4.03 (m, 1H), 4.14 (m, 1H), 4.58 (m, 2H), 6.27 (m, 2H), 6.52 (s, 1H), 6.74 (m, 2H), 7.20 (d, 1H), 7.48 (m, 1H), 7.70 (m, 1H), 7.84 (m, 2H), 8.24 (m, 1H).
Example 217: Synthesis of Compound 217
(217)
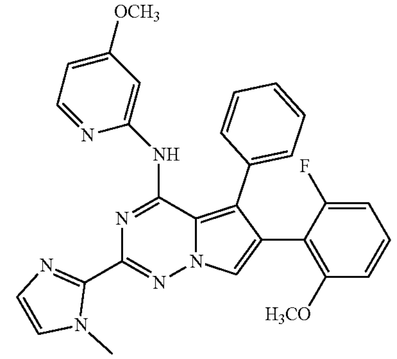
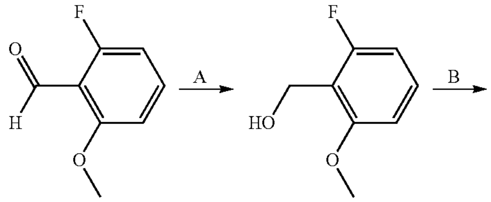
217a
217b
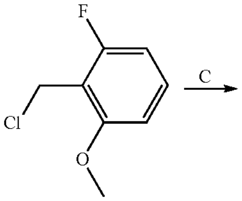
217c
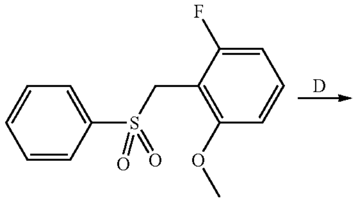
217d
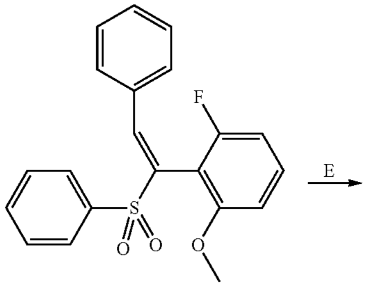
217e
-continued
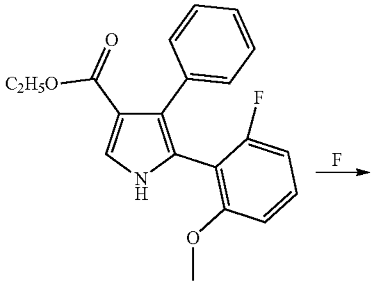
217f
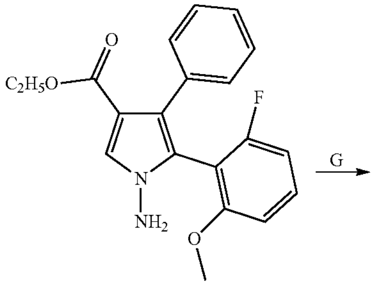
217g
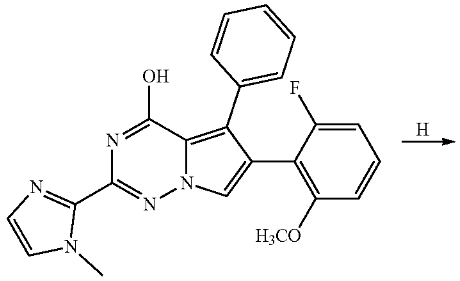
217h
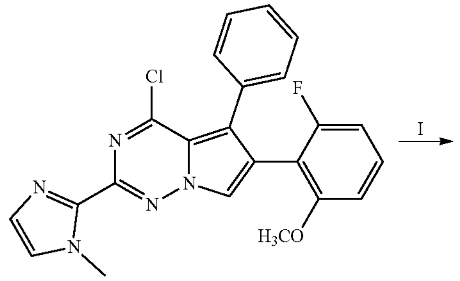
217i
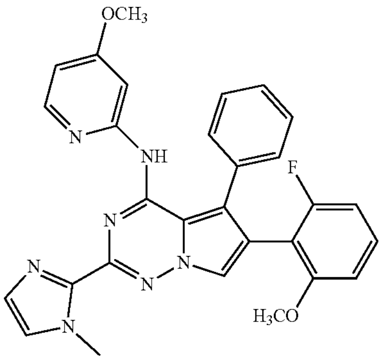
(217)

Step A: (2-Fluoro-6-methoxyphenyl)methanol 217b

To the solution of 2-fluoro-6-methoxybenzaldehyde 217a (49.12 g, 318.87 mmol) in dry MeOH (600 mL), sodium borohydride (14.55 g, 382.64 mmol) was added portionwise at room temperature, and stirred overnight. After reaction mixture was evaporated under reduced pressure, diluted with water (500 mL) and 3 times by EtOAc (3*300 mL). The organic phase washed with water, brine, dried over $Na_2SO_4$ and concentrated in vacuo to give (2-fluoro-6-methoxyphenyl)methanol 217b (49.75 g, 95.0% purity, 302.67 mmol, 94% yield). $^1H$ NMR (400 MHz, DMSO-$d_6$) δ (ppm) 3.87 (s, 3H), 4.62 (s, 3H), 6.70 (m, 2H), 7.20 (dd, 1H).

Step B: 2-(Chloromethyl)-1-fluoro-3-methoxybenzene 217c

To the solution of (2-fluoro-6-methoxyphenyl)methanol 217b (49.75 g, 318.79 mmol) in dry $CH_2Cl_2$ (600 mL) and 2 drops of DMF, sulfuroyl dichloride (82.69 g, 701.34 mmol) was added dropwise at room temperature, and stirred overnight. After reaction mixture was evaporated under reduced pressure to give 2-(chloromethyl)-1-fluoro-3-methoxybenzene 217c (59.0 g, 92.0% purity, 310.88 mmol, 97.5% yield). $^1H$ NMR (400 MHZ, $CDCl_3$) δ (ppm) 3.89 (s, 3H), 4.69 (s, 2H), 6.69 (m, 2H), 7.21 (dd, 1H).

Step C: 1-Fluoro-3-methoxy-2-((phenylsulfonyl)methyl) benzene 217d

To the solution of 2-(chloromethyl)-1-fluoro-3-methoxybenzene 217c (59.0 g, 339.03 mmol) in dry IPA (650 mL), sodium benzenesulfinate (61.16 g, 372.94 mmol) was added portionwise at RT, and heated at 80° C. overnight. After reaction mixture was evaporated under reduced pressure, diluted with water (500 mL) and 3 times with EtOAc (3*300 mL). The organic phase washed with water, brine, dried over $Na_2SO_4$ and concentrated in vacuo to give 1-fluoro-3-methoxy-2-((phenylsulfonyl)methyl) benzene 217d (84.25 g, 90.0% purity, 270.5 mmol, 79.8% yield).

Step D: (E)-1-Fluoro-3-methoxy-2-(2-phenyl-1-(phenylsulfonyl)vinyl)benzene 217e

To 1-fluoro-3-methoxy-2-((phenylsulfonyl)methyl) benzene 217d (50.0 g, 178.37 mmol) in THF (1500 mL) was added LiHMDS (1.1 M in THF/Ethylbenzene, 194 mL), at −78° C. and the mixture was stirred for 10 min. To the solution was added benzaldehyde (22.7 g, 214.05 mmol), and the mixture was stirred for 1 h. Diethyl chlorophosphonate (36.82 g, 214.05 mmol) was added, and the mixture was stirred for 1 hr. Then LiHMDS (1.1 M in THF/ethylbenzene, 194 ml) was added at −78° C., and the mixture was stirred to ambient temperature. The resulting mixture was poured into $NH_4Cl$ (saturated aqueous solution, 800 mL) and extracted with EtOAc (3*400 mL). The organic phase washed with water, brine, dried over $Na_2SO_4$, concentrated in vacuo and purified by FCC (Interchim; 800 g $SiO_2$, petroleum ether/ethyl acetate with ethyl acetate from 0~60%, flow rate=mL/min, Rv=7.5-10 CV) to give (E)-1-fluoro-3-methoxy-2-(2-phenyl-1-(phenylsulfonyl)vinyl) benzene 217e (29.0 g, 85.0% purity, 66.91 mmol, 37.5% yield).

$^1H$ NMR (400 MHZ, $CDCl_3$) δ (ppm) 3.25 (s, 3H), 6.60 (m, 1H), 6.73 (m, 1H), 7.30 (m, 8H), 7.52 (m, 1H), 7.73 (m, 2H), 8.14 (s, 1H).

Step E: Ethyl 5-(2-fluoro-6-methoxyphenyl)-4-phenyl-1H-pyrrole-3-carboxylate 217f Potassium t-butoxide (8.83 g, 78.79 mmol) was added portionwise to the solution of (E)-1-fluoro-3-methoxy-2-(2-phenyl-1-(phenylsulfonyl)vinyl)benzene 217e (29.0 g, 78.79 mmol) and ethyl 2-isocyanoacetate (8.91 g, 78.79 mmol) in dry THF (600 mL) at (−10° C.), and stirred at room temperature overnight. Then reaction mixture was diluted with ice water (400 mL) and extracted 3 times by EtOAc (3*400 mL). The organic phase washed with water, brine, dried over $Na_2SO_4$, concentrated in vacuo and purified by FCC (Interchim, 330 g $SiO_2$, hexane/ethyl acetate (10-32%), flow rate=127 mL/min, 7.1-8.6 CV) to give ethyl 5-(2-fluoro-6-methoxyphenyl)-4-phenyl-1H-pyrrole-3-carboxylate 217f (12.6 g, 95.0% purity, 35.27 mmol, 44.8% yield). LCMS(ESI) Rt=1.264 min. Calculated [M+1] 340.2. Found [M+1] 340.0. $^1H$ NMR (400 MHz, DMSO-$d_6$) δ (ppm) 1.02 (t, 3H), 3.40 (s, 3H), 4.09 (q, 2H), 6.54 (m, 2H), 6.87 (s, 1H), 6.95 (m, 2H), 7.17 (m, 4H), 11.97 (s, 1H).

Step F: Ethyl 1-amino-5-(2-fluoro-6-methoxyphenyl)-4-phenyl-1H-pyrrole-3-carboxylate 217g Sodium hydride (2.2 g, 55 mmol) (60% in mineral oil) was added portionwise to a solution of ethyl 5-(2-fluoro-6-methoxyphenyl)-4-phenyl-1H-pyrrole-3-carboxylate 217f (11.97 g, 35.3 mmol) in DMF (120 mL) at 0° C. The mixture was stirred for 1 h at room temperature. Then, the mixture was cooled to 0° C. and O-(2,4-dinitrophenyl) hydroxylamine (10.54 g, 52.94 mmol) was added portionwise. The reaction mixture was stirred for 16 h at room temperature. Then, it was poured in ice water, and extracted with EtOAc (3*100 mL). The organic phase washed with water, brine, dried over $Na_2SO_4$, concentrated in vacuo to give ethyl 1-amino-5-(2-fluoro-6-methoxyphenyl)-4-phenyl-1H-pyrrole-3-carboxylate 217g (15.94 g, 75.0% purity, 33.74 mmol, 95.6% yield) as dark oil. LCMS(ESI) Rt=3.730 min. Calculated [M+1] 355.2. Found [M+1] 355.2.

Step G: 6-(2-Fluoro-6-methoxyphenyl)-2-(1-methyl-1H-imidazol-2-yl)-5-phenylpyrrolo[2,1-f][1,2,4]triazin-4-ol 217h Sodium hydride (3.6 g, 0.09 mol) (60% in mineral oil) was added portionwise to the solution of ethyl 1-amino-5-(2-fluoro-6-methoxyphenyl)-4-phenyl-1H-pyrrole-3-carboxylate 217g (15.94 g, 45.01 mmol) and 1-methyl-1H-imidazole-2-carbonitrile (5.42 g, 50.64 mmol) in dry dioxane (160 mL). Then, the reaction mixture was heated at 80° C. and stirred at this temperature for 16 h. Then, it was cooled to room temperature, poured in ice water, neutralized with acetic acid and extracted with EtOAc (3*100 mL). The organic phase washed with water, brine, dried over $Na_2SO_4$, concentrated in vacuo to give 6-(2-fluoro-6-methoxyphenyl)-2-(1-methyl-1H-imidazol-2-yl)-5-phenylpyrrolo[2,1-f][1,2,4]triazin-4-ol 217h (16.8 g, 60.0% purity, 24.26 mmol, 71.9% yield). LCMS(ESI) Rt=1.294 min. Calculated [M+1] 416.2. Found [M+1] 416.2.

Step H: 4-Chloro-6-(2-fluoro-6-methoxyphenyl)-2-(1-methyl-1H-imidazol-2-yl)-5-phenylpyrrolo[2,1-f][1,2,4]triazine 217i To the solution of 6-(2-fluoro-6-methoxyphenyl)-2-(1-methyl-1H-imidazol-2-yl)-5-phenylpyrrolo[2,1-f][1,2,4]triazin-4-ol 217h (7.0 g, 16.85 mmol) in $CH_3CN$ (150 mL), phosphoroyl trichloride (7.17 g, 47.19 mmol) was added dropwise. The mixture was heated to 80° C. and stirred at this temperature for 16 h and then concentrated in vacuo, poured in ice water (5 mL) and neutralized with $NaHCO_3$ (aqueous solution). The formed participate was collected by filtration, washed with water (2*20 mL) and dried in vacuo, to give 4-chloro-6-(2-fluoro-6-methoxyphenyl)-2-(1-methyl-1H-imidazol-2-yl)-5-phenylpyrrolo[2,1-f][1,2,4]triazine 217i (7.1 g, 70.0% purity, 11.46 mmol, 97.1% yield) as yellow solid. LCMS(ESI) Rt=2.925 min. Calculated [M+1] 434.2. Found [M+1] 434.0.

Step I: 6-(2-Fluoro-6-methoxyphenyl)-N-(4-methoxypyridin-2-yl)-2-(1-methyl-1H-imidazol-2-yl)-5-phenylpyrrolo[2,1-f][1,2,4]triazin-4-amine (217)

Sodium hydride (46 mg, 1.15 mmol) (60% in mineral oil) was added in portionwise to the solution of 4-methoxypyridin-2-amine (79.93 mg, 644.24 μmol) in DMF (1 mL). The mixture was stirred at room temperature for 30 min, then 4-chloro-6-(2-fluoro-6-methoxyphenyl)-2-(1-methyl-1H-imidazol-2-yl)-5-phenylpyrrolo[2,1-f][1,2,4]triazine 217i (200.0 mg, 460.97 μmol) was added in one portion, and stirred overnight. After this time resulting mixture quenched with $NH_4Cl$ (saturated aqueous solution). The formed precipitate was collected by filtration, washed with water (2*1 mL) and purified by HPLC (column: XBridge BEH C18 100*19 mm, 5 microM (48-55-85% 0-2-10; flow 30 mL/min $MeOH/H_2O/0.1NH_4OH$ (loading pump 4 mL MeOH) to give 6-(2-Fluoro-6-methoxyphenyl)-N-(4-methoxypyridin-2-yl)-2-(1-methyl-1H-imidazol-2-yl)-5-phenylpyrrolo[2,1-f][1,2,4]triazin-4-amine (217) (50.7 mg, 95.0% purity, 92.35 μmol, 28.7% yield). LCMS(ESI) Rt=1.319 min. Calculated [M+1] 522.2. Found [M+1] 522.2.

$^1H$ NMR (500 MHZ, DMSO-$d_6$) δ (ppm) 3.45 (s, 3H), 3.84 (s, 3H), 4.00 (s, 3H), 6.42 (m, 3H), 7.08 (s, 1H), 7.35 (m, 7H), 7.71 (s, 1H), 7.94 (d, 1H), 8.07 (s, 1H), 8.70 (s, 1H).

Example 218-Example 276

Using the methods described in the foregoing Examples, Example Compounds (218)-(276) were synthesized using the appropriate corresponding starting materials. Structures and data for Example Compounds (218)-(276) are in Table C.

Examples 218, 219, 269, 270, 271, and 272 were prepared following the method described in Example 209 for the preparation of Compound (209).

Example 220 was prepared from Example 99, Procedure B, Compound (99) except instead of an amine, using 4-methoxypyridin-2-ol in the procedure of Example 102, Step A.

Examples 221-268 were prepared from Example 99, Procedure B, Compound (99), using the procedure described in Example 102, Step A. Examples 261 and 262 were both products obtained from the reaction of Example 99, Procedure B, Compound (99), with 5-amino-1,2-dihydro-3H-pyrazol-3-one. In the preparation of Example 252, Compound (252), an isomeric by-product was also produced in the last step (10.5 mg, 8.8% yield) (purity 93%). LCMS ESI Calculated [M+1] 405.2. Found [M+1] 405.2. In the preparation of Example 256, Compound (256), an isomeric by-product was also produced in the last step (10.0 mg, 8.8% yield) (purity 98%). LCMS ESI Calculated [M+1] 375.2. Found [M+1] 375.2. In the preparation of Example 260, Compound (260), an isomeric by-product was also produced in the last step (15 mg, 11.5% yield) (purity 96%). LCMS ESI Calculated [M+1] 419.2. Found [M+1] 419.2.

Examples 273, 274, 275, and 276 were prepared following the method described in Example 166, for the preparation of Compound (166). The final step in the synthesis of Example 276 Compound (276) used the conditions described in Example 102, Step A, in place of those described in Example 166, Step G.

TABLE C

| Compounds and Analytical Data | | | | |
|---|---|---|---|---|
| Example | Structure | Name | Amount (Yield)* | Purity |
| 152 | 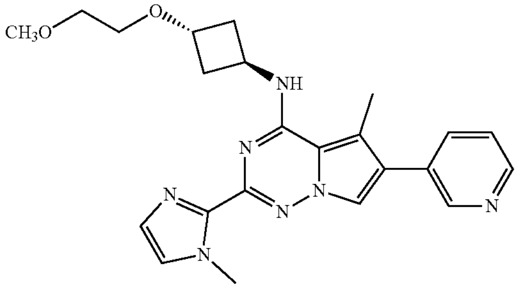 (152) | N-((1r,3r)-3-(2-methoxyethoxy)cyclobutyl)-5-methyl-2-(1-methyl-1H-imidazol-2-yl)-6-(pyridin-3-yl)pyrrolo[2,1-f][1,2,4]triazin-4-amine | 3.0 mg (2.3%) | 90% |

TABLE C-continued

| Compounds and Analytical Data | | | | |
|---|---|---|---|---|
| 153 | 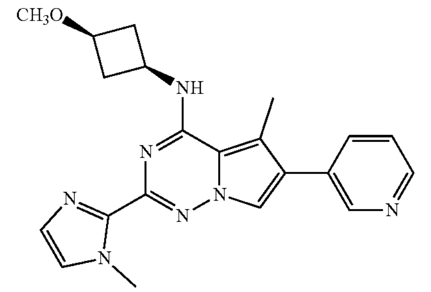 (153) | N-((1s,3s)-3-methoxy-cyclobutyl)-5-methyl-2-(1-methyl-1H-imidazol-2-yl)-6-(pyridin-3-yl)pyrrolo[2,1-f][1,2,4]triazin-4-amine | 3.7 mg (3.1%) | 96% |
| 154 | 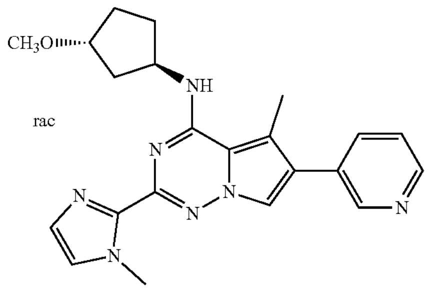 (154) | rac N-((1R,3R)-3-methoxy-cyclopentyl)-5-methyl-2-(1-methyl-1H-imidazol-2-yl)-6-(pyridin-3-yl)pyrrolo[2,1-f][1,2,4]triazin-4-amine | 2.6 mg (2.1%) | 96% |
| 155 | 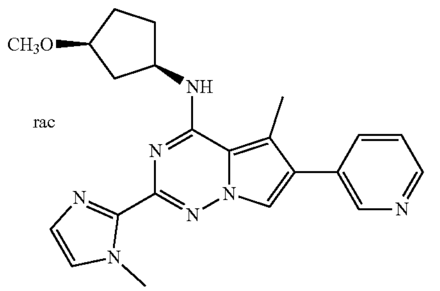 (155) | rac N-((1R,3S)-3-methoxy-cyclopentyl)-5-methyl-2-(1-methyl-1H-imidazol-2-yl)-6-(pyridin-3-yl)pyrrolo[2,1-f][1,2,4]triazin-4-amine | 22.0 mg (17.7%) | 100% |
| 156 | 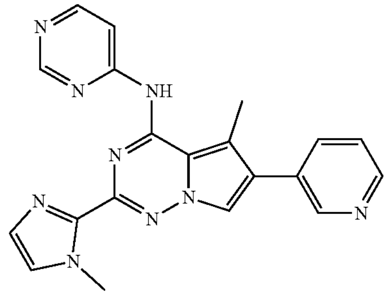 (156) | 5-Methyl-2-(1-methyl-1H-imidazol-2-yl)-6-(pyridin-3-yl)-N-(pyrimidin-4-yl)pyrrolo[2,1-f][1,2,4]triazin-4-amine | 14.0 mg (11.9%) | 100% |

TABLE C-continued

| Compounds and Analytical Data | | | | |
|---|---|---|---|---|
| 157 | 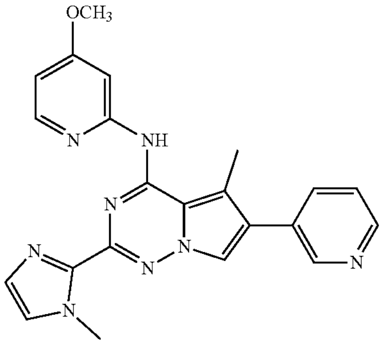 (157) | N-(4-Methoxy-pyridin-2-yl)-5-methyl-2-(1-methyl-1H-imidazol-2-yl)-6-(pyridin-3-yl)pyrrolo[2,1-f][1,2,4]triazin-4-amine | 17.0 mg (13.4%) | 100% |
| 158 | 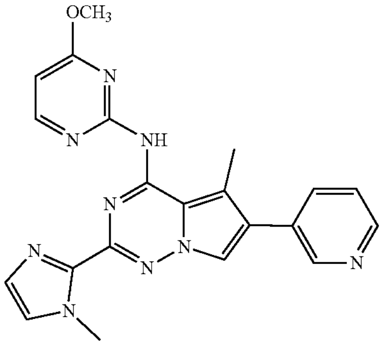 (158) | N-(4-Methoxy-pyrimidin-2-yl)-5-methyl-2-(1-methyl-1H-imidazol-2-yl)-6-(pyridin-3-yl)pyrrolo[2,1-f][1,2,4]triazin-4-amine | 16.0 mg (12.6%) | 100% |
| 161 | 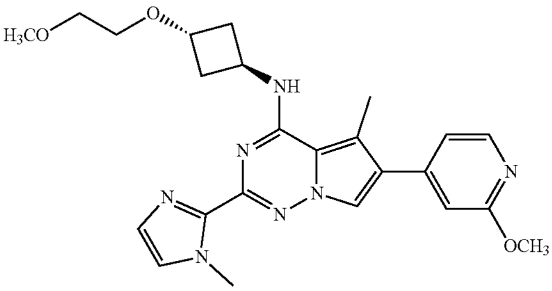 (161) | N-((1r,3r)-3-(2-Methoxy-ethoxy)cyclo-butyl)-6-(2-methoxy-pyridin-4-yl)-5-methyl-2-(1-methyl-1H-imidazol-2-yl)pyrrolo[2,1-f][1,2,4]triazin-4-amine | 8.4 mg (3.2%) | 100% |
| 162 | 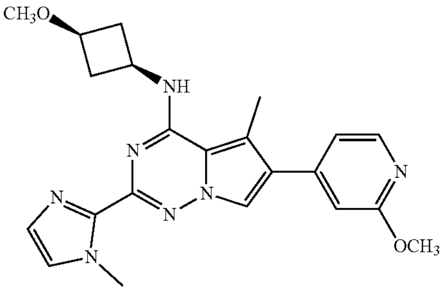 (162) | N-((1s,3s)-3-Methoxycyclobutyl)-6-(2-methoxypyridin-4-yl)-5-methyl-2-(1-methyl-1H-imidazol-2-yl)pyrrolo[2,1-f][1,2,4]triazin-4-amine | 9.2 mg (3.9%) | 100% |

TABLE C-continued

| Compounds and Analytical Data | | | | |
|---|---|---|---|---|
| 163 | 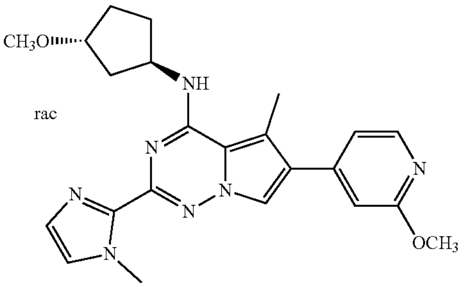 (163) | rac N-((1R,3R)-3-Methoxycyclopentyl)-6-(2-methoxypyridin-4-yl)-5-methyl-2-(1-methyl-1H-imidazol-2-yl)pyrrolo[2,1-f][1,2,4]triazin-4-amine | 23.0 mg (9.5%) | 100% |
| 164 | 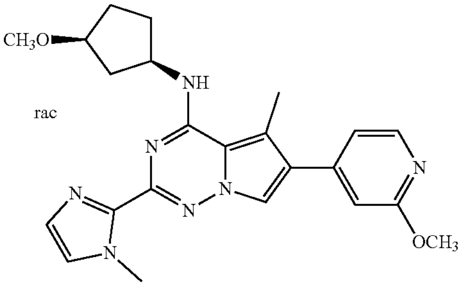 (164) | rac N-((1R,3S)-3-Methoxycyclopentyl)-6-(2-methoxypyridin-4-yl)-5-methyl-2-(1-methyl-1H-imidazol-2-yl)pyrrolo[2,1-f][1,2,4]triazin-4-amine | 4.7 mg (2.0%) | 99% |
| 167 | 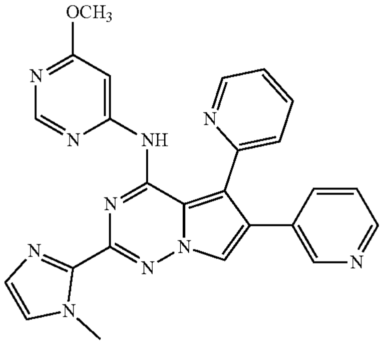 (167) | N-(6-Methoxypyrimidin-4-yl)-2-(1-methyl-1H-imidazol-2-yl)-5-(pyridin-2-yl)-6-(pyridin-3-yl)pyrrolo[2,1-f][1,2,4]triazin-4-amine | 27.7 mg (21.4%) | 100% |
| 168 | 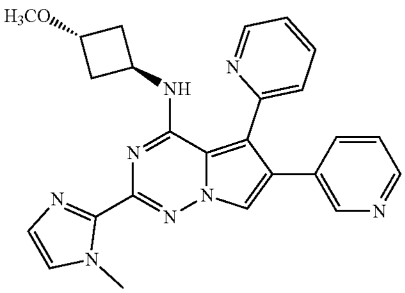 (168) | N-((1r,3r)-3-Methoxycyclobutyl)-2-(1-methyl-1H-imidazol-2-yl)-5-(pyridin-2-yl)-6-(pyridin-3-yl)pyrrolo[2,1-f][1,2,4]triazin-4-amine | 3.0 mg 2.4% | 96% |

TABLE C-continued

| Compounds and Analytical Data | | | | |
|---|---|---|---|---|
| 170 | 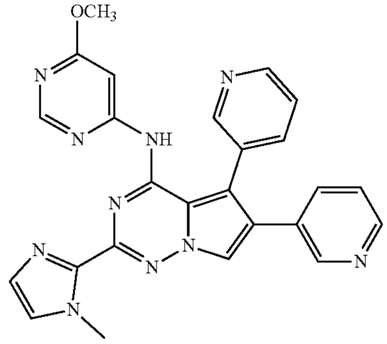 (170) | N-(6-Methoxypyrimidin-4-yl)-2-(1-methyl-1H-imidazol-2-yl)-5,6-di(pyridin-3-yl)pyrrolo[2,1-f][1,2,4]triazin-4-amine | Write up | 100% |
| 171 | 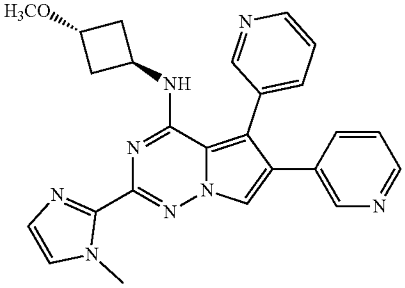 (171) | N-((1r,3r)-3-Methoxycyclobutyl)-2-(1-methyl-1H-imidazol-2-yl)-5,6-di(pyridin-3-yl)pyrrolo[2,1-f][1,2,4]triazin-4-amine | 4.2 mg (3.4%) | 93% |
| 174 | 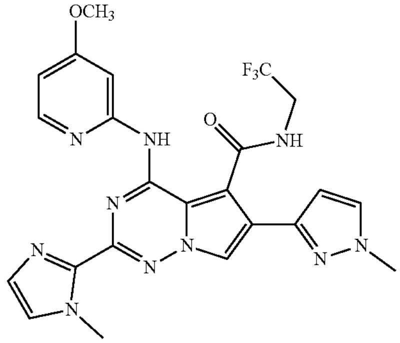 (174) | 4-((4-Methoxypyridin-2-yl)amino)-2-(1-methyl-1H-imidazol-2-yl)-6-(1-methyl-1H-pyrazol-3-yl)-N-(2,2,2-trifluoro-ethyl)pyrrolo[2,1-f][1,2,4]triazine-5-carboxamide | 16.9 mg (9.6%) | 100% |
| 175 | 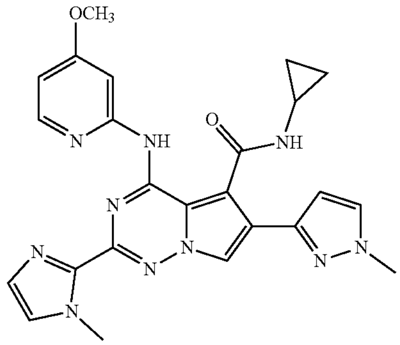 (175) | N-Cyclopropyl-4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxamide | 23.6 mg (10.7%) | 99% |

TABLE C-continued

| Compounds and Analytical Data | | | | |
|---|---|---|---|---|
| 176 | 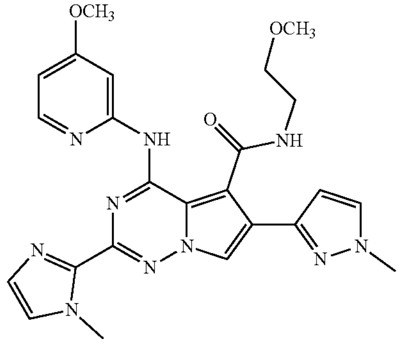 (176) | N-(2-Methoxyethyl)-4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxamide | 13.7 mg (8.2%) | 100% |
| 177 | 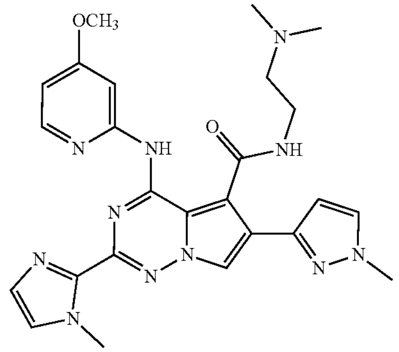 (177) | N-(2-(Dimethylamino)ethyl)-4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxamide | 14.1 mg (8.1%) | 100% |
| 178 | 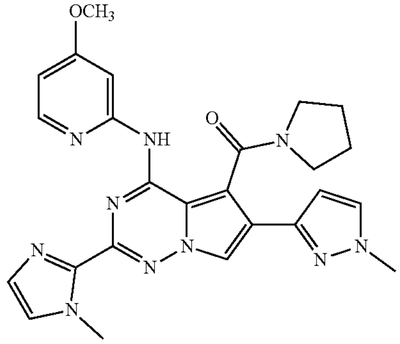 (178) | (4-((4-Methoxypyridin-2-yl)amino)-2-(1-methyl-1H-imidazol-2-yl)-6-(1-methyl-1H-pyrazol-3-yl)pyrrolo[2,1-f][1,2,4]triazin-5-yl)(pyrrolidin-1-yl)methanone | 16.0 mg (9.4%) | 99% |
| 179 | 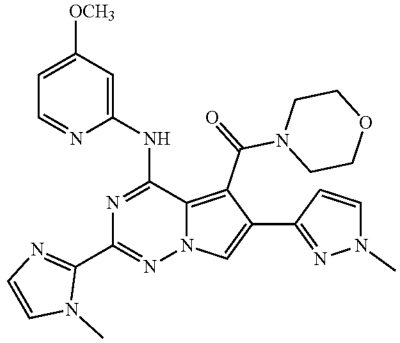 (179) | (4-((4-Methoxypyridin-2-yl)amino)-2-(1-methyl-1H-imidazol-2-yl)-6-(1-methyl-1H-pyrazol-3-yl)pyrrolo[2,1-f][1,2,4]triazin-5-yl)(morpholino)methanone | 24.0 mg (13.8%) | 100% |

TABLE C-continued

| Compounds and Analytical Data | | | | |
|---|---|---|---|---|
| 182 | 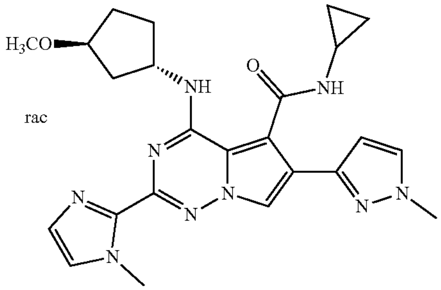 (182) | rac N-Cyclopropyl-4-(((1S,3S)-3-methoxycyclo-pentyl)amino)-2-(1-methyl-1H-imidazol-2-yl)-6-(1-methyl-1H-pyrazol-3-yl)pyrrolo[2,1-f][1,2,4]triazine-5-carboxamide | 10.4 mg (10.9%) | 100% |
| 183 | 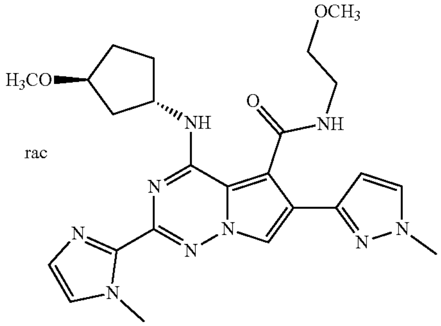 (183) | rac 4-(((1S,3S)-3-Methoxycyclo-pentyl)amino)-N-(2-methoxyethyl)-2-(1-methyl-1H-imidazol-2-yl)-6-(1-methyl-1H-pyrazol-3-yl)pyrrolo[2,1-f][1,2,4]triazine-5-carboxamide | 4.2 mg (47.2%) | 98% |
| 184 | 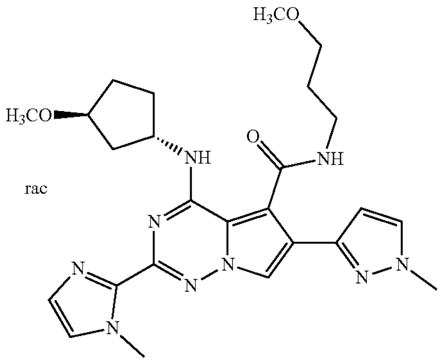 (184) | rac 4-(((1S,3S)-3-methoxycyclo-pentyl)amino)-N-(3-methoxypropyl)-2-(1-methyl-1H-imidazol-2-yl)-6-(1-methyl-1H-pyrazol-3-yl)pyrrolo[2,1-f][1,2,4]triazine-5-carboxamide | 5.8 mg (2.3%) | 100% |
| 185 | 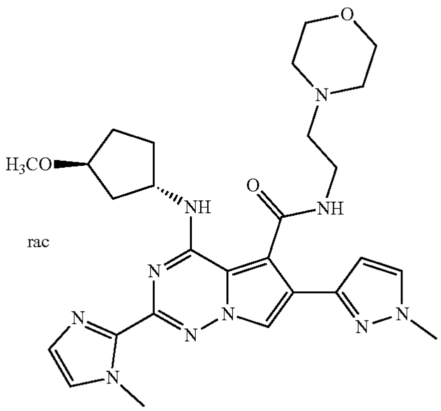 (185) | rac 4-(((1S,3S)-3-methoxycyclo-pentyl)amino)-2-(1-methyl-1H-imidazol-2-yl)-6-(1-methyl-1H-pyrazol-3-yl)-N-(2-morpholino-ethyl)pyrrolo[2,1-f][1,2,4]triazine-5-carboxamide | 15.7 mg (13.9%) | 100% |

TABLE C-continued

| Compounds and Analytical Data | | | | |
|---|---|---|---|---|
| 191 | 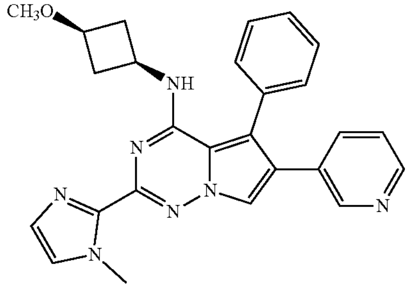<br>(191) | N-((1s,3s)-3-Methoxycyclobutyl)-2-(1-methyl-1H-imidazol-2-yl)-5-phenyl-6-(pyridin-3-yl)pyrrolo[2,1-f][1,2,4]triazin-4-amine | 25.2 mg (20.1%) | 99% |
| 192 | 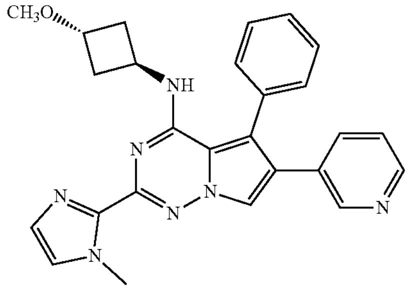<br>(192) | N-((1r,3r)-3-Methoxycyclobutyl)-2-(1-methyl-1H-imidazol-2-yl)-5-phenyl-6-(pyridin-3-yl)pyrrolo[2,1-f][1,2,4]triazin-4-amine | 27.0 mg (21.6%) | 99% |
| 193 | 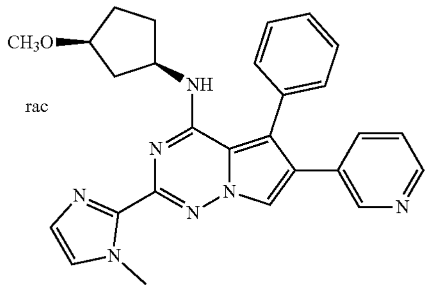<br>(193) | rac N-((1R,3S)-3-Methoxycyclopentyl)-2-(1-methyl-1H-imidazol-2-yl)-5-phenyl-6-(pyridin-3-yl)pyrrolo[2,1-f][1,2,4]triazin-4-amine | 23.6 mg (18.5%) | 100% |
| 194 | 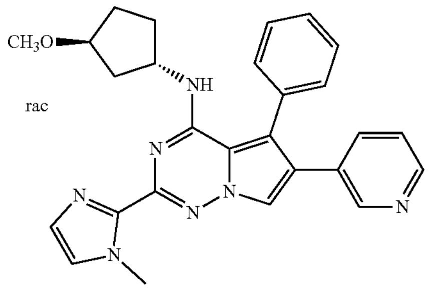<br>(194) | rac N-((1S,3S)-3-Methoxycyclopentyl)-2-(1-methyl-1H-imidazol-2-yl)-5-phenyl-6-(pyridin-3-yl)pyrrolo[2,1-f][1,2,4]triazin-4-amine | 27.8 mg (21.8%) | 100% |

TABLE C-continued

| Compounds and Analytical Data | | | | |
|---|---|---|---|---|
| 195 | 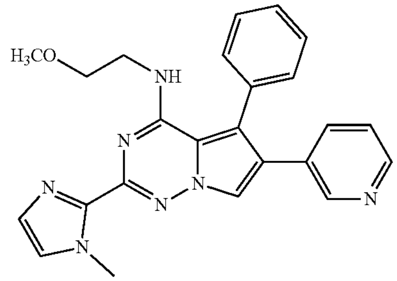 (195) | N-(2-Methoxyethyl)-2-(1-methyl-1H-imidazol-2-yl)-5-phenyl-6-(pyridin-3-yl)pyrrolo[2,1-f][1,2,4]triazin-4-amine | 15.8 mg (13.6%) | 99% |
| 196 | 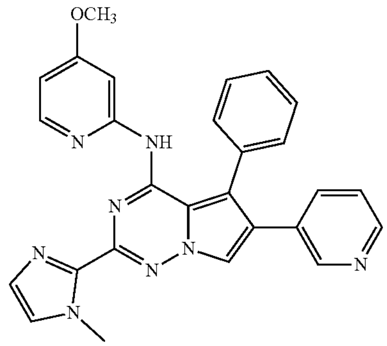 (196) | N-(4-Methoxypyridin-2-yl)-2-(1-methyl-1H-imidazol-2-yl)-5-phenyl-6-(pyridin-3-yl)pyrrolo[2,1-f][1,2,4]triazin-4-amine | 24.1 mg (18.6%) | 100% |
| 197 | 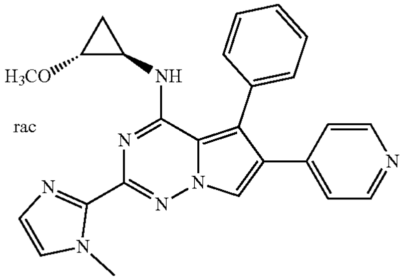 (197) | rac N-((1R,2R)-2-methoxycyclopropyl)-2-(1-methyl-1H-imidazol-2-yl)-5-phenyl-6-(pyridin-4-yl)pyrrolo[2,1-f][1,2,4]triazin-4-amine | 6.0 mg (5.0%) | 100% |
| 198 | 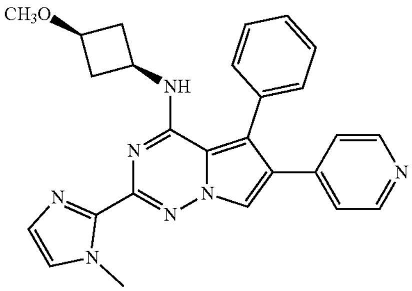 (198) | N-((1s,3s)-3-Methoxycyclobutyl)-2-(1-methyl-1H-imidazol-2-yl)-5-phenyl-6-(pyridin-4-yl)pyrrolo[2,1-f][1,2,4]triazin-4-amine | 19.3 mg (15.7%) | 98% |

TABLE C-continued

| Compounds and Analytical Data | | | | |
|---|---|---|---|---|
| 199 | 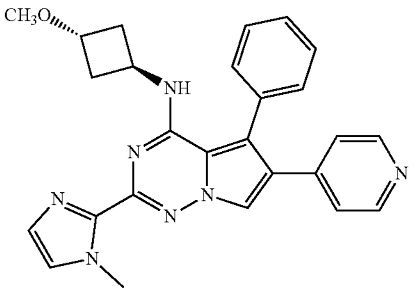<br>(199) | N-((1r,3r)-3-Methoxycyclobutyl)-2-(1-methyl-1H-imidazol-2-yl)-5-phenyl-6-(pyridin-4-yl)pyrrolo[2,1-f][1,2,4]triazin-4-amine | 8.3 mg (6.7%) | 95% |
| 200 | 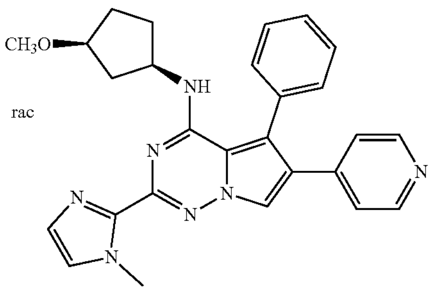<br>(200) | rac N-((1R,3S)-3-Methoxycyclopentyl)-2-(1-methyl-1H-imidazol-2-yl)-5-phenyl-6-(pyridin-4-yl)pyrrolo[2,1-f][1,2,4]triazin-4-amine | 18.4 mg (14.4%) | 98% |
| 201 | 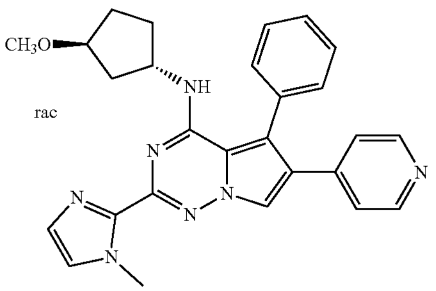<br>(201) | rac N-((1S,3S)-3-Methoxycyclopentyl)-2-(1-methyl-1H-imidazol-2-yl)-5-phenyl-6-(pyridin-4-yl)pyrrolo[2,1-f][1,2,4]triazin-4-amine | 14.8 mg (11.6%) | 98% |
| 202 | 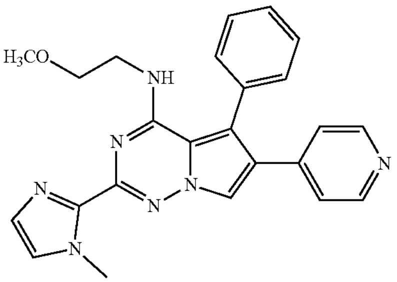<br>(202) | N-(2-Methoxyethyl)-2-(1-methyl-1H-imidazol-2-yl)-5-phenyl-6-(pyridin-4-yl)pyrrolo[2,1-f][1,2,4]triazin-4-amine | 10.2 mg (8.8%) | 95% |

TABLE C-continued

| Compounds and Analytical Data | | | | |
|---|---|---|---|---|
| 206 | 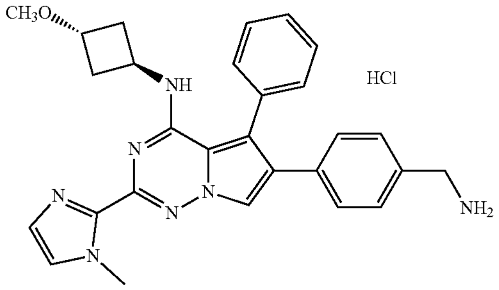<br>(206) | 6-(4-(Aminomethyl)phenyl)-N-((1r,3r)-3-methoxycyclobutyl)-2-(1-methyl-1H-imidazol-2-yl)-5-phenylpyrrolo[2,1-f][1,2,4]triazin-4-amine hydrochloride salt | 8.3 mg (3.0%) | 98% |
| 207 | 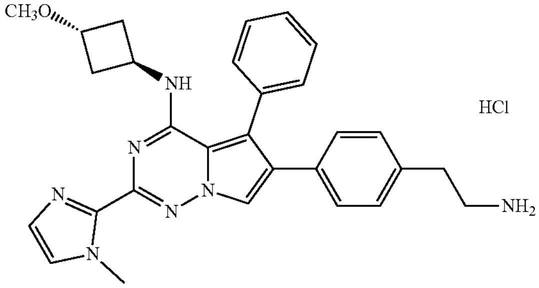<br>(207) | 6-(4-(2-Aminoethyl)phenyl)-N-((1r,3r)-3-methoxycyclobutyl)-2-(1-methyl-1H-imidazol-2-yl)-5-phenylpyrrolo[2,1-f][1,2,4]triazin-4-amine hydrochloride salt | 41 mg (7.7%) | 97% |
| 208 | 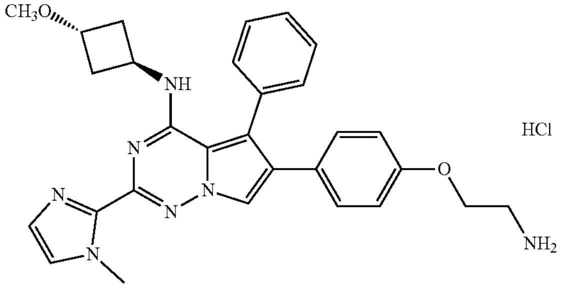<br>(208) | 6-(4-(2-Aminoethoxy)phenyl)-N-((1r,3r)-3-methoxycyclobutyl)-2-(1-methyl-1H-imidazol-2-yl)-5-phenylpyrrolo[2,1-f][1,2,4]triazin-4-amine hydrochloride salt | 41 mg (7.7%) | 95% |
| 209 | 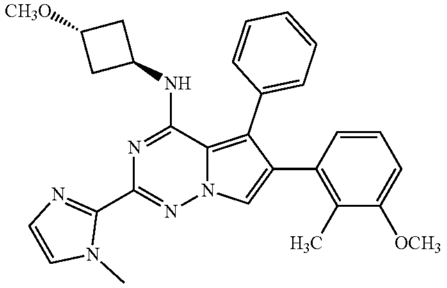<br>(209) | 6-(3-Methoxy-2-methylphenyl)-N-((1r,3r)-3-methoxycyclobutyl)-2-(1-methyl-1H-imidazol-2-yl)-5-phenylpyrrolo[2,1-f][1,2,4]triazin-4-amine | 59.5 mg 96% | 98% |

TABLE C-continued

| Compounds and Analytical Data | | | | |
|---|---|---|---|---|
| 210 | 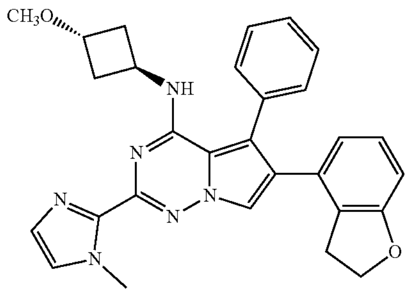 (210) | 6-(2,3-Dihydrobenzofuran-4-yl)-N-((1r,3r)-3-methoxycyclobutyl)-2-(1-methyl-1H-imidazol-2-yl)-5-phenylpyrrolo[2,1-f][1,2,4]triazin-4-amine | 26.8 mg 7.4% | 95% |
| 213 | 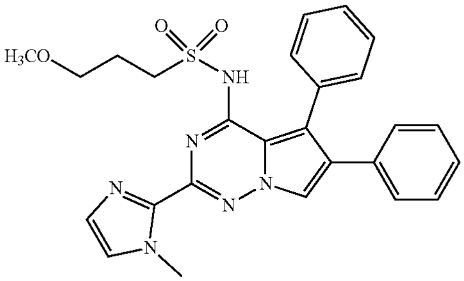 [SMILES: COCCCS(=O)(=O)Nc1nc(-c2nccn2C)nn2cc(-c3ccccc3)c(-c3ccccc3)c12] | 3-Methoxy-N-(2-(1-methyl-1H-imidazol-2-yl)-5,6-diphenylpyrrolo[2,1-f][1,2,4]triazin-4-yl)propane-1-sulfonamide | 47 mg (36.2%) | 100% |
| 214 | 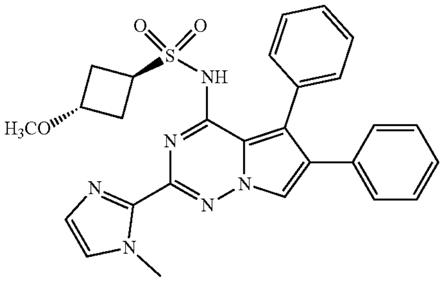 [SMILES: CO[C@H]1C[C@H](S(=O)(=O)Nc2nc(-c3nccn3C)nn3cc(-c4ccccc4)c(-c4ccccc4)c23)C1] | (1r,3r)-3-Methoxy-N-(2-(1-methyl-1H-imidazol-2-yl)-5,6-diphenylpyrrolo[2,1-f][1,2,4]triazin-4-yl)cyclobutane-1-sulfonamide | 8.5 mg (14.8%) | 98% |
| 218 | 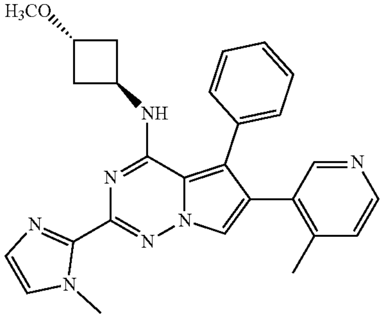 (218) | N-((1r,3r)-3-Methoxycyclobutyl)-2-(1-methyl-1H-imidazol-2-yl)-6-(4-methylpyridin-3-yl)-5-phenylpyrrolo[2,1-f][1,2,4]triazin-4-amine | 5.0 mg (1.1%) | 97% |

TABLE C-continued
| Compounds and Analytical Data | | | | |
|---|---|---|---|---|
| 219 | 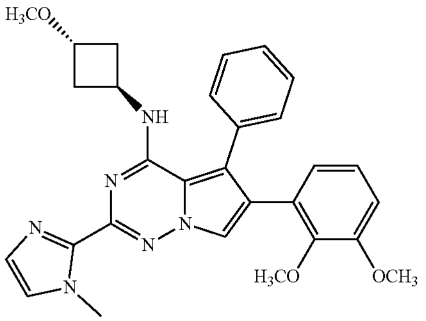 (219) | 6-(2,3-Dimethoxyphenyl)-N-((1r,3r)-3-methoxycyclobutyl)-2-(1-methyl-1H-imidazol-2-yl)-5-phenylpyrrolo[2,1-f][1,2,4]triazin-4-amine | 80.7 mg (10.7%) | 100% |
| 220 | 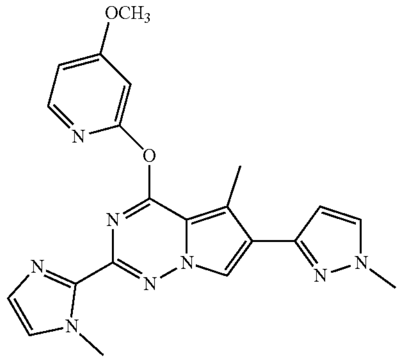 (220) | 4-((4-Methoxypyridin-2-yl)oxy)-5-methyl-2-(1-methyl-1H-imidazol-2-yl)-6-(1-methyl-1H-pyrazol-3-yl)pyrrolo[2,1-f][1,2,4]triazine | 8.4 mg (6.6%) | 95% |
| 221 | 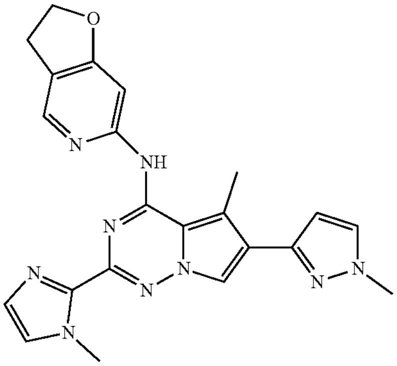 (221) | N-(5-Methyl-2-(1-methyl-1H-imidazol-2-yl)-6-(1-methyl-1H-pyrazol-3-yl)pyrrolo[2,1-f][1,2,4]triazin-4-yl)-2,3-dihydrofuro[3,2-c]pyridin-6-amine | 3.9 mg (3.0%) | 100% |

TABLE C-continued
| Compounds and Analytical Data | | | | |
|---|---|---|---|---|
| 222 | 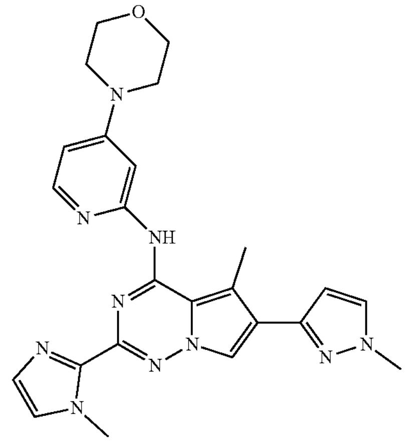 (222) | 5-Methyl-2-(1-methyl-1H-imidazol-2-yl)-6-(1-methyl-1H-pyrazol-3-yl)-N-(4-morpholinopyridin-2-yl)pyrrolo[2,1-f][1,2,4]triazin-4-amine | 60 mg (39.6%) | 100% |
| 223 | 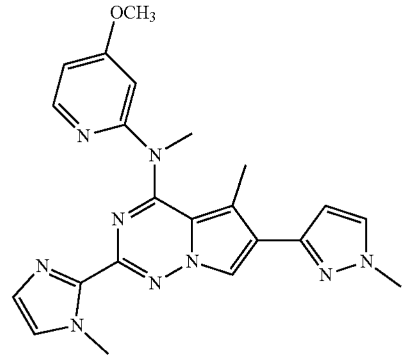 (223) | N-(4-Methoxypyridin-2-yl)-N,5-dimethyl-2-(1-methyl-1H-imidazol-2-yl)-6-(1-methyl-1H-pyrazol-3-yl)pyrrolo[2,1-f][1,2,4]triazin-4-amine | 21.9 mg (15.9%) | 96% |
| 224 | 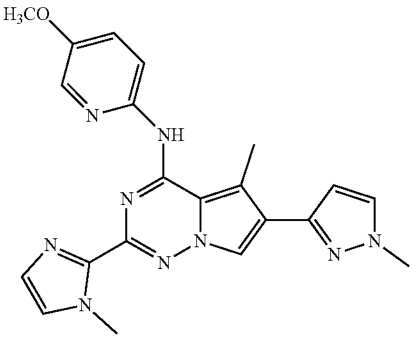 (224) | N-(5-Methoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 21.9 mg (16.4%) | 98% |

TABLE C-continued

| Compounds and Analytical Data | | | | |
|---|---|---|---|---|
| 225 | 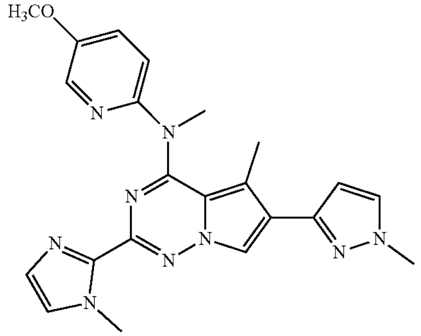 (225) | N-(5-Methoxypyridin-2-yl)-N,5-dimethyl-2-(1-methyl-1H-imidazol-2-yl)-6-(1-methyl-1H-pyrazol-3-yl)pyrrolo[2,1-f][1,2,4]triazin-4-amine | 3.5 mg (2.6%) | 97% |
| 226 | 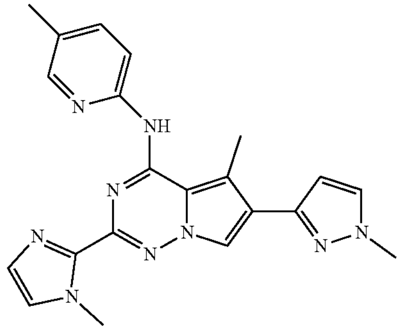 (226) | 5-Methyl-2-(1-methyl-1H-imidazol-2-yl)-6-(1-methyl-1H-pyrazol-3-yl)-N-(5-methylpyridin-2-yl)pyrrolo[2,1-f][1,2,4]triazin-4-amine | 27.5 mg (21.4%) | 100% |
| 227 | 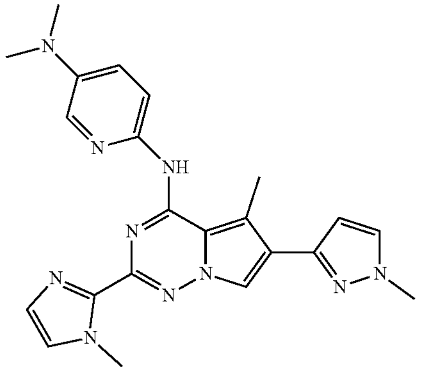 (227) | N5,N5-Dimethyl-N2-(5-methyl-2-(1-methyl-1H-imidazol-2-yl)-6-(1-methyl-1H-pyrazol-3-yl)pyrrolo[2,1-f][1,2,4]triazin-4-yl)pyridine-2,5-diamine | 39.0 mg (29.5%) | 100% |
| 228 | 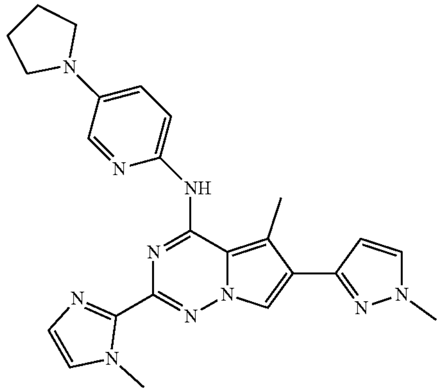 (228) | 5-Methyl-2-(1-methyl-1H-imidazol-2-yl)-6-(1-methyl-1H-pyrazol-3-yl)-N-(5-(pyrrolidin-1-yl)pyridin-2-yl)pyrrolo[2,1-f][1,2,4]triazin-4-amine | 22.0 mg (15.0%) | 100% |

TABLE C-continued

| Compounds and Analytical Data | | | | |
|---|---|---|---|---|
| 229 | 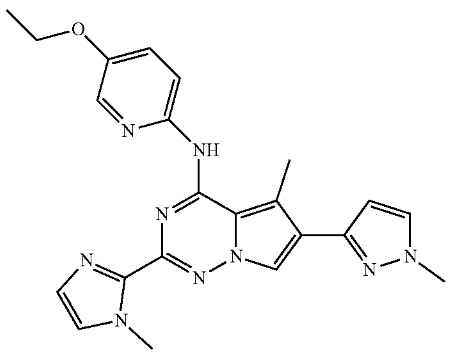 (229) | N-(5-Ethoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 63.5 mg (41.9%) | 100% |
| 230 | 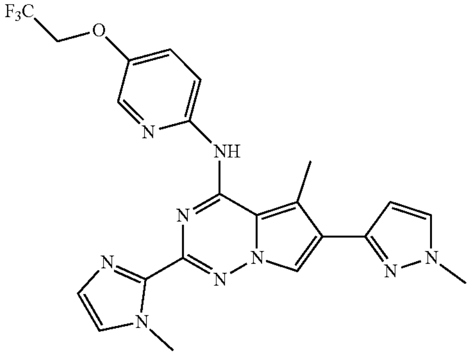 (230) | 5-Methyl-2-(1-methyl-1H-imidazol-2-yl)-6-(1-methyl-1H-pyrazol-3-yl)-N-(5-(2,2,2-trifluoroethoxy)pyridin-2-yl)pyrrolo[2,1-f][1,2,4]triazin-4-amine | 13.9 mg (8.9%) | 99% |
| 231 | 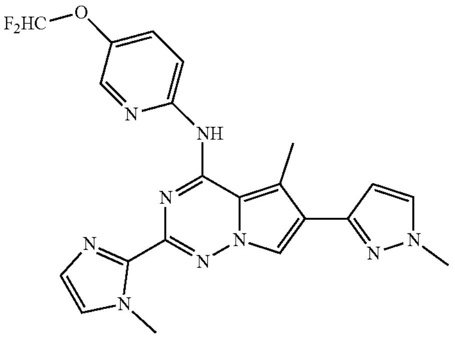 (231) | N-(5-(Difluoromethoxy)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 13.9 mg (9.6%) | 100% |
| 232 | 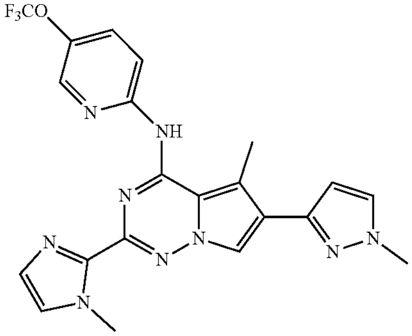 (232) | 5-Methyl-2-(1-methyl-1H-imidazol-2-yl)-6-(1-methyl-1H-pyrazol-3-yl)-N-(5-(trifluoromethoxy)pyridin-2-yl)pyrrolo[2,1-f][1,2,4]triazin-4-amine | 31.0 mg (20.5%) | 100% |

TABLE C-continued

| Compounds and Analytical Data | | | | |
|---|---|---|---|---|
| 233 | 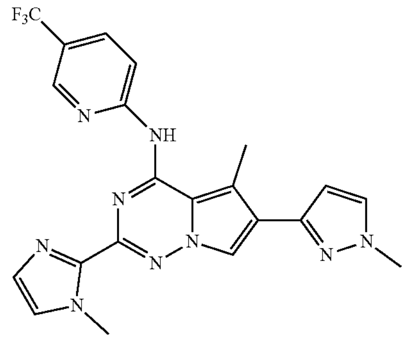 (233) | 5-Methyl-2-(1-methyl-1H-imidazol-2-yl)-6-(1-methyl-1H-pyrazol-3-yl)-N-(5-(trifluoromethyl)pyridin-2-yl)pyrrolo[2,1-f][1,2,4]triazin-4-amine | 26.0 mg (17.8%) | 100% |
| 234 | 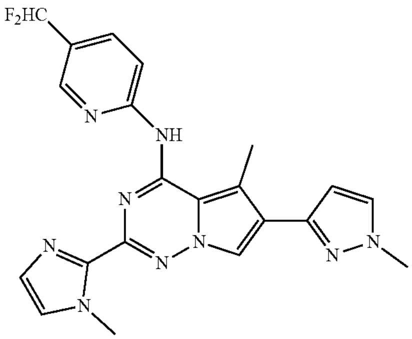 (234) | N-(5-(Difluoromethyl)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 6.5 mg (4.6%) | 99% |
| 235 | 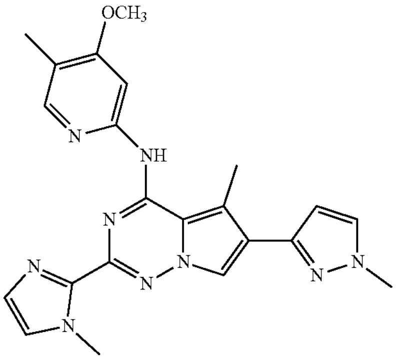 (235) | N-(4-Methoxy-5-methylpyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 33.0 mg (23.9%) | 100% |
| 236 | 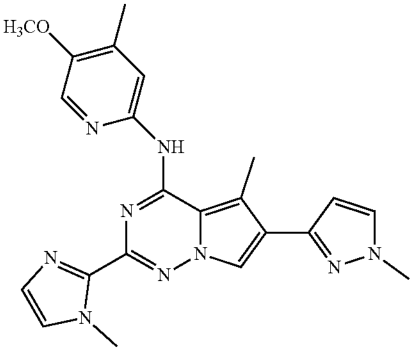 (236) | N-(5-Methoxy-4-methylpyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 32.1 mg (25.8%) | 96% |

TABLE C-continued

| Compounds and Analytical Data | | | | |
|---|---|---|---|---|
| 237 | 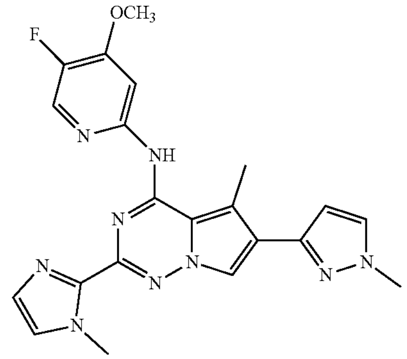 (237) | N-(5-Fluoro-4-methoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 14.0 mg (10.0%) | 100% |
| 238 | 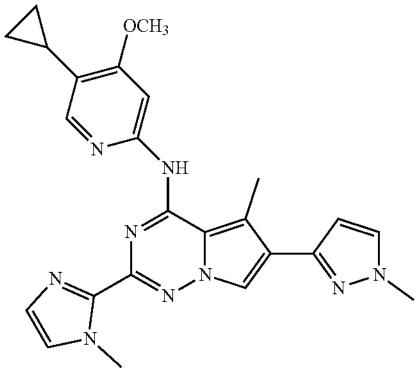 (238) | N-(5-Cyclopropyl-4-methoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 33.0 mg (22.6%) | 100% |
| 239 | 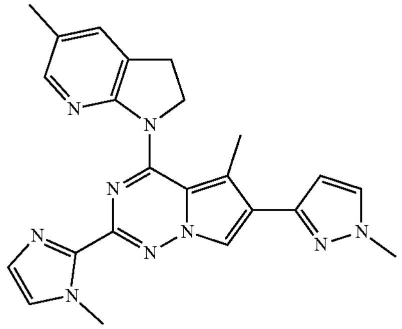 (239) | 5-Methyl-2-(1-methyl-1H-imidazol-2-yl)-6-(1-methyl-1H-pyrazol-3-yl)-4-(5-methyl-2,3-dihydro-1H-pyrrolo[2,3-b]pyridin-1-yl)pyrrolo[2,1-f][1,2,4]triazine | 19.0 mg (13.9%) | 100% |
| 240 | 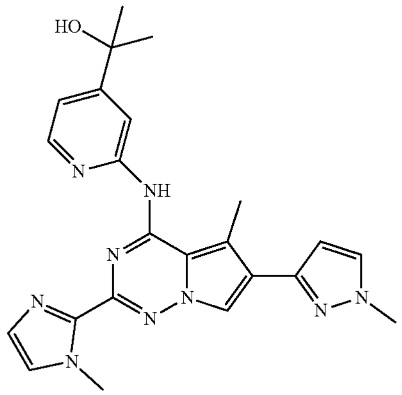 (240) | 2-(2-((5-Methyl-2-(1-methyl-1H-imidazol-2-yl)-6-(1-methyl-1H-pyrazol-3-yl)pyrrolo[2,1-f][1,2,4]triazin-4-yl)amino)pyridin-4-yl)propan-2-ol | 42.0 mg (29.3%) | 100% |

TABLE C-continued
| Compounds and Analytical Data | | | | |
|---|---|---|---|---|
| 241 | 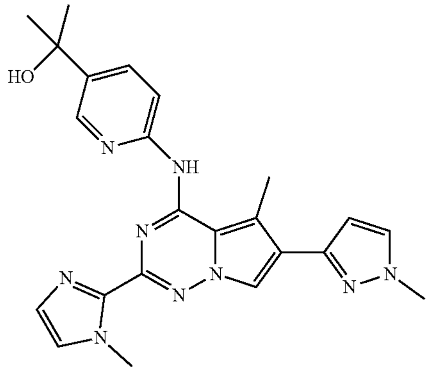 (241) | 2-(6-((5-Methyl-2-(1-methyl-1H-imidazol-2-yl)-6-(1-methyl-1H-pyrazol-3-yl)pyrrolo[2,1-f][1,2,4]triazin-4-yl)amino)pyridin-3-yl)propan-2-ol | 23.2 mg (16.2%) | 100% |
| 242 | 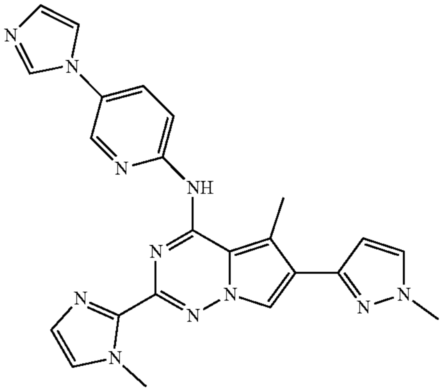 (242) | N-(5-(1H-Imidazol-1-yl)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 47.0 mg (45.2%) | 100% |
| 243 | 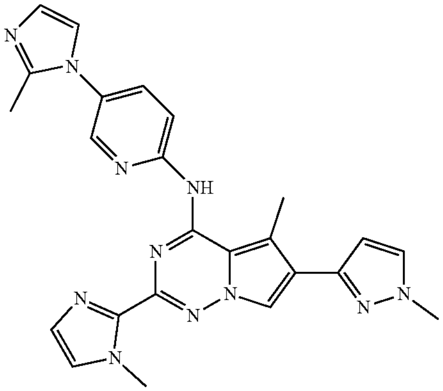 (243) | 5-Methyl-N-(5-(2-methyl-1H-imidazol-1-yl)pyridin-2-yl)-2-(1-methyl-1H-imidazol-2-yl)-6-(1-methyl-1H-pyrazol-3-yl)pyrrolo[2,1-f][1,2,4]triazin-4-amine | 31.0 mg (22.5%) | 100% |

TABLE C-continued

| Compounds and Analytical Data | | | | |
|---|---|---|---|---|
| 244 | 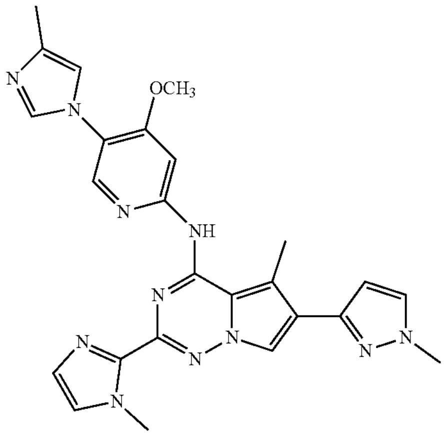<br>(244) | N-(4-Methoxy-5-(4-methyl-1H-imidazol-1-yl)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 16.0 mg (24.2%) | 100% |
| 245 | 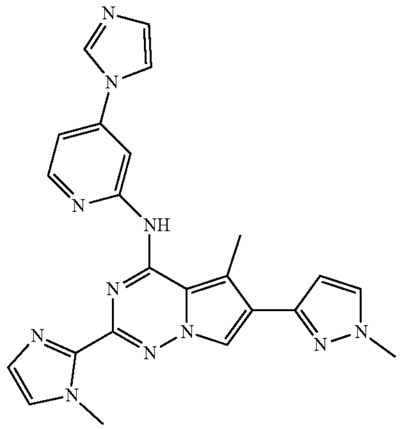<br>(245) | N-(4-(1H-imidazol-1-yl)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine | 46.0 mg (31.7%) | 100% |
| 246 | 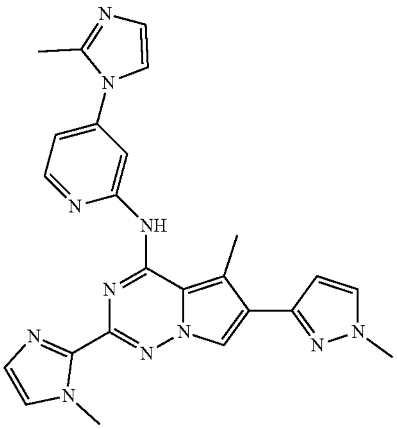<br>(246) | 5-Methyl-N-(4-(2-methyl-1H-imidazol-1-yl)pyridin-2-yl)-2-(1-methyl-1H-imidazol-2-yl)-6-(1-methyl-1H-pyrazol-3-yl)pyrrolo[2,1-f][1,2,4]triazin-4-amine | 23.0 mg (15.4%) | 100% |

TABLE C-continued
| Compounds and Analytical Data | | | | |
|---|---|---|---|---|
| 247 | 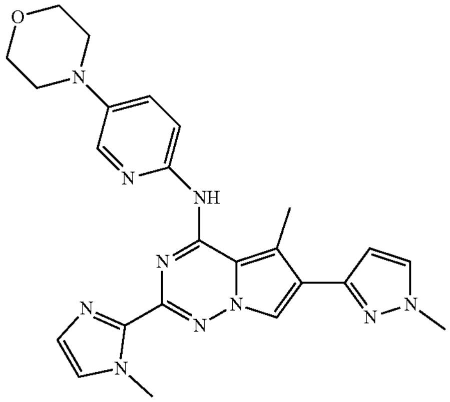<br>(247) | 5-Methyl-2-(1-methyl-1H-imidazol-2-yl)-6-(1-methyl-1H-pyrazol-3-yl)-N-(5-morpholinopyridin-2-yl)pyrrolo[2,1-f][1,2,4]triazin-4-amine | 38.6 mg (26.8%) | 100% |
| 248 | 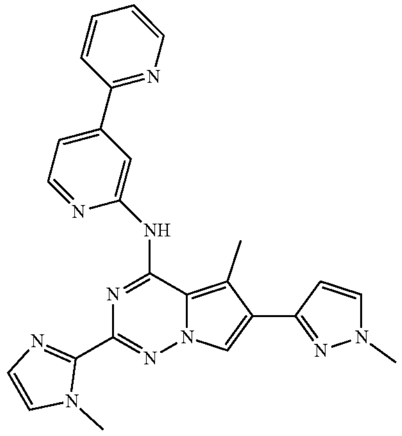<br>(248) | N-([2,4'-Bipyridin]-2'-yl)-5-methyl-2-(1-methyl-1H-imidazol-2-yl)-6-(1-methyl-1H-pyrazol-3-yl)pyrrolo[2,1-f][1,2,4]triazin-4-amine | 43.0 mg (29.0%) | 100% |
| 249 | 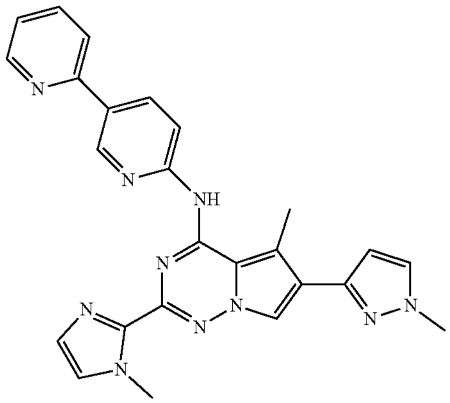<br>(249) | N-([2,3'-Bipyridin]-6'-yl)-5-methyl-2-(1-methyl-1H-imidazol-2-yl)-6-(1-methyl-1H-pyrazol-3-yl)pyrrolo[2,1-f][1,2,4]triazin-4-amine | 84.0 mg (28.2%) | 100% |

TABLE C-continued

| Compounds and Analytical Data | | | | |
|---|---|---|---|---|
| 250 | 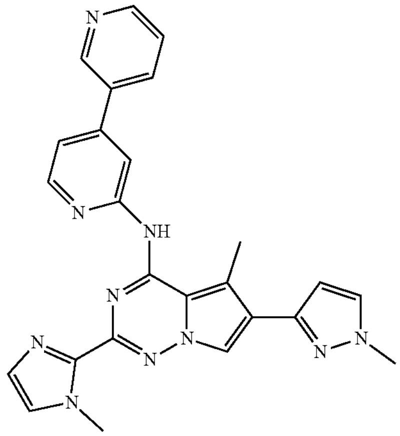 (250) | N-([3,4'-Bipyridin]-2'-yl)-5-methyl-2-(1-methyl-1H-imidazol-2-yl)-6-(1-methyl-1H-pyrazol-3-yl)pyrrolo[2,1-f][1,2,4]triazin-4-amine | 50.0 mg (33.7%) | 100% |
| 251 | 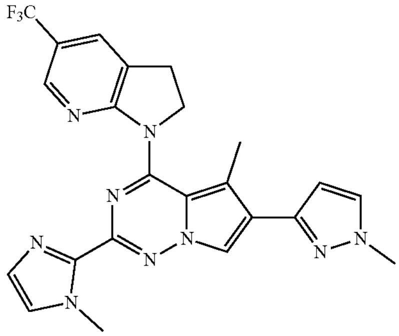 (251) | 5-Methyl-2-(1-methyl-1H-imidazol-2-yl)-6-(1-methyl-1H-pyrazol-3-yl)-4-(5-(trifluoromethyl)-2,3-dihydro-1H-pyrrolo[2,3-b]pyridin-1-yl)pyrrolo[2,1-f][1,2,4]triazine | 18.0 mg (11.6%) | 98% |
| 252 | 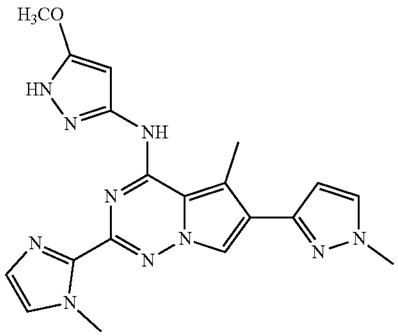 (252) | N-(5-Methoxy-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 11 mg (8.8%) | 93% |
| 253 | 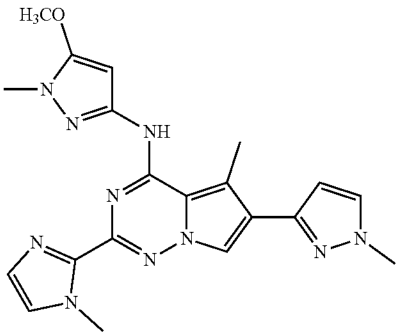 (253) | N-(5-Methoxy-1-methyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 42.0 mg (32.8%) | 100% |

TABLE C-continued

| Compounds and Analytical Data | | | | |
|---|---|---|---|---|
| 254 | 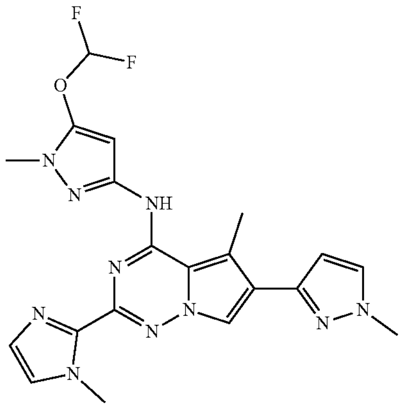 (254) | N-(5-(Difluoromethoxy)-1-methyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 11.1 mg (8.1%) | 100% |
| 255 | 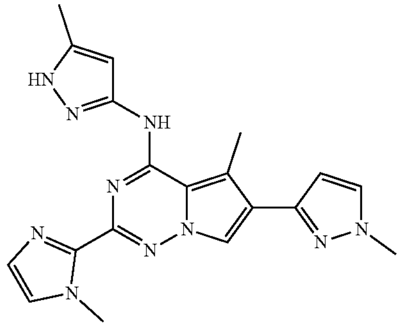 (255) | 5-Methyl-2-(1-methyl-1H-imidazol-2-yl)-6-(1-methyl-1H-pyrazol-3-yl)-N-(5-methyl-1H-pyrazol-3-yl)pyrrolo[2,1-f][1,2,4]triazin-4-amine | 41.0 mg (34.5%) | 100% |
| 256 | 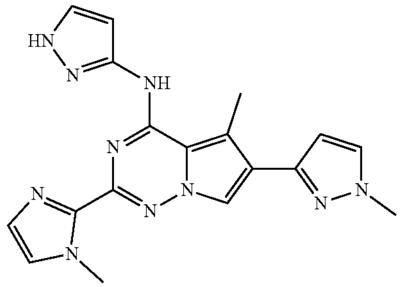 (256) | 5-Methyl-2-(1-methyl-1H-imidazol-2-yl)-6-(1-methyl-1H-pyrazol-3-yl)-N-(1H-pyrazol-3-yl)pyrrolo[2,1-f][1,2,4]triazin-4-amine | 23.0 mg (20.2%) | 100% |
| 257 | 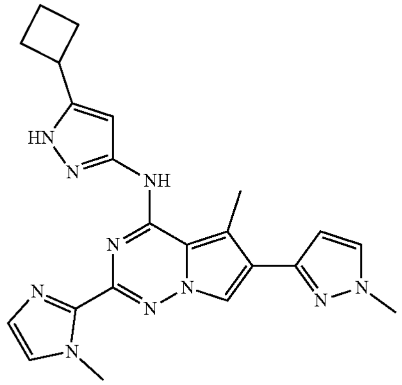 (257) | N-(5-Cyclobutyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 9.8 mg (7.5%) | 100% |

TABLE C-continued

| Compounds and Analytical Data | | | | |
|---|---|---|---|---|
| 258 | 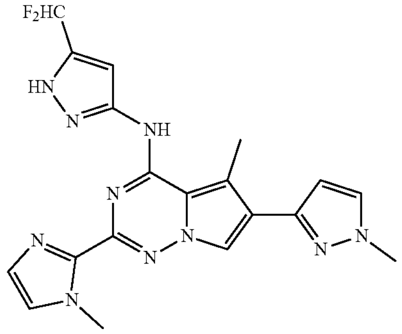 (258) | N-(5-(Difluoromethyl)-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 3.1 mg (2.3%) | 94% |
| 259 | 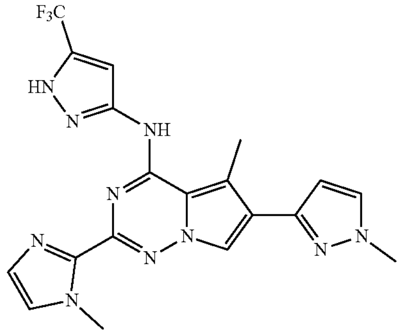 (259) | 5-Methyl-2-(1-methyl-1H-imidazol-2-yl)-6-(1-methyl-1H-pyrazol-3-yl)-N-(5-(trifluoromethyl)-1H-pyrazol-3-yl)pyrrolo[2,1-f][1,2,4]triazin-4-amine | 17.7 mg (13.1%) | 96% |
| 260 | 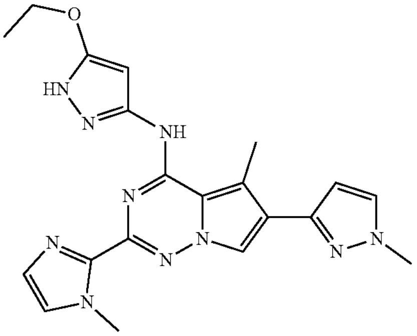 (260) | N-(5-Ethoxy-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 13.0 mg (10.0%) | 100% |
| 261 | 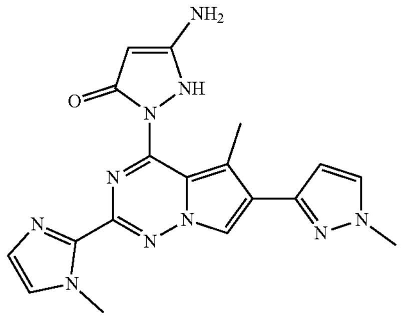 (261) | 5-Amino-2-(5-methyl-2-(1-methyl-1H-imidazol-2-yl)-6-(1-methyl-1H-pyrazol-3-yl)pyrrolo[2,1-f][1,2,4]triazin-4-yl)-1,2-dihydro-3H-pyrazol-3-one | 7.7 mg 6.5% | 100% |

TABLE C-continued
| Compounds and Analytical Data | | | | |
|---|---|---|---|---|
| 262 | 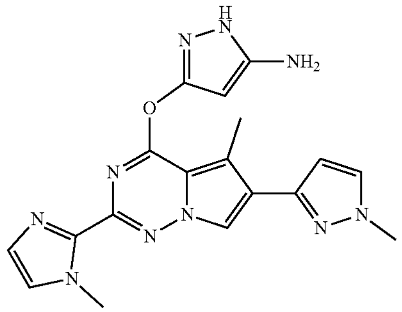<br>(262) | 3-((5-Methyl-2-(1-methyl-1H-imidazol-2-yl)-6-(1-methyl-1H-pyrazol-3-yl)pyrrolo[2,1-f][1,2,4]triazin-4-yl)oxy)-1H-pyrazol-5-amine | 13.9 mg (11.7%) | 92% |
| 263 | 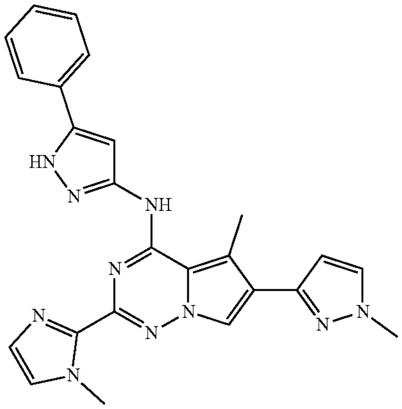<br>(263) | 5-Methyl-2-(1-methyl-1H-imidazol-2-yl)-6-(1-methyl-1H-pyrazol-3-yl)-N-(5-phenyl-1H-pyrazol-3-yl)pyrrolo[2,1-f][1,2,4]triazin-4-amine | 43 mg (31.2%) | 100% |
| 264 | 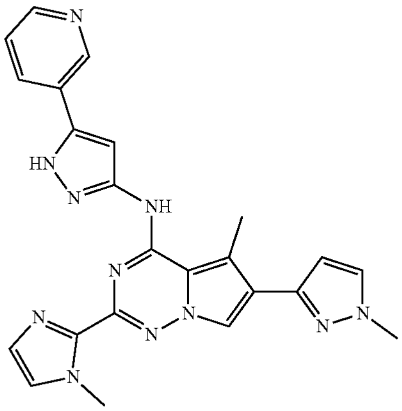<br>(264) | 5-Methyl-2-(1-methyl-1H-imidazol-2-yl)-6-(1-methyl-1H-pyrazol-3-yl)-N-(5-(pyridin-3-yl)-1H-pyrazol-3-yl)pyrrolo[2,1-f][1,2,4]triazin-4-amine | 3.5 mg (2.5%) | 100% |

TABLE C-continued
| Compounds and Analytical Data | | | | |
|---|---|---|---|---|
| 265 | 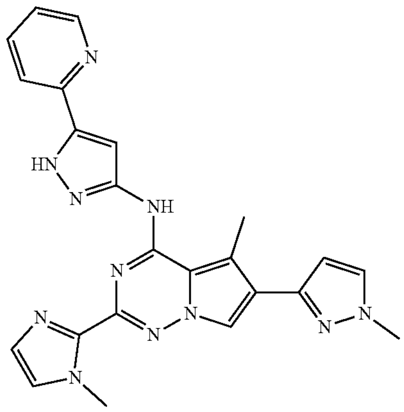 (265) | 5-Methyl-2-(1-methyl-1H-imidazol-2-yl)-6-(1-methyl-1H-pyrazol-3-yl)-N-(5-(pyridin-2-yl)-1H-pyrazol-3-yl)pyrrolo[2,1-f][1,2,4]triazin-4-amine | 31 mg (22.5%) | 100% |
| 266 | 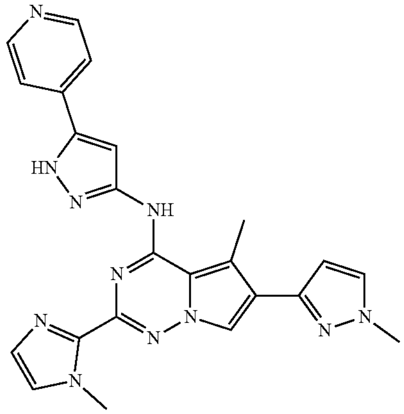 (266) | 5-Methyl-2-(1-methyl-1H-imidazol-2-yl)-6-(1-methyl-1H-pyrazol-3-yl)-N-(5-(pyridin-4-yl)-1H-pyrazol-3-yl)pyrrolo[2,1-f][1,2,4]triazin-4-amine | 31 mg (22.5%) | 100% |
| 267 | 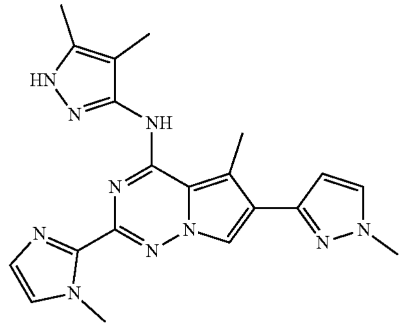 (267) | N-(4,5-Dimethyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 10.6 mg (8.6%) | 100% |

TABLE C-continued

| Compounds and Analytical Data | | | | |
|---|---|---|---|---|
| 268 | 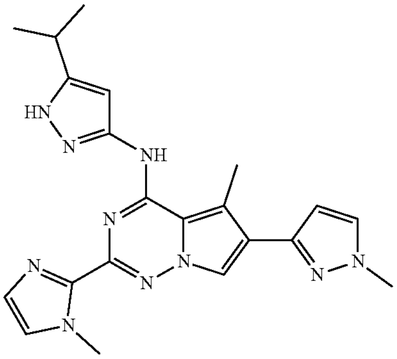 (268) | N-(5-Isopropyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine | 25 mg (19.7%) | 95% |
| 269 | 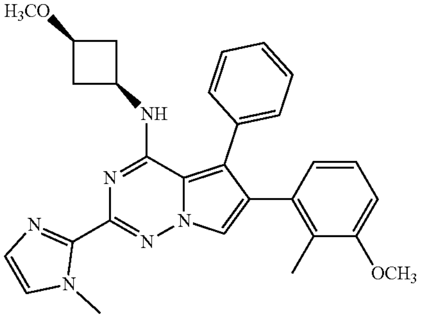 (269) | 6-(3-Methoxy-2-methylphenyl)-N-((1s,3s)-3-methoxycyclobutyl)-2-(1-methyl-1H-imidazol-2-yl)-5-phenylpyrrolo[2,1-f][1,2,4]triazin-4-amine | 77 mg, (22.1%) | 100% |
| 270 | 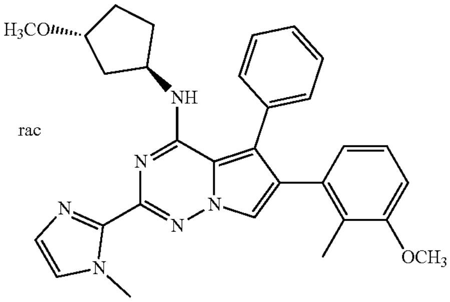 (270) | rac 6-(3-Methoxy-2-methylphenyl)-N-((1R,3R)-3-methoxycyclopentyl)-2-(1-methyl-1H-imidazol-2-yl)-5-phenylpyrrolo[2,1-f][1,2,4]triazin-4-amine | 84 mg (23.6%) | 100% |
| 271 | 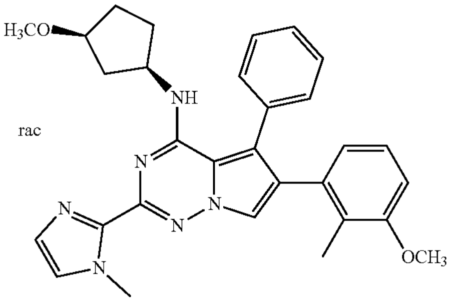 (271) | rac 6-(3-Methoxy-2-methylphenyl)-N-((1R,3S)-3-methoxycyclopentyl)-2-(1-methyl-1H-imidazol-2-yl)-5-phenylpyrrolo[2,1-f][1,2,4]triazin-4-amine | 76.0 mg (21.2%) | 100% |

TABLE C-continued

| Compounds and Analytical Data | | | | |
|---|---|---|---|---|
| 272 | 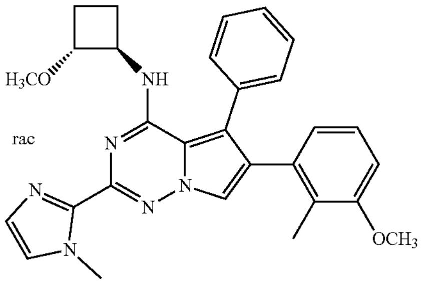 (272) | rac 6-(3-Methoxy-2-methylphenyl)-N-((1R,2R)-2-methoxycyclobutyl)-2-(1-methyl-1H-imidazol-2-yl)-5-phenylpyrrolo[2,1-f][1,2,4]triazin-4-amine | 51.0 mg (14.7%) | 100% |
| 273 | 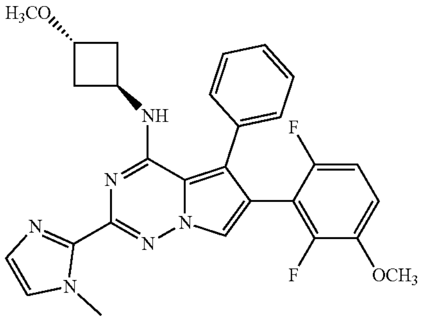 (273) | 6-(2,6-Difluoro-3-methoxyphenyl)-N-((1r,3r)-3-methoxycyclobutyl)-2-(1-methyl-1H-imidazol-2-yl)-5-phenylpyrrolo[2,1-f][1,2,4]triazin-4-amine | 60 mg (31.1%) | 95% |
| 274 | 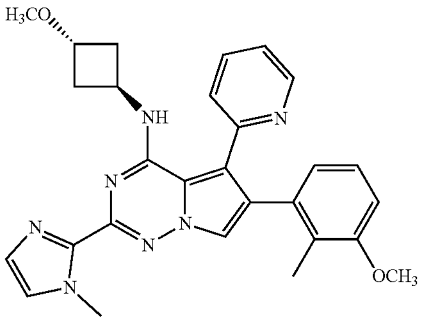 (274) | 6-(3-Methoxy-2-methylphenyl)-N-((1r,3r)-3-methoxycyclobutyl)-2-(1-methyl-1H-imidazol-2-yl)-5-(pyridin-2-yl)pyrrolo[2,1-f][1,2,4]triazin-4-amine | 258.1 mg (53.3%) | 95% |
| 275 | 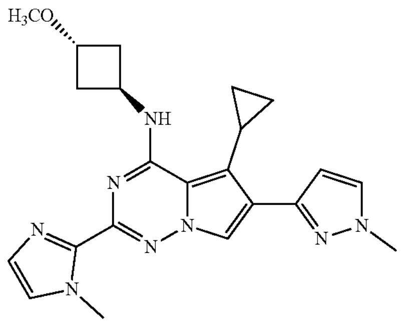 (275) | 5-Cyclopropyl-N-((1r,3r)-3-methoxycyclobutyl)-2-(1-methyl-1H-imidazol-2-yl)-6-(1-methyl-1H-pyrazol-3-yl)pyrrolo[2,1-f][1,2,4]triazin-4-amine | 17.1 mg (22.2%) | 100% |

TABLE C-continued

| Compounds and Analytical Data | | | | |
|---|---|---|---|---|
| 276 | 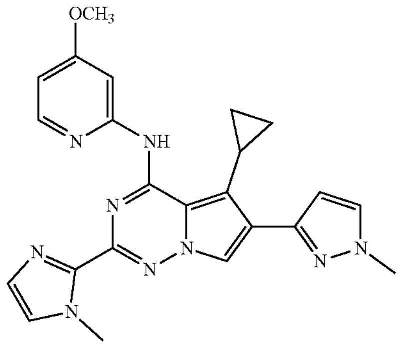 (276) | 5-Cyclopropyl-N-(4-methoxypyridin-2-yl)-2-(1-methyl-1H-imidazol-2-yl)-6-(1-methyl-1H-pyrazol-3-yl)pyrrolo[2,1-f][1,2,4]triazin-4-amine | 35.4 mg (23.6%) | 100% |

| Example | Calc'd [M + 1] | Found [M + 1] | $^{1}$H NMR |
|---|---|---|---|
| 152 | 434.2 | 434.4 | |
| 153 | 390.2 | 390.4 | |
| 154 | 404.2 | 404.4 | |
| 155 | 404.2 | 404.2 | 500 MHz, DMSO-$d_6$) δ (ppm) 1.90 (m, 6H), 2.51 (s, 3H), 3.12 (s, 3H), 3.97 (s, 3H), 4.76 (m, 1H), 6.97 (m, 2H), 7.27 (s, 1H), 7.47 (dd, 1H), 7.88 (d, 1H), 7.96 (s, 1H), 8.52 (d, 1H), 8.67 (d, 1H). |
| 156 | 384.2 | 384.0 | |
| 157 | 413.2 | 413.2 | |
| 158 | 414.2 | 414.2 | (500 MHz, DMSO-$d_6$) δ (ppm) 3.72 (s, 3H), 3.97 (m, 6H), 6.42 (m, 1H), 7.00 (m, 1H), 7.34 (m, 2H), 7.85 (m, 2H), 8.30 (m, 1H), 8.47 (m, 1H), 8.75 (m, 1H). |
| 161 | 464.2 | 464.2 | (500 MHz, DMSO-$d_6$) δ (ppm) 2.31 (m, 4H), 2.57 (s, 3H), 3.45 (m, 5H), 3.85 (s, 3H), 3.91 (s, 3H), 4.15 (m, 2H), 4.73 (m, 2H), 6.90 (m, 1H), 6.97 (m, 1H), 7.12 (m, 1H), 7.25 (m, 2H), 8.02 (m, 1H), 8.15 (d, 1H). |
| 162 | 420.2 | 420.0 | (500 MHz, $CD_3OD$) δ (ppm) 2.06 (m, 2H), 2.61 (s, 3H), 2.80 (m, 2H), 3.27 (s, 3H), 2.68 (m, 1H), 3.91 (s, 3H), 4.08 (s, 3H), 4.53 (m, 1H), 6.88 (m, 1H), 7.10 (m, 3H), 7.80 (m, 1H), 8.12 (d, 1H). |
| 163 | 434.2 | 434.2 | (500 MHz, DMSO-$d_6$) δ (ppm) 1.95 (m, 6H), 2.62 (m, 3H), 3.21 (s, 3H), 3.95 (m, 6H), 4.80 (m, 1H), 6.94 (m, 2H), 7.35 (m, 3H), 8.21 (m, 2H). |
| 164 | 434.2 | 434.2 | (500 MHz, $CD_3OD$) δ (ppm) 1.98 (m, 6H), 2.53 (s, 3H), 3.38 (s, 3H), 3.89 (s, 3H), 3.99 (m, 1H), 4.02 (s, 3H), 4.98 (m, 1H), 6.83 (m, 1H), 7.10 (m, 3H), 7.71 (s, 1H), 8.10 (d, 1H). |
| 167 | 477.1 | 477.2 | (500 MHz, DMSO-$d_6$) δ (ppm) 3.88 (s, 3H), 4.01 (s, 3H), 6.98 (m, 1H), 7.08 (d, 1H), 7.38 (m, 3H), 7.73 (m, 2H), 8.30 (m, 2H), 8.52 (m, 3H), 8.79 (d, 1H), 14.37 (s, 1H). |
| 168 | 453.2 | 453.2 | |
| 170 | 477.2 | 477.2 | |
| 171 | 453.2 | 453.2 | |

TABLE C-continued

| Compounds and Analytical Data | | | |
|---|---|---|---|
| 174 | 527.2 | 527.2 | |
| 175 | 485.2 | 485.2 | |
| 176 | 503.2 | 503.2 | |
| 177 | 516.2 | 516.2 | |
| 178 | 499.2 | 499.2 | |
| 179 | 515.2 | 515.2 | |
| 182 | 476.2 | 476.2 | |
| 183 | 494.2 | 494.2 | |
| 184 | 508.3 | 508.2 | |
| 185 | 549.3 | 549.2 | |
| 191 | 452.2 | 452.2 | (500 MHz, DMSO-$d_6$) δ (ppm) 1.34 (m, 2H), 2.60 (m, 2H), 3.04 (s, 3H), 3.68 (q, 1H), 3.93 (s, 3H), 4.16 (q, 1H), 5.33 (d, 1H), 6.97 (s, 1H), 7.25 (m, 2H), 7.43 (m, 2H), 7.55 (m, 4H), 8.25 (s, 1H), 8.38 (m, 1H), 8.45 (m, 1H). |
| 192 | 452.2 | 452.2 | (500 MHz, DMSO-$d_6$) δ (ppm) 1.80 (m, 2H), 2.21 (m, 2H), 3.05 (s, 3H), 3.78 (m, 1H), 3.91 (s, 3H), 4.43 (m, 1H), 5.41 (d, 1H), 6.97 (s, 1H), 7.26 (m, 2H), 7.45 (m, 2H), 7.55 (m, 4H), 8.26 (s, 1H), 8.42 (m, 1H), 8.46 (d, 1H). |
| 193 | 466.2 | 466.2 | (500 MHz, DMSO-$d_6$) δ (ppm) 1.41 (m, 4H), 1.90 (m, 2H), 2.82 (s, 3H), 3.69 (m, 1H), 3.98 (s, 3H), 4.60 (m, 1H), 5.62 (d, 1H), 6.96 (s, 1H), 7.25 (m, 2H), 7.86 (m, 2H), 7.49 (m, 4H), 8.21 (s, 1H), 8.43 (m, 2H). |
| 194 | 466.2 | 466.2 | |
| 195 | 426.2 | 426.2 | (500 MHz, DMSO-$d_6$) δ (ppm) 3.07 (s, 3H), 3.34 (t, 2H), 3.55 (t, 2H), 3.96 (s, 3H), 5.63 (m, 1H), 6.98 (s, 1H), 7.25 (m, 2H), 7.39 (m, 2H), 7.48 (m, 3H), 7.55 (d, 1H), 8.21 (s, 1H), 8.35 (d, 1H), 8.43 (s, 1H). |
| 196 | 475.2 | 475.2 | |
| 197 | 438.2 | 438.2 | (500 MHz, $CD_3OD$) δ (ppm) 0.51 (m, 1H), 1.02 (m, 1H), 3.00 (m, 3H), 3.30 (s, 3H), 4.13 (s, 3H), 7.25 (m, 6H), 7.51 (m, 3H), 8.30 (m, 3H). |
| 198 | 452.2 | 452.2 | (500 MHz, DMSO-$d_6$) δ (ppm) 1.32 (m, 2H), 2.58 (m, 2H), 3.02 (s, 3H), 3.54 (m, 1H), 3.91 (s, 3H), 4.11 (m, 1H), 5.30 (m, 1H), 6.97 (s, 1H), 7.20 (m, 3H), 7.50 (m, 5H), 8.36 (m, 3H). |
| 199 | 452.2 | 452.2 | (500 MHz, DMSO-$d_6$) δ (ppm) 1.80 (m, 2H), 2.21 (m, 2H), 3.06 (s, 3H), 3.78 (m, 1H), 3.92 (s, 3H), 4.46 (m, 1H), 5.41 (m, 1H), 6.92 (s, 1H), 7.19 (m, 2H), 7.29 (s, 1H), 7.49 (m, 2H), 7.58 (m, 3H), 8.40 (m, 3H). |
| 200 | 466.2 | 466.2 | (500 MHz, DMSO-$d_6$) δ (ppm) 1.60 (m, 6H), 2.89 (s, 3H), 3.66 (m, 1H), 3.96 (s, 3H), 4.60 (m, 1H), 5.60 (d, 1H), 6.93 (s, 1H), 7.09 (m, 2H), 7.22 (m, 1H), 3.38 (m, 2H), 7.50 (m, 3H), 8.32 (m, 3H). |
| 201 | 466.2 | 466.2 | (500 MHz, DMSO-$d_6$) δ (ppm) 1.08 (m, 1H), 1.27 (m, 1H), 1.52 (m, 2H), 1.91 (m, 2H), 3.09 (s, 3H), 3.61 (m, |

TABLE C-continued

| Compounds and Analytical Data | | | |
|---|---|---|---|
| | | | 1H), 3.97 (s, 3H), 4.36 (m, 1H), 5.10 (d, 1H), 6.98 (s, 1H), 7.20 (m, 3H), 7.50 (m, 5H), 8.33 (m, 3H). |
| 202 | 426.2 | 426.2 | (500 MHz, DMSO-$d_6$) δ (ppm) 3.03 (s, 3H), 3.31 (t, 2H), 3.51 (t, 2H), 4.92 (s, 3H), 5.60 (t, 1H), 6.94 (d, 1H), 7.12 (m, 2H), 7.28 (s, 1H), 7.40 (m, 2H), 7.52 (m, 3H), 8.38 (m, 3H). |
| 206 | 480.2 | 480.2 | |
| 207 | 494.3 | 494.2 | |
| 208 | 496.2 | 494.2 | |
| 209 | 495.2 | 495.2 | |
| 210 | 493.2 | 493.2 | |
| 213 | 503.2 | 503.0 | |
| 214 | 515.2 | 515.0 | |
| 218 | 466.2 | 466.2 | |
| 219 | 511.2 | 511.4 | |
| 220 | 417.1 | 417.2 | |
| 221 | 428.2 | 428.0 | (500 MHz, DMSO-$d_6$) δ (ppm) 2.88 (s, 3H), 3.20 (t, 2H), 3.80 (s, 3H), 4.01 (s, 3H), 4.61 (t, 2H), 6.51 (d, 1H), 6.58 (d, 1H), 7.15 (d, 1H), 7.46 (d, 1H), 7.69 (d, 1H), 7.81 (s, 1H), 8.08 (d, 1H), 14.91 (s, 1H). |
| 222 | [M + 2]/2 = 236.1 | [M + 2]/2 = 236.2 | |
| 223 | 430.2 | 430.2 | |
| 224 | 416.2 | 416.2 | |
| 225 | 430.2 | 430.2 | |
| 226 | 400.2 | 400.2 | |
| 227 | 429.2 | 429.2 | |
| 228 | 455.2 | 4.6 | |
| 229 | 430.2 | 430.2 | |
| 230 | 484.1 | 484.0 | |
| 231 | 452.1 | 452.0 | |
| 232 | 470.1 | 470.0 | |
| 233 | 454.1 | 454.0 | |
| 234 | 436.1 | 436.0 | |
| 235 | 430.2 | 430.2 | |
| 236 | 430.2 | 430.2 | |
| 237 | 434.1 | 434.2 | |
| 238 | 456.2 | 456.2 | |
| 239 | 426.2 | 426.2 | |
| 240 | 444.2 | 444.4 | |
| 241 | 444.2 | 444.2 | |
| 242 | 452.2 | 452.2 | |
| 243 | [M + 2]/2 = 233.6 | [M + 2]/2 = 233.6 | |
| 244 | [M + 2]/2 = 248.6 | [M + 2]/2 = 248.6 | |
| 245 | 452.2 | 452.2 | |
| 246 | [M + 2]/2 = 233.6 | [M + 2]/2 = 233.6 | (500 MHz, DMSO-$d_6$) δ (ppm) 2.32 (s, 3H), 2.86 (s, 3H), 3.95 (m, 6H), 6.56 (d, 1H), 6.98 (m, 1H), 7.34 (m, 4H), 7.71 (m, 1H), 8.46 (m, 3H), 14.61 (s, 1H). |
| 247 | 471.2 | 471.2 | |
| 248 | 463.2 | 463.0 | |
| 249 | 463.2 | 463.2 | |
| 250 | 463.2 | 463.0 | |
| 251 | 480.2 | 480.2 | (500 MHz, DMSO-$d_6$) δ (ppm) 2.26 (s, 3H), 3.27 (t, 2H), 3.35 (s, 3H), 3.95 (s, 3H), 4.37 (t, 2H), 6.60 (s, 1H), 7.01 (s, 1H), 7.34 (s, 1H), 7.73 (d, 1H), 7.96 (d, 1H), 8.30 (d, 1H), 8.36 (d, 1H). |
| 252 | 405.1 | 405.2 | (500 MHz, $CD_3OD$) δ (ppm) 2.74 (s, 3H), 3.85 (s, 3H), 3.97 (s, 3H), 4.01 (s, 3H), 5.75 (m, 1H), 6.48 (d, 1H), |

TABLE C-continued

Compounds and Analytical Data

| | | | |
|---|---|---|---|
| | | | 7.07 (d, 1H), 7.20 (d, 1H), 7.70 (d, 1H), 7.96 (s, 1H), NH is not observed. |
| 253 | 419.2 | 419.2 | |
| 254 | 455.1 | 455.0 | |
| 255 | 389.2 | 389.0 | (500 MHz, DMSO-$d_6$) δ (ppm) 2.19 (s, 3H), 2.74 (s, 3H), 3.82 (s, 3H), 4.01 (s, 3H), 5.88 (s, 1H), 6.49 (d, 1H), 7.11 (s, 1H), 7.49 (d, 1H), 7.68 (m, 2H), 12.48 (m, 1H), 12.97 (m, 1H). |
| 256 | 375.2 | 375.0 | |
| 257 | 429.2 | 429.2 | |
| 258 | 425.1 | 425.2 | |
| 259 | 443.1 | 443.2 | |
| 260 | 419.2 | 419.2 | (500 MHz, $CD_3OD$) δ (ppm) 1.31 (t, 3H), 2.71 (s, 3H), 3.89 (s, 3H), 3.98 (s, 3H), 4.11 (m, 2H), 5.77 (m, 1H), 6.48 (d, 1H), 7.08 (d, 1H), 7.21 (d, 1H), 7.61 (d, 1H), 7.96 (m, 1H). |
| 261 | 391.1 | 391.0 | |
| 262 | 391.1 | 391.0 | |
| 263 | 451.2 | 451.0 | |
| 264 | 452.2 | 452.2 | |
| 265 | 452.2 | 452.0 | |
| 266 | 452.2 | 452.2 | |
| 267 | 403.2 | 403.2 | (500 MHz, DMSO-$d_6$) δ (ppm) 1.89 (s, 3H), 2.10 (s, 3H), 2.73 (s, 3H), 3.82 (s, 3H), 3.99 (s, 3H), 6.49 (s, 1H), 7.09 (s, 1H), 7.41 (d, 1H), 7.63 (m, 2H), 12.32 (m, 1H), 12.81 (m, 1H). |
| 268 | 417.2 | 417.2 | |
| 269 | 495.2 | 495.2 | |
| 270 | 509.3 | 509.2 | |
| 271 | 509.3 | 509.2 | |
| 272 | 495.2 | 495.2 | (500 MHz, DMSO-$d_6$) δ (ppm) 1.09 (m, 1H), 1.43 (m, 1H), 1.78 (s, 3H), 1.98 (m, 2H), 3.09 (s, 3H), 3.40 (m, 1H), 3.71 (s, 3H), 3.99 (s, 3H), 4.41 (m, 1H), 5.81 (m, 1H), 6.70 (d, 1H), 6.83 (m, 1H), 7.02 (m, 2H), 7.52 (m, 6H), 7.83 (s, 1H). |
| 273 | 517.2 | 517.2 | |
| 274 | 496.2 | 496.2 | (500 MHz, DMSO-$d_6$) δ (ppm) 1.75 (s, 3H), 2.30 (m, 4H), 3.12 (s, 3H), 3.72 (s, 3H), 3.91 (s, 3H), 4.09 (m, 1H), 4.60 (m, 1H), 6.82 (m, 2H), 6.98 (m, 2H), 7.22 (m, 3H), 7.58 (m, 1H), 7.76 (s, 1H), 8.69 (s, 1H), 11.86 (d, 1H). |
| 275 | 419.2 | 419.2 | |
| 276 | 442.2 | 442.2 | |

Table note:
*Amount and yield refer to the final total amount obtained and yield in the last step of the synthesis of the respective compound, respectively.

4.2 Biological Examples

Biological Example 1: Protocols for Cell-Based Assays

Protocol for Phospho-Smad2/3 Inhibition Assay

This assay is referred to as the "Phospho-Smad2/3 Inhibition Assay" throughout this application.

Cell lines: Human tumor-derived pancreatic cancer cell line Panc-1 (expressing KRas G12D mutant) and mouse muscle myoblast C2C12 were purchased from American Type Culture Collection and grown in complete DMEM-High Glucose, supplemented with penicillin (100 U/mL), streptomycin (100 μg/mL), and 10% heat-inactivated FBS at 37° C. in a humidified incubator with 5% $CO_2$.

Method: Cells were plated at 350000 cells/well density in a 12-well plate, allowed 3 hours to adhere to the plate, then starved in the appropriate medium in the presence of 0.5% FBS overnight. The small molecules to be tested were added to the cells in the final concentration of 10 μM in the presence of 0.3% DMSO for 3 hours incubation at 37° C. For IC50 value determination, serial dilutions of compounds were added to cells under the same conditions. Next, Panc-1 cells were stimulated with 10 ng/ml TGF-b1 for 1 hour, and C2C12 cells were stimulated with 10 ng/ml TGF-b1 for 20 minutes (recombinant human TGF-b1, R&D Systems). After stimulation cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of Smad2/Smad3 was determined by western blot.

Western blot protocol: Equal amounts of protein (15-50 μg) were separated by SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 10% milk and phosphorylation levels of Smad2/Smad3 were assessed by incubating overnight at 4° C. with the following antibodies: Phospho-Smad2 (Ser465/467) and Phosph-Smad3 (Ser423/425), both from Cell Signaling Technology. Then the membranes were incubated with HRP-conjugated secondary antibody (Jackson Immunoresearch, West Grove, PA). Bands were incubated in Amersham ECL Prime Western Blotting Detection Reagent (GE Healthcare) and visualized using the ChemiDoc MP imaging system (Bio-Rad).

Protocol for JNK Activation Assay

This assay is referred to as the "JNK Activation Assay" throughout this application.

Cell lines: Human tumor-derived pancreatic cancer cell line Panc-1 (expressing KRas G12C mutant) was purchased from American Type Culture Collection and grown in complete DMEM-High Glucose medium, supplemented with penicillin (100 U/mL), streptomycin (100 μg/mL), and 10% heat-inactivated FBS at 37° C. in a humidified incubator with 5% $CO_2$.

Method 1: Cells were plated at 350000 cells/well density in a 12-well plate, allowed 3 hours to adhere to the plate, then starved in the appropriate medium in the presence of 0.5% FBS overnight. The small molecules to be tested were added to the cells in the final concentration of 10 μM in the presence of 0.3% DMSO for 6 hours incubation at 37° C. For IC50 value determination, serial dilutions of compounds were added to cells under the same conditions. Next, cells were stimulated with 1.5 ng/ml EGF for 15 minutes then cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of JNK was determined by western blot.

Method 2: Cells were plated at 350000 cells/well density in a 12-well plate in the presence of 10% FBS. The next day small molecules to be tested were added to the cells in the final concentration of 10 μM in the presence of 0.3% DMSO for 6 hours incubation at 37° C. For $IC_{50}$ value determination, serial dilutions of compounds were added to cells under the same conditions. Next, cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of JNK was determined by western blot.

Western blot protocol: Equal amounts of protein (15-50 μg) were separated by SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 10% milk and phosphorylation levels of JNK were assessed by incubating overnight at 4° C. with the antibody Phospho-SAPK/JNK (Thr183/Tyr185), from Cell Signaling Technology. Then the membranes were incubated with HRP-conjugated secondary antibody (Jackson Immunoresearch, West Grove, PA). Bands were incubated in Amersham ECL Prime Western Blotting Detection Reagent (GE Healthcare) and visualized using the ChemiDoc MP imaging system (Bio-Rad).

Protocol for MAPK p38 Activation Assay

This assay is referred to as the "MAPK p38 Activation Assay" throughout this application.

Cell lines: Human tumor-derived pancreatic cancer cell line Panc-1 (expressing KRas G12D mutant) was purchased from American Type Culture Collection and grown in complete DMEM-High Glucose medium, supplemented with penicillin (100 U/mL), streptomycin (100 μg/mL), and 10% heat-inactivated FBS at 37° C. in a humidified incubator with 5% $CO_2$.

Method 1: Cells were plated at 350000 cells/well density in a 12-well plate, allowed 3 hours to adhere to the plate, then starved in the appropriate medium in the presence of 0.5% FBS overnight. The small molecules to be tested were added to the cells in the final concentration of 10 μM in the presence of 0.3% DMSO for 6 hours incubation at 37° C. For $IC_{50}$ value determination, serial dilutions of compounds were added to cells under the same conditions. Next, cells were stimulated with 1.5 ng/ml EGF for 15 minutes then cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of MAPK p38 was determined by western blot.

Method 2: Cells were plated at 350000 cells/well density in a 12-well plate in 10% FBS. The next day small molecules to be tested were added to the cells in the final concentration of 10 μM in the presence of 0.3% DMSO for 6 hours incubation at 37° C. For IC50 value determination, serial dilutions of compounds were added to cells under the same conditions. Next, cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of MAPK p38 was determined by western blot.

Western blot protocol: Equal amounts of protein (15-50 μg) were separated by SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 10% milk and phosphorylation levels of MAPK p38 were assessed by incubating overnight at 4° C. with the following antibody: Phospho-p38 MAPK (Thr180/Tyr182), from Cell Signaling Technology. Then the membranes were incubated with HRP-conjugated secondary antibody (Jackson Immunoresearch, West Grove, PA). Bands were incubated in Amersham ECL Prime Western Blotting Detection Reagent (GE Healthcare) and visualized using the ChemiDoc MP imaging system (Bio-Rad).

Protocol for Western Erk1/2 Cell-Based Phosphorylation Assay

This assay is referred to as the "Erk1/2 Phosphorylation Assay" throughout this application.

Cell lines: Human tumor-derived pancreatic cancer cell line Panc-1 (expressing KRas G12D mutant) was purchased from American Type Culture Collection and grown in complete DMEM-High Glucose medium, supplemented with penicillin (100 U/mL), streptomycin (100 μg/mL), and 10% heat-inactivated FBS at 37° C. in a humidified incubator with 5% $CO_2$.

Method 1: Cells were plated at 350000 cells/well density in a 12-well plate, allowed 3 hours to adhere to the plate, then starved in the appropriate medium in the presence of 0.5% FBS overnight. The small molecules to be tested were added to the cells in the final concentration of 10 μM in the presence of 0.3% DMSO for 6 hours incubation at 37° C. For IC50 value determination, serial dilutions of compounds were added to cells under the same conditions. Next, cells were stimulated with 1.5 ng/ml EGF for 15 minutes then cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of Erk1/2 was determined by western blot.

Method 2: Cells were plated at 350000 cells/well density in a 12-well plate in 10% FBS. The next day small molecules to be tested were added to the cells in the final concentration of 10 μM in the presence of 0.3% DMSO for 6 hours incubation at 37° C. For IC50 value determination, serial dilutions of compounds were added to cells under the same conditions. Next, cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of Erk1/2 was determined by western blot.

Western blot protocol: Equal amounts of protein (15-50 μg) were separated by SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 10% milk and phosphorylation levels of Erk1/2 were assessed by incubating overnight at 4° C. with anti-phospho-p44/42 (Thr202/Tyr204) antibody (Cell Signaling) followed by HRP-conjugated secondary antibody (Jackson Immunoresearch, West Grove, PA). Bands were incubated in Amersham ECL Prime Western Blotting Detection Reagent (GE Healthcare) and visualized using the ChemiDoc MP imaging system (Bio-Rad).

Protocol for Western Akt Cell-Based Phosphorylation Assay

This assay is referred to as the "Akt Phosphorylation Assay" throughout this application.

Human tumor-derived pancreatic cancer cell line Panc-1 (expressing KRas G12D mutant) was purchased from American Type Culture Collection and grown in complete DMEM-High Glucose supplemented with penicillin (100 U/mL), streptomycin (100 μg/mL), and 10% heat-inactivated FBS at 37° C. in a humidified incubator with 5% $CO_2$.

Method 1: Cells were plated at 350000 cells/well density in a 12-well plate, allowed 3 hours to adhere to the plate, then starved in the appropriate medium in the presence of 0.5% FBS overnight. The small molecules to be tested were added to the cells in the final concentration of 10 μM in the presence of 0.3% DMSO for 6 hours incubation at 37° C. Next, cells were stimulated with 1.5 ng/ml EGF for 15 minutes then cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of Akt was determined by western blot.

Method 2: Cells were plated at 350000 cells/well density in a 12-well plate in 10% FBS. The next day small molecules to be tested were added to the cells in the final concentration of 10 μM in the presence of 0.3% DMSO for 6 hours incubation at 37° C. For IC50 value determination, serial dilutions of compounds were added to cells under the same conditions. Next, cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of Akt was determined by western blot.

Western blot protocol: Equal amounts of protein (15-50 μg) were separated by SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 10% milk and phosphorylation levels of Akt were assessed by incubating overnight at 4° C. with anti-phospho-Akt (Ser473) antibody (Cell Signaling) followed by HRP-conjugated secondary antibody (Jackson Immunoresearch, West Grove, PA). Bands were incubated in Amersham ECL Prime Western Blotting Detection Reagent (GE Healthcare) and visualized using the ChemiDoc MP imaging system (Bio-Rad).

Table 3 shows inhibition data for selected compounds tested in one or more of the cellular assays described above.

Protocol for Western S-6 Ribosomal Protein Cell-Based Phosphorylation Assay

Cell lines: Human tumor-derived pancreatic cancer cell line Panc-1 (expressing KRas G12D mutant) and MiaPaca-2 (expressing KRas G12C mutant) were purchased from American Type Culture Collection and grown in complete DMEM-High Glucose medium, supplemented with penicillin (100 U/mL), streptomycin (100 μg/mL), and 10% heat-inactivated FBS at 37° C. in a humidified incubator with 5% $CO_2$.

Method: Cells were plated at 350000 cells/well density in a 12-well plate, allowed 3 hours to adhere to the plate, then starved in the appropriate medium in the presence of 0.5% FBS overnight. The small molecules to be tested were added to the cells in the final concentration of 10 μM in the presence of 0.3% DMSO for 6 hours incubation at 37° C. For IC50 value determination, serial dilutions of compounds were added to cells under the same conditions. Next, cells were stimulated with 1.5 ng/ml EGF for 15 minutes then cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of S-6 Ribosomal Protein was determined by western blot.

Western blot protocol: Equal amounts of protein (15-50 μg) were separated by SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 10% milk and phosphorylation levels of Erk1/2 were assessed by incubating overnight at 4° C. with with phospho S-6 Ribosoma Protein (Ser 235/236) (D57.2.2E) antibody from Cell signaling Technology followed by HRP-conjugated secondary antibody (Jackson Immunoresearch, West Grove, PA). Bands were incubated in Amersham ECL Prime Western Blotting Detection Reagent (GE Healthcare) and visualized using the ChemiDoc MP imaging system (Bio-Rad).

Protocol for Mouse TNF-Alpha and IL6 Quantification Assay

These assays are referred to as the "IL-6 Quantification Assay" and the "TNF-alpha Quantification Assay", respectively, throughout this application.

Cell lines: Abelson murine leukemia virus transformed macrophage cell line RAW 264.7 was purchased from ATCC and grown in complete DMEM-High Glucose medium supplemented with penicillin (100 U/mL), streptomycin (100 μg/mL), and 10% heat-inactivated FBS at 37° C. in a humidified incubator with 5% $CO_2$.

Method: Cells were plated at 40000 cells/well density in a 96-wells plate. After a 3-hour incubation, macrophages were starved with DMEM plus 0.5% FBS o/n. The next day the small molecules to be tested were added to the cells in the final concentration of 30 μM (with 0.3% DMSO) 3 hours prior to LPS stimulation (100 ng/ml). After LPS stimulation cells were incubated at 37° C. for 16h. At the end of the incubation period, culture media were collected and production of LPS-induced TNFα and IL6 cytokine was measured using ELISA detection kits.

Sandwich ELISA: The ELISA Immunoassays Quantikine Mouse TNF-alpha (catalog number MTA00B) and IL6 (catalog number M6000B) were purchased from R&D Systems Inc., Minneapolis, MN. These 4.5 hours solid phase ELISAs were used to measure mouse TNF or IL6 levels in macrophages culture supernatants. Assays were executed according to the manufacturer specifications.

Protocol for Proliferation Assay

This assay is referred to as the "Proliferation Assay" or "Cell Viability Assay" throughout this application.

Cell lines: Human tumor-derived cell lines were purchased from American Type Culture Collection. Human tumor-derived pancreatic cancer cell line MiaPaca-2 (expressing KRAS G12C mutant) and Panc-1 (expressing KRas G12D mutant), and Human non-small cell lung cancer (NSCLC) cell line A549 (expressing KRas G12S mutant) were grown in complete DMEM-High Glucose medium. Human colon cancer cell line SW-620 (expressing KRas G12V mutant) was grown in RPMI 1640 medium. All cell lines were supplemented with penicillin (100 U/mL), streptomycin (100 μg/mL), and 10% heat-inactivated FBS at 37° C. in a humidified incubator with 5% $CO_2$.

Method: Cells were plated at 2000 to 5000 cells/well density in 96-wells plate and cultured overnight. Small molecules to be tested were added to the cells in the final concentration of 10 μM in the presence of 0.3% DMSO and 10% FBS and incubated for 2-4 days at 37° C. in a humidified incubator with 5% CO2. For IC50 value determination, serial dilutions of compounds were added to cells under the same conditions.

Assay: At the end of the incubation period, cell viability was determined using the CellTiter 96® Aqueous One Solution Cell Proliferation Assay according to manufacturer specifications (Promega, Madison, WI). The percentage of small molecules inhibition of cellular proliferation was calculated from raw data.

Tables 2 and 3 show the data for these selected compounds tested in one or more of the cellular assays described above, such as in Human tumor-derived pancreatic cancer cell line Panc-1.

TABLE 2

Inhibition of Smad2/3, JNK, and MAPK p38 (at 10 μM), each in Panc-1 pancreatic cancer cell line

| Compound | % inh of Smad2/3 phosphorylation in Panc-1 | % inh of JNK in Panc-1 | % inh of MAPK p38 in Panc-1 |
|---|---|---|---|
| 1 | ND | F* | H* |
| 2 | ND | F* | H* |
| 3 | ND | H* | H* |
| 4 | ND | G* | G* |
| 5 | ND | ND | ND |
| 6 | 0 | H* | E* |
| 7 | ND | H* | H* |
| 8 | 0 | E* | H* |
| 9 | 0 | F* | G* |
| 10 | A | E* | G* |
| 11 | 0 | G* | G* |
| 12 | 0 | E* | H* |
| 13 | 0 | H* | H* |
| 14 | 0 | F* | H* |
| 15 | 0 | F* | H* |
| 16 | 0 | F* | H* |
| 17 | ND | 0 | 0 |
| 18 | ND | F* | H* |
| 19 | ND | F* | H* |
| 20 | ND | H* | H* |
| 21 | ND | H* | H* |
| 22 | ND | H* | H* |
| 23 | 0 | H* | H* |
| 24 | B | H* | H* |
| 25 | 0 | H* | H* |
| 26 | C | H* | H* |
| 27 | D | H* | H* |
| 28 | 0 | H* | H* |
| 29 | D | H | H |

TABLE 2-continued

Inhibition of Smad2/3, JNK, and MAPK p38 (at 10 μM), each in Panc-1 pancreatic cancer cell line

| Compound | % inh of Smad2/3 phosphorylation in Panc-1 | % inh of JNK in Panc-1 | % inh of MAPK p38 in Panc-1 |
|---|---|---|---|
| 30 | D | F | F |
| 31 | D | H* | H* |
| 32 | D | H | H |
| 33 | D | G | H |
| 34 | ND | H | H |
| 35 | A | H* | H* |
| 36 | D | H* | H* |
| 37 | ND | ND | ND |
| 38 | 0 | ND | ND |
| 39 | ND | ND | ND |
| 40 | B | ND | ND |
| 41 | A* | ND | ND |
| 42 | 0 | H* | H* |
| 43 | D | H* | H* |
| 44 | D | H* | H* |
| 45 | 0 | H* | H* |
| 46 | 0 | H* | H |
| 47 | D | H* | F |
| 48 | B | ND | ND |
| 49 | B | ND | ND |
| 50 | B | ND | ND |
| 51 | D | H* | H* |
| 52 | D | 0 | F* |
| 53 | B | H* | H* |
| 54 | A | H* | H* |
| 55 | D | H* | H* |
| 56 | D* | H* | H* |
| 57 | A* | H* | E* |
| 58 | C | H* | G* |
| 59 | D | H* | H* |
| 60 | C | H* | H* |
| 61 | B | H* | H* |
| 62 | A* | H* | H* |
| 63 | D* | H* | H* |
| 64 | A | H* | H* |
| 65 | A* | H* | H* |
| 66 | A* | H* | H* |
| 67 | 0 | H* | H* |
| 68 | A* | ND | ND |
| 69 | A | H* | H* |
| 70 | 0 | H* | H* |
| 71 | 0 | H* | H* |
| 72 | 0 | H* | H* |
| 73 | B* | ND | ND |
| 74 | A* | ND | ND |
| 75 | A | ND | ND |
| 76 | B | ND | ND |
| 77 | C | ND | ND |
| 78 | A | ND | ND |
| 79 | B* | ND | ND |
| 80 | B* | ND | ND |
| 81 | A* | ND | ND |
| 82 | ND | ND | ND |
| 83 | B* | ND | ND |
| 84 | C* | ND | ND |
| 85 | D | ND | ND |
| 86 | B* | ND | ND |
| 87 | B* | ND | ND |
| 88 | C* | ND | ND |
| 89 | C* | ND | ND |
| 90 | C* | ND | ND |
| 91 | 0 | ND | ND |
| 92 | A* | ND | ND |
| 93 | A | H* | H* |
| 94 | B* | ND | ND |
| 95 | C* | ND | ND |
| 96 | D | ND | ND |
| 97 | D | ND | ND |
| 98 | D | ND | ND |
| 99 | D | ND | ND |
| 100 | C* | ND | ND |
| 101 | D* | ND | ND |
| 102 | A* | ND | ND |

TABLE 2-continued

Inhibition of Smad2/3, JNK, and MAPK p38 (at 10 μM), each in Panc-1 pancreatic cancer cell line

| Compound | % inh of Smad2/3 phosphorylation in Panc-1 | % inh of JNK in Panc-1 | % inh of MAPK p38 in Panc-1 |
|---|---|---|---|
| 103 | C* | ND | ND |
| 104 | D* | ND | ND |
| 105 | A | ND | ND |
| 106 | D* | ND | ND |
| 107 | A | ND | ND |
| 108 | D* | ND | ND |
| 109 | D* | ND | ND |
| 110 | A* | ND | ND |
| 111 | D* | ND | ND |
| 112 | D* | ND | ND |
| 113 | D* | ND | ND |
| 114 | D* | ND | ND |
| 115 | A | ND | ND |
| 116 | D | ND | ND |
| 117 | A | ND | ND |
| 118 | A* | ND | ND |
| 119 | B* | ND | ND |
| 120 | A* | ND | ND |
| 121 | A | ND | ND |
| 122 | C | ND | ND |
| 123 | B | ND | ND |
| 124 | A | ND | ND |
| 125 | B | ND | ND |
| 126 | A* | ND | ND |
| 127 | A | ND | ND |
| 128 | A | ND | ND |
| 129 | D* | ND | ND |
| 130 | C | ND | ND |
| 131 | 0 | ND | ND |
| 132 | A* | ND | ND |
| 133 | A | ND | ND |
| 134 | B | ND | ND |
| 135 | A* | ND | ND |
| 136 | A | ND | ND |
| 137 | C | ND | ND |
| 138 | A* | ND | ND |
| 139 | A* | ND | ND |
| 140 | A | ND | ND |
| 141 | D | ND | ND |
| 142 | C | ND | ND |
| 143 | A | ND | ND |
| 144 | D | ND | ND |
| 145 | B* | ND | ND |
| 146 | C | ND | ND |
| 147 | C | ND | ND |
| 148 | A | ND | ND |
| 149 | A | ND | ND |
| 150 | A | ND | ND |
| 151 | A | ND | ND |
| 152 | A | ND | ND |
| 153 | C | ND | ND |
| 154 | C | ND | ND |
| 155 | A | ND | ND |
| 156 | D | ND | ND |
| 157 | B* | ND | ND |
| 158 | B* | ND | ND |
| 159 | C | ND | ND |
| 160 | A* | ND | ND |
| 161 | B | ND | ND |
| 162 | A | ND | ND |
| 163 | B | ND | ND |
| 164 | A* | ND | ND |
| 165 | B* | ND | ND |
| 166 | C* | ND | ND |
| 167 | 0 | ND | ND |
| 168 | A* | ND | ND |
| 169 | C | ND | ND |
| 170 | A | ND | ND |
| 171 | B | ND | ND |
| 172 | A | ND | ND |
| 173 | D* | ND | ND |
| 174 | A* | ND | ND |
| 175 | B* | ND | ND |

TABLE 2-continued

Inhibition of Smad2/3, JNK, and MAPK p38 (at 10 μM), each in Panc-1 pancreatic cancer cell line

| Compound | % inh of Smad2/3 phosphorylation in Panc-1 | % inh of JNK in Panc-1 | % inh of MAPK p38 in Panc-1 |
|---|---|---|---|
| 176 | B | ND | ND |
| 177 | A | ND | ND |
| 178 | B* | ND | ND |
| 179 | C* | ND | ND |
| 180 | ND | ND | ND |
| 181 | A | ND | ND |
| 182 | A* | ND | ND |
| 183 | D* | ND | ND |
| 184 | B* | ND | ND |
| 185 | B* | ND | ND |
| 186 | D* | ND | ND |
| 187 | A* | ND | E* |
| 188 | B | ND | E |
| 189 | B | ND | ND |
| 190 | A | ND | E |
| 191 | A* | ND | E* |
| 192 | A* | ND | E* |
| 193 | A | ND | E |
| 194 | A | ND | E |
| 195 | A* | ND | E* |
| 196 | C | ND | F |
| 197 | C | ND | F |
| 198 | A | ND | E |
| 199 | B | ND | E |
| 200 | A | ND | E |
| 201 | A | ND | E |
| 202 | A | ND | E |
| 203 | D | ND | G |
| 204 | A | ND | E |
| 205 | D | ND | G |
| 206 | B | ND | E |
| 207 | D | ND | H |
| 208 | D | ND | G |
| 209 | D | ND | H |
| 210 | D | ND | G |
| 211 | D | ND | ND |
| 212 | C | ND | F |
| 213 | B | ND | F |
| 214 | D | ND | G |
| 215 | C | ND | F |
| 216 | C* | ND | ND |
| 217 | C | ND | F |
| 218 | B* | ND | F* |
| 219 | D | ND | ND |
| 220 | C | ND | F |
| 221 | A | ND | E |
| 222 | A* | ND | ND |
| 223 | B | ND | ND |
| 224 | 0 | ND | ND |
| 225 | 0 | ND | ND |
| 226 | D | ND | ND |
| 227 | C | ND | ND |
| 228 | 0 | ND | ND |
| 229 | A* | ND | ND |
| 230 | D | ND | ND |
| 231 | D | ND | ND |
| 232 | B | ND | ND |
| 233 | B | ND | ND |
| 234 | D | ND | ND |
| 235 | 0 | ND | ND |
| 236 | 0 | ND | ND |
| 237 | A | ND | ND |
| 238 | 0 | ND | ND |
| 239 | 0 | ND | ND |
| 240 | 0 | ND | ND |
| 241 | C* | ND | ND |
| 242 | A | ND | ND |
| 243 | A* | ND | ND |
| 244 | A* | ND | ND |
| 245 | B* | ND | ND |
| 246 | C* | ND | ND |
| 247 | C* | ND | ND |
| 248 | D* | ND | ND |

TABLE 2-continued

Inhibition of Smad2/3, JNK, and MAPK p38 (at 10 μM), each in Panc-1 pancreatic cancer cell line

| Compound | % inh of Smad2/3 phosphorylation in Panc-1 | % inh of JNK in Panc-1 | % inh of MAPK p38 in Panc-1 |
|---|---|---|---|
| 249 | 0 | ND | ND |
| 250 | C* | ND | ND |
| 251 | A* | ND | ND |
| 252 | B* | ND | ND |
| 253 | A* | ND | ND |
| 254 | B* | ND | ND |
| 255 | D* | ND | ND |
| 256 | D* | ND | ND |
| 257 | D* | ND | ND |
| 258 | A* | ND | ND |
| 259 | A | ND | ND |
| 260 | A* | ND | ND |
| 261 | B* | ND | ND |
| 262 | B* | ND | ND |
| 263 | C | ND | ND |
| 264 | A | ND | ND |
| 265 | A | ND | ND |
| 266 | D* | ND | ND |
| 267 | B | ND | ND |
| 268 | C | ND | ND |
| 269 | D | ND | ND |
| 270 | ND | ND | ND |
| 271 | ND | ND | ND |
| 272 | D | ND | ND |
| 273 | D | ND | ND |
| 274 | D | ND | ND |
| 275 | B | ND | ND |
| 276 | B | ND | ND |

0 = 0% inhibition,
A = 1-25% inhibition,
B = 26-45% inhibition,
C = 46-75% inhibition,
D = 76-100% inhibition,
E = 1-30% inhibition,
F = 31-74% inhibition,
G = 75-99% inhibition,
H = 100% inhibition,
A* = 1-25% activation,
B* = 26-45% activation,
C* = 46-75% activation,
D* = 76-100% activation,
E* = 1-30% activation,
F* = 31-74% activation,
G* = 75-99% activation,
H* ≥ 100% activation,
ND = not determined.

TABLE 3

% Inhibition at 10 μM of Erk1/2, Akt, IL-6, TNF-alpha and MiaPaca-2 proliferation

| Compound | % inh of Erk1/2 phosphor-ylation in Panc-1 | % inh of Akt phosphor-ylation in Panc-1 | Proliferation in MiaPaca-2: IC50 (uM) | IL-6: % inh. | TNFα: % inh. |
|---|---|---|---|---|---|
| 1 | 0 | C* | I | H | E |
| 2 | B | C* | I | E | F |
| 3 | D | B | I | G | F |
| 4 | D | 0 | I | H | H |
| 5 | 0 | 0 | I | 0 | 0 |
| 6 | 0 | 0 | K | H | F |
| 7 | 0 | 0 | I | E | 0 |
| 8 | 0 | 0 | I | 0 | 0 |
| 9 | 0 | 0 | I | E | 0 |
| 10 | 0 | 0 | I | F | 0 |
| 11 | 0 | 0 | I | 0 | 0 |
| 12 | 0 | 0 | I | F | 0 |

TABLE 3-continued

% Inhibition at 10 μM of Erk1/2, Akt, IL-6, TNF-alpha and MiaPaca-2 proliferation

| Compound | % inh of Erk1/2 phosphor-ylation in Panc-1 | % inh of Akt phosphor-ylation in Panc-1 | Proliferation in MiaPaca-2: IC50 (uM) | IL-6: % inh. | TNFα: % inh. |
|---|---|---|---|---|---|
| 13 | 0 | 0 | K | H | 0 |
| 14 | 0 | 0 | I | G | 0 |
| 15 | 0 | 0 | I | G | 0 |
| 16 | A | 0 | I | G | 0 |
| 17 | A | D | I | G | F |
| 18 | C | D* | I | F | E |
| 19 | 0 | D* | I | H | F |
| 20 | D | D | I | H | E |
| 21 | 0 | C* | I | E | 0 |
| 22 | 0 | A* | K | H | 0 |
| 23 | D | D | I | H | H |
| 24 | 0 | A* | I | F | F |
| 25 | 0 | D | I | E | E |
| 26 | D | C | J | G | E |
| 27 | 0 | A* | I | H | F |
| 28 | 0 | A* | I | F | E |
| 29 | D | D | J | H | H |
| 30 | D | D | J | H | H |
| 31 | D | D | I | H | H |
| 32 | D | D | K | H | H |
| 33 | D | D | J | H | H |
| 34 | D | D | J | H | E |
| 35 | 0 | 0 | I | F | 0 |
| 36 | C | 0 | I | G | E |
| 37 | 0 | 0 | I | 0 | 0 |
| 38 | 0 | 0 | I | F | E |
| 39 | 0 | 0 | I | 0 | 0 |
| 40 | 0 | 0 | I | H | F |
| 41 | 0 | A* | I | E | E |
| 42 | D | D | J | H | H |
| 43 | D | B | I | F | E |
| 44 | B | B | I | F | E |
| 45 | 0 | 0 | I | H | H |
| 46 | 0 | 0 | I | H | H |
| 47 | C | C* | I | 0 | E |
| 48 | A | D* | L | E | E |
| 49 | B* | D* | L | E | E |
| 50 | B* | D* | L | E | 0 |
| 51 | 0 | D* | I | G | F |
| 52 | 0 | B | I | 0 | E |
| 53 | D | A* | L | G | E |
| 54 | C | B* | L | F | E |
| 55 | A | A* | L | E | E |
| 56 | C | B* | K | F | E |
| 57 | A* | D* | L | E | 0 |
| 58 | D | A* | L | F | E |
| 59 | C | C* | K | F | E |
| 60 | A | D* | I | 0 | 0 |
| 61 | A* | C* | J | E | E |
| 62 | A | D* | L | F | E |
| 63 | A | D* | L | E | E |
| 64 | A | D* | L | E | 0 |
| 65 | A | D* | L | E | E |
| 66 | C | D* | I | E | E |
| 67 | D | D* | I | H | G |
| 68 | D* | D* | L | E | F |
| 69 | D* | D* | I | G | E |
| 70 | B* | C* | I | G | E |
| 71 | D* | D* | I | 0 | 0 |
| 72 | D* | D* | I | G | E |
| 73 | D* | D* | L | G | 0 |
| 74 | D* | D* | K | E | E |
| 75 | B | A* | I | E | E |
| 76 | 0 | D* | L | F | F |
| 77 | D* | D* | I | E | F |
| 78 | D* | D* | K | F | F |
| 79 | D* | D* | L | E | F |
| 80 | D* | D* | I | 0 | 0 |
| 81 | 0 | D* | K | H | G |
| 82 | A* | D* | L | H | F |
| 83 | D* | D* | K | F | E |

TABLE 3-continued

% Inhibition at 10 μM of Erk1/2, Akt, IL-6, TNF-alpha and MiaPaca-2 proliferation

| Compound | % inh of Erk1/2 phosphorylation in Panc-1 | % inh of Akt phosphorylation in Panc-1 | Proliferation in MiaPaca-2: IC50 (uM) | IL-6: % inh. | TNFα: % inh. |
|---|---|---|---|---|---|
| 84 | D* | D* | L | F | 0 |
| 85 | C | D* | I | H | G |
| 86 | D* | D* | K | H | E |
| 87 | C* | D* | I | 0 | 0 |
| 88 | 0 | D* | I | E | E |
| 89 | D* | D* | L | H | F |
| 90 | D* | A* | I | 0 | E |
| 91 | D* | D* | L | E | E |
| 92 | A* | A* | I | G | E |
| 93 | D | D* | K | H | H |
| 94 | C* | D* | L | G | F |
| 95 | D* | D* | L | E | E |
| 96 | 0 | D* | K | G | 0 |
| 97 | D* | D* | L | E | 0 |
| 98 | D* | D* | L | E | 0 |
| 99 | D* | A* | I | H | H |
| 100 | C* | D* | L | G | 0 |
| 101 | A* | D* | K | G | 0 |
| 102 | A* | D* | L | H | F |
| 103 | A* | C* | I | 0 | 0 |
| 104 | D* | D* | L | H | 0 |
| 105 | A | C* | J | H | 0 |
| 106 | 0 | D* | L | G | 0 |
| 107 | D* | C* | L | F | E |
| 108 | A* | D* | J | G | 0 |
| 109 | B* | D* | J | G | 0 |
| 110 | B* | C* | L | E | E |
| 111 | A* | D* | K | H | G |
| 112 | A* | D* | L | F | 0 |
| 113 | D* | D* | L | H | F |
| 114 | B* | D* | L | H | G |
| 115 | C | D* | L | G | 0 |
| 116 | D* | D* | L | F | 0 |
| 117 | B | B | L | E | E |
| 118 | D* | D* | L | F | E |
| 119 | A* | D* | J | G | F |
| 120 | C* | B* | L | F | E |
| 121 | D* | B* | J | G | F |
| 122 | A* | C* | L | G | E |
| 123 | A* | B* | L | H | F |
| 124 | C* | C* | L | F | E |
| 125 | A | D* | K | G | E |
| 126 | D* | D* | L | F | 0 |
| 127 | D* | D* | L | G | 0 |
| 128 | D* | D* | L | F | F |
| 129 | D* | C* | L | G | E |
| 130 | B* | D* | I | 0 | E |
| 131 | A* | A | I | 0 | E |
| 132 | 0 | A | I | 0 | 0 |
| 133 | A | B | I | 0 | E |
| 134 | B | A | I | E | E |
| 135 | D* | D* | L | F | E |
| 136 | D* | D* | L | F | E |
| 137 | B* | D* | L | E | E |
| 138 | D* | D* | L | G | 0 |
| 139 | D* | D* | L | G | E |
| 140 | D* | D* | L | G | 0 |
| 141 | B | A | L | F | 0 |
| 142 | C | A | L | F | 0 |
| 143 | D* | D* | L | H | G |
| 144 | A | B* | L | F | E |
| 145 | C* | D* | L | G | E |
| 146 | D* | D* | K | 0 | E |
| 147 | A* | A* | I | 0 | E |
| 148 | C* | A | I | E | E |
| 149 | D* | D* | J | H | H |

TABLE 3-continued

% Inhibition at 10 μM of Erk1/2, Akt, IL-6, TNF-alpha and MiaPaca-2 proliferation

| Compound | % inh of Erk1/2 phosphorylation in Panc-1 | % inh of Akt phosphorylation in Panc-1 | Proliferation in MiaPaca-2: IC50 (uM) | IL-6: % inh. | TNFα: % inh. |
|---|---|---|---|---|---|
| 150 | A | B* | I | E | 0 |
| 151 | D* | C* | I | 0 | 0 |
| 152 | B* | B* | I | E | 0 |
| 153 | A | B | I | 0 | 0 |
| 154 | C* | B* | I | F | 0 |
| 155 | A* | A | I | F | 0 |
| 156 | D* | D* | L | E | 0 |
| 157 | C* | D* | L | E | 0 |
| 158 | A | D* | L | E | 0 |
| 159 | A | B | I | E | 0 |
| 160 | A* | B* | I | H | F |
| 161 | A | A* | I | H | G |
| 162 | A | B | I | F | F |
| 163 | A* | A* | I | H | E |
| 164 | A* | A* | I | H | E |
| 165 | C* | D* | L | G | E |
| 166 | B* | D* | I | H | H |
| 167 | A | B* | I | 0 | 0 |
| 168 | 0 | 0 | I | E | F |
| 169 | B* | C* | L | E | 0 |
| 170 | A* | C* | L | G | 0 |
| 171 | B | B | I | 0 | 0 |
| 172 | 0 | B* | I | E | 0 |
| 173 | C | C* | J | H | 0 |
| 174 | D* | D* | K | E | 0 |
| 175 | D* | D* | K | H | 0 |
| 176 | D* | D* | J | H | 0 |
| 177 | D* | A* | I | H | 0 |
| 178 | D* | D* | I | G | 0 |
| 179 | D* | D* | I | G | 0 |
| 180 | ND | ND | ND | G | F |
| 181 | A | B* | I | G | E |
| 182 | A* | B* | I | F | E |
| 183 | D* | A | I | F | F |
| 184 | A* | A* | I | F | F |
| 185 | B | A | I | F | F |
| 186 | A* | A* | I | E | E |
| 187 | A | C* | I | G | E |
| 188 | A | A* | I | G | 0 |
| 189 | A* | B | I | 0 | E |
| 190 | D* | D* | I | G | E |
| 191 | D* | D* | I | G | E |
| 192 | D* | D* | I | H | F |
| 193 | D* | D* | I | H | F |
| 194 | D* | D* | I | H | G |
| 195 | B* | D* | I | G | 0 |
| 196 | D* | D* | L | H | H |
| 197 | D* | A* | I | G | F |
| 198 | D* | C | I | F | F |
| 199 | D* | A | I | H | E |
| 200 | D* | B | I | E | E |
| 201 | D* | B | I | H | G |
| 202 | D* | B | I | G | E |
| 203 | D | D | J | H | H |
| 204 | D* | C* | I | H | F |
| 205 | D* | C* | I | ND | ND |
| 206 | B | C | I | H | E |
| 207 | D* | C* | I | H | H |
| 208 | C* | D* | I | H | F |
| 209 | D | D | K | H | H |
| 210 | D | D | J | H | H |
| 211 | A* | A | I | G | 0 |
| 212 | B* | A* | I | E | 0 |
| 213 | D* | D* | J | F | 0 |
| 214 | A* | A* | I | E | 0 |

TABLE 3-continued

| % Inhibition at 10 μM of Erk1/2, Akt, IL-6, TNF-alpha and MiaPaca-2 proliferation | | | | | |
|---|---|---|---|---|---|
| Compound | % inh of Erk1/2 phosphorylation in Panc-1 | % inh of Akt phosphorylation in Panc-1 | Proliferation in MiaPaca-2: IC50 (uM) | IL-6: % inh. | TNFα: % inh. |
| 215 | A* | B* | I | E | F |
| 216 | C* | A* | I | G | F |
| 217 | D* | D* | L | H | F |
| 218 | D* | D* | I | E | E |
| 219 | D | D | J | H | H |
| 220 | A | A | I | F | E |
| 221 | A* | D* | L | F | 0 |
| 222 | A* | D* | L | G | 0 |
| 223 | A | B | I | 0 | E |
| 224 | C* | D* | L | G | E |
| 225 | B | A* | I | 0 | 0 |
| 226 | A* | D* | L | G | F |
| 227 | C* | D* | L | G | G |
| 228 | A* | D* | L | F | E |
| 229 | A | D* | K | B | 0 |
| 230 | D* | D* | L | G | E |
| 231 | D* | D* | L | E | 0 |
| 232 | B* | D* | L | F | E |
| 233 | D* | D* | L | F | E |
| 234 | D* | D* | L | E | E |
| 235 | B* | D* | L | C | 0 |
| 236 | D* | B* | K | 0 | 0 |
| 237 | 0 | D* | L | 0 | 0 |
| 238 | A | D* | L | H | G |
| 239 | C* | D* | L | G | E |
| 240 | A* | D* | L | G | 0 |
| 241 | D* | D* | I | F | E |
| 242 | 0 | D* | I | F | 0 |
| 243 | C* | D* | L | 0 | 0 |
| 244 | 0 | D* | L | 0 | 0 |
| 245 | 0 | D* | L | F | 0 |
| 246 | 0 | D* | K | F | 0 |
| 247 | D* | D* | J | H | G |
| 248 | C* | D* | L | H | F |
| 249 | D* | D* | L | H | E |
| 250 | C* | D* | L | H | G |
| 251 | B | A | I | ND | ND |
| 252 | A* | D* | L | E | 0 |
| 253 | C* | D* | J | F | 0 |
| 254 | D* | D* | I | F | 0 |
| 255 | A | D* | L | G | E |
| 256 | C | D* | I | G | 0 |
| 257 | C* | D* | K | H | F |
| 258 | A* | A | I | 0 | 0 |
| 259 | A* | D* | I | G | 0 |
| 260 | A* | C* | I | H | F |
| 261 | B | B | I | G | E |
| 262 | A | B | I | E | 0 |
| 263 | A | D* | L | H | G |
| 264 | B* | D* | K | H | F |
| 265 | A* | D* | L | H | F |
| 266 | D | D* | L | F | 0 |
| 267 | D* | D* | L | G | E |
| 268 | D* | D* | L | H | F |
| 269 | D | C | J | H | H |
| 270 | D | D | K | H | H |
| 271 | D | D | K | H | H |
| 272 | D | D | I | H | H |

TABLE 3-continued

| % Inhibition at 10 μM of Erk1/2, Akt, IL-6, TNF-alpha and MiaPaca-2 proliferation | | | | | |
|---|---|---|---|---|---|
| Compound | % inh of Erk1/2 phosphorylation in Panc-1 | % inh of Akt phosphorylation in Panc-1 | Proliferation in MiaPaca-2: IC50 (uM) | IL-6: % inh. | TNFα: % inh. |
| 273 | D | D | I | H | H |
| 274 | D | D | K | H | H |
| 275 | 0 | D* | I | 0 | 0 |
| 276 | D* | D* | K | G | 0 |

0 = 0% inhibition,
A = 1-25% inhibition,
B = 26-49% inhibition,
C = 50-84% inhibition,
D = 85-100% inhibition,
A* = 1-25% activation,
B* = 26-49% activation,
C* = 46-84% activation,
D* = 85-100% activation,
E = 1-24% inhibition,
F = 25-49% inhibition,
G = 50-74% inhibition,
H = 75-100% inhibition,
E* = 1-24% activation,
F* = 25-49% activation,
G* = 50-74% activation,
H* = 75-100% activation
I = >1 uM $IC_{50}$,
J = 0.51-1 uM $IC_{50}$,
K = 0.15-0.5 uM $IC_{50}$,
L = <0.15 uM $IC_{50}$,
ND = not determined.

Biological Example 2: Cell-Based Proliferation Following Incubation with Compound

Protocol for Proliferation Assay

This assay is referred to as the "Proliferation Assay" or "Cell Viability Assay" throughout this application.

Cell lines: these Human tumor-derived cell lines were purchased from American Type Culture Collection. Human tumor-derived pancreatic cancer cell line MiaPaca-2 (expressing KRAS G12C mutant) and Panc-1 (expressing KRas G12D mutant), and Human non-small cell lung cancer (NSCLC) cell line A549 (expressing KRas G12S mutant), and Human melanoma cell line A375 (wild type Kras) were grown in complete DMEM-High Glucose medium. Human tumor-derived pancreatic cancer cell lines SU86.86 (expressing KRas G12D mutant), BxPC3 (expressing wild type K-Ras), and Human non-small cell lung cancer (NSCLC) cell lines NCI-H441 (expressing KRas G12S mutant), NCI-H1975 (expressing wild type KRas), NCI-H358 (expressing KRas G12C mutant), NCI-H1299 (expressing NRas Q61H mutant), and Human colon cancer cell line SW-620 (expressing KRas G12V mutant), Human triple negative breast cancer cell line HCC-1806 (expressing wild type KRas), and Human tumor-derived multiple myeloma cell line MM.1R (expressing wild type KRAS), were grown in RPMI 1640 medium. Human tumor-derived breast cancer cell line BT-549 (expressing wild type KRAS) was grown in RPMI 1640 medium in the presence of 11.8U insulin. Human tumor-derived pancreatic cancer cell line HPAF-II (expressing KRas G12D mutant), Human triple negative breast cancer cell line BT-20 (expressing wild type KRas), and Human colon cancer cell line LS123 (expressing KRas G12S mutant), were grown in EMEM medium. Human tumor-derived pancreatic cancer cell line CF-PAC1 (expressing KRas G12V mutant) was frown in IMDM medium, and Human colon cancer cell line HT29 (expressing wild type KRas) was grown in McCoy's 5A medium. The colon cancer cell line GP2d (expressing KRas G12D mutant) was purchased from MilliporeSigma and grown in DMEM-High Glucose medium. All cell lines were supplemented with penicillin (100 U/mL), streptomycin (100 μg/mL), and 10% heat-inactivated FBS at 37° C. in a humidified incubator with 5% CO2.

Method: Cells were plated at 2000 to 5000 cells/well density in 96-wells plate and cultured overnight. Small molecules that were tested were added to the cells in the final concentration of 10 μM in the presence of 0.3% DMSO and 10% FBS, and incubated for 2-4 days at 37° C. in a humidified incubator with 5% CO2. For IC50 value determination, serial dilutions of compounds were added to cells under the same conditions.

Assay: At the end of the incubation period, cell viability was determined using the CellTiter 96® Aqueous One Solution Cell Proliferation Assay according to manufacturer specifications (Promega, Madison, WI). The percentage of small molecules inhibition of cellular proliferation was calculated from raw data.

Tables 4a and 4b shows data for these selected compounds tested in one or more of the cellular assays described above, such as in Human tumor-derived pancreatic cancer cell line Panc-1.

TABLE 4a

Proliferation assay IC50 data

| Cell Line | Tumor Type | KRas mutation | Compound 6 $IC_{50}$ (uM) | Compound 58 $IC_{50}$ (uM) |
|---|---|---|---|---|
| BxPC3 | pancreatic | WT | L | ND |
| MiaPaca2 | pancreatic | G12C | L | L |
| Panc1 | pancreatic | G12D | L | L |
| SU86.86 | pancreatic | G12D | K | ND |
| HPAF-II | pancreatic | G12D | L | L |
| CF-PAC1 | pancreatic | G12V | L | ND |
| NCI-H1975 | NSCLC | WT | J | ND |
| NCI-H358 | NSCLC | G12C | L | L |
| A549 | NSCLC | G12S | J | L |
| NCI-H441 | NSCLC | G12S | J | ND |
| NCI-H1299 | NSCLC | Q61H (N-Ras) | L | ND |
| HT29 | colon | WT | L | ND |
| GP2d | colon | G12D | K | L |
| SW-620 | colon | G12V | K | L |
| LS-123 | colon | G12S | L | ND |
| A375 | melanoma | WT | L | L |
| HCC-1806 | Breast (TNBC) | WT | J | ND |
| BT-549 | Breast (TNBC) | WT | L | L |
| BT-20 | Breast (TNBC) | WT | L | L |

I = >1 uM $IC_{50}$,
J = 0.51-1 uM $IC_{50}$,
K = 0.15-0.5 uM $IC_{50}$,
L = <0.15 uM $IC_{50}$,
ND = not determined TABLE 4b Proliferation assay IC50 data

| Compound | MiaPaca-2 IC50 (nM) Pancreatic | NCI-H358 IC50 (nM) NSCLC | A375 IC50 (nM) Melanoma | GP2d IC50 (nM) Colorectal | BT549 IC50 (nM) TNBC | MM.1R IC50 (nM) Multiple Myloma |
|---|---|---|---|---|---|---|
| 6 | N | N | M | M | M | O |
| 58 | O | N | O | N | O | P |
| 84 | O | O | O | O | O | P |

TABLE 4b-continued

Proliferation assay IC50 data

| Compound | MiaPaca-2 IC50 (nM) Pancreatic | NCI-H358 IC50 (nM) NSCLC | A375 IC50 (nM) Melanoma | GP2d IC50 (nM) Colorectal | BT549 IC50 (nM) TNBC | MM.1R IC50 (nM) Multiple Myloma |
|---|---|---|---|---|---|---|
| 91 | N | O | O | ND | O | ND |
| 100 | O | M | M | N | N | P |
| 102 | O | O | O | N | O | P |
| 104 | O | M | M | N | N | P |
| 124 | O | O | O | O | O | P |
| 221 | O | N | M | M | M | P |
| 222 | O | N | M | M | N | P |
| 235 | O | M | M | M | N | P |
| 238 | O | M | M | M | N | P |
| 252 | N | O | M | O | N | P |
| 255 | O | O | N | O | O | P |
| 267 | O | O | O | O | N | P |

M = >50 nM $IC_{50}$,
N = 10-50 nM $IC_{50}$,
O = 1-10 nM $IC_{50}$,
P = <1 nM $IC_{50}$,
ND = not determined

Biological Example 3: Ras GTP Binding Domain Inhibition Assay

The assays described in Example 3 are collectively referred to as the "Ras Superfamily Assay" throughout this application.

A Ras Superfamily Activity Assay (as disclosed in International Application No. PCT/US2018/038613, filed Jun. 20, 2018, which is incorporated by reference in its entirety) was used as a specific assay to evaluate compounds against the following for the following Ras Superfamily proteins: KRas wild type, KRas Q61H mutant, KRas G12C mutant, KRas G12D mutant, Rac-1, and Rho-A.

Buffer-I:
- 25 mM Tris-HCl, pH 7.4
- 27 mM KCl
- 137 mM NaCl
- 1 mM $MgCl_2$
- 1 mM DTT Buffer-II:
- 50 mM Tris-HCl, pH 7.0
- 1 mM $MgCl_2$
- 1 mM DTT The small GTPases proteins: KRas wild type. KRas Q61H mutant, KRas G12C mutant, KRas G12D mutants, Rac-1, and Rho-A were expressed as His-tagged proteins. In addition, the Guanosine nucleotide Exchange Factor (GEF) Sos protein (residues 556-1049) was expressed as a His-tagged protein. In cells, the guanine nucleotide exchange factor Sos protein promotes activation of Ras proteins by stimulating an exchange of GDP for GTP. The inclusion of Sos to the Ras GTP binding domain inhibition assay may be considered as an alternative representation of physiological cellular conditions for evaluating the inhibitory activity of some of the tested small molecules.

For the assay, all purified small GTPases proteins were diluted in Buffer-I or Buffer-II to a final concentration of 10-30 μg/mL. 200 μL of each diluted protein was added to a nickel-coated 96-well plate and incubated overnight at 4° C. Then the protein solution was discarded and 200 μL of Buffer-I or Buffer-II was added to each well in the presence of 1% DMSO. Compounds to be tested were added to the protein-coated wells at final concentration of 20 µM, and incubated for 3 hours at room temperature with and without 10-30 µg/mL of Sos added to the final hour of the incubation. When performing $IC_{50}$ measurements a serial dilution of all tested concentrations was added. Then Cy3-GTP or Cy5-GTP was added to each well to a final concentration of 100 nM. The labeled GTP was incubated for 45 minutes at room temperature. Following GTP incubation, wells were washed 3× in Buffer-I or Buffer-II and 200 µL of Buffer-I or Buffer-II was added to each well. Following washes, the amount of bound labeled-GTP was measured using a SpectraMax M3 (Molecular Devices).

Protocol for Cdc42 and Rheb GTP Binding Domain Inhibition Assay

The following method was developed as specific assay for cdc42 and Rheb proteins.

Buffer-I:

25 mM Tris-HCl, pH 7.4

27 mM KCl 137 mM NaCl 1 mM MgCl2

1 mM DTT

Buffer-II:

50 mM Tris-HCl, pH 7.0

1 mM MgCl2

1 mM DTT

The small GTPases proteins cdc42 and Rheb were expressed as His-tagged proteins. For the assay, the cdc42 and Rheb purified small GTPases proteins were diluted in Buffer-I or Buffer-II to a final concentration of 10-30 µg/mL. 200 µL of each diluted protein was added to a nickel-coated 96-well plate and incubated overnight at 40 C. Then the protein solution was discarded and 200 µL of Buffer-I or Buffer-II was added to each well in the presence of 1% DMSO. Compounds to be tested were added to the protein-coated wells at final concentration of 20 µM, and incubated for 3 hours at room temperature with and without 10-30 µg/mL of Sos added to the final hour of the incubation. When performing IC50 measurements a serial dilution of all tested concentrations was added. Then Cy3-GTP or Cy5-GTP was added to each well to a final concentration of 100 nM. The labeled GTP was incubated for 45 minutes at room temperature. Following GTP incubation, wells were washed 3× in Buffer-I or Buffer-II and 200 µL of Buffer-I or Buffer-II was added to each well. Following washes, the amount of bound labeled-GTP was measured using a SpectraMax M3 (Molecular Devices).

Tables 5-6 show % inhibition data for selected compounds tested in the screening assays described above.

TABLE 5

% Inhibition at 20 µM of K-Ras mutant and wild-type protein

| Compound | KRas wild type: % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 1 | 0 | A | A | 0 | 0 | 0 | 0 | 0 |
| 2 | 0 | 0 | 0 | 0 | 0 | 0 | 0 | 0 |
| 3 | 0 | 0 | 0 | 0 | 0 | 0 | 0 | 0 |
| 4 | A | A | A | 0 | 0 | 0 | 0 | 0 |
| 5 | 0 | 0 | 0 | 0 | 0 | 0 | 0 | 0 |
| 6 | D | C | D | C | C | C | C | C |
| 7 | A | 0 | A | 0 | 0 | A | B | A |
| 8 | A | 0 | 0 | A | 0 | A | 0 | 0 |
| 9 | 0 | 0 | 0 | 0 | B | 0 | A | 0 |
| 10 | A | 0 | A | 0 | B | 0 | A | 0 |
| 11 | 0 | 0 | A | 0 | B | 0 | A | 0 |
| 12 | 0 | 0 | A | 0 | B | 0 | 0 | 0 |
| 13 | A | 0 | A | 0 | A | 0 | 0 | 0 |
| 14 | 0 | A | A | 0 | B | 0 | 0 | 0 |
| 15 | A | A | A | 0 | 0 | 0 | A | A |
| 16 | 0 | A | A | 0 | B | 0 | A | 0 |
| 17 | C | C | C | C | C | C | C | C |
| 18 | B | A | A | 0 | 0 | 0 | 0 | A |
| 19 | A | A | B | A | 0 | A | 0 | B |
| 20 | A | A | A | 0 | A | 0 | 0 | 0 |
| 21 | A | A | B | 0 | 0 | 0 | 0 | A |
| 22 | B | A | B | B | B | A | B | A |
| 23 | 0 | A | A | 0 | A | 0 | A | 0 |
| 24 | 0 | 0 | 0 | 0 | 0 | 0 | 0 | 0 |
| 25 | A | A | A | A | A | A | A | A |
| 26 | A | 0 | 0 | A | 0 | A | A | A |
| 27 | A | A | 0 | 0 | 0 | 0 | A | 0 |
| 28 | A | A | A | A | A | A | A | A |
| 29 | A | 0 | 0 | A | 0 | A | 0 | 0 |
| 30 | A | 0 | 0 | A | A | 0 | 0 | 0 |
| 31 | A | 0 | A | B | A | 0 | 0 | A |
| 32 | A | 0 | 0 | 0 | 0 | 0 | A | A |
| 33 | A | 0 | A | 0 | A | 0 | A | 0 |
| 34 | 0 | A | 0 | 0 | 0 | A | 0 | 0 |
| 35 | A | A | 0 | 0 | A | 0 | A | A |
| 36 | 0 | A | A | A | A | 0 | A | A |
| 37 | B | B | B | B | C | C | 0 | 0 |
| 38 | 0 | 0 | 0 | 0 | 0 | 0 | 0 | 0 |

TABLE 5-continued

% Inhibition at 20 μM of K-Ras mutant and wild-type protein

| Compound | KRas wild type: % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 39 | A | A | A | A | B | A | A | 0 |
| 40 | 0 | 0 | 0 | 0 | 0 | 0 | 0 | A |
| 41 | A | 0 | 0 | A | 0 | 0 | 0 | 0 |
| 42 | 0 | 0 | 0 | 0 | 0 | 0 | B | B |
| 43 | 0 | 0 | A | 0 | 0 | 0 | B | B |
| 44 | 0 | B | B | C | 0 | B | D | D |
| 45 | B | B | B | A | B | A | D | D |
| 46 | A | A | B | A | B | A | D | D |
| 47 | 0 | 0 | A | A | 0 | 0 | A | A |
| 48 | C | B | C | C | C | A | D | D |
| 49 | B | 0 | C | B | A | 0 | D | D |
| 50 | C | B | C | C | A | A | D | D |
| 51 | D | C | D | C | C | C | ND | ND |
| 52 | 0 | A | A | A | 0 | A | ND | ND |
| 53 | C | C | C | C | C | C | D | D |
| 54 | C | C | D | C | D | C | D | D |
| 55 | D | C | D | C | B | C | D | D |
| 56 | B | 0 | B | B | C | A | C | D |
| 57 | D | D | D | D | D | D | D | D |
| 58 | D | D | D | D | D | C | C | D |
| 59 | C | C | D | C | C | B | D | D |
| 60 | A | A | A | A | A | 0 | B | C |
| 61 | D | D | D | D | D | D | D | D |
| 62 | A | 0 | B | A | A | 0 | A | A |
| 63 | D | D | D | D | D | C | D | D |
| 64 | D | D | D | D | D | C | D | D |
| 65 | C | B | C | C | C | A | C | C |
| 66 | D | D | D | D | D | C | D | D |
| 67 | C | C | C | C | C | B | C | C |
| 68 | D | D | D | D | D | D | D | D |
| 69 | A | 0 | A | A | A | 0 | A | 0 |
| 70 | A | 0 | A | A | A | 0 | A | 0 |
| 71 | 0 | A | A | A | 0 | A | 0 | 0 |
| 72 | C | C | D | D | C | C | C | D |
| 73 | C | B | C | B | B | B | C | C |
| 74 | 0 | 0 | A | 0 | 0 | 0 | 0 | 0 |
| 75 | A | A | B | A | A | A | A | B |
| 76 | B | 0 | C | 0 | ND | ND | ND | ND |
| 77 | C | C | D | B | ND | ND | ND | ND |
| 78 | D | D | D | D | ND | ND | ND | ND |
| 79 | C | B | D | C | ND | ND | ND | ND |
| 80 | A | A | A | 0 | ND | ND | ND | ND |
| 81 | C | B | D | C | ND | ND | ND | ND |
| 82 | C | 0 | C | B | ND | ND | ND | ND |
| 83 | D | C | D | D | ND | ND | ND | ND |
| 84 | D | C | C | D | ND | ND | ND | ND |
| 85 | 0 | 0 | 0 | A | ND | ND | ND | ND |
| 86 | B | 0 | A | C | ND | ND | ND | ND |
| 87 | 0 | 0 | A | A | ND | ND | ND | ND |
| 88 | 0 | 0 | A | A | ND | ND | ND | ND |
| 89 | D | D | D | D | ND | ND | ND | ND |
| 90 | B | 0 | 0 | A | ND | ND | ND | ND |
| 91 | D | C | D | D | ND | ND | ND | ND |
| 92 | 0 | 0 | A | A | 0 | 0 | 0 | A |
| 93 | D | D | D | D | D | C | C | D |
| 94 | C | B | C | B | B | B | B | C |
| 95 | C | B | C | C | B | B | C | C |
| 96 | D | D | D | D | ND | ND | ND | ND |
| 97 | D | D | D | D | ND | ND | ND | ND |
| 98 | C | A | C | C | ND | ND | ND | ND |
| 99 | C | B | B | B | B | B | ND | ND |
| 100 | D | D | D | D | ND | ND | ND | ND |
| 101 | D | B | D | C | ND | ND | ND | ND |
| 102 | D | D | D | D | ND | ND | ND | ND |
| 103 | B | A | B | B | ND | ND | ND | ND |
| 104 | D | D | D | D | ND | ND | ND | ND |
| 105 | C | D | D | D | ND | ND | ND | ND |
| 106 | A | 0 | B | A | ND | ND | ND | ND |
| 107 | C | D | C | C | ND | ND | ND | ND |
| 108 | D | C | D | C | ND | ND | ND | ND |
| 109 | D | C | D | C | ND | ND | ND | ND |
| 110 | B | C | C | B | ND | ND | ND | ND |

TABLE 5-continued

| % Inhibition at 20 μM of K-Ras mutant and wild-type protein | | | | | | | | |
|---|---|---|---|---|---|---|---|---|
| Compound | KRas wild type: % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
| 111 | C | A | B | B | ND | ND | ND | ND |
| 112 | A | 0 | A | A | ND | ND | ND | ND |
| 113 | C | D | D | D | ND | ND | ND | ND |
| 114 | D | D | D | D | ND | ND | ND | ND |
| 115 | D | C | C | C | ND | ND | ND | ND |
| 116 | C | D | C | C | ND | ND | ND | ND |
| 117 | A | A | A | A | ND | ND | ND | ND |
| 118 | D | D | D | D | ND | ND | ND | ND |
| 119 | C | A | C | B | ND | ND | ND | ND |
| 120 | A | C | B | A | ND | ND | ND | ND |
| 121 | D | C | D | D | ND | ND | ND | ND |
| 122 | D | D | D | D | ND | ND | ND | ND |
| 123 | D | D | D | D | ND | ND | ND | ND |
| 124 | D | C | C | C | ND | ND | ND | ND |
| 125 | C | B | C | C | ND | ND | ND | ND |
| 126 | A | A | B | B | ND | ND | ND | ND |
| 127 | D | D | D | D | ND | ND | ND | ND |
| 128 | D | D | D | D | ND | ND | ND | ND |
| 129 | B | B | B | B | ND | ND | ND | ND |
| 130 | A | 0 | B | A | ND | ND | ND | ND |
| 131 | B | 0 | A | 0 | ND | ND | ND | ND |
| 132 | B | 0 | B | A | ND | ND | ND | ND |
| 133 | A | 0 | B | 0 | ND | ND | ND | ND |
| 134 | 0 | 0 | A | A | ND | ND | ND | ND |
| 135 | D | D | D | D | ND | ND | ND | ND |
| 136 | C | D | D | D | ND | ND | ND | ND |
| 137 | C | B | C | B | ND | ND | ND | ND |
| 138 | C | D | D | D | ND | ND | ND | ND |
| 139 | D | D | D | D | ND | ND | ND | ND |
| 140 | C | C | C | D | ND | ND | ND | ND |
| 141 | C | B | D | D | ND | ND | ND | ND |
| 142 | D | D | D | D | ND | ND | ND | ND |
| 143 | D | D | D | D | ND | ND | ND | ND |
| 144 | C | D | D | D | ND | ND | ND | ND |
| 145 | D | D | D | D | ND | ND | ND | ND |
| 146 | D | D | D | D | ND | ND | ND | ND |
| 147 | C | A | 0 | 0 | ND | ND | ND | ND |
| 148 | B | A | 0 | 0 | ND | ND | ND | ND |
| 149 | D | D | D | D | ND | ND | ND | ND |
| 150 | D | D | D | D | ND | ND | ND | ND |
| 151 | C | C | B | D | ND | ND | ND | ND |
| 152 | C | B | C | C | ND | ND | ND | ND |
| 153 | B | B | C | C | ND | ND | ND | ND |
| 154 | B | B | D | D | ND | ND | ND | ND |
| 155 | A | A | A | A | ND | ND | ND | ND |
| 156 | D | D | D | D | ND | ND | ND | ND |
| 157 | D | D | D | D | ND | ND | ND | ND |
| 158 | D | D | D | D | ND | ND | ND | ND |
| 159 | A | 0 | 0 | 0 | ND | ND | ND | ND |
| 160 | 0 | 0 | 0 | A | ND | ND | ND | ND |
| 161 | A | 0 | A | 0 | ND | ND | ND | ND |
| 162 | A | 0 | 0 | 0 | ND | ND | ND | ND |
| 163 | 0 | 0 | 0 | 0 | ND | ND | ND | ND |
| 164 | A | A | A | 0 | ND | ND | ND | ND |
| 165 | D | D | D | D | ND | ND | ND | ND |
| 166 | C | D | D | D | ND | ND | ND | ND |
| 167 | A | A | B | A | ND | ND | ND | ND |
| 168 | A | A | B | A | ND | ND | ND | ND |
| 169 | D | D | D | D | ND | ND | ND | ND |
| 170 | D | D | D | D | ND | ND | ND | ND |
| 171 | A | B | A | A | ND | ND | ND | ND |
| 172 | B | B | B | B | ND | ND | ND | ND |
| 173 | C | D | B | C | ND | ND | ND | ND |
| 174 | B | B | B | B | ND | ND | ND | ND |
| 175 | D | D | C | D | ND | ND | ND | ND |
| 176 | D | D | D | D | ND | ND | ND | ND |
| 177 | D | D | C | D | ND | ND | ND | ND |
| 178 | D | D | D | D | ND | ND | ND | ND |
| 179 | D | D | D | D | ND | ND | ND | ND |
| 180 | A | A | A | A | ND | ND | ND | ND |
| 181 | A | A | A | 0 | ND | ND | ND | ND |
| 182 | A | A | A | 0 | ND | ND | ND | ND |

TABLE 5-continued

% Inhibition at 20 μM of K-Ras mutant and wild-type protein

| Compound | KRas wild type: % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 183 | 0 | A | A | A | ND | ND | ND | ND |
| 184 | A | A | B | 0 | ND | ND | ND | ND |
| 185 | A | 0 | A | 0 | ND | ND | ND | ND |
| 186 | D | D | D | D | ND | ND | ND | ND |
| 187 | D | D | D | D | ND | ND | ND | ND |
| 188 | D | D | D | D | ND | ND | ND | ND |
| 189 | 0 | 0 | A | A | ND | ND | ND | ND |
| 190 | A | B | B | B | ND | ND | ND | ND |
| 191 | A | B | B | B | ND | ND | ND | ND |
| 192 | B | B | B | B | ND | ND | ND | ND |
| 193 | A | A | A | A | ND | ND | ND | ND |
| 194 | A | 0 | A | A | ND | ND | ND | ND |
| 195 | A | 0 | A | A | ND | ND | ND | ND |
| 196 | D | D | D | D | ND | ND | ND | ND |
| 197 | 0 | A | A | A | ND | ND | ND | ND |
| 198 | A | B | B | B | ND | ND | ND | ND |
| 199 | A | B | B | B | ND | ND | ND | ND |
| 200 | B | B | B | B | ND | ND | ND | ND |
| 201 | A | B | B | B | ND | ND | ND | ND |
| 202 | B | C | C | C | ND | ND | ND | ND |
| 203 | 0 | 0 | 0 | 0 | ND | ND | ND | ND |
| 204 | A | A | A | A | ND | ND | ND | ND |
| 205 | A | A | A | A | ND | ND | ND | ND |
| 206 | A | A | A | A | ND | ND | ND | ND |
| 207 | B | B | B | A | ND | ND | ND | ND |
| 208 | B | C | B | C | ND | ND | ND | ND |
| 209 | A | 0 | A | A | ND | ND | ND | ND |
| 210 | A | 0 | A | A | ND | ND | ND | ND |
| 211 | C | D | C | C | C | D | ND | ND |
| 212 | C | D | C | D | ND | ND | ND | ND |
| 213 | D | D | D | D | ND | ND | ND | ND |
| 214 | C | C | C | C | ND | ND | ND | ND |
| 215 | D | D | D | D | ND | ND | ND | ND |
| 216 | D | D | D | D | ND | ND | ND | ND |
| 217 | C | B | C | B | ND | ND | ND | ND |
| 218 | A | A | A | A | ND | ND | ND | ND |
| 219 | A | 0 | A | 0 | ND | ND | ND | ND |
| 220 | B | A | B | A | ND | ND | ND | ND |
| 221 | D | D | D | D | ND | ND | ND | ND |
| 222 | D | D | D | D | ND | ND | ND | ND |
| 223 | B | 0 | B | A | ND | ND | ND | ND |
| 224 | D | D | D | D | ND | ND | ND | ND |
| 225 | A | A | B | A | ND | ND | ND | ND |
| 226 | D | D | D | D | ND | ND | ND | ND |
| 227 | D | D | D | D | ND | ND | ND | ND |
| 228 | C | C | D | C | ND | ND | ND | ND |
| 229 | C | D | D | D | ND | ND | ND | ND |
| 230 | D | D | D | D | ND | ND | ND | ND |
| 231 | B | B | C | C | ND | ND | ND | ND |
| 232 | D | D | D | D | ND | ND | ND | ND |
| 233 | D | D | D | D | ND | ND | ND | ND |
| 234 | C | D | D | D | ND | ND | ND | ND |
| 235 | C | B | C | C | ND | ND | ND | ND |
| 236 | B | B | C | B | ND | ND | ND | ND |
| 237 | D | D | D | D | ND | ND | ND | ND |
| 238 | D | D | D | D | ND | ND | ND | ND |
| 239 | D | D | D | D | ND | ND | ND | ND |
| 240 | D | D | D | D | ND | ND | ND | ND |
| 241 | D | D | D | D | ND | ND | ND | ND |
| 242 | A | 0 | B | A | ND | ND | ND | ND |
| 243 | D | D | D | D | ND | ND | ND | ND |
| 244 | C | D | D | D | ND | ND | ND | ND |
| 245 | A | B | C | C | ND | ND | ND | ND |
| 246 | D | D | D | D | ND | ND | ND | ND |
| 247 | D | D | D | D | ND | ND | ND | ND |
| 248 | D | D | D | D | ND | ND | ND | ND |
| 249 | C | C | C | C | ND | ND | ND | ND |
| 250 | D | D | D | D | ND | ND | ND | ND |
| 251 | B | A | C | B | ND | ND | ND | ND |
| 252 | C | D | D | D | ND | ND | ND | ND |
| 253 | D | D | C | D | ND | ND | ND | ND |
| 254 | D | D | D | D | ND | ND | ND | ND |

TABLE 5-continued

% Inhibition at 20 μM of K-Ras mutant and wild-type protein

| Compound | KRas wild type: % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 255 | ND | D | D | D | ND | ND | ND | ND |
| 256 | A | D | D | D | ND | ND | ND | ND |
| 257 | C | D | D | D | ND | ND | ND | ND |
| 258 | A | 0 | 0 | 0 | ND | ND | ND | ND |
| 259 | C | D | C | D | ND | ND | ND | ND |
| 260 | D | D | C | C | ND | ND | ND | ND |
| 261 | C | C | D | C | ND | ND | ND | ND |
| 262 | B | C | D | D | ND | ND | ND | ND |
| 263 | C | D | D | D | ND | ND | ND | ND |
| 264 | C | D | C | D | ND | ND | ND | ND |
| 265 | ND | D | C | D | ND | ND | ND | ND |
| 266 | D | C | D | D | ND | ND | ND | ND |
| 267 | D | D | D | D | ND | ND | ND | ND |
| 268 | C | D | C | D | ND | ND | ND | ND |
| 269 | C | A | B | B | ND | ND | ND | ND |
| 270 | B | A | B | B | ND | ND | ND | ND |
| 271 | B | A | B | B | ND | ND | ND | ND |
| 272 | 0 | 0 | C | A | ND | ND | ND | ND |
| 273 | 0 | A | B | A | ND | ND | ND | ND |
| 274 | 0 | 0 | B | A | ND | ND | ND | ND |
| 275 | A | 0 | A | A | ND | ND | ND | ND |
| 276 | D | D | D | D | ND | ND | ND | ND |

0 = 0% inhibition,
A = 1-25% inhibition,
B = 26-49% inhibition,
C = 50-75% inhibition,
D = 76-100% inhibition,
ND = not determined

TABLE 6

% Inhibition at 20 μM of Rac-1, Rho-A, Cdc42, and Rheb protein

| Compound | Rac-1: % inh. | Rho-A: % inh.. | Cdc42: % inh. | Rheb: % inh. |
|---|---|---|---|---|
| 1 | A | 0 | ND | ND |
| 2 | 0 | 0 | ND | ND |
| 3 | A | 0 | ND | ND |
| 4 | A | A | ND | ND |
| 5 | B | B | ND | ND |
| 6 | C | D | C | D |
| 7 | 0 | 0 | ND | ND |
| 8 | 0 | 0 | ND | ND |
| 9 | 0 | 0 | ND | ND |
| 10 | A | 0 | ND | ND |
| 11 | 0 | 0 | ND | ND |
| 12 | 0 | 0 | ND | ND |
| 13 | 0 | 0 | ND | ND |
| 14 | 0 | 0 | ND | ND |
| 15 | 0 | A | ND | ND |
| 16 | 0 | 0 | ND | ND |
| 17 | C | D | ND | ND |
| 18 | 0 | A | ND | ND |
| 19 | 0 | A | ND | ND |
| 20 | 0 | A | ND | ND |
| 21 | 0 | A | ND | ND |
| 22 | B | C | ND | ND |
| 23 | A | A | ND | ND |
| 24 | 0 | 0 | ND | ND |
| 25 | A | A | ND | ND |
| 26 | 0 | A | ND | ND |
| 27 | A | A | ND | ND |
| 28 | B | A | ND | ND |
| 29 | 0 | A | ND | ND |
| 30 | 0 | A | ND | ND |
| 31 | A | A | ND | ND |
| 32 | 0 | A | A | B |
| 33 | 0 | A | ND | ND |

TABLE 6-continued

% Inhibition at 20 μM of Rac-1, Rho-A, Cdc42, and Rheb protein

| Compound | Rac-1: % inh. | Rho-A: % inh.. | Cdc42: % inh. | Rheb: % inh. |
|---|---|---|---|---|
| 34 | B | A | A | B |
| 35 | 0 | A | ND | ND |
| 36 | 0 | A | ND | ND |
| 37 | 0 | 0 | ND | ND |
| 38 | 0 | A | ND | ND |
| 39 | 0 | 0 | ND | ND |
| 40 | A | A | ND | ND |
| 41 | 0 | 0 | ND | ND |
| 42 | 0 | A | A | A |
| 43 | A | A | A | B |
| 44 | B | A | B | B |
| 45 | C | C | B | C |
| 46 | C | B | C | C |
| 47 | 0 | A | A | A |
| 48 | C | D | C | C |
| 49 | B | B | A | B |
| 50 | B | C | B | B |
| 51 | D | D | C | C |
| 52 | 0 | 0 | A | 0 |
| 53 | D | D | C | D |
| 54 | D | D | C | D |
| 55 | D | D | C | D |
| 56 | C | C | B | C |
| 57 | D | D | D | D |
| 58 | D | D | D | D |
| 59 | D | D | C | C |
| 60 | A | A | A | B |
| 61 | D | D | D | D |
| 62 | C | B | A | 0 |
| 63 | D | D | D | C |
| 64 | D | D | D | C |
| 65 | D | D | B | 0 |
| 66 | D | D | D | C |

TABLE 6-continued

% Inhibition at 20 μM of Rac-1, Rho-A, Cdc42, and Rheb protein

| Compound | Rac-1: % inh. | Rho-A: % inh.. | Cdc42: % inh. | Rheb: % inh. |
|---|---|---|---|---|
| 67 | C | D | B | C |
| 68 | D | D | D | D |
| 69 | A | A | 0 | A |
| 70 | A | A | A | A |
| 71 | A | A | A | A |
| 72 | D | D | C | C |
| 73 | C | D | C | C |
| 74 | A | B | 0 | 0 |
| 75 | B | C | A | A |
| 76 | C | ND | ND | ND |
| 77 | D | ND | ND | ND |
| 78 | D | ND | ND | ND |
| 79 | D | ND | ND | ND |
| 80 | A | ND | ND | ND |
| 81 | D | ND | ND | ND |
| 82 | B | ND | ND | ND |
| 83 | D | ND | ND | ND |
| 84 | D | ND | ND | ND |
| 85 | 0 | ND | ND | ND |
| 86 | C | ND | ND | ND |
| 87 | 0 | ND | ND | ND |
| 88 | A | ND | ND | ND |
| 89 | D | ND | ND | ND |
| 90 | D | ND | ND | ND |
| 91 | D | ND | ND | ND |
| 92 | A | A | A | 0 |
| 93 | D | D | D | D |
| 94 | C | D | B | B |
| 95 | D | D | C | C |
| 96 | D | ND | ND | ND |
| 97 | D | ND | ND | ND |
| 98 | C | ND | ND | ND |
| 99 | C | ND | ND | ND |
| 100 | D | ND | ND | ND |
| 101 | D | ND | ND | ND |
| 102 | D | ND | ND | ND |
| 103 | A | ND | ND | ND |
| 104 | D | ND | ND | ND |
| 105 | D | ND | ND | ND |
| 106 | B | ND | ND | ND |
| 107 | D | ND | ND | ND |
| 108 | D | ND | ND | ND |
| 109 | D | ND | ND | ND |
| 110 | C | ND | ND | ND |
| 111 | B | ND | ND | ND |
| 112 | 0 | ND | ND | ND |
| 113 | D | ND | ND | ND |
| 114 | D | ND | ND | ND |
| 115 | A | ND | ND | ND |
| 116 | C | ND | ND | ND |
| 117 | A | ND | ND | ND |
| 118 | D | ND | ND | ND |
| 119 | B | ND | ND | ND |
| 120 | B | ND | ND | ND |
| 121 | D | ND | ND | ND |
| 122 | D | ND | ND | ND |
| 123 | D | ND | ND | ND |
| 124 | D | ND | ND | ND |
| 125 | C | ND | ND | ND |
| 126 | B | ND | ND | ND |
| 127 | D | ND | ND | ND |
| 128 | D | ND | ND | ND |
| 129 | B | ND | ND | ND |
| 130 | 0 | ND | ND | ND |
| 131 | 0 | ND | ND | ND |
| 132 | A | ND | ND | ND |
| 133 | A | ND | ND | ND |
| 134 | A | ND | ND | ND |
| 135 | D | ND | ND | ND |
| 136 | D | ND | ND | ND |
| 137 | C | ND | ND | ND |
| 138 | C | ND | ND | ND |
| 139 | D | ND | ND | ND |
| 140 | D | ND | ND | ND |
| 141 | D | ND | ND | ND |

TABLE 6-continued

% Inhibition at 20 μM of Rac-1, Rho-A, Cdc42, and Rheb protein

| Compound | Rac-1: % inh. | Rho-A: % inh.. | Cdc42: % inh. | Rheb: % inh. |
|---|---|---|---|---|
| 142 | D | ND | ND | ND |
| 143 | D | ND | ND | ND |
| 144 | D | ND | ND | ND |
| 145 | D | ND | ND | ND |
| 146 | D | ND | ND | ND |
| 147 | 0 | ND | ND | ND |
| 148 | 0 | ND | ND | ND |
| 149 | D | ND | ND | ND |
| 150 | C | ND | ND | ND |
| 151 | C | ND | ND | ND |
| 152 | C | ND | ND | ND |
| 153 | C | ND | ND | ND |
| 154 | C | ND | ND | ND |
| 155 | A | ND | ND | ND |
| 156 | D | ND | ND | ND |
| 157 | D | ND | ND | ND |
| 158 | D | ND | ND | ND |
| 159 | 0 | ND | ND | ND |
| 160 | A | ND | ND | ND |
| 161 | A | ND | ND | ND |
| 162 | 0 | ND | ND | ND |
| 163 | 0 | ND | ND | ND |
| 164 | A | ND | ND | ND |
| 165 | C | ND | ND | ND |
| 166 | D | ND | ND | ND |
| 167 | A | ND | ND | ND |
| 168 | A | ND | ND | ND |
| 169 | D | ND | ND | ND |
| 170 | D | ND | ND | ND |
| 171 | A | ND | ND | ND |
| 172 | B | ND | ND | ND |
| 173 | C | ND | ND | ND |
| 174 | C | ND | ND | ND |
| 175 | B | ND | ND | ND |
| 176 | D | ND | ND | ND |
| 177 | D | ND | ND | ND |
| 178 | D | ND | ND | ND |
| 179 | D | ND | ND | ND |
| 180 | A | ND | ND | ND |
| 181 | A | ND | ND | ND |
| 182 | A | ND | ND | ND |
| 183 | A | ND | ND | ND |
| 184 | A | ND | ND | ND |
| 185 | 0 | ND | ND | ND |
| 186 | D | ND | ND | ND |
| 187 | D | ND | ND | ND |
| 188 | D | ND | ND | ND |
| 189 | A | ND | ND | ND |
| 190 | B | ND | ND | ND |
| 191 | A | ND | ND | ND |
| 192 | A | ND | ND | ND |
| 193 | A | ND | ND | ND |
| 194 | A | ND | ND | ND |
| 195 | A | ND | ND | ND |
| 196 | D | ND | ND | ND |
| 197 | A | ND | ND | ND |
| 198 | B | ND | ND | ND |
| 199 | B | ND | ND | ND |
| 200 | B | ND | ND | ND |
| 201 | B | ND | ND | ND |
| 202 | B | ND | ND | ND |
| 203 | A | ND | ND | ND |
| 204 | A | ND | ND | ND |
| 205 | A | ND | ND | ND |
| 206 | A | ND | ND | ND |
| 207 | A | ND | ND | ND |
| 208 | B | ND | ND | ND |
| 209 | B | ND | ND | ND |
| 210 | A | ND | ND | ND |
| 211 | C | ND | ND | ND |
| 212 | C | ND | ND | ND |
| 213 | C | ND | ND | ND |

TABLE 6-continued

| % Inhibition at 20 μM of Rac-1, Rho-A, Cdc42, and Rheb protein | | | | |
|---|---|---|---|---|
| Compound | Rac-1: % inh. | Rho-A: % inh.. | Cdc42: % inh. | Rheb: % inh. |
| 214 | C | ND | ND | ND |
| 215 | D | ND | ND | ND |
| 216 | D | ND | ND | ND |
| 217 | C | ND | ND | ND |
| 218 | A | ND | ND | ND |
| 219 | A | ND | ND | ND |
| 220 | B | ND | ND | ND |
| 221 | D | ND | ND | ND |
| 222 | D | ND | ND | ND |
| 223 | B | ND | ND | ND |
| 224 | D | ND | ND | ND |
| 225 | A | ND | ND | ND |
| 226 | D | ND | ND | ND |
| 227 | D | ND | ND | ND |
| 228 | D | ND | ND | ND |
| 229 | D | ND | ND | ND |
| 230 | D | ND | ND | ND |
| 231 | D | ND | ND | ND |
| 232 | D | ND | ND | ND |
| 233 | D | ND | ND | ND |
| 234 | D | ND | ND | ND |
| 235 | C | ND | ND | ND |
| 236 | C | ND | ND | ND |
| 237 | D | ND | ND | ND |
| 238 | D | ND | ND | ND |
| 239 | D | ND | ND | ND |
| 240 | D | ND | ND | ND |
| 241 | D | ND | ND | ND |
| 242 | A | ND | ND | ND |
| 243 | D | ND | ND | ND |
| 244 | D | ND | ND | ND |
| 245 | C | ND | ND | ND |
| 246 | D | ND | ND | ND |
| 247 | D | ND | ND | ND |
| 248 | D | ND | ND | ND |
| 249 | D | ND | ND | ND |
| 250 | D | ND | ND | ND |
| 251 | B | ND | ND | ND |
| 252 | D | ND | ND | ND |
| 253 | D | ND | ND | ND |
| 254 | D | ND | ND | ND |
| 255 | D | ND | ND | ND |
| 256 | D | ND | ND | ND |
| 257 | C | ND | ND | ND |
| 258 | 0 | ND | ND | ND |
| 259 | D | ND | ND | ND |
| 260 | C | ND | ND | ND |
| 261 | D | ND | ND | ND |
| 262 | C | ND | ND | ND |
| 263 | D | ND | ND | ND |
| 264 | D | ND | ND | ND |
| 265 | D | ND | ND | ND |
| 266 | D | ND | ND | ND |
| 267 | D | ND | ND | ND |
| 268 | D | ND | ND | ND |
| 269 | B | ND | ND | ND |
| 270 | B | ND | ND | ND |
| 271 | B | ND | ND | ND |
| 272 | A | ND | ND | ND |
| 273 | A | ND | ND | ND |
| 274 | 0 | ND | ND | ND |
| 275 | A | ND | ND | ND |
| 276 | D | ND | ND | ND |

0 = 0% inhibition,
A = 1-25% inhibition,
B = 26-49% inhibition,
C = 50-75% inhibition,
D = 76-100% inhibition,
ND = not determined.

Biological Example 4: Puma Expression and Caspases Activation Assay

Protocols for Cell-Based Puma Expression and Caspase Activation Assays

Cell lines: All human tumor-derived cancer cell lines were purchased from American Type Culture Collection. Human tumor-derived cancer cell lines Panc-1 (expressing KRas G12D mutant), MiaPaca-2 (expressing KRas G12C mutant), A549 (expressing KRas G12S mutant), and A375 (expressing wild type KRas) were grown in complete DMEM-High Glucose medium and NCI-H1975 (expressing wild type KRas), MM.1R (expressing wild type KRas) and IM.9 (expressing wild type KRas) were grown in RPMI1640 medium. Human tumor-derived cancer cell line BT-549 (expressing wild type KRas) was grown in RPMI1640 medium with 11.8U insulin. All mediums were supplemented with penicillin (100 U/mL), streptomycin (100 μg/mL), and 10% heat-inactivated FBS at 37° C. in a humidified incubator with 5% CO2.

Method: Cells were plated at 300,000 to 800,000 cells/well density in a 6-well plate in the presence of 10% FBS. The next day small molecules to be tested were added to the cells in the final concentration of 3 μM in the presence of 0.3% DMSO for 48 hours incubation at 37° C. For IC50 value determination, serial dilutions of compounds were added to cells under the same conditions. Following 48 hours of incubation cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Increase expression of PUMA and active/cleaved forms of caspase 3, caspase 6 and caspase 9 were detected by western blot.

Western blot protocol: Equal amounts of protein (15-50 μg) were separated by SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 10% milk and expression levels of PUMA was assessed by incubating overnight at 4° C. with the antibody PUMA (D30C10) from Cell Signaling Technology (#12450) and active/cleaved forms of caspase 3, caspase 6 and caspase 9 by incubating overnight at 4° C. with the following antibodies: cleaved caspase-3 (Asp175) (5A1E), cleaved caspase-6 (Asp162) and cleaved caspase-9 (Asp330) (D2D4) (all antibodies from Cell Signaling Technology). Then the membranes were incubated with HRP-conjugated secondary antibody (Jackson Immunoresearch, West Grove, PA). Bands were incubated in Amersham ECL Prime Western Blotting Detection Reagent (GE Healthcare) and visualized using the ChemiDoc MP imaging system (Bio-Rad).

Table 7 shows apoptosis-related caspase activation and increased Puma expression after 48 hours for selected compounds tested in the cell-based puma expression and caspase activation assays described above.

TABLE 7

| Apoptosis-related caspase activation and increased Puma expression after 48 hours | | | | | |
|---|---|---|---|---|---|
| Compound | Cell Line | Caspase 3 | Caspase 6 | Caspase 9 | Increased PUMA expression |
| 6 | Panc-1 | yes | yes | ND | ND |
| 6 | MiaPaca2 | yes | yes | yes | yes |
| 6 | A549 | yes | yes | yes | yes |
| 6 | A375 | yes | yes | yes | ND |
| 6 | BT-549 | yes | yes | yes | yes |

TABLE 7-continued

| Apoptosis-related caspase activation and increased Puma expression after 48 hours | | | | | |
|---|---|---|---|---|---|
| Compound | Cell Line | Caspase 3 | Caspase 6 | Caspase 9 | Increased PUMA expression |
| 58 | MiaPaca2 | yes | yes | yes | yes |
| 58 | A549 | yes | yes | yes | yes |
| 58 | BT-549 | yes | yes | yes | yes |
| 84 | MiaPaca2 | yes | yes | yes | yes |
| 91 | MiaPaca2 | yes | yes | yes | yes |
| 91 | BT-549 | yes | yes | yes | yes |
| 91 | A549 | yes | yes | yes | yes |
| 102 | MiaPaca2 | yes | yes | yes | yes |
| 102 | A375 | yes | yes | yes | ND |
| 102 | NCI-H1975 | yes | yes | yes | ND |
| 102 | A549 | yes | yes | yes | yes |
| 102 | IM.9 | yes | yes | yes | ND |
| 102 | MM.1R | yes | yes | yes | ND |
| 124 | MiaPaca2 | yes | yes | yes | yes |
| 124 | A375 | yes | yes | yes | ND |
| 124 | BT-549 | yes | yes | yes | ND |
| 124 | HCC1806 | yes | yes | yes | yes |
| 124 | NCI-H358 | yes | yes | yes | yes |

Biological Example 5: Cell-Based Phosphorylation and Ras-GTP Pulldown Assays for Compound 34 in MiaPaca-2 Cell Line Cell lines: Human tumor-derived pancreatic cell line MiaPaca-2 (expressing KRas G12C mutant) was purchased from American Type Culture Collection and was grown in complete DMEM-High Glucose medium.

Method: Cells were plated at $2\times10^6$ cells/well density in a 6-well plate, allowed 3 hours to adhere to the plate, then starved in the appropriate medium in the presence of 0.5% FBS overnight. Serial dilutions of the small molecules to be tested were added to the cells in the presence of 0.3% DMSO for 6 hours incubation at 37° C. Next, cells were stimulated with 1.5 ng/ml EGF for 15 minutes, rinsed with ice-cold PBS and then lysed with 500 µl of lysis/binding/wash buffer (25 mM Tris-HCl, pH 7.2, 150 mM NaCl, 5 mM MgCl2, 5% glycerol, 1% NP40) from Active Ras Detection kit (Cell Signaling Technology) supplemented with Halt™ Protease & Phosphatase Inhibitor Cocktail (Thermo Scientific). To account for significant differences in cell number due to the treatment, a small sample of lysate was saved for protein quantification and the rest of the lysate was snap frozen. Protein concentration was assessed by BCA protein assay (Thermo Scientific). To ensure that equal amount of protein undergoes RBD pulldown, lysates were subsequently thawed (at 23° C.) and adjusted to 1 mg/ml with lysis/binding/wash buffer (0.5 ml volume). Equal amounts of lysate were then added to 0.5 mL lysis buffer containing RAF-RBD (1 mL total volume). Lysates were vortexed, incubated for 10 min on ice and subsequently pre-cleared at 14,000 rpm for 5 min at 4° C. 90% of the pre-cleared lysates were subsequently added to pre-washed glutathione agarose beads from Active Ras Detection kit (Cell signaling Technology, #8821) for 1 hour at 4° C. under constant rocking. The beads were subsequently pelleted, washed 3 times with lysis/binding/wash buffer, and eluted for western blotting with 50 µl of 1×SDS-PAGE sample buffer. Level of GTP-bound RAS was determined by western blot.

Western blot protocol: The eluted samples were separated by SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 10% milk and Ras bound levels were assessed by incubating overnight at 4° C. with the Ras antibody provided in kit (Cell signaling Technology, #8821). Then the membranes were incubated with HRP-conjugated secondary antibody (Jackson Immunoresearch, West Grove, PA). Bands were incubated in Amersham ECL Prime Western Blotting Detection Reagent (GE Healthcare) and visualized using the ChemiDoc MP imaging system (Bio-Rad).

Biological Example 6: Cell-free MEK1 Kinase Assays

The MEK1 Kinase Enzyme System (catalog number VA7216) was purchased from Promega (Madison, Wisconsin) and executed according to the manufacturer instructions. All components were diluted in kinase reaction buffer and then 10 µL of MEK (final concentration 100 ng/25 µL); 5 µL ATP (final concentration 100 µM)/CHK substrate (final concentration 1 µg/25 µL); and 10 µL of inhibitor solution, (final concentration 10 µM), staurosporine (final concentration 1 µM, Cell Signaling, Danvers, MA), or kinase reaction buffer (blank) was added to each well of a white, 96-well plate and incubated for 1 hour at room temperature. Next, 25 µL of ADP-GLO Kinase Reagent (catalog number V9101, Promega, Madison, Wisconsin) was added to each well, and incubated at room temperature for 40 minutes. Then 50 µL of Kinase Detection Reagent was added to each well, plate was covered with aluminum foil, and incubated at room temperature for 30 minutes. Luminescence, integration time 1 second, was measured using a SpectraMax M3 (Molecular Devices, San Jose, California).

Biological Example 7: Cell-Free B-Raf (V600E Mutant) Kinase Assays

The B-Raf (V600E mutant) Kinase Assay Kit (catalog number 48688) was purchased from BPS BioScience, San Diego, CA. Assay was executed according to the manufacturer instructions. A master mixture consisting of Kinase Buffer+10 mM DTT, 20 µM ATP, Raf substrate, and water was prepared. Then, 25 µL of the master mixture was added to each well. Next, 5 µL of inhibitor solution (final concentration 10 µM), staurosporine (final concentration 1 µM, Cell Signaling, Danvers, MA), or Kinase Buffer (blank) was added to each well of a white, 96-well plate. B-Raf (V600E) or B-Raf (WT) enzyme was thawed on ice and diluted to 2 ng/ml (V600E) or 2.5 ng/ml (WT) with Kinase Buffer then 20 µL was added to all wells, except the blank control well, to initiate the reaction and incubated for 45 minutes at 30° C. To measure the amount of ADP produced during the kinase reaction, Luminescence (integration time 1 second) was measured using a SpectraMax M3 (Molecular Devices, San Jose, California).

Biological Example 8: In Vivo Efficacy of Compound 6 in NCI-H358 (G12C) Model

Cell lines: Human tumor-derived non-small cell lung cancer cell lines NCI-H358 (expressing KRas G12C mutant was grown in RPMI-1640 Medium, ATCC 30-2001, supplemented with 10% fetal bovine serum (FBS) and Penicillin/Streptomycin 100U/ml (Lonza BioWhittaker, Morrisville, NC). Cells were trypsinized, washed in sterile PBS, counted, and resuspended in a 1:1 mix PBS/HC Matrigel (Corning, Glendale, AZ) at a concentration of $25\times10^6$/ml. Cells were kept on ice until injection.

The right flank of Athymic Nude-Foxn1 nu mice (The Jackson Laboratory, Harbor, ME) was injected subcutaneously with $5\times10^6$ cells in 200 μl of sterile PBS/Matrigel solution. Tumor mass was first measured 4 days after injection and mice were randomized on the basis of these measurements. Treatment was begun when tumors reached 150-200 $mm^3$, ~5-8 days after injection. Compound 6 was formulated in 20% captisol (50 mM citrate buffer, PH 5.0), and mice received either daily dose of vehicle or 50 mg/kg body weight of the formulated compound 6. Tumors were measured using digital calipers and volume (v) was calculated using the formula V=(W(2)×L)/2 where V is tumor volume, W is tumor width, and L is tumor length. Mice were housed in accordance with IACUC guidelines. The calculated Tumor Growth Inhibition (TGI) was 80%. No weight loss was detected.

Biological Example 9: Kinetic Solubility

Kinetic solubility assay in pH 7.4 Buffer+2% DMSO ("Kinetic Solubility Assay) was performed according to the following protocol: Briefly, using a 20 mM stock solution of the tested compounds in 100% DMSO, dilutions were prepared to a theoretical concentration of 400 μM in duplicates in phosphate-buffered saline pH 7.4 (138 mM NaCl, 2.7 mM KCl, 10 mM K-phosphate) with 2% final DMSO. The tested compounds dilutions in PBS were further allowed to equilibrate at 25° C. on a thermostatic shaker for two hours and then filtered through HTS filter plates using a vacuum manifold. The filtrates of the test compounds were diluted 2-fold with acetonitrile with 2% DMSO before measuring.

In parallel, using a 20 mM stock solution of the tested compounds in 100% DMSO, dilutions were prepared to theoretical concentrations of 0 μM (blank), 10 μM, 25 μM, 50 μM, 100 μM, and 200 μM in 50% acetonitrile/PBS with 2% final DMSO to generate calibration curves. Ondansetron was used as a reference compound to control proper assay performance. 200 μL of each sample was transferred to a 96-well plate and measured in the 230-550 nm range with a 5 nm step.

The concentrations of compounds in PBS filtrate are calculated using a dedicated Microsoft Excel calculation script. Proper absorbance wavelengths for calculations are selected for each compound manually based on absorbance maximums (absolute absorbance unit values for the minimum and maximum concentration points within the 0-3 OD range). Each final dataset is visually evaluated by the operator, and goodness of fit (R2) is calculated for each calibration curve. The effective range of this assay is approximately 2-400 μM and the compounds returning values close to the upper limit of the range may have higher actual solubility (e.g., 5'-deoxy-5-fluorouridine).

Table 8 show kinetic solubility data for selected compounds tested in the Kinetic Solubility assay described above.

TABLE 8

| Kinetic Solubility in pH 7.4 Buffer + 2% DMSO | |
|---|---|
| Example Number | Solubility (μM) |
| 6 | A |
| 50 | A |
| 53 | B |
| 54 | A |
| 55 | B |
| 57 | B |
| 58 | B |
| 59 | A |
| 62 | A |
| 63 | A |
| 84 | B |
| 91 | C |
| 100 | B |
| 102 | C |
| 104 | A |
| 116 | B |
| 118 | C |
| 124 | B |
| 137 | B |
| 141 | B |
| 142 | B |
| 143 | A |
| 144 | A |
| 145 | B |
| 157 | A |
| 158 | B |
| 221 | B |
| 222 | B |
| 224 | A |
| 226 | A |
| 227 | A |
| 235 | A |
| 238 | A |
| 248 | A |
| 250 | A |
| 252 | A |
| 255 | C |
| 260 | A |
| 265 | A |
| 267 | B |
| 268 | A |

A denotes <10 μM,
B denotes 10-30 μM,
C denotes >30 μM.

Biological Example 10: Assessment of Metabolic Stability in Mouse Liver Microsomes Metabolic Stability Assay: Microsomal incubations were carried out in 96-well plates in 5 aliquots of 30 μL each (one for each time point). Liver microsomal incubation medium comprised of phosphate buffer (100 mM, pH 7.4), MgCl2 (3.3 mM), NADPH (3 mM), glucose-6-phosphate (5.3 mM), glucose-6-phosphate dehydrogenase (0.67 units/ml) with 0.42 mg of liver microsomal protein per mL. In the control reactions the NADPH-cofactor system was substituted with phosphate buffer. Test compounds (2 μM, final solvent concentration 1.6%) were incubated with microsomes at 37° C., shaking at 100 rpm. Each reaction was performed in duplicates. Five time points over 40 minutes were analyzed. The reactions were stopped by adding 5 volumes of methanol containing internal standard to incubation aliquots, followed by protein sedimentation by centrifuging at 5500 rpm for 4 minutes. Supernatants were analyzed using the HPLC system coupled with tandem mass spectrometer.

The elimination constant ($k_{el}$), half-life ($t_{1/2}$) and intrinsic clearance ($Cl_{int}$) were determined in plot of ln(AUC) versus time, using linear regression analysis:

$$k_{el} = -\text{slope} \quad t_{1/2} = \frac{0.693}{k} Cl_{int} = \frac{0.693}{t_{1/2}} \times \frac{\mu l_{incubation}}{mg_{microsomes}}.$$

In order to indicate the quality of the linear regression analysis, the R (correlation coefficient) values are provided. In some cases, the last time point is excluded from the calculations to ensure acceptable logarithmic linearity of decay.

Table 9 show metabolic stability data for selected compounds tested in the Mouse Liver Microsome Metabolic Stability assay described above.

TABLE 9

| Mouse Liver Microsome Metabolic Stability Assay | |
|---|---|
| Example Number | t½ (min) |
| 6 | B |
| 102 | B |
| 104 | B |
| 124 | B |
| 126 | B |
| 127 | A |
| 128 | B |
| 129 | B |
| 137 | B |
| 141 | B |
| 142 | B |
| 143 | A |
| 144 | B |
| 145 | B |
| 156 | B |
| 157 | B |
| 158 | A |
| 222 | A |
| 224 | B |
| 226 | B |
| 227 | B |
| 235 | B |
| 238 | B |
| 248 | B |
| 250 | A |
| 252 | A |
| 255 | B |
| 260 | A |
| 265 | B |
| 267 | B |
| 268 | A |

A denotes <10 min,
B denotes >10 min.

EXEMPLARY EMBODIMENTS

A1. A compound of Formula I:

Formula I

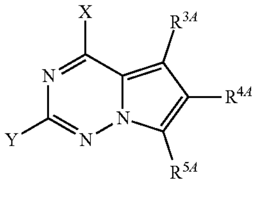

or a pharmaceutically acceptable form thereof, wherein:

X is —$NR^{1A}R^{2A}$ or $OR^{2A}$;

Y is an imidazolyl, a pyridinyl, or an 8-10-membered fused-heteroaryl; wherein the imidazolyl is optionally substituted with 1 $R^{6A}$ substituent and optionally substituted with 1-2 $R^{7A}$ substituents; and the pyridinyl or the 8-10-membered fused-heteroaryl is optionally substituted with 1-4 $R^{7A}$ substituents;

$R^{1A}$ is hydrogen or $C_{1-6}$ alkyl, wherein the $C_{1-6}$ alkyl is optionally substituted with 1-4 $R^{8A}$ substituents;

$R^{2A}$ is hydrogen, $C_{1-6}$ alkyl, $C_{3-7}$ cycloalkyl, $C_{1-6}$ heteroalkyl, $C_{3-7}$ heterocycloalkyl, $C_{5-10}$ membered aryl, —$S(O)_2R^{15A}$, —$P(O)R^{16A}R^{17A}$, or 5-10 membered heteroaryl, wherein the $C_{1-6}$ alkyl, $C_{3-7}$ cycloalkyl, $C_{1-6}$ heteroalkyl, and 5-10 membered heteroaryl are each independently optionally substituted with 1-4 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached, optionally wherein the 3-6 membered heterocycloalkyl formed by $R^{1A}$ and $R^{2A}$ is fused to a 5-6 membered heteroaryl;

$R^{3A}$ is $C_{1-6}$ alkyl, $C_{3-7}$ cycloalkyl, $C_{1-6}$ heteroalkyl, aryl, 5-10 membered heteroaryl, —$(CO)R^{11A}$, or —$C(O)NR^{12A}R^{13A}$ wherein the $C_{1-6}$ alkyl, $C_{3-7}$ cycloalkyl, $C_{1-6}$ heteroalkyl, aryl, and 5-10 membered heteroaryl are each independently optionally substituted with 1-3 $R^{9A}$ substituents;

$R^{4A}$ is hydrogen, aryl, or 5-10 membered heteroaryl, wherein the aryl and 5-10 membered heteroaryl are each independently optionally substituted with 1-4 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, $C_{1-6}$ heteroalkyl, halo, —$NR^{12A}R^{13A}$, $C_{1-6}$ alkoxy, $C_{1-6}$ haloalkoxy, —$C(O)NR^{12A}R^{13A}$, —$(CO)R^{11A}$, —$C(O)OR^{14A}$, or CN, wherein the $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, and $C_{1-6}$ heteroalkyl are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —$(CO)R^{11A}$, —$C(O)OR^{14A}$, —$C(O)NR^{12A}R^{13A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl, wherein the $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, $C_{1-6}$ alkoxy, $C_{3-6}$ cycloalkoxy, $C_{1-6}$ haloalkoxy, or 5-6 membered heteroaryl are each independently optionally substituted with 1-3 $R^{8A}$ substituents;

$R^{11A}$ is —OH, $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-7}$ cycloalkyl, $C_{1-6}$ haloalkyl, $C_{1-6}$ hydroxyalkyl, $C_{1-6}$ heteroalkyl, —OH, $C_{1-6}$ alkoxy, $C_{1-6}$ haloalkoxy, $C_{3-7}$ heterocycloalkyl, aryl, or 5-10 membered heteroaryl, wherein the $C_{1-6}$ alkyl, $C_{3-7}$ cycloalkyl, $C_{1-6}$ haloalkyl, $C_{1-6}$ hydroxyalkyl, $C_{1-6}$ heteroalkyl, $C_{1-6}$ alkoxy, $C_{1-6}$ haloalkoxy, $C_{3-7}$ heterocycloalkyl, aryl, and 5-10 membered heteroaryl are optionally substituted with 1-3 $R^{8A}$ substituents, or $R^{12A}$ and $R^{13A}$ are combined to form a 3-7 membered heterocycloalkyl including the nitrogen atom to which they are both attached;

$R^{14A}$ is hydrogen, $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{15A}$ is $C_{1-6}$ alkyl, $C_{3-6}$ cycloalkyl, $C_{1-6}$ alkoxy, or $C_{1-6}$ heteroalkyl, wherein the $C_{1-6}$ alkyl, $C_{3-6}$ cycloalkyl, $C_{1-6}$ alkoxy, and $C_{1-6}$ heteroalkyl, are each independently optionally substituted with 1-3 $R^{8A}$ substituents;

$R^{16A}$ and $R^{17A}$ are each independently selected from the group consisting $C_{1-6}$ alkyl, $C_{1-6}$ alkoxy, or $C_{1-6}$ heteroalkyl, wherein the $C_{1-6}$ alkyl, $C_{1-6}$ alkoxy, and $C_{1-6}$ heteroalkyl, are each independently optionally substituted with 1-3 $R^{8A}$ substituents, or $R^{16A}$ and $R^{17A}$ are combined to form a 3-7 membered heterocycloalkyl including the phorphorus atom to which they are both attached; and wherein, when X is OH or

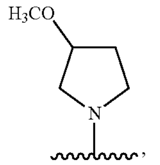

Y is N-methyl imidazoyl, and $R^{5A}$ is H, at least one of $R^{3A}$ and $R^{4A}$ is not unsubstituted phenyl.

A2. The compound of embodiment A1, wherein Y is an imidazolyl optionally substituted with 1 $R^{6A}$ substituent and optionally substituted with 1-2 $R^{7A}$ substituents.

A3. The compound of embodiment A1 or c embodiment A2, wherein Y is a C-linked imidazolyl that is substituted with 1 $R^{6A}$ substituent at a nitrogen of the imidazolyl ring and optionally substituted with 1-2 $R^{7A}$ substituents at carbons of the imidazolyl ring.

A4. The compound of any one of embodiments A1 to A3, wherein the compound is a compound of Formula Ia:

Formula Ia

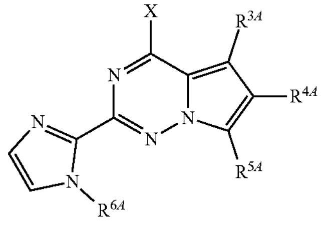

or a pharmaceutically acceptable form thereof.

A5. The of any one of embodiments A1 to A3, wherein the compound is a compound of Formula Ib:

Formula Ib

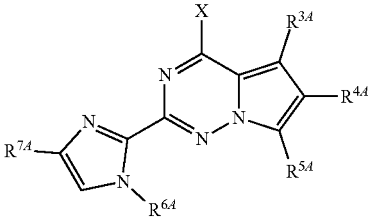

or a pharmaceutically acceptable form thereof.

A6. The compound of embodiment A1, wherein Y is a pyridinyl optionally substituted with 1-4 $R^{7A}$ substituents.

A7. The compound of embodiment A1 or embodiment A6, wherein the compound is a compound of Formula Ib:

Formula Ic

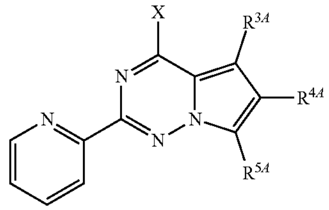

or a pharmaceutically acceptable form thereof.

A8. The compound of embodiment A1, wherein Y is a 8-10-membered fused-heteroaryl which is optionally substituted with 1-4 $R^{7A}$ substituents.

A9. The compound of any one of embodiments A1 to A8, wherein X is —$OR^{2A}$.

A10. The compound of any one of embodiments A1 to A8, wherein X is —$NR^{1A}R^{2A}$.

A11. A compound of Formula II:

Formula II

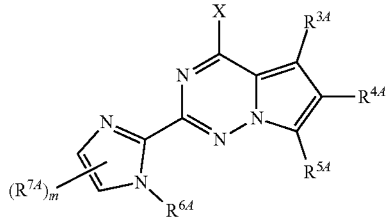

or a pharmaceutically acceptable form thereof, wherein:

X is —$NR^{1A}R^{2A}$ or —$OR^{2A}$;

$R^{1A}$ is hydrogen or $C_{1-6}$ alkyl;

$R^{2A}$ is hydrogen, $C_{1-6}$ alkyl, $C_{3-7}$ cycloalkyl, $C_{1-6}$ heteroalkyl, —$S(O)_2R^{15A}$, —$P(O)R^{16A}R^{17A}$, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached, optionally wherein the 3-6 membered heterocycloalkyl formed by $R^{1A}$ and $R^{2A}$ is fused to a 5-6 membered heteroaryl;

$R^{3A}$ is $C_{1-6}$ alkyl, $C_{3-6}$ cycloalkyl, $C_{1-6}$ heteroalkyl, phenyl, 5-10 membered heteroaryl, —(CO)$R^{11A}$, or —C(O)$NR^{12A}R^{13A}$, wherein the $C_{1-6}$ alkyl, $C_{3-6}$ cycloalkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —(CO)$R^{11A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl, wherein the $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, $C_{1-6}$ alkoxy, $C_{3-6}$ cycloalkoxy, $C_{1-6}$ haloalkoxy, or 5-6 membered heteroaryl are each independently optionally substituted with 1-3 $R^{8A}$ substituents;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-7}$ cycloalkyl, $C_{1-6}$ haloalkyl, $C_{1-6}$ hydroxyalkyl, $C_{1-6}$ heteroalkyl, —OH, $C_{1-6}$ alkoxy, or $C_{1-6}$ haloalkoxy, or $R^{12A}$ and $R^{13A}$ are combined to form a 3-6 membered heterocycloalkyl including the nitrogen atom to which they are both attached;

$R^{15A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{16A}$ and $R^{17A}$ are each independently selected from the group consisting $C_{1-6}$ alkyl, $C_{1-6}$ alkoxy, or $C_{1-6}$ heteroalkyl, wherein the $C_{1-6}$ alkyl, $C_{1-6}$ alkoxy, and $C_{1-6}$ heteroalkyl, are each independently optionally substituted with 1-3 $R^{8A}$ substituents, or $R^{16A}$ and $R^{17A}$ are combined to form a 3-7 membered heterocycloalkyl including the phorphorus atom to which they are both attached;

m is 0, 1 or 2; and wherein, when X is OH or

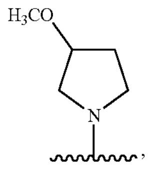

Y is N-methyl imidazoyl, and $R^{5A}$ is H, at least one of $R^{3A}$ and $R^{4A}$ is not unsubstituted phenyl.

A12. A compound of Formula IIa:

Formula IIa

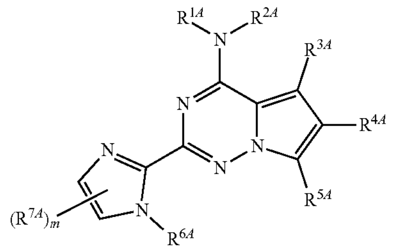

or a pharmaceutically acceptable form thereof, wherein:

$R^{1A}$ is hydrogen;

$R^{2A}$ is hydrogen, $C_{1-6}$ alkyl, $C_{3-6}$ cycloalkyl, $C_{1-6}$ heteroalkyl, —$S(O)_2R^{15A}$, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{3A}$ is $C_{1-3}$ alkyl, $C_{3-6}$ cycloalkyl, $C_{1-6}$ heteroalkyl, phenyl, 5-, 6- or 9-membered heteroaryl, —(CO)$R^{11A}$, or —C(O)$NR^{12A}R^{13A}$, wherein the $C_{1-3}$ alkyl, $C_{3-6}$ cycloalkyl, $C_{1-6}$ heteroalkyl, phenyl, and 5-, 6-, or 9-membered heteroaryl are each independently optionally substituted with 1-3 $R^{9A}$ substituents;

$R^{4A}$ is hydrogen, phenyl, or 5, 6, or 9 membered heteroaryl, wherein the phenyl and 5, 6, or 9 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is $C_{1-3}$ alkyl or $C_{1-3}$ heteroalkyl, wherein the $C_{1-3}$ alkyl or $C_{1-3}$ heteroalkyl is optionally substituted with biotinamide;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —(CO)$R^{11A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{11A}R^{12A}$, or 5-6 membered heteroaryl, wherein the $C_{1-6}$ alkyl or $C_{1-6}$ heteroalkyl is optionally substituted with biotinamide;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy, or $R^{12A}$ and $R^{13A}$ are combined to form a 5 or 6 membered heterocycloalkyl including the nitrogen atom to which they are both attached;

$R^{15A}$ is $C_{1-3}$ alkyl, $C_{3-6}$ cycloalkyl, or $C_{1-4}$ heteroalkyl;

$R^{16A}$ and $R^{17A}$ are each independently selected from the group consisting $C_{1-3}$ alkyl or $C_{1-3}$ alkoxy, or $R^{16A}$ and $R^{17A}$ are combined to form a 5 membered heterocycloalkyl including the phorphorus atom to which they are both attached; and m is 0 or 1.

A13. The compound of embodiment A12, wherein:

$R^{1A}$ and $R^{2A}$ together with the nitrogen to which they are attached, have a structure of: —$NH_2$,

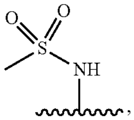,
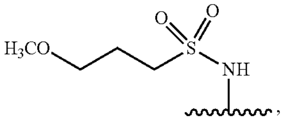,
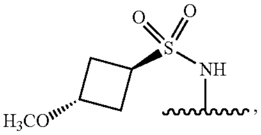,
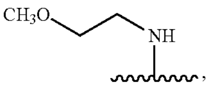,
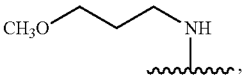,
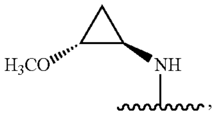,
(cis)
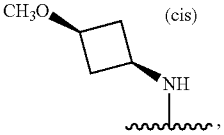,
(trans)
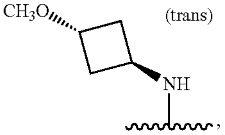,
(+/- trans)
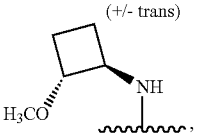,
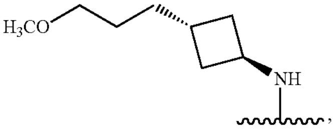,
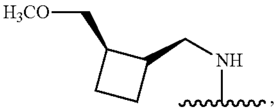,
(+/- cis)
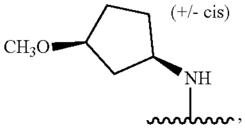,
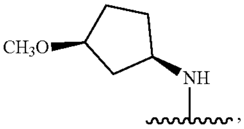,
(+/- trans)
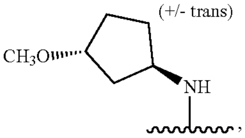,
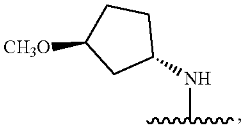,
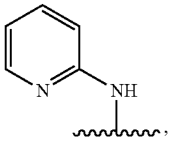, -continued

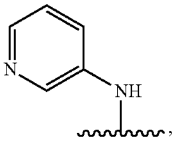,
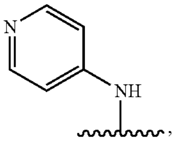,
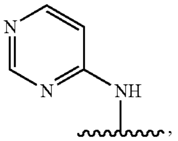,
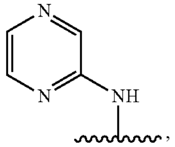,
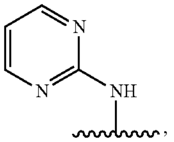,
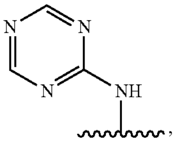,
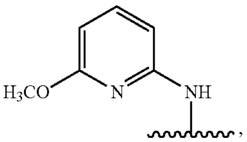,
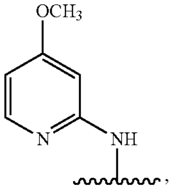,
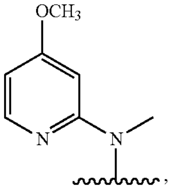,
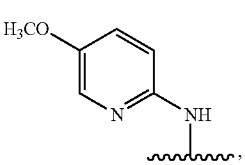,
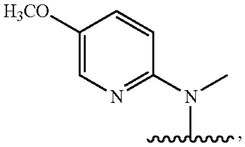,
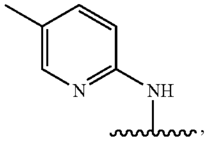,
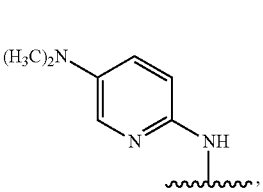,
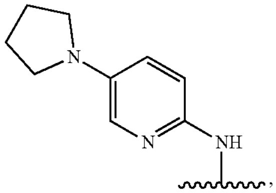,
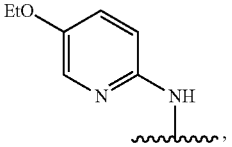,
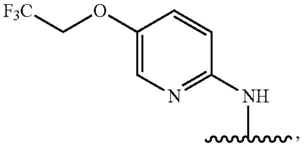,
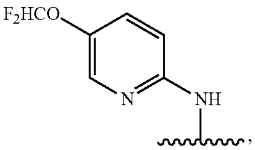,
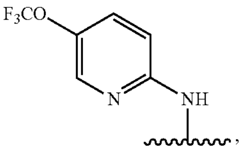,
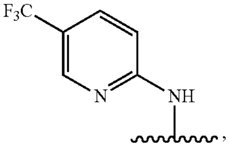,
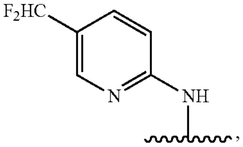,
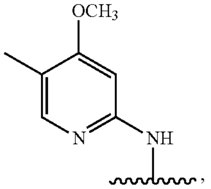,
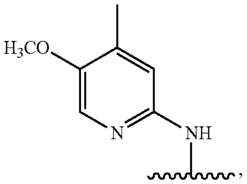, -continued
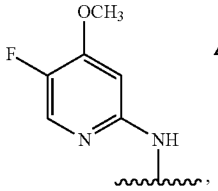 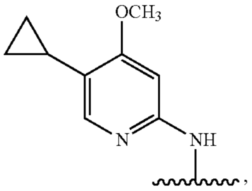
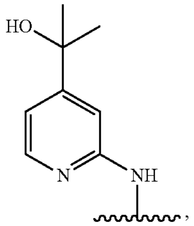 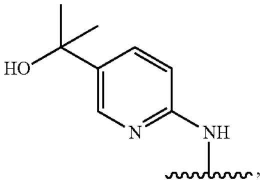
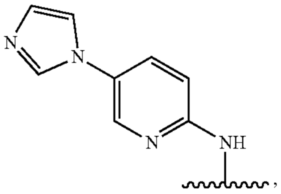 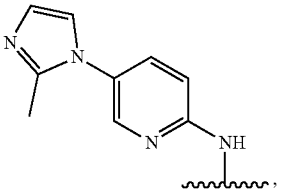
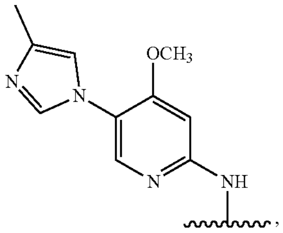 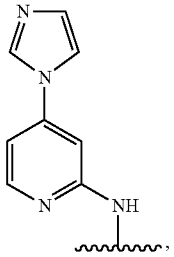
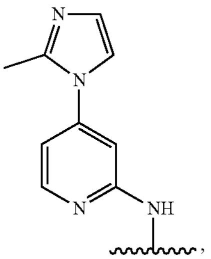 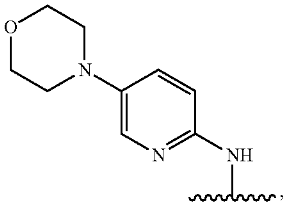
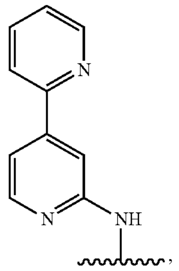 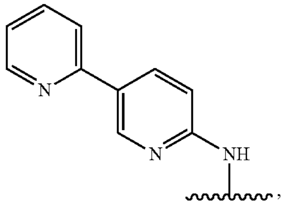
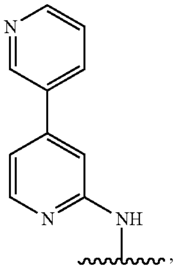 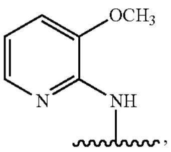 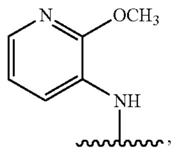
-continued
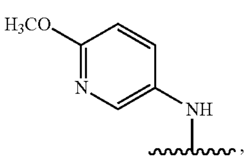 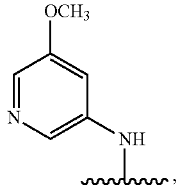
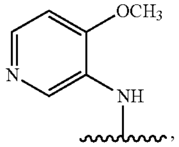 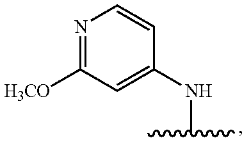
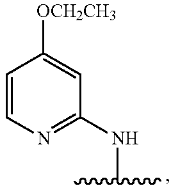 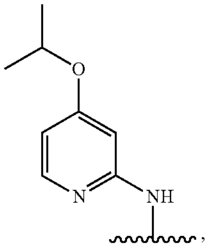
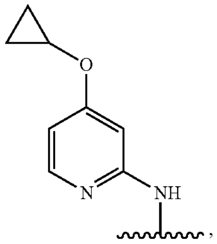 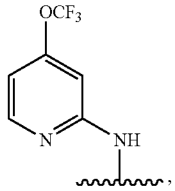 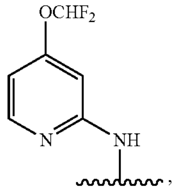
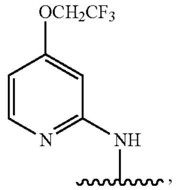 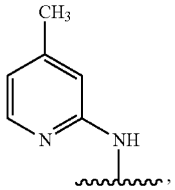 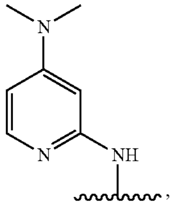
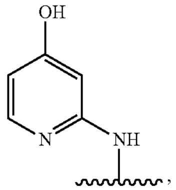 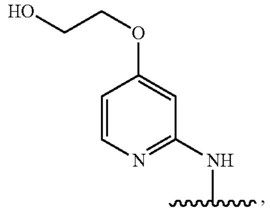
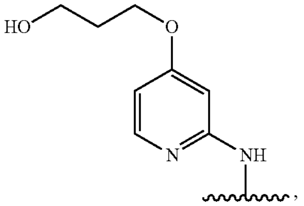
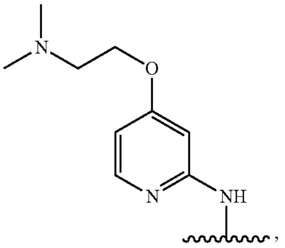

-continued
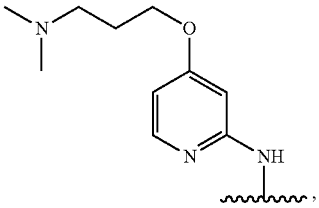,
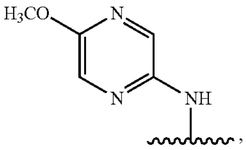,
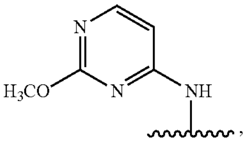,
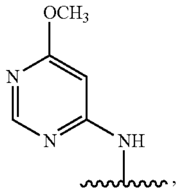,
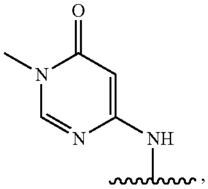,
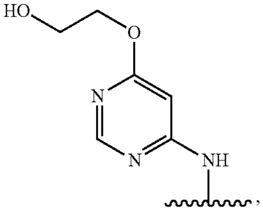,
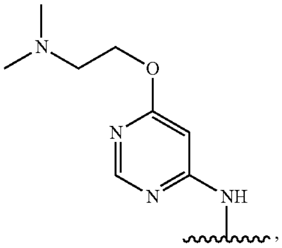,
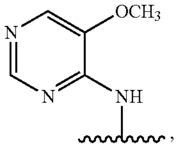,
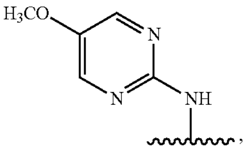,
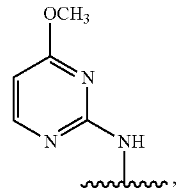,
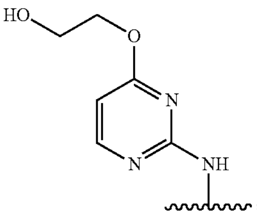,
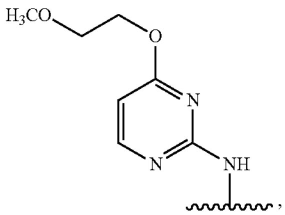,
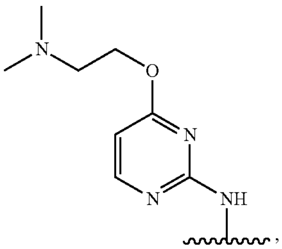,
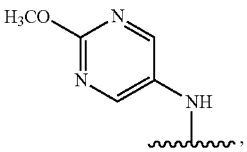,
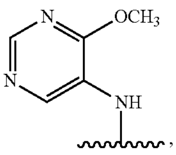,
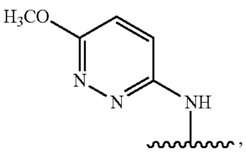,
-continued
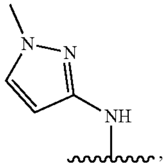,
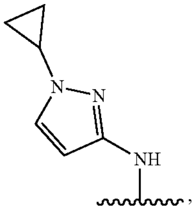,
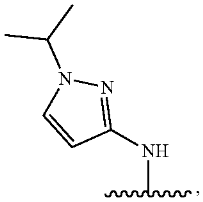,
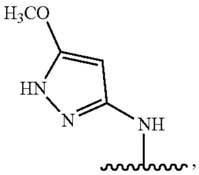,
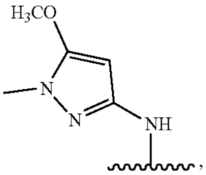,
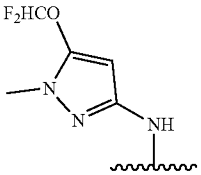,
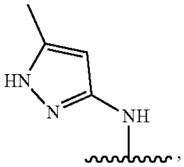,
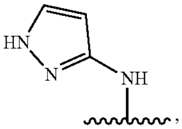,
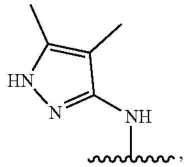,
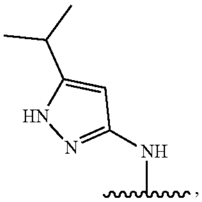,
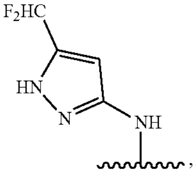,
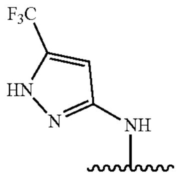,
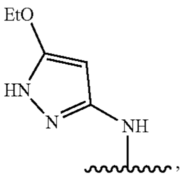,
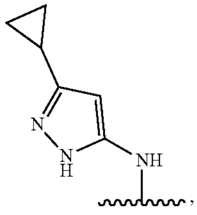,
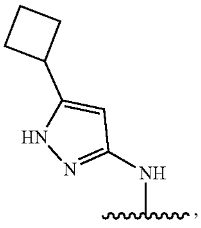,
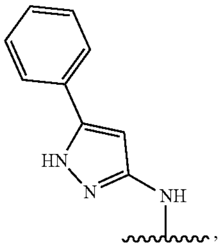,
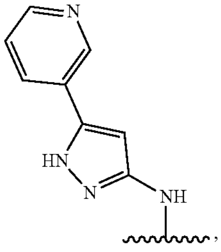, -continued
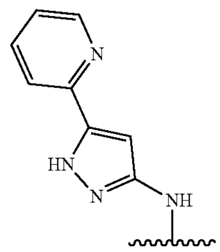,
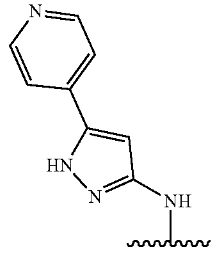,
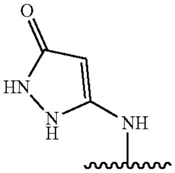,
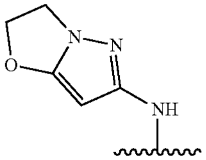,
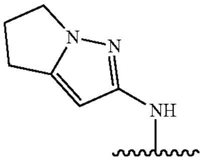,
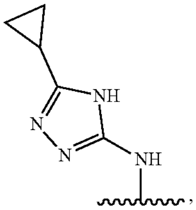,
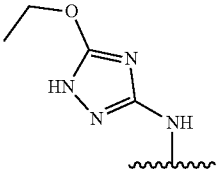,
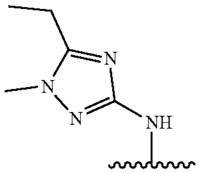,
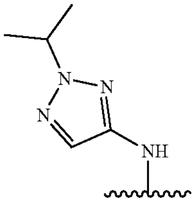,
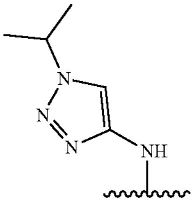,
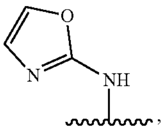,
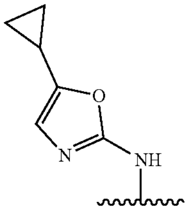,
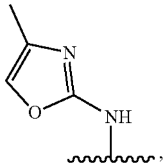,
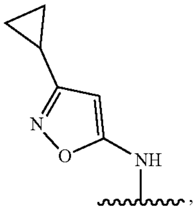,
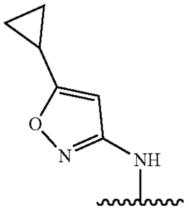,
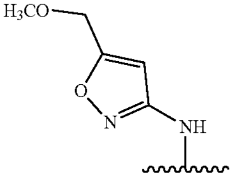,
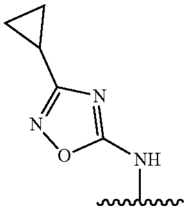,
-continued
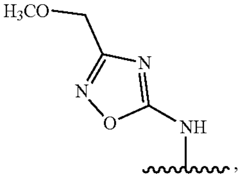,
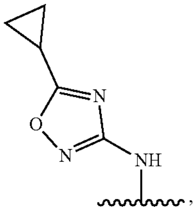,
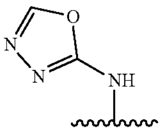,
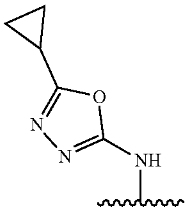,
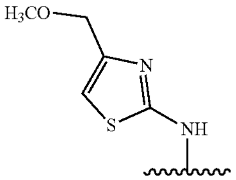,
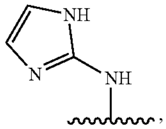,
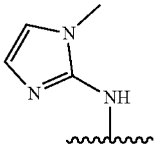,
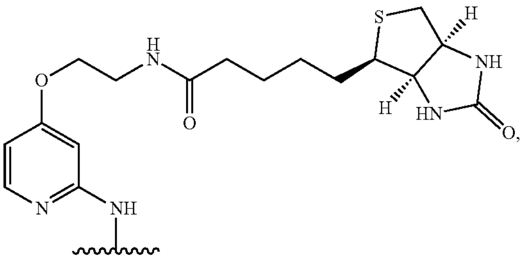,
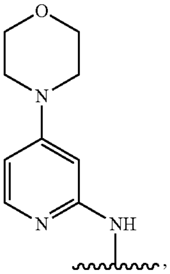,
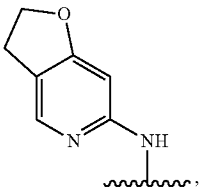,
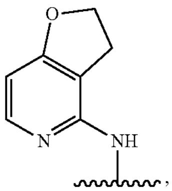, or
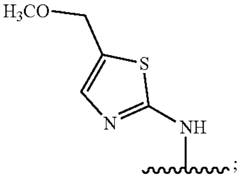;
$R^{3A}$ is —$CH_3$, unsubstituted phenyl, isopropyl, cyclopropyl,

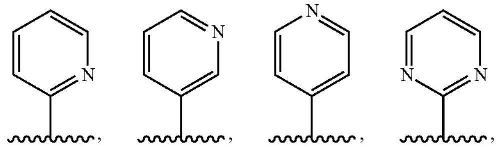
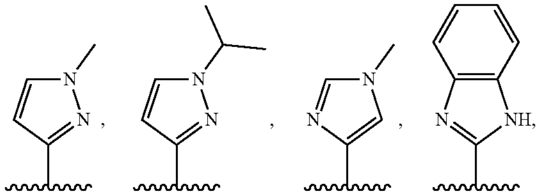
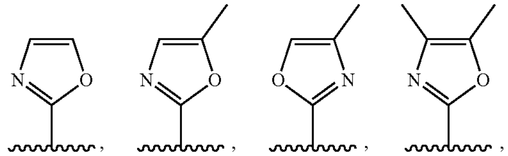
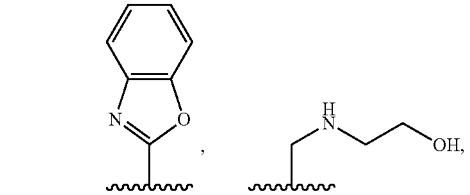
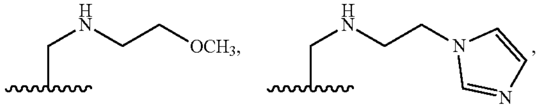
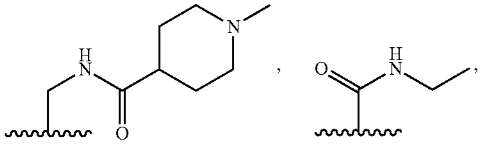
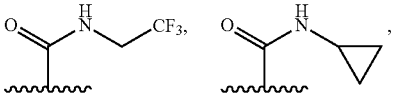
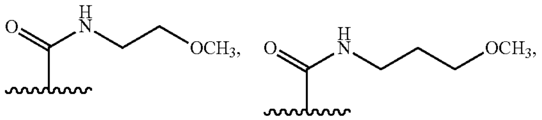
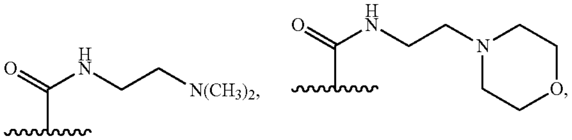
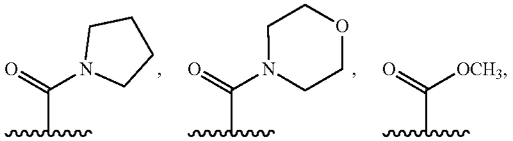
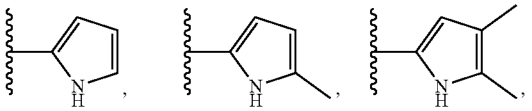
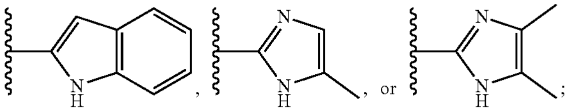
or ;
$R^{4A}$ hydrogen, unsubstituted phenyl,
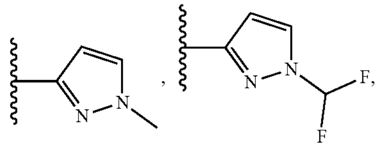
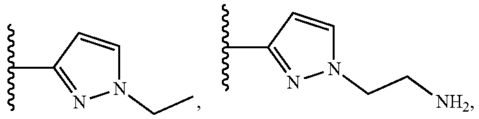
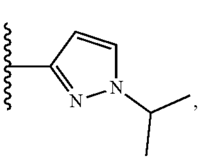
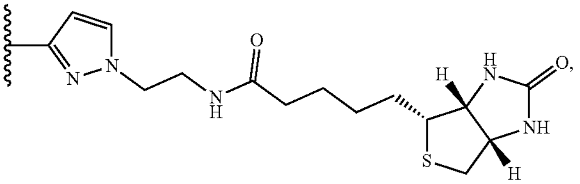
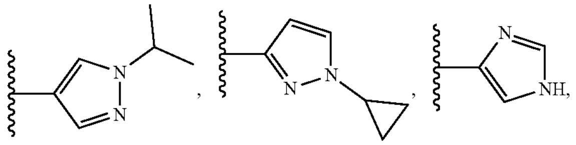
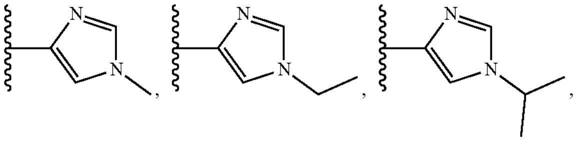
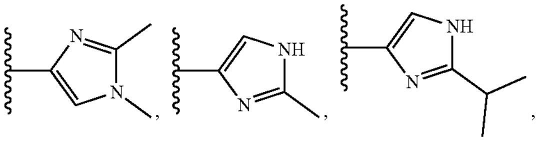
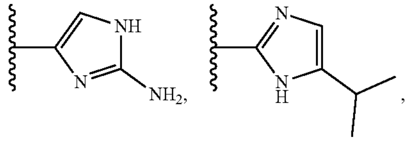
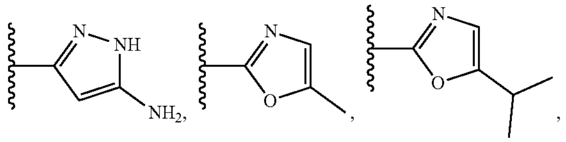
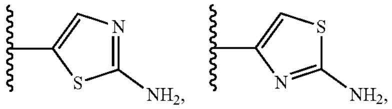
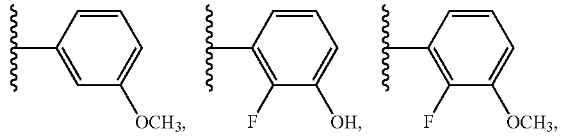

-continued
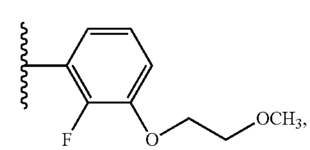, 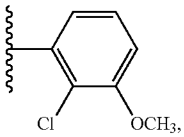,
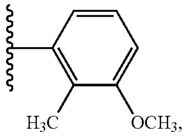, 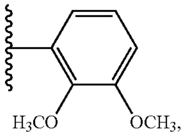,
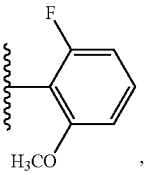, 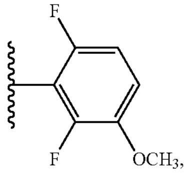, 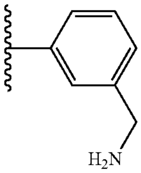,
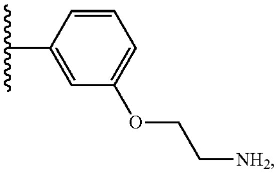, 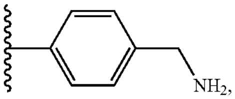,
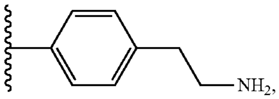,
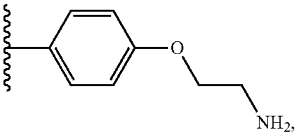, 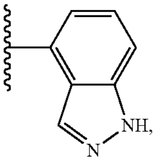,
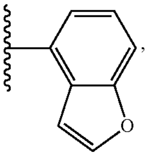, 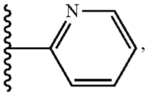, 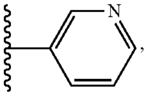,
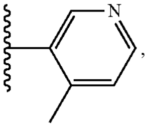, 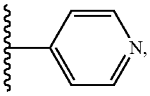, 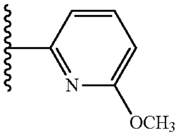,
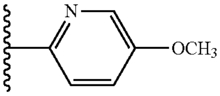, 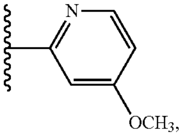,
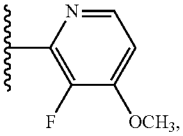, 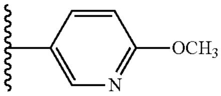,
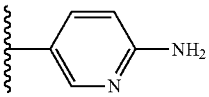, 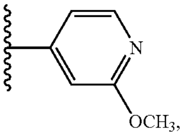 or
-continued
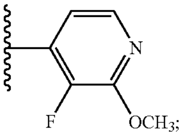;
$R^{5A}$ is hydrogen;
$R^{6A}$ is methyl, $—CH_2CH_2NH_2$, or
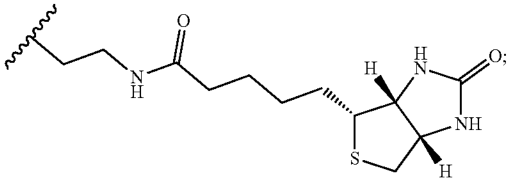 [SMILES: *CCNC(=O)CCCC[C@H]1SC[C@H]2NC(=O)N[C@H]21];
$R^{7A}$ is methyl; and
m is 0 or 1.
A14. The compound of embodiment A12, wherein:
$R^{1A}$ and $R^{2A}$ together with the nitrogen to which they are attached, have a structure of: $—NH_2$,
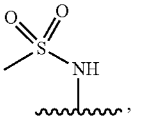, 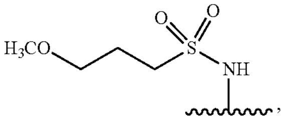,
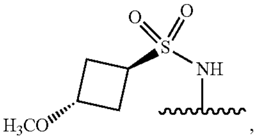, 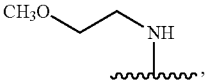,
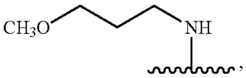, 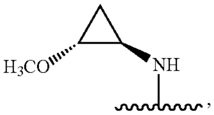,
(cis) (trans)
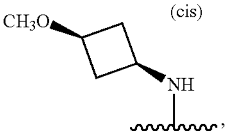, 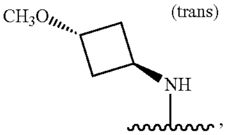,
(+/- trans)
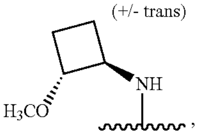, 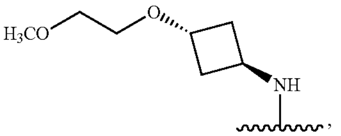,
(+/- cis)
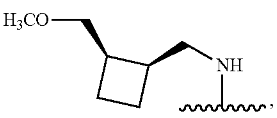, 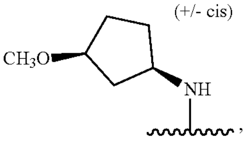,
(+/- trans)
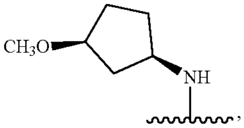, 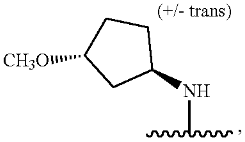, -continued
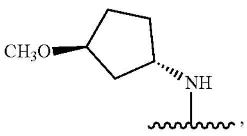
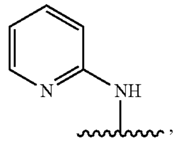
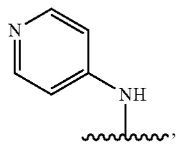
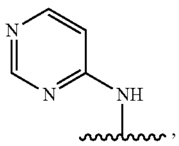
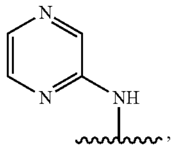
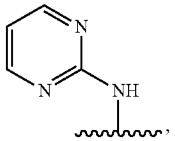
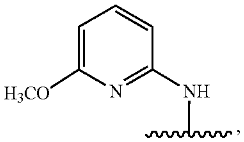
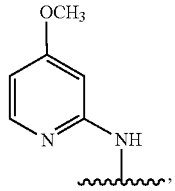
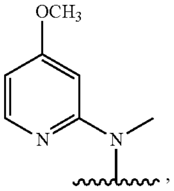
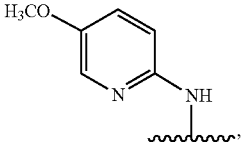
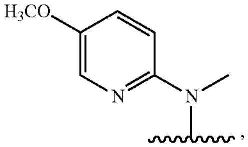
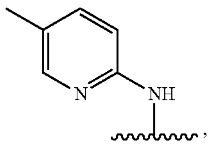
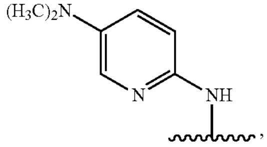
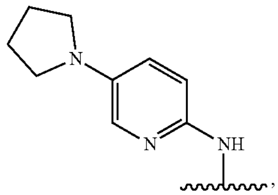
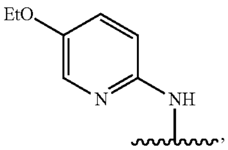
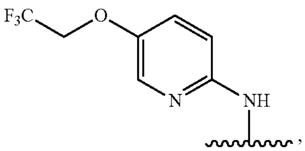
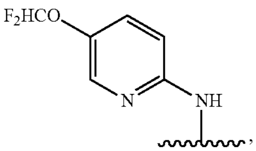
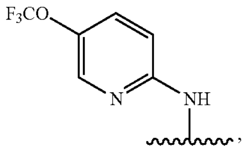
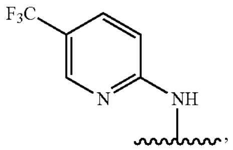
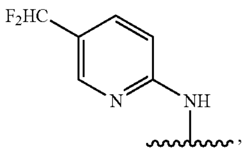
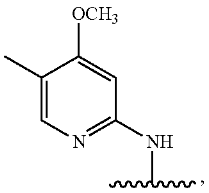
-continued
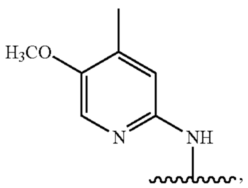
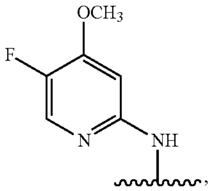
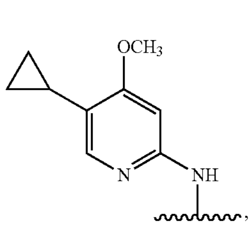
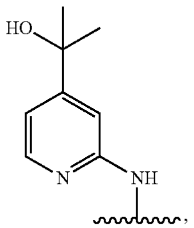
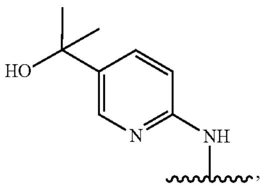
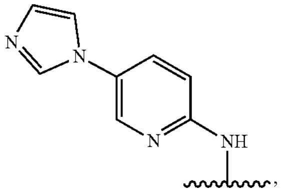
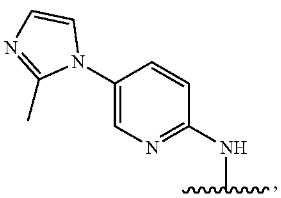
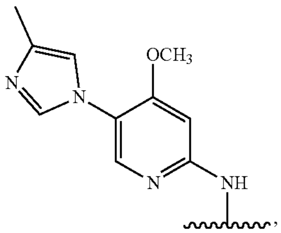
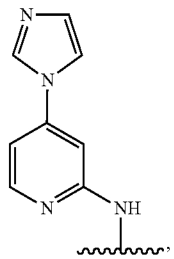
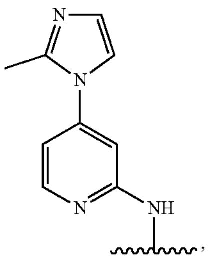
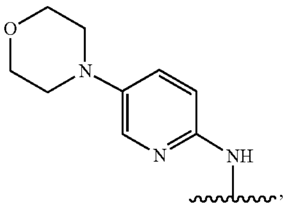
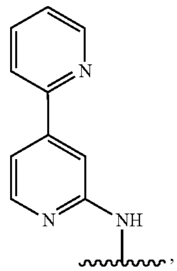
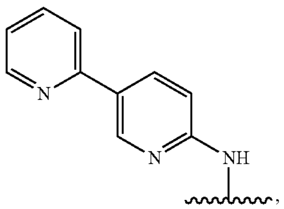
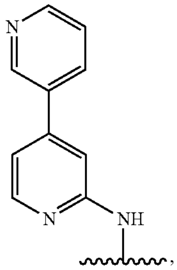

-continued
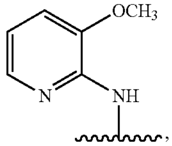, 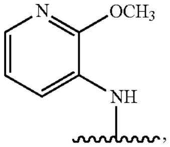,
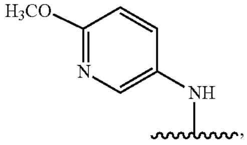, 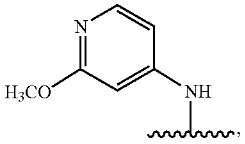,
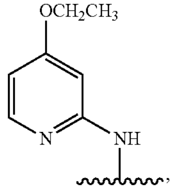, 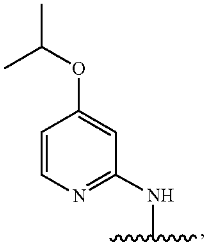,
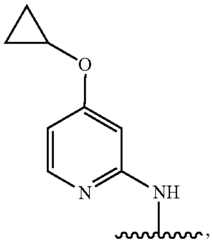, 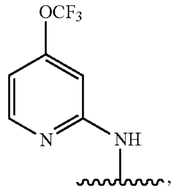, 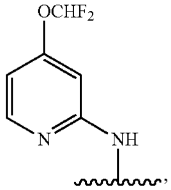,
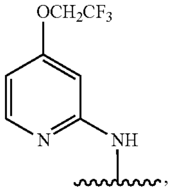, 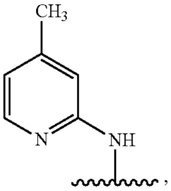, 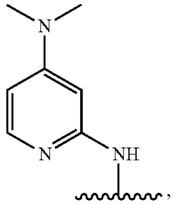,
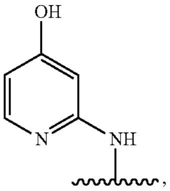, 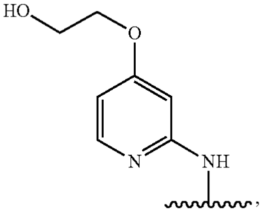,
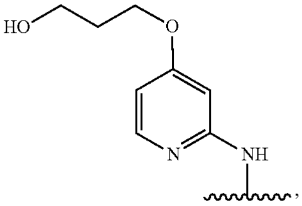,
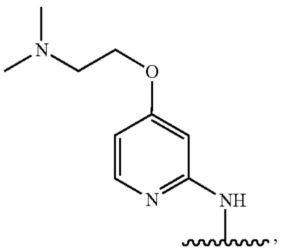,
-continued
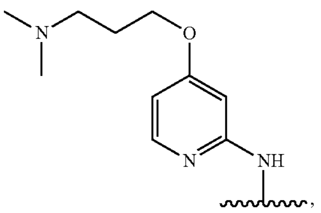, 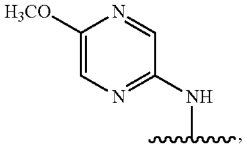,
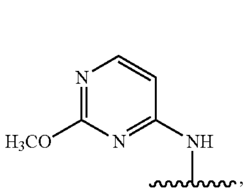, 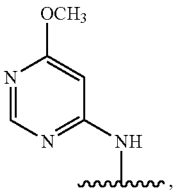,
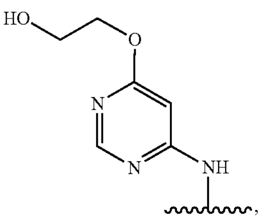, 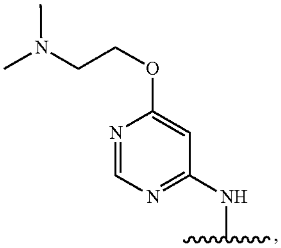,
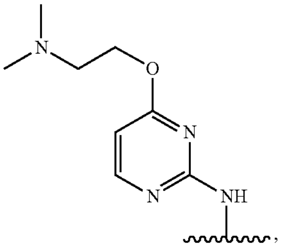, 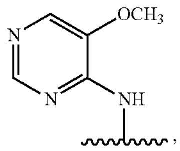,
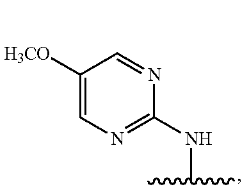, 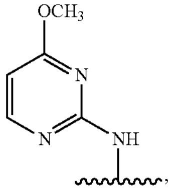,
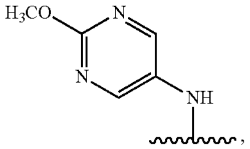, 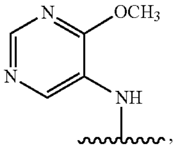,
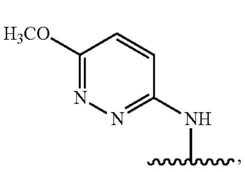, 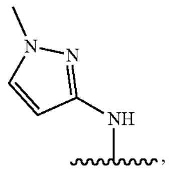,
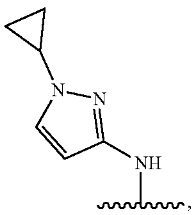, 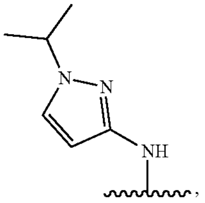, -continued
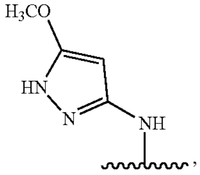
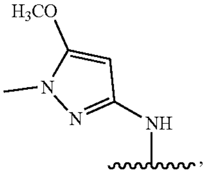
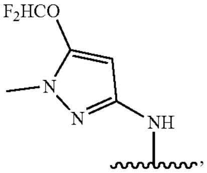
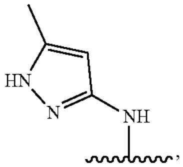
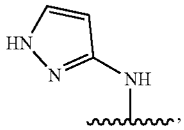
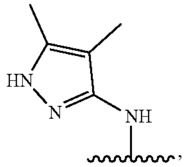
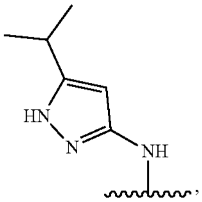
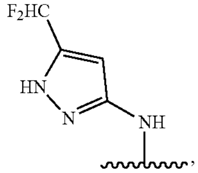
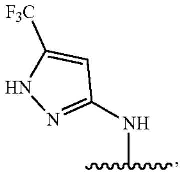
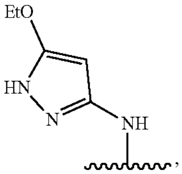
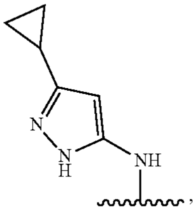
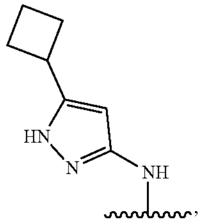
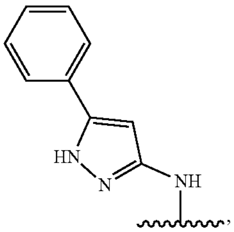
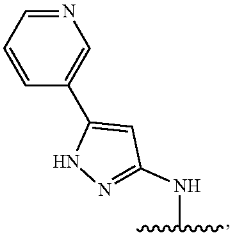
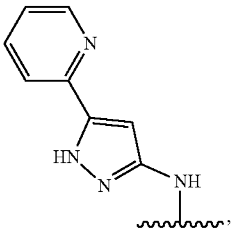
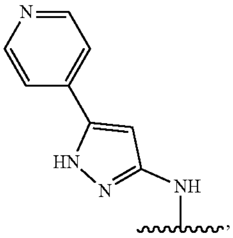
-continued
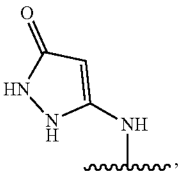
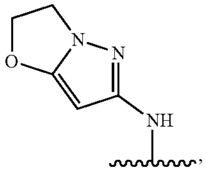
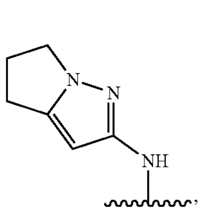
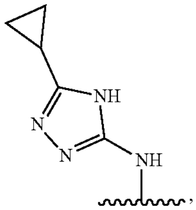
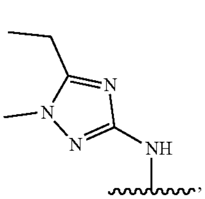
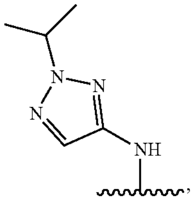
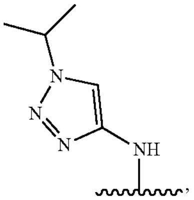
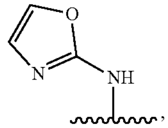
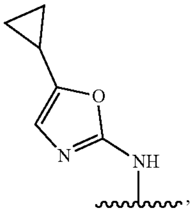
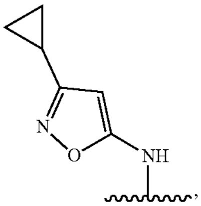
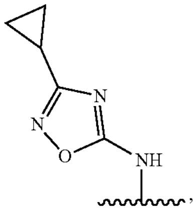
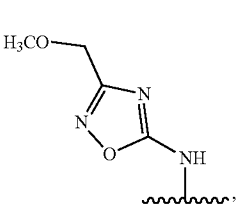
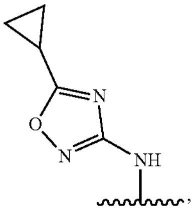
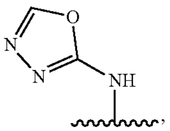
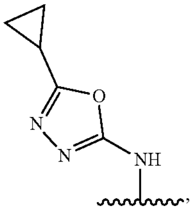
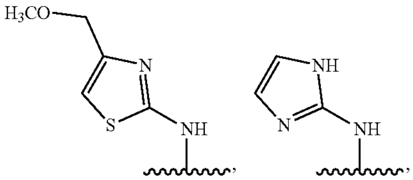

-continued
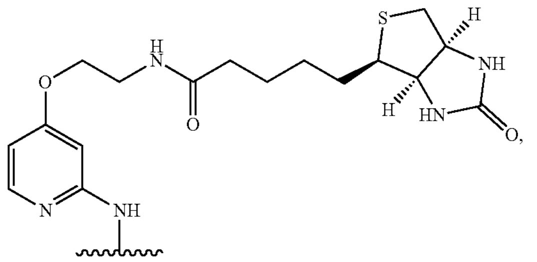
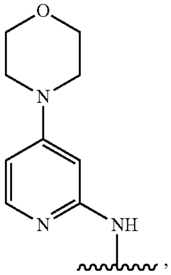, 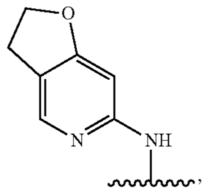,
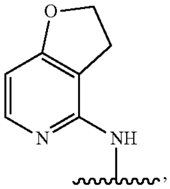, or 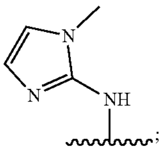;
$R^{3A}$ is —$CH_3$, unsubstituted phenyl, isopropyl, cyclopropyl,
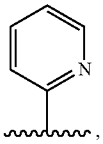, 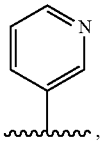, 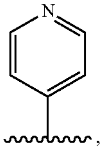, 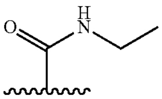,
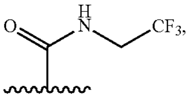 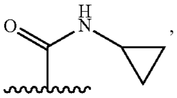,
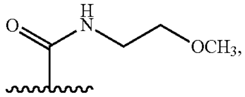 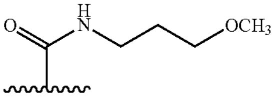,
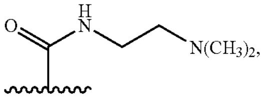 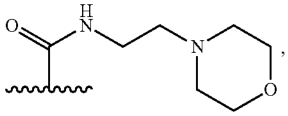,
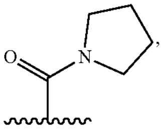, 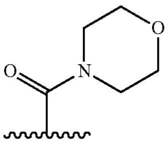, 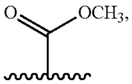 or
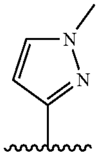;
$R^{4A}$ hydrogen, unsubstituted phenyl,
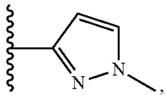, 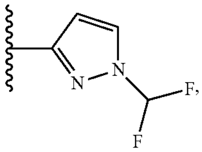
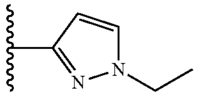, 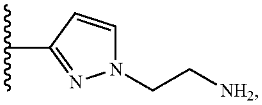
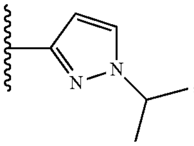,
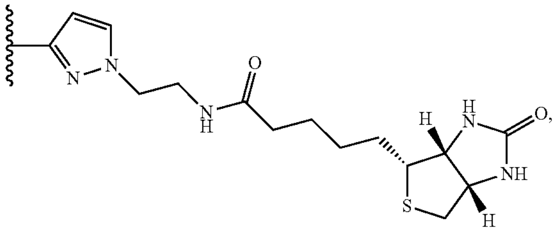
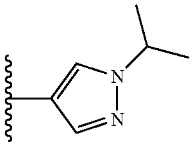, 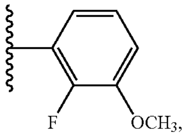
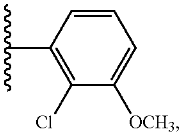 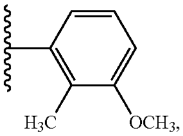 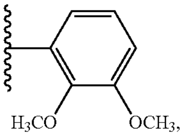
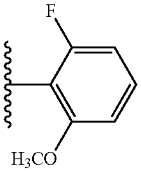, 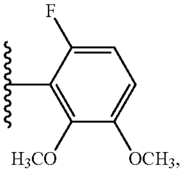 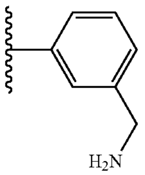,
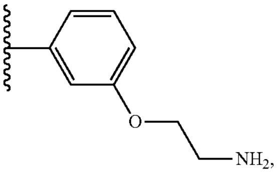 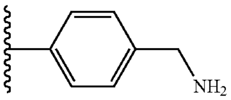,
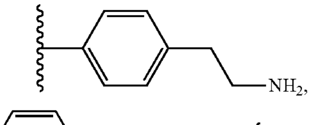
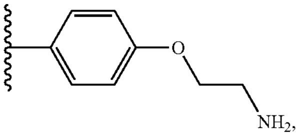 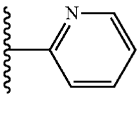,
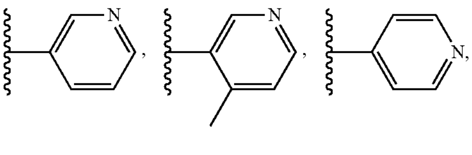

-continued

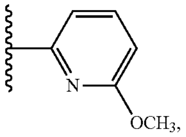

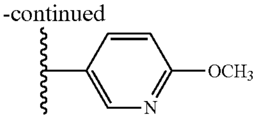

,

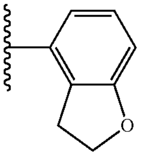

, or

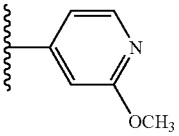

$R^{5A}$ is hydrogen;

$R^{6A}$ is methyl, $—CH_2CH_2NH_2$, or

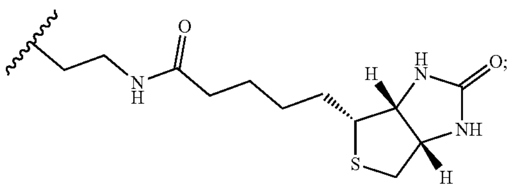 [SMILES: *CCNC(=O)CCCC[C@H]1SC[C@H]2NC(=O)N[C@H]21]

and m is 0.

A15. A compound of Formula IIb:

Formula IIb

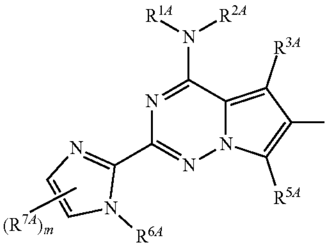

or a pharmaceutically acceptable form thereof, wherein:

$R^{1A}$ and $R^{2A}$ are combined to form a 4-6 membered heterocycloalkyl including the nitrogen atom to which they are both attached, optionally wherein the 4-6 membered heterocycloalkyl formed by $R^{1A}$ and $R^{2A}$ is fused to a 6 membered heteroaryl;

$R^{3A}$ is $C_{1-3}$ alkyl or phenyl, wherein the $C_{1-3}$ alkyl and phenyl are each independently optionally substituted with 1-3 $R^{9A}$ substituents;

$R^{4A}$ is phenyl or 5 membered heteroaryl, wherein the phenyl and 5 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is methyl;

$R^{7A}$ is methyl;

$R^{9A}$ is each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, $—(CO)R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, $—NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy;

m is 0 or 1; and wherein, when $R^{1A}$ and $R^{2A}$ are combined to form

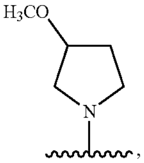

$R^{6A}$ is methyl, m is 0, and $R^{5A}$ is H, at least one of $R^{3A}$ and $R^{4A}$ is not unsubstituted phenyl.

A16. The compound of embodiment A15, wherein:

$R^{1A}$ and $R^{2A}$ are combined to form

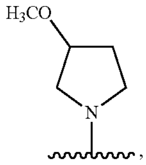

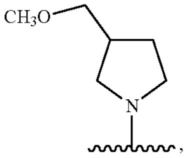

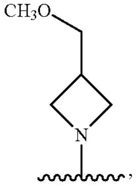

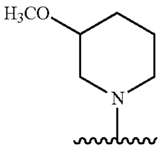

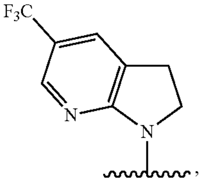

or

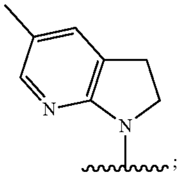

$R^{3A}$ is $—CH_3$, unsubstituted phenyl, (4-methoxy)-phenyl, or isopropyl;

$R^{4A}$ is

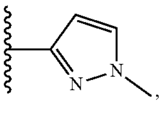

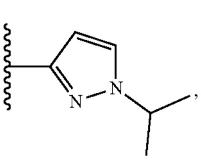 [SMILES: *c1ccn(C(C)C)n1]

-continued

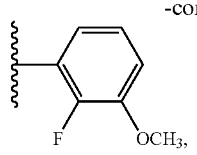, or 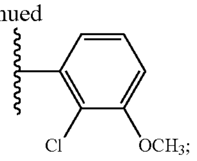;

$R^{5A}$ is hydrogen;

$R^{6A}$ is methyl; and m is 0.

A17. The compound of embodiment A15, wherein:

$R^{1A}$ and $R^{2A}$ are combined to form

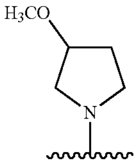, 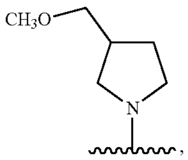, 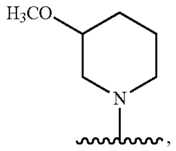, 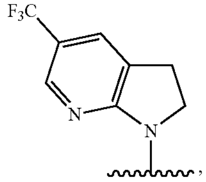, or 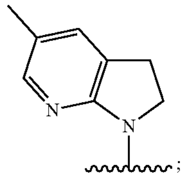;

$R^{3A}$ is —$CH_3$ or substituted phenyl;

$R^{4A}$ is

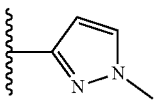 or 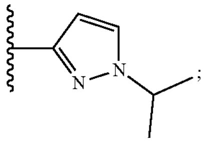;

$R^{5A}$ is hydrogen;

$R^{6A}$ is methyl; and m is 0.

A18. A compound of Formula IIc:

Formula IIc

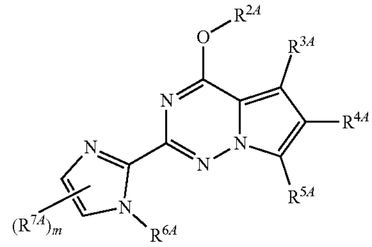

or a pharmaceutically acceptable form thereof, wherein:

$R^{2A}$ is hydrogen $C_{1-6}$ heteroalkyl, or 6 membered heteroaryl, wherein the $C_{1-6}$ heteroalkyl and 5-6 membered heteroaryl are each optionally substituted with 1-3 $R^{8A}$ substituents;

$R^{3A}$ is $C_{1-3}$ alkyl or phenyl, wherein the $C_{1-3}$ alkyl or phenyl are each independently optionally substituted with 1-3 $R^{9A}$ substituents;

$R^{4A}$ is hydrogen, phenyl, or 5 or 6 membered heteroaryl, wherein the phenyl and 5 or 6 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is methyl;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy;

m is 0 or 1; and wherein, when $R^{2A}$ is H, $R^{6A}$ is methyl, m is 0, and $R^{5A}$ is H, at least one of $R^{3A}$ and $R^{4A}$ is not unsubstituted phenyl.

A19. The compound of embodiment A18, wherein:

$R^{2A}$ together with the oxygen to which it is attached have a structure of: —OH,

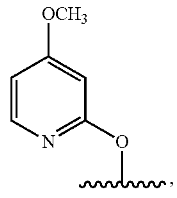, or 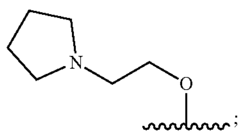;

$R^{3A}$ is —$CH_3$ or unsubstituted phenyl;

$R^{4A}$ hydrogen, unsubstituted phenyl,

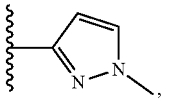, 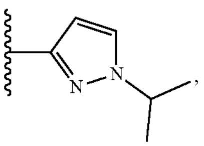 [SMILES: *c1ccn(C(C)C)n1], 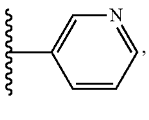, or 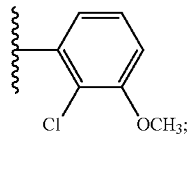;

$R^{5A}$ is hydrogen;

$R^{6A}$ is methyl; and m 0.

A20. A compound of Formula III:

Formula III

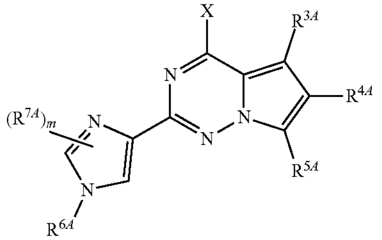

or a pharmaceutically acceptable form thereof, wherein:

X is $NR^{1A}R^{2A}$ or —$OR^{2A}$;

$R^{1A}$ is hydrogen or $C_{1-6}$ alkyl;

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

A21. A compound of Formula IIIa:

Formula IIIa

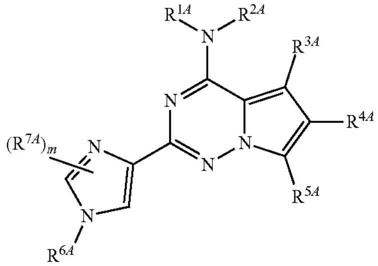

or a pharmaceutically acceptable form thereof, wherein:

$R^{1A}$ is hydrogen;

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

A22. A compound of Formula IIIb:

Formula IIIb

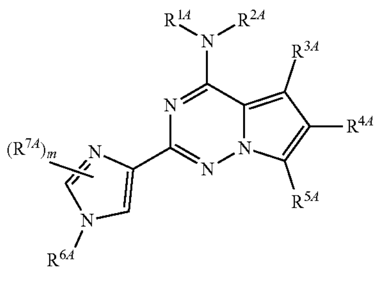

or a pharmaceutically acceptable form thereof, wherein:

$R^{1A}$ and $R^{2A}$ are combined to form a 4-6 membered heterocycloalkyl including the nitrogen atom to which they are both attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

A23. A compound of Formula IIIc:

Formula IIIc

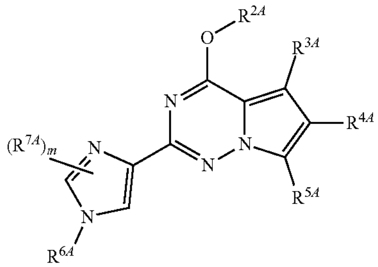

or a pharmaceutically acceptable form thereof, wherein:

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1 or 2.

A24. A compound of Formula IV:

Formula IV

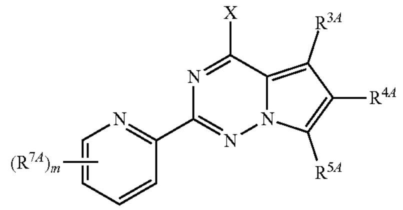

or a pharmaceutically acceptable form thereof, wherein:

X is —$NR^{1A}R^{2A}$ or —$OR^{2A}$;

$R^{1A}$ is hydrogen or $C_{1-6}$ alkyl;

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen or $C_{1-6}$ alkyl;

$R^{7A}$ is $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, $C_{1-6}$ heteroalkyl, halo, —$NR^{12A}R^{13A}$, $C_{1-6}$ alkoxy, $C_{1-6}$ haloalkoxy, —C(O)$NR^{12A}R^{13A}$, —(CO)$R^{11A}$, —C(O)$OR^{14A}$, or CN, wherein the $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, and $C_{1-6}$ heteroalkyl are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

A25. A compound of Formula IVa:

Formula IVa

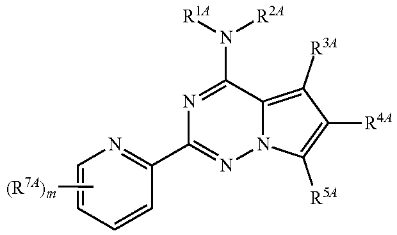

or a pharmaceutically acceptable form thereof, wherein:

$R^{1A}$ is hydrogen;

$R^{2A}$ is hydrogen, $C_{1-6}$ alkyl, $C_{3-6}$ cycloalkyl, $C_{1-6}$ heteroalkyl, or 6 membered heteroaryl, wherein the $C_{1-6}$ alkyl, $C_{3-6}$ cycloalkyl, $C_{1-6}$ heteroalkyl, and 6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{3A}$ is $C_{1-6}$ alkyl or phenyl, wherein the $C_{1-6}$ alkyl and phenyl are each independently optionally substituted with 1-3 $R^{9A}$ substituents;

$R^{4A}$ is 5 membered heteroaryl, wherein the 5 membered heteroaryl is optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

A26. The compound of embodiment A25, wherein:

$R^{1A}$ and $R^{2A}$ together with the nitrogen to which they are attached have a structure of:

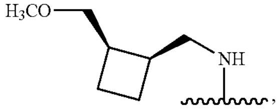,

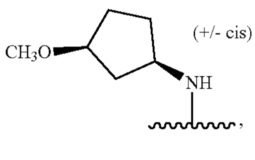

(+/- cis),

-continued

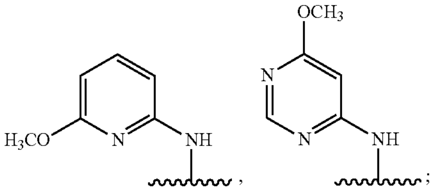

$R^{3A}$ is —$CH_3$ or unsubstituted phenyl;

$R^{4A}$ is

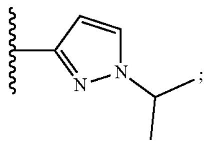

$R^{5A}$ is hydrogen;

$R^{7A}$ is methyl; and m is 0.

A27. A compound of Formula IVb:

Formula IVb

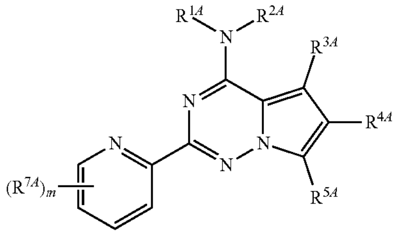

or a pharmaceutically acceptable form thereof, wherein:

$R^{1A}$ and $R^{2A}$ are combined to form a 4-6 membered heterocycloalkyl including the nitrogen atom to which they are both attached;

$R^{3A}$ is $C_{1-6}$ alkyl or phenyl, wherein the $C_{1-6}$ alkyl and phenyl are each independently optionally substituted with 1-3 $R^{9A}$ substituents;

$R^{4A}$ is 5 membered heteroaryl, wherein the 5 membered heteroaryl is optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

A28. The compound of embodiment A27, wherein:

$R^{1A}$ and $R^{2A}$ are combined to form

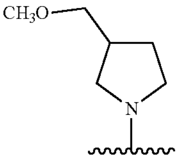
or
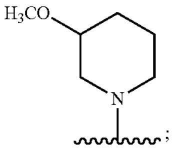

$R^{3A}$ is —$CH_3$ or unsubstituted phenyl;

$R^{4A}$ is

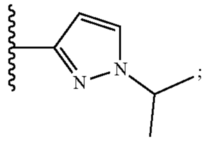 [SMILES: *c1ccn(C(C)C)n1]

$R^{5A}$ is hydrogen;

$R^{7A}$ is methyl; and m is 0.

A29. A compound of Formula IVc:

Formula IVc

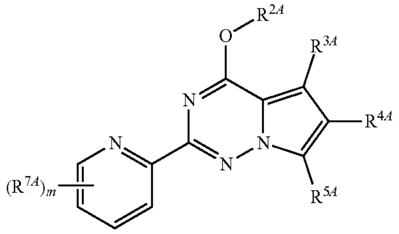

or a pharmaceutically acceptable form thereof, wherein:

$R^{2A}$ is hydrogen, $C_{1-6}$ alkyl, $C_{3-6}$ cycloalkyl, $C_{1-6}$ heteroalkyl, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents;

$R^{3A}$ is $C_{1-6}$ alkyl, $C_{1-6}$ heteroalkyl, phenyl, or 5-10 membered heteroaryl, wherein the $C_{1-6}$ alkyl, $C_{1-6}$ heteroalkyl, phenyl, and 5-10 membered heteroaryl are each independently optionally substituted with 1-3 $R^{9A}$ substituents;

$R^{4A}$ is hydrogen, phenyl, or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{7A}$ is $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy; and m is 0, 1, 2, 3 or 4.

A30. The compound of embodiment A29, wherein:

$R^{2A}$ is hydrogen;

$R^{3A}$ is —$CH_3$;

$R^{4A}$ is

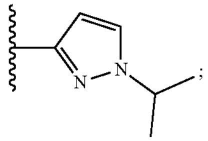

$R^{5A}$ is hydrogen;

$R^{7A}$ is methyl;

m is 0.

A31. The compound of any one of embodiments A1 to A30, wherein no more than one of $R^{4A}$ and $R^{5A}$ is hydrogen.

A32. The compound of any one of embodiments A1 to A31, wherein $R^{5A}$ is hydrogen, methyl, ethyl, or isopropyl.

A33. The compound of any one of embodiments A1 to A32, wherein $R^{5A}$ is hydrogen.

A34. The compound of any one of embodiments A1 to A33, wherein $R^{6A}$ is $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, $C_{1-6}$ heteroalkyl, $C_{1-6}$ alkoxy, $C_{1-6}$ haloalkoxy, —C(O)$NR^{12A}R^{13A}$, —(CO)$R^{11A}$, or —C(O)$OR^{14A}$, wherein the $C_{1-6}$ alkyl, $C_{3-6}$ cycloalkyl, $C_{1-6}$ haloalkyl, aryl, $C_{5-10}$ heteroaryl, $C_{3-7}$ heterocycloalkyl, and $C_{1-6}$ heteroalkyl are each independently optionally substituted with 1-3 $R^{8A}$ substituents.

A35. The compound of any one of embodiments A1 to A34, wherein $R^{6A}$ is $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents.

A36. The compound of any one of embodiments A1 to A35, wherein $R^{6A}$ is methyl, ethyl, or isopropyl, wherein the methyl, ethyl, and isopropyl are each independently optionally substituted with 1-3 $R^{8A}$, wherein $R^{8A}$ is —OH, $C_{1-3}$ alkoxy, or $C_{1-3}$ haloalkoxy.

A37. The compound of any one of embodiments A1 to A36, wherein $R^{6A}$ is methyl, ethyl, or isopropyl.

A38. The compound of any one of embodiments A1 to A37, wherein $R^{6A}$ is methyl.

A39. The compound of any one of embodiments A1 to A38, wherein $R^{7A}$ is $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents.

A40. The compound of any one of embodiments A1 to A39, wherein $R^{7A}$ is methyl, ethyl, or isopropyl, wherein the methyl, ethyl, and isopropyl are each independently optionally substituted with 1-3 $R^{8A}$, wherein $R^{8A}$ is —OH, $C_{1-3}$ alkoxy, or $C_{1-3}$ haloalkoxy.

A41. The compound of any one of embodiments A1 to A40, wherein $R^{7A}$ is methyl, ethyl, or isopropyl.

A42. The compound of any one of embodiments A1 to A41, wherein $R^{7A}$ is methyl.

A43. The compound of any one of embodiments A1 to A42, wherein m is 1.

A44. The compound of any one of embodiments A1 to A42, wherein m is 0.

A45. The compound of any one of embodiments A1 to A44, wherein X is nitrogen, and $R^{1A}$ and $R^{2A}$ are combined to form a 3-6 membered heterocycloalkyl including the nitrogen atom to which they are both attached.

A46. The compound of any one of embodiments A1 to A44, wherein $R^{1A}$ is hydrogen or $C_{1-3}$ alkyl.

A47. The compound of any one of embodiments A1 to A44, or A46, wherein $R^{1A}$ is methyl, ethyl, or isopropyl.

A48. The compound of any one of embodiments A1 to A44, or A46 wherein $R^{1A}$ is hydrogen.

A49. The compound of any one of embodiments A1 to A44, or A46 to A48, wherein $R^{2A}$ is $C_{1-4}$ alkyl, $C_{4-5}$ cycloalkyl, $C_{1-4}$ heteroalkyl, or 5-6 membered heteroaryl, wherein the $C_{1-4}$ alkyl, $C_{4-5}$ cycloalkyl, $C_{1-4}$ heteroalkyl, or 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached.

A50. The compound of any one of embodiments A1 to A44, or A46 to A49, wherein $R^{2A}$ is a 5-6 membered heteroaryl, wherein each are independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached.

A51. The compound of any one of embodiments A1 to A44, or A46 to A50, wherein $R^{2A}$ is a 5-6 membered heteroaryl selected from the group consisting of a pyridinyl, a pyrimidinyl, a pyrazinyl, a pyridazinyl, a triazinyl, an imidazolyl, a pyrazolyl, a triazolyl, a tetrazolyl, an oxazolyl, an isoxazolyl, an oxadiazolyl, a thiazolyl, a isothiazolyl, or a thiadiazolyl, each independently optionally substituted with 1-3 $R^{8A}$ substituents.

A52. The compound of embodiment A51, wherein the 5-6 membered heteroaryl is substituted with 2 independent $R^{8A}$ substituents which are combined to form a 5-6 membered cycloalkyl fused to the 5-6 membered heteroaryl including the atom or atoms to which each are attached.

A53. The compound of embodiment A51, wherein the 5-6 membered heteroaryl is substituted with 2 independent $R^{8A}$ substituents which are combined to form a 5-6 membered heterocycloalkyl fused to the 5-6 membered heteroaryl including the atom or atoms to which each are attached.

A54. The compound of embodiment A53, wherein the 2 $R^{8A}$ substituents are combined to form a 2,3-dihydropyrazolo[5,1-b]oxazolyl ring.

A55. The compound of embodiment A54, wherein the 5-6 membered heteroaryl is a pyrazolyl.

A56. The compound of embodiment A51, wherein $R^{8A}$ is independently selected from the group consisting of $C_{1-6}$ alkyl, $C_{1-6}$ haloalkyl, $C_{3-6}$ cycloalkyl, $—NR^{12A}R^{13A}$, $—(CO)R^{11A}$, oxo, $C_{1-6}$ hydroxyalkyl, $C_{1-6}$ heteroalkyl, 3-6 membered heterocycloalkyl, $C_{1-6}$ alkoxy, $C_{3-6}$ cycloalkoxy, biotinamide, or a biotinylated substituent.

A57. The compound of embodiment A51 or embodiment A56 wherein $R^{8A}$ is independently selected from the group consisting of $C_{1-4}$ alkyl, $C_{1-4}$ haloalkyl, $C_{3-5}$ cycloalkyl, $—NR^{12A}R^{13A}$, $—(CO)R^{11A}$, oxo, $C_{1-4}$ hydroxyalkyl, $C_{1-4}$ heteroalkyl, 3-5 membered heterocycloalkyl, $C_{1-4}$ alkoxy, $C_{3-5}$ cycloalkoxy, biotinamide, or a biotinylated substituent.

A58. The compound of any one of embodiments A51 to A57, wherein $R^{8A}$ is independently selected from the group consisting of methyl, ethyl, isopropyl, cyclopropyl, cyclobutyl, $—(CO)R^{11A}$, oxo, $C_{2-3}$ hydroxyalkyl, $C_{2-4}$ heteroalkyl, methoxy, ethoxy, isopropoxy, cyclopropoxy, or cyclobutoxy.

A59. The compound of any one of embodiments A1 to A58, wherein X is: —OH, $—NH_2$,

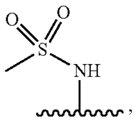,
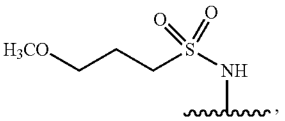,
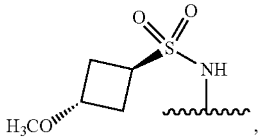,
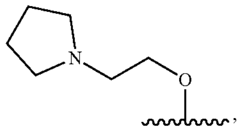,
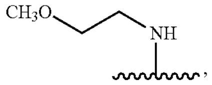,
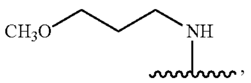,
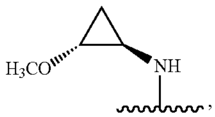,
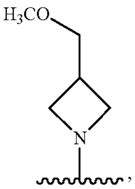,
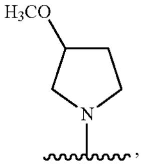,
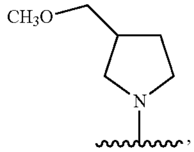,
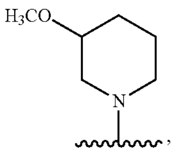, (cis)

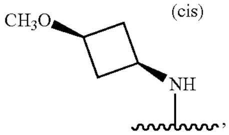, (trans)

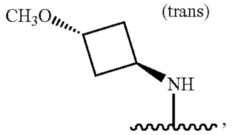, (+/- trans)

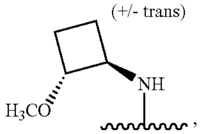,
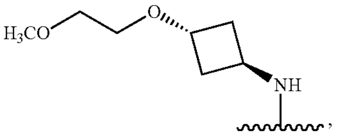,

-continued

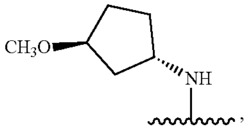,
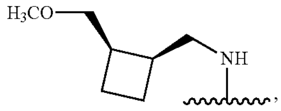, (+/- cis)

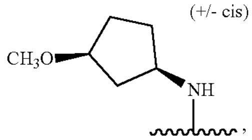,
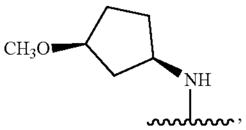, (+/- trans)

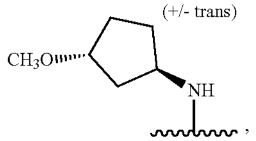,
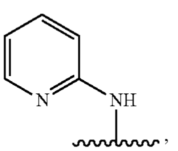,
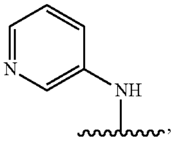,
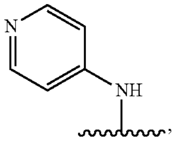,
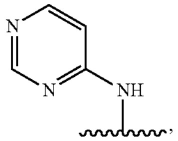,
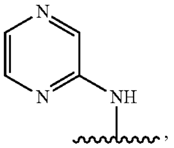,
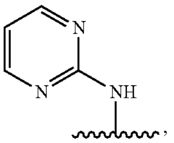,
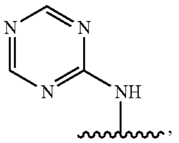,
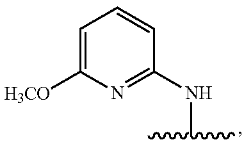,
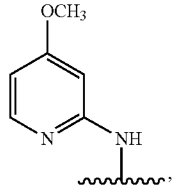,
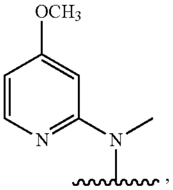,
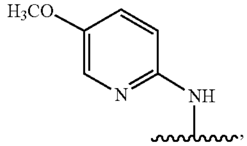,
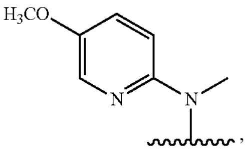,
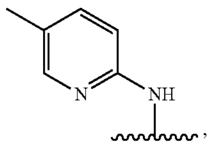,
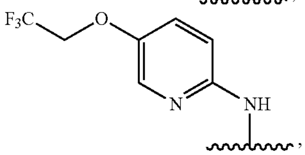,
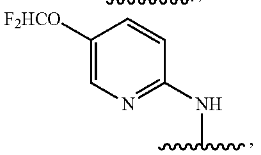,
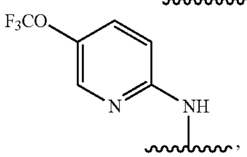,
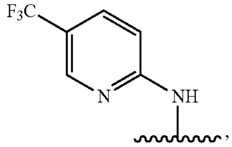,
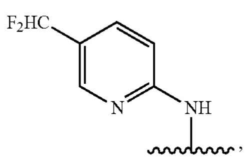,
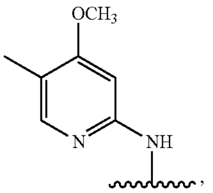, -continued
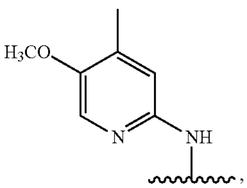
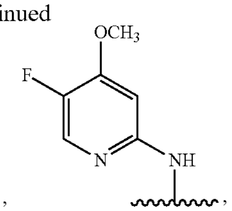
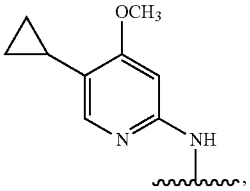
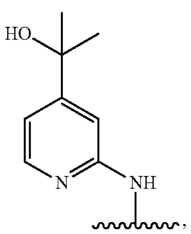
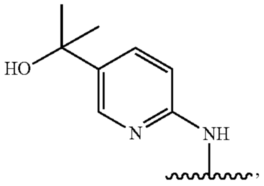
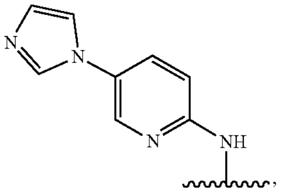
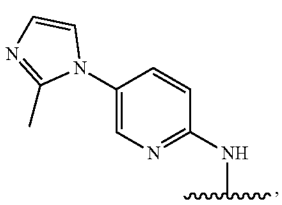
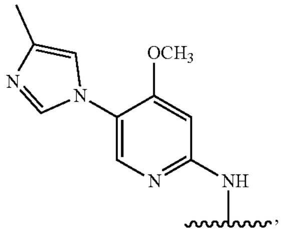
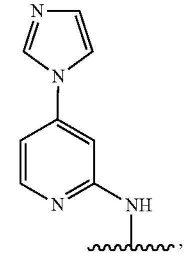
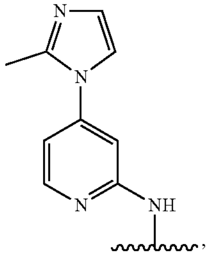
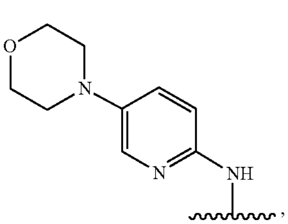
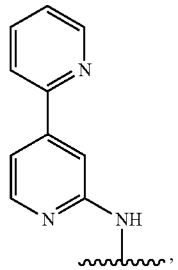
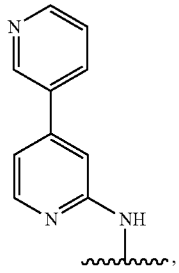
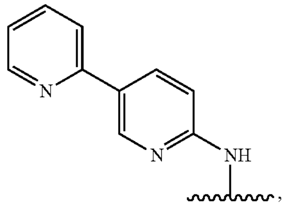
-continued
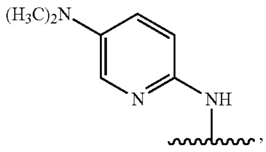
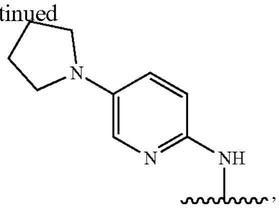
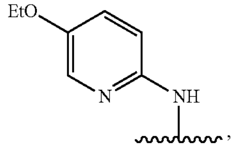
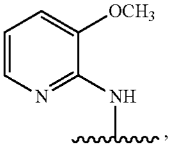
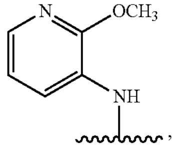
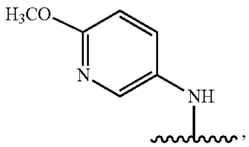
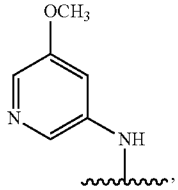
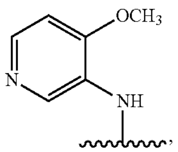
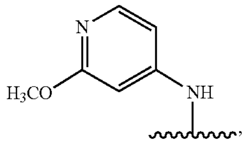
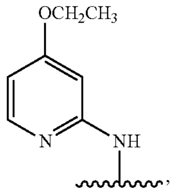
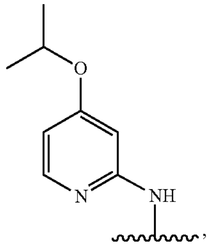
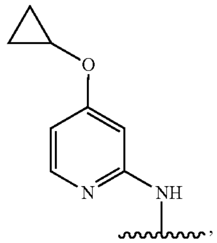
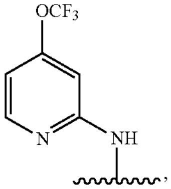
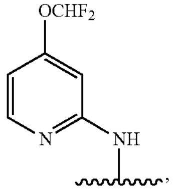
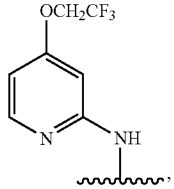
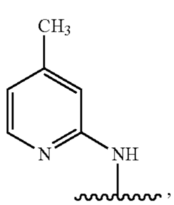
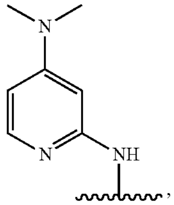
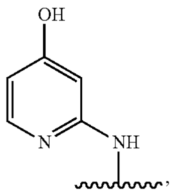
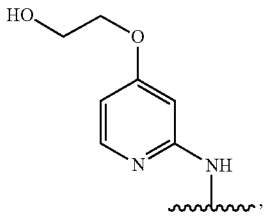
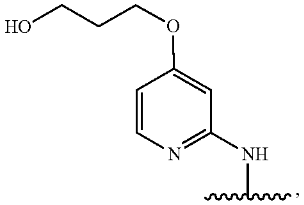

-continued
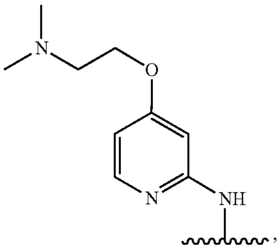,
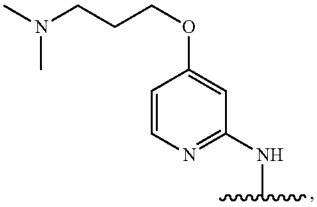,
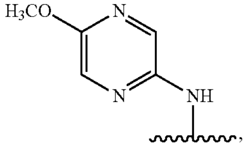,
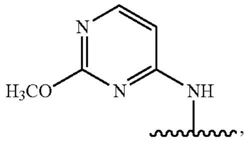,
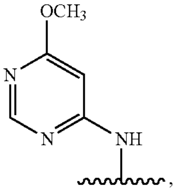,
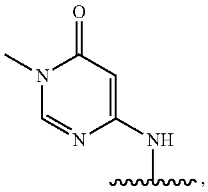,
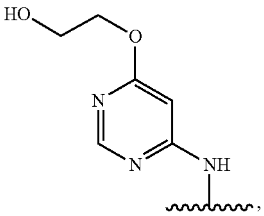,
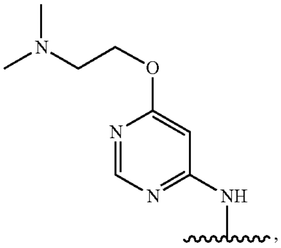,
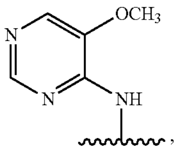,
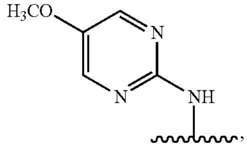,
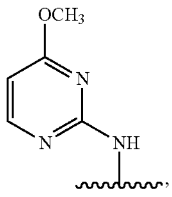,
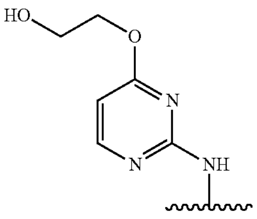,
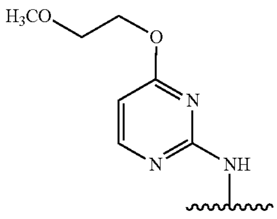,
-continued
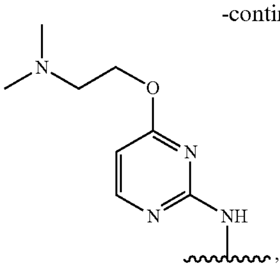,
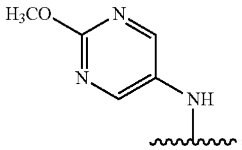,
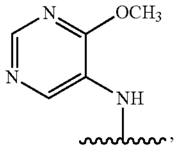,
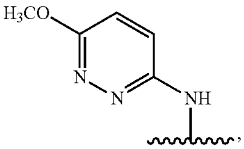,
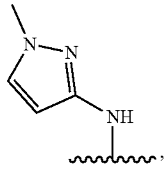,
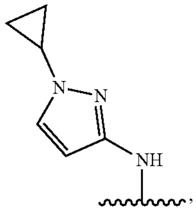,
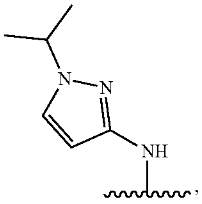,
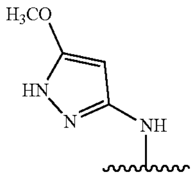,
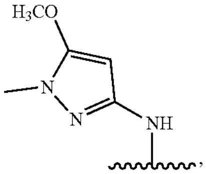,
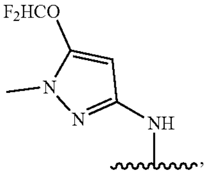,
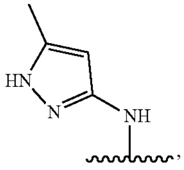,
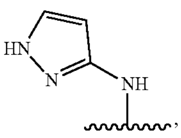,
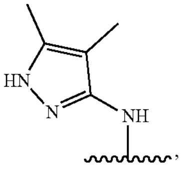,
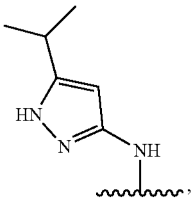,
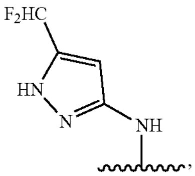,
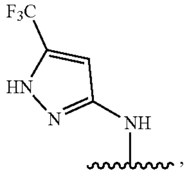,
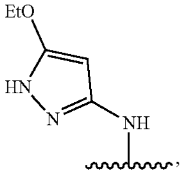, -continued
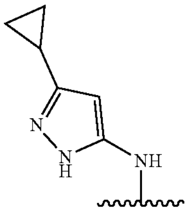,
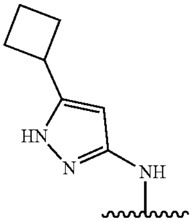,
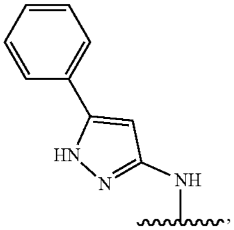,
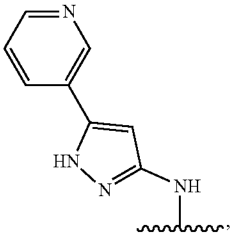,
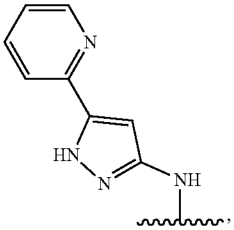,
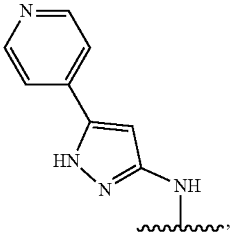,
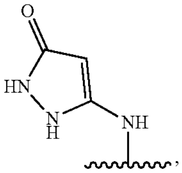,
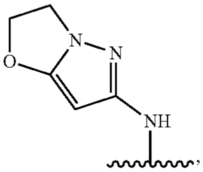,
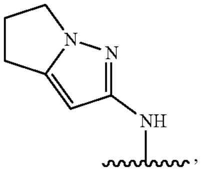,
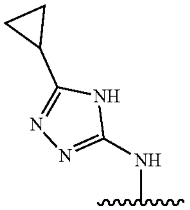,
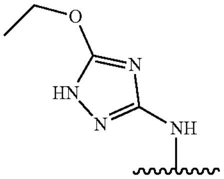,
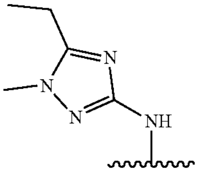,
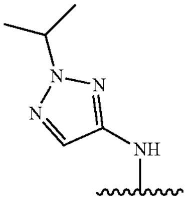,
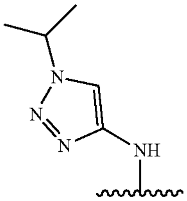,
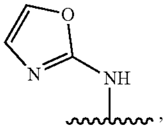,
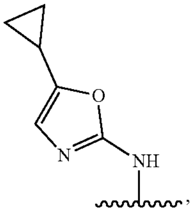,
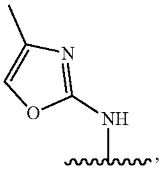,
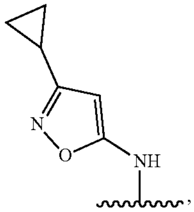,
-continued
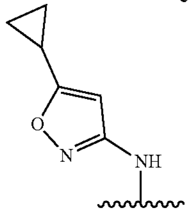,
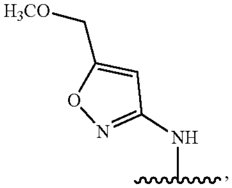,
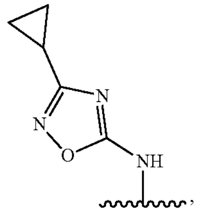,
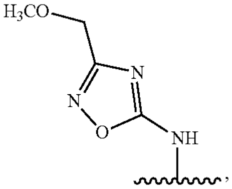,
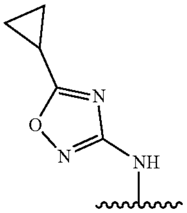,
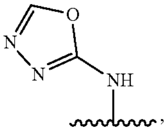,
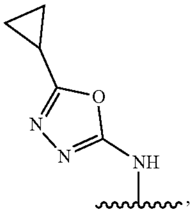,
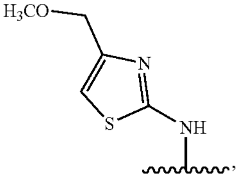,
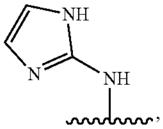,
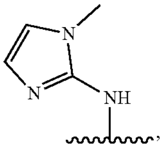,
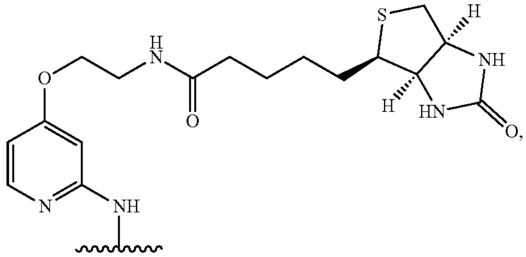
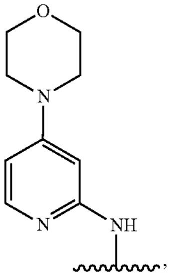,
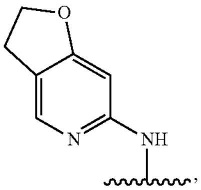,
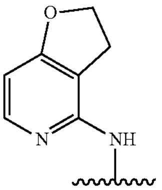,
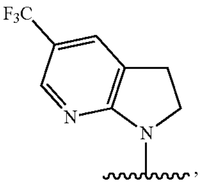,
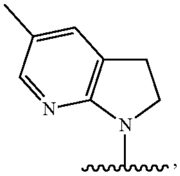, or
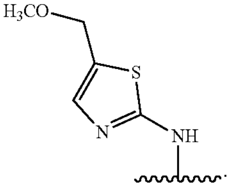.

A60. The compound of embodiment A59, wherein X is: —OH, —$NH_2$,
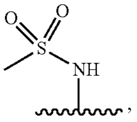
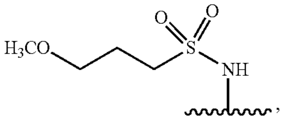
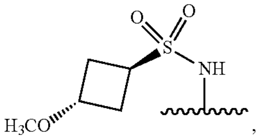
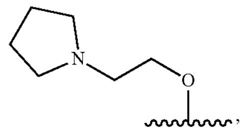
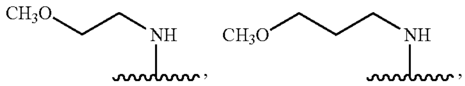
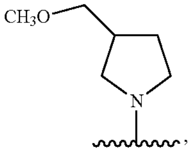
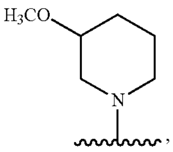
(cis)
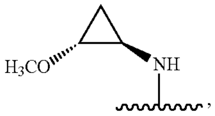
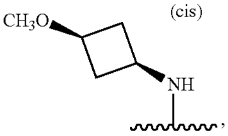
(trans)
(+/- trans)
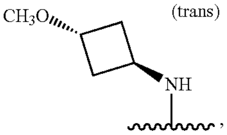
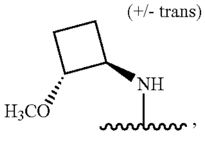
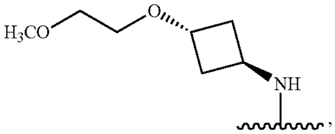
(+/- cis)
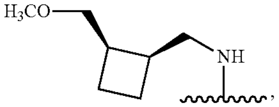
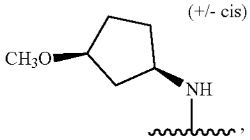
(+/- trans)
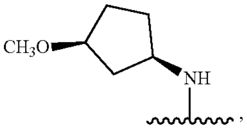
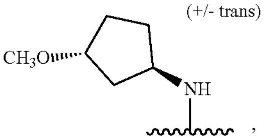
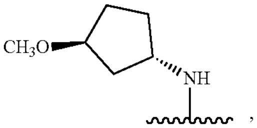
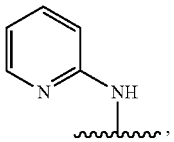
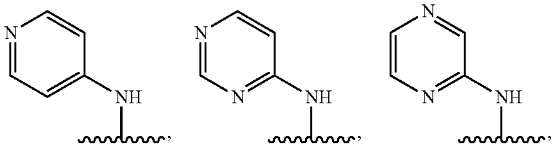
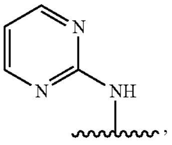
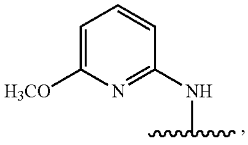
-continued
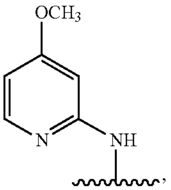
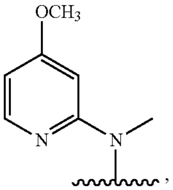
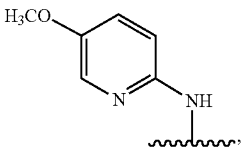
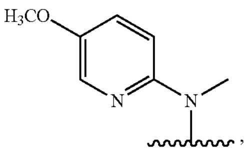
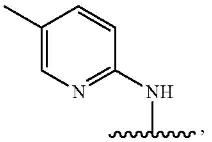
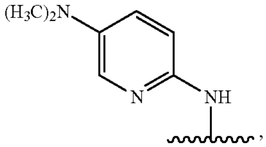
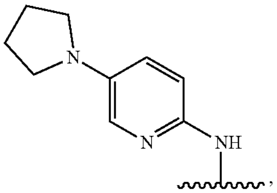
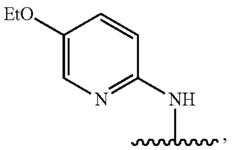
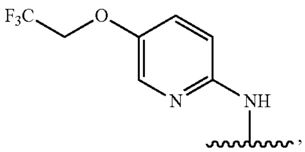
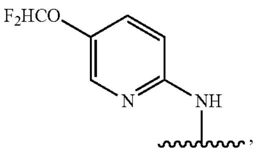
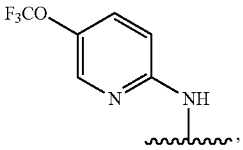
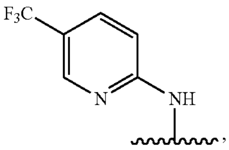
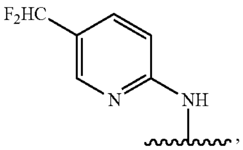
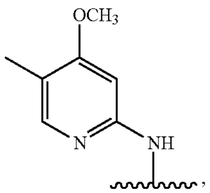
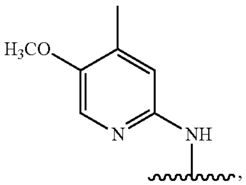
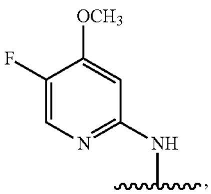
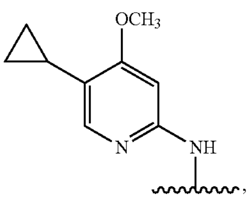
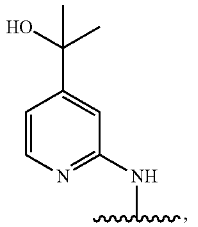

-continued
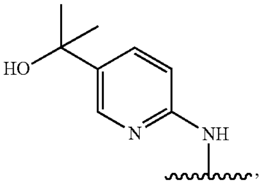
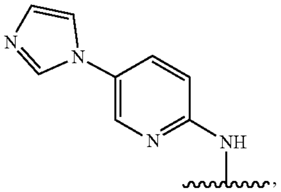
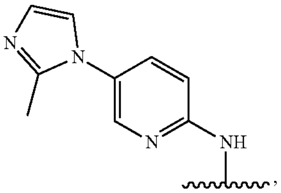
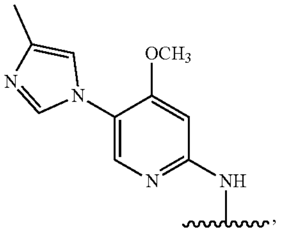
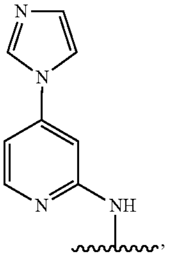
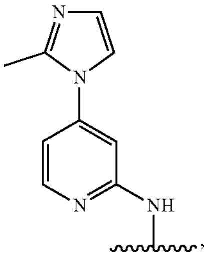
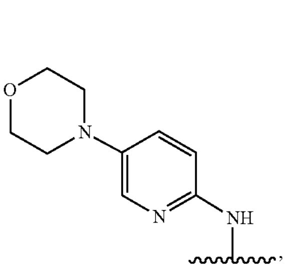
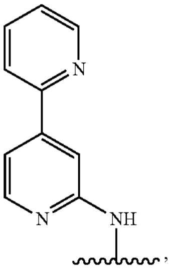
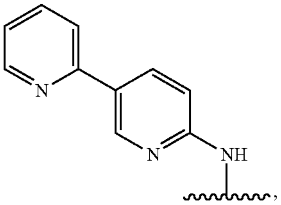
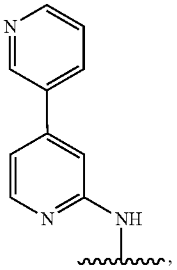
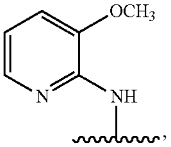
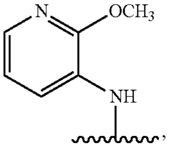
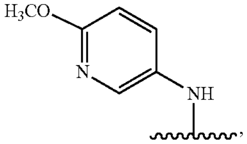
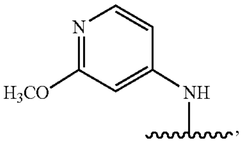
-continued
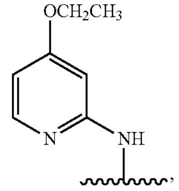
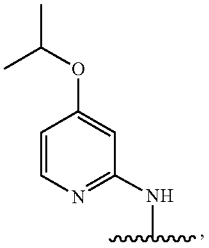
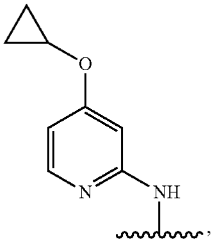
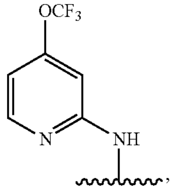
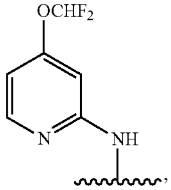
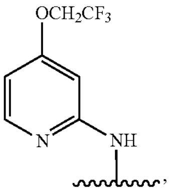
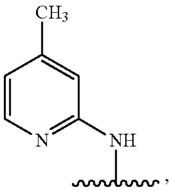
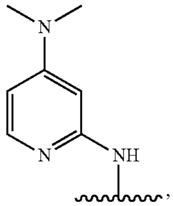
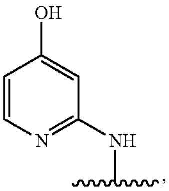
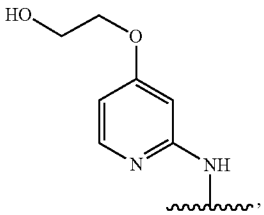
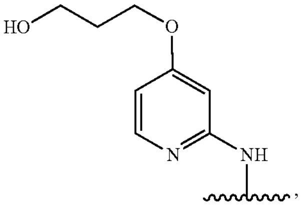
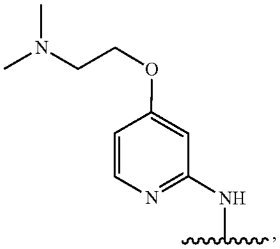
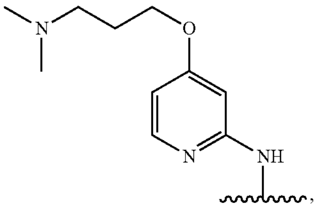
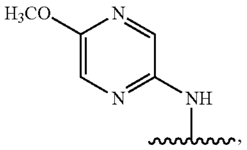

-continued
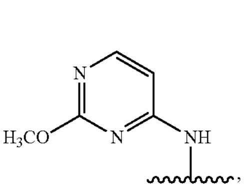
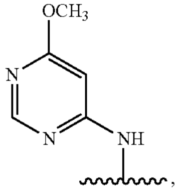
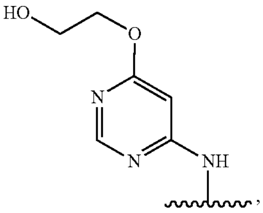
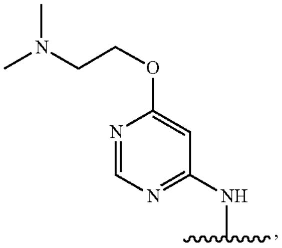
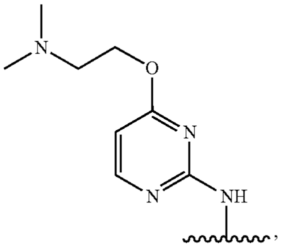
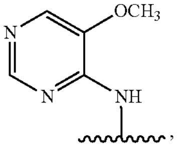
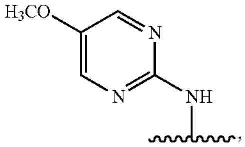
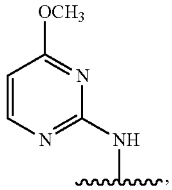
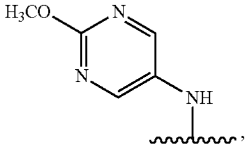
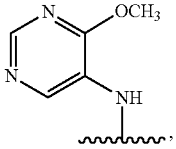
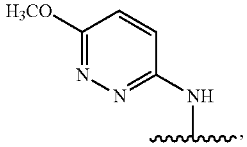
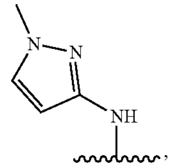
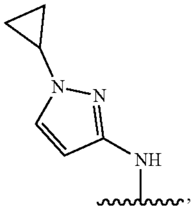
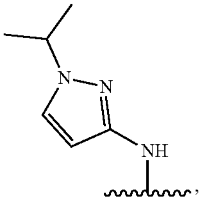
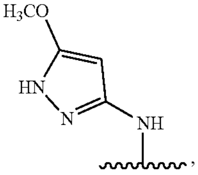
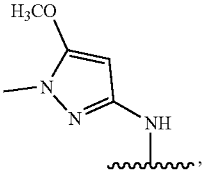
-continued
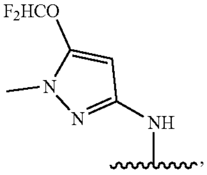
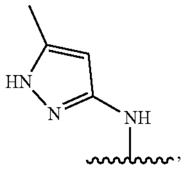
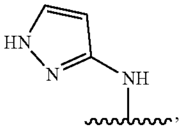
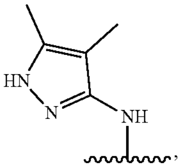
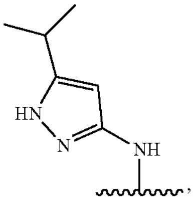
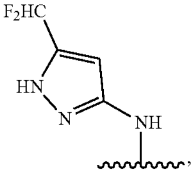
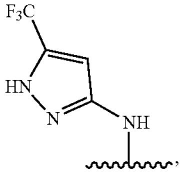
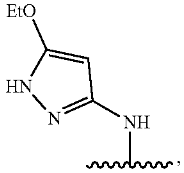
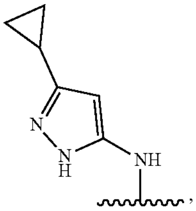
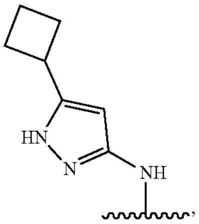
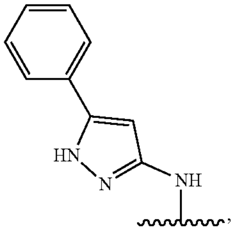
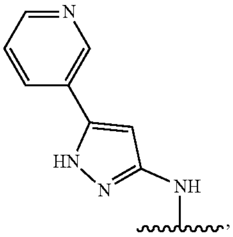
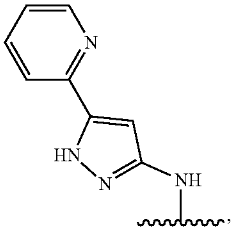
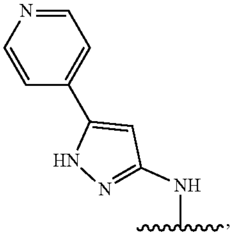
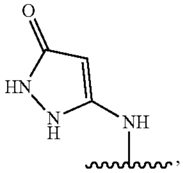
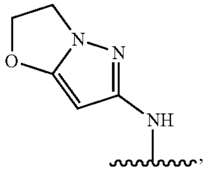
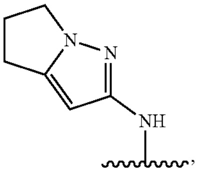
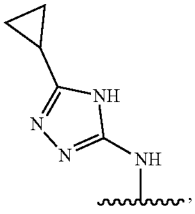

-continued

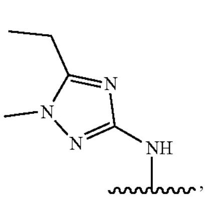,
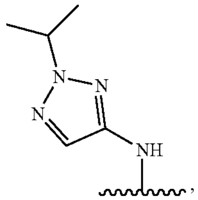,
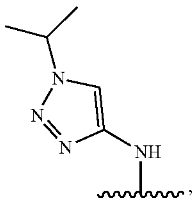,
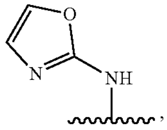,
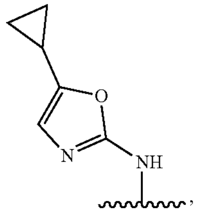,
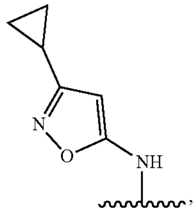,
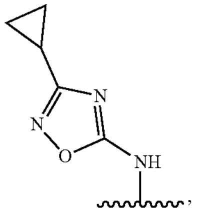,
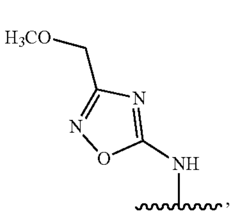,
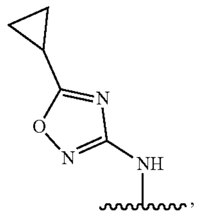,
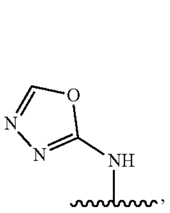,
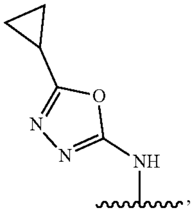,
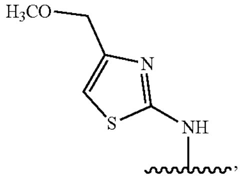,
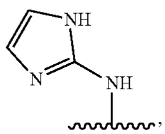,
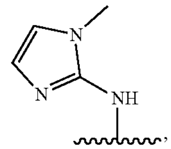,
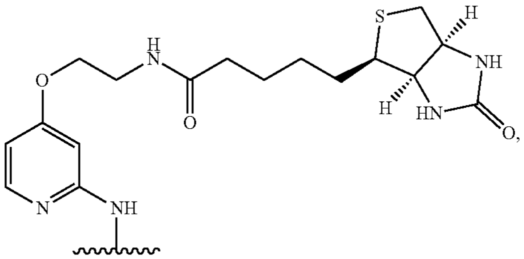

-continued

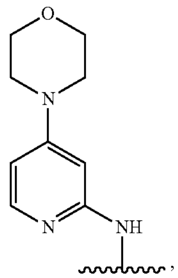,
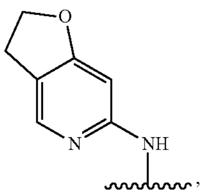,
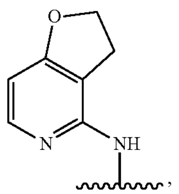,
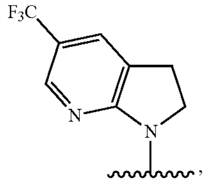,
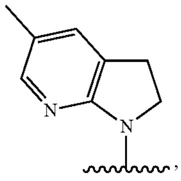, or
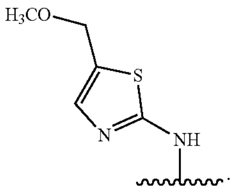.

A61. The compound of any one of embodiments A1 to A60, wherein $R^{3A}$ is $C_{1-4}$ alkyl, $C_{3-6}$ cycloalkyl, $C_{1-4}$ heteroalkyl, phenyl, 5-6 membered heteroaryl, —(CO)$R^{11A}$, or —C(O)$NR^{12A}R^{13A}$, wherein the $C_{1-4}$ alkyl, $C_{3-6}$ cycloalkyl, $C_{1-4}$ heteroalkyl, phenyl, or 5-6 membered heteroaryl, are each independently optionally substituted with 1-3 $R^{9A}$ substituents.

A62. The compound of embodiment A61, wherein $R^{9A}$ is independently selected from the group consisting of $C_{1-4}$ alkyl, $C_{3-5}$ cycloalkyl, —(CO)$R^{11A}$, $C_{1-4}$ hydroxyalkyl, $C_{1-4}$ heteroalkyl, 4-6 membered heterocycloalkyl, $C_{1-4}$ alkoxy, or $C_{3-5}$ cycloalkoxy.

A63. The compound of embodiment A61 or embodiment A62, wherein $R^{9A}$ is independently selected from the group consisting of methyl, ethyl, isopropyl, cyclopropyl, cyclobutyl, —(CO)$R^{11A}$, $C_{2-3}$ hydroxyalkyl, $C_{2-4}$ heteroalkyl, methoxy, ethoxy, isopropoxy, cyclopropoxy, cyclobutoxy, imidazolyl, or piperidinyl.

A64. The compound of any one of embodiments A1 to A63, wherein $R^{3A}$ is: —$CH_3$, unsubstituted phenyl, (4-methoxy)-phenyl, ispropyl, cyclopropyl,

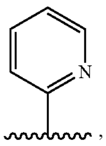,
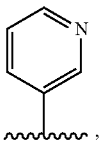,
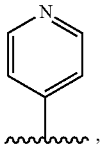,
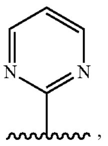,
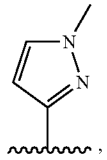,
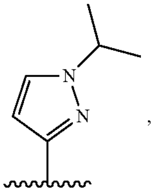,
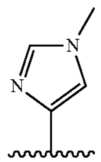,
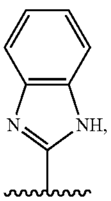,
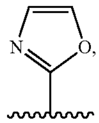

-continued

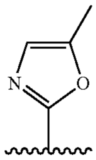, 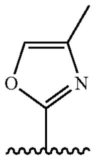, 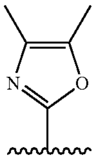,

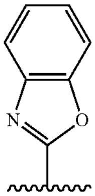, 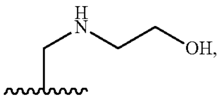

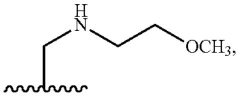 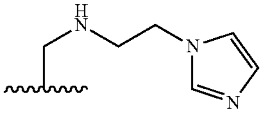,

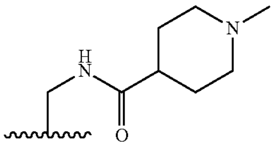, 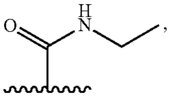,

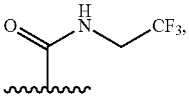 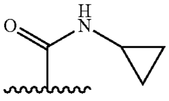,

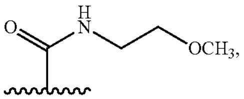 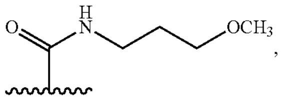,

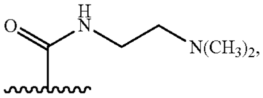 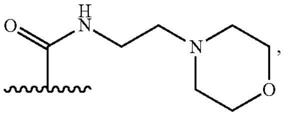,

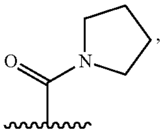, 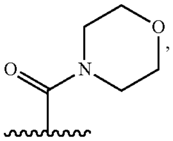, or 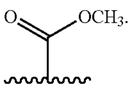.

A65. The compound of embodiment A64, wherein $R^{3A}$ is: —$CH_3$, unsubstituted phenyl, isopropyl, cyclopropyl,

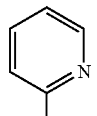, 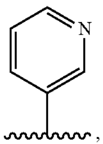, 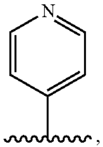, 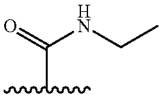,

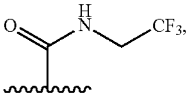 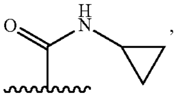,

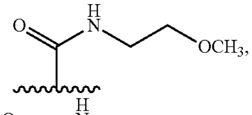 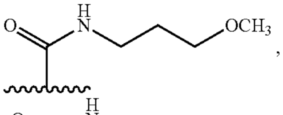,

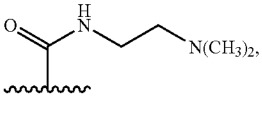 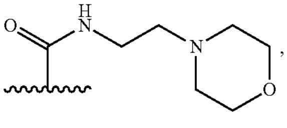,

-continued

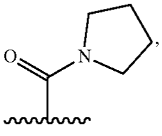, 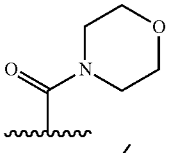, 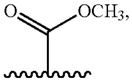 or

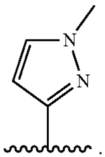.

A66. The compound of any one of embodiments A1 to A65, wherein $R^{4A}$ is phenyl or 5-10 membered heteroaryl, wherein the phenyl or 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached.

A67. The compound of any one of embodiments A1 to A66, wherein $R^{4A}$ is phenyl optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached.

A68. The compound of any one of embodiments A1 to A66, wherein $R^{4A}$ is 5-6 membered heteroaryl optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached.

A69. The compound of any one of embodiments A66 to A68, wherein $R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl.

A70. The compound of any one of embodiments A66 to A69, wherein $R^{10A}$ is independently selected from the group consisting of halo, $C_{1-4}$ alkyl, $C_{3-5}$ cycloalkyl, $C_{1-4}$ haloalkyl, $C_{1-4}$ hydroxyalkyl, $C_{1-4}$ heteroalkyl, 3-5 membered heterocycloalkyl, —OH, $C_{1-4}$ alkoxy, $C_{3-5}$ cycloalkoxy, $C_{1-4}$ haloalkoxy, or —$NR^{12A}R^{13A}$.

A71. The compound of any one of embodiments A66 to A70, wherein $R^{10A}$ is independently selected from the group consisting of halo, methyl, ethyl, isopropyl, cyclopropyl, cyclobutyl, $C_{1-3}$ haloalkyl, $C_{2-3}$ hydroxyalkyl, $C_{2-4}$ heteroalkyl, —OH, methoxy, ethoxy, isopropoxy, cyclopropoxy, cyclobutoxy, $C_{1-4}$ haloalkoxy, or —$NR^{12A}R^{13A}$.

A72. The compound of any one of embodiments A69 to A71, wherein $R^{12A}$ and $R^{13A}$ are each independently selected from the group consisting of hydrogen, $C_{1-4}$ alkyl, $C_{3-5}$ cycloalkyl, $C_{1-4}$ hydroxyalkyl, $C_{1-4}$ heteroalkyl, —OH, or $C_{1-4}$ alkoxy.

A73. The compound of any one of embodiments A69 to A72, wherein $R^{12A}$ and $R^{13A}$ are each independently selected from the group consisting of hydrogen, methyl, ethyl, isopropyl, cyclopropyl, cyclobutyl, methoxy, or ethoxy.

A74. The compound of any one of embodiments A69 to A73, wherein $R^{12A}$ and $R^{13A}$ are each independently selected from the group consisting of hydrogen or methyl.

A75. The compound of any one of embodiments A69 to A74, wherein $R^{12A}$ and $R^{13A}$ are each hydrogen.

A76. The compound of any one of embodiments A1 to A75, wherein $R^{4A}$ is: hydrogen, unsubstituted phenyl,
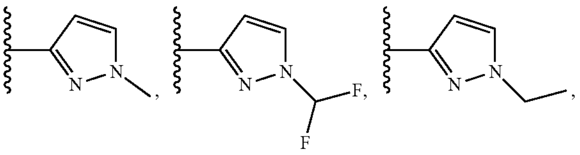
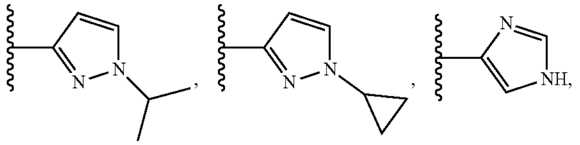
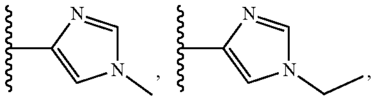
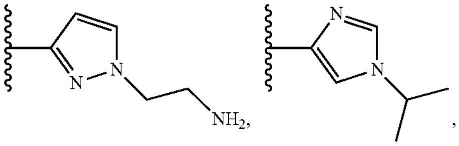
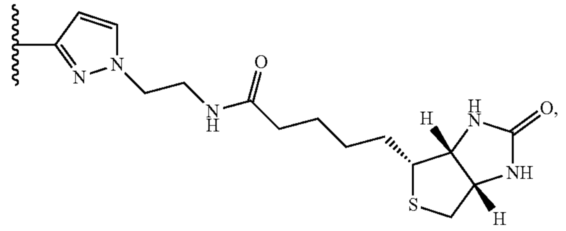
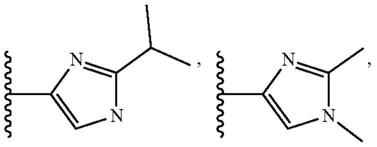
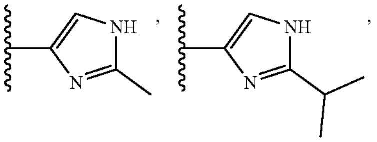
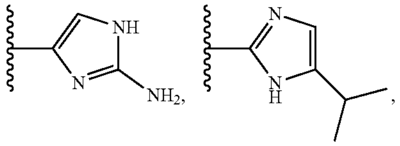
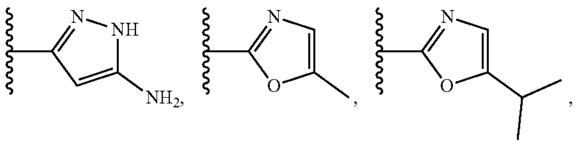
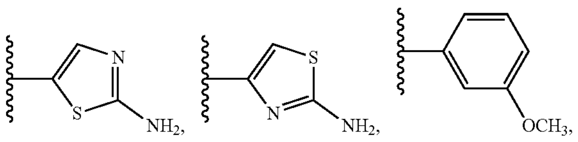
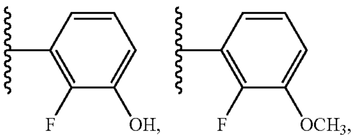
-continued
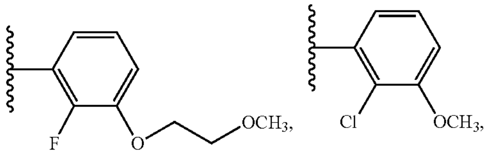
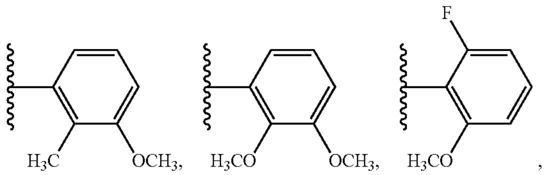
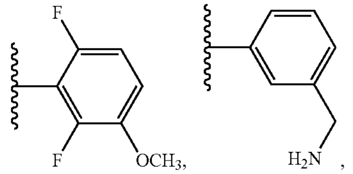
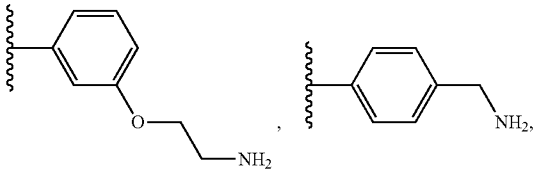
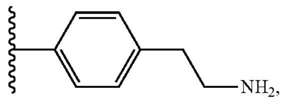
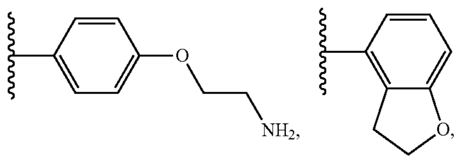
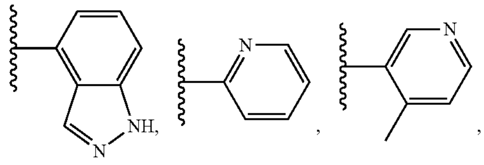
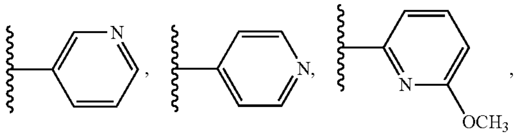
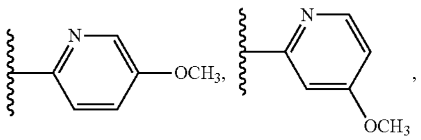
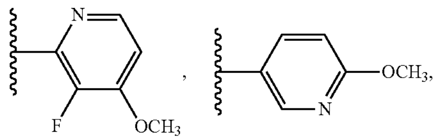
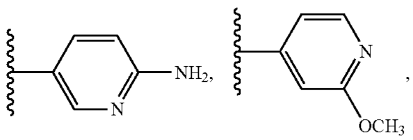
, or -continued

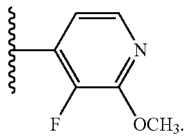

A77. The compound of embodiment A76, wherein $R^{4A}$ is: hydrogen, unsubstituted phenyl,

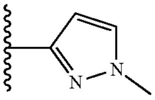,
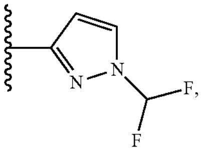,
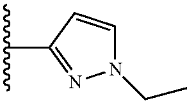,
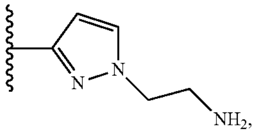,
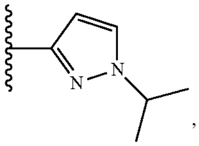,
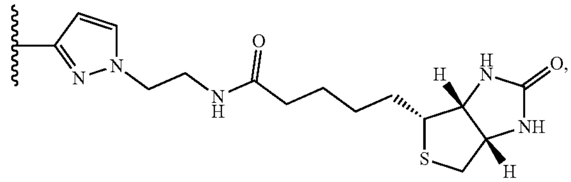,
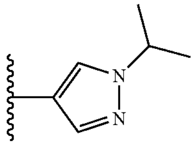,
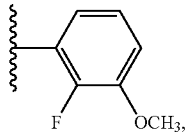,
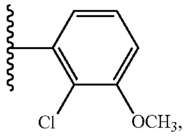,
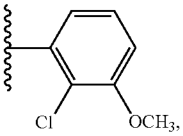,
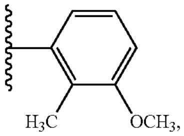,
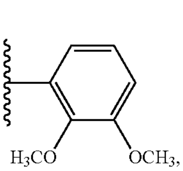,
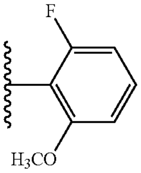,
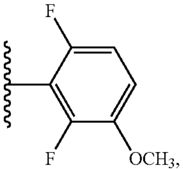,
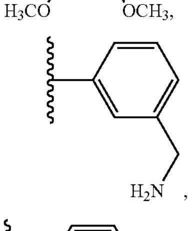,
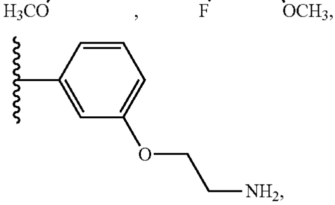,
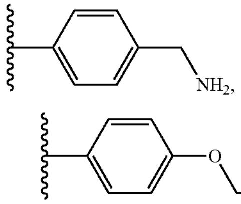,
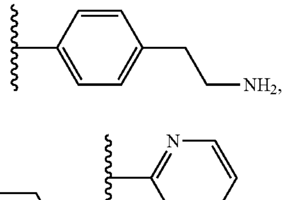,
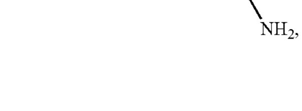,
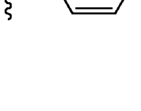, -continued

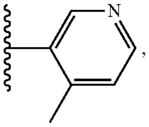,
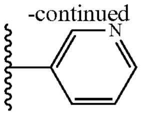,
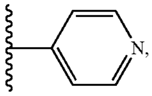,
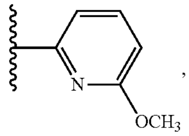,
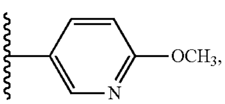,
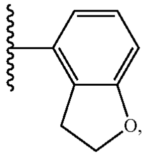
or
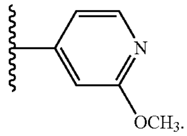

A78. A compound of Formula IIa(1):

Formula IIa(1)

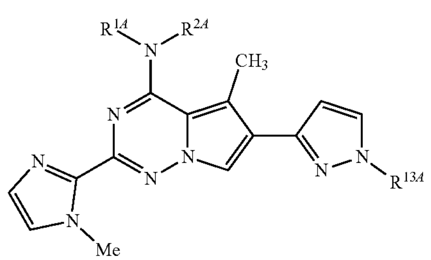

or a pharmaceutically acceptable form thereof, wherein:

$R^{1A}$ is hydrogen;

$R^{2A}$ is 5 or 6 membered heteroaryl, wherein the 5 or 6 membered heteroaryl is optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{8A}$ is selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —(CO)$R^{11A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy, or $R^{12A}$ and $R^{13A}$ are combined to form a 5 or 6 membered heterocycloalkyl including the nitrogen atom to which they are both attached; and $R^{18A}$ is $C_{1-3}$ alkyl or $C_{3-6}$ cycloalkyl.

A79. The compound of embodiment A78, wherein $R^{18A}$ is methyl, ethyl, isopropyl, or cyclopropyl.

A80. The compound of embodiment A79, wherein $R^{18A}$ is methyl.

A81. The compound of embodiment A79, wherein $R^{18A}$ is ethyl.

A82. The compound of embodiment A79, wherein $R^{18A}$ is isopropyl.

A83. The compound of embodiment A79, wherein $R^{18A}$ is cyclopropyl.

A84. The compound of any one of embodiments A78-A83, wherein $R^{8A}$ is selected from the group consisting of $C_{1-6}$ alkyl, $C_{3-6}$ cycloalkyl, 3-6 membered heterocycloalkyl, $C_{1-6}$ alkoxy, or $C_{3-6}$ cycloalkoxy, —$NR^{12A}R^{13A}$, or 5-6 membered heteroaryl.

A85. The compound of any one of embodiments A78-A84, wherein $R^{2A}$ is pyridyl, pyrimidyl, pyrazyl, or pyrazolyl, wherein the pyridyl, pyrimidyl, pyrazyl, or pyrazolyl is optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached.

A86. The compound of embodiment A85, wherein $R^{2A}$ is pyridyl, optionally substituted with 1-2 $R^{8A}$ substituents.

A87. The compound of embodiment A86, wherein $R^{2A}$ is

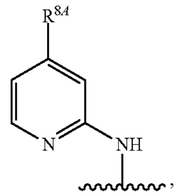,
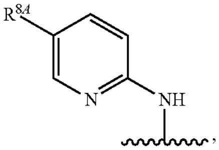,
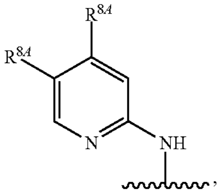, or
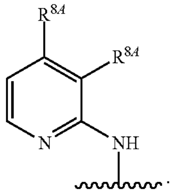.

A88. The compound of embodiment A85, wherein $R^{2A}$ is pyrimidyl, optionally substituted with 1-2 $R^{8A}$ substituents.

A89. The compound of embodiment A88, wherein $R^{2A}$ is

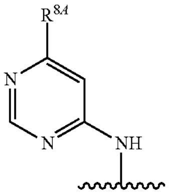 or
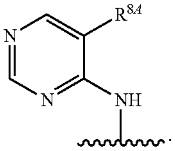.

A90. The compound of embodiment A85, wherein $R^{2A}$ is pyrazyl, optionally substituted with 1-2 $R^{8A}$ substituents.

A91. The compound of embodiment A85, wherein $R^{2A}$ is pyrazolyl, optionally substituted with 1-2 $R^{8A}$ substituents.

A92. The compound of embodiment A91, wherein $R^{2A}$ is

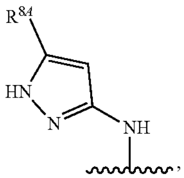,
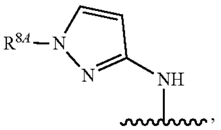,

-continued

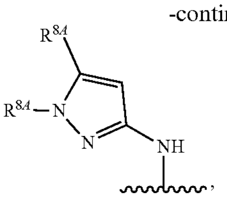, or
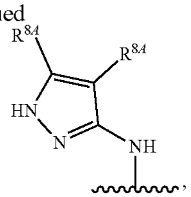,

A93. The compound of any one of embodiments A85-A92, wherein the 2 independent $R^{8A}$ substituents are combined to form a 5 membered cycloalkyl or 5 membered heterocycloalkyl including the atom or atoms to which each are attached.

A94. The compound of any one of embodiments A78-A93, wherein $R^{1A}$ and $R^{2A}$ together with the nitrogen to which they are attached have a structure of:

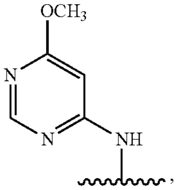,
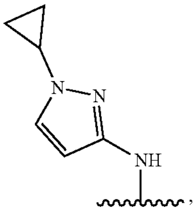,
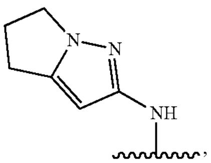,
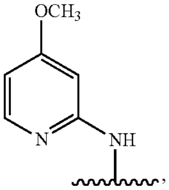,
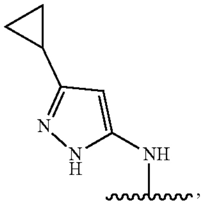,
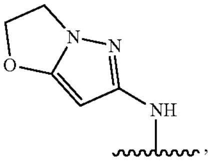,
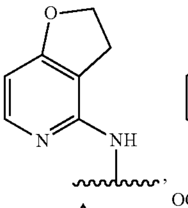,
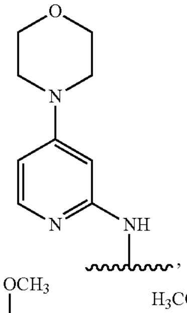,
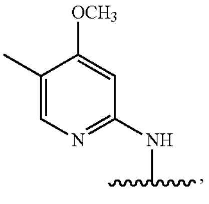,
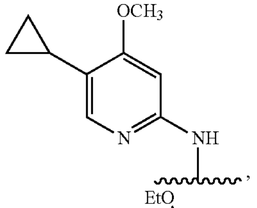,
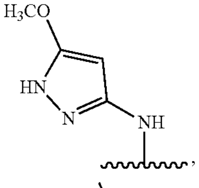,
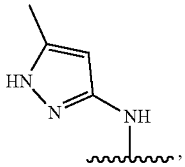,
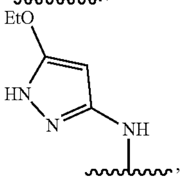,
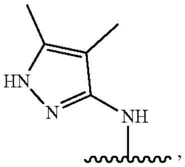, -continued

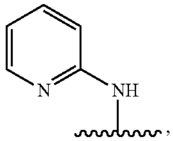, 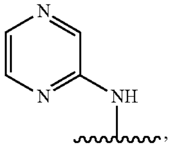, 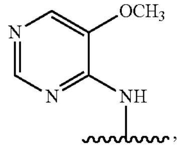,

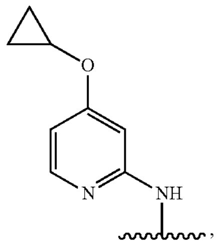, 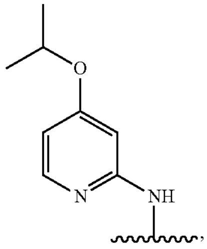,

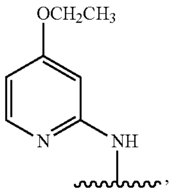, 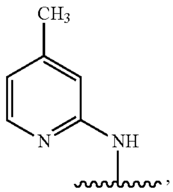, 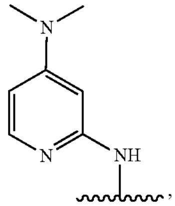,

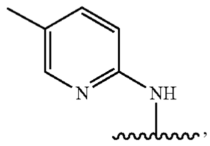, 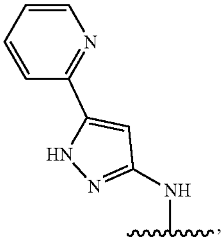, or

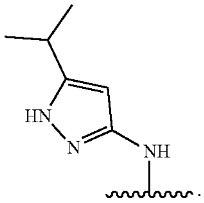.

A95. The compound of any one of embodiments A78-A94, wherein $R^{1A}$ and $R^{2A}$ together with the nitrogen to which they are attached have a structure of:

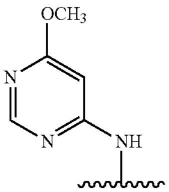, 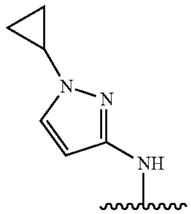,

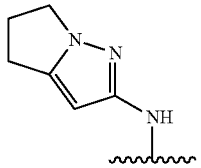, 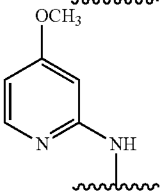,

-continued

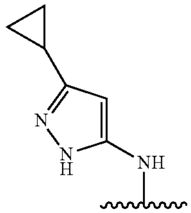, 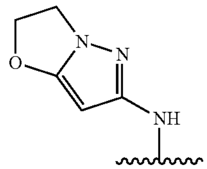,

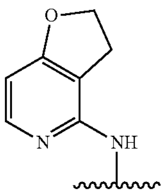, 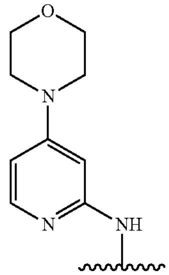, 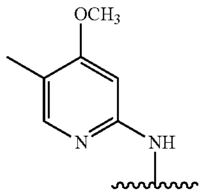,

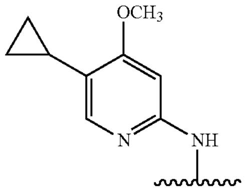, 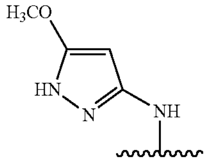,

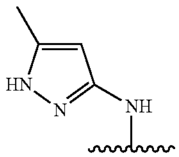, 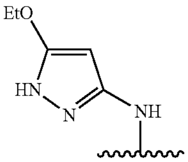, or

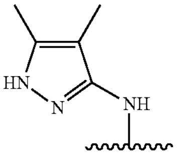,

A96. The compound of any one of embodiments A78-A95, wherein the compound is selected from the group consisting of Compounds 6, 57, 58, 62, 63, 64, 68, 84, 91, 100, 102, 104, 107, 124, 126, 136, 137, 141, 142, 143, 144, 145, 157, 221, 222, 226, 235, 238, 252, 255, 260, 265, 267, and 268.

A97. The compound of any one of embodiments A78-A96, wherein the compound is selected from the group consisting of Compounds 6, 84, 100, 102, 104, 124, 221, 222, 235, 238, 252, 255, 260, and 267.

A98. The compound of any one of embodiments A1 to A97, wherein the compound has a MW of no more than 1,000 g/mol.

A99. The compound of any one of embodiments A1 to A98, wherein the compound has a MW of no more than 900 g/mol, no more than 800 g/mol, no more than 700 g/mol, no more than 600 g/mol, or no more than 500 g/mol.

A100. The compound of any one of embodiments A1 to A99, wherein the compound has a MW of no more than 600 g/mol.

A101. The compound of any one of embodiments A1 to A100, wherein the compound has a MW of no more than 500 g/mol.

A102. The compound of any one of claims A1 to A101, wherein the compound is selected from the group consisting of Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, and 276, or a pharmaceutically acceptable form thereof.

A103. The compound of any one of embodiments A1 to A102, wherein the compound is selected from the group consisting of Compounds 6, 17, 22, 32, 34, 37, 42, 43, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 126, 127, 135, 136, 137, 138, 139, 140, 141, 142, 143, 144, 145, 146, 147, 148, 149, 150, 151, 152, 153, 154, 156, 157, 158, 165, 166, 167, 169, 170, 172, 173, 174, 175, 176, 177, 178, 179, 186, 187, 188, 196, 200, 202, 208, 211, 212, 213, 214, 215, 216, 217, 220, 221, 222, 223, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof.

A104. The compound of any one of embodiments A1 to A103, wherein the compound is selected from the group consisting of Compounds 6, 17, 22, 37, 44, 45, 46, 48, 49, 50, 51, 53, 54, 55, 56, 57, 58, 59, 60, 61, 62, 63, 64, 65, 66, 67, 68, 72, 73, 75, 76, 77, 78, 79, 81, 82, 83, 84, 86, 89, 90, 91, 93, 94, 95, 96, 97, 98, 99, 100, 101, 102, 104, 105, 107, 108, 109, 110, 111, 113, 114, 116, 118, 119, 120, 121, 122, 123, 124, 125, 127, 135, 136, 137, 138, 139, 140, 141, 142, 143, 144, 145, 146, 147, 149, 150, 151, 152, 153, 154, 156, 157, 158, 165, 166, 169, 170, 173, 175, 176, 177, 178, 179, 186, 187, 188, 196, 202, 208, 211, 212, 213, 214, 215, 216, 217, 221, 222, 224, 226, 227, 228, 229, 230, 231, 232, 233, 234, 235, 236, 237, 238, 239, 240, 241, 243, 244, 245, 246, 247, 248, 249, 250, 252, 253, 254, 255, 256, 257, 259, 260, 261, 262, 263, 264, 265, 266, 267, 268, 269, 270, and 276, or a pharmaceutically acceptable form thereof.

A105. The compound of any one of embodiments A1 to A104, wherein the compound is selected from the group consisting of Compounds 3, 4, 20, 23, 26, 29, 30, 31, 32, 33, 34, 36, 42, 43, 53, 58, 67, 93, 203, 209, 210, 219, 266, 269, 270, 271, 272, 273, and 274, or a pharmaceutically acceptable form thereof.

A106. The compound of any one of embodiments A1 to A105, wherein the compound is selected from the group consisting of Compounds 3, 4, 20, 23, 26, 29, 30, 31, 32, 33, 34, 42, 43, 53, 58, 67, 93, 203, 209, 210, 219, 266, 269, 270, 271, 272, 273, and 274, or a pharmaceutically acceptable form thereof.

A107. The compound of any one of embodiments A1 to A104, wherein the compound is selected from the group consisting of Compounds 49, 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 130, 135, 136, 138, 143, 145, 148, 149, 151, 154, 156, 157, 165, 174, 175, 176, 177, 178, 179, 183, 190, 191, 192, 193, 194, 195, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof.

A108. The compound of any one of embodiments A1 to A104 or A107, wherein the compound is selected from the group consisting of Compounds 68, 69, 71, 72, 73, 74, 77, 78, 79, 80, 83, 84, 86, 87, 89, 90, 91, 94, 95, 97, 98, 99, 100, 104, 107, 113, 116, 118, 120, 121, 124, 126, 127, 128, 129, 135, 136, 138, 143, 145, 148, 149, 151, 154, 156, 157, 165, 174, 175, 176, 177, 178, 179, 183, 190, 191, 192, 193, 194, 196, 197, 198, 199, 200, 201, 202, 204, 205, 207, 208, 213, 216, 217, 218, 224, 227, 230, 231, 233, 234, 236, 239, 243, 247, 248, 249, 250, 253, 254, 257, 267, 268, and 276, or a pharmaceutically acceptable form thereof.

A109. The compound of any one of embodiments A1 to A108, wherein the compound is selected from the group consisting of Compounds 17, 20, 23, 25, 29, 30, 31, 32, 33, 34, 42, 203, 209, 210, 219, 270, 271, 272, 273, and 274, or a pharmaceutically acceptable form thereof.

A110. The compound of any one of embodiments A1 to A108, wherein the compound is selected from the group consisting of Compounds 1, 2, 18, 19, 21, 47, 48, 49, 50, 51, 57, 59, 60, 61, 62, 63, 64, 65, 66, 67, 68, 69, 70, 71, 72, 73, 74, 76, 77, 78, 79, 80, 81, 82, 83, 84, 85, 86, 87, 88, 89, 91, 93, 94, 95, 96, 97, 98, 100, 101, 102, 103, 104, 106, 107, 108, 109, 110, 111, 112, 113, 114, 115, 116, 118, 119, 122, 124, 125, 126, 127, 128, 129, 130, 135, 136, 137, 138, 143, 145, 149, 151, 156, 157, 158, 165, 166, 169, 170, 173, 174, 175, 176, 178, 179, 187, 190, 191, 192, 193, 194, 195, 196, 204, 205, 207, 208, 213, 217, 218, 221, 222, 224, 226, 227, 228, 229, 230, 231, 232, 233, 234, 235, 237, 238, 240, 241, 242, 243, 244, 245, 246, 247, 248, 249, 250, 252, 253, 254, 255, 256, 257, 259, 260, 263, 264, 265, 266, 267, 268, 275, and 276, or a pharmaceutically acceptable form thereof.

A111. The compound of any one of embodiments A1 to A110, wherein the compound is selected from the group consisting of Compounds 27, 29, 30, 31, 32, 33, 36, 43, 44, 47, 51, 52, 55, 59, 85, 96, 97, 98, 99, 116, 141, 144, 156, 203, 205, 207, 208, 209, 210, 211, 214, 219, 230, 269, 272, 273, and 274, or a pharmaceutically acceptable form thereof.

A112. The compound of any one of embodiments A1 to A111, wherein the compound is selected from the group consisting of Compounds 29, 30, 31, 32, 33, 36, 44, 47, 59, 85, 97, 98, 99, 116, 141, 144, 156, 203, 205, 207, 208, 209, 210, 211, 214, 219, 230, 269, 272, 273, and 274, or a pharmaceutically acceptable form thereof.

A113. The compound of any one of embodiments A1 to A110, wherein the compound is selected from the group consisting of Compounds 56, 63, 84, 88, 89, 90, 95, 100, 101, 103, 104, 106, 108, 109, 111, 112, 113, 114, 129, 166, 173, 179, 183, 186, 216, 241, 247, 248, 250, 255, 256, 257, and 266, or a pharmaceutically acceptable form thereof.

A114. The compound of any one of embodiments A1 to A113, wherein the compound is selected from the group consisting of Compounds 29, 30, 32, 33, and 34, or a pharmaceutically acceptable form thereof.

A115. The compound of any one of embodiments A1 to A114, wherein the compound is selected from the group consisting of Compounds 29, 32, 33, and 34, or a pharmaceutically acceptable form thereof.

A116. The compound of any one of embodiments A1 to A115, wherein the compound is selected from the group consisting of Compounds 29, 32, and 34, or a pharmaceutically acceptable form thereof.

A117. The compound of any one of embodiments A1 to A113, wherein the compound is selected from the group consisting of Compounds 1, 2, 3, 4, 6, 7, 8, 9, 11, 13, 14, 15, 16, 18, 19, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof.

A118. The compound of any one of embodiments A1 to A113 or A117, wherein the compound is selected from the group consisting of Compounds 3, 4, 6, 7, 11, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof.

A119. The compound of any one of embodiments A1 to A113, A117, or A118, wherein the compound is selected from the group consisting of Compounds 3, 6, 7, 13, 20, 21, 22, 23, 24, 25, 26, 27, 28, 31, 35, 36, 42, 43, 44, 45, 46, 47, 51, 53, 54, 55, 56, 57, 58, 59, 60, 61, 62, 63, 64, 65, 66, 67, 69, 70, 71, 72, and 93, or a pharmaceutically acceptable form thereof.

A120. The compound of any one of embodiments A1 to A119, wherein the compound is selected from the group consisting of Compounds 29, 30, 32, 33, 34, 46, 47, 188, 196, 197, 203, 205, 207, 208, 209, 210, 212, 213, 214, 215, 217, and 220, or a pharmaceutically acceptable form thereof.

A121. The compound of any one of embodiments A1 to A120, wherein the compound is selected from the group consisting of Compounds 29, 32, 33, 34, 46, 207, and 209, or a pharmaceutically acceptable form thereof.

A122. The compound of any one of embodiments A1 to A119, wherein the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 52, 53, 54, 55, 56, 57, 58, 59, 60, 61, 62, 63, 64, 65, 66, 67, 69, 70, 71, 72, 93, and 218, or a pharmaceutically acceptable form thereof.

A123. The compound of any one of embodiments A1 to A119 or A122, wherein the compound is selected from the group consisting of Compounds 1, 2, 3, 4, 7, 8, 9, 10, 11, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof.

A124. The compound of any one of embodiments A1 to A119, A122 or A123, wherein the compound is selected from the group consisting of Compounds 1, 2, 3, 7, 8, 12, 13, 14, 15, 16, 18, 19, 20, 21, 22, 23, 24, 25, 26, 27, 28, 31, 35, 36, 42, 43, 44, 45, 51, 53, 54, 55, 56, 59, 60, 61, 62, 63, 64, 65, 66, 67, 69, 70, 71, 72, and 93, or a pharmaceutically acceptable form thereof.

A125. The compound of any one of embodiments A1 to A124, wherein the compound is selected from the group consisting of Compounds 6, 13, 22, 26, 29, 30, 32, 33, 34, 42, 45, 46, 48, 49, 50, 53, 54, 55, 56, 57, 58, 59, 61, 62, 63, 64, 65, 68, 72, 73, 74, 76, 78, 79, 81, 82, 83, 84, 86, 89, 91, 93, 94, 95, 96, 97, 98, 100, 101, 102, 104, 105, 106, 107, 108, 109, 110, 111, 112, 113, 114, 115, 116, 117, 118, 119, 120, 121, 122, 123, 124, 125, 126, 127, 128, 129, 135, 136, 137, 138, 139, 140, 141, 142, 143, 144, 145, 146, 149, 156, 157, 158, 165, 169, 170, 173, 174, 175, 176, 196, 203, 209, 210, 213, 214, 217, 219, 221, 222, 224, 226, 227, 228, 229, 230, 231, 232, 233, 234, 235, 236, 237, 238, 239, 240, 243, 244, 245, 246, 247, 248, 249, 250, 252, 253, 255, 257, 263, 264, 265, 266, 267, 268, 269, 270, 271, 274, and 276, or a pharmaceutically acceptable form thereof.

A126. The compound of any one of embodiments A1 to A125, wherein the compound is selected from the group consisting of Compounds 6, 13, 22, 26, 29, 30, 32, 33, 34, 42, 48, 49, 50, 53, 54, 55, 56, 57, 58, 59, 61, 62, 63, 64, 65, 68, 72, 73, 74, 76, 78, 79, 81, 82, 83, 84, 86, 89, 91, 93, 94, 95, 96, 97, 98, 100, 101, 102, 104, 105, 106, 107, 108, 109, 110, 111, 112, 113, 114, 115, 116, 117, 118, 120, 122, 123, 124, 125, 126, 127, 128, 129, 135, 136, 137, 138, 139, 140, 141, 142, 143, 144, 145, 146, 149, 156, 157, 158, 165, 169, 170, 173, 174, 175, 176, 196, 203, 209, 210, 213, 217, 219, 221, 222, 224, 226, 227, 228, 229, 230, 231, 232, 233, 234, 235, 236, 237, 238, 239, 240, 243, 244, 245, 246, 247, 248, 249, 250, 252, 253, 255, 257, 263, 264, 265, 266, 267, 268, 269, 270, 271, 274, and 276, or a pharmaceutically acceptable form thereof.

A127. The compound of any one of embodiments A1 to A126, wherein the compound is selected from the group consisting of Compounds 6, 13, 22, 32, 34, 48, 49, 50, 53, 54, 55, 56, 57, 58, 59, 62, 63, 64, 65, 68, 73, 74, 76, 78, 79, 81, 82, 83, 84, 86, 89, 91, 93, 94, 95, 96, 97, 98, 100, 101, 102, 104, 106, 107, 110, 111, 112, 113, 114, 115, 116, 117, 118, 120, 122, 123, 124, 125, 126, 127, 128, 129, 135, 136, 137, 138, 139, 140, 141, 142, 143, 144, 145, 146, 156, 157, 158, 165, 169, 170, 174, 175, 196, 209, 221, 222, 224, 226, 227, 228, 229, 230, 231, 232, 233, 234, 235, 236, 237, 238, 239, 240, 243, 244, 245, 246, 247, 248, 249, 250, 252, 255, 257, 263, 264, 265, 266, 267, 268, 270, 271, 274, and 276, or a pharmaceutically acceptable form thereof.

A128. The compound of any one of embodiments A1 to A127, wherein the compound is selected from the group consisting of Compounds 6, 48, 49, 50, 53, 54, 55, 57, 58, 62, 63, 64, 65, 68, 73, 76, 79, 82, 84, 89, 91, 94, 95, 97, 98, 100, 102, 104, 106, 107, 110, 112, 113, 114, 115, 117, 118, 120, 122, 123, 124, 126, 127, 128, 129, 135, 136, 137, 138, 139, 140, 141, 142, 143, 144, 145, 156, 157, 158, 165, 169, 170, 196, 221, 222, 224, 226, 227, 228, 230, 231, 232, 233, 234, 235, 236, 237, 238, 239, 240, 243, 244, 245, 248, 249, 250, 252, 255, 257, 263, 265, 266, 267, and 268, or a pharmaceutically acceptable form thereof.

A129. The compound of any one of embodiments A1 to A128, wherein the compound is selected from the group consisting of Compounds 1, 4, 6, 13, 19, 20, 22, 23, 27, 29, 30, 31, 32, 33, 34, 40, 42, 45, 46, 67, 81, 82, 85, 86, 89, 93, 99, 104, 105, 111, 113, 143, 149, 160, 161, 163, 164, 166, 173, 175, 176, 177, 192, 193, 194, 196, 199, 201, 203, 204, 206, 207, 208, 209, 210, 217, 219, 238, 247, 248, 249, 250, 257, 260, 263, 264, 265, 268, 269, 270, 271, 272, 273, and 274, or a pharmaceutically acceptable form thereof.

A130. The compound of any one of embodiments A1 to A129, wherein the compound is selected from the group consisting of Compounds 4, 23, 29, 30, 31, 32, 33, 42, 45, 46, 93, 99, 149, 166, 196, 203, 207, 209, 210, 219, 269, 270, 271, 272, 273, and 274, or a pharmaceutically acceptable form thereof.

A131. The compound of any one of embodiments A1 to A130, wherein the compound is selected from the group consisting of Compounds 53, 55, 57, 58, 84, 91, 100, 102, 116, 118, 124, 137, 141, 142, 145, 158, 221, 222, 255, and 267, or a pharmaceutically acceptable form thereof.

A132. The compound of any one of embodiments A1 to A131, wherein the compound is selected from the group consisting of Compounds 91, 102, 118, and 255, or a pharmaceutically acceptable form thereof.

A133. The compound of any one of embodiments A1 to A132, wherein the compound is selected from the group consisting of Compounds 6, 102, 104, 124, 126, 128, 129, 137, 141, 142, 144, 145, 156, 157, 224, 226, 227, 235, 238, 248, 255, 265, and 267, or a pharmaceutically acceptable form thereof.

A134. The compound of any one of embodiments A1 to A133, wherein the compound is selected from the group consisting of Compounds 6, 58, 84, 100, 102, 104, 124, 221, 222, 235, 238, 252, 255, and 267, or a pharmaceutically acceptable form thereof.

A135. The compound of any one of embodiments A1 to A134, wherein the pharmaceutically acceptable form of the compound is an isomer, isotopic variant, pharmaceutically acceptable salt, polymorph, or solvate of said compound.

A136. The compound of any one of embodiments A1 to A134, wherein the pharmaceutically acceptable form of the compound is exclusive of a salt form.

A137. The compound of any one of embodiments A1 to A136, wherein the isomer of the compound is a diastereomer or enantiomer of the compound.

A138. The compound of any one of embodiments A1 to A137, wherein the compound is a tautomer of the compound.

A139. The compound of any one of embodiments A1 to A138, wherein the compound is a racemate or a mixture of diasteromers.

A140. The compound of any one of embodiments A1 to A138, wherein the compound is a single enantiomer or a single diastereomer.

A141. The compound of embodiment A140, wherein the compound is an (R)-enantiomer.

A142. The compound of embodiment A140 or embodiment A141, wherein the compound has an enantiomeric excess of greater than 10% of the ®-enantiomer.

A143. The compound of any one of embodiments A140 to A142, wherein the compound has an enantiomeric excess of 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, 98% or more, or 99% or more of the ®-enantiomer.

A144. The compound of any one of embodiments A140 to A143, wherein the compound has an enantiomeric excess of about 90%, about 91%, about 92%, about 93%, about 94%, about 95%, about 96%, about 97%, about 98%, or about 99%, of the (R)-enantiomer.

A145. The compound of embodiment A140, wherein the compound is an (S)-enantiomer.

A146. The compound of embodiment A140 or embodiment A145, wherein the compound has an enantiomeric excess of greater than 10% of the (S)-enantiomer.

A147. The compound of any one of embodiments A140, A145, or A146 wherein the compound has an enantiomeric excess of 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, 98% or more, or 99% or more of the (S)-enantiomer.

A148. The compound of any one of embodiments A140, or A145 to A147, wherein the compound has an enantiomeric excess of about 90%, about 91%, about 92%, about 93%, about 94%, about 95%, about 96%, about 97%, about 98%, or about 99%, of the (S)-enantiomer.

A149. The compound of any one of embodiments A1 to A148, wherein the compound or pharmaceutically acceptable form thereof is a modulator of Ras superfamily activity according to a Ras Superfamily Activity Assay.

A150. The compound of embodiment A149, wherein the compound or pharmaceutically acceptable form thereof modulates Ras superfamily activity of one or more GTPase by 50% or more, 55% or more, 60% or more, 65% or more, 70% or more, 75% or more, 80% or more, 85% or more, 90% or more, or 95% or more at 20 μM according to a Ras Superfamily Activity Assay.

A151. The compound of any one of embodiments A1 to A150, wherein the compound or pharmaceutically acceptable form thereof inhibits phosphorylation of Erk1/2 according to Erk1/2 Phosphorylation Assay.

A152. The compound of embodiment A151, wherein the compound or pharmaceutically acceptable form thereof inhibits phosphorylation of Erk1/2 by 50% or more, 55% or more, 60% or more, 65% or more, 70% or more, 75% or more, 80% or more, 85% or more, 90% or more, or 95% or more at 10 μM according to Erk1/2 Phosphorylation Assay.

A153. The compound of any one of embodiments A1 to A150, wherein the compound or pharmaceutically acceptable form thereof activates phosphorylation of Erk1/2 according to Erk1/2 Phosphorylation Assay.

A154. The compound of embodiment 153, wherein the compound or pharmaceutically acceptable form thereof activates phosphorylation of Erk1/2 by 50% or more, 55% or more, 60% or more, 65% or more, 70% or more, 75% or more, 80% or more, 85% or more, 90% or more, 95% or more, or equal or greater than 100% at 10 μM according to Erk1/2 Phosphorylation Assay.

A155. The compound of any one of embodiments A1 to A154, wherein the compound or pharmaceutically acceptable form thereof inhibits phosphorylation of Akt according to Akt Phosphorylation Assay.

A156. The compound of embodiment A155, wherein the compound or pharmaceutically acceptable form thereof inhibits phosphorylation of Akt by 50% or more, 55% or more, 60% or more, 65% or more, 70% or more, 75% or more, 80% or more, 85% or more, 90% or more, or 95% or more at 10 μM according to Akt Phosphorylation Assay.

A157. The compound of any one of embodiments A1 to A154, wherein the compound or pharmaceutically acceptable form thereof activates phosphorylation of Akt according to Akt Phosphorylation Assay.

A158. The compound of embodiment A157, wherein the compound or pharmaceutically acceptable form thereof activates phosphorylation of Akt by 50% or more, 55% or more, 60% or more, 65% or more, 70% or more, 75% or more, 80% or more, 85% or more, 90% or more, 95% or more, or equal or greater than 100% at 10 μM according to Akt Phosphorylation Assay.

A159. The compound of any one of embodiments A1 to A158, wherein the compound or pharmaceutically acceptable form thereof inhibits phosphorylation of Smad2/3 according to Phospho-Smad2/3 Inhibition Assay.

A160. The compound of embodiment A159, wherein the compound or pharmaceutically acceptable form thereof inhibits phosphorylation of Smad2/3 by 50% or more, 55% or more, 60% or more, 65% or more, 70% or more, 75% or more, 80% or more, 85% or more, 90% or more, or 95% or more at 10 μM according to Phospho-Smad2/3 Inhibition Assay.

A161. The compound of any one of embodiments A1 to A158, wherein the compound or pharmaceutically acceptable form thereof activates phosphorylation of Smad2/3 according to Phospho-Smad2/3 Inhibition Assay.

A162. The compound of embodiment A161, wherein the compound or pharmaceutically acceptable form thereof activates phosphorylation of Smad2/3 by 50% or more, 55% or more, 60% or more, 65% or more, 70% or more, 75% or more, 80% or more, 85% or more, 90% or more, 95% or more, or equal or greater than 100% at 10 μM according to Phospho-Smad2/3 Inhibition Assay.

A163. The compound of any one of embodiments A1 to A162, wherein the compound or pharmaceutically acceptable form thereof inhibits JNK according to JNK Activation Assay.

A164. The compound of embodiment A163, wherein the compound or pharmaceutically acceptable form thereof inhibits JNK by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to JNK Activation Assay.

A165. The compound of any one of embodiments A1 to A162, wherein the compound or pharmaceutically acceptable form thereof activates JNK according to JNK Activation Assay.

A166. The compound of embodiment A165, wherein the compound or pharmaceutically acceptable form thereof activates JNK by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to JNK Activation Assay.

A167. The compound of any one of embodiments A1 to A166, wherein the compound or pharmaceutically acceptable form thereof inhibits MAPK p38 according to MAPK p38 Activation Assay.

A168. The compound of embodiment A167, wherein the compound or pharmaceutically acceptable form thereof inhibits MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more at 10 μM according to MAPK p38 Activation Assay.

A169. The compound of any one of embodiments A1 to A166, wherein the compound or pharmaceutically acceptable form thereof activates MAPK p38 according to MAPK p38 Activation Assay.

A170. The compound of embodiment A169, wherein the compound or pharmaceutically acceptable form thereof activates MAPK p38 by 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or equal or greater than 100% at 10 μM according to MAPK p38 Activation Assay.

A171. The compound of any one of embodiments A1 to A170, wherein the compound or pharmaceutically acceptable form thereof inhibits proliferation in MiaPaca2 according to Proliferation Assay.

A172. The compound of embodiment A171, wherein the compound or pharmaceutically acceptable form thereof inhibits proliferation in MiaPaca2 with an $IC_{50}$ value of 1 μM or less, 0.9 μM or less, 0.8 μM or less, 0.75 μM or less, 0.7 μM or less, 0.6 μM or less, 0.5 μM or less, 0.4 μM or less, 0.3 μM or less, 0.25 μM or less, 0.2 μM or less, 0.15 μM or less, or 0.1 μM or less according to Proliferation Assay.

A173. The compound of any one of embodiments A1 to A172, wherein the compound or pharmaceutically acceptable form thereof inhibits IL-6 according to IL-6 Quantification Assay.

A174. The compound of embodiment A173, wherein the compound or pharmaceutically acceptable form thereof inhibits IL-6 by 50% or more, 55% or more, 60% or more, 65% or more, 70% or more, 75% or more, 80% or more, 85% or more, 90% or more, or 95% or more at 10 μM according to IL-6 Quantification Assay.

A175. The compound of any one of embodiments A1 to A174, wherein the compound or pharmaceutically acceptable form thereof inhibits TNF-alpha according to TNF-alpha Quantification Assay.

A176. The compound of embodiment A175, wherein the compound or pharmaceutically acceptable form thereof inhibits TNF-alpha by 50% or more, 55% or more, 60% or more, 65% or more, 70% or more, 75% or more, 80% or more, 85% or more, 90% or more, or 95% or more at 10 μM according to TNF-alpha Quantification Assay.

A177. The compound of any one of embodiments A1 to A176, wherein the compound or pharmaceutically acceptable form thereof has a half-life of 10 minutes or more, 20 minutes or more, 30 minutes or more, 40 minutes or more, or 50 minutes or more in mouse liver microsomes according to Mouse Liver Microsome Metabolic Stability Assay.

A178. The compound of any one of embodiments A1 to A177, wherein the compound or pharmaceutically acceptable form thereof has a kinetic solubility of 10 μM or more, 20 μM or more, 30 μM or more, 40 μM or more, 50 μM or more, 60 μM or more, 70 μM or more, 80 μM or more, 90 μM or more, 100 μM or more, 150 μM or more, or 200 μM or more in pH 7.4 buffer comprising 2% DMSO according to Kinetic Solubility Assay A179. The compound of any one of embodiments A1 to A178, wherein the compound or pharmaceutically acceptable form thereof inhibits proliferation in NCI-H358, A375, GP2d, BT549, or MM.R1 according to Proliferation Assay.

A180. The compound of embodiment A179, wherein the compound or pharmaceutically acceptable form thereof inhibits proliferation in NCI-H358, A375, GP2d, BT549, or MM.R1 with an $IC_{50}$ value of 50 nM or less, 40 nM or less, 30 nM or less, 20 nM or less, 10 nM or less, 1 nM or less, 0.1 nM or less, or 0.01 nM or less according to Proliferation Assay.

A181. The compound of embodiment A180, wherein the compound or pharmaceutically acceptable form thereof inhibits proliferation in MM.R1 with an $IC_{50}$ value of 1 nM or less, 0.1 nM or less, or 0.01 nM or less according to Proliferation Assay.

A182. A pharmaceutical composition comprising the compound or pharmaceutically acceptable form thereof, of any one of embodiments A1 to A181, and a pharmaceutically acceptable carrier, excipient or diluent.

A183. A method of modulating a Ras superfamily protein, comprising contacting the Ras superfamily protein with an effective amount of the compound of any one of embodiments A1-A181, or pharmaceutically acceptable form thereof.

A184. A method of modulating a Ras superfamily protein, comprising contacting the Ras superfamily protein with an effective amount of the pharmaceutical composition of embodiment A182.

A185. The method of embodiment A183 or embodiment A184, wherein the Ras superfamily protein is present in a cell.

A186. The method of any one of embodiments A183 to A185, wherein the method inhibits the Ras superfamily protein.

A187. The method of any one of embodiments A183 to A186, wherein the Ras superfamily protein is a Ras protein, or a mutant thereof.

A188. The method of embodiment A187, wherein the Ras protein is DIRAS I; DIRAS2; DIRAS3; ERAS; GEM; HRAS; KRAS; MRAS; NKIRASI; NKIRAS2; NRAS; RALA; RALB; RAP1A; RAP1B; RAP2A; RAP2B; RAP2C; RASD1; RASD2; RASLIOA; RASLIOB; RASLI IA; RASLIIB; RASL12; REMI; REM2; RERG; RERGL; RRAD; RRAS; or RRAS2.

A189. The method of embodiment A187 or embodiment A188, wherein the Ras protein is HRAS; KRAS; or NRAS, or a mutant thereof.

A190. The method of any one of embodiments A187 to A189, wherein the Ras protein is a KRAS mutant.

A191. The method of embodiment A190, wherein the KRAS mutant is a KRas G12D mutant, KRas G12C mutant, or KRas Q61H mutant.

A192. The method of any one of embodiments A187 to A189, wherein the Ras protein is HRAS or a mutant thereof.

A193. The method of any one of embodiments A187 to A189, wherein the Ras protein is NRAS or a mutant thereof.

A194. The method of any one of embodiments A183 to A186, wherein the Ras superfamily protein is a Rac protein, or a mutant thereof.

A195. The method of embodiment A194, wherein the Rac protein is RAC1; RAC2; RAC3; RHOG, or a mutant thereof.

A196. The method of embodiment A194 or embodiment A195, wherein the Rac protein is wild-type RAC1.

A197. The method of any one of embodiments A183 to A186, wherein the Ras superfamily protein is a Rho protein, or a mutant thereof.

A198. The method of embodiment A197, wherein the Rho protein is RHOA; RHOB; RHOBTB1; RHOBTB2; RHOBTB3; RHOC; RHOD; RHOF; RHOH; RHOJ; RHOQ; RHOU; RHOV; RND1; RND2; RND3; CDC42, or a mutant thereof.

A199. The method of embodiment A197 or embodiment A198, wherein the Rho protein is wild-type RHOA.

A200. The method of any one of embodiments A183 to A186, wherein the Ras superfamily protein is a Cdc42 protein, or a mutant thereof.

A201. The method of any one of embodiments A183 to A186, wherein the Ras superfamily protein is a Rheb protein, or a mutant thereof.

A202. The method of any one of embodiments A183 to A201, wherein the contacting of the Ras superfamily protein takes place in a cell.

A203. The method of embodiment A202, wherein the cell is in a subject.

A204. The method of embodiment A202 or embodiment A203, wherein the cell is a mammalian cell.

A205. The method of any one of embodiments A202 to A204, wherein the cell is a human cell.

A206. The method of any one of embodiment A203 to A205, wherein the subject suffers from a cancer.

A207. The method of any one of embodiment A183 to A206, wherein the modulation takes place in a subject suffering from a cancer.

A208. The method of embodiment A206 or embodiment A207, wherein the cancer is a solid tumor or is a blood borne tumor (or a hematological cancer).

A209. The method of any one of embodiments A206 to A208, wherein the cancer is hepatocellular carcinoma, prostate cancer, pancreatic cancer, lung cancer, breast cancer, ovarian cancer, colon cancer, small intestine cancer, biliary tract cancer, endometrium cancer, skin cancer (melanoma), cervix cancer, urinary tract cancer, glioblastoma, or multiple myeloma.

A210. The method of embodiment A209, wherein the cancer is pancreatic cancer.

A211. The method of embodiment A209, wherein the cancer is colon cancer.

A212. The method of embodiment A209, wherein the cancer is triple negative breast cancer.

A213. The method of embodiment A209, wherein the cancer is multiple myeloma.

A214. The method of any one of embodiments A206 to A213 wherein the cancer is a cancer dependent on a Ras superfamily protein.

A215. The method of any one of embodiments A202 to A214, wherein the subject is a human.

A216. A method of modulating caspase activity, comprising contacting the caspase with an effective amount of the compound of any one of embodiments A1-A181, or pharmaceutically acceptable form thereof.

A217. A method of modulating caspase activity, comprising contacting the caspase with an effective amount of the pharmaceutical composition of embodiment A182.

A218. The method of embodiment A216 or embodiment A217, wherein the method activates the caspase.

A219. The method of any one of embodiments A216 to A218, wherein the caspase is caspase 3, caspase 6, or caspase 9.

A220. The method of any one of embodiments A216 to A219, wherein the contacting of the caspase takes place in a cell.

A221. The method of embodiment A220, wherein the modulation caspase activity induces apoptosis of the cell.

A222. The method of embodiment A220 or A221, wherein the cell is in a subject.

A223. The method of any one of embodiments A220 to A222, wherein the cell is a mammalian cell.

A224. The method of any one of embodiments A220 to A223, wherein the cell is a human cell.

A225. The method of any one of embodiments A220 to A224, wherein the subject suffers from a cancer.

A226. The method of any one of embodiment A216 to A225, wherein the modulation takes place in a subject suffering from a cancer.

A227. The method of embodiment A225 or embodiment A226, wherein the cancer is a solid tumor or is a blood borne tumor (or a hematological cancer).

A228. The method of any one of embodiments A225 to A227, wherein the cancer is hepatocellular carcinoma, prostate cancer, pancreatic cancer, lung cancer, breast cancer, ovarian cancer, colon cancer, small intestine cancer, biliary tract cancer, endometrium cancer, skin cancer (melanoma), cervix cancer, urinary tract cancer, glioblastoma, or multiple myeloma.

A229. The method of embodiment A228, wherein the cancer is pancreatic cancer.

A230. The method of embodiment A228, wherein the cancer is colon cancer.

A231. The method of embodiment A228, wherein the cancer is triple negative breast cancer.

A232. The method of embodiment A228, wherein the cancer is multiple myeloma.

A233. The method of any one of embodiments A222 to A232, wherein the subject is a human.

A234. A method of treating cancer in a subject, comprising administering a therapeutically effective amount of the compound of any one of embodiments A1-A181, or pharmaceutically acceptable form thereof, to the subject having cancer.

A235. A method of treating cancer in a subject, comprising administering a therapeutically effective amount of the pharmaceutical composition of embodiment A182 to the subject having cancer.

A236. The method of embodiment A234 or embodiment A235, wherein the cancer is a solid tumor or is a blood borne tumor (or a hematological cancer).

A237. The method of any one of embodiments A234 to A236, wherein the cancer is hepatocellular carcinoma, prostate cancer, pancreatic cancer, lung cancer, breast cancer, ovarian cancer, colon cancer, small intestine cancer, biliary tract cancer, endometrium cancer, skin cancer (melanoma), cervix cancer, urinary tract cancer, glioblastoma, or multiple myeloma.

A238. The method of embodiment A237, wherein the cancer is pancreatic cancer.

A239. The method of embodiment A237, wherein the cancer is colon cancer.

A240. The method of embodiment A237, wherein the cancer is triple negative breast cancer.

A241. The method of embodiment A237, wherein the cancer is multiple myeloma.

A242. The method of any one of embodiments A234 to A241, wherein the cancer is a cancer dependent on a Ras superfamily protein.

A243. The method of embodiment A242, wherein the Ras superfamily protein is a Ras protein, or a mutant thereof.

A244. The method of embodiment A243, wherein the Ras protein is DIRAS I; DIRAS2; DIRAS3; ERAS; GEM; HRAS; KRAS; MRAS; NKIRASI; NKIRAS2; NRAS; RALA; RALB; RAP1A; RAP1B; RAP2A; RAP2B; RAP2C; RASD1; RASD2; RASLIOA; RASLIOB; RASLI IA; RASLIIB; RASL12; REMI; REM2; RERG; RERGL; RRAD; RRAS; or RRAS2.

A245. The method of embodiment A244, wherein the Ras protein is HRAS; KRAS; or NRAS, or a mutant thereof.

A246. The method of embodiment A245, wherein the Ras protein is a KRAS mutant.

A247. The method of embodiment A246, wherein the KRAS mutant is a KRas G12D mutant, KRas G12C mutant, or KRas Q61H mutant.

A248. The method of embodiment A245, wherein the Ras protein is HRAS or a mutant thereof.

A249. The method of embodiment A245, wherein the Ras protein is NRAS or a mutant thereof.

A250. The method of embodiment A242, wherein the Ras superfamily protein is a Rac protein, or a mutant thereof.

A251. The method of embodiment A250, wherein the Rac protein is RAC1; RAC2; RAC3; RHOG, or a mutant thereof.

A252. The method of embodiment A251, wherein the Rac protein is wild-type RAC1.

A253. The method of embodiment A242, wherein the Ras superfamily protein is a Rho protein, or a mutant thereof.

A254. The method of embodiment A253, wherein the Rho protein is RHOA; RHOB; RHOBTB1; RHOBTB2; RHOBTB3; RHOC; RHOD; RHOF; RHOH; RHOJ; RHOQ; RHOU; RHOV; RND1; RND2; RND3; CDC42, or a mutant thereof.

A255. The method of embodiment A254, wherein the Rho protein is wild-type RHOA.

A256. The method of embodiment A242, wherein the Ras superfamily protein is a Cdc42 protein, or a mutant thereof.

A257. The method of embodiment A242, wherein the Ras superfamily protein is a Rheb protein, or a mutant thereof.

A258. The method of any one of embodiments A234 to A240, wherein the administration activates caspase activity in a cancerous cell of the subject.

A259. The method of embodiment A258, wherein the activation induces apoptosis of the cancerous cell.

A260. The method of any one of embodiments A234 to A259, wherein the subject is a human.

A261. A method of modulating Erk1/2 activity, comprising contacting an Erk1/2 protein with an effective amount of the compound of any one of embodiments A1-A181, or pharmaceutically acceptable form thereof.

A262. A method of modulating Erk1/2 activity, comprising contacting an Erk1/2 protein with an effective amount of the pharmaceutical composition of embodiment A182.

A263. The method of embodiment A261 or embodiment A262, wherein the method inhibits phosphorylation of the Erk1/2 protein.

A264. The method of embodiment A261 or embodiment A262, wherein the method activates phosphorylation of the Erk1/2 protein.

A265. A method of modulating Akt activity, comprising contacting an Akt protein with an effective amount of the compound of any one of embodiments A1-A181, or pharmaceutically acceptable form thereof.

A266. A method of modulating Akt activity, comprising contacting an AKT protein with an effective amount of the pharmaceutical composition of embodiment A182.

A267. The method of embodiment A265 or embodiment A266, wherein the method inhibits phosphorylation of the Akt protein.

A268. The method of embodiment A265 or embodiment A266, wherein the method activates phosphorylation of the Akt protein.

A269. A method of modulating Smad2/3 activity, comprising contacting a Smad2/3 protein with an effective amount of the compound of any one of embodiments A1-A181, or pharmaceutically acceptable form thereof.

A270. A method of modulating Smad2/3 activity, comprising contacting a Smad2/3 protein with an effective amount of the pharmaceutical composition of embodiment A182.

A271. The method of embodiment A269 or embodiment A270, wherein the method inhibits phosphorylation of the Smad2/3 protein.

A272. The method of embodiment A269 or embodiment A270, wherein the method activates phosphorylation of the Smad2/3 protein.

A273. A method of modulating JNK activity, comprising contacting a JNK protein with an effective amount of the compound of any one of embodiments A1-A181, or pharmaceutically acceptable form thereof.

A274. A method of modulating JNK activity, comprising contacting a JNK protein with an effective amount of the pharmaceutical composition of embodiment A182.

A275. The method of embodiment A273 or embodiment A274, wherein the method inhibits phosphorylation of the JNK protein.

A276. The method of embodiment A273 or embodiment A274, wherein the method activates phosphorylation of the JNK protein.

A277. A method of modulating MAPK p38 activity, comprising contacting a MAPK p38 protein with an effective amount of the compound of any one of embodiments A1-A181, or pharmaceutically acceptable form thereof.

A278. A method of modulating MAPK p38 activity, comprising contacting a MAPK p38 protein with an effective amount of the pharmaceutical composition of embodiment A182.

A279. The method of embodiment A277 or embodiment A278, wherein the method inhibits phosphorylation of the MAPK p38 protein.

A280. The method of embodiment A277 or embodiment A278, wherein the method activates phosphorylation of the MAPK p38 protein.

A281. A method of modulating IL-6 activity, comprising contacting a IL-6 protein with an effective amount of the compound of any one of embodiments A1-A181, or pharmaceutically acceptable form thereof.

A282. A method of modulating IL-6 activity, comprising contacting a IL-6 protein with an effective amount of the pharmaceutical composition of embodiment A182.

A283. The method of embodiment A281 or embodiment A282, wherein the method inhibits IL-6 activity.

A284. A method of modulating TNF-alpha activity, comprising contacting a TNF-alpha protein with an effective amount of the compound of any one of embodiments A1-A181, or pharmaceutically acceptable form thereof.

A285. A method of modulating TNF-alpha activity, comprising contacting a TNF-alpha protein with an effective amount of the pharmaceutical composition of embodiment A182.

A286. The method of embodiment A284 or embodiment A285, wherein the method inhibits TNF-alpha activity.

A287. A method of treating a fibrotic disease in a subject, comprising administering a therapeutically effective amount of the compound of any one of embodiments A1-A181, or pharmaceutically acceptable form thereof, to the subject.

A288. A method of treating a fibrotic disease in a subject, comprising administering a therapeutically effective amount of the pharmaceutical composition of embodiment A182 to the subject.

A289. A method of treating an inflammatory disease in a subject, comprising administering a therapeutically effective amount of the compound of any one of embodiments A1-A181, or pharmaceutically acceptable form thereof, to the subject.

A290. A method of treating an inflammatory disease in a subject, comprising administering a therapeutically effective amount of the pharmaceutical composition of embodiment A182 to the subject.

This disclosure is not to be limited in scope by the embodiments disclosed in the examples which are intended as single illustrations of individual aspects, and any methods which are functionally equivalent are within the scope of this disclosure. Indeed, various modifications in addition to those shown and described herein will become apparent to those skilled in the art from the foregoing description. Such modifications are intended to fall within the scope of the appended claims. This disclosure is not to be limited in scope, or cabined in any way, by the use of any subheadings, which are provided only for the convenience of the reader.

All references, such as publications, patents, and patent applications, mentioned in this specification are herein incorporated by reference in their entirety to the same extend as if each individual publication, patent, and patent application, was specifically and individually indicated to incorporated by reference in its entirety.

What is claimed is:

1. A compound of Formula II:

Formula II

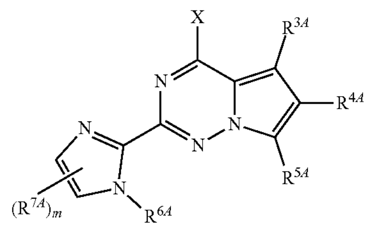

or a pharmaceutically acceptable salt, solvate, stereoisomer, isotopic variant, and/or polymorph thereof, wherein:

X is —$NR^{1A}R^{2A}$ or —$OR^{2A}$, $R^{1A}$ is hydrogen or C1-6 alkyl;

$R^{2A}$ is hydrogen, C1-6 alkyl, C3-7 cycloalkyl, C1-6 heteroalkyl, —$S(O)_2R^{15A}$, —$P(O)R^{16A}R^{17A}$, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached; or $R^{1A}$ and $R^{2A}$ are combined to form a 3-6 membered heterocycloalkyl including the nitrogen atom to which they are both attached, optionally wherein the 3-6 membered heterocycloalkyl formed by $R^{1A}$ and $R^{2A}$ is fused to a 5-6 membered heteroaryl;

$R^{3A}$ is $C_{1-6}$ alkyl, $C_{3-6}$ cycloalkyl, $C_{1-6}$ heteroalkyl, phenyl, 5-10 membered heteroaryl, —$(CO)R^{11A}$, or —$C(O)NR^{12A}R^{13A}$, wherein the $C_{1-6}$ alkyl, $C_{3-6}$ cycloalkyl, $C_{1-6}$ heteroalkyl, phenyl, and 5-10 membered heteroaryl are each independently optionally substituted with 1-3 $R^{9A}$ substituents;

$R^{4A}$ is phenyl or 5-10 membered heteroaryl, wherein the phenyl and 5-10 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ and $R^{7A}$ are each independently $C_{1-6}$ alkyl, $C_{3-6}$ cycloalkyl, $C_{1-6}$ haloalkyl, or $C_{1-6}$ heteroalkyl, wherein the $C_{1-6}$ alkyl, $C_{3-6}$ cycloalkyl, $C_{1-6}$ haloalkyl, and $C_{1-6}$ heteroalkyl, are each independently optionally substituted with 1-3 $R^{8A}$ substituents;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —$(CO)R^{11A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl, wherein the $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, $C_{1-6}$ alkoxy, $C_{3-6}$ cycloalkoxy, $C_{1-6}$ haloalkoxy, or 5-6 membered heteroaryl are each independently optionally substituted with 1-3 $R^{8A}$ substituents;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-7}$ cycloalkyl, $C_{1-6}$ haloalkyl, $C_{1-6}$ hydroxyalkyl, $C_{1-6}$ heteroalkyl, —OH, $C_{1-6}$ alkoxy, or $C_{1-6}$ haloalkoxy, or $R^{12A}$ and $R^{13A}$ are combined to form a 3-6 membered heterocycloalkyl including the nitrogen atom to which they are both attached;

$R^{15A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{16A}$and $R^{17A}$are each independently selected from the group consisting $C_{1-6}$ alkyl, $C_{1-6}$ alkoxy, or $C_{1-6}$ heteroalkyl, wherein the $C_{1-6}$ alkyl, $C_{1-6}$ alkoxy, and $C_{1-6}$ heteroalkyl, are each independently optionally substituted with 1-3 $R^{8A}$ substituents, or $R^{16A}$and $R^{17A}$are combined to form a 3-7 membered heterocycloalkyl including the phorphorus atom to which they are both attached;

m is 0, 1 or 2; and wherein, when X is OH or

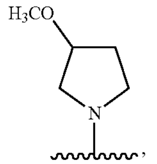,

Y is N-methyl imidazoyl, and $R^{5A}$ is H, at least one of $R^{3A}$ and $R^{4A}$ is not unsubstituted phenyl.

2. The compound of claim 1, wherein $R^{6A}$ is $C_{1-3}$ alkyl or $C_{1-3}$ heteroalkyl, wherein the $C_{1-3}$ alkyl or $C_{1-3}$ heteroalkyl is optionally substituted with biotinamide.

3. The compound of claim 1, wherein $R^{6A}$ and $R^{7A}$ are each independently methyl, and m is 0 or 1.

4. The compound of claim 1, wherein $R^{3A}$ is $C_{1-3}$ alkyl or phenyl, wherein the $C_{1-3}$ alkyl and phenyl are each independently optionally substituted with 1-3 $R^{9A}$ substituents.

5. The compound of claim 1, wherein $R^{3A}$ is —$CH_3$, unsubstituted phenyl, (4-methoxy)-phenyl, isopropyl, cyclopropyl,

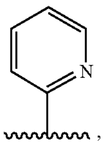, 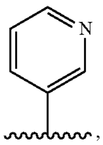, 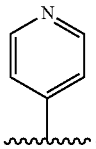, 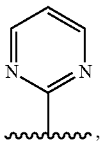,

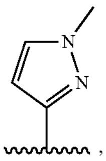, 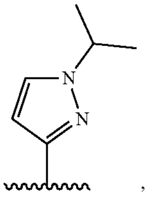, 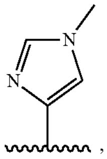, 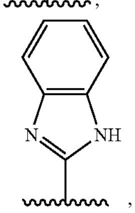,

-continued

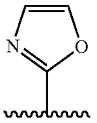, 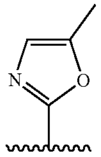, 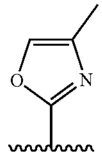, 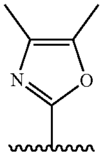,

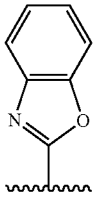, 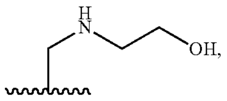,

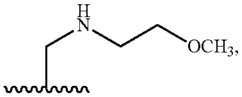, 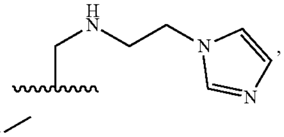,

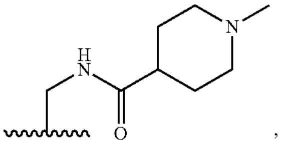, 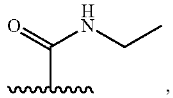,

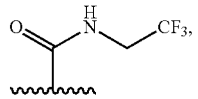, 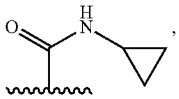,

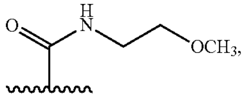, 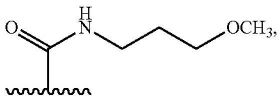,

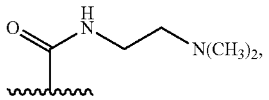, 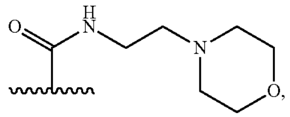,

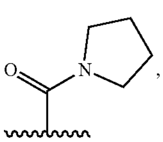, 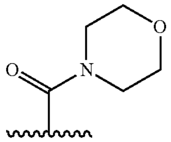, or 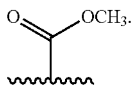.

6. The compound of claim 1, wherein $R^{3A}$ is —$CH_3$, unsubstituted phenyl, isopropyl, cyclopropyl,

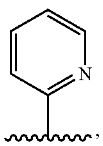, 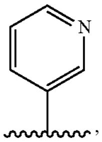, 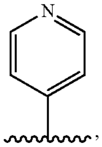,

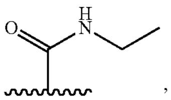, 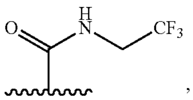, 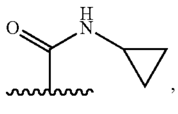,

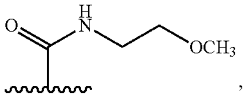, 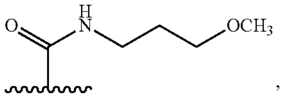,

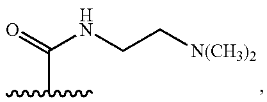, 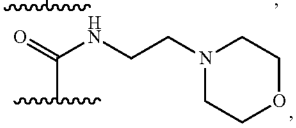,

-continued
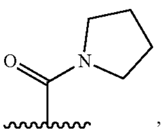,
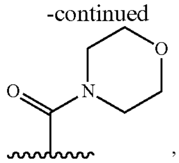,
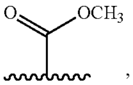, or
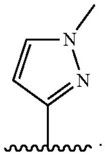.
7. The compound of claim 1, wherein $R^{4A}$ is phenyl or 5-6 membered heteroaryl, wherein the phenyl and 5-6 membered heteroaryl are each independently optionally substituted with 1-3 $R^{10A}$ substituents.
8. The compound of claim 7, wherein $R^{4A}$ is: unsubstituted phenyl,
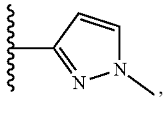,
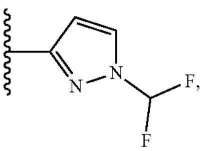,
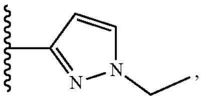,
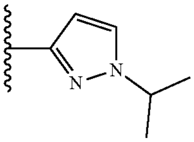,
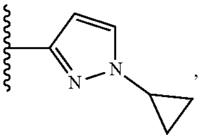,
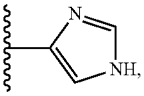,
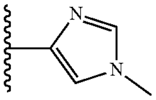,
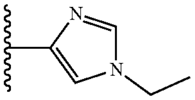,
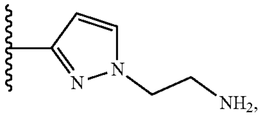,
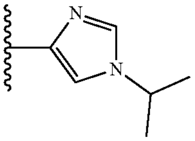,
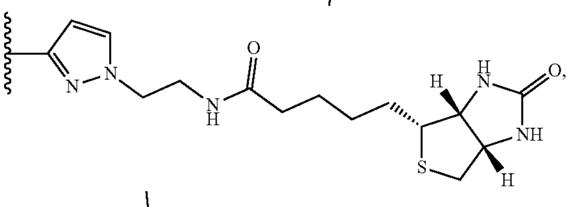,
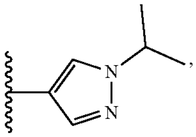,
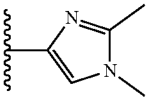,
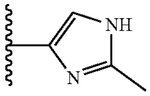,
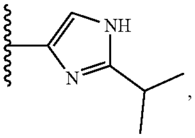,
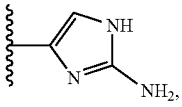,
-continued
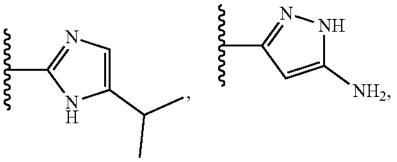,
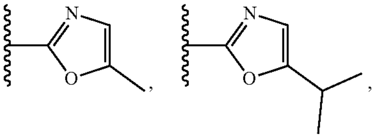,
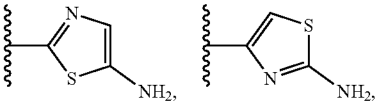,
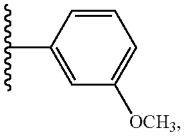,
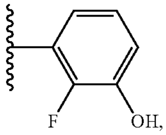,
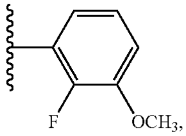,
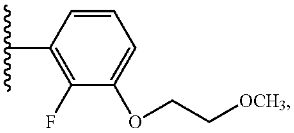,
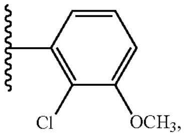,
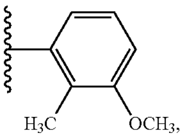,
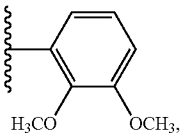,
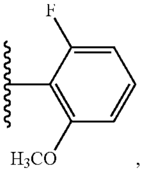,
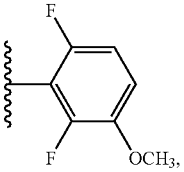,
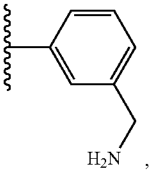,
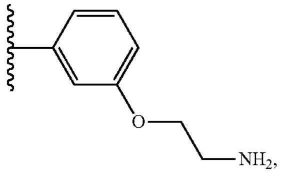,
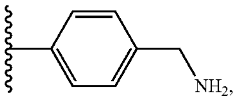,
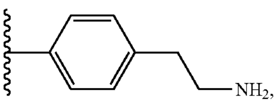,
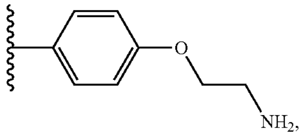,
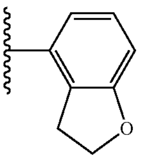,
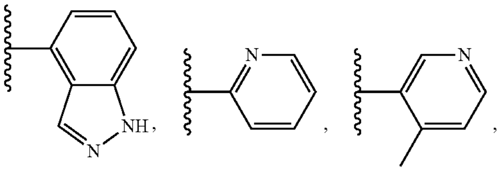, -continued

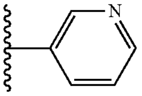, 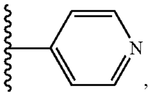, 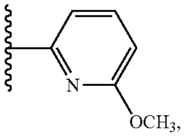,

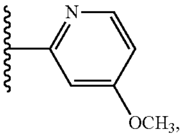,

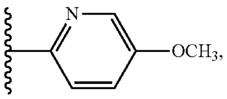,

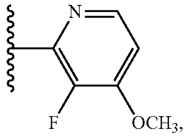, 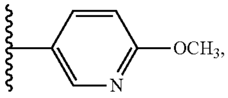,

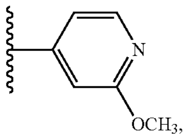 or

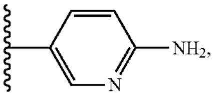,

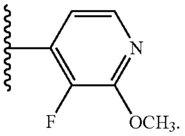.

9. The compound of claim 7, wherein $R^{4A}$ unsubstituted phenyl,

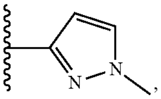, 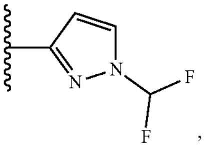,

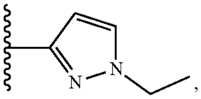, 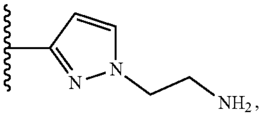,

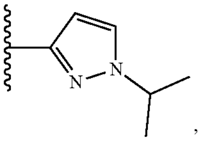,

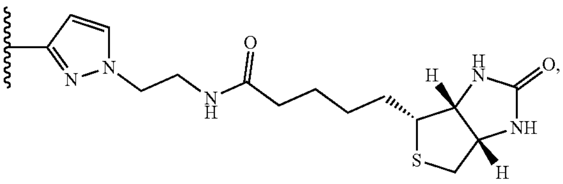

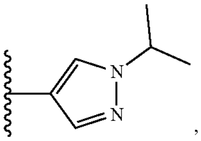, 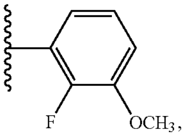, 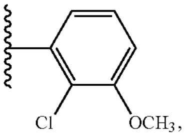,

-continued

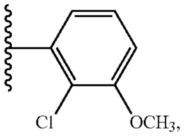, 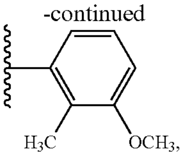, 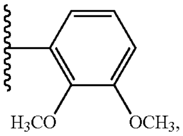,

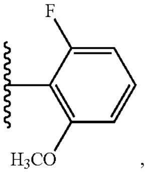, 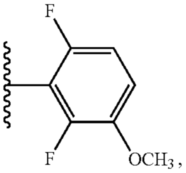, 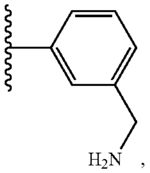,

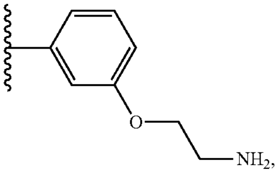, 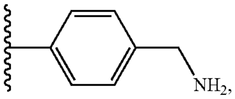,

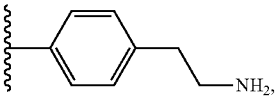,

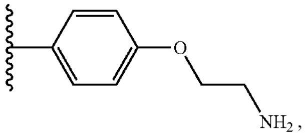, 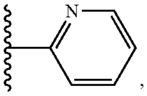,

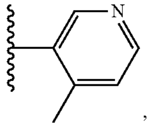, 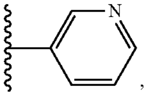, 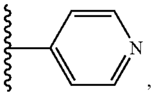,

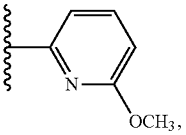, 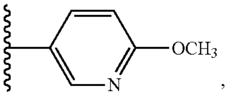,

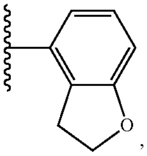, or 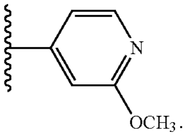.

10. The compound of claim 1, wherein the compound of Formula II is a compound of Formula IIa:

Formula IIa

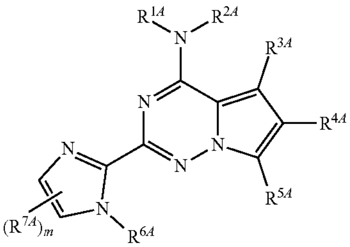

or a pharmaceutically acceptable salt, solvate, stereoisomer, isotopic variant, and/or polymorph thereof, wherein:

$R^{1A}$ is hydrogen;

$R^{2A}$ is hydrogen, $C_{1-6}$ alkyl, $C_{3-6}$ cycloalkyl, $C_{1-6}$ heteroalkyl, $-S(O)_2R^{15A}$, or 5-6 membered heteroaryl, wherein the $C_{1-6}$ alkyl, $C_{3-6}$ cycloalkyl, $C_{1-6}$ heteroalkyl, and 5-6 membered heteroaryl are each independently optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{3A}$ is $C_{1-3}$ alkyl, $C_{3-6}$ cycloalkyl, $C_{1-6}$ heteroalkyl, phenyl, 5-, 6- or 9-membered heteroaryl, —(CO)$R^{11A}$, or —C(O)$NR^{12A}R^{13A}$, wherein the $C_{1-3}$ alkyl, $C_{3-6}$ cycloalkyl, $C_{1-6}$ heteroalkyl, phenyl, and 5-, 6-, or 9-membered heteroaryl are each independently optionally substituted with 1-3 $R^{9A}$ substituents;

$R^{4A}$ is phenyl or 5, 6, or 9 membered heteroaryl, wherein the phenyl and 5, 6, or 9 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is $C_{1-3}$ alkyl or $C_{1-3}$ heteroalkyl, wherein the $C_{1-3}$ alkyl or $C_{1-3}$ heteroalkyl is optionally substituted with biotinamide;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —(CO)$R^{11A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{11A}R^{12A}$, or 5-6 membered heteroaryl, wherein the $C_{1-6}$ alkyl or $C_{1-6}$ heteroalkyl is optionally substituted with biotinamide;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy, or $R^{12A}$ and $R^{13A}$ are combined to form a 5 or 6 membered heterocycloalkyl including the nitrogen atom to which they are both attached;

$R^{15A}$ is $C_{1-3}$ alkyl, $C_{3-6}$ cycloalkyl, or $C_{1-4}$ heteroalkyl;

$R^{16A}$and $R^{17A}$are each independently selected from the group consisting $C_{1-3}$ alkyl or $C_{1-3}$ alkoxy, or $R^{16A}$and $R^{17A}$are combined to form a 5 membered heterocycloalkyl including the phorphorus atom to which they are both attached; and m is 0 or 1.

11. The compound of claim 1, wherein the compound of Formula II is a compound of Formula IIb:

Formula IIb

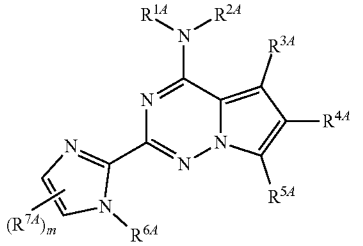

or a pharmaceutically acceptable salt, solvate, stereoisomer, isotopic variant, and/or polymorph thereof, wherein:

$R^{1A}$ and $R^{2A}$ are combined to form a 4-6 membered heterocycloalkyl including the nitrogen atom to which they are both attached, optionally wherein the 4-6 membered heterocycloalkyl formed by $R^{1A}$ and $R^{2A}$ is fused to a 6 membered heteroaryl;

$R^{3A}$ is $C_{1-3}$ alkyl or phenyl, wherein the $C_{1-3}$ alkyl and phenyl are each independently optionally substituted with 1-3 $R^{9A}$ substituents;

$R^{4A}$ is phenyl or 5 membered heteroaryl, wherein the phenyl and 5 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is methyl;

$R^{7A}$ is methyl;

$R^{9A}$ is each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $R^{10A}$ $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy;

m is 0 or 1; and wherein, when $R^{1A}$ and $R^{2A}$ are combined to form

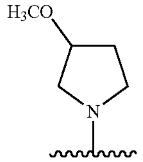, $R^{6A}$ is methyl, m is 0, and $R^{5A}$ is H, at least one of $R^{3A}$ and $R^{4A}$ is not unsubstituted phenyl.

12. The compound of claim 1, wherein the compound of Formula II is a compound of Formula IIc:

Formula IIc

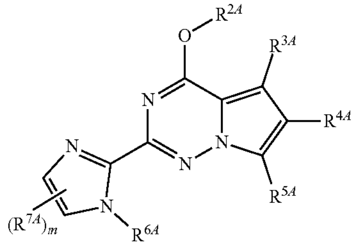

or a pharmaceutically acceptable salt, solvate, stereoisomer, isotopic variant, and/or polymorph thereof, wherein:

$R^{2A}$ is hydrogen $C_{1-6}$ heteroalkyl, or 6 membered heteroaryl, wherein the $C_{1-6}$ heteroalkyl and 5-6 membered heteroaryl are each optionally substituted with 1-3 $R^{8A}$ substituents;

$R^{3A}$ is $C_{1-3}$ alkyl or phenyl, wherein the $C_{1-3}$ alkyl or phenyl are each independently optionally substituted with 1-3 $R^{9A}$ substituents;

$R^{4A}$ is phenyl or 5 or 6 membered heteroaryl, wherein the phenyl and 5 or 6 membered heteroaryl are each independently optionally substituted with 1-3 $R^{10A}$ substituents, optionally wherein 2 independent $R^{10A}$ substituents are combined to form a 5-6 membered cycloalkyl or 5-6 membered heterocycloalkyl including the atom or atoms to which each are attached;

$R^{5A}$ is hydrogen;

$R^{6A}$ is methyl;

$R^{7A}$ is methyl;

$R^{8A}$ and $R^{9A}$ are each independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —(CO)$R^{11A}$, oxo, —OH, $C_{1-6}$ alkoxy, $C_{3-6}$ cycloalkoxy, $C_{1-6}$ haloalkoxy, or 5-6 membered heteroaryl;

$R^{10A}$ is independently selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —OH, $C_{1-6}$ alkoxy, $C_{3-6}$ cycloalkoxy, $C_{1-6}$ haloalkoxy, —$NR^{12A}R^{13A}$, or 5-6 membered heteroaryl;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy;

m is 0 or 1; and wherein, when $R^{2A}$ is H, $R^{6A}$ is methyl, m is 0, and $R^{5A}$ is H, at least one of $R^{3A}$ and $R^{4A}$ is not unsubstituted phenyl.

13. The compound of claim 1, the compound of Formula II is a compound of Formula IIa(1):

Formula IIa(1)

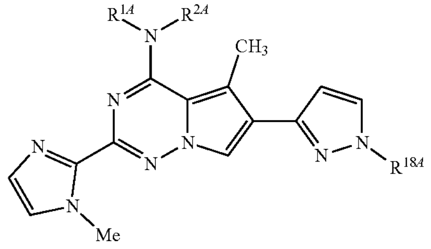

or a pharmaceutically acceptable salt, solvate, stereoisomer, isotopic variant, and/or polymorph thereof, wherein:

$R^{1A}$ is hydrogen;

$R^{2A}$ is 5 or 6 membered heteroaryl, wherein the 5 or 6 membered heteroaryl is optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached;

$R^{8A}$ is selected from the group consisting of halo, CN, $C_{1-6}$ alkyl, $C_{3-6}$ cycloalkyl, $C_{1-6}$ haloalkyl, $C_{1-6}$ hydroxyalkyl, $C_{1-6}$ heteroalkyl, 3-6 membered heterocycloalkyl, —$NR^{12A}R^{13A}$, —(CO)$R^{11A}$, oxo, —OH, $C_{1-6}$ alkoxy, $C_{3-6}$ cycloalkoxy, $C_{1-6}$ haloalkoxy, 5-6 membered heteroaryl, biotinamide, or a biotinylated substituent;

$R^{11A}$ is $C_{1-6}$ alkyl, $C_{3-6}$ cycloalkyl, or $C_{1-6}$ heteroalkyl, wherein the $C_{1-6}$ alkyl, $C_{3-6}$ cycloalkyl, and $C_{1-6}$ heteroalkyl, are each independently optionally substituted with 1-3 $R^{8A}$ substituents;

$R^{12A}$ and $R^{13A}$ are each independently selected from the group consisting of hydrogen, $C_{1-6}$ alkyl, $C_{3-6}$ cycloalkyl, $C_{1-6}$ hydroxyalkyl, $C_{1-6}$ heteroalkyl, —OH, or $C_{1-6}$ alkoxy, or $R^{12A}$ and $R^{13A}$ are combined to form a 5 or 6 membered heterocycloalkyl including the nitrogen atom to which they are both attached; and $R^{18A}$ is $C_{1-3}$ alkyl or $C_{3-6}$ cycloalkyl.

14. The compound of claim 13, wherein $R^{18A}$ is methyl, ethyl, isopropyl, or cyclopropyl.

15. The compound of claim 13, wherein $R^{8A}$ is selected from the group consisting of $C_{1-6}$ alkyl, $C_{3-6}$ cycloalkyl, 3-6 membered heterocycloalkyl, $C_{1-6}$ alkoxy, or $C_{3-6}$ cycloalkoxy, —$NR^{12A}R^{13A}$, or 5-6 membered heteroaryl.

16. The compound of claim 13, wherein $R^{2A}$ is pyridyl, pyrimidyl, pyrazyl, or pyrazolyl, wherein the pyridyl, pyrimidyl, pyrazyl, or pyrazolyl is optionally substituted with 1-3 $R^{8A}$ substituents, optionally wherein 2 independent $R^{8A}$ substituents are combined to form a 5-6 membered cycloalkyl or 5-6 membered heterocycloalkyl including the atom or atoms to which each are attached.

17. The compound of claim 13, wherein $R^{1A}$ and $R^{2A}$ together with the nitrogen to which they are attached have a structure of:

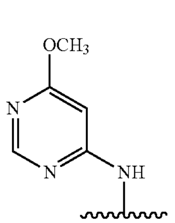 , 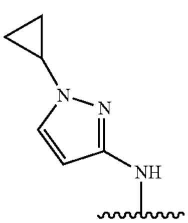 ,

-continued

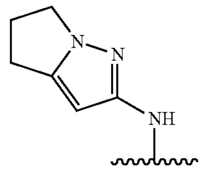 , 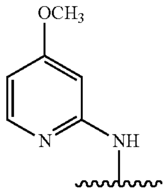 ,

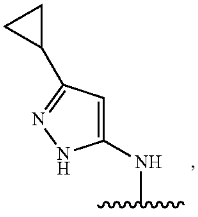 , 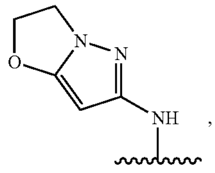 ,

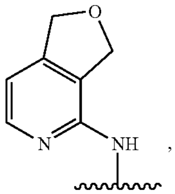 , 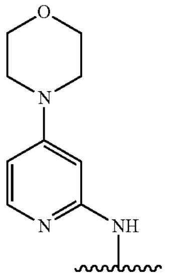 , 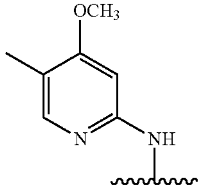 ,

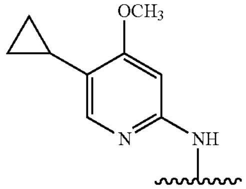 , 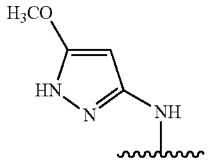 ,

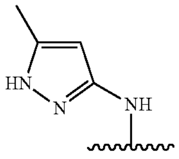 , 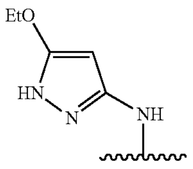 ,

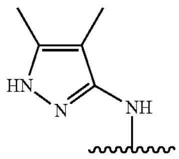 , 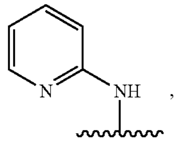 , 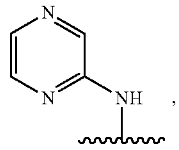 ,

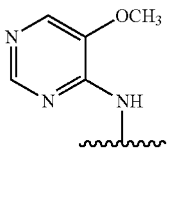 , 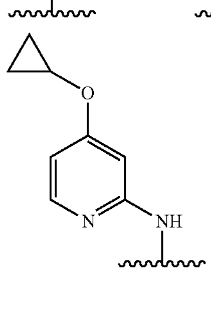 ,

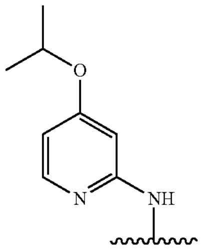 , 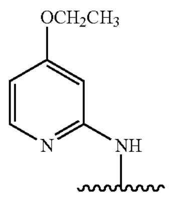 , 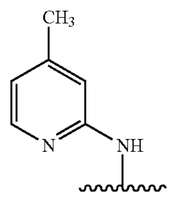 ,

-continued

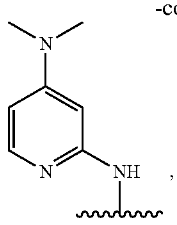 , 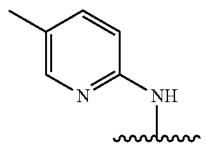 ,

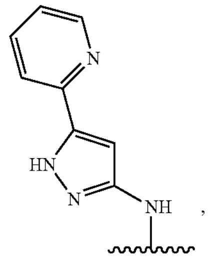 , or 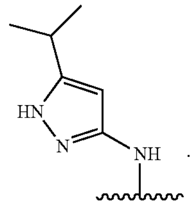 .

18. The compound of claim 13, wherein the compound has a MW of no more than 1,000 g/mol.

19. The compound of claim 1, wherein the compound is selected from the group consisting of:

rac 6-(1-Isopropyl-1H-pyrazol-3-yl)-N-((1R,3S)-3-methoxycyclopentyl)-5-methyl-2-(1-methyl-1H-imidazol-2-yl)pyrrolo[2,1-f][1,2,4]triazin-4-amine, rac 6-(1-Isopropyl-1H-pyrazol-3-yl)-4-(3-(methoxymethyl)pyrrolidin-1-yl)-5-methyl-2-(1-methyl-1H-imidazol-2-yl)pyrrolo[2,1-f][1,2,4]triazine, rac 6-(1-Isopropyl-1H-pyrazol-3-yl)-N-(((1S,2R)-2-(methoxymethyl)cyclobutyl)methyl)-5-methyl-2-(1-methyl-1H-imidazol-2-yl)pyrrolo[2,1-f][1,2,4]triazin-4-amine, rac 6-(1-Isopropyl-1H-pyrazol-3-yl)-5-methyl-2-(1-methyl-1H-imidazol-2-yl)-4-(3-(oxo-λ6-methyl)piperidin-1-yl)pyrrolo[2,1-f][1,2,4]triazine, 6-(1-Isopropyl-1H-pyrazol-3-yl)-N-(2-methoxyethyl)-5-methyl-2-(1-methyl-1H-imidazol-2-yl)pyrrolo[2,1-f][1,2,4]triazin-4-amine, 6-(1-Isopropyl-1H-pyrazol-3-yl)-N-(6-methoxypyrimidin-4-yl)-5-methyl-2-(1-methyl-1H-imidazol-2-yl)pyrrolo[2,1-f][1,2,4]triazin-4-amine, 6-(1-isopropyl-1H-pyrazol-3-yl)-N-(6-methoxypyridin-2-yl)-5-methyl-2-(1-methyl-1H-imidazol-2-yl)pyrrolo[2,1-f][1,2,4]triazin-4-amine, 6-(2-Chloro-3-methoxyphenyl)-5-methyl-2-(1-methyl-1H-imidazol-2-yl)pyrrolo[2,1-f][1,2,4]triazin-4-ol, 6-(2-Chloro-3-methoxyphenyl)-N-(2-methoxyethyl)-5-methyl-2-(1-methyl-1H-imidazol-2-yl)pyrrolo[2,1-f][1,2,4]triazin-4-amine, 6-(1-Isopropyl-1H-pyrazol-3-yl)-2-(1-methyl-1H-imidazol-2-yl)-5-phenylpyrrolo[2,1-f][1,2,4]triazin-4-ol, rac 6-(1-Isopropyl-1H-pyrazol-3-yl)-N-((1R,3S)-3-methoxycyclopentyl)-2-(1-methyl-1H-imidazol-2-yl)-5-phenylpyrrolo[2,1-f][1,2,4]triazin-4-amine, rac 6-(1-Isopropyl-1H-pyrazol-3-yl)-4-(3-(methoxymethyl)pyrrolidin-1-yl)-2-(1-methyl-1H-imidazol-2-yl)-5-phenylpyrrolo[2,1-f][1,2,4]triazine, rac 6-(1-Isopropyl-1H-pyrazol-3-yl)-N-(((1S,2R)-2-(methoxymethyl)cyclobutyl)methyl)-2-(1-methyl-1H-imidazol-2-yl)-5-phenylpyrrolo[2,1-f][1,2,4]triazin-4-amine, rac 6-(1-Isopropyl-1H-pyrazol-3-yl)-4-(3-methoxypiperidin-1-yl)-2-(1-methyl-1H-imidazol-2-yl)-5-phenylpyrrolo[2,1-f][1,2,4]triazine, 6-(1-Isopropyl-1H-pyrazol-3-yl)-N-(6-methoxypyrimidin-4-yl)-2-(1-methyl-1H-imidazol-2-yl)-5-phenylpyrrolo[2,1-f][1,2,4]triazin-4-amine, 6-(1-Isopropyl-1H-pyrazol-3-yl)-N-(6-methoxypyridin-2-yl)-2-(1-methyl-1H-imidazol-2-yl)-5-phenylpyrrolo[2,1-f][1,2,4]triazin-4-amine, 6-(2-Chloro-3-methoxyphenyl)-2-(1-methyl-1H-imidazol-2-yl)-5-phenylpyrrolo[2,1-f][1,2,4]triazin-4-ol, 6-(2-Chloro-3-methoxyphenyl)-N-(2-methoxyethyl)-2-(1-methyl-1H-imidazol-2-yl)-5-phenylpyrrolo[2,1-f][1,2,4]triazin-4-amine, 6-(2-Chloro-3-methoxyphenyl)-N-(3-methoxypropyl)-2-(1-methyl-1H-imidazol-2-yl)-5-phenylpyrrolo[2,1-f][1,2,4]triazin-4-amine, 6-(2-Chloro-3-methoxyphenyl)-N-((1s,3s)-3-methoxycyclobutyl)-2-(1-methyl-1H-imidazol-2-yl)-5-phenylpyrrolo[2,1-f][1,2,4]triazin-4-amine, 6-(2-Chloro-3-methoxyphenyl)-N-((1r,3r)-3-methoxycyclobutyl)-2-(1-methyl-1H-imidazol-2-yl)-5-phenylpyrrolo[2,1-f][1,2,4]triazin-4-amine, rac 6-(2-Chloro-3-methoxyphenyl)-N-((1R,3S)-3-methoxycyclopentyl)-2-(1-methyl-1H-imidazol-2-yl)-5-phenylpyrrolo[2,1-f][1,2,4]triazin-4-amine, rac 6-(2-Chloro-3-methoxyphenyl)-N-((1R,3R)-3-methoxycyclopentyl)-2-(1-methyl-1H-imidazol-2-yl)-5-phenylpyrrolo[2,1-f][1,2,4]triazin-4-amine, 5-Isopropyl-6-(1-isopropyl-1H-pyrazol-3-yl)-N-(2-methoxyethyl)-2-(1-methyl-1H-imidazol-2-yl)pyrrolo[2,1-f][1,2,4]triazin-4-amine, rac 5-Isopropyl-6-(1-isopropyl-1H-pyrazol-3-yl)-N-((1R,3S)-3-methoxycyclopentyl)-2-(1-methyl-1H-imidazol-2-yl)pyrrolo[2,1-f][1,2,4]triazin-4-amine, 6-(2-Fluoro-3-methoxyphenyl)-N-((1r,3r)-3-methoxycyclobutyl)-2-(1-methyl-1H-imidazol-2-yl)-5-phenylpyrrolo[2,1-f][1,2,4]triazin-4-amine, rac 6-(2-Fluoro-3-methoxyphenyl)-N-((1R,3R)-3-methoxycyclopentyl)-2-(1-methyl-1H-imidazol-2-yl)-5-phenylpyrrolo[2,1-f][1,2,4]triazin-4-amine, 6-(2-Fluoro-3-methoxyphenyl)-N-((1r,3r)-3-(2-methoxyethoxy)cyclobutyl)-2-(1-methyl-1H-imidazol-2-yl)-5-phenylpyrrolo[2,1-f][1,2,4]triazin-4-amine, 6-(2-Fluoro-3-methoxyphenyl)-N-((1r,3r)-3-methoxycyclobutyl)-2-(1-methyl-1H-imidazol-2-yl)-5-(pyridin-2-yl)pyrrolo[2,1-f][1,2,4]triazin-4-amine, 6-(2-Fluoro-3-methoxyphenyl)-N-((1R,3R)-3-methoxycyclopentyl)-2-(1-methyl-1H-imidazol-2-yl)-5-(pyridin-2-yl)pyrrolo[2,1-f][1,2,4]triazin-4-amine, 6-(2-Fluoro-3-methoxyphenyl)-N-((1r,3r)-3-methoxycyclobutyl)-2-(1-methyl-1H-imidazol-2-yl)-5-(1-methyl-1H-pyrazol-3-yl)pyrrolo[2,1-f][1,2,4]triazin-4-amine, N-(6-Methoxypyrimidin-4-yl)-5-methyl-2-(1-methyl-1H-imidazol-2-yl)-6-(pyridin-3-yl)pyrrolo[2,1-f][1,2,4]triazin-4-amine, N-(6-Methoxypyrimidin-4-yl)-5-methyl-2-(1-methyl-1H-imidazol-2-yl)-6-(pyridin-4-yl)pyrrolo[2,1-f][1,2,4]triazin-4-amine, 6-(2-Methoxypyridin-4-yl)-N-(6-methoxypyrimidin-4-yl)-5-methyl-2-(1-methyl-1H-imidazol-2-yl)pyrrolo[2,1-f][1,2,4]triazin-4-amine, 6-(1-Isopropyl-1H-pyrazol-3-yl)-N-(5-methoxy-1H-pyrazol-3-yl)-5-methyl-2-(1-methyl-1H-imidazol-2-yl)pyrrolo[2,1-f][1,2,4]triazin-4-amine, 6-(1-Isopropyl-1H-pyrazol-3-yl)-5-methyl-2-(1-methyl-1H-imidazol-2-yl)-N-(pyridin-4-yl)pyrrolo[2,1-f][1,2,4]triazin-4-amine, 6-(1-Isopropyl-1H-pyrazol-3-yl)-N-(4-methoxypyrimidin-2-yl)-5-methyl-2-(1-methyl-1H-imidazol-2-yl)pyrrolo[2,1-f][1,2,4]triazin-4-amine, 6-(1-Isopropyl-1H-pyrazol-3-yl)-5-methyl-2-(1-methyl-1H-imidazol-2-yl)-N-(pyrimidin-2-yl)pyrrolo[2,1-f][1,2,4]triazin-4-amine, 6-(1-Isopropyl-1H-pyrazol-3-yl)-5-methyl-2-(1-methyl-1H-imidazol-2-yl)-N-(pyrimidin-4-yl)pyrrolo[2,1-f][1,2,4]triazin-4-amine, 6-(1-Isopropyl-1H-pyrazol-3-yl)-N-(5-methoxypyrimidin-2-yl)-5-methyl-2-(1-methyl-1H-imidazol-2-yl)pyrrolo[2,1-f][1,2,4]triazin-4-amine, 6-(1-Isopropyl-1H-pyrazol-3-yl)-5-methyl-2-(1-methyl-1H-imidazol-2-yl)-N-(pyridin-2-yl)pyrrolo[2,1-f][1,2,4]triazin-4-amine, 6-(1-Isopropyl-1H-pyrazol-3-yl)-N-(4-methoxypyridin-2-yl)-5-methyl-2-(1-methyl-1H-imidazol-2-yl)pyrrolo[2,1-f][1,2,4]triazin-4-amine, N-(6-(1-Isopropyl-1H-pyrazol-3-yl)-5-methyl-2-(1-methyl-1H-imidazol-2-yl)pyrrolo[2,1-f][1,2,4]triazin-4-yl)-1,3,4-oxadiazol-2-amine, N-(6-(1-Isopropyl-1H-pyrazol-3-yl)-5-methyl-2-(1-methyl-1H-imidazol-2-yl)pyrrolo[2,1-f][1,2,4]triazin-4-yl)oxazol-2-amine, 6-(1-Isopropyl-1H-pyrazol-3-yl)-5-methyl-2-(1-methyl-1H-imidazol-2-yl)-N-(1-methyl-1H-pyrazol-3-yl)pyrrolo[2,1-f][1,2,4]triazin-4-amine, 6-(1-Isopropyl-1H-pyrazol-3-yl)-5-methyl-2-(1-methyl-1H-imidazol-2-yl)-N-(pyrazin-2-yl)pyrrolo[2,1-f][1,2,4]triazin-4-amine, N-(6-Methoxypyrimidin-4-yl)-5-methyl-2-(1-methyl-1H-imidazol-2-yl)-6-(1-methyl-1H-pyrazol-3-yl)pyrrolo[2,1-f][1,2,4]triazin-4-amine, 6-(1-Ethyl-1H-pyrazol-3-yl)-N-(6-methoxypyrimidin-4-yl)-5-methyl-2-(1-methyl-1H-imidazol-2-yl)pyrrolo[2,1-f][1,2,4]triazin-4-amine, 6-(6-Methoxypyridin-2-yl)-N-(6-methoxypyrimidin-4-yl)-5-methyl-2-(1-methyl-1H-imidazol-2-yl)pyrrolo[2,1-f][1,2,4]triazin-4-amine, 6-(6-Methoxypyridin-3-yl)-N-(6-methoxypyrimidin-4-yl)-5-methyl-2-(1-methyl-1H-imidazol-2-yl)pyrrolo[2,1-f][1,2,4]triazin-4-amine, 5-Cyclopropyl-N-(6-(1-isopropyl-1H-pyrazol-3-yl)-5-methyl-2-(1-methyl-1H-imidazol-2-yl)pyrrolo[2,1-f][1,2,4]triazin-4-yl)-1,3,4-oxadiazol-2-amine, N-(3-Cyclopropyl-1H-pyrazol-5-yl)-6-(1-isopropyl-1H-pyrazol-3-yl)-5-methyl-2-(1-methyl-1H-imidazol-2-yl)pyrrolo[2,1-f][1,2,4]triazin-4-amine, 3-Cyclopropyl-N-(6-(1-isopropyl-1H-pyrazol-3-yl)-5-methyl-2-(1-methyl-1H-imidazol-2-yl)pyrrolo[2,1-f][1,2,4]triazin-4-yl)isoxazol-5-amine, 3-Cyclopropyl-N-(6-(1-isopropyl-1H-pyrazol-3-yl)-5-methyl-2-(1-methyl-1H-imidazol-2-yl)pyrrolo[2,1-f][1,2,4]triazin-4-yl)-1,2,4-oxadiazol-5-amine, 6-(1-Isopropyl-1H-pyrazol-3-yl)-N-(6-methoxypyridin-3-yl)-5-methyl-2-(1-methyl-1H-imidazol-2-yl)pyrrolo[2,1-f][1,2,4]triazin-4-amine, N,6-bis(1-Isopropyl-1H-pyrazol-3-yl)-5-methyl-2-(1-methyl-1H-imidazol-2-yl)pyrrolo[2,1-f][1,2,4]triazin-4-amine, 6-(1-Isopropyl-1H-pyrazol-3-yl)-N-(5-methoxypyrimidin-4-yl)-5-methyl-2-(1-methyl-1H-imidazol-2-yl)pyrrolo[2,1-f][1,2,4]triazin-4-amine, 6-(1-Isopropyl-1H-pyrazol-3-yl)-N-(6-methoxypyridazin-3-yl)-5-methyl-2-(1-methyl-1H-imidazol-2-yl)pyrrolo[2,1-f][1,2,4]triazin-4-amine, 5-Cyclopropyl-N-(6-(1-isopropyl-1H-pyrazol-3-yl)-5-methyl-2-(1-methyl-1H-imidazol-2-yl)pyrrolo[2,1-f][1,2,4]triazin-4-yl)-1,2,4-oxadiazol-3-amine, N-(5-Ethyl-I-methyl-1H-1,2,4-triazol-3-yl)-6-(I-isopropyl-1H-pyrazol-3-yl)-5-methyl-2-(1-methyl-1H-imidazol-2-yl)pyrrolo[2,1-f][1,2,4]triazin-4-amine, 6-(1-Isopropyl-1H-pyrazol-3-yl)-N-(2-isopropyl-2H-1,2,3-triazol-4-yl)-5-methyl-2-(1-methyl-1H-imidazol-2-yl)pyrrolo[2,1-f][1,2,4]triazin-4-amine, N-(1-Isopropyl-1H-1,2,3-triazol-4-yl)-6-(1-isopropyl-1H-pyrazol-3-yl)-5-methyl-2-(1-methyl-1H-imidazol-2-yl)pyrrolo[2,1-f][1,2,4]triazin-4-amine, N-(6-(1-Isopropyl-1H-pyrazol-3-yl)-5-methyl-2-(1-methyl-1H-imidazol-2-yl)pyrrolo[2,1-f][1,2,4]triazin-4-yl)-4-(methoxymethyl)thiazol-2-amine, 6-(1-Isopropyl-1H-pyrazol-3-yl)-N-(2-methoxypyrimidin-5-yl)-5-methyl-2-(1-methyl-1H-imidazol-2-yl)pyrrolo[2,1-f][1,2,4]triazin-4-amine, N-(5-Cyclopropyl-4H-1,2,4-triazol-3-yl)-6-(1-isopropyl-1H-pyrazol-3-yl)-5-methyl-2-(1-methyl-1H-imidazol-2-yl)pyrrolo[2,1-f][1,2,4]triazin-4-amine, N-(6-(1-Isopropyl-1H-pyrazol-3-yl)-5-methyl-2-(1-methyl-1H-imidazol-2-yl)pyrrolo[2,1-f][1,2,4]triazin-4-yl)-3-(methoxymethyl)-1,2,4-oxadiazol-5-amine, 6-(1-Isopropyl-1H-pyrazol-3-yl)-N-(5-methoxypyrazin-2-yl)-5-methyl-2-(1-methyl-1H-imidazol-2-yl)pyrrolo[2,1-f][1,2,4]triazin-4-amine, N-(1-Cyclopropyl-1H-pyrazol-3-yl)-6-(1-isopropyl-1H-pyrazol-3-yl)-5-methyl-2-(1-methyl-1H-imidazol-2-yl)pyrrolo[2,1-f][1,2,4]triazin-4-amine, 6-(1-Isopropyl-1H-pyrazol-3-yl)-N-(2-methoxypyridin-3-yl)-5-methyl-2-(1-methyl-1H-imidazol-2-yl)pyrrolo[2,1-f][1,2,4]triazin-4-amine, 6-(1-Isopropyl-1H-pyrazol-3-yl)-N-(2-methoxypyrimidin-4-yl)-5-methyl-2-(1-methyl-1H-imidazol-2-yl)pyrrolo[2,1-f][1,2,4]triazin-4-amine, 6-(1-Isopropyl-1H-pyrazol-3-yl)-N-(2-methoxypyridin-4-yl)-5-methyl-2-(1-methyl-1H-imidazol-2-yl)pyrrolo[2,1-f][1,2,4]triazin-4-amine, 6-(1-Isopropyl-1H-pyrazol-3-yl)-N-(4-methoxypyrimidin-5-yl)-5-methyl-2-(1-methyl-1H-imidazol-2-yl)pyrrolo[2,1-f][1,2,4]triazin-4-amine, 6-(1-Isopropyl-1H-pyrazol-3-yl)-N-(3-methoxypyridin-2-yl)-5-methyl-2-(1-methyl-1H-imidazol-2-yl)pyrrolo[2,1-f][1,2,4]triazin-4-amine, 5-Cyclopropyl-N-(6-(1-isopropyl-1H-pyrazol-3-yl)-5-methyl-2-(1-methyl-1H-imidazol-2-yl)pyrrolo[2,1-f][1,2,4]triazin-4-yl)oxazol-2-amine, N-(6-(1-Isopropyl-1H-pyrazol-3-yl)-5-methyl-2-(1-methyl-1H-imidazol-2-yl)pyrrolo[2,1-f][1,2,4]triazin-4-yl)-2,3-dihydropyrazolo[5,1-b]oxazol-6-amine, 6-(1-Isopropyl-1H-pyrazol-3-yl)-N-((1r,3r)-3-(2-methoxyethoxy)cyclobutyl)-5-methyl-2-(1-methyl-1H-imidazol-2-yl)pyrrolo[2,1-f][1,2,4]triazin-4-amine, 6-(1-Isopropyl-1H-pyrazol-3-yl)-5-methyl-N,2-bis(1-methyl-1H-imidazol-2-yl)pyrrolo[2,1-f][1,2,4]triazin-4-amine, N-(6-Methoxypyrimidin-4-yl)-5-methyl-2-(1-methyl-1H-imidazol-2-yl)-6-(pyridin-2-yl)pyrrolo[2,1-f][1,2,4]triazin-4-amine, 6-(1-(Difluoromethyl)-1H-pyrazol-3-yl)-N-(4-methoxypyrimidin-2-yl)-5-methyl-2-(1-methyl-1H-imidazol-2-yl)pyrrolo[2,1-f][1,2,4]triazin-4-amine, N-(4-(2-(Dimethylamino)ethoxy)pyrimidin-2-yl)-6-(1-isopropyl-1H-pyrazol-3-yl)-5-methyl-2-(1-methyl-1H-imidazol-2-yl)pyrrolo[2,1-f][1,2,4]triazin-4-amine, 2-((6-((6-(1-Isopropyl-1H-pyrazol-3-yl)-5-methyl-2-(1-methyl-1H-imidazol-2-yl)pyrrolo[2,1-f][1,2,4]triazin-4-yl)amino)pyrimidin-4-yl)oxy)ethan-1-ol, 6-(1-(Difluoromethyl)-1H-pyrazol-3-yl)-N-(6-methoxypyrimidin-4-yl)-5-methyl-2-(1-methyl-1H-imidazol-2-yl)pyrrolo[2,1-f][1,2,4]triazin-4-amine, N-(5, 6-Dihydro-4H-pyrrolo[1,2-b]pyrazol-2-yl)-5-methyl-2-(1-methyl-1H-imidazol-2-yl)-6-(1-methyl-1H-pyrazol-3-yl)pyrrolo[2,1-f][1,2,4]triazin-4-amine, 2-((6-((5-Methyl-2-(1-methyl-1H-imidazol-2-yl)-6-(1-methyl-1H-pyrazol-3-yl)pyrrolo[2,1-f][1,2,4]triazin-4-yl)amino)pyrimidin-4-yl)oxy)ethan-1-ol, N-(4-Methoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine, N-((1r,3r)-3-Methoxycyclobutyl)-5-methyl-2-(1-methyl-1H-imidazol-2-yl)-6-(1-methyl-1H-pyrazol-3-yl)pyrrolo[2,1-f][1,2,4]triazin-4-amine hydrochloride salt, N-(5-Cyclopropyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine, N-(4-(2-(Dimethylamino)ethoxy)pyrimidin-2-yl)-5-methyl-2-(1-methyl-1H-imidazol-2-yl)-6-(1-methyl-1H-pyrazol-3-yl)pyrrolo[2,1-f][1,2,4]triazin-4-amine, 5-Methyl-N,2-bis(1-methyl-1H-imidazol-2-yl)-6-(1-methyl-1H-pyrazol-3-yl)pyrrolo[2,1-f][1,2,4]triazin-4-amine, N-(5-Methoxypyrimidin-4-yl)-5-methyl-2-(1-methyl-1H-imidazol-2-yl)-6-(1-methyl-1H-pyrazol-3-yl)pyrrolo[2,1-f][1,2,4]triazin-4-amine, N-(5-Ethyl-1-methyl-1H-1,2,4-triazol-3-yl)-5-methyl-2-(1-methyl-H-imidazol-2-yl)-6-(1-methyl-1H-pyrazol-3-yl)pyrrolo[2,1-f][1,2,4]triazin-4-amine, N-(1-Isopropyl-1H-1,2,3-triazol-4-yl)-5-methyl-2-(1-methyl-1H-imidazol-2-yl)-6-(1-methyl-1H-pyrazol-3-yl)pyrrolo[2,1-f][1,2,4]triazin-4-amine, N-(5-Methoxypyrazin-2-yl)-5-methyl-2-(1-methyl-1H-imidazol-2-yl)-6-(1-methyl-1H-pyrazol-3-yl)pyrrolo[2,1-f][1,2,4]triazin-4-amine, N-(1-Cyclopropyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine, N-(3-Methoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine, N-(5-Cyclopropyl-1H-1,2,4-triazol-3-yl)-5-methyl-2-(1-methyl-1H-imidazol-2-yl)-6-(1-methyl-1H-pyrazol-3-yl)pyrrolo[2,1-f][1,2,4]triazin-4-amine, N-(4-Methoxypyrimidin-2-yl)-5-methyl-2-(1-methyl-1H-imidazol-2-yl)-6-(1-methyl-1H-pyrazol-3-yl)pyrrolo[2,1-f][1,2,4]triazin-4-amine, 5-Methyl-2-(1-methyl-1H-imidazol-2-yl)-6-(1-methyl-1H-pyrazol-3-yl)-N-(pyrimidin-2-yl)pyrrolo[2,1-f][1,2,4]triazin-4-amine, 5-Methyl-2-(1-methyl-1H-imidazol-2-yl)-6-(1-methyl-1H-pyrazol-3-yl)-N-(pyrimidin-4-yl)pyrrolo[2,1-f][1,2,4]triazin-4-amine, N-(5-Methoxypyrimidin-2-yl)-5-methyl-2-(1-methyl-1H-imidazol-2-yl)-6-(1-methyl-1H-pyrazol-3-yl)pyrrolo[2,1-f][1,2,4]triazin-4-amine, 5-Methyl-2-(1-methyl-1H-imidazol-2-yl)-6-(1-methyl-1H-pyrazol-3-yl)-N-(pyridin-2-yl)pyrrolo[2,1-f][1,2,4]triazin-4-amine, N-(5-Methyl-2-(1-methyl-1H-imidazol-2-yl)-6-(1-methyl-1H-pyrazol-3-yl)pyrrolo[2,1-f][1,2,4]triazin-4-yl)-1,3,4-oxadiazol-2-amine, 5-Methyl-2-(1-methyl-1H-imidazol-2-yl)-6-(1-methyl-1H-pyrazol-3-yl)-N-(pyrazin-2-yl)pyrrolo[2,1-f][1,2,4]triazin-4-amine, 2-((2-((6-(1-Isopropyl-1H-pyrazol-3-yl)-5-methyl-2-(1-methyl-1H-imidazol-2-yl)pyrrolo[2,1-f][1,2,4]triazin-4-yl)amino)pyrimidin-4-yl)oxy)ethan-1-ol, 6-(1-Isopropyl-1H-pyrazol-3-yl)-N-(6-(2-methoxyethoxy)pyrimidin-4-yl)-5-methyl-2-(1-methyl-1H-imidazol-2-yl)pyrrolo[2,1-f][1,2,4]triazin-4-amine, N-(6-(2-(Dimethylamino)ethoxy)pyrimidin-4-yl)-6-(1-isopropyl-1H-pyrazol-3-yl)-5-methyl-2-(1-methyl-1H-imidazol-2-yl)pyrrolo[2,1-f][1,2,4]triazin-4-amine, N-(5-Methyl-2-(1-methyl-1H-imidazol-2-yl)-6-(1-methyl-1H-pyrazol-3-yl)pyrrolo[2,1-f][1,2,4]triazin-4-yl)-2,3-dihydropyrazolo[5,1-b]oxazol-6-amine, N-(1H-Imidazol-2-yl)-6-(1-isopropyl-1H-pyrazol-3-yl)-5-methyl-2-(1-methyl-1H-imidazol-2-yl)pyrrolo[2,1-f][1,2,4]triazin-4-amine, N-(4-Cyclopropoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine, 5-Methyl-2-(1-methyl-1H-imidazol-2-yl)-6-(1-methyl-1H-pyrazol-3-yl)-N-(4-(trifluoromethoxy)pyridin-2-yl)pyrrolo[2,1-f][1,2,4]triazin-4-amine, N-(4-(Difluoromethoxy)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine, 5-Methyl-2-(1-methyl-1H-imidazol-2-yl)-6-(1-methyl-1H-pyrazol-3-yl)-N-(4-(2,2,2-trifluoroethoxy)pyridin-2-yl)pyrrolo[2,1-f][1,2,4]triazin-4-amine, N-((1r,3r)-3-(2-Methoxyethoxy)cyclobutyl)-5-methyl-2-(1-methyl-1H-imidazol-2-yl)-6-(1-methyl-1H-pyrazol-3-yl)pyrrolo[2,1-f][1,2,4]triazin-4-amine, N-((1s,3s)-3-Methoxycyclobutyl)-5-methyl-2-(1-methyl-1H-imidazol-2-yl)-6-(1-methyl-1H-pyrazol-3-yl)pyrrolo[2,1-f][1,2,4]triazin-4-amine, rac N-((1R,3R)-3-Methoxycyclopentyl)-5-methyl-2-(1-methyl-1H-imidazol-2-yl)-6-(1-methyl-1H-pyrazol-3-yl)pyrrolo[2,1-f][1,2,4]triazin-4-amine, rac N-((1R,3S)-3-Methoxycyclopentyl)-5-methyl-2-(1-methyl-1H-imidazol-2-yl)-6-(1-methyl-1H-pyrazol-3-yl)pyrrolo[2,1-f][1,2,4]triazin-4-amine, 6-(1-cyclopropyl-1H-pyrazol-3-yl)-5-methyl-2-(1-methyl-1H-imidazol-2-yl)pyrrolo[2,1-f][1,2,4]triazin-4-ol, 6-(1-cyclopropyl-1H-pyrazol-3-yl)-N-(6-methoxypyrimidin-4-yl)-5-methyl-2-(1-methyl-1H-imidazol-2-yl)pyrrolo[2,1-f][1,2,4]triazin-4-amine, N-(4-isopropoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine, 6-(1-cyclopropyl-1H-pyrazol-3-yl)-N-(4-methoxypyridin-2-yl)-5-methyl-2-(1-methyl-1H-imidazol-2-yl)pyrrolo[2,1-f][1,2,4]triazin-4-amine, 6-(1-cyclopropyl-1H-pyrazol-3-yl)-5-methyl-2-(1-methyl-1H-imidazol-2-yl)-N-(4-(trifluoromethoxy)pyridin-2-yl)pyrrolo[2,1-f][1,2,4]triazin-4-amine, 6-(1-cyclopropyl-1H-pyrazol-3-yl)-N-(4-(difluoromethoxy)pyridin-2-yl)-5-methyl-2-(1-methyl-1H-imidazol-2-yl)pyrrolo[2,1-f][1,2,4]triazin-4-amine, 6-(1-cyclopropyl-1H-pyrazol-3-yl)-5-methyl-2-(1-methyl-1H-imidazol-2-yl)-N-(4-(2,2,2-trifluoroethoxy)pyridin-2-yl)pyrrolo[2,1-f][1,2,4]triazin-4-amine, 6-(1-cyclopropyl-1H-pyrazol-3-yl)-N-(4-ethoxypyridin-2-yl)-5-methyl-2-(1-methyl-1H-imidazol-2-yl)pyrrolo[2,1-f][1,2,4]triazin-4-amine, N-(4-cyclopropoxypyridin-2-yl)-6-(1-cyclopropyl-1H-pyrazol-3-yl)-5-methyl-2-(1-methyl-1H-imidazol-2-yl)pyrrolo[2,1-f][1,2,4]triazin-4-amine, 6-(1-cyclopropyl-1H-pyrazol-3-yl)-5-methyl-2-(1-methyl-1H-imidazol-2-yl)-N-(pyridin-2-yl)pyrrolo[2,1-f][1,2,4]triazin-4-amine, 6-(1-cyclopropyl-1H-pyrazol-3-yl)-5-methyl-2-(1-methyl-1H-imidazol-2-yl)-N-(4-methylpyridin-2-yl)pyrrolo[2,1-f][1,2,4]triazin-4-amine, N2-(6-(1-cyclopropyl-1H-pyrazol-3-yl)-5-methyl-2-(1-methyl-1H-imidazol-2-yl)pyrrolo[2,1-f][1,2,4]triazin-4-yl)-N4,N4-dimethylpyridine-2,4-diamine, 2-((2-((6-(1-cyclopropyl-1H-pyrazol-3-yl)-5-methyl-2-(1-methyl-1H-imidazol-2-yl)pyrrolo[2,1-f][1,2,4]triazin-4-yl)amino)pyridin-4-yl)oxy)ethan-1-ol, 6-(1-cyclopropyl-1H-pyrazol-3-yl)-N-(4-(2-(dimethylamino)ethoxy)pyridin-2-yl)-5-methyl-2-(1-methyl-1H-imidazol-2-yl)pyrrolo[2,1-f][1,2,4]triazin-4-amine, 6-(1-cyclopropyl-1H-pyrazol-3-yl)-N-(4-(3-(dimethylamino)propoxy)pyridin-2-yl)-5-methyl-2-(1-methyl-1H-imidazol-2-yl)pyrrolo[2,1-f][1,2,4]triazin-4-amine, 3-((2-((6-(1-cyclopropyl-1H-pyrazol-3-yl)-5-methyl-2-(1-methyl-1H-imidazol-2-yl)pyrrolo[2,1-f][1,2,4]triazin-4-yl)amino)pyridin-4-yl)oxy)propan-1-ol, 2-((6-(1-cyclopropyl-1H-pyrazol-3-yl)-5-methyl-2-(1-methyl-1H-imidazol-2-yl)pyrrolo[2,1-f][1,2,4]triazin-4-yl)amino)pyridin-4-ol, N-((1r,3r)-3-Methoxycyclobutyl)-5-methyl-2-(1-methyl-1H-imidazol-2-yl)-6-(pyridin-3-yl)pyrrolo[2,1-f][1,2,4]triazin-4-amine, N-((1r,3r)-3-(2-Methoxyethoxy)cyclobutyl)-5-methyl-2-(1-methyl-1H-imidazol-2-yl)-6-(pyridin-3-yl)pyrrolo[2,1-f][1,2,4]triazin-4-amine, N-((1s,3s)-3-Methoxycyclobutyl)-5-methyl-2-(1-methyl-1H-imidazol-2-yl)-6-(pyridin-3-yl)pyrrolo[2,1-f][1,2,4]triazin-4-amine, rac N-((1R,3R)-3-Methoxycyclopentyl)-5-methyl-2-(1-methyl-1H-imidazol-2-yl)-6-(pyridin-3-yl)pyrrolo[2,1-f][1,2,4]triazin-4-amine, rac N-((1R,3S)-3-Methoxycyclopentyl)-5-methyl-2-(1-methyl-1H-imidazol-2-yl)-6-(pyridin-3-yl)pyrrolo[2,1-f][1,2,4]triazin-4-amine, 5-Methyl-2-(1-methyl-1H-imidazol-2-yl)-6-(pyridin-3-yl)-N-(pyrimidin-4-yl)pyrrolo[2,1-f][1,2,4]triazin-4-amine, N-(4-Methoxypyridin-2-yl)-5-methyl-2-(1-methyl-1H-imidazol-2-yl)-6-(pyridin-3-yl)pyrrolo[2,1-f][1,2,4]triazin-4-amine, N-(4-Methoxypyrimidin-2-yl)-5-methyl-2-(1-methyl-1H-imidazol-2-yl)-6-(pyridin-3-yl)pyrrolo[2,1-f][1,2,4]triazin-4-amine, N-((1r,3r)-3-Methoxycyclobutyl)-5-methyl-2-(1-methyl-1H-imidazol-2-yl)-6-(pyridin-4-yl)pyrrolo[2,1-f][1,2,4]triazin-4-amine, N-((1r,3r)-3-Methoxycyclobutyl)-6-(2-methoxypyridin-4-yl)-5-methyl-2-(1-methyl-1H-imidazol-2-yl)pyrrolo[2,1-f][1,2,4]triazin-4-amine, N-((1r,3r)-3-(2-Methoxyethoxy)cyclobutyl)-6-(2-methoxypyridin-4-yl)-5-methyl-2-(1-methyl-1H-imidazol-2-yl)pyrrolo[2,1-f][1,2,4]triazin-4-amine, N-((1s,3s)-3-Methoxycyclobutyl)-6-(2-methoxypyridin-4-yl)-5-methyl-2-(1-methyl-1H-imidazol-2-yl)pyrrolo[2,1-f][1,2,4]triazin-4-amine, rac N-((1R,3R)-3-Methoxycyclopentyl)-6-(2-methoxypyridin-4-yl)-5-methyl-2-(1-methyl-1H-imidazol-2-yl)pyrrolo[2,1-f][1,2,4]triazin-4-amine, rac N-((1R,3S)-3-Methoxycyclopentyl)-6-(2-methoxypyridin-4-yl)-5-methyl-2-(1-methyl-1H-imidazol-2-yl)pyrrolo[2,1-f][1,2,4]triazin-4-amine, 6-(1-Isopropyl-1H-pyrazol-4-yl)-N-(4-methoxypyridin-2-yl)-5-methyl-2-(1-methyl-1H-imidazol-2-yl)pyrrolo[2,1-f][1,2,4]triazin-4-amine, N-(4-Methoxypyridin-2-yl)-2-(1-methyl-1H-imidazol-2-yl)-5-(pyridin-2-yl)-6-(pyridin-3-yl)pyrrolo[2,1-f][1,2,4]triazin-4-amine, N-(6-Methoxypyrimidin-4-yl)-2-(1-methyl-1H-imidazol-2-yl)-5-(pyridin-2-yl)-6-(pyridin-3-yl)pyrrolo[2,1-f][1,2,4]triazin-4-amine, N-((1r,3r)-3-Methoxycyclobutyl)-2-(1-methyl-1H-imidazol-2-yl)-5-(pyridin-2-yl)-6-(pyridin-3-yl)pyrrolo[2,1-f][1,2,4]triazin-4-amine, N-(4-Methoxypyridin-2-yl)-2-(1-methyl-1H-imidazol-2-yl)-5, 6-di(pyridin-3-yl)pyrrolo[2,1-f][1,2,4]triazin-4-amine, N-(6-Methoxypyrimidin-4-yl)-2-(1-methyl-1H-imidazol-2-yl)-5, 6-di(pyridin-3-yl)pyrrolo[2,1-f][1,2,4]triazin-4-amine, N-((1r,3r)-3-Methoxycyclobutyl)-2-(1-methyl-1H-imidazol-2-yl)-5,6-di(pyridin-3-yl)pyrrolo[2,1-f][1,2,4]triazin-4-amine, 5-Methyl-2-(1-methyl-1H-imidazol-2-yl)-6-(1-methyl-1H-pyrazol-3-yl)pyrrolo[2,1-f][1,2,4]triazin-4-ol, N-Ethyl-4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxamide, 4-((4-Methoxypyridin-2-yl)amino)-2-(1-methyl-1H-imidazol-2-yl)-6-(1-methyl-1H-pyrazol-3-yl)-N-(2,2,2-trifluoroethyl)pyrrolo[2,1-f][1,2,4]triazine-5-carboxamide, N-Cyclopropyl-4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxamide, N-(2-Methoxyethyl)-4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxamide, N-(2-(Dimethylamino)ethyl)-4-((4-methoxypyridin-2-yl)amino)-2-(1-methyl-1H-imidazol-2-yl)-6-(1-methyl-1H-pyrazol-3-yl)pyrrolo[2,1-f][1,2,4]triazine-5-carboxamide, (4-((4-Methoxypyridin-2-yl)amino)-2-(1-methyl-1H-imidazol-2-yl)-6-(1-methyl-1H-pyrazol-3-yl)pyrrolo[2,1-f][1,2,4]triazin-5-yl)(pyrrolidin-1-yl)methanone, (4-((4-Methoxypyridin-2-yl)amino)-2-(1-methyl-1H-imidazol-2-yl)-6-(1-methyl-1H-pyrazol-3-yl)pyrrolo[2,1-f][1,2,4]triazin-5-yl)(morpholino)methanone, rac Methyl 4-(((1S,3S)-3-methoxycyclopentyl)amino)-2-(1-methyl-1H-imidazol-2-yl)-6-(1-methyl-1H-pyrazol-3-yl)pyrrolo[2,1-f][1,2,4]triazine-5-carboxylate, rac 4-(((1S,3S)-3-Methoxycyclopentyl)amino)-2-(1-methyl-1H-imidazol-2-yl)-6-(1-methyl-1H-pyrazol-3-yl)-N-(2,2,2-trifluoroethyl)pyrrolo[2,1-f][1,2,4]triazine-5-carboxamide, rac N-Cyclopropyl-4-(((1S,3S)-3-methoxycyclopentyl)amino)-2-(1-methyl-1H-imidazol-2-yl)-6-(1-methyl-1H-pyrazol-3-yl)pyrrolo[2,1-f][1,2,4]triazine-5-carboxamide, rac 4-(((1S,3S)-3-Methoxycyclopentyl)amino)-N-(2-methoxyethyl)-2-(1-methyl-1H-imidazol-2-yl)-6-(1-methyl-1H-pyrazol-3-yl)pyrrolo[2,1-f][1,2,4]triazine-5-carboxamide, rac 4-(((1S,3S)-3-Methoxycyclopentyl)amino)-N-(3-methoxypropyl)-2-(1-methyl-1H-imidazol-2-yl)-6-(1-methyl-1H-pyrazol-3-yl)pyrrolo[2,1-f][1,2,4]triazine-5-carboxamide, rac 4-(((1S,3S)-3-Methoxycyclopentyl)amino)-2-(1-methyl-1H-imidazol-2-yl)-6-(1-methyl-1H-pyrazol-3-yl)-N-(2-morpholinoethyl)pyrrolo[2,1-f][1,2,4]triazine-5-carboxamide, N-(2-((2-((5-Methyl-2-(1-methyl-1H-imidazol-2-yl)-6-(1-methyl-1H-pyrazol-3-yl)pyrrolo[2,1-f][1,2,4]triazin-4-yl)amino)pyridin-4-yl)oxy)ethyl)-5-((3aR,4R,6aS)-2-oxohexahydro-1H-thieno[3,4-d]imidazol-4-yl)pentanamide, 6-(1-(2-Aminoethyl)-1H-pyrazol-3-yl)-N-(4-methoxypyridin-2-yl)-5-methyl-2-(1-methyl-1H-imidazol-2-yl)pyrrolo[2,1-f][1,2,4]triazin-4-amine, 2-(1-(2-Aminoethyl)-1H-imidazol-2-yl)-N-(4-methoxypyridin-2-yl)-5-methyl-6-(1-methyl-1H-pyrazol-3-yl)pyrrolo[2,1-f][1,2,4]triazin-4-amine, 2-(1-Methyl-1H-imidazol-2-yl)-5-phenyl-6-(pyridin-3-yl)pyrrolo[2,1-f][1,2,4]triazin-4-ol, rac N-((1R,2R)-2-methoxycyclopropyl)-2-(1-methyl-1H-imidazol-2-yl)-5-phenyl-6-(pyridin-3-yl)pyrrolo[2,1-f][1,2,4]triazin-4-amine, N-((1s,3s)-3-Methoxycyclobutyl)-2-(1-methyl-1H-imidazol-2-yl)-5-phenyl-6-(pyridin-3-yl)pyrrolo[2,1-f][1,2,4]triazin-4-amine, N-((1r,3r)-3-Methoxycyclobutyl)-2-(1-methyl-1H-imidazol-2-yl)-5-phenyl-6-(pyridin-3-yl)pyrrolo[2,1-f][1,2,4]triazin-4-amine, rac N-((1R,3S)-3-Methoxycyclopentyl)-2-(1-methyl-1H-imidazol-2-yl)-5-phenyl-6-(pyridin-3-yl)pyrrolo[2,1-f][1,2,4]triazin-4-amine, rac N-((1S,3S)-3-methoxycyclopentyl)-2-(1-methyl-1H-imidazol-2-yl)-5-phenyl-6-(pyridin-3-yl)pyrrolo[2,1-f][1,2,4]triazin-4-amine, N-(2-Methoxyethyl)-2-(1-methyl-1H-imidazol-2-yl)-5-phenyl-6-(pyridin-3-yl)pyrrolo[2,1-f][1,2,4]triazin-4-amine, N-(4-Methoxypyridin-2-yl)-2-(1-methyl-1H-imidazol-2-yl)-5-phenyl-6-(pyridin-3-yl)pyrrolo[2,1-f][1,2,4]triazin-4-amine, rac N-((1R,2R)-2-Methoxycyclopropyl)-2-(1-methyl-1H-imidazol-2-yl)-5-phenyl-6-(pyridin-4-yl)pyrrolo[2,1-f][1,2,4]triazin-4-amine, N-((1s,3s)-3-methoxycyclobutyl)-2-(1-methyl-1H-imidazol-2-yl)-5-phenyl-6-(pyridin-4-yl)pyrrolo[2,1-f][1,2,4]triazin-4-amine, N-((1r,3r)-3-methoxycyclobutyl)-2-(1-methyl-1H-imidazol-2-yl)-5-phenyl-6-(pyridin-4-yl)pyrrolo[2,1-f][1,2,4]triazin-4-amine, rac N-((1R,3S)-3-methoxycyclopentyl)-2-(1-methyl-1H-imidazol-2-yl)-5-phenyl-6-(pyridin-4-yl)pyrrolo[2,1-f][1,2,4]triazin-4-amine, rac N-((1S,3S)-3-Methoxycyclopentyl)-2-(1-methyl-1H-imidazol-2-yl)-5-phenyl-6-(pyridin-4-yl)pyrrolo[2,1-f][1,2,4]triazin-4-amine, N-(2-Methoxyethyl)-2-(1-methyl-1H-imidazol-2-yl)-5-phenyl-6-(pyridin-4-yl)pyrrolo[2,1-f][1,2,4]triazin-4-amine, N-((1r,3r)-3-Methoxycyclobutyl)-2-(1-methyl-1H-imidazol-2-yl)-5, 6-diphenylpyrrolo[2,1-f][1,2,4]triazin-4-amine, 6-(3-(Aminomethyl)phenyl)-N-((1r,3r)-3-methoxycyclobutyl)-2-(1-methyl-1H-imidazol-2-yl)-5-phenylpyrrolo[2,1-f][1,2,4]triazin-4-amine, 6-(3-(2-Aminoethoxy)phenyl)-N-((1r,3r)-3-methoxycyclobutyl)-2-(1-methyl-1H-imidazol-2-yl)-5-phenylpyrrolo[2,1-f][1,2,4]triazin-4-amine,
6-(4-(Aminomethyl)phenyl)-N-((1r,3r)-3-methoxycyclobutyl)-2-(1-methyl-1H-imidazol-2-yl)-5-phenylpyrrolo[2,1-f][1,2,4]triazin-4-amine,
6-(4-(2-Aminoethyl)phenyl)-N-((1r,3r)-3-methoxycyclobutyl)-2-(1-methyl-1H-imidazol-2-yl)-5-phenylpyrrolo[2,1-f][1,2,4]triazin-4-amine,
6-(4-(2-Aminoethoxy)phenyl)-N-((1r,3r)-3-methoxycyclobutyl)-2-(1-methyl-1H-imidazol-2-yl)-5-phenylpyrrolo[2,1-f][1,2,4]triazin-4-amine,
6-(3-Methoxy-2-methylphenyl)-N-((1r,3r)-3-methoxycyclobutyl)-2-(1-methyl-1H-imidazol-2-yl)-5-phenylpyrrolo[2,1-f][1,2,4]triazin-4-amine,
6-(2,3-Dihydrobenzofuran-4-yl)-N-((1r,3r)-3-methoxycyclobutyl)-2-(1-methyl-1H-imidazol-2-yl)-5-phenylpyrrolo[2,1-f][1,2,4]triazin-4-amine,
5-Methyl-2-(1-methyl-1H-imidazol-2-yl)-6-(1-methyl-1H-pyrazol-3-yl)pyrrolo[2,1-f][1,2,4]triazin-4-amine,
N-(2-(1-Methyl-1H-imidazol-2-yl)-5,6-diphenylpyrrolo[2,1-f][1,2,4]triazin-4-yl)methanesulfonamide,
3-Methoxy-N-(2-(1-methyl-1H-imidazol-2-yl)-5,6-diphenylpyrrolo[2,1-f][1,2,4]triazin-4-yl)propane-1-sulfonamide,
(1r,3r)-3-Methoxy-N-(2-(1-methyl-1H-imidazol-2-yl)-5,6-diphenylpyrrolo[2,1-f][1,2,4]triazin-4-yl)cyclobutane-1-sulfonamide,
N-(2-(3-(4-((4-Methoxypyridin-2-yl)amino)-5-methyl-2-(1-methyl-1H-imidazol-2-yl)pyrrolo[2,1-f][1,2,4]triazin-6-yl)-1H-pyrazol-1-yl)ethyl)-5-((3aR,4R,6aS)-2-oxohexahydro-1H-thieno[3,4-d]imidazol-4-yl)pentanamide,
N-(2-(2-(4-((4-Methoxypyridin-2-yl)amino)-5-methyl-6-(1-methyl-1H-pyrazol-3-yl)pyrrolo[2,1-f][1,2,4]triazin-2-yl)-1H-imidazol-1-yl)ethyl)-5-((3aR,4R,6aS)-2-oxohexahydro-1H-thieno[3,4-d]imidazol-4-yl)pentanamide,
6-(2-Fluoro-6-methoxyphenyl)-N-(4-methoxypyridin-2-yl)-2-(1-methyl-1H-imidazol-2-yl)-5-phenylpyrrolo[2,1-f][1,2,4]triazin-4-amine,
N-((1r,3r)-3-Methoxycyclobutyl)-2-(1-methyl-1H-imidazol-2-yl)-6-(4-methylpyridin-3-yl)-5-phenylpyrrolo[2,1-f][1,2,4]triazin-4-amine,
6-(2,3-Dimethoxyphenyl)-N-((1r,3r)-3-methoxycyclobutyl)-2-(1-methyl-1H-imidazol-2-yl)-5-phenylpyrrolo[2,1-f][1,2,4]triazin-4-amine,
4-((4-Methoxypyridin-2-yl)oxy)-5-methyl-2-(1-methyl-1H-imidazol-2-yl)-6-(1-methyl-1H-pyrazol-3-yl)pyrrolo[2,1-f][1,2,4]triazine,
N-(5-Methyl-2-(1-methyl-1H-imidazol-2-yl)-6-(1-methyl-1H-pyrazol-3-yl)pyrrolo[2,1-f][1,2,4]triazin-4-yl)-2,3-dihydrofuro[3,2-c]pyridin-4-amine,
5-Methyl-2-(1-methyl-1H-imidazol-2-yl)-6-(1-methyl-1H-pyrazol-3-yl)-N-(4-morpholinopyridin-2-yl)pyrrolo[2,1-f][1,2,4]triazin-4-amine,
N-(4-Methoxypyridin-2-yl)-N,5-dimethyl-2-(1-methyl-1H-imidazol-2-yl)-6-(1-methyl-1H-pyrazol-3-yl)pyrrolo[2,1-f][1,2,4]triazin-4-amine,
N-(5-Methoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine,
N-(5-Methoxypyridin-2-yl)-N,5-dimethyl-2-(1-methyl-1H-imidazol-2-yl)-6-(1-methyl-1H-pyrazol-3-yl)pyrrolo[2,1-f][1,2,4]triazin-4-amine,
5-Methyl-2-(1-methyl-1H-imidazol-2-yl)-6-(1-methyl-1H-pyrazol-3-yl)-N-(5-methylpyridin-2-yl)pyrrolo[2,1-f][1,2,4]triazin-4-amine,
N5,N5-Dimethyl-N2-(5-methyl-2-(1-methyl-1H-imidazol-2-yl)-6-(1-methyl-1H-pyrazol-3-yl)pyrrolo[2,1-f][1,2,4]triazin-4-yl)pyridine-2,5-diamine,
5-Methyl-2-(1-methyl-1H-imidazol-2-yl)-6-(1-methyl-1H-pyrazol-3-yl)-N-(5-(pyrrolidin-1-yl)pyridin-2-yl)pyrrolo[2,1-f][1,2,4]triazin-4-amine,
N-(5-Ethoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine,
5-Methyl-2-(1-methyl-1H-imidazol-2-yl)-6-(1-methyl-1H-pyrazol-3-yl)-N-(5-(2,2,2-trifluoroethoxy)pyridin-2-yl)pyrrolo[2,1-f][1,2,4]triazin-4-amine,
N-(5-(Difluoromethoxy)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine,
5-Methyl-2-(1-methyl-1H-imidazol-2-yl)-6-(1-methyl-1H-pyrazol-3-yl)-N-(5-(trifluoromethoxy)pyridin-2-yl)pyrrolo[2,1-f][1,2,4]triazin-4-amine,
5-Methyl-2-(1-methyl-1H-imidazol-2-yl)-6-(1-methyl-1H-pyrazol-3-yl)-N-(5-(trifluoromethyl)pyridin-2-yl)pyrrolo[2,1-f][1,2,4]triazin-4-amine,
N-(5-(Difluoromethyl)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine,
N-(4-Methoxy-5-methylpyridin-2-yl)-5-methyl-2-(1-methyl-1H-imidazol-2-yl)-6-(1-methyl-1H-pyrazol-3-yl)pyrrolo[2,1-f][1,2,4]triazin-4-amine,
N-(5-Methoxy-4-methylpyridin-2-yl)-5-methyl-2-(1-methyl-1H-imidazol-2-yl)-6-(1-methyl-1H-pyrazol-3-yl)pyrrolo[2,1-f][1,2,4]triazin-4-amine,
N-(5-Fluoro-4-methoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine,
N-(5-Cyclopropyl-4-methoxypyridin-2-yl)-5-methyl-2-(1-methyl-1H-imidazol-2-yl)-6-(1-methyl-1H-pyrazol-3-yl)pyrrolo[2,1-f][1,2,4]triazin-4-amine,
5-Methyl-2-(1-methyl-1H-imidazol-2-yl)-6-(1-methyl-1H-pyrazol-3-yl)-4-(5-methyl-2,3-dihydro-1H-pyrrolo[2,3-b]pyridin-1-yl)pyrrolo[2,1-f][1,2,4]triazine,
2-(2-((5-Methyl-2-(1-methyl-1H-imidazol-2-yl)-6-(1-methyl-1H-pyrazol-3-yl)pyrrolo[2,1-f][1,2,4]triazin-4-yl)amino)pyridin-4-yl)propan-2-ol,
2-(6-((5-Methyl-2-(1-methyl-1H-imidazol-2-yl)-6-(1-methyl-1H-pyrazol-3-yl)pyrrolo[2,1-f][1,2,4]triazin-4-yl)amino)pyridin-3-yl)propan-2-ol,
N-(5-(1H-Imidazol-1-yl)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine,
5-Methyl-N-(5-(2-methyl-1H-imidazol-1-yl)pyridin-2-yl)-2-(1-methyl-1H-imidazol-2-yl)-6-(1-methyl-1H-pyrazol-3-yl)pyrrolo[2,1-f][1,2,4]triazin-4-amine,
N-(4-Methoxy-5-(4-methyl-1H-imidazol-1-yl)pyridin-2-yl)-5-methyl-2-(1-methyl-1H-imidazol-2-yl)-6-(1-methyl-1H-pyrazol-3-yl)pyrrolo[2,1-f][1,2,4]triazin-4-amine,
5-Methyl-N-(4-(2-methyl-1H-imidazol-1-yl)pyridin-2-yl)-2-(1-methyl-1H-imidazol-2-yl)-6-(1-methyl-1H-pyrazol-3-yl)pyrrolo[2,1-f][1,2,4]triazin-4-amine,
5-Methyl-2-(1-methyl-1H-imidazol-2-yl)-6-(1-methyl-1H-pyrazol-3-yl)-N-(5-morpholinopyridin-2-yl)pyrrolo[2,1-f][1,2,4]triazin-4-amine,
N-([2,4'-Bipyridin]-2'-yl)-5-methyl-2-(1-methyl-1H-imidazol-2-yl)-6-(1-methyl-1H-pyrazol-3-yl)pyrrolo[2,1-f][1,2,4]triazin-4-amine, N-([2,3'-Bipyridin]-6'-yl)-5-methyl-2-(1-methyl-1H-imidazol-2-yl)-6-(1-methyl-1H-pyrazol-3-yl)pyrrolo[2,1-f][1,2,4]triazin-4-amine, N-([3,4'-Bipyridin]-2'-yl)-5-methyl-2-(1-methyl-1H-imidazol-2-yl)-6-(1-methyl-1H-pyrazol-3-yl)pyrrolo[2,1-f][1,2,4]triazin-4-amine, 5-Methyl-2-(1-methyl-1H-imidazol-2-yl)-6-(1-methyl-1H-pyrazol-3-yl)-4-(5-(trifluoromethyl)-2,3-dihydro-1H-pyrrolo[2,3-b]pyridin-1-yl)pyrrolo[2,1-f][1,2,4]triazine, N-(5-Methoxy-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine, N-(5-Methoxy-I-methyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine, N-(5-(Difluoromethoxy)-1-methyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine, 5-Methyl-2-(1-methyl-1H-imidazol-2-yl)-6-(1-methyl-1H-pyrazol-3-yl)-N-(5-methyl-1H-pyrazol-3-yl)pyrrolo[2,1-f][1,2,4]triazin-4-amine, 5-Methyl-2-(1-methyl-1H-imidazol-2-yl)-6-(1-methyl-1H-pyrazol-3-yl)-N-(1H-pyrazol-3-yl)pyrrolo[2,1-f][1,2,4]triazin-4-amine, N-(5-Cyclobutyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine, N-(5-(Difluoromethyl)-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine, 5-Methyl-2-(1-methyl-1H-imidazol-2-yl)-6-(1-methyl-1H-pyrazol-3-yl)-N-(5-(trifluoromethyl)-1H-pyrazol-3-yl)pyrrolo[2,1-f][1,2,4]triazin-4-amine, N-(5-Ethoxy-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine, 5-((5-Methyl-2-(1-methyl-1H-imidazol-2-yl)-6-(1-methyl-1H-pyrazol-3-yl)pyrrolo[2,1-f][1,2,4]triazin-4-yl)amino)-1,2-dihydro-3H-pyrazol-3-one, 3-((5-methyl-2-(1-methyl-1H-imidazol-2-yl)-6-(1-methyl-1H-pyrazol-3-yl)pyrrolo[2,1-f][1,2,4]triazin-4-yl)oxy)-1H-pyrazol-5-amine, 5-Methyl-2-(1-methyl-1H-imidazol-2-yl)-6-(1-methyl-1H-pyrazol-3-yl)-N-(5-phenyl-1H-pyrazol-3-yl)pyrrolo[2,1-f][1,2,4]triazin-4-amine, 5-Methyl-2-(1-methyl-1H-imidazol-2-yl)-6-(1-methyl-1H-pyrazol-3-yl)-N-(5-(pyridin-3-yl)-1H-pyrazol-3-yl)pyrrolo[2,1-f][1,2,4]triazin-4-amine, 5-Methyl-2-(1-methyl-1H-imidazol-2-yl)-6-(1-methyl-1H-pyrazol-3-yl)-N-(5-(pyridin-2-yl)-1H-pyrazol-3-yl)pyrrolo[2,1-f][1,2,4]triazin-4-amine, 5-Methyl-2-(1-methyl-1H-imidazol-2-yl)-6-(1-methyl-1H-pyrazol-3-yl)-N-(5-(pyridin-4-yl)-1H-pyrazol-3-yl)pyrrolo[2,1-f][1,2,4]triazin-4-amine, N-(4,5-Dimethyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine, N-(5-Isopropyl-1H-pyrazol-3-yl)-5-methyl-2-(1-methyl-1H-imidazol-2-yl)-6-(1-methyl-1H-pyrazol-3-yl)pyrrolo[2,1-f][1,2,4]triazin-4-amine, 6-(3-Methoxy-2-methylphenyl)-N-((1s,3s)-3-methoxycyclobutyl)-2-(1-methyl-1H-imidazol-2-yl)-5-phenylpyrrolo[2,1-f][1,2,4]triazin-4-amine, rac 6-(3-methoxy-2-methylphenyl)-N-((1R,3R)-3-methoxycyclopentyl)-2-(1-methyl-1H-imidazol-2-yl)-5-phenylpyrrolo[2,1-f][1,2,4]triazin-4-amine, rac 6-(3-Methoxy-2-methylphenyl)-N-((1R,3S)-3-methoxycyclopentyl)-2-(1-methyl-1H-imidazol-2-yl)-5-phenylpyrrolo[2,1-f][1,2,4]triazin-4-amine, rac 6-(3-Methoxy-2-methylphenyl)-N-((1R,2R)-2-methoxycyclobutyl)-2-(1-methyl-1H-imidazol-2-yl)-5-phenylpyrrolo[2,1-f][1,2,4]triazin-4-amine, 6-(2,6-Difluoro-3-methoxyphenyl)-N-((1r,3r)-3-methoxycyclobutyl)-2-(1-methyl-1H-imidazol-2-yl)-5-phenylpyrrolo[2,1-f][1,2,4]triazin-4-amine, 6-(3-Methoxy-2-methylphenyl)-N-((1r,3r)-3-methoxycyclobutyl)-2-(1-methyl-1H-imidazol-2-yl)-5-(pyridin-2-yl)pyrrolo[2,1-f][1,2,4]triazin-4-amine, 5-Cyclopropyl-N-((1r,3r)-3-methoxycyclobutyl)-2-(1-methyl-1H-imidazol-2-yl)-6-(1-methyl-1H-pyrazol-3-yl)pyrrolo[2,1-f][1,2,4]triazin-4-amine, and 5-Cyclopropyl-N-(4-methoxypyridin-2-yl)-2-(1-methyl-1H-imidazol-2-yl)-6-(1-methyl-1H-pyrazol-3-yl)pyrrolo[2,1-f][1,2,4]triazin-4-amine, or a pharmaceutically acceptable salt, solvate, stereoisomer, isotopic variant, or polymorph thereof.

20. The compound of claim 1, which is a pharmaceutically acceptable salt of said compound, optionally wherein the pharmaceutically acceptable salt of the compound is a hydrochloride, sulfate, acetate, lactate, malate, tartrate, citrate, ascorbate, succinate, butyrate, valerate, mesylate, or fumarate salt of said compound.

21. The compound of claim 1, wherein the compound or pharmaceutically acceptable salt, solvate, stereoisomer, isotopic variant, and/or polymorph thereof:

i) is a modulator of Ras superfamily activity according to a Ras Superfamily Activity Assay;

ii) inhibits phosphorylation of Erk1/2 according to Erk1/2 Phosphorylation Assay;

iii) activates phosphorylation of Erk1/2 according to Erk1/2 Phosphorylation Assay;

iv) inhibits phosphorylation of Akt according to Akt Phosphorylation Assay;

v) activates phosphorylation of Akt according to Akt Phosphorylation Assay;

vi) inhibits phosphorylation of Smad2/3 according to Phospho-Smad2/3 Inhibition Assay;

vii) activates phosphorylation of Smad2/3 according to Phospho-Smad2/3 Inhibition Assay;

viii) inhibits JNK according to JNK Activation Assay;

ix) activates JNK according to JNK Activation Assay;

x) inhibits MAPK p38 according to MAPK p38 Activation Assay;

xi) activates MAPK p38 according to MAPK p38 Activation Assay;

xii) inhibits IL-6 according to IL-6 Quantification Assay;

xiii) inhibits TNF-alpha according to TNF-alpha Quantification Assay; or xiv) inhibits proliferation in MiaPaca2, NCI-H358, A375, GP2d, BT549, or MM.R1 according to Proliferation Assay.

22. The compound of claim 1, wherein the compound or pharmaceutically acceptable salt, solvate, stereoisomer, isotopic variant, and/or polymorph thereof has a half-life of 10 minutes or more in mouse liver microsomes according to Mouse Liver Microsome Metabolic Stability Assay.

23. The compound of claim 1, wherein the compound or pharmaceutically acceptable salt, solvate, stereoisomer, isotopic variant, and/or polymorph thereof has a kinetic solubility of 10 μM or more in pH 7.4 buffer comprising 2% DMSO according to Kinetic Solubility Assay.

24. A pharmaceutical composition comprising the compound of claim 1, or pharmaceutically acceptable salt, solvate, stereoisomer, isotopic variant, and/or polymorph thereof, and a pharmaceutically acceptable carrier, excipient or diluent.

25. A method of modulating a Ras superfamily protein, comprising contacting the Ras superfamily protein with an effective amount of the compound of claim 1, or pharmaceutically acceptable salt, solvate, stereoisomer, isotopic variant, and/or polymorph thereof.

26. A method of modulating caspase activity, comprising contacting the caspase with an effective amount of the compound of claim 1, and/or pharmaceutically acceptable salt, solvate, stereoisomer, isotopic variant, or polymorph thereof.

27. A method of treating cancer in a subject, comprising administering a therapeutically effective amount of the compound of claim 1, or pharmaceutically acceptable salt, solvate, stereoisomer, isotopic variant, and/or polymorph thereof, to the subject having cancer.

28. A method of modulating Erk1/2 activity, Akt activity, Smad2/3 activity, JNK activity, MAPK p38 activity, IL-6 activity, or TNF-alpha activity, comprising contacting an Erk1/2 protein, an Akt protein, a Smad2/3 protein, a JNK protein, a MAPK p38 protein, a IL-6 protein, or a TNF-alpha protein with an effective amount of the compound of claim 1, or pharmaceutically acceptable salt, solvate, stereoisomer, isotopic variant, and/or polymorph thereof.

29. A method of treating a fibrotic disease in a subject, comprising administering a therapeutically effective amount of the compound of claim 1, or pharmaceutically acceptable salt, solvate, stereoisomer, isotopic variant, and/or polymorph thereof, to the subject.

30. A method of treating an inflammatory disease in a subject, comprising administering a therapeutically effective amount of the compound of claim 1, or pharmaceutically acceptable salt, solvate, stereoisomer, isotopic variant, and/or polymorph thereof, to the subject.

31. The pharmaceutical composition of claim 24, wherein the compound is N-(4-Methoxypyridin-2-yl)-5-methyl-2-(1-methyl-1H-imidazol-2-yl)-6-(1-methyl-1H-pyrazol-3-yl) pyrrolo [2,1-*f*] [1,2,4] triazin-4-amine, or a pharmaceutically acceptable salt, solvate, and/or isotopic variant thereof.

32. The compound of claim 17, wherein $R^{1A}$ and $R^{2A}$ together with the nitrogen to which they are attached have a structure of:

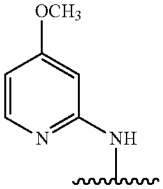,

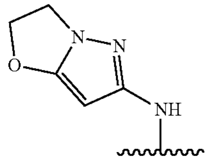,

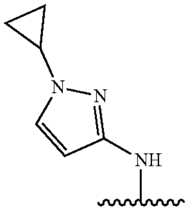,

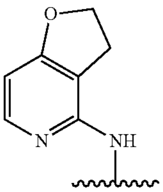,

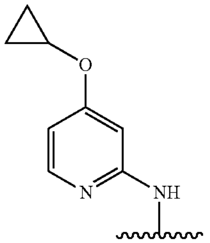, or

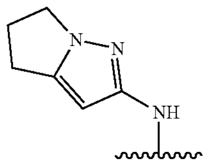.

33. The compound of claim 32, wherein $R^{18A}$ is methyl, ethyl, isopropyl, or cyclopropyl.

34. The compound of claim 32, wherein $R^{18A}$ is methyl.

35. The compound of claim 34, wherein the compound is:

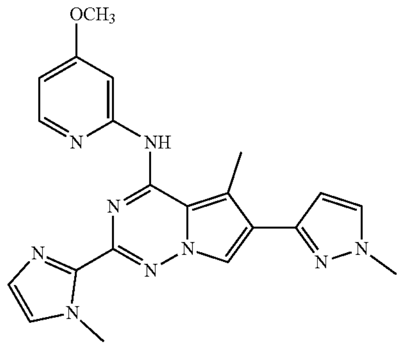 [SMILES: COc1ccnc(Nc2nc(-c3nccn3C)nn3cc(-c4ccn(C)n4)c(C)c23)c1]

or a pharmaceutically acceptable salt, solvate, and/or isotopic variant thereof.

36. The compound of claim 35, wherein the compound is a pharmaceutically acceptable salt of:

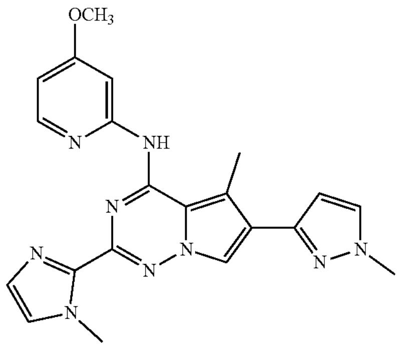.

37. The compound of claim 35, wherein the compound is a pharmaceutically acceptable solvate of:

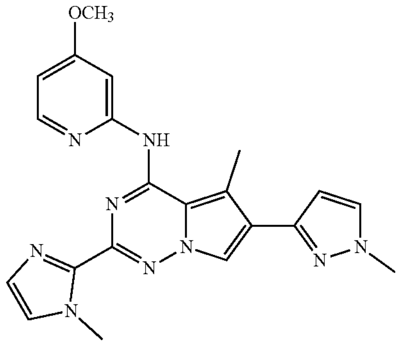.

38. The compound of claim 35, wherein the compound is:

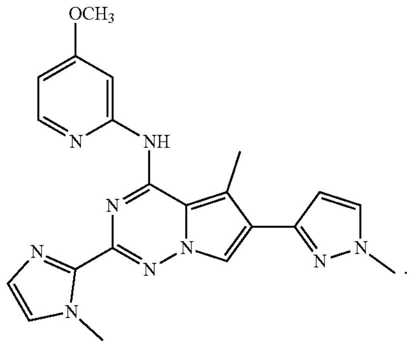 [SMILES: COc1ccnc(Nc2nc(-c3nccn3C)nn3cc(-c4ccn(C)n4)c(C)c23)c1]

39. The compound of claim 19, wherein the compound is N-(4-Methoxypyridin-2-y1)-5-methyl-2-(1-methyl-1H-imidazol-2-yl)-6-(1-methyl-1H-pyrazol-3-yl) pyrrolo [2,1-*f*] [1,2,4] triazin-4-amine, or a pharmaceutically acceptable salt and/or a pharmaceutically acceptable solvate.

40. The compound of claim 39, wherein the compound is a pharmaceutically acceptable salt and a pharmaceutically acceptable solvate of N-(4-Methoxypyridin-2-yl)-5-methyl-2-(1-methyl-1H-imidazol-2-yl)-6-(1-methyl-1H-pyrazol-3-yl) pyrrolo [2,1-*f*] [1,2,4] triazin-4-amine.

41. The method of modulating a Ras superfamily protein of claim 25, wherein the compound is N-(4-Methoxypyridin-2-yl)-5-methyl-2-(1-methyl-1H-imidazol-2-yl)-6-(1-methyl-1H-pyrazol-3-yl) pyrrolo [2,1-*f*] [1,2,4] triazin-4-amine, or a pharmaceutically acceptable salt, solvate, and/or isotopic variant thereof.

42. The method of modulating caspase activity of claim 26, wherein the compound is N-(4-Methoxypyridin-2-yl)-5-methyl-2-(1-methyl-1H-imidazol-2-yl)-6-(1-methyl-1H-pyrazol-3-yl) pyrrolo [2,1-*f*] [1,2,4] triazin-4-amine, or a pharmaceutically acceptable salt, solvate, and/or isotopic variant thereof.

43. The method of treating cancer of claim 27, wherein the compound is N-(4-Methoxypyridin-2-yl)-5-methyl-2-(1-methyl-1H-imidazol-2-yl)-6-(1-methyl-1H-pyrazol-3-yl) pyrrolo [2,1-*f*] [1,2,4] triazin-4-amine, or a pharmaceutically acceptable salt, solvate, and/or isotopic variant thereof.

44. The method of modulating Erk1/2 activity, Akt activity, Smad2/3 activity, JNK activity, MAPK p38 activity, IL-6 activity, or TNF-alpha activity, of claim 28, wherein the compound is N-(4-Methoxypyridin-2-yl)-5-methyl-2-(1-methyl-1H-imidazol-2-yl)-6-(1-methyl-1H-pyrazol-3-yl) pyrrolo [2,1-*f*] [1,2,4] triazin-4-amine, or a pharmaceutically acceptable salt, solvate, and/or isotopic variant thereof.

45. The method of treating fibrotic disease of claim 29, wherein the compound is N-(4-Methoxypyridin-2-yl)-5-methyl-2-(1-methyl-1H-imidazol-2-yl)-6-(1-methyl-1H-pyrazol-3-y1) pyrrolo [2,1-71 ] [1,2,4] triazin-4-amine, or a pharmaceutically acceptable salt, solvate, and/or isotopic variant thereof.

46. The method of treating inflammatory disease of claim 30, wherein the compound is N-(4-Methoxypyridin-2-yl)-5-methyl-2-(1-methyl-1H-imidazol-2-yl)-6-(1-methyl-1H-pyrazol-3-yl) pyrrolo [2,1-*f*] [1,2,4] triazin-4-amine, or a pharmaceutically acceptable salt, solvate, and/or isotopic variant thereof.

* * * * *